United States Patent
Meng et al.

(10) Patent No.: US 10,155,725 B2
(45) Date of Patent: Dec. 18, 2018

(54) ANTHELMINTIC COMPOUNDS AND COMPOSITIONS AND METHOD OF USING THEREOF

(71) Applicant: MERIAL, INC., Duluth, GA (US)

(72) Inventors: Charles Q. Meng, Johns Creek, GA (US); Alan Long, Hillsborough, NC (US); Scot Huber, Raleigh, NC (US); Srinivas Reddy Gurrala, Cary, NC (US); Douglas Edward Wilkinson, Wake Forest, NC (US); Gregory Pacofsky, Raleigh, NC (US)

(73) Assignee: MERIAL, INC., Duluth, GA (US)

( * ) Notice: Subject to any disclaimer, the term of this patent is extended or adjusted under 35 U.S.C. 154(b) by 0 days.

(21) Appl. No.: 14/981,847

(22) Filed: Dec. 28, 2015

(65) Prior Publication Data
US 2016/0185726 A1 Jun. 30, 2016

Related U.S. Application Data

(62) Division of application No. 14/083,879, filed on Nov. 19, 2013, now Pat. No. 9,249,102.
(Continued)

(51) Int. Cl.
| | |
|---|---|
| *A61K 31/497* | (2006.01) |
| *C07D 215/38* | (2006.01) |
| *A61K 31/167* | (2006.01) |
| *A61K 31/4704* | (2006.01) |
| *A61K 31/495* | (2006.01) |
| *A61K 31/496* | (2006.01) |
| *A61K 31/4995* | (2006.01) |
| *A61K 45/06* | (2006.01) |
| *C07D 241/04* | (2006.01) |
| *C07D 277/64* | (2006.01) |
| *C07D 307/81* | (2006.01) |
| *C07D 401/06* | (2006.01) |
| *C07D 401/12* | (2006.01) |
| *C07D 417/06* | (2006.01) |

(Continued)

(52) U.S. Cl.
CPC ..........  *C07D 215/38* (2013.01); *A61K 31/167* (2013.01); *A61K 31/47* (2013.01); *A61K 31/472* (2013.01); *A61K 31/4704* (2013.01); *A61K 31/495* (2013.01); *A61K 31/496* (2013.01); *A61K 31/4995* (2013.01); *A61K 45/06* (2013.01); *C07C 233/56* (2013.01); *C07C 235/16* (2013.01); *C07D 211/58* (2013.01); *C07D 213/74* (2013.01); *C07D 215/42* (2013.01); *C07D 217/06* (2013.01); *C07D 241/04* (2013.01); *C07D 263/58* (2013.01); *C07D 277/64* (2013.01); *C07D 277/82* (2013.01); *C07D 295/15* (2013.01); *C07D 295/16* (2013.01); *C07D 295/185* (2013.01); *C07D 295/215* (2013.01); *C07D 307/14* (2013.01); *C07D 307/81* (2013.01); *C07D 307/82* (2013.01); *C07D 333/60* (2013.01); *C07D 333/66* (2013.01); *C07D 401/06* (2013.01); *C07D 401/12* (2013.01); *C07D 403/12* (2013.01); *C07D 405/12* (2013.01); *C07D 409/12* (2013.01); *C07D 413/12* (2013.01); *C07D 417/06* (2013.01); *C07D 417/12* (2013.01); *C07D 471/08* (2013.01); *C07C 2601/14* (2017.05)

(58) Field of Classification Search
USPC .................................................... 514/253.06
See application file for complete search history.

(56) References Cited

U.S. PATENT DOCUMENTS

| | | | | |
|---|---|---|---|---|
| 6,635,658 | B2 * | 10/2003 | Madera ................ | C07D 211/58 514/235.5 |
| 2007/0270422 | A1 | 11/2007 | Fukushima et al. | |
| 2014/0275063 | A1 * | 9/2014 | Carley ................ | C07D 471/04 514/232.5 |

FOREIGN PATENT DOCUMENTS

| | | |
|---|---|---|
| EP | 2468096 A1 | 6/2012 |
| WO | 02/26720 A1 | 4/2002 |

(Continued)

OTHER PUBLICATIONS

"Antihelminthic activity of some newly synthesized 5(6)-(un)substituted-1H-benzimidazol-2-ylthioacetylpiperazine derivatives", Mavrova et al., European Journal of Medicinal Chemistry, 2006, 41(12), 1412-1420.

(Continued)

*Primary Examiner* — Marcos L Sznaidman
(74) *Attorney, Agent, or Firm* — Judy Jarecki-Black; John Ezcurra; Merial, Inc.

(57) ABSTRACT

The present invention relates to novel anthelmintic compounds of formula (I) below:

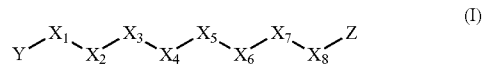

wherein
Y and Z are independently a bicyclic carbocyclic or a bicyclic heterocyclic group, or one of Y or Z is a bicyclic carbocyclic or a bicyclic heterocyclic group and the other of Y or Z is alkyl, alkenyl, alkynyl, cycloalkyl, phenyl, heterocyclyl or heteroaryl, and variables $X_1$, $X_2$, $X_3$, $X_4$, $X_5$, $X_6$, $X_7$ and $X_8$ are as defined herein. The invention also provides for veterinary compositions comprising the anthelmintic compounds of the invention, and their uses for the treatment and prevention of parasitic infections in animals.

16 Claims, No Drawings

Related U.S. Application Data

(60) Provisional application No. 61/728,782, filed on Nov. 20, 2012.

(51) Int. Cl.

| | | |
|---|---|---|
| *C07D 471/08* | (2006.01) | |
| *C07D 403/12* | (2006.01) | |
| *C07D 213/74* | (2006.01) | |
| *C07D 215/42* | (2006.01) | |
| *C07D 217/06* | (2006.01) | |
| *C07D 333/66* | (2006.01) | |
| *C07D 405/12* | (2006.01) | |
| *C07D 409/12* | (2006.01) | |
| *C07D 413/12* | (2006.01) | |
| *C07D 417/12* | (2006.01) | |
| *C07D 263/58* | (2006.01) | |
| *C07D 277/82* | (2006.01) | |
| *C07D 295/15* | (2006.01) | |
| *C07D 295/185* | (2006.01) | |
| *C07D 295/215* | (2006.01) | |
| *C07D 307/14* | (2006.01) | |
| *C07D 307/82* | (2006.01) | |
| *C07C 233/56* | (2006.01) | |
| *C07C 235/16* | (2006.01) | |
| *A61K 31/47* | (2006.01) | |
| *A61K 31/472* | (2006.01) | |
| *C07D 211/58* | (2006.01) | |
| *C07D 295/16* | (2006.01) | |
| *C07D 333/60* | (2006.01) | |

(56) References Cited

FOREIGN PATENT DOCUMENTS

| WO | 2004/111004 A1 | 12/2004 |
|---|---|---|
| WO | 2004/111007 A1 | 12/2004 |
| WO | 2004/111032 A1 | 12/2004 |
| WO | 2005/056550 A2 | 6/2005 |
| WO | 2006/103545 A1 | 10/2006 |
| WO | 2009/077527 A1 | 6/2009 |
| WO | 2010/080357 A1 | 7/2010 |
| WO | 2010/115688 A1 | 10/2010 |
| WO | 2010/146083 A1 | 12/2010 |
| WO | 2012/058134 A1 | 5/2012 |

OTHER PUBLICATIONS

"Chemotherapy of filariasis—on the search of new agents effective on the reproductive system female adult worms," Singh et al., Zeitschrift Fuer Naturforschung, Section C. Biosciences, 1990, 45(11/12), 1210-1214.
"Discovery of pyrimidine carboxamides as potent and selective CCK1 receptor agonists," Wang et al., Bioorganic & Medicinal Chemistry Letters, 2011, 21, 2911-2915.
"A new class of 5-HT2B antagonists possesses favorable potency, selectivity, and rat pharmacokinetic properties," Moss et al., Bioorganic & Medicinal Chemistry Letters, 2009, 19, 2206-2210.
"Calcitonin gene-related peptide (CGRP) receptor antagonists: Pyridine as a replacement for a core amide group," Luo et al., Bioorganic & Medicinal Chemistry Letters, 2012, 22, 2917-2921.
Database Registry [Online], Chemical Abstracts Service, Columbus, Ohio, US; 2007, XP002719957, retrieved from STN, Database accession No. 924169-66-4, compounds 924169-66-4.
Database Registry [Online], Chemical Abstracts Service, Columbus, Ohio, US; 2007, XP002719958, retrieved from STN Database, accession No. 927571-60-6 compounds 927571-60-6.
Database Registry [Online], Chemical Abstracts Service, Columbus, Ohio, US; 2008, XP002719959, retrieved from STN, Database accession No. 1048639-02-6 compounds 1048639-02-6.
Database Registry [Online], Chemical Abstracts Service, Columbus, Ohio, US; 2008, XP002719960, retrieved from STN, Database accession No. 1058200-26-2 compounds 1058200-26-2.
Database Registry [Online], Chemical Abstracts Service, Columbus, Ohio, US; 2008, XP002719961, retrieved from STN, Database accession No. 1058204-48-0 compounds 1058204-48-0.
Database Registry [Online], Chemical Abstracts Service, Columbus, Ohio, US; 2008, XP002719962, retrieved from STN, Database accession No. 1058204-80-0 compounds 1058204-80-0.
Database Registry [Online], Chemical Abstracts Service, Columbus, Ohio, US; 2008, XP002719963, retrieved from STN, Database accession No. 1058228-61-7 compounds 1058228-61-7.
Database Registry [Online], Chemical Abstracts Service, Columbus, Ohio, US; 2008,, XP002719964, retrieved from STN, Database accession No. 1058228-86-6 compounds 1058228-86-6.
Database Registry [Online], Chemical Abstracts Service, Columbus, Ohio, US; 2008, XP002719965, retrieved from STN, Database accession No. 1058229-31-4 compounds 1058229-31-4.
Database Registry [Online], Chemical Abstracts Service, Columbus, Ohio, US; 2008, XP002719966, retrieved from STN, Database accession No. 1058234-57-3 compounds 1058234-57-3.
Database Registry [Online], Chemical Abstracts Service, Columbus, Ohio, US; 2008, XP002719967, retrieved from STN, Database accession No. 1058234-68-6 compounds 1058234-68-6.
Database Registry [Online], Chemical Abstracts Service, Columbus, Ohio, US; 2008, XP002719968, retrieved from STN, Database accession No. 1058236-89-7 compounds 1058236-89-7.
Database Registry [Online], Chemical Abstracts Service, Columbus, Ohio, US; 2008, XP002719969, retrieved from STN, Database accession No. 1058237-30-1 compounds 1058237-30-1.
Database Registry [Online], Chemical Abstracts Service, Columbus, Ohio, US; 2008, XP002719970, retrieved from STN, Database accession No. 1058256-03-3 compounds 1058256-03-3.
Database Registry [Online], Chemical Abstracts Service, Columbus, Ohio, US; 2008, XP002719971, retrieved from STN, Database accession No. 1058256-09-9 compounds 1058256-09-9.
Database Registry [Online], Chemical Abstracts Service, Columbus, Ohio, US; 2008, XP002719972 , retrieved from STN, Database accession No. 1058256-34-0 compounds 1058256-34-0.
Database Registry [Online], Chemical Abstracts Service, Columbus, Ohio, US; 2008, XP002719973, retrieved from STN, Database accession No. 1058447-24-7 compounds 1058447-24-7.
Database Registry [Online], Chemical Abstracts Service, Columbus, Ohio, US; 2008, XP002719974, retrieved from STN, Database accession No. 1058447-68-9 compounds 1058447-68-9.
Database Registry [Online], Chemical Abstracts Service, Columbus, Ohio, US; 2008, XP002719975, retrieved from STN, Database accession No. 1060174-64-2 compounds 1060174-64-2.
Database Registry [Online], Chemical Abstracts Service, Columbus, Ohio, US; 2008, XP002719976, retrieved from STN, Database accession No. 1060179-21-6 compounds 1060179-21-6.
Database Registry [Online], Chemical Abstracts Service, Columbus, Ohio, US; 2008, XP002719977 , retrieved from STN, Database accession No. 1060209-32-6 compounds 1060209-32-6.
Database Registry [Online], Chemical Abstracts Service, Columbus, Ohio, US; 2009, XP002719978, retrieved from STN, Database accession No. 1185021-40-2 compounds 1185021-40-2.
Database Registry [Online], Chemical Abstracts Service, Columbus, Ohio, US; 2011, XP002719979, retrieved from STN, Database accession No. 1278085-47-4 compounds 1278085-47-4.
Database Registry [Online], Chemical Abstracts Service, Columbus, Ohio, US; 2011, XP002719980, retrieved from STN, Database accession No. 1293525-19-5 compounds 1293525-19-5.
Database Registry [Online], Chemical Abstracts Service, Columbus, Ohio, US; 2011, XP002719981, Database accession No. 1302832-45-6 compounds 1302832-45-6.

\* cited by examiner

ANTHELMINTIC COMPOUNDS AND COMPOSITIONS AND METHOD OF USING THEREOF

CROSS REFERENCE TO RELATED APPLICATIONS

This application is a divisional application of U.S. patent application Ser. No. 14/083,879 filed on Nov. 19, 2013, now U.S. Pat. No. 9,249,102, which claims the benefit of priority to U.S. Provisional Patent Application No. 61/728,782 filed Nov. 20, 2012, both incorporated herein by reference in their entirety.

INCORPORATION BY REFERENCE

The foregoing applications and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to novel anthelmintic compounds of formula (I) and compositions containing the compounds:

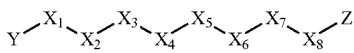

wherein, at least one of variables Y and Z is a bicyclic carbocyclyl or heterocyclyl group. Variables Y, $X_1$, $X_2$, $X_3$, $X_4$, $X_5$, $X_6$, $X_7$, $X_8$ and Z are as defined below. The invention also relates to parasiticidal compositions comprising the compounds, and methods and uses of the compounds for treating and preventing parasitic infections and infestations in animals.

BACKGROUND OF THE INVENTION

Animals such as mammals and birds are often susceptible to parasite infestations/infections. These parasites may be ectoparasites, such as insects, and endoparasites such as nematodes and other worms. Domesticated animals, such as cats and dogs, are often infested with one or more of the following ectoparasites:
  fleas (e.g. *Ctenocephalides* spp., such as *Ctenocephalides felis* and the like);
  ticks (e.g. *Rhipicephalus* spp., *Ixodes* spp., *Dermacentor* spp., *Amblyoma* spp., and the like);
  mites (e.g. *Demodex* spp., *Sarcoptes* spp., *Otodectes* spp., and the like);
  lice (e.g. *Trichodectes* spp., *Cheyletiella* spp., *Linognathus* spp. and the like);
  mosquitoes (*Aedes* spp., *Culex* spp., *Anopheles* spp. and the like); and
  flies (*Hematobia* spp., *Musca* spp., *Stomoxys* spp., *Dermatobia* spp., *Cochliomyia* spp. and the like).

Fleas are a particular problem because not only do they adversely affect the health of the animal or human, but they also cause a great deal of psychological stress. Moreover, fleas may also transmit pathogenic agents to animals and humans, such as tapeworm (*Dipylidium caninum*).

Similarly, ticks are also harmful to the physical and psychological health of the animal or human. However, the most serious problem associated with ticks is that they are vectors of pathogenic agents in both humans and animals. Major diseases which may be transmitted by ticks include borrelioses (Lyme disease caused by *Borrelia burgdorferi*), babesioses (or piroplasmoses caused by *Babesia* spp.) and rickettsioses (e.g. Rocky Mountain spotted fever). Ticks also release toxins which cause inflammation or paralysis in the host. Occasionally, these toxins are fatal to the host.

Likewise, farm animals are also susceptible to parasite infestations. For example, cattle are affected by a large number of parasites. Parasites prevalent among cattle in some regions are ticks of the genus *Rhipicephalus*, especially those of the species *microplus* (cattle tick), *decoloratus* and *annulatus*. Ticks such as *Rhipicephalus microplus* (formerly *Boophilus microplus*) are difficult to control because they lay eggs in the pasture where farm animals graze. This species of ticks is considered a one-host tick and spends immature and adult stages on one animal before the female engorges and falls off the host to lay eggs in the environment. The life cycle of the tick is approximately three to four weeks. In addition to cattle, *Rhipicephalus microplus* may infest buffalo, horses, donkeys, goats, sheep, deer, pigs, and dogs. A heavy tick burden on animals can decrease production and damage hides as well as transmit diseases such as babesioses ("cattle fever") and anaplasmosis.

Animals and humans also suffer from endoparasitic infections including, for example, helminthiasis which is caused by of parasitic worms categorized as cestodes (tapeworm), nematodes (roundworm) and trematodes (flatworm or flukes). These parasites adversely affect the nutrition of the animal and cause severe economic losses in pigs, sheep, horses, and cattle as well as affecting domestic animals and poultry. Other parasites which occur in the gastrointestinal tract of animals and humans include *Ancylostoma, Necator, Ascaris, Strongyloides, Trichinella, Capillaria, Toxocara, Toxascaris, Trichiris, Enterobius* and parasites which are found in the blood or other tissues and organs such as filarial worms and the extra intestinal stages of *Strogyloides, Toxocara* and *Trichinella*.

Another endoparasite which seriously harms animals is *Dirofilaria immitis*, also known as Heartworm. The most common hosts are dogs and cats but other animals such as ferrets and raccoons may also be infected. The parasitic worm is transmitted by the mosquitoe bites, which carry the heartworm larvae. The adult worms live in the major blood vessels of the lung, causing inflammation of the blood vessels and potentially resulting in heart damage and early death. In advanced infections, the worms enter the heart as well.

Recently, anthelmintic compounds with activity against various endoparasitic species were reported in WO 2009/077527 A1, WO 2010/115688 A1, WO 2010/146083 A1 and EP 2 468 096 A1 (all incorporated herein by reference). Although many parasitic infections can be treated with known antiparasitic compounds and compositions, there is a need for new parasiticidal active agents and veterinary compositions and methods with improved efficacy, bioavailability, and spectrum of coverage to protect animals against endoparasites and/or ectoparasites. This invention addresses this need.

SUMMARY OF THE INVENTION

The present invention is directed to novel and inventive anthelmintic compounds of formulae (I), (IA), (IA-1), (IA-2), (IB), (IB-1), (IB-2), (IB-3), (IB-4), (IC) and (IC-1):

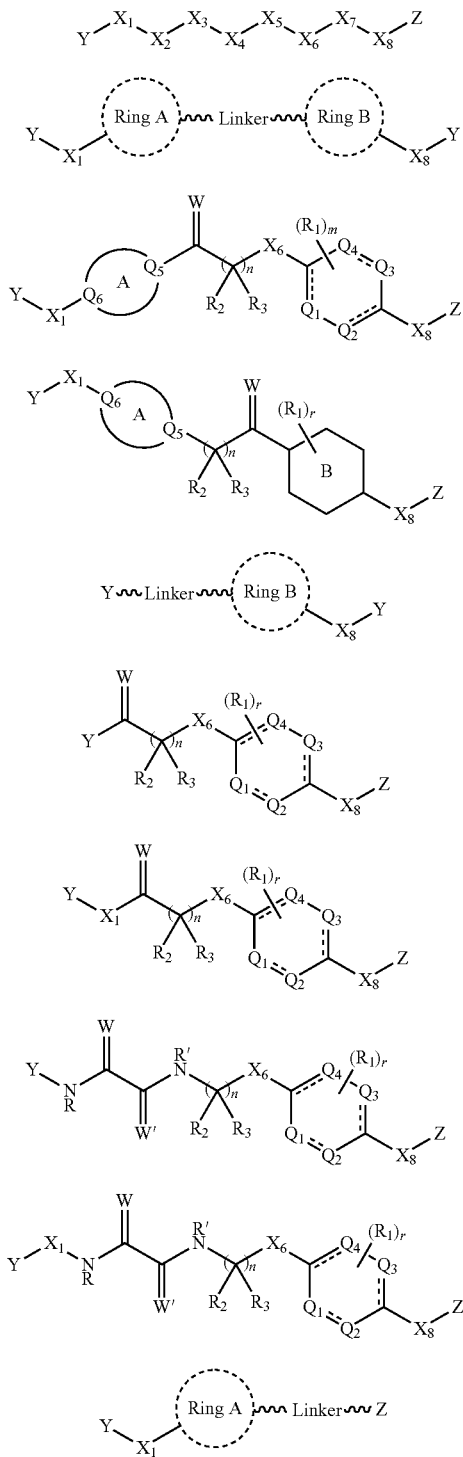

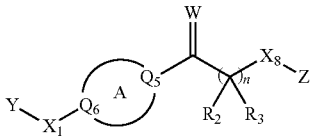

as described herein and compositions comprising the compounds in combination with a pharmaceutically acceptable carrier or diluent.

The present invention is also directed to methods for the treatment and prevention of a parasitic infection in an animal comprising administering at least one of the compounds of the invention to the animal. Also included in the present invention are uses of the compounds for the treatment and/or prevention of parasitic infections in animals and the use of the compounds in the preparation of a medicament for the treatment and/or prevention of a parasitic infection in an animal.

The compounds of the invention are intended to encompass racemic mixtures, specific stereoisomers and tautomeric forms of the compound. Another aspect of the invention is a salt form of the compound of the invention.

Another aspect of the invention are solid state forms of the compounds of the invention which consists of crystalline forms including single crystals, nanocrystals, co-crystals, molecular complexes, hydrates, anhydrates, solvates, desolvates, clathrates and inclusion complexes and non-crystalline forms including non-crystalline glass and non-crystalline amorphous forms.

It is noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right and hereby disclose a disclaimer of any previously described product, method of making the product or process of using the product.

It is further noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are apparent from and encompassed by, the following Detailed Description.

DETAILED DESCRIPTION OF THE INVENTION

The present invention provides novel and inventive anthelmintic compounds of formulae (I), (IA), (IA-1), (IA-2), (IB), (IB-1), (IB-2), (IB-3), (IB-4), (IC) and (IC-1) as described herein, and compositions comprising the compounds together with a pharmaceutically acceptable carrier or diluent. The compounds of the invention have been found to be highly efficacious against internal parasites (endoparasites) that cause harm to animals. In certain embodiments, the compounds of the invention may also be used to combat external parasites (ectoparasites) that cause harm to animals.

The compounds may be combined with one or more additional active agents in compositions to broaden the scope of coverage against both endoparasites and ectoparasites.

Also provided are methods and uses of the compounds and compositions for the treatment and/or prophylaxis of parasitic infections and infestations of animals, comprising administering an effective amount of a compound or composition of the invention to the animal.

Definitions

Terms used herein will have their customary meaning in the art unless specified otherwise. The organic moieties mentioned in the definitions of the variables of formula (I) are—like the term halogen—collective terms for individual listings of the individual group members. The prefix $C_n$-$C_m$ indicates in each case the possible number of carbon atoms in the group.

The term "animal" is used herein to include all mammals, birds and fish and also include all vertebrate animals. Animals include, but are not limited to, cats, dogs, cattle, chickens, cows, deer, goats, horses, llamas, pigs, sheep and yaks. It also includes an individual animal in all stages of development, including embryonic and fetal stages. In some embodiments, the animal will be a non-human animal.

Unless otherwise specifically noted or apparent by context, "active agent" or "active ingredient" or "therapeutic agent" as used in this specification, means an anthelmintic compound of the invention.

The term "fatty acid" refers to carboxylic acids having from 4 to 26 carbon atoms.

The terms "fatty alcohol" or "long-chain aliphatic alcohol" refer to aliphatic alcohols containing from 6 to 20 carbon atoms.

The term "alkyl" refers to saturated straight, branched, cyclic, primary, secondary or tertiary hydrocarbons, including those having 1 to 20 atoms. In some embodiments, alkyl groups will include $C_1$-$C_{12}$, $C_1$-$C_{10}$, $C_1$-$C_8$, $C_1$-$C_6$ or $C_1$-$C_4$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "carbocyclyl" refers to carbon-containing ring systems, including both "cycloalkyl" and "aryl" groups as defined herein.

Cyclic alkyl groups or "cycloalkyl", which are encompassed by alkyl include those with 3 to 10 carbon atoms having single or multiple condensed rings. In some embodiments, cycloalkyl groups include $C_4$-$C_7$ or $C_3$-$C_4$ cyclic alkyl groups. Non-limiting examples of cycloalkyl groups include adamantyl, cyclopropyl, cyclobutyl, cyclopentyl, cyclohexyl, cycloheptyl, cyclooctyl and the like.

The alkyl groups described herein can be unsubstituted or substituted with one or more moieties selected from the group consisting of alkyl, alkenyl, alkynyl, alkoxy, haloalkoxy, aryl, aryloxy, arylalkoxy, heteroaryl, heteroaryloxy, heteroarylalkoxy, halogen, haloalkyl, hydroxyl, hydroxyalkyl, carboxyl, alkylcarbonyl, arylcarbonyl, alkoxycarbonyl, aryloxycarbonyl, aminocarbonyl, alkylaminocarbonyl, dialkylaminocarbonyl, acyl, acyloxy, sulfanyl, sulfamonyl, amino, alkyl- or dialkylamino, amido, arylamino, alkoxy, haloalkoxy, aryloxy, nitro, cyano, azido, thiol, imino, sulfonic acid; alkyl, haloalkyl or aryl sulfate; alkyl, haloalkyl or aryl sulfonyl; arylalkylsulfonyl; alkyl, haloalkyl or aryl sulfinyl; arylalkylsulfinyl; alkyl haloalkyl or aryl thio; arylalkylthio; heteroarylthio, heteroarylalkylthio, heteroarylsulfinyl, heteroarylalkylsulfinyl, heteroarylsulfonyl, heteroarylalkylsulfonyl, an alkyl, haloalkyl or aryl ester, phosphonyl, phosphinyl, phosphoryl, phosphine, thioester, thioether, acid halide, anhydride, oxime, hydrazine, carbamate, phosphoric acid, phosphate, phosphonate, or any other viable functional group that does not inhibit the biological activity of the compounds of the invention, either unprotected, or protected as necessary, as known to those skilled in the art, for example, as taught in Greene, et al., Protective Groups in Organic Synthesis, John Wiley and Sons, Third Edition, 1999, hereby incorporated by reference.

Terms including the term "alkyl" such as "alkylcycloalkyl," "cycloalkylalkyl," "alkylamino," or "dialkylamino" will be understood to comprise an alkyl group as defined above linked to the other functional group, where the group is linked to the compound through the last group listed, as understood by those of skill in the art.

The term "alkenyl" refers to both straight and branched carbon chains which have at least one carbon-carbon double bond. In some embodiments, alkenyl groups may include $C_2$-$C_{20}$ alkenyl groups. In other embodiments, alkenyl includes $C_2$-$C_{12}$, $C_2$-$C_{10}$, $C_2$-$C_8$, $C_2$-$C_6$ or $C_2$-$C_4$ alkenyl groups. In one embodiment of alkenyl, the number of double bonds is 1-3, in another embodiment of alkenyl, the number of double bonds is one or two. Other ranges of carbon-carbon double bonds and carbon numbers are also contemplated depending on the location of the alkenyl moiety on the molecule. "$C_2$-$C_{10}$-alkenyl" groups may include more than one double bond in the chain. Examples include, but are not limited to, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3- butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Alkynyl" refers to both straight and branched carbon chains which have at least one carbon-carbon triple bond. In one embodiment of alkynyl, the number of triple bonds is 1-3; in another embodiment of alkynyl, the number of triple bonds is one or two. In some embodiments, alkynyl groups include from $C_2$-$C_{20}$ alkynyl groups. In other embodiments, alkynyl groups may include $C_2$-$C_{12}$, $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "haloalkyl" refers to an alkyl group, as defined herein, which is substituted by one or more halogen atoms. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "haloalkenyl" refers to an alkenyl group, as defined herein, which is substituted by one or more halogen atoms.

The term "haloalkynyl" refers to an alkynyl group, as defined herein, which is substituted by one or more halogen atoms.

"Alkoxy" refers to alkyl-O—, wherein alkyl is as defined above. Similarly, the terms "alkenyloxy," "alkynyloxy," "haloalkoxy," "haloalkenyloxy," "haloalkynyloxy," "cycloalkoxy," "cycloalkenyloxy," "halocycloalkoxy," and "halocycloalkenyloxy" refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined above. Examples of $C_1$-$C_6$-alkoxy include, but are not limited to, methoxy, ethoxy, $C_2H_5$—$CH_2O$—, $(CH_3)_2CHO$—, n-butoxy, $C_2H_5$—$CH(CH_3)O$—, $(CH_3)_2CH$—$CH_2O$—, $(CH_3)_3CO$—, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

The term "alkylthio" refers to alkyl-S—, wherein alkyl is as defined above. Similarly, the terms "haloalkylthio," "cycloalkylthio," and the like, refer to haloalkyl-S— and cycloalkyl-S— where haloalkyl and cycloalkyl are as defined above.

The term "halothio" refers to (halogen)$_5$-S—, wherein halogen is as defined above. An example of "halothio" is the group $F_5S$—.

The term "alkylsulfinyl" refers to alkyl-S(O)—, wherein alkyl is as defined above.

Similarly, the term "haloalkylsulfinyl" refers to haloalkyl-S(O)— where haloalkyl is as defined above.

The term "alkylsulfonyl" refers to alkyl-S(O)$_2$—, wherein alkyl is as defined above. Similarly, the term "haloalkylsulfonyl" refers to haloalkyl-S(O)$_2$— where haloalkyl is as defined above.

The term alkylamino and dialkylamino refer to alkyl-NH— and (alkyl)$_2$N— where alkyl is as defined above. Similarly, the terms "haloalkylamino" refers to haloalkyl-NH— where haloalkyl is as defined above.

The terms "alkylcarbonyl," "alkoxycarbonyl," "alkylaminocarbonyl," and "dialkylaminocarbonyl" refer to alkyl-C(O)—, alkoxy-C(O)—, alkylamino-C(O)— and dialkylamino-C(O)— where alkyl, alkoxy, alkylamino and dialkylamino are as defined above. Similarly, the terms "haloalkylcarbonyl," "haloalkoxycarbonyl," "haloalkylaminocarbonyl," and "dihaloalkylaminocarbonyl" refer to the groups haloalkyl-C(O)—, haloalkoxy-C(O)—, haloalkylamino-C(O)— and dihaloalkylamino-C(O)— where haloalkyl, haloalkoxy, haloalkylamino and dihaloalkylamino are as defined above.

"Aryl" refers to a monovalent aromatic carbocyclic group of from 6 to 14 carbon atoms having a single ring or multiple condensed rings. In some embodiments, aryl groups include $C_6$-$C_{10}$ aryl groups. Aryl groups include, but are not limited to, phenyl, biphenyl, naphthyl, tetrahydronaphthyl, phenylcyclopropyl, biphenylene, fluorene, anthracene, acenaphthene, phenanthrene and indanyl. Examples of bicyclic aryl groups include naphthyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylamino, alkenylamino, alkynylamino, di(alkyl)amino, di(alkenyl)-amino, di(alkynyl)amino, or trialkylsilyl.

The terms "aralkyl" or "arylalkyl" refers to an aryl group that is bonded to the parent compound through a diradical alkylene bridge, (—$CH_2$—)$_6$, where n is 1-12 and where "aryl" is as defined above.

"Heteroaryl" refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple condensed rings provided that the point of attachment is through a heteroaryl ring atom. Preferred heteroaryls include pyridyl, piridazinyl, pyrimidinyl, pyrazinyl, triazinyl, pyrrolyl, indolyl, quinolinyl, isoquinolinyl, quinazolinyl, quinoxalinyl, furanyl, thiophenyl, pyrrolyl, imidazolyl, oxazolyl, isoxazolyl, isothiazolyl, pyrazolyl, benzofuranyl, dihydrobenzofuranyl and benzothiophenyl. Heteroaryl rings may be unsubstituted or substituted by one or more moieties as described for aryl above.

"Heterocyclyl," "heterocyclic" or "heterocyclo" refer to fully saturated or unsaturated, cyclic groups, for example, 3 to 8 membered monocyclic or 4 to 7 membered monocyclic; 7 to 11 membered bicyclic, or 10 to 15 membered tricyclic ring systems, which have one or more oxygen, sulfur or nitrogen heteroatoms in ring, preferably 1 to 4 or 1 to 3 heteroatoms. The nitrogen and sulfur heteroatoms may optionally be oxidized and the nitrogen heteroatoms may optionally be quaternized. The heterocyclic group may be attached at any heteroatom or carbon atom of the ring or ring system and may be unsubstituted or substituted by one or more moieties as described for aryl groups above.

Exemplary monocyclic heterocyclic groups include, but are not limited to, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuranyl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, isoindolyl, benzothiazolyl, benzoxazolyl, benz[d]isoxazolyl, benzotriazolyl, benzodioxolyl, benzothienyl, quinuclidinyl, quinazolinyl, quinoxalinyl, quinolinyl, isoquinolinyl, benzimidazolyl, benzopyranyl, indolizinyl, benzofuranyl, dihydrobenzofuranyl, chromonyl, coumarinyl, cinnolinyl, indazolyl, pyrrolopyridyl, phthalazinyl, 1,2,3-benzotriazinyl, 1,2,4-benzotriazinyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl, tetrahydroisoquinolinyl, and the like.

Exemplary tricyclic heterocyclic groups include carbazolyl, benzidolyl, phenanthrolinyl, acridinyl, phenanthridinyl, xanthenyl, and the like.

Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—CH$_2$Cl), dichloromethyl (—CHCl$_2$), trichloromethyl (—CCl$_3$)).

Anthelmintic Compounds of the Invention

In a first aspect of the invention, an anthelmintic compound of Formula (I) is provided

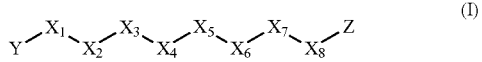

(I)

wherein:

Y and Z are independently a bicyclic carbocyclic or a bicyclic heterocyclic group optionally substituted by one or more of halogen, nitro, cyano, hydroxy, hydroxyalkyl, amino, alkylamino, dialkylamino, aminoalkyl, alkyl, haloalkyl, alkoxy, haloalkoxy, alkylcarbonyl, haloalkylcarbonyl, alkoxycarbonyl, haloalkoxycarbonyl, aminocarbonyl, alkyl- or dialkylaminocarbonyl, alkylthio, halothio, haloalkylthio, alkylsulfinyl, haloalkylsulfinyl, alkylsulfonyl, haloalkylsulfonyl, aryl, aryloxy, arylalkoxy, arylthio, arylalkylthio, arylsulfinyl, arylsulfonyl, arylalkylsulfinyl, arylalkylsulfonyl, heteroaryl, heteroaryloxy, heteroarylalkoxy, heteroarylthio, heteroarylsulfinyl, heteroarylsulfonyl, heteroarylalkylthio, heteroarylalkylsulfinyl or heteroarylalkylsulfonyl; or one of Y or Z is a bicyclic carbocyclic or a bicyclic heterocyclic group optionally substituted by one or more of halogen, nitro, cyano, hydroxy, hydroxyalkyl, amino, alkylamino, dialkylamino, aminoalkyl, alkyl, haloalkyl, alkoxy, haloalkoxy, alkylcarbonyl, haloalkylcarbonyl, alkoxycarbonyl, haloalkoxycarbonyl, aminocarbonyl, alkyl- or dialkylaminocarbonyl, alkylthio, halothio, haloalkylthio, alkylsulfinyl, haloalkylsulfinyl, alkylsulfonyl, haloalkylsulfonyl, aryl, aryloxy, arylalkoxy, arylthio, arylalkylthio, arylsulfinyl, arylsulfonyl, arylalkylsulfinyl, arylalkylsulfonyl, heteroaryl, heteroaryloxy, heteroarylalkoxy, heteroarylthio, heteroarylsulfinyl, heteroarylsulfonyl, heteroarylalkylthio, heteroarylalkylsulfinyl or heteroarylalkylsulfonyl; and the other of Y or Z is alkyl, alkenyl, alkynyl, cycloalkyl, phenyl, heterocyclyl or heteroaryl;

wherein the alkyl, alkenyl, alkynyl, cycloalkyl, phenyl, heterocyclyl and heteroaryl groups are optionally substituted with one or more substituents independently selected from the group consisting of halogen, nitro, cyano, alkyl, haloalkyl, hydroxy, hydroxyalkyl, amino, alkyl- or dialkylamino, aminoalkyl, alkoxy, haloalkoxy, alkylcarbonyl, haloalkylcarbonyl, alkoxycarbonyl, haloalkoxycarbonyl, aminocarbonyl, alkyl- or dialkylaminocarbonyl, alkylthio, halothio, haloalkylthio, alkylsulfinyl, haloalkylsulfinyl, alkylsulfonyl, haloalkylsulfonyl, aryl, aryloxy, arylalkoxy, arylthio, arylalkylthio, arylsulfinyl, arylsulfonyl, arylalkylsulfinyl, arylalkylsulfonyl, heteroaryl, heteroaryloxy, heteroarylalkoxy, heteroarylthio, heteroarylsulfinyl, heteroarylsulfonyl, heteroarylalkylthio, heteroarylalkylsulfinyl and heteroarylalkylsulfonyl;

$X_1$ is a bond, —O—, —C(O)—, —C(S)—, —NH—, —S, —S(O), —S(O)$_2$—, —NHS(O)—, —S(O)—NH—, —NHSO$_2$—, —SO$_2$NH—, —(CH$_2$)$_n$— where n is 1 to 3, —C(O)—CH$_2$—, —CH$_2$—C(O)—, —O—CH$_2$—, —CH$_2$—O—, —NHCH$_2$—, —CH$_2$—NH—, —S—CH$_2$—, —CH$_2$—S—, —S(O)—CH$_2$—, —CH$_2$—S(O)—, —S(O)$_2$—CH$_2$—, or —CH$_2$—S(O)$_2$—, wherein each —NH—, —NHS(O)—, —S(O)—NH—, —NHSO$_2$—, —SO$_2$NH—, —(CH$_2$)$_n$—, —C(O)CH$_2$—, —CH$_2$—C(O)—, —O—CH$_2$—, —CH$_2$—O, —NH—CH$_2$, —CH$_2$—NH—, —S—CH$_2$—, —CH$_2$—S—, —S(O)—CH$_2$—, —CH$_2$—S(O)—, —S(O)$_2$—CH$_2$— and —CH$_2$—S(O)$_2$— are optionally substituted with oxo (=O) or one or more halogen, cyano, hydroxy, hydroxyalkyl, amino, alkylamino, dialkylamino, aminoalkyl, alkyl, haloalkyl, cycloalkyl or aryl groups;

$X_2$ is a linker selected from a $C_1$-$C_8$-alkylene group, a $C_2$-$C_8$-alkenylene group, a $C_2$-$C_8$-alkynylene group, a 3-8 membered carbocyclylene and 3-8 membered heterocyclylene group, wherein the 3-8 membered heterocyclylene group contains one to four nitrogen, oxygen or sulfur atoms, and wherein one to three of the carbon atoms in the $C_1$-$C_8$-alkylene group, the $C_2$-$C_8$-alkenylene group and the $C_2$-$C_8$-alkynylene group may be replaced by a nitrogen, an oxygen or sulfur atom; and wherein the $C_1$-$C_8$-alkylene group, the $C_2$-$C_8$-alkenylene group, the $C_2$-$C_8$-alkynylene group, the 3-8 membered carbocyclylene and the 3-8 membered heterocyclylene group are optionally substituted with one or more substituents independently selected from halogen, alkyl, haloalkyl, alkoxy, haloalkoxy, alkylthio, haloalkylthio, hydroxy, hydroxyalkyl, amino, alkylamino, dialkylamino, aminoalkyl, and oxo (=O);

$X_3$ is a diradical group selected from the group consisting of a bond, —$(CH_2)_n$— where n is 1 to 3, —O—, —C(S)—, —C(O)—, —S(O)—, —S(O)$_2$—, and an oxetane group (4-membered ring containing one oxygen), wherein $X_2$ and $X_4$ may be bonded to any carbon atom of the oxetane group; and wherein each —$CH_2$— in the —$(CH_2)_n$— group is optionally substituted with one or two substituents independently selected from the group consisting of halogen, hydroxy, hydroxyalkyl, amino, alkylamino, dialkylamino, aminoalkyl, alkyl, haloalkyl, alkenyl, haloalkenyl, alkynyl, haloalkynyl, carbocyclyl and halocarbocyclyl;

$X_4$ is a bond, —$(CH_2)_n$— where n is 1 to 3, carbocyclylene or heterocyclylene, wherein the —$CH_2$—, the carbocyclylene and the heterocyclylene groups are optionally substituted with one or more substituents independently selected from the group consisting of halogen, hydroxy, hydroxyalkyl, amino, alkylamino, dialkylamino, aminoalkyl, alkyl, haloalkyl, alkenyl, haloalkenyl, alkynyl, haloalkynyl, carbocyclyl and halocarbocyclyl;

$X_5$ is absent or is a bond, —$(CH_2)_n$ where n is 1 to 3, carbocyclylene or heterocyclylene, wherein each —$CH_2$— in the —$(CH_2)_n$ group, the carbocyclylene and the heterocyclylene groups are optionally substituted with one or more substituents independently selected from the group consisting of halogen, hydroxy, hydroxyalkyl, amino, alkylamino, dialkylamino, aminoalkyl, alkyl, haloalkyl, alkenyl, haloalkenyl, alkynyl, haloalkynyl, carbocyclyl and halocarbocyclyl;

$X_6$ is —$(CH_2)_n$— where n is 1 to 3, —O—, —C(O)—, —C(S)—, —S—, —S(O)—, —S(O)$_2$—, —NH—, —C(O)—NH—, —C(S)—NH—, —NH—C(O)—, —NH—C(S)—, wherein each —$CH_2$— in the —$(CH_2)_n$— group, —NH—, —C(O)—NH—, —C(S)—NH—, —NH—C(O)—, —NH—C(S)— are optionally substituted with one or more substituents independently selected from the group consisting of halogen, hydroxy, hydroxyalkyl, amino, alkylamino, dialkylamino, aminoalkyl, alkyl, haloalkyl, alkenyl, haloalkenyl, alkynyl, haloalkynyl, carbocyclyl, halocarbocyclyl, carbocyclylalkyl and halocarbocyclylalkyl;

$X_7$ is a bond, —$(CH_2)_n$— where n is 1 to 3, alkenylene, alkynylene, carbocyclylene or heterocyclylene, wherein each $CH_2$ in —$(CH_2)_n$—, alkenylene, alkynylene, carbocyclylene and heterocyclylene is optionally substituted with one or more halogen, hydroxy, hydroxyalkyl, alkyl, haloalkyl, alkoxy, haloalkoxy, amino, alkylamino, dialkylamino or aminoalkyl group; and $X_8$ is a bond, —$(CH_2)_n$ where n is 1 to 3, —O—, —C(O)—, —S—, —S(O)—, —S(O)$_2$—, —NHS(O)—, —S(O)—NH—, —NHSO$_2$—, —SO$_2$NH— or —NH—, wherein each $CH_2$ in —$(CH_2)_n$—, —NHS(O)—, —S(O)—NH—, —NHSO$_2$—, —SO$_2$NH— or —NH— is optionally independently substituted with one or two substituents selected from the group consisting of halogen, hydroxy, amino, alkylamino, dialkylamino, hydroxyalkyl, aminoalkyl, alkyl, haloalkyl, alkenyl, haloalkenyl, alkynyl, haloalkynyl, alkoxyalkyl, carbocyclyl, halocarbocyclyl, carbocyclylalkyl and halocarbocyclylalkyl.

In one embodiment, at least one of Y or Z is an optionally substituted bicyclic carbocyclic group. In another embodiment, at least one of Y or Z is an optionally substituted bicyclic aromatic carbocyclic group. In still another embodiment, at least one of Y or Z is an optionally substituted non-aromatic bicyclic carbocyclic group. In still another embodiment, at least one of Y or Z is optionally substituted naphthyl, tetrahydronaphthyl or indanyl.

In another embodiment, at least one of Y or Z is a bicyclic heterocyclic group. In another embodiment, at least one of Y or Z is an optionally substituted bicyclic heteroaryl group. In still another embodiment, at least one of Y or Z is optionally substituted indolyl, benzothiazolyl, benzoxazolyl, benzodioxolyl, benzothienyl, quinuclidinyl, quinolinyl, tetrahydroquinolinyl, isoquinolinyl, tetra-hydroisoquinolinyl, benzimidazolyl, benzopyranyl, indolizinyl, benzofuranyl, dihydrobenzofuranyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl or dihydroquinazolinyl (such as 3,4-dihydro-4-oxo-quinazolinyl).

In one embodiment, $X_1$ is a bond, —C(O)—, —$CH_2$—, —$CH_2CH_2$—, —C(O)—$CH_2$—, —$CH_2$—C(O), —O—$CH_2$—, —$CH_2$—O—, —NH$CH_2$— or —$CH_2$—NH—, wherein each —$CH_2$—, —$CH_2CH_2$—, —C(O)$CH_2$—, —$CH_2$—C(O)—, —O—$CH_2$—, —$CH_2$—O, —NH—$CH_2$, —$CH_2$—NH— are optionally substituted with one or more halogen, alkyl, haloalkyl or cycloalkyl groups.

In another embodiment, $X_1$ is NH—, —NHS(O)—, —S(O)—NH—, —NHSO$_2$— or —SO$_2$NH—.

In another embodiment, $X_1$ is a bond, —$CH_2$— or —$CH_2CH_2$—, wherein each —$CH_2$— or —$CH_2CH_2$— is optionally substituted with one or more halogen, alkyl or haloalkyl groups.

In one embodiment, $X_2$ is a $C_1$-$C_8$alkylene group, a 3-8 membered carbocyclylene or a 3-8 membered heterocyclylene group containing one to four nitrogen, oxygen or sulfur heteroatoms, wherein one or more of the carbon atoms in the $C_1$-$C_8$-alkylene group may be replaced by a nitrogen, oxygen or sulfur atom; and wherein the $C_1$-$C_8$-alkylene group, the 3-8 membered carbocyclylene and the 3-8 membered heterocyclylene group are optionally substituted with one or more substituents independently selected from halogen, alkyl, haloalkyl, alkoxy, haloalkoxy, hydroxy, hydroxyalkyl, amino, alkylamino, dialkylamino, aminoalkyl and oxo (=O).

In one preferred embodiment, $X_2$ is —C(=O)— or optionally substituted $C_1$-$C_3$-alkylene.

In another embodiment, $X_2$ comprises a chain of from 3 to 6 atoms (as an acyclic chain or part of a ring) that bridges $X_1$ to $X_3$, wherein 1 or 2 of the chain atoms are nitrogen. In this embodiment, the nitrogen atoms in $X_2$ are typically bonded to $X_1$ and/or $X_3$.

In yet another embodiment, $X_2$ comprises a chain of from 3 to 6 atoms (as an acyclic chain or as part of a ring) that bridges $X_1$ to $X_3$, wherein 1 or 2 of the chain atoms are nitrogen and wherein one or more of the alkylene groups in the chain are substituted with oxo (=O).

In another embodiment, $X_2$ is a 3-8 membered heterocyclylene group containing at least one nitrogen atom. In still another embodiment, $X_2$ is a heterocyclylene group containing at least two nitrogen atoms. In yet another embodiment, $X_2$ is a 5- or 6-membered heterocyclylene group containing one or two nitrogen atoms.

In certain preferred embodiments, $X_2$ and/or $X_7$ are selected from one of the linkers L1 to L18 in Table 1 below, wherein variables R and R' are each independently hydrogen, alkyl, haloalkyl or arylalkyl; $R_2$ and $R_3$ are independently hydrogen, halogen, cyano, alkyl, haloalkyl or carbocyclyl; $R_4$ is H, OH, halogen or $C_{1-3}$alkyl; $R_5$, $R_6$, $R_7$ and $R_8$ are independently hydrogen, $C_{1-3}$alkyl or $C_{1-3}$haloalkyl; W and W' are each independently O or S; and each linker L1 to L18 in the table may be substituted by one or more of halogen, cyano, $C_1$-$C_6$alkyl, hydroxy, thiol, $C_1$-$C_6$alkoxy, oxo or thiocarbonyl.

TABLE 1

Examples of $X_2$ and $X_7$ Linkers

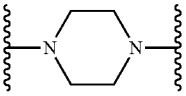 L1

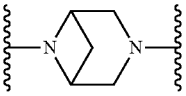 L2

 L3

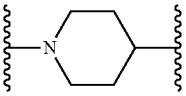 L4

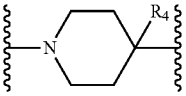 L5

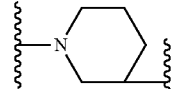 L6

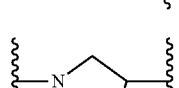 L7

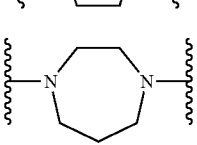 L8

 L9

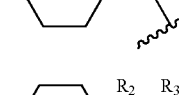 L10

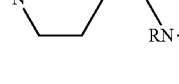 L11

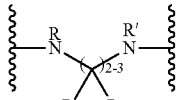 L12

TABLE 1-continued

Examples of $X_2$ and $X_7$ Linkers

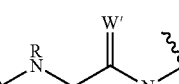 L13

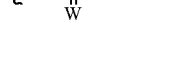 L14

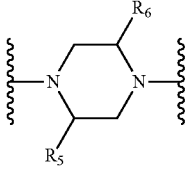 L15

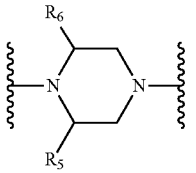 L16

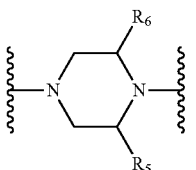 L17

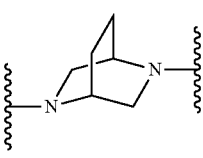 [SMILES: *N1CC2CCC1CN2*] L18

It will be understood that the $X_2$ and $X_7$ linkers presented in Table 1 may be bonded to $X_1$ and/or $X_3$ or $X_6$ and/or $X_8$ at any possible atom in the linker group. Typically, when the $X_2$ and/or the $X_7$ linker contains one or more nitrogen atoms, the nitrogen atom(s) will be bonded to $X_1$ and/or $X_3$ or $X_6$ and/or $X_7$.

In one embodiment, $X_2$ and/or $X_7$ is L1. In another preferred embodiment, $X_2$ and/or $X_7$ is L2. In yet another preferred embodiment, $X_2$ and/or $X_7$ is L11 or L12. In another embodiment, $X_2$ and/or $X_7$ is L13 or L14. In still another embodiment, $X_2$ and/or $X_7$ is L13 where the $R_6$ and $R_7$ groups are in a trans relationship to each other. In yet another embodiment, $X_2$ and/or $X_7$ are L13 where the $R_6$ and $R_7$ groups are in a cis-relationship to each other. In another embodiment, $X_2$ and/or $X_7$ are L14 where the $R_6$ and $R_7$ groups are in a trans-relationship to each other. In still another embodiment, $X_2$ and/or $X_7$ are L14 where the $R_6$ and $R_7$ are in a cis-relationship to each other. In yet another embodiment, $X_2$ and/or $X_7$ are L15 where the $R_6$ and $R_7$ are trans to each other. In still another embodiment, $X_2$ and/or $X_7$ are L15 where $R_6$ and $R_7$ are cis- to each other. In still another embodiment, $X_2$ and/or $X_7$ are L16, L17 or L18.

In certain embodiments, $X_3$ is a bond, —(CH$_2$)$_n$— where n is 1 to 3, —C(S)— or —C(O)—, wherein each carbon atom in the —(CH$_2$)$_n$— group is optionally substituted with one or two substituents independently selected from the group consisting of halogen, alkyl or haloalkyl. In one preferred embodiment, $X_3$ is C(O)—. In another preferred embodiment, $X_3$ is CH$_2$CH$_2$— or —CH$_2$CH$_2$CH$_2$— wherein each of the carbon atoms may be substituted by one or two methyl groups. In yet another embodiment, $X_3$ is an oxetane group.

In one embodiment, $X_4$ is a bond. In another embodiment, $X_4$ is —(CH$_2$)$_n$— where n is 1 or 2, wherein each —CH$_2$— is optionally independently substituted with one or two substituents selected from the group consisting of halogen, alkyl, haloalkyl and carbocyclyl;

In another embodiment, $X_5$ is a bond or —(CH$_2$)$_n$— where n is 1 or 2 and wherein each —CH$_2$— in the —(CH$_2$)$_n$ group is optionally independently substituted with one or two halogen, alkyl, haloalkyl, or carbocyclyl groups;

In yet another embodiment of formula (I), $X_6$ is —(CH$_2$)$_n$ where n is 1 or 2, —O—, —C(O)—, —S—, —S(O)—, —S(O)$_2$— or —NH—, wherein each —CH$_2$— in the —(CH$_2$)$_n$— group or the NH, is optionally independently substituted with one or two substituents is selected from the group consisting of halogen, alkyl, haloalkyl and carbocyclyl. In one preferred embodiment, $X_6$ is CH$_2$. In another preferred embodiment, $X_6$ is —O—.

In another embodiment of formula (I), $X_7$ is a bond, —(CH$_2$)$_n$— where n is 1 to 3, carbocyclylene or heterocyclylene, wherein each CH$_2$ in —(CH$_2$)$_n$—, carbocyclylene and heterocyclylene is optionally substituted with one or more halogen, alkyl, haloalkyl, hydroxy, hydroxyalkyl, alkoxy, haloalkoxy, amino, alkylamino or dialkylamino or aminoalkyl. In another embodiment, $X_7$ is a 5- or 6-membered carbocyclylene group such as cyclohexylene or cyclopentylene. In yet another embodiment, $X_7$ is a phenylene group.

In yet another embodiment of formula (I), $X_8$ is absent or is a bond, —(CH$_2$)$_n$ where n is 1 to 3, —O—, —C(O)— or —NH—, wherein each CH$_2$ in —(CH$_2$)$_n$— and the —NH— is optionally independently substituted with one or two substituents selected from the group consisting of halogen, alkyl, and haloalkyl. In one particularly preferred embodiment, $X_8$ is NH—. In another embodiment, $X_8$ is —C(O)—. In yet another preferred embodiment, $X_8$ is —CH$_2$—, —CF$_2$—, —CH(CH$_3$)— or C(CH$_3$)$_2$—. In still another embodiment, $X_8$ is —NHS(O)—, —S(O)—NH—, —NHSO$_2$— or —SO$_2$NH—.

In one aspect of the invention, the compounds of formula (I) have the structure (IA) shown below:

(IA)

Wherein variables Y, $X_1$, $X_8$ and Z are as defined for formula (I) above, Ring A and Ring B are independently a 3 to 8-membered monocyclic or a 7 to 11-membered bicyclic carbocyclylene or heterocyclylene ring, wherein the heterocyclic ring contains 1 to 4 heteroatoms selected from N, O and S; and the Linker is the segment —X$_3$—X$_4$—X$_5$—X$_6$— where X$_3$, X$_4$, X$_5$ and X$_6$ are as defined for formula (I).

In one embodiment of formula (IA), Ring A is one of L1 to L10; or L13 to L18 as defined in Table 1, which may optionally be substituted with halogen, alkyl or haloalkyl. In another embodiment, Ring A is cyclohexylene or phenylene, which may optionally be substituted with halogen, alkyl or haloalkyl. In another embodiment of formula (IA), Ring B is cyclohexylene or phenylene, which may optionally be substituted with halogen, alkyl or haloalkyl. In still another embodiment, Ring B is one of L1 to L10; or L13 to L18 as defined in Table 1, which may optionally be substituted with halogen, alkyl or haloalkyl.

In one embodiment of formula (IA), $X_1$ is a bond, an optionally substituted —(CH$_2$)$_n$— where n is 1 to 3, or —C(O)—.

In another embodiment of formula (IA), $X_8$ is —C(O)—, —NH— or —(CH$_2$)$_n$— where n is 1 to 3, wherein the each CH$_2$ in (CH$_2$)$_n$— or the NH— may optionally be substituted.

In still another embodiment of formula (IA), Y and/or Z is phenyl or naphthyl optionally substituted with one or more of halogen, nitro, cyano, hydroxy, hydroxyalkyl, amino, alkylamino, dialkylamino, aminoalkyl, alkyl, haloalkyl, alkoxy, haloalkoxy, alkylthio, halothio, haloalkylthio, alkylsulfinyl, haloalkylsulfinyl, alkylsulfonyl, haloalkylsulfonyl, aryl, aryloxy, arylalkoxy, arylthio, arylalkylthio, arylsulfinyl, arylsulfonyl, arylalkylsulfinyl, arylalkylsulfonyl, heteroaryl, heteroaryloxy, heteroarylalkoxy, heteroarylthio, heteroarylsulfinyl, heteroarylsulfonyl, heteroarylalkylthio, heteroarylalkylsulfinyl or heteroarylalkylsulfonyl, with the proviso that at least one or Y or Z is naphthyl.

In yet another embodiment of formula (IA), Y and/or Z are independently phenyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more halogen, nitro, cyano, hydroxy, hydroxyalkyl, amino, alkylamino, dialkylamino, aminoalkyl, alkyl, haloalkyl, alkoxy, haloalkoxy, alkylthio, halothio, haloalkylthio, alkylsulfinyl, haloalkylsulfinyl, alkylsulfonyl, haloalkylsulfonyl, aryl, aryloxy, arylalkoxy, arylthio, arylalkylthio, arylsulfinyl, arylsulfonyl, arylalkylsulfinyl, arylalkylsulfonyl, heteroaryl, heteroaryloxy, heteroarylalkoxy, heteroarylthio, heteroarylsulfinyl, heteroarylsulfonyl, heteroarylalkylthio, heteroarylalkylsulfinyl or heteroarylalkylsulfonyl, with the proviso that at least one of Y or Z is a bicyclic ring.

In certain embodiments of formula (IA), the compound has the structure of formula (IA-1) or (IA-2) shown below:

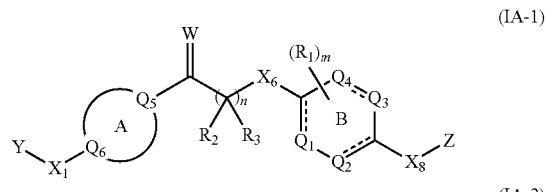

(IA-1)

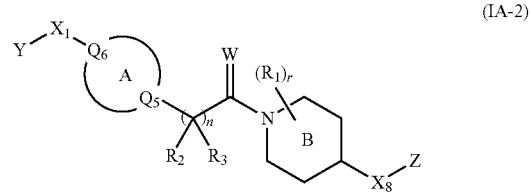

(IA-2)

wherein variables Y, $X_6$, $X_8$ and Z are as defined for formula (I) above; $X_1$ is a bond, —C(O)—, —C(S)—, —NH—, —S(O)—, —S(O)$_2$—, —NHS(O)—, —S(O)—NH—, —NHSO$_2$—, —SO$_2$NH—, —(CH$_2$)$_n$— where n is 1 to 3, —O—CH$_2$—, —NHCH$_2$—, —S—CH$_2$—, —S(O)—CH$_2$—, —CH$_2$—S(O)—, —S(O)$_2$—CH$_2$—, and —CH$_2$—S(O)$_2$—, wherein each —NH—, —(CH$_2$)$_n$—, —O—CH$_2$—, —NHCH$_2$—, —S—CH$_2$—, —S(O)—CH$_2$—, —CH$_2$—S(O)—, —S(O)$_2$—CH$_2$—, and —CH$_2$—S(O)$_2$— are optionally substituted with oxo (=O) or one or more halogen, cyano, alkyl, haloalkyl, cycloalkyl or aryl groups; Ring A is a 3- to 8-membered carbocyclic ring where Q5 and Q6 are independently N or CR$_4$ where R$_4$ is H, OH, halogen or C$_{1-3}$alkyl; W is O, S or an oxetane group (—CH$_2$OCH$_2$—); Q$_1$, Q$_2$, Q$_3$ and Q$_4$ are each independently C—H or a heteroatom selected from N, S or O; each R$_1$ is independently halogen, cyano, hydroxyl, amino, alkylamino, dialkylamino, alkyl, haloalkyl, carbocyclyl, heterocyclyl, alkenyl, haloalkenyl, alkynyl or haloalkynyl; R$_2$ and R$_3$ are independently hydrogen, halogen, cyano, alkyl, haloalkyl or carbocyclyl; n is 0, 1, 2 or 3; m is 0, 1, 2, 3 or 4; and r is 0 to 5.

In one embodiment of formula (IA-1), W is O. In another embodiment, W is an oxetane group. In another embodiment, Ring B is optionally substituted phenylene.

In another embodiment of formula (IA-1) or (IA-2), Ring A is one of linkers L1, L2, L3, L8, L13, L14, L15, L16, L17 or L18. In another embodiment, Ring A is one of L1, L13, L14 or L15. In yet another embodiment, Ring A is L16, L17 or L18. In another embodiment, Ring A is L4, L5, L6, L7, L9 or L10. In another embodiment, Ring B is L1, L13, L14 or L15. In still another embodiment of formula (IA-1), Y and/or Z is naphthyl optionally substituted by one or more of halogen, nitro, cyano, alkyl, haloalkyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl.

In yet another embodiment of formula (IA-1), Y and/or Z are independently benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of halogen, nitro, cyano, alkyl, haloalkyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl.

In another embodiment of formula (IA-1), one of Y or Z is naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of halogen, nitro, cyano, alkyl, haloalkyl, phenyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl and the other of Y or Z is phenyl, a 3-8 membered heterocyclyl group or a 5 or 6-membered heteroaryl group, each of which is optionally substituted by one or more of halogen, nitro, cyano, alkyl, haloalkyl, phenyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl.

In still another embodiment of formula (IA-1), one of Y or Z is naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of halogen, nitro, cyano, alkyl, haloalkyl, phenyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl and the other of Y or Z is phenyl or a 5- or 6-membered heteroaryl group, each of which is optionally substituted by one or more of halogen, nitro, cyano, alkyl, haloalkyl, phenyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl.

In another embodiment, one of Y or Z is naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of chloro, fluoro, bromo, CF$_3$, OCF$_3$, SCF$_3$ or SF$_5$; and the other of Y or Z is phenyl optionally substituted by cyano, nitro, CF$_3$, SF$_5$, S(O)C$_{1-3}$alkyl, S(O)$_2$—C$_{1-3}$alkyl, S(O)C$_{1-3}$haloalkyl or S(O)$_2$C$_{1-3}$haloalkyl.

In another embodiment of formula (IA-1), Y and Z are independently phenyl, naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of halogen, nitro, cyano, C$_{1-3}$alkyl, C$_{1-3}$haloalkyl, phenyl, hydroxy, C$_{1-3}$hydroxyalkyl, amino, C$_{1-3}$alkyl- or C$_{1-3}$dialkylamino, C$_{1-3}$alkoxy, C$_{1-3}$haloalkoxy, halothio, C$_{1-3}$haloalkylthio, C$_{1-3}$ alkylsulfinyl C$_{1-3}$alkylsulfonyl or C$_{1-3}$haloalkylsulfonyl, with the proviso that at least one of Y and Z is a bicyclic ring;

Ring A is one of L1, L2, L3, L4, L5, L6, L7, L8, L9, L10, L13, L14, L15, L16, L17 or L18 shown in Table 1;

$X_1$ is a bond, —C(O)—, —(CH$_2$)$_n$— where n is 1 to 3, —O—CH$_2$—, —NHCH$_2$—, —S—CH$_2$—, —S(O)—CH$_2$—, —CH$_2$—S(O)—, —S(O)$_2$—CH$_2$—, and —CH$_2$—S(O)$_2$—, wherein each —(CH$_2$)$_n$—, —O—CH$_2$—, —NHCH$_2$—, —S(O)—CH$_2$—, —CH$_2$—S(O)—, —S(O)$_2$—CH$_2$—, and —CH$_2$—S(O)$_2$— are optionally substituted with oxo (=O) or one or more halogen, cyano, alkyl, haloalkyl, cycloalkyl or aryl groups;

W is O, S or an oxetane group;

each R$_1$ is independently halogen, cyano, hydroxyl, amino, C$_{1-3}$alkylamino, C$_{1-3}$ dialkylamino, C$_{1-3}$alkyl or C$_{1-3}$haloalkyl;

R$_2$ and R$_3$ are independently H, halogen, C$_1$-C$_3$alkyl or C$_1$-C$_3$haloalkyl;

$X_6$ is a bond, —(CH$_2$)$_n$— where n is 1 to 3, —O—, —NH—, —C(O)—NH— and —NH—C(O)—, wherein each —CH$_2$— in the —(CH$_2$)$_n$— group, —NH—, —C(O)—NH— and —NH—C(O)— are optionally substituted with one or more substituents independently selected from the group consisting of halogen, hydroxy, C$_{1-3}$hydroxyalkyl, amino, C$_{1-3}$alkylamino, C$_{1-3}$dialkylamino, C$_{1-3}$ aminoalkyl, C$_{1-3}$alkyl and C$_{1-3}$haloalkyl;

$X_8$ is a bond, —(CH$_2$)$_n$ where n is 1 to 3, —O—, —C(O)—, —S—, —S(O)—, —S(O)$_2$—, —NHS(O)—, —S(O)—NH—, —NHSO$_2$—, —SO$_2$NH— or —NH—, wherein each CH$_2$ in —(CH$_2$)$_n$—, —NHS(O)—, —S(O)—NH—, —NHSO$_2$—, —SO$_2$NH— or —NH— is optionally independently substituted with one or two substituents selected from the group consisting of halogen, hydroxy, amino, C$_{1-3}$alkylamino, C$_{1-3}$dialkylamino, C$_{1-3}$hydroxyalkyl, C$_{1-3}$aminoalkyl, C$_{1-3}$alkyl, C$_{1-3}$haloalkyl and C$_{1-3}$alkoxyalkyl;

$Q_1$, $Q_2$, $Q_3$ and $Q_4$ are each independently C—H or a heteroatom selected from N, S or O;

the dashed lines represent a single or double bond;

n is 0, 1, 2 or 3; and m is 0, 1, 2, 3 or 4. In another embodiment of formula (IA-1), one of Y or Z is naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of chloro, fluoro, bromo, $CF_3$, $OCF_3$, $SCF_3$ or $SF_5$; and the other of Y or Z is phenyl optionally substituted by cyano, nitro, $CF_3$, $SF_5$, $S(O)C_{1-3}$alkyl, $S(O)_2$—$C_{1-3}$alkyl, $S(O)C_{1-3}$haloalkyl or $S(O)_2C_{1-3}$haloalkyl;

Ring A is one of L1, L2, L3, L4, L5, L13, L14, L15, L16, L17 or L18; Ring B is trans-cyclohexylene or phenylene;

W is O;

$X_6$ is a bond, —O—, —$(CH_2)_n$— where n is 1 to 3 or —NH—;

$X_8$ is a bond, —$(CH_2)_n$— where n is 1 to 3, —O— or —NH—, wherein each $CH_2$ in —$(CH_2)_n$— and —NH— is optionally independently substituted with one or two substituents selected from the group consisting of halogen, $C_{1-3}$alkyl or $C_{1-3}$haloalkyl;

$R_2$ and $R_3$ are H; n is 1 or 2; and m is 0.

In another embodiment, $X_1$ is optionally substituted —$(CH_2)_n$— or —C(O)—. In another embodiment, $X_8$ is —C(O)— or optionally substituted —NH— or —$(CH_2)_n$—. In still another embodiment of formula (IA-1), $R_2$ and $R_3$ are H. In still another embodiment of formula (IA-1), n is 1 or 2. In another embodiment of formula (IA-1), $X_6$ is —O—, —NH— which may optionally be substituted by alkyl or haloalkyl; —S—, —S(O)— or —S(O)$_2$—. In yet another embodiment of formula (IA-1), $X_1$ is a bond, —C(O)— or —$CH_2$—; W is O, $X_6$ is —O—, n is 0, 1 or 2, $R_2$ and $R_3$ are H and m is 0.

In one embodiment of formula (IA-1), $Q_1$ is N. In another embodiment, $Q_2$ is N. In another embodiment, $Q_3$ is N. In yet another embodiment, $Q_4$ is N.

In one embodiment, $Q_1$ and $Q_4$ are N. In another embodiment, $Q_2$ and $Q_3$ are N. In still another embodiment, $Q_1$ and $Q_2$ are N. In another embodiment, $Q_3$ and $Q_4$ are N.

In another embodiment, $Q_1$ and $Q_3$ are N. In still another embodiment, $Q_2$ and $Q_4$ are N.

In an embodiment, $Q_5$ is N and $Q_6$ is CH. In another embodiment, $Q_5$ is CH and $Q_6$ is N. In yet another embodiment, $Q_5$ and $Q_6$ are both N. In still another embodiment, $Q_5$ and $Q_6$ are both CH.

In another embodiment of formula (IA-1), Ring A is one of L1, L2, L3, L4, L5, L6, L7, L8, L9, L10, L13, L14, L15, L16, L17 or L18; Ring B is a optionally substituted cyclohexylene or phenylene, Y and/or Z are independently phenyl, naphthyl, quinolinyl, isoquinolinyl, tetrahydroquinolyl, tetrahydroisoquinolyl, benzofuranyl, dihydrobenzofuranyl, benzimidazolyl or benzothiazolyl, each of which is optionally substituted by one or more of halogen, nitro, cyano, alkyl, haloalkyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl, with the proviso that at least one of Y or Z is a bicyclic ring; $X_1$ is bond, —C(O)— or —$CH_2$—; W is O or an oxetane group, $X_6$ is —O—, n is 0, 1 or 2, $R_2$ and $R_3$ are H, m is 0 and $X_8$ is —NH—, —C(O)—, —$CH_2$—, —$CF_2$—, —CH($CH_3$)— or —C($CH_3$)$_2$—.

In another embodiment of formula (IA-1), Ring A is one of L1, L4, L13, L14, L15 or L16; Ring B is an optionally substituted diradical pyridine ring linker where one of $Q_1$, $Q_2$, $Q_3$ or $Q_4$ is N, Y and/or Z are independently phenyl, naphthyl, quinolinyl, isoquinolinyl, tetrahydroquinolyl, tetrahydroisoquinolyl, benzofuranyl, dihydrobenzofuranyl, benzimidazolyl or benzothiazolyl, each of which is optionally substituted by one or more of halogen, nitro, cyano, alkyl, haloalkyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl, with the proviso that at least one of Y or Z is a bicyclic ring; $X_1$ is bond, —C(O)— or —$CH_2$—; W is O or an oxetane group, $X_6$ is —O—, n is 0, 1 or 2, $R_2$ and $R_3$ are H, m is 0 and $X_8$ is —NH—, —C(O)—, —$CH_2$—, —$CF_2$—, —CH($CH_3$)— or —C($CH_3$)$_2$—.

In another embodiment of formula (IA-1), Ring A is L1, L2, L3, L4, L5, L6, L7, L8, L13, L14, L15, L16, L17 or L18; Ring B is a optionally substituted cyclohexylene or phenylene, Y and/or Z are independently phenyl, naphthyl, quinolinyl, isoquinolinyl, tetrahydroquinolyl, tetrahydroisoquinolyl, benzofuranyl, dihydrobenzofuranyl, benzimidazolyl or benzothiazolyl, each of which is optionally substituted by one or more of halogen, nitro, cyano, alkyl, haloalkyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl, with the proviso that one of Y or Z is a bicyclic ring; $X_1$ is bond, —C(O)— or —$CH_2$—; W is O, $X_6$ is —O—, n is 1 or 2, $R_2$ and $R_3$ are H, m is 0 and $X_8$ is —NH—, —C(O)—, —$CH_2$—, —$CF_2$—, —CH($CH_3$)— or —C($CH_3$)$_2$—.

In other embodiments of formula (IA-1), the invention provides the compounds in Table 2 below:

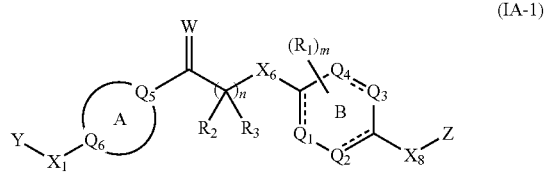

(IA-1)

TABLE 2

Compounds of formula (IA-1) where $R_1$ is not present; OX. = oxetane group; B = bond

| Y | $X_1$ | Ring A | W | n | $R_2$ | $R_3$ | $X_6$ | Ring B | $X_8$ | Z | # |
|---|---|---|---|---|---|---|---|---|---|---|---|
|  | B | L1 | O | 1 | H | H | O | trans-$C_6H_{10}$ | NH |  | 14 |

TABLE 2-continued
Compounds of formula (IA-1) where R₁ is not present; OX. = oxetane group; B = bond
| Y | X₁ | Ring A | W | n | R₂ | R₃ | X₆ | Ring B | X₈ | Z | # |
|---|---|---|---|---|---|---|---|---|---|---|---|
| 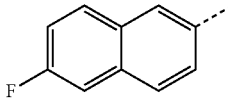 | B | L1 | O | 1 | H | H | O | trans-C₆H₁₀ | NH | 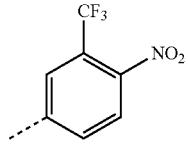 | 17 |
| 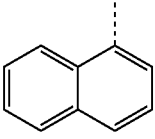 | B | L1 | O | 1 | H | H | O | trans-C₆H₁₀ | NH | 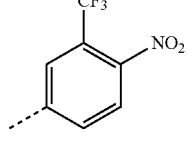 | 20 |
| 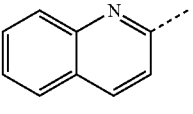 | B | L1 | O | 1 | H | H | O | trans-C₆H₁₀ | NH | 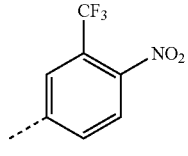 | 88 |
| 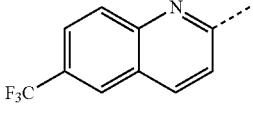 | B | L1 | O | 1 | H | H | O | trans-C₆H₁₀ | NH | 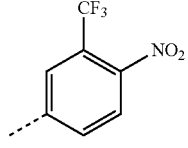 | 89 |
| 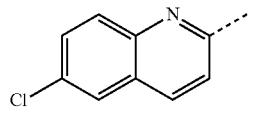 | B | L1 | O | 1 | H | H | O | trans-C₆H₁₀ | NH | 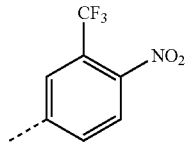 | 90 |
| 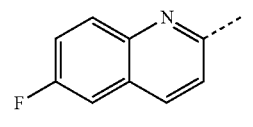 | B | L1 | O | 1 | H | H | O | trans-C₆H₁₀ | NH | 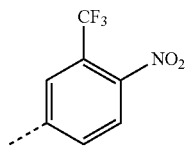 | 97 |
| 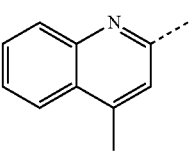 | B | L1 | O | 1 | H | H | O | trans-C₆H₁₀ | NH | 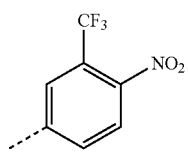 | 98 |
| 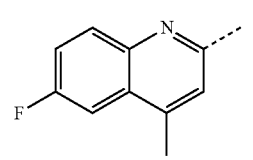 | B | L1 | O | 1 | H | H | O | trans-C₆H₁₀ | NH | 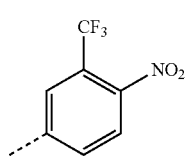 | 99 |
| 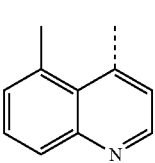 | B | L1 | O | 1 | H | H | O | trans-C₆H₁₀ | NH | 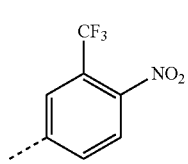 | 160 |

TABLE 2-continued
Compounds of formula (IA-1) where R₁ is not present; OX. = oxetane group; B = bond
| Y | X₁ | Ring A | W | n | R₂ | R₃ | X₆ | Ring B | X₈ | Z | # |
|---|---|---|---|---|---|---|---|---|---|---|---|
| 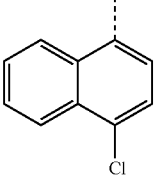 | B | L1 | O | 1 | H | H | O | trans-C₆H₁₀ | NH | 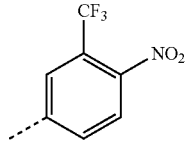 | 161 |
| 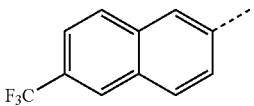 | B | L1 | O | 1 | H | H | O | trans-C₆H₁₀ | NH | 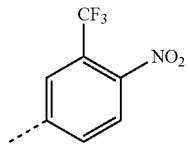 | 232 |
| 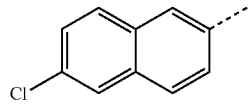 | B | L1 | O | 1 | H | H | O | trans-C₆H₁₀ | NH | 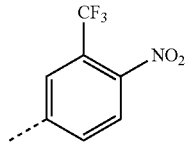 | 233 |
| 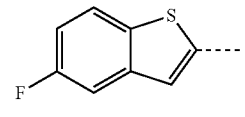 | B | L1 | O | 1 | H | H | O | trans-C₆H₁₀ | NH | 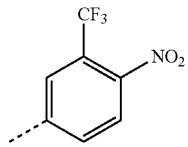 | 236 |
| 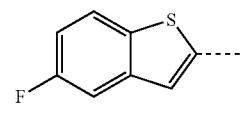 | B | L1 | O | 1 | H | H | O | trans-C₆H₁₀ | NH | 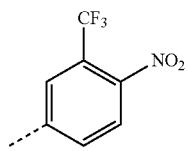 | 237 |
| 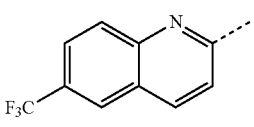 | B | L1 | O | 1 | H | H | O | trans-C₆H₁₀ | NMe | 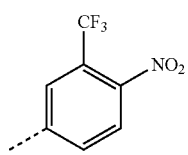 | 245 |
| 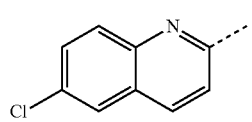 | B | L1 | O | 1 | H | H | O | trans-C₆H₁₀ | NMe | 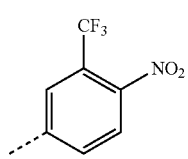 | 246 |
| 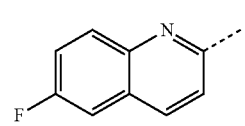 | B | L1 | O | 1 | H | H | O | trans-C₆H₁₀ | NMe | 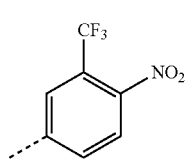 | 247 |
| 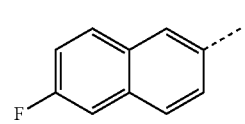 | B | L1 | O | 1 | H | H | O | trans-C₆H₁₀ | NMe | 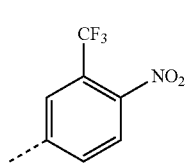 | 248 |

TABLE 2-continued
Compounds of formula (IA-1) where $R_1$ is not present; OX. = oxetane group; B = bond
| Y | $X_1$ | Ring A | W | n | $R_2$ | $R_3$ | $X_6$ | Ring B | $X_8$ | Z | # |
|---|---|---|---|---|---|---|---|---|---|---|---|
| 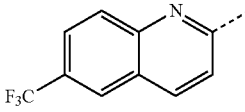 | B | L1 | O | 1 | H | H | O | trans-$C_6H_{10}$ | NH | 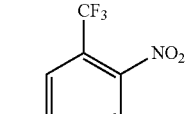 | 249 |
| 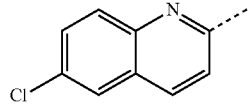 | B | L1 | O | 1 | H | Me | O | trans-$C_6H_{10}$ | NH | 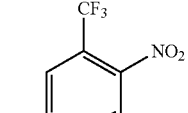 | 250 |
| 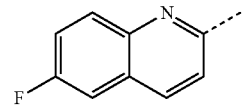 | B | L1 | O | 1 | H | Me | O | trans-$C_6H_{10}$ | NH | 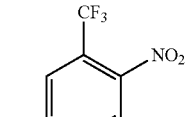 | 251 |
| 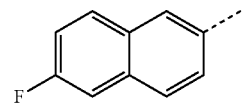 | B | L1 | O | 1 | H | Me | O | trans-$C_6H_{10}$ | NH | 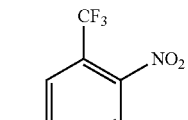 | 252 |
| 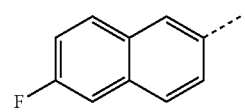 | B | L1 | S | 1 | H | H | O | trans-$C_6H_{10}$ | NH | 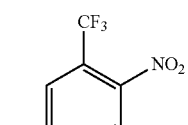 | 263 |
| 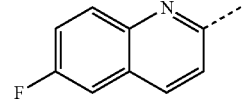 | B | L1 | S | 1 | H | H | O | trans-$C_6H_{10}$ | NH | 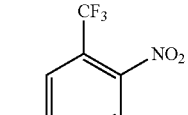 | 264 |
| 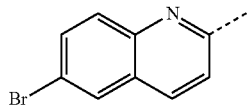 | B | L1 | O | 1 | H | H | O | trans-$C_6H_{10}$ | NH | 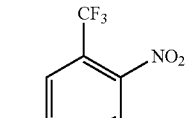 | 266 |
| 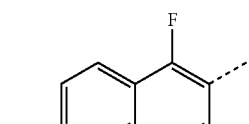 | B | L1 | O | 1 | H | H | O | trans-$C_6H_{10}$ | NH | 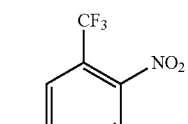 | 267 |
| 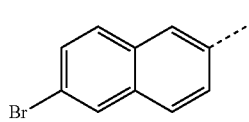 | B | L1 | O | 1 | H | H | O | trans-$C_6H_{10}$ | NH | 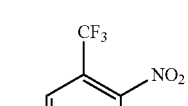 | 268 |

TABLE 2-continued
Compounds of formula (IA-1) where R₁ is not present; OX. = oxetane group; B = bond
| Y | X₁ | Ring A | W | n | R₂ | R₃ | X₆ | Ring B | X₈ | Z | # |
|---|---|---|---|---|---|---|---|---|---|---|---|
| 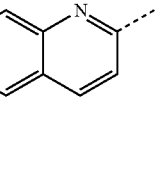 | B | L1 | O | 1 | H | H | O | trans-C₆H₁₀ | NMe | 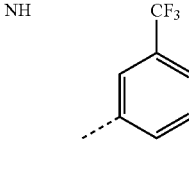 | 269 |
| 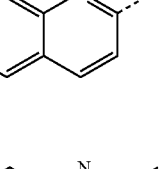 | B | L1 | O | 1 | H | H | O | trans-C₆H₁₀ | NH | 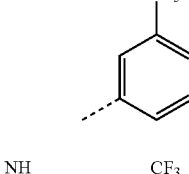 | 270 |
| 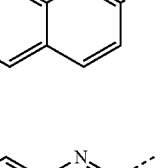 | B | L1 | O | 1 | H | H | O | trans-C₆H₁₀ | NH | 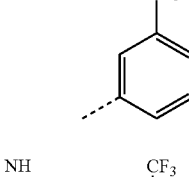 | 271 |
| 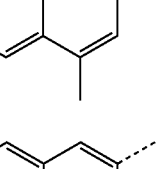 | B | L1 | O | 1 | H | H | O | trans-C₆H₁₀ | NH | 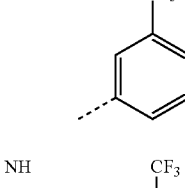 | 272 |
| 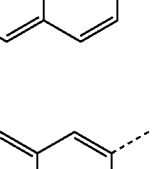 | B | L1 | O | 1 | H | H | O | trans-C₆H₁₀ | NH | 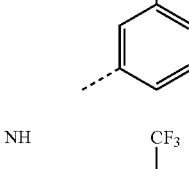 | 273 |
| 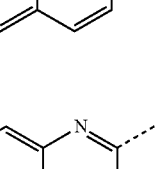 | B | L1 | O | 1 | H | H | O | trans-C₆H₁₀ | NH | 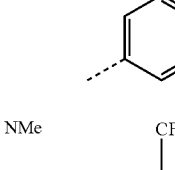 | 277 |
| 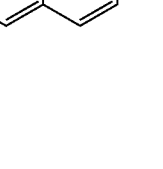 | B | L1 | O | 1 | H | H | O | trans-C₆H₁₀ | NH | 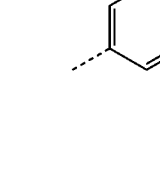 | 278 |
|  | B | L1 | O | 1 | H | H | O | trans-C₆H₁₀ | NH |  | 279 |
|  | B | L1 | O | 1 | H | H | O | trans-C₆H₁₀ | NMe |  | 281 |

TABLE 2-continued
Compounds of formula (IA-1) where R₁ is not present; OX. = oxetane group; B = bond
| Y | X₁ | Ring A | W | n | R₂ | R₃ | X₆ | Ring B | X₈ | Z | # |
|---|----|--------|---|---|----|----|----|--------|----|---|---|
| 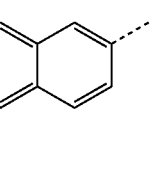 | B | L1 | O | 1 | H | H | O | trans-C₆H₁₀ | NMe | 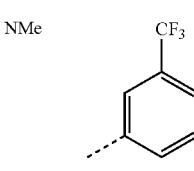 | 282 |
| 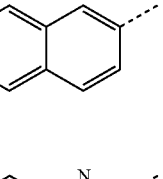 | B | L1 | O | 1 | H | H | O | trans-C₆H₁₀ | NMe | 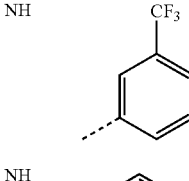 | 283 |
| 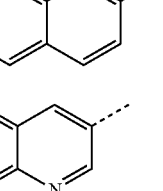 | B | L1 | O | 1 | H | H | O | trans-C₆H₁₀ | NH | 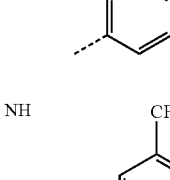 | 289 |
| 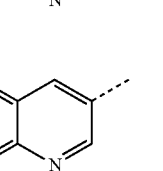 | B | L1 | O | 1 | H | H | O | trans-C₆H₁₀ | NH | 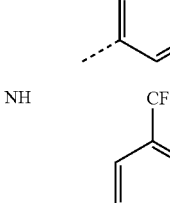 | 290 |
| 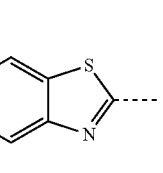 | B | L1 | O | 1 | H | H | O | trans-C₆H₁₀ | NMe | 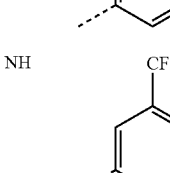 | 293 |
|  | B | L1 | O | 1 | H | H | O | trans-C₆H₁₀ | NH | 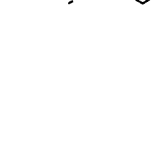 | 314 |
|  | B | L1 | O | 1 | H | H | O | trans-C₆H₁₀ | NH |  | 331 |
|  | B | L1 | O | 1 | H | H | O | trans-C₆H₁₀ | NH |  | 335 |
|  | B | L1 | O | 1 | H | H | O | trans-C₆H₁₀ | NH |  | 336 |
|  | B | L1 | O | 1 | H | H | O | trans-C₆H₁₀ | NH |  | 342 |

TABLE 2-continued

Compounds of formula (IA-1) where R₁ is not present; OX. = oxetane group; B = bond

| Y | X₁ | Ring A | W | n | R₂ | R₃ | X₆ | Ring B | X₈ | Z | # |
|---|---|---|---|---|---|---|---|---|---|---|---|
| 5-CF₃-benzothiazol-2-yl | B | L1 | O | 1 | H | H | O | trans-C₆H₁₀ | NH | 2-CF₃-4-CN-phenyl | 358 |
| 5-CF₃-benzothiazol-2-yl | B | L1 | O | 1 | H | H | O | trans-C₆H₁₀ | NH | 4-SO₂CF₃-phenyl | 364 |
| 5-CF₃-benzothiazol-2-yl | B | L1 | O | 1 | F | F | O | trans-C₆H₁₀ | NH | 2-CF₃-4-NO₂-phenyl | 390 |
| 5-CF₃O-benzoxazol-2-yl | B | L1 | O | 1 | H | H | O | trans-C₆H₁₀ | NH | 2-CF₃-4-NO₂-phenyl | 399 |
| 5-CF₃-benzoxazol-2-yl | B | L1 | O | 1 | H | H | O | trans-C₆H₁₀ | NH | 2-CF₃-4-NO₂-phenyl | 400 |
| 5-CF₃-benzothiazol-2-yl | B | L1 | O | 1 | H | H | O | trans-C₆H₁₀ | NH—SO₂ | 4-NO₂-phenyl | 402 |
| 5-CF₃-benzothiazol-2-yl | CH₂ | L1 | O | 1 | H | H | O | trans-C₆H₁₀ | NH—SO₂ | 4-NO₂-phenyl | 403 |
| 5-CF₃-benzothiazol-2-yl | B | L1 | O | 1 | H | H | O | trans-C₆H₁₀ | NH—SO₂ | 2-CF₃-4-CN-phenyl | 404 |
| 5-CF₃-benzothiazol-2-yl | CH₂ | L1 | O | 1 | H | H | O | trans-C₆H₁₀ | NH—SO₂ | 2-CF₃-4-CN-phenyl | 405 |
| 5-Cl-2,3-dihydrobenzofuran-2-yl | CH₂ | L1 | O | 1 | H | H | O | C₆H₄ | CH₂ | 2-CF₃-4-CN-phenyl | 132 |

TABLE 2-continued
Compounds of formula (IA-1) where R₁ is not present; OX. = oxetane group; B = bond
| Y | X₁ | Ring A | W | n | R₂ | R₃ | X₆ | Ring B | X₈ | Z | # |
|---|---|---|---|---|---|---|---|---|---|---|---|
| 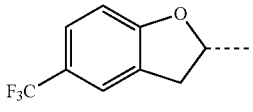 | CH₂ | L1 | O | 1 | H | H | O | C₆H₄ | CH₂ | 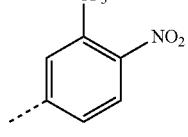 | 133 |
| 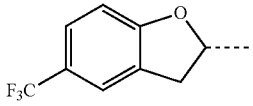 | CH₂ | L1 | O | 1 | H | H | O | C₆H₄ | CO | 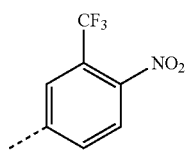 | 134 |
| 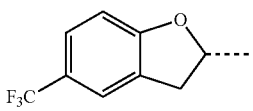 | CH₂ | L1 | O | 1 | H | H | O | C₆H₄ | CO | 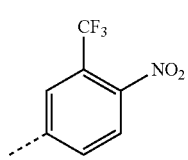 | 135 |
| 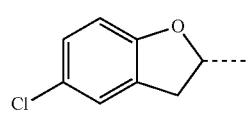 | CH₂ | L1 | O | 1 | H | H | O | C₆H₄ |  | 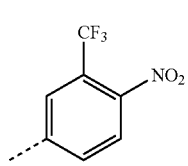 | 136 |
| 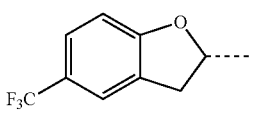 | CH₂ | L1 | O | 1 | H | H | O | C₆H₄ |  | 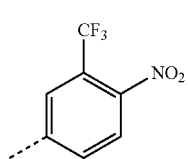 | 137 |
| 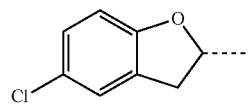 | CH₂ | L1 | O | 1 | H | H | O | C₆H₄ |  | 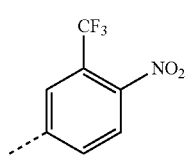 | 138 |
| 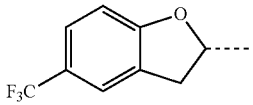 | CH₂ | L1 | O | 1 | H | H | O | C₆H₄ |  | 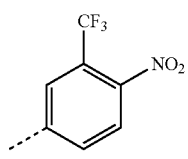 | 139 |
| 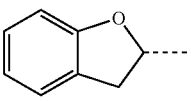 | CH₂ | L1 | O | 1 | H | H | O | C₆H₄ |  | 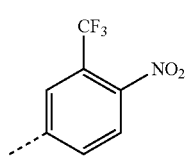 | 140 |
| 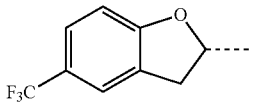 | CH₂ | L1 | O | 1 | H | H | O | C₆H₄ |  | 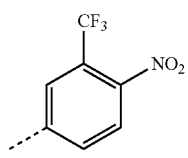 | 141 |

TABLE 2-continued

Compounds of formula (IA-1) where R₁ is not present; OX. = oxetane group; B = bond

| Y | X₁ | Ring A | W | n | R₂ | R₃ | X₆ | Ring B | X₈ | Z | # |
|---|---|---|---|---|---|---|---|---|---|---|---|
| 2,3-dihydrobenzofuran-2-yl | CH₂ | L1 | O | 1 | H | H | O | C₆H₄ | CF₂ | 2-CF₃-4-NO₂-phenyl | 142 |
| 5-CF₃-2,3-dihydrobenzofuran-2-yl | CH₂ | L1 | O | 1 | H | H | O | C₆H₄ | CF₂ | 2-CF₃-4-NO₂-phenyl | 143 |
| 6-CF₃-quinolin-2-yl | B | L1 | O | 1 | H | H | O | pyridinyl | NH | 2-CF₃-4-NO₂-phenyl | 144 |
| 5-CF₃-benzothiazol-2-yl | B | L1 | O | 1 | H | H | O | pyridinyl | NH | 4-SO₂CF₃-phenyl | 145 |
| 5-CF₃-benzothiazol-2-yl | CH₂ | L1 | O | 1 | H | H | O | pyridinyl | NH | 2-CF₃-4-NO₂-phenyl | 146 |
| 3-Cl-5-CF₃-benzofuran-2-yl | CH₂ | L1 | O | 1 | H | H | O | pyridinyl | NH | 2-CF₃-4-NO₂-phenyl | 147 |
| 5,6-difluoro-benzoxazol-2-yl | B | L1 | O | 1 | H | H | O | pyridinyl | O | 2-CF₃-4-NO₂-phenyl | 152 |
| 6-Cl-quinolin-2-yl | B | L1 | O | 1 | H | H | O | pyridinyl | O | 2-CF₃-4-NO₂-phenyl | 153 |
| 5-F-benzothiophen-2-yl | B | L1 | O | 1 | H | H | O | pyridinyl | O | 2-CF₃-4-NO₂-phenyl | 154 |
| 7-CF₃-quinolin-2-yl | CH₂ | L1 | O | 1 | H | H | O | pyridinyl | O | 2-CF₃-4-NO₂-phenyl | 155 |

TABLE 2-continued
Compounds of formula (IA-1) where R₁ is not present; OX. = oxetane group; B = bond
| Y | X₁ | Ring A | W | n | R₂ | R₃ | X₆ | Ring B | X₈ | Z | # |
|---|---|---|---|---|---|---|---|---|---|---|---|
| 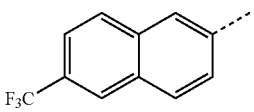 | B | L1 | O | 1 | H | H | bond | 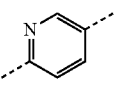 | NH | 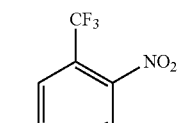 | 148 |
| 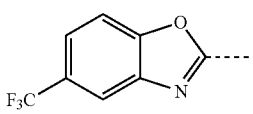 | CH₂ | L1 | O | 1 | H | H | bond | 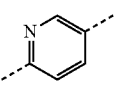 | NH | 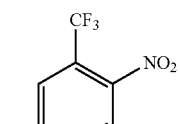 | 149 |
| 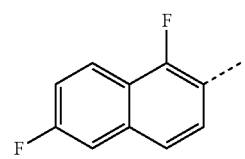 | B | L1 | O | 1 | H | H | bond | 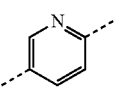 | NH | 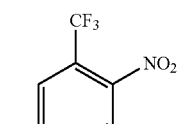 | 150 |
| 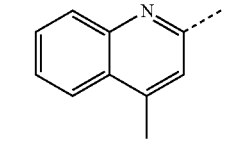 | B | L1 | O | 1 | H | H | bond | 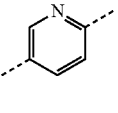 | NH | 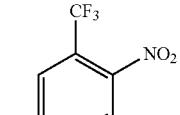 | 151 |
| 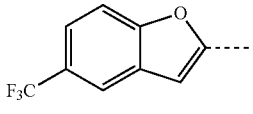 | CO | L1 | O | 1 | H | H | bond | 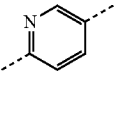 | O | 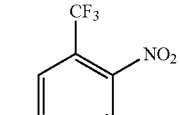 | 156 |
| 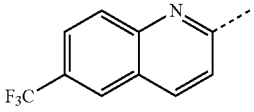 | B | L1 | O | 1 | H | H | bond | 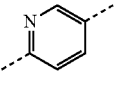 | O | 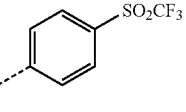 | 157 |
| 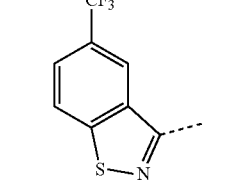 | B | L1 | O | 1 | H | H | bond | 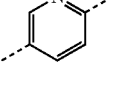 | O | 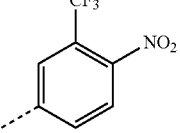 | 158 |
| 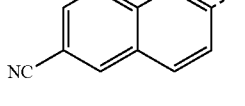 | B | L1 | O | 1 | H | H | bond | 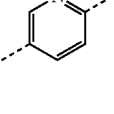 | O | 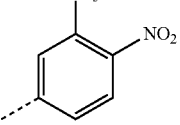 | 159 |
| 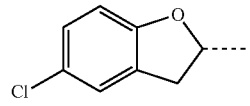 | CH₂ | L1 | O | 1 | H | H | O | C₆H₄ | NH | 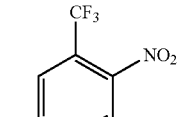 | 68 |

TABLE 2-continued

Compounds of formula (IA-1) where R₁ is not present; OX. = oxetane group; B = bond

| Y | X₁ | Ring A | W | n | R₂ | R₃ | X₆ | Ring B | X₈ | Z | # |
|---|---|---|---|---|---|---|---|---|---|---|---|
| 5-Cl-benzofuran-2-yl | CH₂ | L1 | O | 1 | H | H | O | C₆H₄ | NH | 4-(CF₃)(NO₂)-phenyl | 184 |
| 5-Cl-2,3-dihydrobenzofuran-2-yl | CH₂ | L1 | O | 1 | H | H | O | C₆H₄ | NH | 4-(CF₃)(NO₂)-phenyl | 185 |
| 5-F-benzofuran-2-yl | CH₂ | L1 | O | 1 | H | H | O | C₆H₄ | NH | 4-(CF₃)(NO₂)-phenyl | 186 |
| 5-CF₃-2,3-dihydrobenzofuran-2-yl | CH₂ | L1 | O | 1 | H | H | O | C₆H₄ | NH | 4-(CF₃)(NO₂)-phenyl | 187 |
| 5-CF₃-benzofuran-2-yl | CH₂ | L1 | O | 1 | H | H | O | C₆H₄ | NH | 4-(CF₃)(NO₂)-phenyl | 188 |
| 5-Cl-benzofuran-2-yl | O | L1 | O | 1 | H | H | O | C₆H₄ | NH | 4-(CF₃)(NO₂)-phenyl | 189 |
| 5-Cl-benzofuran-2-yl | CO | L1 | O | 1 | H | H | O | C₆H₄ | NH | 4-(CF₃)(NO₂)-phenyl | 190 |
| 5-CF₃-benzofuran-2-yl | CO | L1 | O | 1 | H | H | O | C₆H₄ | NH | 4-(CF₃)(NO₂)-phenyl | 191 |
| 5-CF₃-benzothiazol-2-yl | B | L1 | O | 1 | H | H | O | trans-C₆H₁₀ | B | 6-CF₃-5-NO₂-indol-1-yl | 409 |
| 5-CF₃-benzothiazol-2-yl | B | L1 | O | 1 | H | H | O | trans-C₆H₁₀ | B | 4-CF₃-5-NO₂-indol-1-yl | 410 |

TABLE 2-continued

Compounds of formula (IA-1) where R₁ is not present; OX. = oxetane group; B = bond

| Y | X₁ | Ring A | W | n | R₂ | R₃ | X₆ | Ring B | X₈ | Z | # |
|---|---|---|---|---|---|---|---|---|---|---|---|
| 5-CF₃-benzothiazol-2-yl | B | L1 | O | 1 | H | H | O | trans-C₆H₁₀ | B | 6-CF₃-5-NO₂-indolin-1-yl | 411 |
| 5-CF₃-benzothiazol-2-yl | B | L1 | O | 1 | H | H | O | trans-C₆H₁₀ | B | 4-CF₃-5-NO₂-indol-1-yl | 412 |
| 5-CF₃-benzothiazol-2-yl | B | L1 | O | 1 | H | H | O | trans-C₆H₁₀ | B | 3,3-difluoro-6-CF₃-5-NO₂-indolin-1-yl | 413 |
| 5-CF₃-benzothiazol-2-yl | B | L1 | O | 1 | H | H | O | trans-C₆H₁₀ | B | 3,3-difluoro-4-CF₃-5-NO₂-indolin-1-yl | 414 |
| 5-CF₃-benzothiazol-2-yl | B | L1 | OX | 1 | H | H | O | trans-C₆H₁₀ | —NH— | 2-CF₃-4-NO₂-phenyl | 415 |
| 5-CF₃-benzothiazol-2-yl | CH₂ | L1 | OX | 1 | H | H | O | trans-C₆H₁₀ | —NH— | 2-CF₃-4-NO₂-phenyl | 416 |
| 5-CF₃-benzothiazol-2-yl | B | L1 | O | 0 | — | — | —NH— | trans-C₆H₁₀ | —NH— | 2-CF₃-4-NO₂-phenyl | 395 |
| 5-CF₃-benzothiazol-2-yl | B | L1 | O | 0 | — | — | —NMe— | trans-C₆H₁₀ | —NH— | 2-CF₃-4-NO₂-phenyl | 397 |
| 2,3-dihydrobenzofuran-2-yl | CH₂ | L1 | O | 1 | H | H | O | trans-C₆H₁₀ | NH | 2-CF₃-4-NO₂-phenyl | 24 |
| 5-Cl-2,3-dihydrobenzofuran-2-yl | CH₂ | L1 | O | 1 | H | H | O | trans-C₆H₁₀ | NH | 2-CF₃-4-NO₂-phenyl | 76 |

TABLE 2-continued

Compounds of formula (IA-1) where $R_1$ is not present; OX. = oxetane group; B = bond

| Y | $X_1$ | Ring A | W | n | $R_2$ | $R_3$ | $X_6$ | Ring B | $X_8$ | Z | # |
|---|---|---|---|---|---|---|---|---|---|---|---|
| 5-F-2,3-dihydrobenzofuran-2-yl | $CH_2$ | L1 | O | 1 | H | H | O | trans-$C_6H_{10}$ | NH | 2-$NO_2$-3-$CF_3$-phenyl | 77 |
| 5-$CF_3$-2,3-dihydrobenzofuran-2-yl | $CH_2$ | L1 | O | 1 | H | H | O | trans-$C_6H_{10}$ | NH | 2-$NO_2$-3-$CF_3$-phenyl | 78 |
| 5-Cl-2,3-dihydrobenzofuran-2-yl | C(O) | L1 | O | 1 | H | H | O | trans-$C_6H_{10}$ | NH | 2-$NO_2$-3-$CF_3$-phenyl | 79 |
| 5-F-2,3-dihydrobenzofuran-2-yl | C(O) | L1 | O | 1 | H | H | O | trans-$C_6H_{10}$ | NH | 2-$NO_2$-3-$CF_3$-phenyl | 80 |
| 5-$CF_3$-2,3-dihydrobenzofuran-2-yl | C(O) | L1 | O | 1 | H | H | O | trans-$C_6H_{10}$ | NH | 2-$NO_2$-3-$CF_3$-phenyl | 81 |
| 5-Cl-2,3-dihydrobenzofuran-2-yl | $CH_2$ | L1 | O | 1 | H | H | O | trans-$C_6H_{10}$ | NH | 2-$NO_2$-3-$CF_3$-phenyl | 82 |
| 5-F-2,3-dihydrobenzofuran-2-yl | $CH_2$ | L1 | O | 1 | H | H | O | trans-$C_6H_{10}$ | NH | 2-CN-3-$CF_3$-phenyl | 83 |
| 5-$CF_3$-2,3-dihydrobenzofuran-2-yl | $CH_2$ | L1 | O | 1 | H | H | O | trans-$C_6H_{10}$ | NH | 2-CN-3-$CF_3$-phenyl | 84 |
| 5-F-2,3-dihydrobenzofuran-2-yl | C(O) | L1 | O | 1 | H | H | O | trans-$C_6H_{10}$ | NH | 2-CN-3-$CF_3$-phenyl | 85 |

TABLE 2-continued

Compounds of formula (IA-1) where R₁ is not present; OX. = oxetane group; B = bond

| Y | X₁ | Ring A | W | n | R₂ | R₃ | X₆ | Ring B | X₈ | Z | # |
|---|---|---|---|---|---|---|---|---|---|---|---|
| 5-F-2,3-dihydrobenzofuran-2-yl | C(O) | L1 | O | 1 | H | H | O | trans-C₆H₁₀ | NH | 4-CN-3-CF₃-phenyl | 86 |
| 5-CF₃-2,3-dihydrobenzofuran-2-yl | C(O) | L1 | O | 1 | H | H | O | trans-C₆H₁₀ | NH | 4-CN-3-CF₃-phenyl | 87 |
| 5-F-2,3-dihydrobenzofuran-2-yl | CH₂ | L1 | O | 1 | H | H | O | trans-C₆H₁₀ | NH | 4-NO₂-3-CF₃-phenyl | 260 |
| 5-F-2,3-dihydrobenzofuran-2-yl | CH₂ | L1 | O | 1 | H | H | O | trans-C₆H₁₀ | NMe | 4-NO₂-3-CF₃-phenyl | 261 |
| 5-F-2,3-dihydrobenzofuran-2-yl | CH(CH₃) | L1 | O | 1 | H | H | O | trans-C₆H₁₀ | NMe | 4-NO₂-3-CF₃-phenyl | 262 |
| 5-F-2,3-dihydrobenzofuran-2-yl | CH₂ | L1 | S | 1 | H | H | O | trans-C₆H₁₀ | NH | 4-NO₂-3-CF₃-phenyl | 265 |
| 5-F-2,3-dihydrobenzofuran-2-yl | CH₂ | L1 | O | 1 | H | H | O | trans-C₆H₁₀ | NMe | 4-CN-3-CF₃-phenyl | 280 |
| 5-Br-2,3-dihydrobenzofuran-2-yl | CH₂ | L1 | O | 1 | H | H | O | trans-C₆H₁₀ | NH | 4-NO₂-3-CF₃-phenyl | 299 |
| 5-pFPH-2,3-dihydrobenzofuran-2-yl | CH₂ | L1 | O | 1 | H | H | O | trans-C₆H₁₀ | NH | 4-NO₂-3-CF₃-phenyl | 310 |

TABLE 2-continued

Compounds of formula (IA-1) where $R_1$ is not present; OX. = oxetane group; B = bond

| Y | $X_1$ | Ring A | W | n | $R_2$ | $R_3$ | $X_6$ | Ring B | $X_8$ | Z | # |
|---|---|---|---|---|---|---|---|---|---|---|---|
| 5-F, 2-Me-2,3-dihydrobenzofuran-2-yl | $CH_2$ | L1 | O | 1 | H | H | O | trans-$C_6H_{10}$ | NH | 2-$CF_3$, 4-$NO_2$-phenyl | 377 |
| 5-$CF_3$-2,3-dihydrobenzofuran-2-yl | $CH_2$ | L1 | O | 1 | H | H | O | trans-$C_6H_{10}$ | NH | 4-$SO_2CF_3$-phenyl | 378 |
| 5-F-2,3-dihydrobenzofuran-2-yl | $CH_2$ | L1 | O | 1 | H | H | O | trans-$C_6H_{10}$ | NH | 4-$SO_2CF_3$-phenyl | 379 |
| 5-(p$CF_3$Ph)-2,3-dihydrobenzofuran-2-yl | $CH_2$ | L1 | O | 1 | H | H | O | trans-$C_6H_{10}$ | NH | 2-$CF_3$, 4-$NO_2$-phenyl | 380 |
| 5-F, 2-Me-2,3-dihydrobenzofuran-2-yl | $CH_2$ | L1 | O | 1 | H | H | O | trans-$C_6H_{10}$ | NH | 2-$CF_3$, 4-CN-phenyl | 401 |
| 5-F-2,3-dihydrobenzofuran-2-yl | $CH_2$ | L13 | O | 1 | H | H | O | trans-$C_6H_{10}$ | NH | 2-$CF_3$, 4-$NO_2$-phenyl | 307 |
| 5-F-2,3-dihydrobenzofuran-2-yl | $CH_2$ | L13 | O | 1 | H | H | O | trans-$C_6H_{10}$ | NH | 2-$CF_3$, 4-CN-phenyl | 308 |
| 5-F-2,3-dihydrobenzofuran-2-yl | B | L15 | O | 1 | H | H | O | trans-$C_6H_{10}$ | NH | 2-$CF_3$, 4-$NO_2$-phenyl | 309 |
| 5-Cl-benzofuran-2-yl | $CH_2$ | L1 | O | 1 | H | H | O | trans-$C_6H_{10}$ | NH | 2-$CF_3$, 4-$NO_2$-phenyl | 178 |
| 5-F-benzofuran-2-yl | $CH_2$ | L1 | O | 1 | H | H | O | trans-$C_6H_{10}$ | NH | 2-$CF_3$, 4-$NO_2$-phenyl | 179 |

TABLE 2-continued

Compounds of formula (IA-1) where R₁ is not present; OX. = oxetane group; B = bond

| Y | X₁ | Ring A | W | n | R₂ | R₃ | X₆ | Ring B | X₈ | Z | # |
|---|---|---|---|---|---|---|---|---|---|---|---|
| 5-CF₃-benzofuran-2-yl | CH₂ | L1 | O | 1 | H | H | O | trans-C₆H₁₀ | NH | 4-CF₃-3-NO₂-phenyl | 180 |
| 5-Cl-benzofuran-2-yl | C(O) | L1 | O | 1 | H | H | O | trans-C₆H₁₀ | NH | 4-CF₃-3-NO₂-phenyl | 181 |
| 5-F-benzofuran-2-yl | C(O) | L1 | O | 1 | H | H | O | trans-C₆H₁₀ | NH | 4-CF₃-3-NO₂-phenyl | 182 |
| 6-F-benzofuran-2-yl | C(O) | L1 | O | 1 | H | H | O | trans-C₆H₁₀ | NH | 4-CF₃-3-NO₂-phenyl | 183 |
| 5-F-benzothiophene-2-yl | CH₂ | L1 | O | 1 | H | H | O | trans-C₆H₁₀ | NH | 4-CF₃-3-NO₂-phenyl | 234 |
| 5-F-benzothiazol-2-yl | CH₂ | L1 | O | 1 | H | H | O | trans-C₆H₁₀ | NH | 4-CF₃-3-NO₂-phenyl | 235 |
| 3-Cl-5-CF₃-benzofuran-2-yl | CH₂ | L1 | O | 1 | H | H | O | trans-C₆H₁₀ | NH | 4-CF₃-3-NO₂-phenyl | 253 |
| 5-CF₃-benzofuran-2-yl | C(CH₃)₂ | L1 | O | 1 | H | H | O | trans-C₆H₁₀ | NH | 4-CF₃-3-NO₂-phenyl | 254 |
| 3-Cl-5-CF₃-benzofuran-2-yl | CH(CH₃) | L1 | O | 1 | H | H | O | trans-C₆H₁₀ | NH | 4-CF₃-3-NO₂-phenyl | 255 |

TABLE 2-continued

Compounds of formula (IA-1) where R₁ is not present; OX. = oxetane group; B = bond

| Y | X₁ | Ring A | W | n | R₂ | R₃ | X₆ | Ring B | X₈ | Z | # |
|---|---|---|---|---|---|---|---|---|---|---|---|
| 5-CF₃-benzofuran-2-yl | CH₂ | L1 | O | 1 | H | H | O | trans-C₆H₁₀ | NMe | 2-CF₃-4-NO₂-phenyl | 256 |
| 5-CF₃-benzofuran-2-yl | CH(CH₃) | L1 | O | 1 | H | H | O | trans-C₆H₁₀ | NMe | 2-CF₃-4-NO₂-phenyl | 257 |
| 5-CF₃-3-Cl-benzofuran-2-yl | CH₂ | L1 | O | 1 | H | H | O | trans-C₆H₁₀ | NMe | 2-CF₃-4-NO₂-phenyl | 258 |
| 5-CF₃-3-Cl-benzofuran-2-yl | CH(CH₃) | L1 | O | 1 | H | H | O | trans-C₆H₁₀ | NMe | 2-CF₃-4-NO₂-phenyl | 259 |
| 5-Cl-benzofuran-2-yl | CH₂ | L1 | O | 1 | H | H | O | trans-C₆H₁₀ | NH | 2-CF₃-4-CN-phenyl | 274 |
| 5-Cl-benzofuran-2-yl | CH₂ | L1 | O | 1 | H | H | O | trans-C₆H₁₀ | NMe | 2-CF₃-4-NO₂-phenyl | 275 |
| 5-Cl-benzofuran-2-yl | CH₂ | L1 | O | 1 | H | H | O | trans-C₆H₁₀ | NMe | 2-CF₃-4-CN-phenyl | 284 |
| 5-F-benzoxazol-2-yl | CH₂ | L1 | O | 1 | H | H | O | trans-C₆H₁₀ | NH | 2-CF₃-4-NO₂-phenyl | 285 |
| 5-F-benzoxazol-2-yl | CH₂ | L1 | O | 1 | H | H | O | trans-C₆H₁₀ | NH | 2-CF₃-4-CN-phenyl | 286 |

TABLE 2-continued
Compounds of formula (IA-1) where $R_1$ is not present; OX. = oxetane group; B = bond
| Y | $X_1$ | Ring A | W | n | $R_2$ | $R_3$ | $X_6$ | Ring B | $X_8$ | Z | # |
|---|---|---|---|---|---|---|---|---|---|---|---|
| 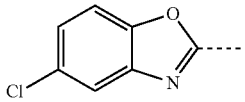 | $CH_2$ | L1 | O | 1 | H | H | O | trans-$C_6H_{10}$ | NH | 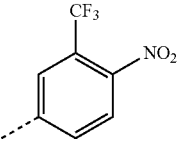 | 287 |
| 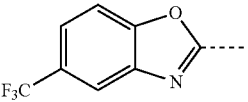 | $CH_2$ | L1 | O | 1 | H | H | O | trans-$C_6H_{10}$ | NH | 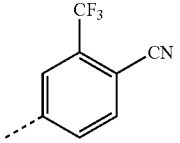 | 288 |
| 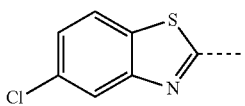 | $CH_2$ | L1 | O | 1 | H | H | O | trans-$C_6H_{10}$ | NH | 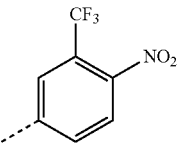 | 291 |
| 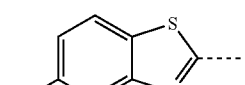 | $CH_2$ | L1 | O | 1 | H | H | O | trans-$C_6H_{10}$ | NH | 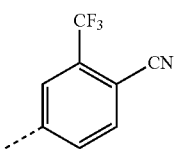 | 292 |
| 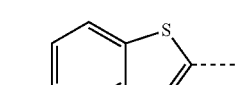 | $CH_2$ | L1 | O | 1 | H | H | O | trans-$C_6H_{10}$ | NH | 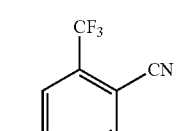 | 294 |
| 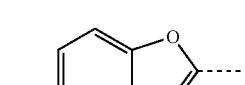 |  | L1 | O | 1 | H | H | O | trans-$C_6H_{10}$ | NH | 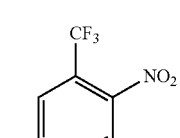 | 300 |
| 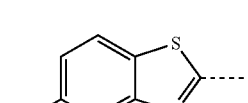 | $CH_2$ | L1 | O | 1 | H | H | O | trans-$C_6H_{10}$ | NH | 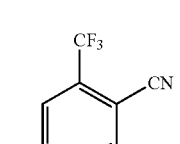 | 301 |
| 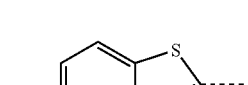 | $CH_2$ | L1 | O | 1 | H | H | O | trans-$C_6H_{10}$ | NH | 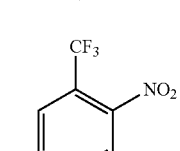 | 302 |
| 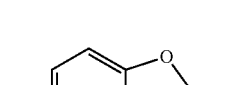 |  | L1 | O | 1 | H | H | O | trans-$C_6H_{10}$ | NH | 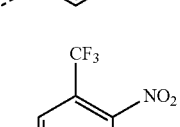 | 304 |

TABLE 2-continued

Compounds of formula (IA-1) where $R_1$ is not present; OX. = oxetane group; B = bond

| Y | $X_1$ | Ring A | W | n | $R_2$ | $R_3$ | $X_6$ | Ring B | $X_8$ | Z | # |
|---|---|---|---|---|---|---|---|---|---|---|---|
| 5-trifluoromethyl-benzothiazol-2-yl | C(CH$_3$)$_2$ | L1 | O | 1 | H | H | O | trans-C$_6$H$_{10}$ | NH | 2-CF$_3$-4-NO$_2$-phenyl | 406 |
| 5-trifluoromethyl-3-chloro-benzofuran-2-yl | CH$_2$ | L1 | O | 1 | H | H | O | trans-C$_6$H$_{10}$ | NH | 2-CF$_3$-4-CN-phenyl | 305 |
| 5-trifluoromethyl-benzofuran-2-yl | CH$_2$ | L1 | O | 1 | H | H | O | trans-C$_6$H$_{10}$ | NH | 2-CF$_3$-4-CN-phenyl | 306 |
| 5-fluoro-3-chloro-benzofuran-2-yl | CH$_2$ | L1 | O | 1 | H | H | O | trans-C$_6$H$_{10}$ | NH | 2-CF$_3$-4-NO$_2$-phenyl | 312 |
| 5-fluoro-3-chloro-benzofuran-2-yl | CH$_2$ | L1 | O | 1 | H | H | O | trans-C$_6$H$_{10}$ | NH | 2-CF$_3$-4-NO$_2$-phenyl | 313 |
| 5-chloro-3-chloro-benzofuran-2-yl | CH$_2$ | L1 | O | 1 | H | H | O | trans-C$_6$H$_{10}$ | NH | 2-CF$_3$-4-NO$_2$-phenyl | 315 |
| 5-chloro-3-chloro-benzofuran-2-yl | CH$_2$ | L1 | O | 1 | H | H | O | trans-C$_6$H$_{10}$ | NH | 2-CF$_3$-4-NO$_2$-phenyl | 316 |
| 4,6-dichloro-benzofuran-2-yl | CH$_2$ | L1 | O | 1 | H | H | O | trans-C$_6$H$_{10}$ | NH | 2-CF$_3$-4-NO$_2$-phenyl | 318 |
| 5,7-dichloro-benzofuran-2-yl | CH$_2$ | L1 | O | 1 | H | H | O | trans-C$_6$H$_{10}$ | NH | 2-CF$_3$-4-NO$_2$-phenyl | 319 |

TABLE 2-continued

Compounds of formula (IA-1) where R₁ is not present; OX. = oxetane group; B = bond

| Y | X₁ | Ring A | W | n | R₂ | R₃ | X₆ | Ring B | X₈ | Z | # |
|---|---|---|---|---|---|---|---|---|---|---|---|
| 4,5-difluorobenzofuran-2-yl | CH₂ | L1 | O | 1 | H | H | O | trans-C₆H₁₀ | NH | 4-nitro-3-(trifluoromethyl)phenyl | 320 |
| 7-bromo-5-chlorobenzofuran-2-yl | CH₂ | L1 | O | 1 | H | H | O | trans-C₆H₁₀ | NH | 4-nitro-3-(trifluoromethyl)phenyl | 321 |
| 6-chlorobenzofuran-2-yl | CH₂ | L1 | O | 1 | H | H | O | trans-C₆H₁₀ | NH | 4-nitro-3-(trifluoromethyl)phenyl | 322 |
| 5-methoxybenzofuran-2-yl | CH₂ | L1 | O | 1 | H | H | O | trans-C₆H₁₀ | NH | 4-nitro-3-(trifluoromethyl)phenyl | 323 |
| 5-(trifluoromethyl)benzofuran-2-yl | CH₂ | L1 | O | 1 | H | H | O | trans-C₆H₁₀ | NH | 4-nitro-3-(trifluoromethyl)phenyl | 324 |
| 5,6-difluorobenzofuran-2-yl | CH₂ | L1 | O | 1 | H | H | O | trans-C₆H₁₀ | NH | 4-nitro-3-(trifluoromethyl)phenyl | 325 |
| 5-(trifluoromethoxy)benzofuran-2-yl | CH₂ | L1 | O | 1 | H | H | O | trans-C₆H₁₀ | NH | 4-nitro-3-(trifluoromethyl)phenyl | 326 |
| 5-(trifluoromethyl)benzofuran-2-yl | —CH₂—CH(CH₃)— | L1 | O | 1 | H | H | O | trans-C₆H₁₀ | NH | 4-nitro-3-(trifluoromethyl)phenyl | 330 |
| 5-(trifluoromethyl)benzoxazol-2-yl | C(O) | L1 | O | 1 | H | H | O | trans-C₆H₁₀ | NH | 4-nitro-3-(trifluoromethyl)phenyl | 338 |

TABLE 2-continued

Compounds of formula (IA-1) where R₁ is not present; OX. = oxetane group; B = bond

| Y | X₁ | Ring A | W | n | R₂ | R₃ | X₆ | Ring B | X₈ | Z | # |
|---|---|---|---|---|---|---|---|---|---|---|---|
| 5-CF₃-benzothiazol-2-yl | CH(CH₃) | L1 | O | 1 | H | H | O | trans-C₆H₁₀ | NH | 2-NO₂-4-(CF₃)-phenyl | 343 |
| 5-CF₃-benzothiazol-2-yl | CH₂ | L1 | O | 1 | H | H | O | trans-C₆H₁₀ | NH | 4-(SO₂CF₃)-phenyl | 344 |
| 5,7-difluorobenzofuran-2-yl | CH₂ | L1 | O | 1 | H | H | O | trans-C₆H₁₀ | NH | 2-NO₂-4-(CF₃)-phenyl | 375 |
| 5-CF₃-benzoxazol-2-yl | CH₂ | L1 | O | 1 | H | H | O | trans-C₆H₁₀ | NH | 2-NO₂-4-(CF₃)-phenyl | 376 |
| 5-CF₃-benzothiazol-2-yl | CH₂ | L13 | O | 1 | H | H | O | trans-C₆H₁₀ | NH | 2-NO₂-4-(CF₃)-phenyl | 365 |
| 5-F-benzothiazol-2-yl | CH₂ | L13 | O | 1 | H | H | O | trans-C₆H₁₀ | NH | 2-NO₂-4-(CF₃)-phenyl | 370 |
| 5-F-benzothiazol-2-yl | CH₂ | L14 | O | 1 | H | H | O | trans-C₆H₁₀ | NH | 2-NO₂-4-(CF₃)-phenyl | 371 |
| 5-CF₃-benzothiazol-2-yl | CH₂ | L1 | O | 1 | H | H | O | trans-C₆H₁₀ | NH | 2-NO₂-4-(CF₃)-phenyl | 311 |
| 6-F-naphth-2-yl | CH₂ | L1 | O | 1 | H | H | O | trans-C₆H₁₀ | NH | 2-NO₂-4-(CF₃)-phenyl | 297 |
| 6-F-naphth-2-yl | CH(CH₃) | L1 | O | 1 | H | H | O | trans-C₆H₁₀ | NH | 2-NO₂-4-(CF₃)-phenyl | 298 |

TABLE 2-continued
Compounds of formula (IA-1) where $R_1$ is not present; OX. = oxetane group; B = bond
| Y | $X_1$ | Ring A | W | n | $R_2$ | $R_3$ | $X_6$ | Ring B | $X_8$ | Z | # |
|---|---|---|---|---|---|---|---|---|---|---|---|
| 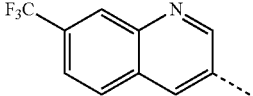 | $CH_2$ | L1 | O | 1 | H | H | O | trans-$C_6H_{10}$ | NH | 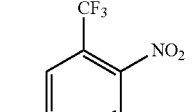 | 327 |
| 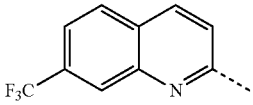 | $CH_2$ | L1 | O | 1 | H | H | O | trans-$C_6H_{10}$ | NH | 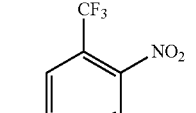 | 328 |
| 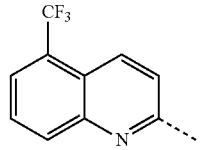 | $CH_2$ | L1 | O | 1 | H | H | O | trans-$C_6H_{10}$ | NH | 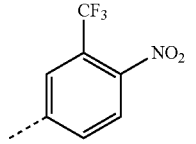 | 329 |
| 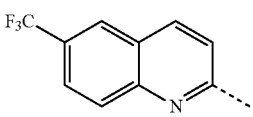 | $CH_2$ | L1 | O | 1 | H | H | O | trans-$C_6H_{10}$ | NH | 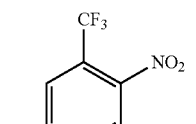 | 332 |
| 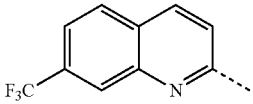 | $CH_2$ | L1 | O | 1 | H | H | O | trans-$C_6H_{10}$ | NH | 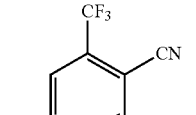 | 333 |
| 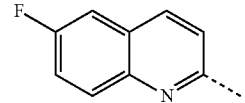 | $CH_2$ | L1 | O | 1 | H | H | O | trans-$C_6H_{10}$ | NH | 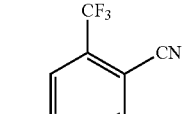 | 334 |
| 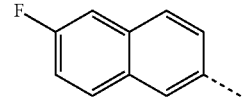 | $CH_2$ | L13 | O | 1 | H | H | O | trans-$C_6H_{10}$ | NH | 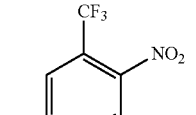 | 357 |
| 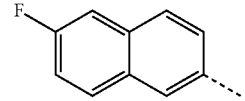 | $CH_2$ | L14 | O | 1 | H | H | O | trans-$C_6H_{10}$ | NH | 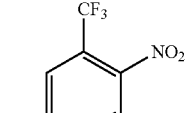 | 372 |
| 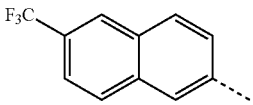 | $CH_2$ | L13 | O | 1 | H | H | O | trans-$C_6H_{10}$ | NH | 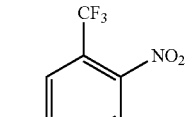 | 373 |

TABLE 2-continued

Compounds of formula (IA-1) where R₁ is not present; OX. = oxetane group; B = bond

| Y | X₁ | Ring A | W | n | R₂ | R₃ | X₆ | Ring B | X₈ | Z | # |
|---|---|---|---|---|---|---|---|---|---|---|---|
| 6-(trifluoromethyl)naphthalen-2-yl | CH₂ | L14 | O | 1 | H | H | O | trans-C₆H₁₀ | NH | 4-nitro-3-(trifluoromethyl)phenyl | 374 |
| 5-(trifluoromethyl)benzothiazol-2-yl | B | L1 | O | 1 | H | H | O | trans-C₆H₁₀ | NH | 4-nitro-3-(trifluoromethyl)phenyl | 391 |
| 6-(trifluoromethyl)quinolin-2-yl | B | L1 | O | 1 | H | H | O | trans-C₆H₁₀ | NH | 4-nitro-3-(trifluoromethyl)phenyl | 392 |
| 5-(trifluoromethyl)benzothiazol-2-yl | CH₂ | L1 | O | 1 | H | H | O | trans-C₆H₁₀ | NH | 4-nitro-3-(trifluoromethyl)phenyl | 393 |
| 6-chloroquinolin-2-yl | B | L1 | O | 1 | H | H | O | trans-C₆H₁₀ | NH | 4-nitro-3-(trifluoromethyl)phenyl | 394 |
| 5-(trifluoromethyl)benzothiazol-2-yl | B | L16 | O | 1 | H | H | O | trans-C₆H₁₀ | NH | 4-nitro-3-(trifluoromethyl)phenyl | 407 |
| 5-(trifluoromethyl)benzothiazol-2-yl | CH₂ | L16 | O | 1 | H | H | O | trans-C₆H₁₀ | NH | 4-nitro-3-(trifluoromethyl)phenyl | 408 |
| 5-(pentafluoro-λ⁶-sulfanyl)benzoxazol-2-yl | B | L1 | O | 1 | H | H | O | trans-C₆H₁₀ | NH | 4-nitro-3-(trifluoromethyl)phenyl | 417 |
| 6-(pentafluoro-λ⁶-sulfanyl)benzoxazol-2-yl | B | L1 | O | 1 | H | H | O | trans-C₆H₁₀ | NH | 4-nitro-3-(trifluoromethyl)phenyl | 418 |

TABLE 2-continued

Compounds of formula (IA-1) where R₁ is not present; OX. = oxetane group; B = bond

| Y | X₁ | Ring A | W | n | R₂ | R₃ | X₆ | Ring B | X₈ | Z | # |
|---|---|---|---|---|---|---|---|---|---|---|---|
| F₅C-benzoxazol-2-yl (5-pentafluoroethyl) | CH₂ | L1 | O | 1 | H | H | O | trans-C₆H₁₀ | NH | 2-NO₂-4-(attached)-CF₃-phenyl | 419 |
| F₅S-benzoxazol-2-yl (6-SF₅) | CH₂ | L1 | O | 1 | H | H | O | trans-C₆H₁₀ | NH | 2-NO₂-4-(attached)-CF₃-phenyl | 420 |
| F₃C-5-(1H-benzimidazol-2-yl) | B | L1 | O | 1 | H | H | O | trans-C₆H₁₀ | NH | 2-NO₂-4-(attached)-CF₃-phenyl | 421 |
| F₃C-5-(1-Me-benzimidazol-2-yl) | B | L1 | O | 1 | H | H | O | trans-C₆H₁₀ | NH | 2-NO₂-4-(attached)-CF₃-phenyl | 422 |
| F₃C-6-(3-Me-benzimidazol-2-yl) | B | L1 | O | 1 | H | H | O | trans-C₆H₁₀ | NH | 2-NO₂-4-(attached)-CF₃-phenyl | 423 |
| F₃C-6-(1H-benzimidazol-2-yl) | CH₂ | L1 | O | 1 | H | H | O | trans-C₆H₁₀ | NH | 2-NO₂-4-(attached)-CF₃-phenyl | 424 |
| F₃C-6-(1-Me-benzimidazol-2-yl) | CH₂ | L1 | O | 1 | H | H | O | trans-C₆H₁₀ | NH | 2-NO₂-4-(attached)-CF₃-phenyl | 425 |
| F₃C-5-(3-Me-benzimidazol-2-yl) | CH₂ | L1 | O | 1 | H | H | O | trans-C₆H₁₀ | NH | 2-NO₂-4-(attached)-CF₃-phenyl | 426 |
| F₃C-6-(quinolin-2-yl) | B | L15 | O | 1 | H | H | O | trans-C₆H₁₀ | NH | 2-NO₂-4-(attached)-CF₃-phenyl | 427 |

In one embodiment of formula (IA-2), W is O. In another embodiment, W is an oxetane group.

In another embodiment of formula (IA-2), Ring A is one of linkers L1, L2, L3, L4, L5, L6, L7, L8, L9, L10, L13, L14, L15, L16, L17 or L18. In another embodiment, Ring A is one of L1, L2, L3, L8, L13, L14, L15, L16, L17 or L18. In another embodiment, Ring A is L1, L13, L14 or L15. In yet another embodiment, Ring A is L16, L17 or L18.

In still another embodiment of formula (IA-2), Y and/or Z is naphthyl optionally substituted with one or more of halogen, nitro, cyano, alkyl, haloalkyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl.

In yet another embodiment of formula (IA-2), Y and/or Z are independently benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more halogen, nitro, cyano, alkyl, haloalkyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl.

In another embodiment of formula (IA-2), one of Y or Z is naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of halogen, nitro, cyano, alkyl, haloalkyl, phenyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl and the other of Y or Z is phenyl, a 3-7 membered heterocyclyl group or a 5 or 6-membered heteroaryl group, each of which is optionally substituted by one or more of halogen, nitro, cyano, alkyl, haloalkyl, phenyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl.

In still another embodiment of formula (IA-2), one of Y or Z is naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of halogen, nitro, cyano, alkyl, haloalkyl, phenyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl and the other of Y or Z is phenyl or a 5- or 6-membered heteroaryl group, each of which is optionally substituted by one or more of halogen, nitro, cyano, alkyl, haloalkyl, phenyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl.

In another embodiment, one of Y or Z is naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of chloro, fluoro, bromo, $CF_3$, $OCF_3$, $SCF_3$ or $SF_5$; and the other of Y or Z is phenyl optionally substituted by cyano, nitro, $CF_3$, $SF_5$, $S(O)C_{1-3}$alkyl, $S(O)_2$—$C_{1-3}$alkyl, $S(O)C_{1-3}$haloalkyl or $S(O)_2C_{1-3}$haloalkyl.

In another embodiment of formula (IA-2), Y and Z are independently phenyl, naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of halogen, nitro, cyano, $C_{1-3}$alkyl, $C_{1-3}$haloalkyl, phenyl, hydroxy, $C_{1-3}$hydroxyalkyl, amino, $C_{1-3}$alkyl- or $C_{1-3}$ dialkylamino, $C_{1-3}$alkoxy, $C_{1-3}$haloalkoxy, $C_{1-3}$alkylthio, $C_{1-3}$haloalkylthio, $C_{1-3}$ alkylsulfinyl, $C_{1-3}$haloalkylsulfinyl, $C_{1-3}$alkylsulfonyl, $C_{1-3}$haloalkylsulfonyl or $SF_5$, with the proviso that at least one of Y and Z is a bicyclic ring;

Ring A is one of linkers L1, L2, L3, L4, L5, L6, L7, L8, L9, L10, L13, L14, L15, L16, L17 or L18;

$X_1$ is a bond, —C(O)—, —$(CH_2)_n$— where n is 1 to 3, —O—$CH_2$—, —$NHCH_2$—, —S—$CH_2$—, —S(O)—$CH_2$—, —$CH_2$—S(O)—, —$S(O)_2$—$CH_2$—, and —$CH_2$—$S(O)_2$—, wherein each —$(CH_2)_n$—, —O—$CH_2$—, —$NHCH_2$—, —S—$CH_2$—, —S(O)—$CH_2$—, —$CH_2$—S(O)—, —$S(O)_2$—$CH_2$—, and —$CH_2$—$S(O)_2$— are optionally substituted with oxo (=O) or one or more halogen, cyano, alkyl, haloalkyl, cycloalkyl or aryl groups;

W is O, S or an oxetane group;

each $R_1$ is independently halogen, cyano, hydroxyl, amino, $C_{1-3}$alkylamino, $C_{1-3}$ dialkylamino, $C_{1-3}$alkyl or $C_{1-3}$haloalkyl;

$R_2$ and $R_3$ are independently H, halogen, $C_1$-$C_3$alkyl or $C_1$-$C_3$haloalkyl;

$X_8$ is a bond, —$(CH_2)_n$ where n is 1 to 3, —O—, —C(O)—, —S—, —S(O)—, —$S(O)_2$—, —NHS(O)—, —S(O)—NH—, —$NHSO_2$—, —$SO_2NH$— or —NH—, wherein each $CH_2$ in —$(CH_2)_n$—, —NHS(O)—, —S(O)—NH—, —$NHSO_2$—, —$SO_2NH$— or —NH— is optionally independently substituted with one or two substituents selected from the group consisting of halogen, hydroxy, amino, $C_{1-3}$alkylamino, $C_{1-3}$dialkylamino, $C_{1-3}$hydroxyalkyl, $C_{1-3}$aminoalkyl, $C_{1-3}$alkyl, $C_{1-3}$haloalkyl and $C_{1-3}$ alkoxyalkyl; n is 0, 1, 2 or 3; and r is 0, 1, 2, 3 or 4.

In another embodiment, $X_1$ is optionally substituted —$(CH_2)_n$— or —C(O)—. In another embodiment, $X_8$ is —C(O)— or optionally substituted NH— or —$(CH_2)_n$—. In still another embodiment of formula (IA-2), $R_2$ and $R_3$ are H. In still another embodiment of formula (IA-2), n is 1 or 2. In yet another embodiment of formula (IA-2), $X_1$ is a bond, —C(O)— or —$CH_2$—; W is O, n is 1 or 2, $R_2$ and $R_3$ are H and r is 0. In another embodiment of formula (IA-2), Y and/or Z are independently naphthyl, quinolinyl, isoquinolinyl, tetrahydroquinolyl, tetrahydroisoquinolyl, benzofuranyl, dihydrobenzofuranyl, benzimidazolyl or benzothiazolyl, each of which is optionally substituted with one or more halogen, nitro, cyano, alkyl, haloalkyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl; $X_1$ is bond, —C(O)— or —$CH_2$—; W is O, n is 1 or 2, $R_2$ and $R_3$ are H, r is 0 and $X_8$ is —NH—, —C(O)—, —$CH_2$—, —$CF_2$—, —$CH(CH_3)$— or $C(CH_3)_2$—.

In other embodiments of formula (IA-2), the invention provides the compounds in Table 3 below:

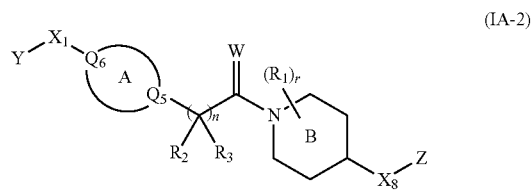

(IA-2)

TABLE 3
Compounds of formula (IA-2) wherein $X_1$ = bond, $R_1$ is not present, $R_2$ = H and $X_8$ is —NH—
| Y | Ring A | n | $R_3$ | Z | Compound # |
|---|---|---|---|---|---|
| 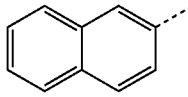 | L1 | 2 | Me | 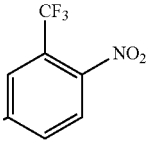 | 13 |
| 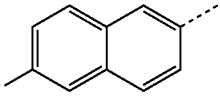 | L1 | 2 | Me | 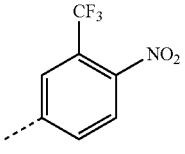 | 16 |
| 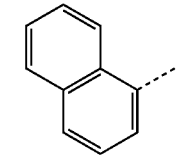 | L1 | 2 | Me | 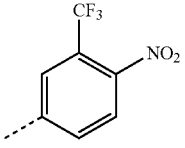 | 19 |
| 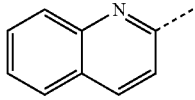 | L1 | 2 | Me | 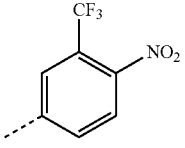 | 91 |
| 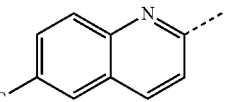 | L1 | 2 | Me | 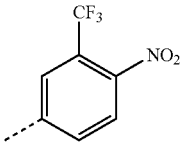 | 92 |
| 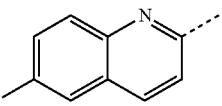 | L1 | 2 | Me | 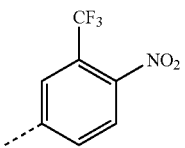 | 93 |
| 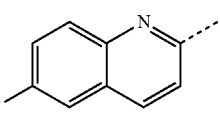 | L1 | 2 | Me | 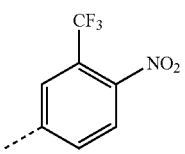 | 100 |
| 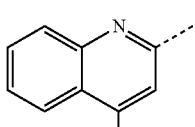 | L1 | 2 | Me | 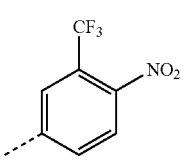 | 101 |
| 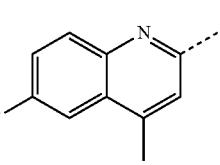 | L1 | 2 | Me | 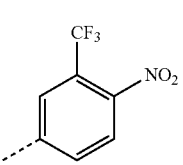 | 102 |

TABLE 3-continued
Compounds of formula (IA-2) wherein $X_1$ = bond,
$R_1$ is not present, $R_2$ = H and $X_8$ is —NH—
| Y | Ring A | n | $R_3$ | Z | Compound # |
|---|---|---|---|---|---|
| 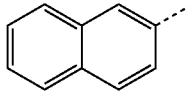 | L1 | 3 | H | 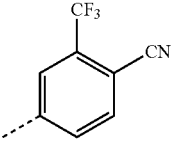 | 15 |
| 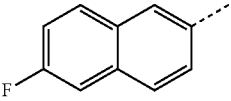 | L1 | 3 | H | 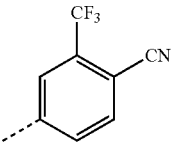 | 18 |
| 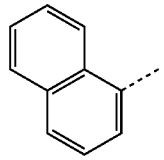 | L1 | 3 | H | 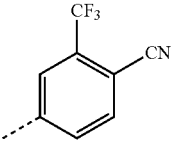 | 21 |
| 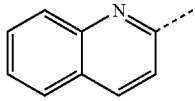 | L1 | 3 | H | 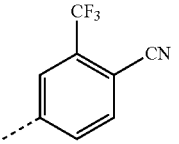 | 94 |
| 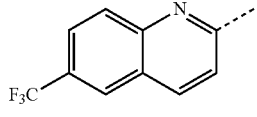 | L1 | 3 | H | 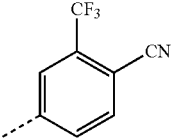 | 95 |
| 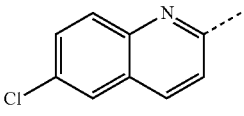 | L1 | 3 | H | 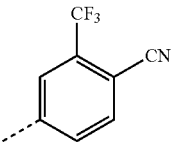 | 96 |
| 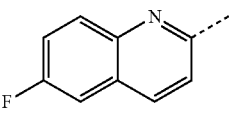 | L1 | 3 | H | 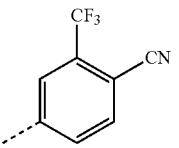 | 103 |
| 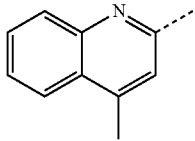 | L1 | 3 | H | 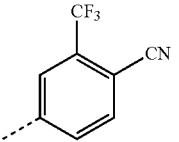 | 104 |
| 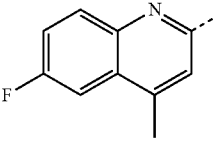 | L1 | 3 | H | 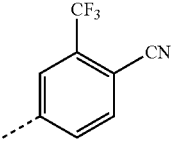 | 105 |

In another aspect of the invention, the compounds of formula (I) have the structure (TB) shown below:

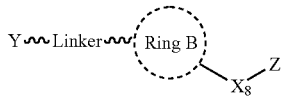

(IB)

Wherein variables Y, $X_8$ and Z are as defined for formula (I), Ring B is independently a 3- to 8-membered carbocyclylene or a 3- to 8-membered heterocyclylene ring with 1 to 3 heteroatoms selected from oxygen, sulfur and nitrogen; or a 7- to 11-membered bicyclic carbocyclylene or 7- to 11-membered heterocyclylene ring containing 1 to 4 heteroatoms selected from oxygen, sulfur and nitrogen; and the Linker is the segment $X_1$—$X_2$—$X_3$—$X_4$—$X_5$—$X_6$— where $X_1$, $X_2$, $X_3$, $X_4$, $X_5$ and $X_6$ are as defined for formula (I).

In an embodiment of formula (TB), variables $X_4$ and/or $X_5$ in the Linker segment $X_1$—$X_2$—$X_3$—$X_4$—$X_5$—$X_6$— are absent. In another embodiment of formula (IB), Ring B is one of L1 to L10 or L13 to L18 as defined in Table 1, which may optionally be substituted with halogen, alkyl or haloalkyl. In another embodiment of formula (IB), Ring B is cyclohexylene or phenylene, which may optionally be substituted with halogen, alkyl or haloalkyl.

In still another embodiment of formula (IB), Y and/or Z is naphthyl optionally substituted with one or more of halogen, nitro, cyano, hydroxy, hydroxyalkyl, amino, alkylamino, dialkylamino, aminoalkyl, alkyl, haloalkyl, alkoxy, haloalkoxy, alkylthio, halothio, haloalkylthio, alkylsulfinyl, haloalkylsulfinyl, alkylsulfonyl, haloalkylsulfonyl, aryl, aryloxy, arylalkoxy, arylthio, arylalkylthio, arylsulfinyl, arylsulfonyl, arylalkylsulfinyl, arylalkylsulfonyl, heteroaryl, heteroaryloxy, heteroarylalkoxy, heteroarylthio, heteroarylsulfinyl, heteroarylsulfonyl, heteroarylalkylthio, heteroarylalkylsulfinyl or heteroarylalkylsulfonyl.

In yet another embodiment of formula (IB), Y and/or Z are independently benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of halogen, nitro, cyano, hydroxy, hydroxyalkyl, amino, alkylamino, dialkylamino, aminoalkyl, alkyl, haloalkyl, alkoxy, haloalkoxy, alkylthio, halothio, haloalkylthio, alkylsulfinyl, haloalkylsulfinyl, alkylsulfonyl, haloalkylsulfonyl, aryl, aryloxy, arylalkoxy, arylthio, arylalkylthio, arylsulfinyl, arylsulfonyl, arylalkylsulfinyl, arylalkylsulfonyl, heteroaryl, heteroaryloxy, heteroarylalkoxy, heteroarylthio, heteroarylsulfinyl, heteroarylsulfonyl, heteroarylalkylthio, heteroarylalkylsulfinyl or heteroarylalkylsulfonyl.

In another embodiment of formula (IB), the compound has the structure of formula (IB-1), (IB-2), (IB-3), (IB-4) or (IB-5) shown below:

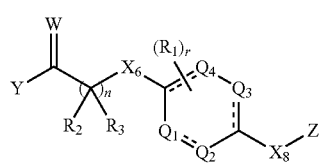

(IB-1)

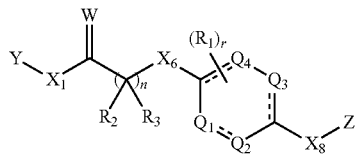

(IB-2)

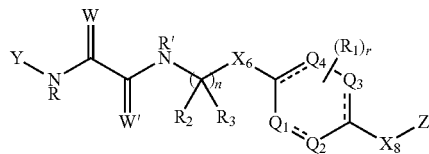

(IB-3)

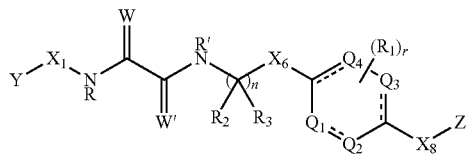

(IB-4)

wherein Y, $X_1$, $X_6$, $X_8$ and Z are as defined above for formula (I); W and W' are each independently O, S or oxetane; $Q_1$, $Q_2$, $Q_3$ and $Q_4$ are each independently C—H or a heteroatom selected from N, S or O; R and R' are each independently hydrogen, alkyl, haloalkyl or arylalkyl; $R_1$ is independently halogen, cyano, hydroxyl, amino, alkylamino, dialkylamino, alkyl, haloalkyl, carbocyclyl, heterocyclyl, alkenyl, haloalkenyl, alkynyl or haloalkynyl; $R_2$ and $R_3$ are independently hydrogen, halogen, cyano, alkyl, haloalkyl or carbocyclyl; n is 0, 1, 2 or 3; r is 0, 1, 2, 3 or 4; and the dotted lines in the ring represent single or double bonds.

In one embodiment of formulae (IB-1), (IB-2), (IB-3) and (IB-4), Y and/or Z is naphthyl optionally substituted with one or more of halogen, nitro, cyano, alkyl, haloalkyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl. In yet another embodiment of formulae (IB-1), (IB-2), (IB-3) and (IB-4), Y and/or Z are independently benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl each of which is optionally substituted by one or more halogen, nitro, cyano, alkyl, haloalkyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl.

In another embodiment of formulae (IB-1), (IB-2), (IB-3) and (IB-4), one of Y or Z is naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of halogen, nitro, cyano, alkyl, haloalkyl, phenyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl and the other of Y or Z is phenyl, a 3-8 membered heterocyclyl group or a 5 or 6-membered heteroaryl group, each of which is optionally substituted by one or more of halogen, nitro, cyano, alkyl, haloalkyl, phenyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl.

In still another embodiment of formulae (IB-1), (IB-2), (IB-3) and (IB-4), one of Y or Z is naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of halogen, nitro, cyano, alkyl, haloalkyl, phenyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl and the other of Y or Z is phenyl or a 5- or 6-membered heteroaryl group, each of which is optionally substituted by one or more of halogen, nitro, cyano, alkyl, haloalkyl, phenyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl. In another embodiment, one of Y or Z is naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of chloro, fluoro, bromo, $CF_3$, $OCF_3$, $SCF_3$ or $SF_5$, and the other of Y or Z is phenyl optionally substituted by cyano, nitro, $CF_3$, $SF_5$, $S(O)C_{1-3}$alkyl, $S(O)_2$—$C_{1-3}$alkyl, $S(O)C_{1-3}$haloalkyl or $S(O)_2C_{1-3}$haloalkyl.

In one embodiment of formulae (IB-1), (IB-2), (IB-3) and (IB-4), $Q_1$ is N. In another embodiment, $Q_2$ is N. In another embodiment, $Q_3$ is N. In yet another embodiment, $Q_4$ is N.

In one embodiment, $Q_1$ and $Q_4$ are N. In another embodiment, $Q_2$ and $Q_3$ are N. In still another embodiment, $Q_1$ and $Q_2$ are N. In another embodiment, $Q_3$ and $Q_4$ are N.

In another embodiment, $Q_1$ and $Q_3$ are N. In still another embodiment, $Q_2$ and $Q_4$ are N.

In one embodiment of formula (IB-1), W is O. In another embodiment, W is an oxetane group. In another embodiment, the ring is an optionally substituted cyclohexylene group. In yet another embodiment, the ring is an optionally substituted phenylene group. In yet another embodiment, $X_6$ is —NH— in which the hydrogen may be replaced by alkyl, haloalkyl or arylalkyl, —O—, —S—, —S(O)— or —S(O)$_2$—. In another embodiment, $X_6$ is —(CH$_2$)$_n$-optionally substituted by halogen, alkyl or haloalkyl. In still another embodiment of formula (IB-1), $R_2$ and $R_3$ are H. In still another embodiment of formula (IB-1), n is 1 or 2. In another embodiment of formula (IB-1), $X_6$ is —O— or —NH— which may optionally be substituted by alkyl or haloalkyl or arylalkyl.

In another embodiment of formula (IB-1), Y and Z are independently phenyl, naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of halogen, nitro, cyano, $SF_5$, $C_{1-3}$alkyl, $C_{1-3}$haloalkyl, phenyl, hydroxy, $C_{1-3}$hydroxyalkyl, amino, $C_{1-3}$alkyl- or $C_{1-3}$dialkylamino, $C_{1-3}$alkoxy, $C_{1-3}$haloalkoxy, $C_{1-3}$alkylthio, $C_{1-3}$haloalkylthio, $C_{1-3}$ alkylsulfinyl, $C_{1-3}$haloalkylsulfinyl, $C_{1-3}$alkylsulfonyl or $C_{1-3}$haloalkylsulfonyl, with the proviso that at least one of Y and Z is a bicyclic ring;

W is O, S or an oxetane group;

each $R_1$ is independently halogen, cyano, hydroxyl, amino, $C_{1-3}$alkylamino, $C_{1-3}$ dialkylamino, $C_{1-3}$alkyl or $C_{1-3}$haloalkyl;

$R_2$ and $R_3$ are independently H, halogen, $C_1$-$C_3$alkyl or $C_1$-$C_3$haloalkyl;

$X_6$ is a bond, —(CH$_2$)$_n$— where n is 1 to 3, —O—, —NH—, —C(O)—NH— and —NH—C(O)—, wherein each —CH$_2$— in the —(CH$_2$)$_n$— group, —NH—, —C(O)—NH— and —NH—C(O)— are optionally substituted with one or more substituents independently selected from the group consisting of halogen, hydroxy, $C_{1-3}$hydroxyalkyl, amino, $C_{1-3}$alkylamino, $C_{1-3}$dialkylamino, $C_{1-3}$ aminoalkyl, $C_{1-3}$alkyl and $C_{1-3}$haloalkyl;

$X_8$ is a bond, —(CH$_2$)$_n$ where n is 1 to 3, —O—, —C(O)—, —S—, —S(O)—, —S(O)$_2$—, —NHS(O)—, —S(O)—NH—, —NHSO$_2$—, —SO$_2$NH— or —NH—, wherein each CH$_2$ in —(CH$_2$)$_n$—, —NHS(O)—, —S(O)—NH—, —NHSO$_2$—, —SO$_2$NH— or —NH— is optionally independently substituted with one or two substituents selected from the group consisting of halogen, hydroxy, amino, $C_{1-3}$alkylamino, $C_{1-3}$dialkylamino, $C_{1-3}$hydroxyalkyl, $C_{1-3}$aminoalkyl, $C_{1-3}$alkyl, $C_{1-3}$haloalkyl and $C_{1-3}$ alkoxyalkyl; n is 0, 1, 2 or 3; and r is 0, 1, 2, 3 or 4;

$Q_1$, $Q_2$, $Q_3$ and $Q_4$ are each independently C—H or a heteroatom selected from N, S or O;

the dashed lines represent a single or double bond; n is 0, 1, 2 or 3; and r is 0, 1, 2, 3 or 4.

In yet another embodiment of formula (IB-1), W is O, $X_6$ is —O—, Y and/or Z are independently phenyl, naphthyl, quinolinyl, isoquinolinyl, tetrahydroquinolyl, tetrahydroisoquinolyl, benzofuranyl, dihydrobenzofuranyl, benzimidazolyl or benzothiazolyl, each of which is optionally substituted with one or more halogen, nitro, cyano, alkyl, haloalkyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl, with the proviso that at least one of Y or Z is a bicyclic ring; n is 1 or 2, $R_2$ and $R_3$ are H and r is 0.

In another embodiment of formula (IB-1), one of Y or Z is naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of chloro, fluoro, bromo, $CF_3$, $OCF_3$, $SCF_3$ or $SF_5$, and the other of Y or Z is phenyl optionally substituted by cyano, nitro, $CF_3$, $SF_5$, $S(O)C_{1-3}$alkyl, $S(O)_2$—$C_{1-3}$alkyl, $S(O)C_{1-3}$haloalkyl or $S(O)_2C_{1-3}$haloalkyl;

the ring is a trans-cyclohexylene or phenylene ring;

W is O; $X_6$ is a bond, —O—, —(CH$_2$)$_n$— where n is 1 to 3 or —NH—;

$X_8$ is a bond, —(CH$_2$)$_n$— where n is 1 to 3, —O— or NH—;

$R_2$ and $R_3$ are H;

n is 1 or 2; and r is 0.

In another embodiment of formula (IB-1), the ring is optionally substituted cyclohexylene or phenylene, W is O, Y and/or Z are independently optionally substituted naphthyl, benzofuranyl, dihydrobenzofuranyl, benzimidazolyl or benzothiazolyl, $X_6$ is —O—, n is 1 or 2, $R_2$ and $R_3$ are H, r is 0; and $X_8$ is NH—, —C(O)—, —CH$_2$—, —CF$_2$—, —CH(CH$_3$)— or C(CH$_3$)$_2$—.

In another embodiment, the invention provides the compounds of formula (IB-1) in Table 4 below.

TABLE 4

Compounds of Formula (IB-1) where W is O, $R_2$ and $R_3$ are H, n is 1, $R^1$ is not present, $X_6$ is —O— and $X_8$ is —NH—.

(IB-1)

| Y | Ring | Z | # |
|---|---|---|---|
| 1,2,3,4-tetrahydroisoquinolin-2-yl | trans-$C_6H_{10}$ | 2-$CF_3$-4-$NO_2$-phenyl | 192 |
| 6-F-1,2,3,4-tetrahydroisoquinolin-2-yl | trans-$C_6H_{10}$ | 2-$CF_3$-4-$NO_2$-phenyl | 193 |
| 6-$CF_3$-1,2,3,4-tetrahydroisoquinolin-2-yl | trans-$C_6H_{10}$ | 2-$CF_3$-4-$NO_2$-phenyl | 194 |
| 6-Cl-1,2,3,4-tetrahydroisoquinolin-2-yl | trans-$C_6H_{10}$ | 2-$CF_3$-4-$NO_2$-phenyl | 195 |
| 1,2,3,4-tetrahydroisoquinolin-2-yl | $C_6H_4$ | 2-$CF_3$-4-$NO_2$-phenyl | 196 |
| 6-F-1,2,3,4-tetrahydroisoquinolin-2-yl | $C_6H_4$ | 2-$CF_3$-4-$NO_2$-phenyl | 197 |
| 6-$CF_3$-1,2,3,4-tetrahydroisoquinolin-2-yl | $C_6H_4$ | 2-$CF_3$-4-$NO_2$-phenyl | 198 |
| 6-Cl-1,2,3,4-tetrahydroisoquinolin-2-yl | $C_6H_4$ | 2-$CF_3$-4-$NO_2$-phenyl | 199 |

In one embodiment of formula (IB-2), W is O. In another embodiment, $X_1$ is —O—, —S—, or —NH— in which the hydrogen atom may be replaced with alkyl, haloalkyl or arylalkyl. In yet another embodiment of formula (IB-2), $X_6$ is —NH— in which the hydrogen may be replaced by alkyl, haloalkyl or arylalkyl; —O—, —S—, —S(O)— or —S$(O)_2$—. In another embodiment, $X_6$ is —$(CH_2)_n$— optionally substituted by halogen, alkyl or haloalkyl. In another embodiment, the ring is an optionally substituted cyclohexylene group. In yet another embodiment, the ring is an optionally substituted phenylene group. In still another embodiment of formula (IB-2), $R_2$ and $R_3$ are H. In still another embodiment of formula (IB-2), n is 1 or 2.

In yet another embodiment of formula (IB-2), W is O, Y and/or Z are independently phenyl, naphthyl, quinolinyl, isoquinolinyl, tetrahydroquinolyl, tetrahydroisoquinolyl, benzofuranyl, dihydrobenzofuranyl, benzimidazolyl or benzothiazolyl, each of which is optionally substituted with one or more halogen, nitro, cyano, alkyl, haloalkyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl, with the proviso that at least one of Y or Z is a bicyclic ring; $X_6$ is —O—, $X_1$ and $X_8$ are —NH—, n is 1 or 2, $R_2$ and $R_3$ are H and r is 0.

In another embodiment of formula (IB-2), Y and Z is phenyl, naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of halogen, nitro, cyano, $C_{1-3}$alkyl, $C_{1-3}$haloalkyl, phenyl, hydroxy, $C_{1-3}$hydroxyalkyl, amino, $C_{1-3}$alkyl- or $C_{1-3}$dialkylamino, $C_{1-3}$alkoxy, $C_{1-3}$haloalkoxy, $C_{1-3}$alkylthio, $C_{1-3}$haloalkylthio, $C_{1-3}$alkylsulfinyl, $C_{1-3}$haloalkylsulfinyl, $C_{1-3}$ alkylsulfonyl, $C_{1-3}$haloalkylsulfonyl or $SF_5$, with the proviso that at least one of Y and Z is a bicyclic ring;

$Q_1$, $Q_2$, $Q_3$ and $Q_4$ are CH or one or two of $Q_1$, $Q_2$, $Q_3$ and $Q_4$ are independently N, O or S and the remaining of $Q_1$, $Q_2$, $Q_3$ and $Q_4$ are CH;

the dashed lines represent a single or double bond;

$X_1$ is a bond, —C(O)—, —$(CH_2)_n$— where n is 1 to 3, —O—$CH_2$—, —$NHCH_2$—, —S—$CH_2$—, —S(O)—$CH_2$—, —$CH_2$—S(O)—, —$S(O)_2$—$CH_2$—, and —$CH_2$—$S(O)_2$—, wherein each —$(CH_2)_n$—, —O—$CH_2$—, —$NHCH_2$—, —S—$CH_2$—, —S(O)—$CH_2$—, —$CH_2$—S(O)—, —$S(O)_2$—$CH_2$—, and —$CH_2$—$S(O)_2$— are optionally substituted with oxo (=O) or one or more halogen, cyano, alkyl, haloalkyl, cycloalkyl or aryl groups;

W is O, S or an oxetane group;

each $R_1$ is independently halogen, cyano, hydroxyl, amino, $C_{1-3}$alkylamino, $C_{1-3}$ dialkylamino, $C_{1-3}$alkyl or $C_{1-3}$haloalkyl;

$R_2$ and $R_3$ are independently H, halogen, $C_1$-$C_3$alkyl or $C_1$-$C_3$haloalkyl;

$X_8$ is a bond, —$(CH_2)_n$ where n is 1 to 3, —O—, —C(O)—, —S—, —S(O)—, —$S(O)_2$—, —NHS(O)—, —S(O)—NH—, —$NHSO_2$—, —$SO_2NH$— or —NH—, wherein each $CH_2$ in —$(CH_2)_n$—, —NHS(O)—, —S(O)—NH—, —$NHSO_2$—, —$SO_2NH$— or —NH— is optionally independently substituted with one or two substituents selected from the group consisting of halogen, hydroxy, amino, $C_{1-3}$alkylamino, $C_{1-3}$dialkylamino, $C_{1-3}$hydroxyalkyl, $C_{1-3}$aminoalkyl, $C_{1-3}$alkyl, $C_{1-3}$haloalkyl and $C_{1-3}$ alkoxyalkyl; n is 0, 1, 2 or 3; and r is 0, 1, 2, 3 or 4.

In another embodiment of formula (IB-2), one of Y or Z is naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of chloro, fluoro, bromo, $CF_3$, $OCF_3$, $SCF_3$ or SF$_5$, and the other of Y or Z is phenyl optionally substituted by cyano, nitro, CF$_3$, SF$_5$, S(O)C$_{1-3}$alkyl, S(O)$_2$—C$_{1-3}$alkyl, S(O)C$_{1-3}$haloalkyl or S(O)$_2$C$_{1-3}$haloalkyl;

the ring is a trans-cyclohexylene or phenylene ring;
W is O;
X$_6$ is a bond, —O—, —(CH$_2$)$_n$— where n is 1 to 3 or —NH—;
X$_8$ is a bond, —(CH$_2$)$_n$— where n is 1 to 3, —O— or NH—;
R$_2$ and R$_3$ are H; n is 1 or 2; and r is 0.

In another embodiment of formula (IB-2), the ring is cyclohexylene or phenylene, W is O, Y and/or Z are independently phenyl, naphthyl, quinolinyl, isoquinolinyl, tetrahydroquinolyl, tetrahydroisoquinolyl, benzofuranyl, dihydrobenzofuranyl, benzimidazolyl or benzothiazolyl, each of which is optionally substituted with one or more halogen, nitro, cyano, alkyl, haloalkyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl, with the proviso that one of Y or Z is a bicyclic ring; X$_6$ is —O—, X$_1$ is —NH—, n is 1 or 2, R$_2$ and R$_3$ are H, r is 0 and X$_8$ is —NH—, —C(O)—, —CH$_2$—, —CF$_2$—, —CH(CH$_3$)— or C(CH$_3$)$_2$—.

In another embodiment, the invention provides the compounds of formula (IB-2) in Table 5 below.

TABLE 5

Compounds of formula (IB-2) where W is O, R$_2$ and R$_3$ are H, n is 1, R$^1$ is not present, X$_6$ is —O— and X$_8$ is —NH—.

(IB-2)

| Y | X$_1$ | Ring | Z | # |
|---|---|---|---|---|
| naphthyl | —NH— | trans-C$_6$H$_{10}$ | 2-CF$_3$-4-NO$_2$-phenyl | 200 |
| 6-F-naphthyl | —NH— | trans-C$_6$H$_{10}$ | 2-CF$_3$-4-NO$_2$-phenyl | 201 |
| 6-F$_3$C-naphthyl | —NH— | trans-C$_6$H$_{10}$ | 2-CF$_3$-4-NO$_2$-phenyl | 202 |
| 6-Cl-naphthyl | —NH— | trans-C$_6$H$_{10}$ | 2-CF$_3$-4-NO$_2$-phenyl | 203 |
| naphthyl | —NH— | C$_6$H$_4$ | 2-CF$_3$-4-NO$_2$-phenyl | 204 |
| 6-F-naphthyl | —NH— | C$_6$H$_4$ | 2-CF$_3$-4-NO$_2$-phenyl | 205 |
| 6-F$_3$C-naphthyl | —NH— | C$_6$H$_4$ | 2-CF$_3$-4-NO$_2$-phenyl | 206 |
| 6-Cl-naphthyl | —NH— | C$_6$H$_4$ | 2-CF$_3$-4-NO$_2$-phenyl | 207 |
| quinolinyl | —NH— | trans-C$_6$H$_{10}$ | 2-CF$_3$-4-NO$_2$-phenyl | 208 |
| 6-F-quinolinyl | —NH— | trans-C$_6$H$_{10}$ | 2-CF$_3$-4-NO$_2$-phenyl | 209 |
| 6-F$_3$C-quinolinyl | —NH— | trans-C$_6$H$_{10}$ | 2-CF$_3$-4-NO$_2$-phenyl | 210 |
| 6-Cl-quinolinyl | —NH— | trans-C$_6$H$_{10}$ | 2-CF$_3$-4-NO$_2$-phenyl | 211 |

TABLE 5-continued

Compounds of formula (IB-2) where W is O, $R_2$ and $R_3$ are H, n is 1, $R^1$ is not present, $X_6$ is —O— and $X_8$ is —NH—.

| Y | $X_1$ | Ring | Z | # |
|---|---|---|---|---|
| quinolin-2-yl | —NH— | $C_6H_4$ | 2-$CF_3$-4-$NO_2$-phenyl | 212 |
| 6-fluoroquinolin-2-yl | —NH— | $C_6H_4$ | 2-$CF_3$-4-$NO_2$-phenyl | 213 |
| 6-trifluoromethylquinolin-2-yl | —NH— | $C_6H_4$ | 2-$CF_3$-4-$NO_2$-phenyl | 214 |
| 6-chloroquinolin-2-yl | —NH— | $C_6H_4$ | 2-$CF_3$-4-$NO_2$-phenyl | 215 |

In one embodiment of formula (IB-3), W and W' are each O. In yet another embodiment of formula (IB-3), $X_6$ is —NH— in which the hydrogen may be replaced by alkyl, haloalkyl or arylalkyl, —O—, —S—, —S(O)— or —S(O)$_2$—. In another embodiment, $X_6$ is (CH$_2$)$_n$-optionally substituted by halogen, alkyl or haloalkyl. In another embodiment of formula (IB-3), the ring is an optionally substituted cyclohexylene group. In yet another embodiment, the ring is an optionally substituted phenylene group. In still another embodiment of formula (IB-3), $R_2$ and $R_3$ are H. In still another embodiment of formula (IB-3), n is 1 or 2. In another embodiment of formula (IB-3), R and R' is each independently hydrogen or alkyl.

In another embodiment of formula (IB-3), Y and Z are independently phenyl, naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of halogen, nitro, cyano, SF$_5$, C$_{1-3}$alkyl, C$_{1-3}$haloalkyl, phenyl, hydroxy, C$_{1-3}$hydroxyalkyl, amino, C$_{1-3}$alkyl- or C$_{1-3}$ dialkylamino, C$_{1-3}$alkoxy, C$_{1-3}$haloalkoxy, C$_{1-3}$alkylthio, C$_{1-3}$haloalkylthio, C$_{1-3}$alkylsulfinyl, C$_{1-3}$haloalkylsulfinyl, C$_{1-3}$alkylsulfonyl or C$_{1-3}$haloalkylsulfonyl, with the proviso that at least one of Y and Z is a bicyclic ring;

W and W' are independently O, S or an oxetane group;
R and R' are independently H, C$_{1-3}$alkyl or C$_{1-3}$haloalkyl;
each R$_1$ is independently halogen, cyano, hydroxyl, amino, C$_{1-3}$alkylamino, C$_{1-3}$dialkylamino, C$_{1-3}$alkyl or C$_{1-3}$haloalkyl;

$R_2$ and $R_3$ are independently H, halogen, C$_1$-C$_3$alkyl or C$_1$-C$_3$haloalkyl;

$X_6$ is a bond, —(CH$_2$)$_n$— where n is 1 to 3, —O—, —NH—, —C(O)—NH— and —NH—C(O)—, wherein each —CH$_2$— in the —(CH$_2$)$_n$— group, —NH—, —C(O)—NH— and —NH—C(O)— are optionally substituted with one or more substituents independently selected from the group consisting of halogen, hydroxy, C$_{1-3}$hydroxyalkyl, amino, C$_{1-3}$alkylamino, C$_{1-3}$dialkylamino, C$_{1-3}$ aminoalkyl, C$_{1-3}$alkyl and C$_{1-3}$haloalkyl;

Q$_1$, Q$_2$, Q$_3$ and Q$_4$ are CH or one or two of Q$_1$, Q$_2$, Q$_3$ and Q$_4$ are independently N, O or S and the remaining of Q$_1$, Q$_2$, Q$_3$ and Q$_4$ are CH;

the dashed lines represent a single or double bond;

$X_8$ is absent or is a bond, —(CH$_2$) where n is 1 to 3, —O—, —C(O)—, —S—, —S(O)—, —S(O)$_2$—, —NHS(O)—, —S(O)—NH—, —NHSO$_2$—, —SO$_2$NH— or —NH—, wherein each CH$_2$ in —(CH$_2$)$_n$—, —NHS(O)—, —S(O)—NH—, —NHSO$_2$—, —SO$_2$NH— or —NH— is optionally independently substituted with one or two substituents selected from the group consisting of halogen, hydroxy, amino, C$_{1-3}$alkylamino, C$_{1-3}$dialkylamino, C$_{1-3}$hydroxyalkyl, C$_{1-3}$aminoalkyl, C$_{1-3}$alkyl, C$_{1-3}$ haloalkyl and C$_{1-3}$alkoxyalkyl; n is 0, 1, 2 or 3; and r is 0, 1, 2, 3 or 4.

In yet another embodiment of formula (IB-3), W and W' are O, $X_6$ is —O— or —NH—, n is 1 or 2, $R_2$ and $R_3$ are H, Y and/or Z are independently phenyl, naphthyl, quinolinyl, isoquinolinyl, tetrahydroquinolyl, tetrahydroisoquinolyl, benzofuranyl, dihydrobenzofuranyl, benzimidazolyl or benzothiazolyl, each of which is optionally substituted with one or more halogen, nitro, cyano, alkyl, haloalkyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl, with the proviso that at least one of Y or Z is a bicyclic ring; and r is 0.

In another embodiment of formula (IB-3), one of Y or Z is naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of chloro, fluoro, bromo, CF$_3$, OCF$_3$, SCF$_3$ or SF$_5$, and the other of Y or Z is phenyl optionally substituted by cyano, nitro, CF$_3$, SF$_5$, S(O)C$_{1-3}$alkyl, S(O)$_2$—C$_{1-3}$alkyl, S(O)C$_{1-3}$haloalkyl or S(O)$_2$C$_{1-3}$haloalkyl;

the ring is a trans-cyclohexylene or phenylene ring;
W and W' are O;
R and R' are H or C$_{1-3}$alkyl;
$X_6$ is a bond, —O—, —(CH$_2$)$_n$— where n is 1 to 3 or —NH—;
$X_8$ is a bond, —(CH$_2$)$_n$— where n is 1 to 3, —O— or —NH—;
$R_2$ and $R_3$ are H; n is 1 or 2; and r is 0.

In another embodiment of formula (IB-3), the ring is optionally substituted cyclohexylene or phenylene, W and W' are O, Y and/or Z are independently optionally substituted phenyl, naphthyl, benzofuranyl, dihydrobenzofuranyl, benzimidazolyl or benzothiazolyl, wherein at least one of Y or Z is a bicyclic ring; $X_6$ is —O—, n is 1 or 2, $R_2$ and $R_3$ are H, r is 0 and $X_8$ is —NH—, —C(O)—, —CH$_2$—, —CF$_2$—, —CH(CH$_3$)— or —C(CH$_3$)$_2$—.

In one embodiment of formula (IB-4), W and W' are each O. In yet another embodiment of formula (IB-4), $X_6$ is —NH— in which the hydrogen may be replaced by alkyl, haloalkyl or arylalkyl; —O—, —S—, —S(O)— or —S(O)$_2$—. In another embodiment, $X_6$ is —(CH$_2$)$_n$-optionally substituted by halogen, alkyl or haloalkyl. In another embodiment of formula (IB-4), the ring is an optionally substituted cyclohexylene group. In yet another embodiment, the ring is an optionally substituted phenylene group. In another embodiment, $X_1$ is —(CH$_2$)$_n$-optionally substituted by halogen, alkyl or haloalkyl.

In still another embodiment of formula (IB-4), $R_2$ and $R_3$ are H. In still another embodiment of formula (IB-4), n is 1 or 2. In another embodiment of formula (IB-4), R and R' are independently hydrogen or alkyl. In yet another embodiment of formula (IB-4), W and W' are O, Y and/or Z are independently phenyl, naphthyl, quinolinyl, isoquinolinyl, tetrahydroquinolyl, tetrahydroisoquinolyl, benzofuranyl, dihydrobenzofuranyl, benzimidazolyl or benzothiazolyl, each of which is optionally substituted with one or more halogen, nitro, cyano, alkyl, haloalkyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl, with the proviso that one of Y or Z are a bicyclic ring; $X_6$ is —O— or —NH—, n is 1 or 2, $R_2$ and $R_3$ are H and r is 0.

In another embodiment of formula (IB-4), Y and Z are independently phenyl, naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of halogen, nitro, cyano, SF$_5$, C$_{1-3}$alkyl, C$_{1-3}$haloalkyl, phenyl, hydroxy, C$_{1-3}$hydroxyalkyl, amino, C$_{1-3}$alkyl- or C$_{1-3}$dialkylamino, C$_{1-3}$alkoxy, C$_{1-3}$haloalkoxy, C$_{1-3}$alkylthio, C$_{1-3}$haloalkylthio, C$_{1-3}$ alkylsulfinyl, C$_{1-3}$haloalkylsulfinyl, C$_{1-3}$alkylsulfonyl or C$_{1-3}$haloalkylsulfonyl, with the proviso that at least one of Y and Z is a bicyclic ring;

W and W' are independently O, S or an oxetane group;

$Q_1$, $Q_2$, $Q_3$ and $Q_4$ are CH or one or two of $Q_1$, $Q_2$, $Q_3$ and $Q_4$ are independently N, O or S and the remaining of $Q_1$, $Q_2$, $Q_3$ and $Q_4$ are CH;

the dashed lines represent a single or double bond;

R and R' are independently H, C$_{1-3}$alkyl or C$_{1-3}$haloalkyl;

each $R_1$ is independently halogen, cyano, hydroxyl, amino, C$_{1-3}$alkylamino, C$_{1-3}$ dialkylamino, C$_{1-3}$alkyl or C$_{1-3}$haloalkyl;

$R_2$ and $R_3$ are independently H, halogen, C$_1$-C$_3$alkyl or C$_1$-C$_3$haloalkyl;

$X_6$ is a bond, —(CH$_2$)$_n$— where n is 1 to 3, —O—, —NH—, —C(O)—NH— and —NH—C(O)—, wherein each —CH$_2$— in the —(CH$_2$)$_n$— group, —NH—, —C(O)—NH— and —NH—C(O)— are optionally substituted with one or more substituents independently selected from the group consisting of halogen, hydroxy, C$_{1-3}$hydroxyalkyl, amino, C$_{1-3}$alkylamino, C$_{1-3}$dialkylamino, C$_{1-3}$ aminoalkyl, C$_{1-3}$alkyl and C$_{1-3}$haloalkyl;

$X_8$ is a bond, —(CH$_2$)$_n$ where n is 1 to 3, —O—, —C(O)—, —S—, —S(O)—, —S(O)$_2$—, —NHS(O)—, —S(O)—NH—, —NHSO$_2$—, —SO$_2$NH— or —NH—, wherein each CH$_2$ in —(CH$_2$)$_n$—, —NHS(O)—, —S(O)—NH—, —NHSO$_2$—, —SO$_2$NH— or —NH— is optionally independently substituted with one or two substituents selected from the group consisting of halogen, hydroxy, amino, C$_{1-3}$alkylamino, C$_{1-3}$dialkylamino, C$_{1-3}$hydroxyalkyl, C$_{1-3}$aminoalkyl, C$_{1-3}$alkyl, C$_{1-3}$haloalkyl and C$_{1-3}$ alkoxyalkyl; n is 0, 1, 2 or 3; and r is 0, 1, 2, 3 or 4.

In another embodiment of formula (IB-4), one of Y or Z is naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of chloro, fluoro, bromo, CF$_3$, OCF$_3$, SCF$_3$ or SF$_5$, and the other of Y or Z is phenyl optionally substituted by cyano, nitro, CF$_3$, SF$_5$, S(O)C$_{1-3}$alkyl, S(O)$_2$—C$_{1-3}$alkyl, S(O)C$_{1-3}$haloalkyl or S(O)$_2$C$_{1-3}$haloalkyl;

the ring is a trans-cyclohexylene or phenylene ring;

W and W' are O;

R and R' are H or C$_{1-3}$alkyl;

$X_6$ is a bond, —O—, —(CH$_2$)$_n$— where n is 1 to 3 or —NH—;

$X_8$ is a bond, —(CH$_2$)$_n$— where n is 1 to 3, —O— or —NH—;

$R_2$ and $R_3$ are H; n is 1 or 2; and r is 0.

In yet another embodiment of formula (IB-4), the ring is optionally substituted cyclohexylene or phenylene, W and W' are O, Y and/or Z are independently phenyl, naphthyl, quinolinyl, isoquinolinyl, tetrahydroquinolyl, tetrahydroisoquinolyl, benzofuranyl, dihydrobenzofuranyl, benzimidazolyl or benzothiazolyl, each of which is optionally substituted with one or more halogen, nitro, cyano, alkyl, haloalkyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl, with the proviso that at least one of Y or Z is a bicyclic ring; $X_1$ is —(CH$_2$)$_n$— where n is 1 or 2 optionally substituted by halogen, alkyl or haloalkyl; $X_6$ is —O—, n is 1 or 2; $R_2$ and $R_3$ are H; r is 0 and $X_8$ is —NH—, —C(O)—, —CH$_2$—, —CF$_2$—, —CH(CH$_3$)— or —C(CH$_3$)$_2$—.

In another embodiment, the invention provides the compounds of formula (IB-4) in Table 6 below:

TABLE 6

Compounds of formula (IB-4), wherein W and W' are O, $R_2$ and $R_3$ are H, n is 2 and $X_8$ is —NH—:

(IB-4)

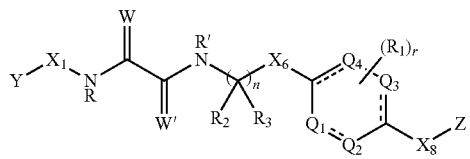

| Y | $X_1$ | R | R' | $X_6$ | Ring | Z | # |
|---|---|---|---|---|---|---|---|
| naphthyl | bond | H | H | O | trans-C$_6$H$_{10}$ | 2-CF$_3$-4-NO$_2$-phenyl | 75 |

TABLE 6-continued

Compounds of formula (IB-4), wherein W and W' are O, $R_2$ and $R_3$ are H, n is 2 and $X_8$ is —NH—:

(IB-4)

| Y | $X_1$ | R | R' | $X_6$ | Ring | Z | # |
|---|---|---|---|---|---|---|---|
| 6-F-naphthalen-2-yl | bond | H | H | O | trans-$C_6H_{10}$ | 2-$CF_3$-4-$NO_2$-phenyl | 172 |
| 6-$F_3C$-naphthalen-2-yl | bond | H | H | O | trans-$C_6H_{10}$ | 2-$CF_3$-4-$NO_2$-phenyl | 173 |
| 6-Cl-naphthalen-2-yl | bond | H | H | O | trans-$C_6H_{10}$ | 2-$CF_3$-4-$NO_2$-phenyl | 174 |
| 6-F-naphthalen-2-yl | bond | Me | H | O | trans-$C_6H_{10}$ | 2-$CF_3$-4-$NO_2$-phenyl | 175 |
| 6-F-naphthalen-2-yl | bond | H | Me | O | trans-$C_6H_{10}$ | 2-$CF_3$-4-$NO_2$-phenyl | 176 |
| 6-F-naphthalen-2-yl | bond | Me | Me | O | trans-$C_6H_{10}$ | 2-$CF_3$-4-$NO_2$-phenyl | 177 |
| 2,3-dihydrobenzofuran-2-yl | $CH_2$ | H | H | O | trans-$C_6H_{10}$ | 2-$CF_3$-4-$NO_2$-phenyl | 216 |
| 5-F-2,3-dihydrobenzofuran-2-yl | $CH_2$ | H | H | O | trans-$C_6H_{10}$ | 2-$CF_3$-4-$NO_2$-phenyl | 217 |

TABLE 6-continued

Compounds of formula (IB-4), wherein W and W' are O, $R_2$ and $R_3$ are H, n is 2 and $X_8$ is —NH—:

(IB-4)

| Y | $X_1$ | R | R' | $X_6$ | Ring | Z | # |
|---|---|---|---|---|---|---|---|
| 5-Cl-2,3-dihydrobenzofuran-2-yl | $CH_2$ | H | H | O | trans-$C_6H_{10}$ | 2-$CF_3$-4-$NO_2$-phenyl | 218 |
| 5-$CF_3$-2,3-dihydrobenzofuran-2-yl | $CH_2$ | H | H | O | trans-$C_6H_{10}$ | 2-$CF_3$-4-$NO_2$-phenyl | 219 |
| benzofuran-2-yl | $CH_2$ | H | H | O | trans-$C_6H_{10}$ | 2-$CF_3$-4-$NO_2$-phenyl | 220 |
| 5-F-benzofuran-2-yl | $CH_2$ | H | H | O | trans-$C_6H_{10}$ | 2-$CF_3$-4-$NO_2$-phenyl | 221 |
| 5-Cl-benzofuran-2-yl | $CH_2$ | H | H | O | trans-$C_6H_{10}$ | 2-$CF_3$-4-$NO_2$-phenyl | 222 |
| 5-$CF_3$-benzofuran-2-yl | $CH_2$ | H | H | O | trans-$C_6H_{10}$ | 2-$CF_3$-4-$NO_2$-phenyl | 223 |
| quinolin-2-yl | bond | H | H | O | trans-$C_6H_{10}$ | 2-$CF_3$-4-$NO_2$-phenyl | 238 |
| 6-F-quinolin-2-yl | bond | H | H | O | trans-$C_6H_{10}$ | 2-$CF_3$-4-$NO_2$-phenyl | 239 |

TABLE 6-continued

Compounds of formula (IB-4), wherein W and W' are O, $R_2$ and $R_3$ are H, n is 2 and $X_8$ is —NH—:

(IB-4)

| Y | $X_1$ | R | R' | $X_6$ | Ring | Z | # |
|---|---|---|---|---|---|---|---|
| 6-(trifluoromethyl)quinolin-2-yl | bond | H | H | O | trans-$C_6H_{10}$ | 3-CF$_3$-4-NO$_2$-phenyl | 240 |
| 6-chloroquinolin-2-yl | bond | H | H | O | trans-$C_6H_{10}$ | 3-CF$_3$-4-NO$_2$-phenyl | 241 |
| 6-fluoroquinolin-2-yl | bond | Me | H | O | trans-$C_6H_{10}$ | 3-CF$_3$-4-NO$_2$-phenyl | 242 |
| 6-fluoroquinolin-2-yl | bond | Me | Me | O | trans-$C_6H_{10}$ | 3-CF$_3$-4-NO$_2$-phenyl | 244 |
| 5-(trifluoromethyl)benzo[d]thiazol-2-yl | bond | H | H | O | trans-$C_6H_{10}$ | 3-CF$_3$-4-NO$_2$-phenyl | 382 |
| 5-(trifluoromethyl)benzo[d]thiazol-2-yl | bond | Me | H | O | trans-$C_6H_{10}$ | 3-CF$_3$-4-NO$_2$-phenyl | 383 |
| 5-(trifluoromethyl)benzo[d]thiazol-2-yl | bond | H | Me | O | trans-$C_6H_{10}$ | 3-CF$_3$-4-NO$_2$-phenyl | 384 |

TABLE 6-continued

Compounds of formula (IB-4), wherein W and W' are O, R₂ and R₃ are H, n is 2 and X₈ is —NH—:

(IB-4)

| Y | X₁ | R | R' | X₆ | Ring | Z | # |
|---|---|---|---|---|---|---|---|
| 5-(trifluoromethyl)benzothiazol-2-yl | bond | Me | Me | O | trans-C₆H₁₀ | 3-CF₃-4-NO₂-phenyl | 385 |
| 5-(trifluoromethyl)benzoxazol-2-yl | bond | H | H | O | trans-C₆H₁₀ | 3-CF₃-4-NO₂-phenyl | 386 |
| 5-(trifluoromethyl)benzoxazol-2-yl | bond | Me | H | O | trans-C₆H₁₀ | 3-CF₃-4-NO₂-phenyl | 387 |
| 5-(trifluoromethyl)benzoxazol-2-yl | bond | H | Me | O | trans-C₆H₁₀ | 3-CF₃-4-NO₂-phenyl | 388 |
| 5-(trifluoromethyl)benzoxazol-2-yl | bond | Me | Me | O | trans-C₆H₁₀ | 3-CF₃-4-NO₂-phenyl | 389 |
| 2,3-dihydrobenzofuran-2-yl | CH₂ | H | H | O | C₆H₄ | 3-CF₃-4-NO₂-phenyl | 224 |
| 5-fluoro-2,3-dihydrobenzofuran-2-yl | CH₂ | H | H | O | C₆H₄ | 3-CF₃-4-NO₂-phenyl | 225 |

TABLE 6-continued

Compounds of formula (IB-4), wherein W and W' are O, $R_2$ and $R_3$ are H, n is 2 and $X_8$ is —NH—:

(IB-4)

| Y | $X_1$ | R | R' | $X_6$ | Ring | Z | # |
|---|---|---|---|---|---|---|---|
| 5-Cl-2,3-dihydrobenzofuran-2-yl | $CH_2$ | H | H | O | $C_6H_4$ | 2-CF$_3$-4-NO$_2$-phenyl | 226 |
| 5-CF$_3$-2,3-dihydrobenzofuran-2-yl | $CH_2$ | H | H | O | $C_6H_4$ | 2-CF$_3$-4-NO$_2$-phenyl | 227 |
| benzofuran-2-yl | $CH_2$ | H | H | O | $C_6H_4$ | 2-CF$_3$-4-NO$_2$-phenyl | 228 |
| 5-F-benzofuran-2-yl | $CH_2$ | H | H | O | $C_6H_4$ | 2-CF$_3$-4-NO$_2$-phenyl | 229 |
| 5-Cl-benzofuran-2-yl | $CH_2$ | H | H | O | $C_6H_4$ | 2-CF$_3$-4-NO$_2$-phenyl | 230 |
| 5-CF$_3$-benzofuran-2-yl | $CH_2$ | H | H | O | $C_6H_4$ | 2-CF$_3$-4-NO$_2$-phenyl | 231 |

In another aspect of the invention, the compounds of formula (I) have the structure (IC) shown below:

(IC)

Wherein variables Y, $X_1$, and Z are as defined for formula (I), Ring A is independently a monocyclic 3- to 8-membered carbocyclylene or heterocyclylene ring or a 7- to 11-membered carbocyclylene or heterocyclylene ring, wherein the heterocyclylene ring may contain 1 to 4 heteroatoms selected from O, S and N; and the Linker is the segment —$X_3$—$X_4$—$X_5$—$X_6$—$X_7$—$X_8$— where $X_3$, $X_4$, $X_5$, $X_6$, $X_7$ and $X_8$ are as defined for formula (I).

In one embodiment of formula (IC), Y and/or Z is naphthyl which is optionally substituted with one or more of halogen, nitro, cyano, hydroxy, hydroxyalkyl, amino, alkylamino, dialkylamino, aminoalkyl, alkyl, haloalkyl, alkoxy, haloalkoxy, alkylthio, halothio, haloalkylthio, alkylsulfinyl, haloalkylsulfinyl, alkylsulfonyl, haloalkylsulfonyl, aryl, aryloxy, arylalkoxy, arylthio, arylalkylthio, arylsulfinyl, arylsulfonyl, arylalkylsulfinyl, arylalkylsulfonyl, heteroaryl, heteroaryloxy, heteroarylalkoxy, heteroarylthio, heteroarylsulfinyl, heteroarylsulfonyl, heteroarylalkylthio, heteroarylalkylsulfinyl or heteroarylalkylsulfonyl.

In another embodiment of formula (IC), Y and/or Z are independently benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl each of which is optionally substituted with one or more of halogen, nitro, cyano, hydroxy, hydroxyalkyl, amino, alkylamino, dialkylamino, aminoalkyl, alkyl, haloalkyl, alkoxy, haloalkoxy, alkylthio, halothio, haloalkylthio, alkylsulfinyl, haloalkylsulfinyl, alkylsulfonyl, haloalkylsulfonyl, aryl, aryloxy, arylalkoxy, arylthio, arylalkylthio, arylsulfinyl, arylsulfonyl, arylalkylsulfinyl, arylalkylsulfonyl, heteroaryl, heteroaryloxy, heteroarylalkoxy, heteroarylthio, heteroarylsulfinyl, heteroarylsulfonyl, heteroarylalkylthio, heteroarylalkylsulfinyl or heteroarylalkylsulfonyl.

In another embodiment of formula (IC), one of Y or Z is naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of halogen, nitro, cyano, alkyl, haloalkyl, phenyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl and the other of Y or Z is phenyl, a 3-7 membered heterocyclyl group or a 5 or 6-membered heteroaryl group, each of which is optionally substituted by one or more of halogen, nitro, cyano, alkyl, haloalkyl, phenyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl.

In still another embodiment of formula (IC), one of Y or Z is naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of halogen, nitro, cyano, alkyl, haloalkyl, phenyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl and the other of Y or Z is phenyl or a 5- or 6-membered heteroaryl group, each of which is optionally substituted by one or more of halogen, nitro, cyano, alkyl, haloalkyl, phenyl, hydroxy, hydroxyalkyl, amino, alkyl- or dialkylamino, aminoalkyl, alkoxy, haloalkoxy, alkylthio, halothio, haloalkylthio, alkylsulfinyl, haloalkylsulfinyl, alkylsulfonyl or haloalkylsulfonyl.

In another embodiment, one of Y or Z is naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of chloro, fluoro, bromo, $CF_3$, $OCF_3$, $SCF_3$ halothio, and the other of Y or Z is phenyl optionally substituted by cyano, nitro, $CF_3$, $S(O)C_{1-3}$alkyl, $S(O)_2$—$C_{1-3}$alkyl, $S(O)C_{1-3}$haloalkyl or $S(O)_2C_{1-3}$haloalkyl.

In one embodiment of formula (IC), Ring A is a 5- or -6-membered heterocycle containing one or more nitrogen atoms. In another embodiment, Ring A is an optionally substituted cyclohexylene ring. In still another embodiment, Ring A is an optionally substituted phenylene ring. In yet another embodiment, Ring A is L1 to L10 or L13 to L18 in Table 1 above. In another embodiment, Ring A is L1, L2, L3, L4, L5, L6, L7, L8, L13, L14, L15, L16, L17 or L18. In still another embodiment, Ring A is L1, L4, L13, L14 or L15.

In one embodiment of formula (IC), the compound has the structure (IC-1) shown below:

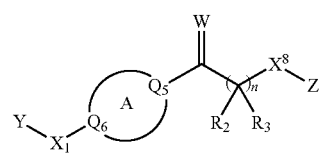

(IC-1)

wherein Y, $X_8$ and Z are as defined for formula (I) above; Ring A is a 3 to 8-membered monocyclic carbocyclic or heterocylic ring wherein $Q_5$ and $Q_6$ are independently N or $CR_4$ where $R_4$ is H, halogen, OH or $C_{1-3}$alkyl; $X_1$ is a bond, —C(O)—, —C(S)—, —NH—, —S(O)—, —S(O)$_2$—, —(CH$_2$)$_n$— where n is 1 to 3, —O—CH$_2$—, —NHCH$_2$—, —S—CH$_2$—, —S(O)—CH$_2$—, —CH$_2$—S(O)—, —S(O)$_2$—CH$_2$—, or —CH$_2$—S(O)$_2$—, wherein each —NH—, —(CH$_2$)$_n$—, —O—CH$_2$—, —NHCH$_2$—, —S—CH$_2$—, —S(O)—CH$_2$—, —CH$_2$—S(O)—, —S(O)$_2$—CH$_2$—, and —CH$_2$—S(O)$_2$— are optionally substituted with oxo (=O) or one or more halogen, cyano, alkyl, haloalkyl, cycloalkyl or aryl groups; W is O, S or oxetane; $R_2$ and $R_3$ are independently hydrogen, halogen, cyano, alkyl, haloalkyl or carbocyclyl; and n is 1, 2 or 3.

In one embodiment of formula (IC-1), W is O. In another embodiment, Ring A is one of linkers L1, L2, L3, L4, L5, L6, L7, L8, L9, L10, L13, L14, L15, L16, L17 or L18. In another embodiment, Ring A is one of L1, L2, L3, L4, L5, L6, L7, L8, L13, L14, L15, L16, L17 or L18. In yet another embodiment, Ring A is L1, L4, L5, L13, L14 or L15. In another embodiment, Ring A is L1 or L4.

In still another embodiment of formula (IC-1), Y and/or Z is naphthyl which is optionally substituted with one or more halogen, nitro, cyano, alkyl, haloalkyl, hydroxy, hydroxyalkyl, amino, alkyl- or dialkylamino, aminoalkyl, alkoxy, haloalkoxy, alkylthio, haloalkylthio, alkylsulfinyl, haloalkylsulfinyl, alkylsulfonyl or haloalkylsulfonyl.

In yet another embodiment of formula (IC-1), Y and/or Z are independently benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted with one or more halogen, nitro, cyano, alkyl, haloalkyl, hydroxy, hydroxyalkyl, amino, alkyl- or dialkylamino, aminoalkyl, alkoxy, haloalkoxy, alkylthio, haloalkylthio, alkylsulfinyl, haloalkylsulfinyl, alkylsulfonyl or haloalkylsulfonyl.

In another embodiment of formulae (IC-1), one of Y or Z is naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of halogen, nitro, cyano, alkyl, haloalkyl, phenyl, hydroxy, hydroxyalkyl, amino, alkyl- or dialkylamino, aminoalkyl, alkoxy, haloalkoxy, alkylthio, haloalkylthio, alkylsulfinyl, haloalkylsulfinyl, alkylsulfonyl or haloalkylsulfonyl and the other of Y or Z is phenyl, a 3-8 membered heterocyclyl group or a 5 or 6-membered heteroaryl group, each of which is optionally substituted by one or more of halogen, nitro, cyano, alkyl, haloalkyl, phenyl, hydroxy, hydroxyalkyl, amino, alkyl- or dialkylamino, aminoalkyl, alkoxy, haloalkoxy, alkylthio, haloalkylthio, alkylsulfinyl, haloalkylsulfinyl, alkylsulfonyl or haloalkylsulfonyl.

In still another embodiment of formula (IC-1), one of Y or Z is naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of halogen, nitro, cyano, alkyl, haloalkyl, phenyl, hydroxy, hydroxyalkyl, amino, alkyl- or dialkylamino, aminoalkyl, alkoxy, haloalkoxy, alkylthio, haloalkylthio, alkylsulfinyl, haloalkylsulfinyl, alkylsulfonyl or haloalkylsulfonyl, and the other of Y or Z is phenyl or a 5- or 6-membered heteroaryl group, each of which is optionally substituted by one or more of halogen, nitro, cyano, alkyl, haloalkyl, phenyl, hydroxy, hydroxyalkyl, amino, alkyl- or dialkylamino, aminoalkyl, alkoxy, haloalkoxy, alkylthio, haloalkylthio, alkylsulfinyl, haloalkylsulfinyl, alkylsulfonyl or haloalkylsulfonyl.

In another embodiment, one of Y or Z is naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of chloro, fluoro, bromo, $CF_3$, $OCF_3$ or $SCF_3$, and the other of Y or Z is phenyl optionally substituted by cyano, nitro, $CF_3$, $S(O)C_{1-3}$alkyl, $S(O)_2$—$C_{1-3}$alkyl, $S(O)C_{1-3}$haloalkyl or $S(O)_2C_{1-3}$haloalkyl.

In another embodiment, $X_1$ is optionally substituted —$(CH_2)_n$— or —C(O)—. In another embodiment, $X_8$ is —C(O)— or optionally substituted —NH— or —$(CH_2)_n$—. In still another embodiment of formula (IC-1), $R_2$ and $R_3$ are H. In still another embodiment of formula (IC-1), n is 1 or 2. In yet another embodiment of formula (IC-1), $X_1$ is a bond, —C(O)— or —$CH_2$—; W is O, n is 1 or 2, and $R_2$ and $R_3$ are H.

In another embodiment of formula (IC-1), Y and Z are independently phenyl, naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of halogen, nitro, cyano, $C_{1-3}$alkyl, $C_{1-3}$haloalkyl, phenyl, hydroxy, $C_{1-3}$hydroxyalkyl, amino, $C_{1-3}$alkyl- or $C_{1-3}$ dialkylamino, $C_{1-3}$alkoxy, $C_{1-3}$haloalkoxy, $C_{1-3}$alkylthio, $C_{1-3}$haloalkylthio, $C_{1-3}$ alkylsulfinyl, $C_{1-3}$haloalkylsulfinyl, $C_{1-3}$alkylsulfonyl or $C_{1-3}$haloalkylsulfonyl, with the proviso that at least one of Y and Z is a bicyclic ring;

$X_1$ is a bond, —C(O)—, —$(CH_2)_n$— where n is 1 to 3, —O—$CH_2$—, —$NHCH_2$—, —S—$CH_2$—, —S(O)—$CH_2$—, —$CH_2$—S(O)—, —S(O)$_2$—$CH_2$—, and —$CH_2$—S(O)$_2$—, wherein each —$(CH_2)_n$—, —O—$CH_2$—, —$NHCH_2$—, —S—$CH_2$—, —S(O)—$CH_2$—, —$CH_2$—S(O)—, —S(O)$_2$—$CH_2$—, and —$CH_2$—S(O)$_2$— are optionally substituted with oxo (=O) or one or more halogen, cyano, alkyl, haloalkyl, cycloalkyl or aryl groups;

Ring A is a 3-8 membered heterocyclic ring wherein $Q_5$ and $Q_6$ are independently N or $CR_4$ where $R_4$ is H, OH, halogen or $C_1$-$C_3$alkyl;

W is O, S or an oxetane group;

$R_2$ and $R_3$ are independently H, halogen, $C_1$-$C_3$alkyl or $C_1$-$C_3$haloalkyl;

$X_8$ is a bond, —$(CH_2)_n$ where n is 1 to 3, —O—, —C(O)—, —S—, —S(O)—, —S(O)$_2$—, —NHS(O)—, —S(O)—NH—, —NHSO$_2$—, —SO$_2$NH— or —NH—, wherein each $CH_2$ in —$(CH_2)_n$—, —NHS(O)—, —S(O)—NH—, —NHSO$_2$—, —SO$_2$NH— or —NH— is optionally independently substituted with one or two substituents selected from the group consisting of halogen, hydroxy, amino, $C_{1-3}$alkylamino, $C_{1-3}$dialkylamino, $C_{1-3}$hydroxyalkyl, $C_{1-3}$aminoalkyl, $C_{1-3}$alkyl, $C_{1-3}$haloalkyl and $C_{1-3}$ alkoxyalkyl; and n is 0, 1, 2 or 3.

In another embodiment of formula (IC-1), one of Y or Z is naphthyl, benzofuranyl, dihydrobenzofuranyl, quinolinyl, isoquinolinyl, tetrahydroquinolyl, tetrahydroisoquinolyl, indolyl, isoindolyl, benzothiophenyl, benzimidazolyl, or benzothiazolyl, each of which is optionally substituted by one or more of chloro, fluoro, bromo, $CF_3$, $OCF_3$ or $SCF_3$, and the other of Y or Z is phenyl optionally substituted by cyano, nitro, $CF_3$, $S(O)C_{1-3}$alkyl, $S(O)_2$—$C_{1-3}$alkyl, $S(O)C_{1-3}$haloalkyl or $S(O)_2C_{1-3}$haloalkyl;

Ring A is L1, L2, L3, L8, L13, L14, L15 or L16;

W is O; $X_6$ is a bond, —O—, —$(CH_2)_n$— where n is 1 to 3 or —NH—;

$X_8$ is a bond, —$(CH_2)_n$— where n is 1 to 3, —O— or —NH—;

$R_2$ and $R_3$ are H; and n is 1 or 2. In another embodiment of formula (IC-1), Ring A is optionally substituted cyclohexylene or phenylene, Y and/or Z are independently naphthyl, quinolinyl, isoquinolinyl, tetrahydroquinolyl, tetrahydroisoquinolyl, benzofuranyl, dihydrobenzofuranyl, benzimidazolyl or benzothiazolyl, each of which is optionally substituted with one or more halogen, nitro, cyano, alkyl, haloalkyl, hydroxy, hydroxyalkyl, amino, alkyl- or dialkylamino, aminoalkyl, alkoxy, haloalkoxy, alkylthio, haloalkylthio, alkylsulfinyl, haloalkylsulfinyl, alkylsulfonyl or haloalkylsulfonyl; $X_1$ is bond, —C(O)— or —$CH_2$—; W is O, n is 1 or 2, $R_2$ and $R_3$ are H, and $X_8$ is —NH—, —C(O)—, —$CH_2$—, —$CF_2$—, —$CH(CH_3)$— or —$C(CH_3)_2$—.

In another embodiment, the invention provides the compounds of formula (IC) in table 7 below:

TABLE 7

Compounds of formula (IC-1), wherein X1 is a bond, W is O, $R_2$ and $R_3$ are H, n is 1 and $X_8$ is —O—.

(IC-1)

| Y | Ring A | Z | # |
|---|---|---|---|
| F₃C-phenyl | L1 | naphthyl with CF₃, NO₂ | 111 |
| Cl-phenyl | L1 | naphthyl with CF₃, NO₂ | 112 |
| F₃C-pyridyl | L1 | naphthyl with CF₃, NO₂ | 113 |

TABLE 7-continued

Compounds of formula (IC-1), wherein X1 is a bond, W is O, R$_2$ and R$_3$ are H, n is 1 and X$_8$ is —O—.

(IC-1)

| Y | Ring A | Z | # |
|---|---|---|---|
| 5-Cl-pyridin-2-yl | L1 | 1-CF$_3$-2-NO$_2$-naphthyl | 114 |
| naphthyl | L1 | 1-CF$_3$-2-NO$_2$-naphthyl | 127 |
| 6-F-naphthyl | L1 | 1-CF$_3$-2-NO$_2$-naphthyl | 128 |
| quinolin-2-yl | L1 | 1-CF$_3$-2-NO$_2$-naphthyl | 129 |
| 6-Cl-quinolin-2-yl | L1 | 1-CF$_3$-2-NO$_2$-naphthyl | 130 |
| 6-CF$_3$-quinolin-2-yl | L1 | 1-CF$_3$-2-NO$_2$-naphthyl | 131 |

The compounds of the invention were found to exhibit superior permeability compared with prior art compounds. For an orally-dosed compound the permeability of a compound across the epithelium cells along the gastrointestinal tract is an important limiting factor for the oral absorption and systemic availability of the compound. Thus, the permeability of a systemically-acting compound is a feature that can significantly impact the efficacy of a compound against internal and/or external parasites when administered orally or topically.

In one embodiment, the compounds of the invention exhibit surprisingly improved permeability compared with the compounds of the prior art having only monocyclic rings at the position corresponding to Y and/or Z (for example compounds of WO 2009/077527 and EP 2468096). The significantly higher permeability of the compounds of the invention is expected to result in higher in vivo efficacy against internal parasites such as nematodes and external parasites that consume blood meals. This is because the increased permeability across the mammalian gut enhances the amount of the active compounds present in the blood circulation for delivery and uptake at the required sites. Furthermore, the increased permeability of the compounds is likely to result in increased permeability across the nematode tissue. In addition, increased permeability of the active compounds may result in improved transdermal passage of the compounds into the bloodstream following topical administration.

In one embodiment, the compounds of the invention exhibit about 20% to about 30% higher permeability than the prior art compounds. In another embodiment, the compounds of the invention exhibit about 40% to about 60% or about 50% to about 70% higher permeability than the prior art compounds. In still other embodiments, the compounds of the invention exhibit about 60% to about 100% higher permeability. In yet other embodiments, the compounds of the invention exhibit about 20% to about 50% or about 30% to about 75% higher permeability compared with the prior art compounds. In yet other embodiments, the compounds of the invention exhibit about 50% to about 100% higher permeability compared with the prior art compounds.

In other embodiments, the compounds of the invention exhibit about 50% to about 500% greater permeability than the prior art compounds. In other embodiments, the compounds of the invention exhibit about 100% to about 500% greater permeability than the prior art compounds. In yet other embodiments, the compounds of the invention exhibit about 200% to about 400% greater permeability. In other embodiments, the compounds of the invention exhibit In yet other embodiments, the compounds of the invention exhibit about 100% to about 300% higher permeability or about 200% to about 300% greater permeability than the prior art compounds. In yet other embodiments, the compounds of the invention exhibit about 100% to about 200% higher permeability compared with the prior art compounds. In other embodiments, the compounds of the invention exhibit about 300% to about 500% higher permeability or about 400% to about 500% higher permeability compared with the prior art compounds.

Compositions of the Invention

In another aspect, the invention provides parasiticidal compositions which comprise at least one anthelmintic compound of formula (I) of the invention and a pharmaceutically acceptable carrier. The composition of the invention can also be in a variety of forms which include, but are not limited to, oral formulations, injectable formulations, and topical, dermal or subdermal formulations. The formulations are intended to be administered to an animal which includes but is not limited to mammals, birds and fish. Examples of mammals include but are not limited to humans, cattle, sheep, goats, llamas, alpacas, pigs, horses, donkeys, dogs, cats and other livestock or domestic mammals. Examples of birds include turkeys, chickens, ostriches and other livestock or domestic birds.

The composition of the invention may be in a form suitable for oral use, for example, as baits (see, e.g., U.S. Pat. No. 4,564,631, incorporated herein by reference), dietary supplements, troches, lozenges, chewables, tablets, hard or soft capsules, emulsions, aqueous or oily suspensions, aqueous or oily solutions, oral drench formulations, dispersible powders or granules, premixes, syrups or elixirs, enteric formulations or pastes. Compositions intended for oral use may be prepared according to any method known in the art for the manufacture of pharmaceutical compositions and such compositions may contain one or more agents selected from the group consisting of sweetening agents, buttering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc, the tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874 (incorporated herein by reference) to form osmotic therapeutic tablets for controlled release.

Formulations for oral use may be hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example peanut oil, liquid paraffin, or olive oil.

The compositions of the invention may also be in the form of oil-in-water or water-in-oil emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soybean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and/or preservatives.

In one embodiment of the formulation, the composition of the invention is in the form of a microemulsion. Microemulsions are well suited as the liquid carrier vehicle. Microemulsions are quaternary systems comprising an aqueous phase, an oily phase, a surfactant and a co-surfactant. They are translucent and isotropic liquids.

Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides; in another embodiment of the oily phase, the triglycerides are medium-chain triglycerides, for example $C_8$-$C_{10}$ caprylic/capric triglyceride. In another embodiment of the oily phase will represent a % v/v range selected from the group consisting of about 2 to about 15%; about 7 to about 10%; and about 8 to about 9% v/v of the microemulsion.

The aqueous phase includes, for example water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion.

Surfactants for the microemulsion include diethylene glycol monoethyl ether, dipropyelene glycol monomethyl ether, polyglycolized $C_8$-$C_{10}$ glycerides or polyglyceryl-6 dioleate. In addition to these surfactants, the co-surfactants include short-chain alcohols, such as ethanol and propanol.

Some compounds are common to the three components discussed above, i.e., aqueous phase, surfactant and co-surfactant. However, it is well within the skill level of the practitioner to use different compounds for each component of the same formulation. In one embodiment for the amount of surfactant/co-surfactant, the co-surfactant to surfactant ratio will be from about ½ to about ½. In another embodiment for the amount of co-surfactant, there will be from about 25 to about 75% v/v of surfactant and from about 10 to about 55% v/v of co-surfactant in the microemulsion.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an antioxidant such as ascorbic acid, or other known preservatives.

Aqueous suspensions may contain the active material in admixture with excipients suitable for the manufacture of aqueous suspensions. Such excipients are suspending agents, for example, sodium carboxymethylcellulose, methylcellulose, hydroxy-propylmethylcellulose, sodium alginate, polvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s) and/or coloring agent(s).

In another embodiment of the invention, the composition can be in paste form. Examples of embodiments in a paste form include but are not limited to those described in U.S. Pat. Nos. 6,787,342 and 7,001,889 (each of which are incorporated herein by reference). In addition to the anthelmintic compounds of the invention, the paste can also contain fumed silica; a viscosity modifier; a carrier; optionally, an absorbent; and optionally, a colorant, stabilizer, surfactant, or preservative.

The process for preparing a paste formulation comprises the steps of:
(a) dissolving or dispersing the anthelmintic compound into the carrier by mixing;
(b) adding the fumed silica to the carrier containing the dissolved anthelmintic compound and mixing until the silica is dispersed in the carrier;
(c) allowing the intermediate formed in (b) to settle for a time sufficient in order to allow the air entrapped during step (b) to escape; and
(d) adding the viscosity modifier to the intermediate with mixing to produce a uniform paste.

The above steps are illustrative, but not limiting. For example, step (a) can be the last step.

In one embodiment of the formulation, the formulation is a paste containing at least one anthelmintic compound of formula (I), fumed silica, a viscosity modifier, an absorbent, a colorant; and a hydrophilic carrier which is triacetin, a monoglyceride, a diglyceride, or a triglyceride.

The paste may also include, but is not limited to, a viscosity modifier selected from the group consisting of PEG 200, PEG 300, PEG 400, PEG 600, monoethanolamine, triethanolamine, glycerol, propylene glycol, polyoxyethylene (20) sorbitan mono-oleate (POLYSORBATE 80 or TWEEN 80), and poloxomers (e.g., PLURONIC L 81); an absorbent selected from the group consisting of magnesium carbonate, calcium carbonate, starch, and cellulose and its derivatives; and a colorant selected from the group consisting of titanium dioxide iron oxide, and FD&C Blue #1 ALUMINUM LAKE.

The compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Co-solvents such as ethanol, propylene glycol glycerol formal or polyethylene glycols may also be used. Preservatives, such as phenol or benzyl alcohol, may be used.

In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectable compositions.

Topical, dermal and subdermal formulations can include emulsions, creams, ointments, gels, pastes, powders, shampoos, pour-on formulations, ready-to-use formulations, spot-on solutions and suspensions, dips and sprays. Topical application of an inventive compound or of a composition including at least one inventive compound among active agent(s) therein, a spot-on or pour-on composition, can allow for the inventive compound to be absorbed through the skin to achieve systemic levels, distributed through the sebaceous glands or on the surface of the skin achieving levels throughout the hair coat. When the compound is distributed through the sebaceous glands, they can act as a reservoir, whereby there can be a long-lasting effect (up to several months) effect. Spot-on formulations are typically applied in a localized region which refers to an area other than the entire animal. In one embodiment of a localized region, the location is between the shoulders. In another embodiment of a localized region it is a stripe, e.g. a stripe from head to tail of the animal.

Pour-on formulations are described in U.S. Pat. No. 6,010,710, incorporated herein by reference. The pour-on formulations may be advantageously oily, and generally comprise a diluent or vehicle and also a solvent (e.g. an organic solvent) for the active ingredient if the latter is not soluble in the diluent.

Organic solvents that can be used in the invention include but are not limited to: acetyltributyl citrate, fatty acid esters such as the dimethyl ester, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone including N-methylpyrrolidone, diethylene glycol monoethyl ether, propylene glycol monomethyl ether, propylene glycol monoethyl ether, ethylene glycol, diisobutyl adipate, diisopropyl adipate (also known as CERAPHYL 230), triacetin, butyl acetate, octyl acetate, propylene carbonate, butylene carbonate, dimethylsulfoxide, organic amides including dimethylformamide and dimethylacetamide, and diethyl phthalate, or a mixture of at least two of these solvents.

In one embodiment of the invention, the pharmaceutically or veterinarily acceptable carrier of the formulation comprises $C_1$-$C_{10}$ alcohols or esters thereof (including acetates, such as ethyl acetate, butyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycols, glycol ethers, glycol esters or glycol carbonates, polyethylene glycols of various grades (PEGs) or monoethers, diethers, monoesters or diesters thereof (e.g. diethylene glycol monoethyl ether), or mixtures thereof.

As vehicle or diluent, mention may be made of plant oils such as, but not limited to soybean oil, groundnut oil, castor oil, corn oil, cotton oil, olive oil, grape seed oil, sunflower oil, coconut oils etc.; mineral oils such as, but not limited to, petrolatum, paraffin, silicone, etc.; aliphatic or cyclic hydrocarbons or alternatively, for example, medium-chain (such as C8 to C12) triglycerides.

In another embodiment of the invention, an emollient and/or spreading and/or film-forming agent can be added. One embodiment of the emollient and/or spreading and/or film-forming agent are those agents selected from the group consisting of:
(a) polyvinylpyrrolidone, polyvinyl alcohols, copolymers of vinyl acetate and vinylpyrrolidone, polyethylene glycols, benzyl alcohol, 2-pyrrolidones including, but not limited to N-methylpyrrolidone, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, (b) anionic surfactants such as alkaline stearates, sodium, potassium or ammonium stearates; calcium stearate, triethanolamine stearate; sodium abietate; alkyl sulfates (e.g. sodium lauryl sulfate and sodium cetyl sulfate); sodium dodecylbenzenesulfonate, sodium dioctylsulfosuccinate; fatty acids (e.g. those derived from coconut oil), (c) cationic surfactants such as water-soluble quaternary ammonium salts of formula $N^+R'R''R'''R''''$, $Y^-$ in which the radicals R are optionally hydroxylated hydrocarbon radicals and $Y^-$ is an anion of a strong acid such as the halide, sulfate and sulfonate anions; cetyltrimethylammonium bromide is among the cationic surfactants which can be used, (d) amine salts of formula $N^+HR'R''R'''$ in which the radicals R, R', R'' and R''' are optionally independently hydroxylated hydrocarbon radicals; octadecylamine hydrochloride is among the cationic surfactants which can be used, (e) nonionic surfactants such as sorbitan esters, which are optionally polyoxyethylenated (e.g. POLYSORBATE 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine; or (g) a mixture of at least two of these agents.

The solvent will be used in proportion with the concentration of the anthelmintic compound of formula (I) and its solubility in this solvent. It will be sought to have the lowest possible volume. The vehicle makes up the difference to 100%.

In one embodiment of the amount of emollient, the emollient is used in a proportion of from 0.1 to 50% and 0.25 to 5%, by volume.

In another embodiment of the invention, the composition can be in ready-to-use solution form as is described in U.S. Pat. No. 6,395,765, incorporated herein by reference. In addition to the anthelmintic compound of the invention, the ready-to-use solution can contain a crystallization inhibitor, an organic solvent and an organic co-solvent.

In one embodiment of the amount of crystallization inhibitor, the crystallization inhibitor can be present in a proportion of about 1 to about 30% (w/v) in the composition. In other embodiments, the crystallization inhibitor may be present in a proportion of about 1 to about 20% (w/v) and about 5 to about 15%. Acceptable inhibitors are those whose addition to the formulation inhibits the formation of crystals when the formulation is applied. In some embodiments, formulations may include compounds that function as crystallization inhibitors other than those listed herein. In these embodiments, the suitability of a crystallization inhibitor may be determined by a test in which 0.3 ml of a solution comprising 10% (w/v) of an anthelmintic compound of the invention in the liquid carrier and 10% of the inhibitor are deposited on a glass slide at 20° C. and allowed to stand for 24 hours. The slide is then observed with the naked eye. Acceptable inhibitors are those whose addition provides for few (e.g. less than ten crystals) or no crystal.

In one embodiment, the organic solvent has a dielectric constant of a range selected from the group consisting of between about 2 to about 35, about 10 to about 35 or about 20 to about 30. In other embodiments, the solvent will have a dielectric constant of between about 2 and about 20, or between about 2 and about 10. The content of this organic solvent in the overall composition represents the complement to 100% of the composition.

As discussed above, the solvent may comprise a mixture of solvents including a mixture of an organic solvent and an organic co-solvent. In one embodiment, and the organic co-solvent has a boiling point of less than about 300° C. or less than about 250° C. In other embodiments, the co-solvent has a boiling point of below about 200° C., or below about 130° C. In still another embodiment of the invention, the organic co-solvent has a boiling point of below about 100° C., or below about 80° C. In still other embodiments, the organic co-solvent will have a dielectric constant of a range selected from the group consisting of about 2 to about 40, about 10 to about 40, or typically about 20 to about 30. In some embodiments of the invention, this co-solvent may be present in the composition in an organic co-solvent/organic solvent weight/weight (W/W) ratio of about $\frac{1}{15}$ to about $\frac{1}{2}$. In some embodiments, the co-solvent is volatile so as to act as a drying promoter, and is miscible with water and/or with the organic solvent.

The formulation can also comprise an antioxidizing agent intended to inhibit oxidation in air, this agent being present in a proportion selected from a range consisting of about 0.005 to about 1% (w/v) and about 0.01 to about 0.05%.

Crystallization inhibitors which are useful for the invention include but are not limited to:

(a) polyvinylpyrrolidone, polyvinyl alcohols, copolymers of vinyl acetate and of vinylpyrrolidone, polyethylene glycols of various grades, benzyl alcohol, 2-pyrrolidones including, but not limited to N-methylpyrrolidone, dimethylsulfoxide, mannitol, glycerol, sorbitol or polyoxyethylenated esters of sorbitan; lecithin or sodium carboxymethylcellulose; a solvent as described herein that is capable of inhibiting crystal formation; acrylic derivatives, such as acrylates and methacrylates or other polymers derived from acrylic monomers, and others;

(b) anionic surfactants, such as alkaline stearates (e.g. sodium, potassium or ammonium stearate); calcium stearate or triethanolamine stearate; sodium abietate; alkyl sulfates, which include but are not limited to sodium lauryl sulfate and sodium cetyl sulfate; sodium dodecylbenzenesulfonate or sodium dioctyl sulfosuccinate; or fatty acids (e.g. coconut oil);

(c) cationic surfactants, such as water-soluble quaternary ammonium salts of formula $N^+R'R''R'''R''''Y^-$, in which the R radicals are identical or different optionally hydroxylated hydrocarbon radicals and Y is an anion of a strong acid, such as halide, sulfate and sulfonate anions; cetyltrimethylammonium bromide is one of the cationic surfactants which can be used;

(d) amine salts of formula $N^+HR'R''R'''$, in which the R radicals are identical or different optionally hydroxylated hydrocarbon radicals; octadecylamine hydrochloride is one of the cationic surfactants which can be used;

(e) non-ionic surfactants, such as optionally polyoxyethylenated esters of sorbitan, e.g. POLYSORBATE 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine; or (g) a mixture of at least two of the compounds listed in (a)-(f) above.

In one embodiment of the crystallization inhibitor, a crystallization inhibitor pair will be used. Such pairs include, for example, the combination of a film-forming agent of polymeric type and of a surface-active agent. These agents will be selected from the compounds mentioned above as crystallization inhibitor.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants; in another embodiment of the surface active agents, the agent is a polyoxyethylenated esters of sorbitan and in yet another embodiment of the surface-active agent, the agents include the various grades of POLYSORBATE, for example POLYSORBATE 80.

In another embodiment of the invention, the film-forming agent and the surface-active agent can be incorporated in similar or identical amounts within the limit of the total amounts of crystallization inhibitor mentioned elsewhere.

The pair thus constituted secures, in a noteworthy way, the objectives of absence of crystallization on the coat and of maintenance of the cosmetic appearance of the skin or fur, that is to say without a tendency towards sticking or towards a sticky appearance, despite the high concentration of active material.

In one embodiment of the antioxidizing agents, the agents are those conventional in the art and include but is not limited to butylated hydroxyanisole, butylated hydroxytoluene, ascorbic acid, sodium metabisulphite, propyl gallate, sodium thiosulfate or a mixture of not more than two of them.

The formulation adjuvants discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients or adjuvants are added.

The volume applied is not restricted as long as the amount of substance administered is shown to be safe and efficacious. Typically, the volume applied depends on the size and weight of the animal as well as the concentration of active, the extent of infestation by parasites and the type of administration. In some embodiments, the volume applied can be of the order of about 0.3 to about 5 ml or about 0.3 ml to about 1 ml. In one embodiment for the volume, the volume is on the order of about 0.5 ml, for cats and on the order of about 0.3 to about 3 ml for dogs, depending on the weight of the animal.

In another embodiment of the invention, application of a spot-on formulation according to the present invention can also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type).

For spot-on formulations, the carrier can be a liquid carrier vehicle as described in U.S. Pat. No. 6,426,333 (incorporated herein by reference), which in one embodiment of the spot-on formulation comprises a solvent and a co-solvent wherein the solvent is selected from the group consisting of acetone, acetonitrile, benzyl alcohol, butyl diglycol, dimethylacetamide, dimethylformamide, dipropylene glycol n-butyl ether, propylene glycol monomethyl ether, propylene glycol monoethyl ether, diisobutyl adipate, diisopropyl adipate (also known as CERAPHYL 230), triacetin, butyl acetate, octyl acetate, propylene carbonate, butylene carbonate, dimethylsulfoxide, organic amides including dimethylformamide and dimethylacetamide, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone including N-methylpyrrolidone, diethylene glycol monoethyl ether, ethylene glycol, diethyl phthalate fatty acid esters, such as the diethyl ester or diisobutyl adipate, and a mixture of at least two of these solvents and the co-solvent is selected from the group consisting of absolute ethanol, isopropanol or methanol.

In one embodiment of the invention, the pharmaceutically or veterinarily acceptable carrier of the formulation comprises $C_1$-$C_{10}$ alcohols or esters thereof (including acetates, such as ethyl acetate, butyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycols, glycol ethers, glycol esters or glycol carbonates, polyethylene glycols of various grades (PEGs) or monoethers, diethers, monoesters or diesters thereof (e.g. diethylene glycol monoethyl ether), or mixtures thereof.

The liquid carrier vehicle can optionally contain a crystallization inhibitor including an anionic surfactant, a cationic surfactant, a non-ionic surfactant, an amine salt, an amphoteric surfactant or polyvinylpyrrolidone, polyvinyl alcohols, copolymers of vinyl acetate and vinylpyrrolidone, 2-pyrrolidone including N-methylpyrrolidone (NMP), dimethylsulfoxide, polyethylene glycols, benzyl alcohol, mannitol, glycerol, sorbitol, polyoxyethylenated sorbitan esters; lecithin, sodium carboxymethylcellulose, solvents as defined herein that can inhibit the formation of crystals, and acrylic derivatives such acrylates or methacrylates as well as other polymers derived from acrylic monomers, or a mixture of these crystallization inhibitors.

Spot-on formulations may be prepared by dissolving the active ingredients into the pharmaceutically or veterinary acceptable vehicle. Alternatively, the spot-on formulation can be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

Dosage forms may contain from about 0.5 mg to about 5 g of an active agent. In one embodiment of the dosage form, the dosage is from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

In one embodiment of the invention, the active agent is present in the formulation at a concentration of about 0.05% to about 50% weight/volume. In other embodiments, the active agent may be present in the formulation at a concentration of about 0.1% to about 30%, about 0.5% to about 20% (w/v) or about 1% to about 10% (w/v). In another embodiment of the invention, the active agent is present in the formulation as a concentration from about 0.1 to 2% weight/volume. In yet another embodiment of the invention, the active agent is present in the formulation as a concentration from about 0.25 to about 1.5% weight/volume. In still another embodiment of the invention, the active agent is present in the formulation as a concentration about 1% weight/volume.

In a particular advantageous embodiment of the invention, the dose of the inventive compounds is about 0.1 mg/kg to about 100 mg/kg. In other embodiments, the dose of the inventive compounds is about 0.5 mg/kg to about 70 mg/kg, about 0.5 mg/kg to about 50 mg/kg or about 0.5 mg/kg to about 30 mg/kg. In other preferred embodiments, the dose is 0.5 mg/kg to about 30 mg/kg, 0.5 mg/kg to about 20 mg/kg or 0.5 mg/kg to about 10 mg/kg. More typically, in some embodiments the dose of the active compounds is about 0.1 mg/kg to 5 mg/kg, 0.1 mg/kg to about 3 mg/kg, or about 0.1 mg/kg to 1.5 mg/kg. In still other embodiments of the invention, the dose may be as low as 0.1 mg/kg (0.02 mg/ml), about 0.2 mg/kg (0.04 mg/ml), about 0.3 mg/kg (0.06 mg/ml), about 0.4 mg/kg (0.08 mg/ml), about 0.5 mg/kg (0.1 mg/ml), about 0.6 mg/kg (0.12 mg/ml), about 0.7 mg/kg (0.14 mg/ml), about 0.8 mg/kg (0.16 mg/ml), about 0.9 mg/kg (0.18 mg/ml), about 1.0 mg/kg (0.2 mg/ml).

Another embodiment of the invention is directed toward a method of treating endoparasitic infestation or infection in an animal, comprising administering an effective amount of the compound of the invention to the animal in need thereof. The compounds of the invention have been shown to have superior efficacy against endoparasites, and in particular against parasites that are resistant to active agents of the macrocyclic lactone class.

For example, a compound of the invention has been shown to have superior efficacy against ivermectin-resistant endoparasites in sheep. Figure 2 shows that a compound of the invention (compound 3.024) administered at a dosage of 1.5 mg/kg or 3 mg/kg orally had greater than 95% efficacy against ivermectin-resistant strains of *Haemonchus contortus, Ostertagia circumcincta* and *Trichostrongylus columbriformis*. In contrast, ivermectin administered orally at a dose of 0.2 mg/kg was almost completely inactive against *Haemonchus contortus*, less than 30% effective against *Ostertagia circumcincta* and less than 60% effective against *Trichostrongylus columbriformis*. It is surprising that the compounds of the invention have superior efficacy against endoparasites that are resistant to ivermectin, which is one of the most potent active agents known against endo- and ectoparasites.

Accordingly, in another embodiment, the invention provides a method for treating an endoparasitic infestation or infection in an animal, comprising administering an effective amount of an anthelmintic compound of the invention in combination with an effective amount of activators of invertebrate GABA receptors including an avermectin or milbemycin to the animal in need thereof. Avermectins that may be used in combination with the compounds of the invention include, but are not limited to abamectin, dimadectin, doramectin, emamectin, eprinomectin, ivermectin, latidectin, lepimectin, and selamectin Milbemycins compounds that may be used in combination with the compounds of the invention include, but are not limited to, milbemectin, milbemycin D, moxidectin and nemadectin. Also included are the 5-oxo and 5-oxime derivatives of said avermectins and milbemy cins.

In one embodiment, the compounds and compositions of the invention may be used for treating endoparasiticidal infection or infestation an endoparasite including, but not limited to, *Anaplocephala (Anoplocephala), Ancylostoma, Anecator, Ascaris, Brugia, Bunostomum, Capillaria, Chabertia, Cooperia, Cyathostomum, Cylicocyclus, Cylicodontophorus, Cylicostephanus, Craterostomum, Dictyocaulus, Dipetalonema, Dipylidium, Dirofilaria, Dracunculus, Echinococcus, Enterobius, Fasciola, Filaroides, Habronema, Haemonchus, Metastrongylus, Moniezia, Necator, Nematodirus, Nippostrongylus, Oesophagostumum, Onchocerca, Ostertagia, Oxyuris, Parascaris, Schistosoma, Strongylus, Taenia, Toxocara, Strongyloides, Toxascaris, Trichinella, Trichuris, Trichostrongylus, Triodontophorus, Uncinaria, Wuchereria*, and combinations thereof.

In a particularly preferred embodiment of the invention, the compounds and compositions of the invention are used to treat or prevent an infection by *Dirofilaria immitis*. In another embodiment the compounds and compositions of the invention are used to treat or prevent an infection by Dirofilaria repens.

In another embodiment of the invention, the helminth is *Haemonchus contortus, Ostertagia circumcincta, Trichostrongylus axei, Trichostrongylus colubriformis, Cooperia curticei, Nematodirus battus* and combinations thereof.

Another embodiment of the invention is directed toward a method of treating ectoparasitic infestation or infection in an animal in need thereof which comprises administering an effective amount of the compound of the invention to the animal in need thereof.

In one embodiment, the infection or infestation is caused by fleas, ticks, mites, mosquitoes, flies, lice, blowfly and combinations thereof.

In still another embodiment, invention provides a method for treating an ectoparasitic infestation or infection in an animal, comprising administering an effective amount of an anthelmintic compound of the invention in combination with an effective amount of an avermectin or milbemycin active agent to the animal in need thereof.

In certain embodiments, the compounds of the invention may be used to protect plants and crops. In other embodiments, the compounds may be used to treat environmental surfaces and structures.

The compounds of formula (I) or their salts can be employed as such or in the form of their preparations (formulations) as combinations with other active substances, such as, for example, insecticides, attractants, sterilants, acaricides, nematicides, and with growth regulators.

Bactericides include, but are not limited to, bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/acaricides/nematicides include those compounds mentioned in U.S. Pat. Nos. 7,420,062 and 7,001,903, U.S. Patent publication 2008/0234331, each incorporated herein by reference, the literature known to the person skilled in the art, and the compounds classified by IRAC (Insecticide Resistance Action Committee). Examples of insecticides/acaricides/nematicides include, but are limited to, carbamates; triazemate; organophosphates; cyclodiene organochlorines; phenylpyrazoles; DDT; methoxychlor; pyrethroids; pyrethrins; neonicotinoids; nicotine; bensultap; cartap hydrochloride; nereistoxin analogues; spinosyns; avermectins and milbemycins; juvenile hormone analogues; fenoxycarb; fenoxycarb; alkyl halides; chloropicrin; sulfuryl fluoride; cryolite; pymetrozine; flonicamid; clofentezine; hexythiazox; etoxazole; *Bacillus sphaericus*; diafenthiuron; organotin miticides; propargite; tetradifon; chlorfenapyr; DNOC; benzoylureas; buprofezin; cyromazine; diacylhydrazines; azadirachtin; amitraz; hydramethylnon; acequinocyl; fluacrypyrim; METI acaricides; rotenone; indoxacarb; metaflumizone; tetronic acid derivatives; aluminium phosphide; cyanide; phosphine; bifenazate; fluoroacetate; P450-dependent monooxygenase inhibitors; esterase inhibitors; diamides; benzoximate; chinomethionat; dicofol; pyridalyl; borax; tartar emetic; fumigants, such as methyl bromide; ditera; clandosan; sincocin.

The compounds of formula (I) can be formulated in various ways, depending on the prevailing biological and/or chemico-physical parameters. Examples of possible formulations which are suitable are: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water basis, solutions which are miscible with oil, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

Solid state forms of the compounds of formula (I) can be prepared by methods known in the art, e.g. Byrn et al., "Solid-State Chemistry of Drugs", $2^{nd}$ Edition, SSCI Inc., (1999); Glusker et al., "Crystal Structure Analysis—A Primer", $2^{nd}$ Edition, Oxford University Press, (1985).

The formulations mentioned can be prepared in a manner known per se, for example by mixing the active compounds with at least one solvent or diluent, emulsifier, dispersant and/or binder or fixative, water repellent and optionally one or more of a desiccant, UV stabilizer, a colorant, a pigment and other processing auxiliaries.

These individual formulation types are known in principle and described, for example, in: Winnacker-Küchler, "Chemische Technologie" [Chemical Technology], Volume 7, C. Hauser Verlag, Munich, 4th Edition 1986; Wade van Valkenburg, "Pesticide Formulations", Marcel Dekker, N. Y., 1973; K. Martens, "Spray Drying Handbook", 3rd Ed. 1979, G. Goodwin Ltd. London.

The necessary formulation auxiliaries such as inert materials, surfactants, solvents and other additives are also known and described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; C. Marsden, "Solvents Guide", 2nd Ed., Interscience, N. Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag, Munich, 4th Ed. 1986.

Wettable powders are preparations which are uniformly dispersible in water and which, besides the compounds of formula (I), also comprise ionic and/or nonionic surfactants (welters, dispersants), for example, polyoxyethylated alkylphenols, polyoxyethylated fatty alcohols, polyoxyethylated fatty amines, fatty alcohol polyglycol ether sulfates, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, in addition to a diluent or inert substance. To prepare the wettable powders, the compounds of formula (I) are, for example, ground finely in conventional apparatuses such as hammer mills, blower mills and air-jet mills and mixed with the formulation auxiliaries, either concomitantly or thereafter.

Emulsifiable concentrates are prepared, for example, by dissolving the compounds of formula (I) in an organic solvent, for example butanol, cyclohexanone, dimethylformamide, xylene or else higher-boiling aromatics or hydrocarbons or mixtures of these, with addition of one or more ionic and/or nonionic surfactants (emulsifiers). Emulsifiers which can be used are, for example: calcium salts of alkylarylsulfonic acids, such as calcium dodecylbenzenesulfonate or nonionic emulsifiers, such as fatty acid polyglycol esters, alkylaryl polyglycol ethers, fatty alcohol polyglycol ethers, propylene oxide/ethylene oxide condensates, alkyl polyethers, sorbitan esters such as sorbitan fatty acid esters or polyoxyethylene sorbitan esters such as polyoxyethylene sorbitan fatty acid esters.

Dusts are obtained by grinding the active substance with finely divided solid substances, for example talc or natural clays, such as kaolin, bentonite or pyrophyllite, or diatomaceous earth.

Suspension concentrates may be water- or oil-based. They can be prepared, for example, by wet grinding by means of commercially available bead mills, if appropriate with addition of surfactants, as they have already been mentioned above for example in the case of the other formulation types.

Emulsions, for example oil-in-water emulsions (EW), can be prepared for example by means of stirrers, colloid mills and/or static mixtures using aqueous organic solvents and, if appropriate, surfactants as they have already been mentioned above for example in the case of the other formulation types.

Granules can be prepared either by spraying the compounds of formula (I) onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils. Suitable active substances can also be granulated in the manner which is conventional for the production of fertilizer granules, if desired in a mixture with fertilizers.

Water-dispersible granules are prepared, as a rule, by the customary processes such as spray-drying, fluidized-bed granulation, disk granulation, mixing in high-speed mixers and extrusion without solid inert material. To prepare disk, fluidized-bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8-57. In general, the agrochemical preparations comprise a range selected from the group consisting of about 0.1 to about 99% by weight and about 0.1 to about 95% by weight, of compounds of formula (I).

The concentration of compounds of formula (I) in wettable powders is, for example, about 10 to about 90% by weight, the remainder to 100% by weight being composed of customary formulation components. In the case of emulsifiable concentrates, the concentration of compounds of formula (I) can amount to ranges selected from the group consisting of about 1% to about 90% and about 5% to about 80% by weight. Formulations in the form of dusts usually comprise in the range selected from the group consisting of about 1% to about 30% by weight of compounds of formula (I) and about 5% to about 20% by weight of compounds of formula (I). For sprayable solutions comprise a range selected from the group consisting of about 0.05% to about 80% by weight of compounds of formula (I) and about 2% to about 50% by weight of compounds of formula (I). In the case of water-dispersible granules, the content of compounds of formula (I) depends partly on whether the compounds of formula (I) are in liquid or solid form and on which granulation auxiliaries, fillers and the like are being used. The water-dispersible granules, for example, comprise a range selected from the group consisting of between about 1 and about 95% and between about 10% and about 80% by weight.

In addition, the formulations of compounds of formula (I) mentioned comprise, if appropriate, the adhesives, wetters, dispersants, emulsifiers, penetrants, preservatives, antifreeze agents, solvents, fillers, carriers, colorants, antifoams, evaporation inhibitors, pH regulators and viscosity regulators which are conventional in each case.

Additional pharmaceutically or veterinarily active ingredients may also be added to the compositions of the invention. In some embodiments, the additional active agents may be one or more parasiticidal compounds including acaricides, anthelmintics, endectocides and insecticides. Antiparasitic agents can include both ectoparasiticisal and endoparasiticidal agents.

Additional pharmaceutical agents that may be included in the compositions of the invention with the inventive anthelmintic compounds are well-known in the art (see e.g. *Plumb' Veterinary Drug Handbook*, 5$^{th}$ Edition, ed. Donald C. Plumb, Blackwell Publishing, (2005) or *The Merck Veterinary Manual*, 9$^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, clorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (OXYGLOBIN®®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenytoin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxine chloride, prazosin, prednisolone/prednisone, primidone, procainamide, procarbazine, prochlorperazine, propantheline bromide, propionibacterium acnes injection, propofol, propranolol, protamine sulfate, pseudoephedrine, psyllium hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/l-deprenyl, sertraline, sevelamer, sevoflurane, silymarin/milk thistle, sodium bicarbonate, sodium polystyrene sulfonate, sodium stiboglucon-ate, sodium sulfate, soduim thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocainide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, arylpyrazole compounds such as phenylpyrazoles, known in the art may be combined with the anthelmintic compounds of the invention. Examples of such arylpyrazole compounds include but are not limited to those described in U.S. Pat. Nos. 6,001,384; 6,010,710; 6,083,519; 6,096,329; 6,174,540; 6,685,954 and 6,998,131 (all of which are incorporated herein by reference, each assigned to Merial, Ltd., Duluth, Ga.). On particularly preferred arylpyrazole compound is fipronil.

In another embodiment of the invention, one or more macrocyclic lactones or lactams, which act as an acaricide, anthelmintic agent and/or insecticide, can be added to the compositions of the invention.

The macrocyclic lactones include, but are not limited to, avermectins such as abamectin, dimadectin, doramectin, emamectin, eprinomectin, ivermectin, latidectin, lepimectin, selamectin and ML-1,694,554, and milbemycins such as milbemectin, milbemycin D, moxidectin and nemadectin. Also included are the 5-oxo and 5-oxime derivatives of said avermectins and milbemycins. Examples of combinations of arylpyrazole compounds with macrocyclic lactones include but are not limited to those described in U.S. Pat. Nos. 6,426,333; 6,482,425; 6,962,713 and 6,998,131 (all incorporated herein by reference—each assigned to Merial, Ltd., Duluth, Ga.).

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schonberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alio, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054, both incorporated herein by reference.

Macrocyclic lactones are either natural products or are semi-synthetic derivatives thereof. The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569. Mention is also made of U.S. Pat. Nos. 4,468,390, 5,824,653, EP 0 007 812 A1, U.K. Patent Specification 1 390 336, EP 0 002 916, and New Zealand Patent No. 237 086, inter alia, all incorporated herein by reference. Naturally occurring milbemycins are described in U.S. Pat. No. 3,950,360 (incorporated herein by reference) as well as in the various references cited in "The Merck Index" 12$^{th}$ ed., S. Budavari, Ed., Merck & Co., Inc. Whitehouse Station, N.J. (1996). Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. Nos. 5,077,308, 4,859, 657, 4,963,582, 4,855,317, 4,871,719, 4,874,749, 4,427,663, 4,310,519, 4,199,569, 5,055,596, 4,973,711, 4,978,677, 4,920,148 and EP 0 667 054, all incorporated herein by reference.

In another embodiment of the invention, the compositions may include a class of acaricides or insecticides known as insect growth regulators (IGRs). Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225, 598, 4,798,837, 4,751,225, EP 0 179 022 or U.K. 2 140 010 as well as U.S. Pat. Nos. 6,096,329 and 6,685,954 (all incorporated herein by reference).

In one embodiment the IGR that may be included in the composition is a compound that mimics juvenile hormone. Examples of juvenile hormone mimics include azadirachtin, diofenolan, fenoxycarb, hydroprene, kinoprene, methoprene, pyriproxyfen, tetrahydroazadirachtin and 4-chloro-2 (2-chloro-2-methyl-propyl)-5-(6-iodo-3-pyridylmethoxy) pyridazine-3(2H)-one. In a particularly preferred embodiment, the compositions of the invention comprise methoprene or pyriproxyfen.

In another embodiment, the compositions of the invention may include an IGR compound that is a chitin synthesis inhibitor. Chitin synthesis inhibitors include chlorofluazuron, cyromazine, diflubenzuron, fluazuron, flucycloxuron, flufenoxuron, hexaflumoron, lufenuron, tebufenozide, teflubenzuron, triflumoron, novaluron, 1-(2,6-difluorobenzoyl)-3-(2-fluoro-4-(trifluoromethyl)phenylurea, 1-(2,6-difluoro-benzoyl)-3-(2-fluoro-4-(1,1,2,2-tetrafluoroethoxy)-phenylurea and 1-(2,6-difluorobenzoyl)-3-(2-fluoro-4-trifluoromethyl)phenylurea.

In yet another embodiment of the invention, adulticide insecticides and acaricides can also be added to the composition of the invention. These include pyrethrins (which include cinerin I, cinerin II, jasmolin I, jasmolin II, pyrethrin I, pyrethrin II and mixtures thereof) and pyrethroids, and carbamates including, but are not limited to, benomyl, carbanolate, carbaryl, carbofuran, meththiocarb, metolcarb, promacyl, propoxur, aldicarb, butocarboxim, oxamyl, thiocarboxime and thiofanox.

In some embodiments, the compositions of the invention may include one or more antinematodal agents including, but not limited to, active agents in the benzimidazoles, imidazothiazoles, tetrahydropyrimidines, and organophosphate class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the compositions may include an imidazothiazole compounds including, but not limited to, tetramisole, levamisole and butamisole. In still other embodiments, the compositions of the invention may include tetrahydropyrimidine active agents including, but not limited to, pyrantel, oxantel, and morantel. Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the compositions may include the antinematodal compounds phenothiazine and piperazine as the neutral compound or in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, the compositions of the invention may include antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, brotianide, bromoxanide and closantel; triclabendazole, diamfenetide, clorsulon, hetolin and emetine.

Anticestodal compounds may also be advantageously used in the compositions of the invention including, but not limited to, arecoline in various salt forms, bunamidine, niclosamide, nitroscanate, paromomycin and paromomycin II.

In yet other embodiments, the compositions of the invention may include other active agents that are effective against arthropod parasites. Suitable active agents include, but are not limited to, bromocyclen, chlordane, DDT, endosulfan, lindane, methoxychlor, toxaphene, bromophos, bromophos-ethyl, carbophenothion, chlorfenvinphos, chlorpyrifos, crotoxyphos, cythioate, diazinon, dichlorenthion diemthoate, dioxathion, ethion, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfiram, isobornyl thiocyanato acetate, methoprene, monosulfiram, pirenonylbutoxide, rotenone, triphenyltin acetate, triphenyltin hydroxide, deet, dimethyl phthalate, and the compounds 1,5a,6,9,9a,9b-hexahydro-4a (4H)-dibenzofurancarboxaldehyde (MGK-11), 2-(2-ethylhexyl)-3a,4,7,7a-tetrahydro-4,7-methano-1H-isoindole-1,3 (2H)dione (MGK-264), dipropyl-2,5-pyridinedicarboxylate (MGK-326) and 2-(octylthio)ethanol (MGK-874). In a particularly preferred embodiment, the compositions of the invention will include permethrin in combination with the anthelmintic compounds of the invention.

An antiparasitic agent that can be combined with the compound of the invention to form a composition can be a biologically active peptide or protein including, but not limited to, depsipeptides, which act at the neuromuscular junction by stimulating presynaptic receptors belonging to the secretin receptor family resulting in the paralysis and death of parasites. In one embodiment of the depsipeptide, the depsipeptide is emodepside (see Willson et al., *Parasitology*, January 2003, 126(Pt 1):79-86).

In another embodiment, the compositions of the invention may comprise an active agent from the neonicotinoid class of pesticides. The neonicotinoids bind and inhibit insect specific nicotinic acetylcholine receptors. In one embodiment, the neonicotinoid insecticidal agent that may be included in a composition of the invention is imidacloprid. Imidacloprid is a well-known neonicotinoid active agent and is the key active ingredient in the topical parasiticide products Advantage®, Advantage® II, K9 Advantix®, and K9 Advantix® II sold by Bayer Animal Health. Agents of this class are described, for example, in U.S. Pat. No. 4,742,060 or in EP 0 892 060.

In another embodiment, the compositions of the invention may comprise nitenpyram, another active agent of the neonicotinoid class of pesticides. Nitenpyram has the following chemical structure and is the active ingredient in the oral product CAPSTAR™ Tablets sold by Novartis Animal Health.

In certain embodiments, an insecticidal agent that can be combined with the compositions of the invention is a semicarbazone, such as metaflumizone.

In another embodiment of the invention, nodulisporic acid and its derivatives (a class of known acaricidal, anthelmintic, anti-parasitic and insecticidal agents) may be added to the compositions of the invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The compositions may include one or more of the known nodulisporic acid derivatives in the art, including all stereoisomers, such as those described in the patents cited above.

In another embodiment, anthelmintic compounds of the amino acetonitrile class (AAD) of compounds such as monepantel (ZOLVIX), and the like, may be added to the compositions of the invention. These compounds are described, for example, in WO 2004/024704 and U.S. Pat. No. 7,084,280 (both incorporated by reference); Sager et al., Veterinary Parasitology, 2009, 159, 49-54; Kaminsky et al., Nature vol. 452, 13 Mar. 2008, 176-181. The compositions of the invention may also include aryloazol-2-yl cyanoethylamino compounds such as those described in U.S. Pat. No. 8,088,801 to Soll et al., which is incorporated herein in its entirety, and thioamide derivatives of these compounds, as described in U.S. Pat. No. 7,964,621, which is incorporated herein by reference.

The compositions of the invention may also be combined with paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11, 407-408). The paraherquamide family of compounds is a known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004432, U.S. Pat. No. 5,703,078 and U.S. Pat. No. 5,750,695, all of which are hereby incorporated by reference in their entirety.

In another particularly preferred embodiment, the compositions of the invention may advantageously include one or more compounds of the isoxazoline class of compounds. These active agents are described in WO 2007/079162, WO 2007/075459 and US 2009/0133319, WO 2007/070606 and US 2009/0143410, WO 2009/003075, WO 2009/002809, WO 2009/024541, U.S. Pat. No. 7,662,972, WO 2008/122375, WO 2010/003877, WO 2010/003923, WO 2009/025983, WO 2008/150393, WO 2008/154528, WO 2009/045999, WO 2009/051956, WO 2009/126668, WO 2009/0259832, WO 2008/109760, US 2009/0156643, US 2010/0144797, US 2010/0137612, US 2011/009438 and WO 2011/075591, all of which are incorporated herein by reference in their entirety.

Where appropriate the anthelmintic, parasiticidal and insecticial agent may also be selected from the group of compounds described above as suitable for agrochemical use.

In general, the additional active agent is included in a dose of between about 0.1 μg and about 500 mg. In some embodiments, the additional active agent may be present in a dose of about 1 mg to about 500 mg, about 1 mg to about 300 mg, or about 1 mg to about 100 mg. In other embodiments, the additional active agent may be present in a dose of about 1 mg to about 50 mg or about 1 mg to about 20 mg. In other embodiment of the invention, the additional active agent is included in a dose of about 1 μg to about 10 mg.

In another embodiment of the invention, the additional active agent is included in a dose of about 5 μg/kg to about 50 mg/kg. In other embodiments, the additional active agent may be included in a dose of about 5 μg/kg to about 30 mg/kg, about 5 μg/kg to about 20 mg/kg or about 5 μg/kg to about 10 mg/kg. In still other embodiments, the additional active agent may be included in a dose of about 10 μg/kg to about 1 mg/kg or about 50 μg/kg to about 500 μg/kg of weight of the animal. In yet another embodiment of the invention, the additional active agent is included in a dose between about 0.1 mg/kg to about 10 mg/kg of weight of animal. In still another embodiment of the invention, the additional active agent is included in a dose between about 0.5 mg/kg to 50 mg/kg.

The proportions, by weight, of the aryloazol-2-yl-cyanoethylamino compound and the additional active agent are for example between about 5/1 and about 10,000/1. However, one of ordinary skill in the art would be able to select the appropriate ratio of aryloazol-2-yl-cyanoethylamino compound and the additional active agent for the intended host and use thereof.

Processes of Preparation

Another aspect of the invention is the process of making the novel anthelmintic compounds of the invention. The compounds of the invention may be prepared according to the processes described herein or by the application or adaptation of known methods (i.e. methods heretofore used or described in the chemical literature). For example, in some embodiments, the compounds of the invention may be prepared by methods described in WO 2009/077527 A1, WO 2010/115688 A1, WO 2010/146083 A1 and EP 2 468 096 A1 (all incorporated herein by reference), or by adaptation of methods described in these publications.

LIST OF ABBREVIATIONS

AIBN azobisisobutyronitrile
BINAP 2,2'-bis(diphenylphosphino)-1,1'-binaphthyl
BSA bovine serum albumin
BOC ter t-butoxy carbonyl
dba dibenzylidineacetone
CDI 1,1'-carbonyl diimidazole
CI chemical ionization
DEGMME diethylene glycol monomethyl ether
DIAD diisopropylazodicarboxylate
DIEA diisopropylethylamine
DMF N,N-dimethylformamide
DMSO dimethylsulfoxide
DPPA diphenylphosphoryl azide
EDAC.HCl 1-ethyl-3-(3-dimethylaminopropyl) carbodiimide hydrochloride
ES electrospray
EtOAc ethyl acetate
HATU 1-[bis(dimethylamino)methylene]-1H-1,2,3-triazolo[4,5 b]pyridinium 3-oxide hexafluorophosphate
HBSS Hank's Balanced Salt Solution
HOBt 1-hydroxybenzotriazole
NBS N-bromosuccinimde
NMM N-methylmorpholine
POM polyoxymethylene (formaldehyde polymer)
TBAF tert-butyl ammonium fluoride
TBHP tert-butyl hydrogen peroxide
TFA trifluoroacetic acid
TFAA trifluoroacetic acid anhydride
THF tetrahydrofuran EXAMPLE 1: Synthesis of Common Intermediate (Acid #1)

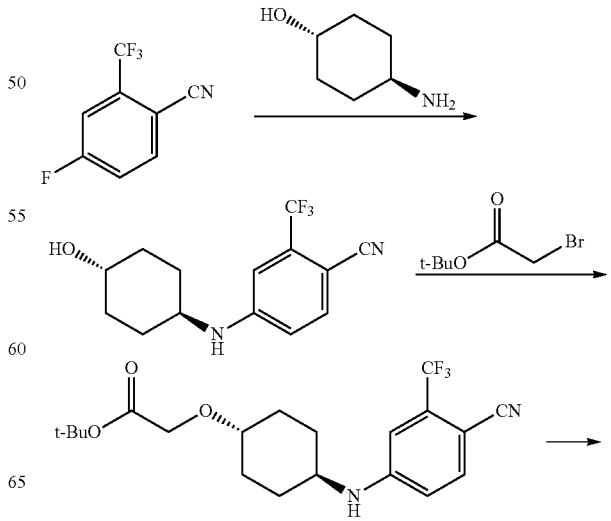

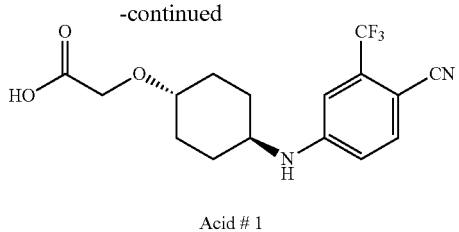

Acid # 1

Step 1. Formation of 4-(4-cyano-3-trifluoromethyl-phenylamino)-cyclohexanol

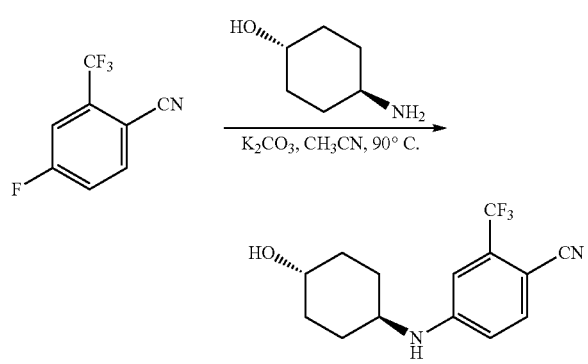

The aryl fluoride (2 g, 10.6 mmol) was placed in a 100 ml round-bottomed flask and stirred in 20 ml acetonitrile at room temperature. Potassium carbonate (3.3 g, 23.9 mmol, 2.2 eq) and 1,4-trans-amino-cyclohexanol (1.34 g, 11.6 mmol, 1.1 eq) were added and the mixture was then heated at 90° C. overnight. The mixture was cooled to room temperature and then concentrated under vacuum. The crude material was purified by silica gel chromatography using 20-40% ethyl acetate in petroleum ether to elute. The product-containing fractions were combined and concentrated under vacuum to provide 1 g (33%) of the desired aniline as a yellow oil. (ES, m/z): [M+H]$^+$ 285.0; $^1$H NMR (300 MHz, DMSO): δ 8.04 (d, J=9.3 Hz, 1H), 7.42 (d, J=7.8 Hz, 1H), 7.06 (d, J=1.8 Hz, 1H), 6.82-6.86 (m, 1H), 4.59 (d, J=4.2 Hz, 1H), 3.39-3.49 (m, 2H), 1.78-1.94 (m, 4H), 1.18-1.32 (m, 4H).

Step 2. Formation of [4-(4-cyano-3-trifluoromethyl-phenylamino)-cyclohexyloxy]-acetic acid tert-butyl ester

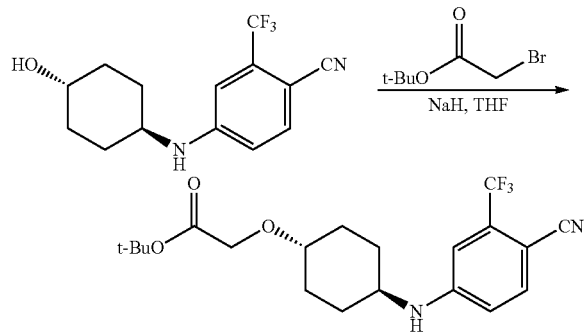

In a 250 ml round-bottomed flask under nitrogen, a solution of 4-(4-nitro-3-trifluoromethyl-phenylamino)-cyclohexanol (1 g, 3.5 mmol) in 20 ml of THF was cooled using an external ice bath. Sodium hydride (254 mg, 10.6 mmol, 3 eq) was then added and the mixture was stirred at ~0-5° C. for 20 minutes before adding the tert-butyl-2-bromoacetate (700 mg, 3.6 mmol, 1 eq). The solution was allowed to warm to room temperature while stirring for 2 hours. The reaction was then diluted using 50 ml of water. The mixture was then extracted with 3×50 ml of ethyl acetate. The organic layers were combined, dried over sodium sulfate, filtered, and concentrated under vacuum. The crude material was purified by silica gel chromatography using 10-20% ethyl acetate in petroleum ether to elute. The product-containing fractions were combined and concentrated under vacuum to provide 0.5 g (36%) of the desired ester as an off-white powder. (ES, m/z): [M+H]$^+$ 399.0. $^1$H NMR (300 MHz, CDCl$_3$): δ 7.53 (d, J=8.7 Hz, 1H), 6.83 (s, 1H), 6.65-6.83 (t, J=6.9 Hz, 1H), 4.01 (s, 2H), 3.36-3.42 (m, 2H), 2.12-2.15 (m, 4H), 1.49 (s, 9H), 1.24-1.32 (m, 4H).

Step 3. Formation of [4-(4-cyano-3-trifluoromethyl-phenylamino)-cyclohexyloxy]-acetic acid

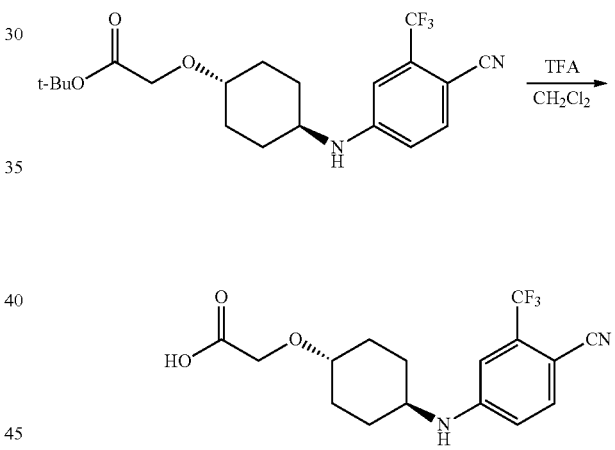

To a solution of tert-butyl 2-(4-(4-nitro-3-(trifluoromethyl)phenylamino)cyclohexyloxy)acetate (150 mg, 0.38 mmol) in dichloromethane (20 ml) was added trifluoroacetic acid (500 mg, 4.4 mmol, 2.6 eq). The resulting solution was stirred for 2 hours at room temperature and then concentrated under vacuum. The residue was dissolved in water (10 ml) and then extracted with n-butanol (2×50 ml). The organic layers were combined, dried over sodium sulfate, filtered, and concentrated under vacuum. The crude material was purified by silica gel chromatography using 3% methanol in dichloromethane to elute. The product-containing fractions were combined and concentrated under vacuum to afford 41.7 mg (32%) of 2-(4-(4-cyano-3-(trifluoromethyl)phenylamino)cyclohexyloxy)acetic acid as a light yellow oil. (ES, m/z):

[M+H]$^+$ 343.1; $^1$H NMR (300 MHz, CD$_3$OD): δ 7.58 (d, J=8.7 Hz, 1H), 6.94 (d, J=2.1 Hz, 1H), 6.79-6.83 (dd, J=2.1 Hz, 8.7 Hz, 1H), 4.12 (s, 2H), 3.35-3.51 (m, 2H), 2.04-2.20 (m, 4H), 1.24-1.53 (m, 4H).

EXAMPLE 2: Synthesis of Common Intermediate (Acid #2)

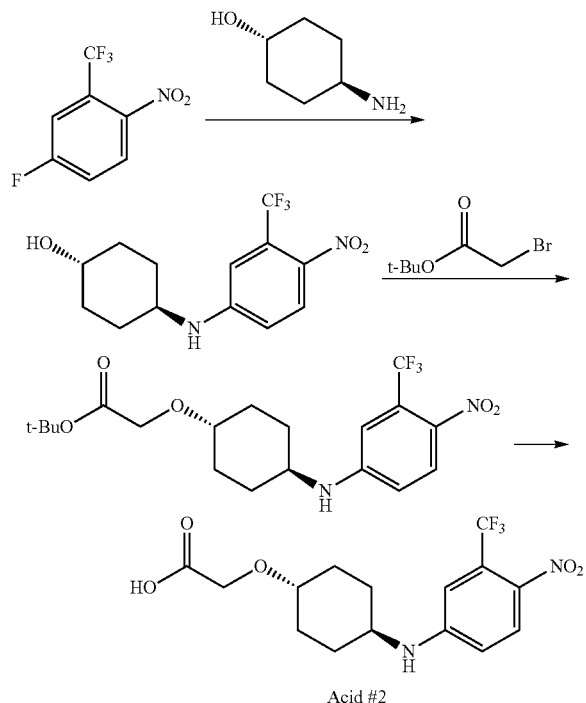

Acid #2

Step 1. Formation of 4-(4-nitro-3-trifluoromethyl-phenylamino)-cyclohexanol

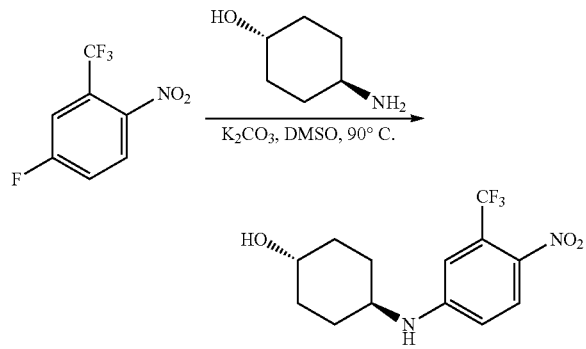

The aryl fluoride (500 mg, 2.4 mmol) was placed in a 100 ml round-bottomed flask and stirred in 10 ml DMSO at room temperature. Potassium carbonate (661 mg, 4.75 mmol, 2 eq) and 1,4-trans-amino-cyclohexanol (413 mg, 3.59 mmol, 1.5 eq) were added and the mixture was then heated at 90° C. overnight. The mixture was cooled to room temperature and then partitioned between water and ethyl acetate (3×80 ml). The organic layers were combined, washed with saturated aqueous sodium chloride, dried over sodium sulfate, filtered, and concentrated under vacuum to provide 400 mg (55%) of the desired aniline as a yellow solid. On both the 10 g and 50 g scale, similar reaction conditions (using acetonitrile as the solvent) provided a 76% yield of the desired product.

Step 2. Formation of [4-(4-nitro-3-trifluoromethyl-phenylamino)-cyclohexyloxy]-acetic acid tert-butyl ester

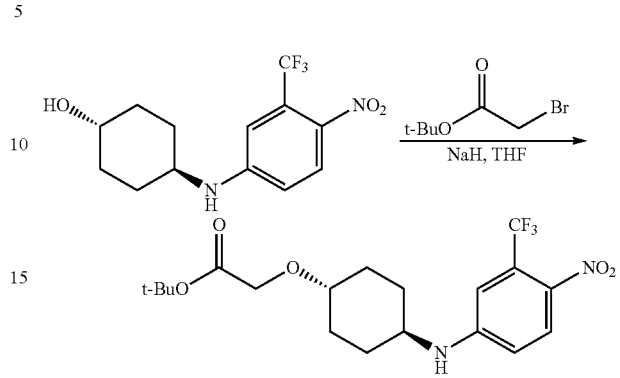

In a 250 ml round-bottomed flask under nitrogen, a solution of 4-(4-nitro-3-trifluoromethyl-phenylamino)-cyclohexanol (10 g, 33 mmol) in 150 ml of THF was cooled using an external ice bath. Sodium hydride (3.65 g, 152 mmol, 3 eq) was then added and the mixture was stirred at ~0° C. for 30 minutes before adding the tert-butyl-2-bromoacetate (9.6 g, 49.2 mmol, 1.5 eq). The solution was allowed to warm to room temperature while stirring overnight. The reaction was then diluted using 500 ml of ice-water. The mixture was then extracted with 3×200 ml of ethyl acetate. The organic layers were combined, dried over sodium sulfate, filtered, and concentrated under vacuum. The crude material was purified by silica gel chromatography using 10% ethyl acetate in petroleum ether to elute. The product-containing fractions were combined and concentrated under vacuum to provide 5 g (36%) of the desired ester as a yellow oil. Repeating this reaction on a larger scale yielded 51% of the desired product.

Step 3. Formation of [4-(4-nitro-3-trifluoromethyl-phenylamino)-cyclohexyloxy]-acetic acid

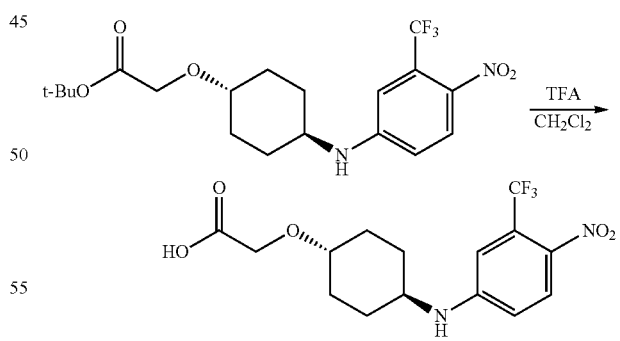

To a solution of tert-butyl 2-(4-(4-nitro-3-(trifluoromethyl)phenylamino)cyclohexyloxy)acetate (1 g, 2.39 mmol) in dichloromethane (30 ml) was added trifluoroacetic acid (5 ml). The resulting solution was stirred for 2 hours at room temperature and then concentrated under vacuum. The resulting solution was diluted with dichloromethane (200 ml), washed with water (100 ml), dried over anhydrous sodium sulfate, filtered, and then concentrated under vacuum to afford 800 mg (92%) of 2-(4-(4-nitro-3-(trifluoromethyl)phenylamino)cyclohexyloxy)acetic acid as yellow oil. ¹H NMR (300 MHz, DMSO): δ 12.5 (broad s, 1H), 8.07 (d, J=9.3 Hz, 1H), 7.45 (d, J=7.8 Hz, 1H), 7.07 (s, 1H), 6.87 (dd, J=2.4 Hz, 9.3 Hz, 1H), 4.03 (s, 2H), 3.32-3.46 (m, 2H), 1.91-2.03 (m, 4H), 1.17-1.41 (m, 4H).

EXAMPLE 3: Synthesis of Common Intermediate (Amine #1)

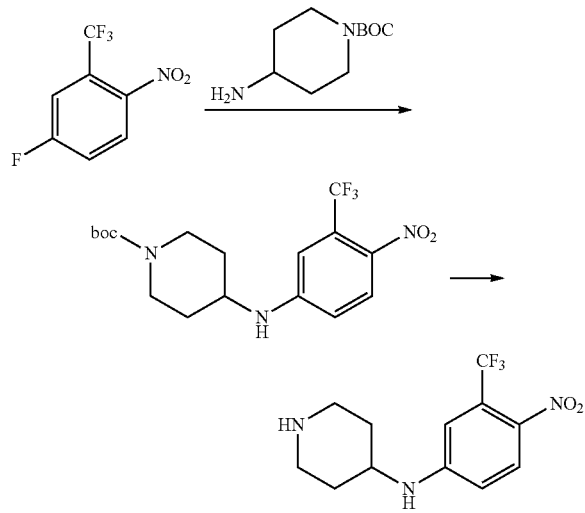

Step 1. Formation of tert-butyl 4-[[4-nitro-3-(trifluoromethyl)phenyl]amino]piperidine-1-carboxylate

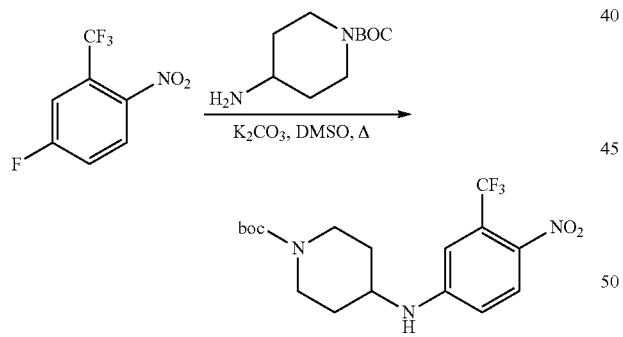

To a solution of 4-fluoro-1-nitro-2-(trifluoromethyl)benzene (5 g, 24 mmol) in DMSO (50 ml) was added tert-butyl 4-aminopiperidine-1-carboxylate (4.78 g, 23.9 mmol, 1 eq.) and potassium carbonate (9.9 g, 72 mmol, 3 eq.). The resulting mixture was stirred with heating overnight at 100° C. (oil bath) and then diluted with water (300 ml). The solids were collected by filtration to afford tert-butyl 4-[[4-nitro-3-(trifluoromethyl)phenyl]amino]piperidine-1-carboxylate as a yellow powder (8 g, 86%); (ES, m/z): [M+H]⁺ 390.0; ¹H NMR (300 MHz, DMSO-d6): δ 8.06 (d, J=9.3 Hz, 1H), 7.47 (d, J=7.8 Hz, 1H), 7.08 (d, J=2.1 Hz, 1H), 6.89 (dd, J=2.4, 9.3 Hz, 1H), 3.87 (d, J=13.5 Hz, 2H), 3.68 (m, 1H), 2.95 (m, 2H), 2.54 (s, 0.6H), 1.89 (m, 2H), 1.39 (s, 9H), 1.28 (m, 2H).

Step 2. Formation of N-[4-nitro-3-(trifluoromethyl)phenyl]piperidin-4-amine (Amine #1)

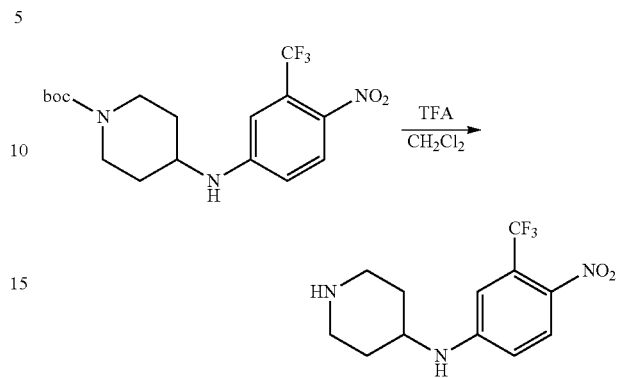

To a solution of tert-butyl 4-[[4-nitro-3-(trifluoromethyl)phenyl]amino]piperidine-1-carboxylate (1 g, 2.6 mmol) in dichloromethane (10 mL) was added trifluoroacetic acid (3 ml). The solution was stirred for 2 hours at room temperature and then concentrated under vacuum. The crude material was diluted with water (50 ml), adjusted pH to 9 with sodium bicarbonate (saturated aqueous), and extracted with dichloromethane (3×100 ml). The organic layers were combined and dried over anhydrous sodium sulfate, filtered, and concentrated under vacuum to afford N-[4-nitro-3-(trifluoromethyl)phenyl]piperidin-4-amine as a yellow powder (800 mg, crude); (ES, m/z): [M+H]⁺ 290.1; ¹H NMR (300 MHz, DMSO-d6): δ 8.08 (d, J=9.0 Hz, 1H), 7.20-7.80 (br s), 7.60 (d, J=7.8 Hz, 1H), 7.11 (d, J=2.4 Hz, 1H), 6.91 (dd, J=2.4, 9.0 Hz, 1H), 3.70 (m, 1H), 3.22 (d, J=12.6 Hz, 2H), 2.91 (dd, J=10.5, 11.4 Hz, 2H), 1.99 (d, J=11.4 Hz, 2H), 1.52 (m, 2H).

EXAMPLE 4: Synthesis of Common Intermediate (Amine #2)

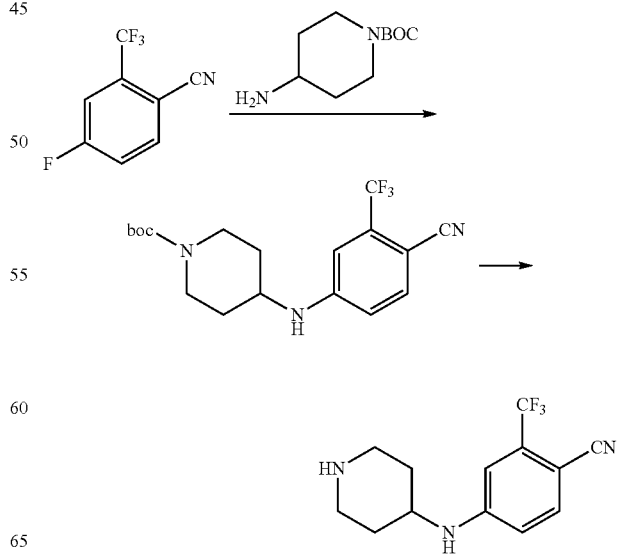

Step 1. Formation of tert-butyl 4-[[4-cyano-3-trifluoromethyl)phenyl]amino]piperidine-1-carboxylate

Step 2. Formation of N-[4-cyano-3-(trifluoromethyl)phenyl]piperidin-4-amine (Amine #2)

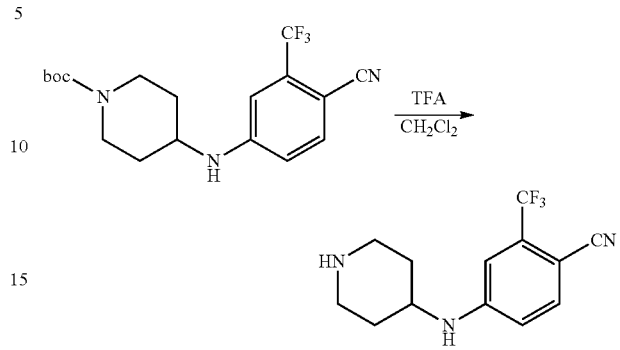

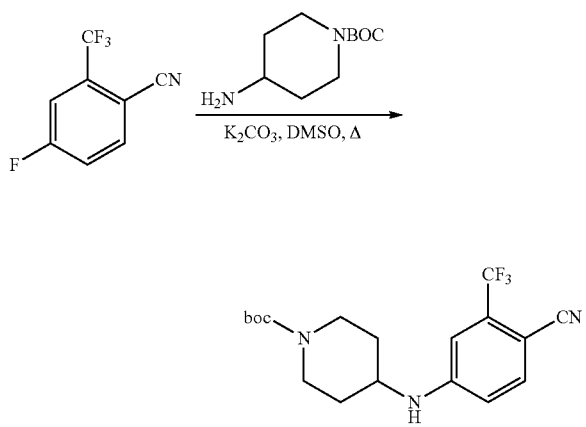

To a solution of 4-fluoro-2-(trifluoromethyl)benzonitrile (5 g, 26 mmol,) in DMSO (50 ml) was added tert-butyl 4-aminopiperidine-1-carboxylate (5.3 g, 26.5 mmol, 1 eq.) and potassium carbonate (7.3 g, 52.8 mmol, 2 eq.). The resulting solution was stirred with heating overnight at 100° C. (oil bath). The resulting solution was diluted with of ethyl acetate (300 ml) and washed with sodium chloride (sat., 300 ml). The organic layer was dried over anhydrous sodium sulfate, filtered, and concentrated under vacuum to give a residue, which was applied onto a silica gel column and eluted with ethyl acetate to afford tert-butyl 4-[[4-cyano-3-(trifluoromethyl)phenyl]amino]piperidine-1-carboxylate as a white powder (5 g, 51%). (ES, m/z): [M+H]$^+$ 370.1.

To a solution of tert-butyl 4-[[4-cyano-3-(trifluoromethyl)phenyl]amino]piperidine-1-carboxylate (150 mg, 0.41 mmol) in dichloromethane (4 mL) was added trifluoroacetic acid (1 ml). The solution was stirred for 2 hours at room temperature and then concentrated under vacuum. The crude material was diluted with 100 ml of EtOAc and washed with sodium bicarbonate (saturated aqueous) and then brine. The organic layer was dried over anhydrous sodium sulfate, filtered, and concentrated under vacuum. The crude solids were recrystallized from EtOAc/PE to afford N-[4-cyano-3-(trifluoromethyl)phenyl]piperidin-4-amine as a yellow powder (93.1 mg, 85% yield); (ES, m/z): [M+H]$^+$ 270.1; $^1$H NMR (300 MHz, CDCl$_3$): δ 7.69 (d, J=8.7 Hz, 1H), 7.16 (d, J=7.8 Hz, 1H), 7.03 (d, J=1.2 Hz, 1H), 6.85 (dd, J=2.1, 8.7 Hz, 1H), 3.42 (m, 1H), 2.94 (m, 2H), 2.53 (m, 2H), 1.82 (d, J=10.2 Hz, 2H), 1.27 (m, 2H).

EXAMPLE 5: Preparation of Compound 104

Compound 014

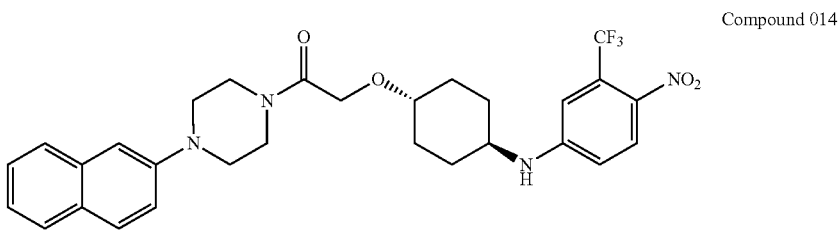

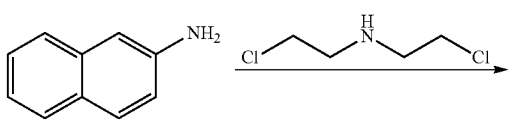

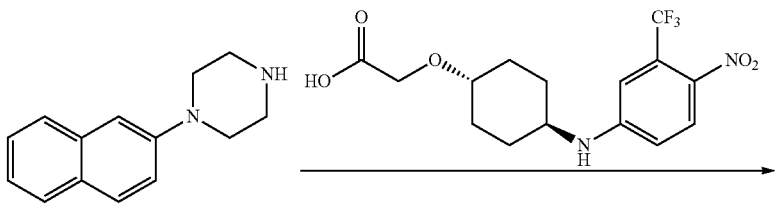

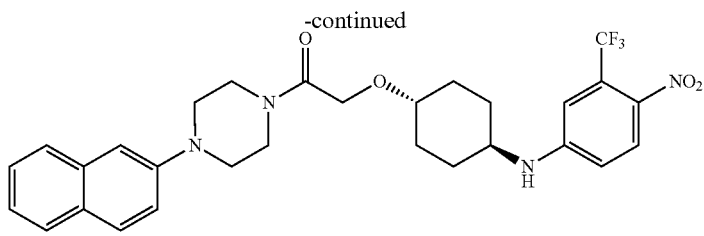

Step 1. Formation of 1-naphthalen-2-yl-piperazine hydrochloride

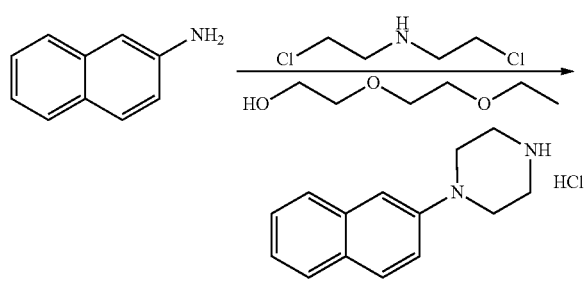

A solution of naphthalen-2-amine (2 g, 14 mmol) and bis(2-chloroethyl)amine hydrochloride (2.51 g, 14.1 mmol, 1 eq) in diethylene glycol monoethyl ether (3 mL) was stirred overnight at 149° C. (oil bath). The resulting solution was diluted with methanol (2 ml). The crude product was re-crystallized from diethyl ether to afford 1-(naphthalen-2-yl)piperazine hydrochloride as a yellow solid (2 g, 58%). (ES, m/z): [M+H]$^+$ 213.0

Step 2. Formation of 1-(4-(naphthalen-2-yl)piperazin-1-yl)-2-(4-(4-nitro-3-(trifluoromethyl) phenyl amino)cyclohexyloxy)ethanone (#14)

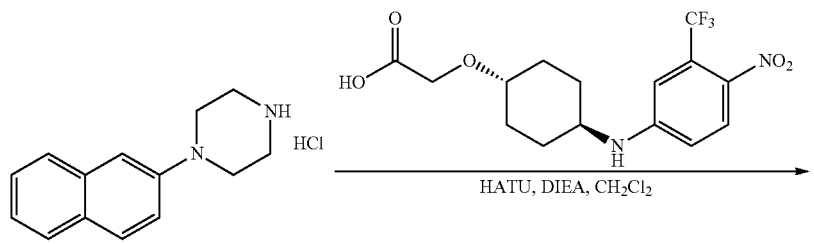

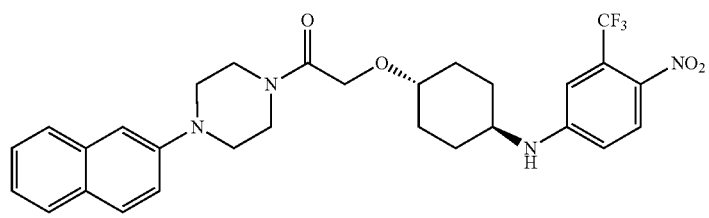

To a solution of 1-(naphthalen-2-yl)piperazine hydrochloride (100 mg, 0.40 mmol) in dichloromethane (20 ml) was added 2-(4-(4-nitro-3-trifluoromethyl)phenylamino)cyclohexyloxy)acetic acid (145 mg, 0.40 mmol, 1 eq), HATU (153 mg, 0.40 mmol, 1 eq), diisopropylethylamine (104 mg, 0.80 mmol, 2 eq). The resulting solution was stirred overnight at room temperature and diluted with dichloromethane (150 ml) and washed with water (100 ml), dried over anhydrous sodium sulfate, filtered, and concentrated under vacuum to give a residue, which was applied onto a silica gel column with 0.5% methanol in dichloromethane to afford crude product (50 mg), which was purified by Flash-Prep-HPLC to afford 1-[4-(naphthalen-2-yl)piperazin-1-yl]-2-[(4-[[4-nitro-3-(trifluoromethyl)phenyl]amino]cyclohexyl)oxy]ethan-1-one trifluoroacetic acid salt as a yellow solid (39.4 mg, 15%). (ES, m/z): [M+H]$^+$ 557; $^1$H NMR (300 MHz, CD$_3$OD): δ 8.000 (d, J=9.0 Hz, 1H), 7.70-7.80 (m, 3H), 7.30-7.45 (m, 4H), 6.97 (d, J=2.1 Hz, 1H), 6.75-6.79 (m, 1H), 4.33 (s, 2H), 3.75-3.88 (m, 4H), 3.40-3.52 (m, 2H), 3.32-3.40 (m, 4H), 2.08-2.22 (m, 4H), 1.42-1.58 (m, 2H), 1.27-1.42 (m, 2H).

EXAMPLE 6: Preparation of Compound 17

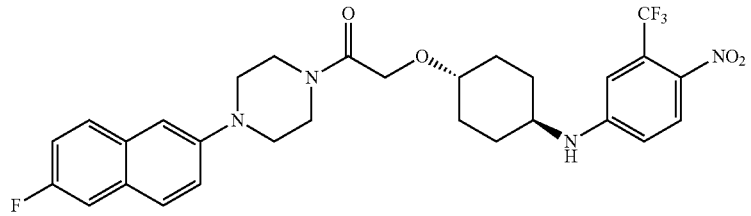

Compound 17

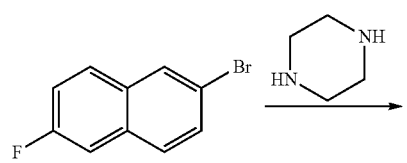

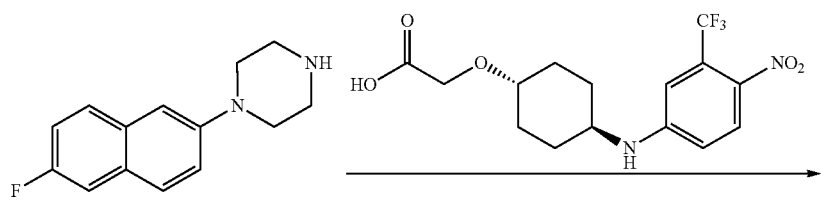

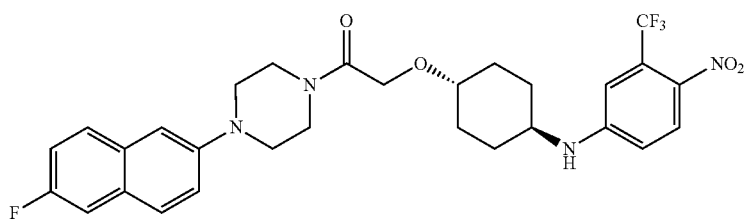

Step 1. Formation of 1-(6-fluoronaphthalen-2-yl)piperazine

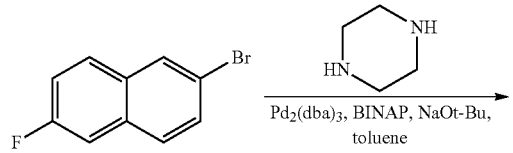

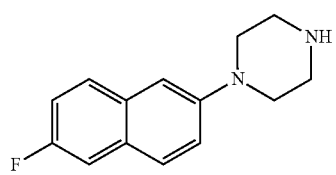

To a solution of 2-bromo-6-fluoronaphthalene (1 g, 4.44 mmol) in 30 ml of toluene was added sodium tert-butoxide (0.854 g, 8.89 mmol, 2.0 eq), piperazine (0.764 g, 8.87 mmol, 2.0 eq), BINAP (28 mg, 0.045 mmol, 1 mol %) and Pd$_2$(dba)$_3$.CHCl$_3$ (92 mg, 0.089 mmol, 2 mol %) at 70° C. in an oil bath under an inert atmosphere of nitrogen. The resulting solution was stirred overnight and then concentrated under vacuum. The crude material was purified by silica gel chromatography using 10-20% methanol in dichloromethane to elute. The product-containing fractions were combined and concentrated under vacuum to afford 1-(6-fluoronaphthalen-2-yl)piperazine as a light yellow solid (0.75 g, 73%). (ES, m/z): [M+H]$^+$ 231.1; $^1$H NMR (300 MHz, CDCl$_3$): δ 7.67-7.73 (m, 2H), 7.29-7.38 (m, 2H), 7.18-7.23 (m, 1H), 7.14 (d, J=1.8 Hz, 1H), 3.24 (dd, J=3.6, 3.9 Hz, 4H), 3.12 (dd, J=3.6, 3.9 Hz, 4H).

Step 2. Formation of 1-[4-(6-fluoronaphthalen-2-yl)piperazin-1-yl]-2-[(4-[[4-nitro-3-(trifluoro-methyl)phenyl]amino]cycl-ohexyl)oxy]ethan-1-one (#17)

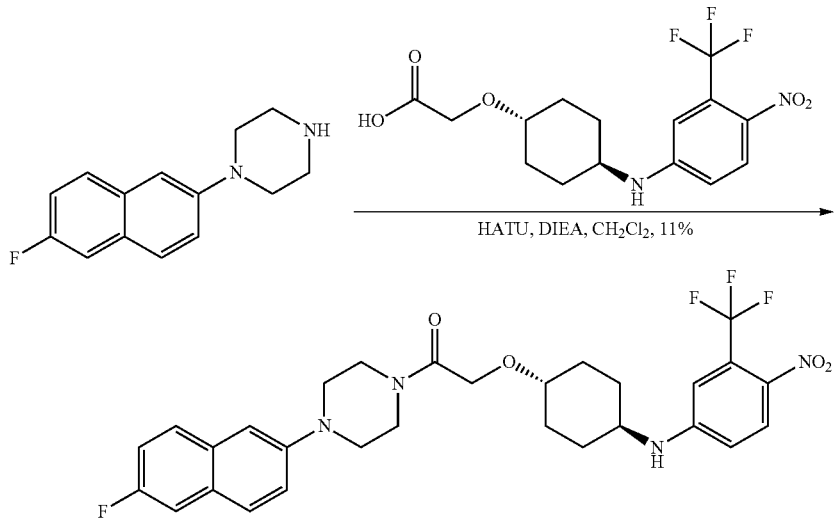

To a solution of 2-[(4-[4-nitro-3-(trifluoromethyl)phenyl]aminocyclohexyl)-oxy]acetic acid (173 mg, 0.48 mmol, 1 eq) in dichloromethane (50 ml) was added DIEA (61.8 mg, 0.48 mmol, 1 eq), HATU (182 mg, 0.48 mmol, 1 eq) and 1-(6-fluoronaphthalen-2-yl)piperazine (110 mg, 0.48 mmol, 1 eq) at room temperature under an inert atmosphere of nitrogen. The resulting solution was stirred overnight. The reaction was then quenched by the addition of water (100 ml) and extracted with dichloromethane (3×50 ml) and the organic layers were combined and then dried over anhydrous sodium sulfate. The solids were filtered off. The resulting mixture was concentrated under vacuum to give a residue, which was applied onto a silica gel column and eluted with 2% methanol in dichloromethane. The product-containing fractions were combined and concentrated under vacuum to afford 1-[4-(6-fluoronaphthalen-2-yl)piperazin-1-yl]-2-[(4-[[4-nitro-3-(trifluoromethyl)phenyl]amino]cyclohexyl)oxy]ethan-1-one as a yellow solid (31.1 mg, 11%); (ES, m/z): [M−H]⁻ 573.2; ¹H NMR (300 MHz, DMSO/D₂O): δ 8.05 (d, J=6.9 Hz, 1H), 7.77-7.82 (m, 2H), 7.53-7.56 (dd, J=1.8, 7.5 Hz, 1H), 7.43-7.46 (dd, J=1.5, 6.9 Hz, 1H), 7.28-7.33 (m, 1H), 7.25 (d, J=1.2 Hz, 1H), 7.06 (s, 1H), 6.83-6.86 (dd, J=1.8, 6.9 Hz, 1H), 4.21 (s, 2H), 3.63 (broad s, 4H), 3.37-3.52 (m, 2H), 3.21-3.26 (m, 4H), 1.94-2.05 (m, 4H), 1.34-1.39 (m, 2H), 1.23-1.29 (m, 2H).

EXAMPLE 7: Preparation of Compound 088

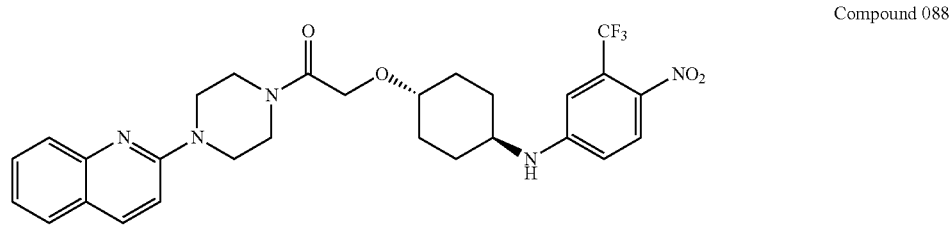

Compound 088

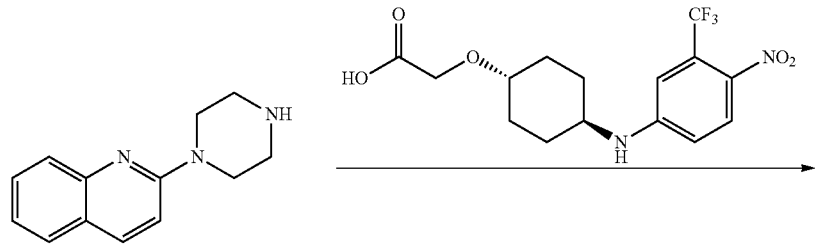

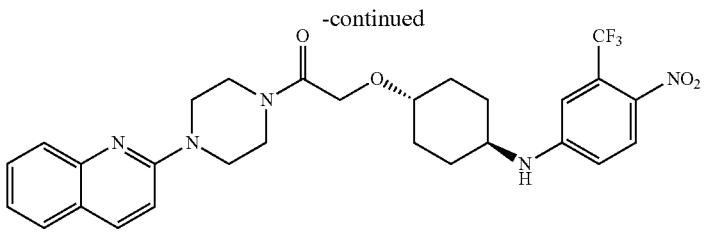

Step 1. Formation of 2-((1R,4R)-4-(4-nitro-3-(trifluoromethyl)phenylamino)cyclohexyloxy)-1-(4-(quinolin-2-yl)piperazin-1-yl)ethanone (#88)

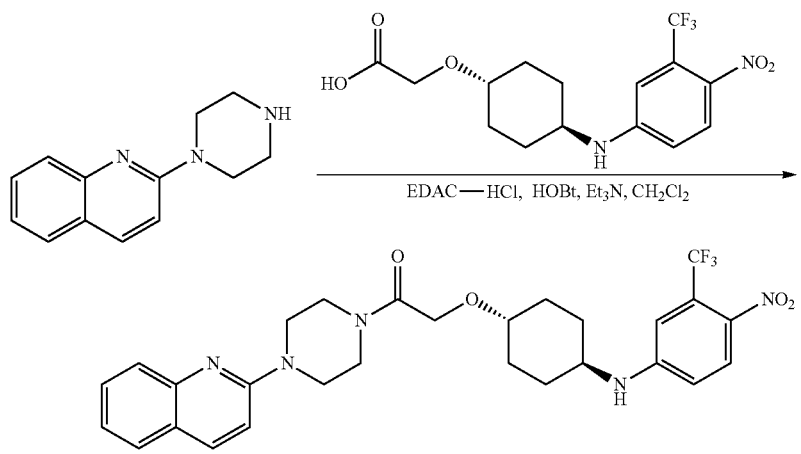

To a solution of 2-(piperazin-1-yl)quinoline (150 mg, 0.70 mmol) in dichloromethane (30 ml) was added 2-[(4-[4-nitro-3-(trifluoromethyl)phenyl]aminocyclohexyl)oxy]acetic acid (300 mg, 0.83 mmol, 1.2 eq), EDAC.HCl (201 mg, 1.05 mmol, 1.5 eq), HOBt (142.6 mg, 1.06 mmol, 1.5 eq) and triethylamine (213 mg, 2.10 mmol, 3 eq). The resulting solution was stirred overnight at room temperature, quenched by the addition of water (50 ml), and then extracted with dichloromethane (3×50 ml). The organic layers were combined, dried over anhydrous sodium sulfate, filtered, and then concentrated under vacuum to give a residue. The crude material was purified by Pre-TLC using 5% methanol in dichloromethane to elute. The product-containing fractions were combined and then concentrated under vacuum to afford 229 mg (58%) of 2-[(4-[[4-nitro-3-(trifluoromethyl)phenyl]amino]cyclohexyl)oxy]-1-[4-(quinolin-2-yl)piperazin-1-yl]ethan-1-one as a yellow solid. (ES, m/z): [M+H]$^+$ 558.40; $^1$H NMR (300 MHz, CDCl$_3$): δ 7.94-8.03 (m, 2H), 7.71 (s, 1H), 7.55-7.65 (m, 2H), 7.28-7.30 (t, J=5.4 Hz, 1H), 6.99 (d, J=9.0 Hz, 1H), 6.84 (d, J=2.4 Hz, 1H), 6.61-6.65 (m, 1H), 4.51 (d, J=7.5 Hz, 1H), 4.27 (s, 2H), 3.74-3.96 (m, 8H), 3.34-3.51 (m, 2H), 2.14-2.17 (m, 4H), 1.50-1.60 (m, 2H), 1.36-1.47 (m, 2H).

EXAMPLE 8: Preparation of Compound 097

Compound 097

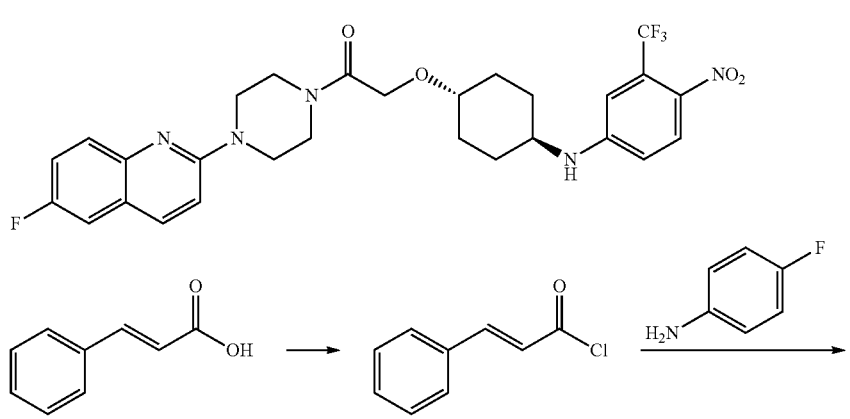

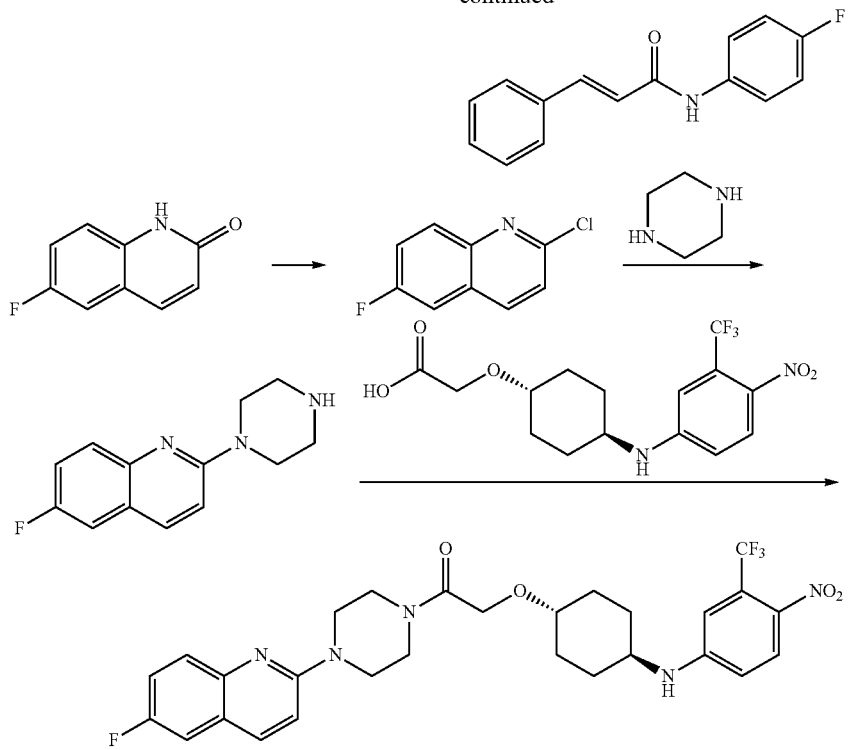

Step 1. Formation of cinnamoyl chloride

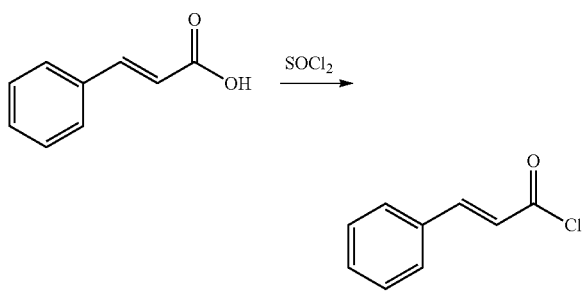

Cinnamic acid (25 g, 168.74 mmol) was treated with SOCl$_2$ (150 ml) for 2 hours at 70° C. in a round-bottomed flask. The volatiles were distilled out under vacuum to afford cinnamoyl chloride as a yellow oil (25.2 g, crude), which was used in the next step without further purification.

Step 2. Formation of N-(4-fluorophenyl)cinnamamide

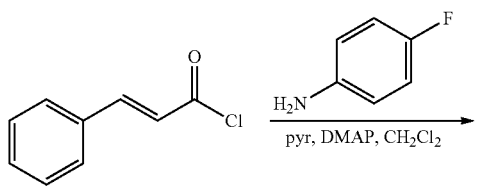

-continued

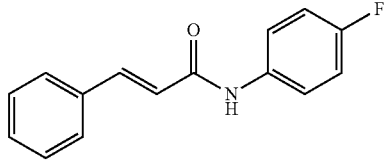

In a round-bottomed flask, a solution of the crude cinnamoyl chloride (25.2 g) in dichloromethane (50 ml) was added to a stirring mixture of pyridine (14.4 g, 182 mmol) and 4-dimethylaminopyridine (1.44 g, 11.8 mmol) in dichloromethane (100 ml) at 0° C. and stirred for 15 minutes before a solution of 4-fluoroaniline (13.2 g, 118.79 mmol) in dichloromethane (50 ml) was added over 20 min. After being stirred for 3 h at room temperature, the mixture was quenched with water (500 ml) and extracted with dichloromethane (3×150 ml). The organic layers were combined, dried over anhydrous magnesium sulfate, filtered, and concentrated under vacuum to give a residue. The crude material was purified by silica gel chromatography using 1-5% ethyl acetate in petroleum to elute. The product-containing fractions were combined to afford N-(4-fluorophenyl)cinnamamide as a light yellow solid (17.8 g, 61%); (ES, m/z): [M+H]$^+$ 242; $^1$H NMR (300 MHz, CDCl$_3$): δ 10.28 (s, 1H), 7.70-7.75 (m, 5H), 7.39-7.65 (m, 3H), 7.15 (t, J=9.0 Hz, 2H), 6.79 (d, J=15.6 Hz, 1H).

Step 3. Formation of 6-fluoro-1,2-dihydroquinolin-2-one

An intimate mixture of N-(4-fluorophenyl)cinnamamide (10 g, 42 mmol) and aluminum trichloride (16.4 g, 123 mmol, 3 eq) was heated rapidly to melting and then heated at 100° C. for 3 h. After cooling to room temperature, ice-water was added and the resultant precipitate was washed with water (300 ml) and then with 5% aqueous hydrochloric acid (3×100 ml) to afford 6-fluoro-1,2-dihydroquinolin-2-one as a brown solid (7.8 g, 88%) which was used without further purification; (ES, m/z): [M+H]⁺ 164; ¹H NMR (300 MHz, DMSO): δ 11.82 (broad s, 1H), 7.86 (d, J=9.4 Hz, 1H), 7.61 (d, J=8.7 Hz, 1H), 7.29-7.40 (m, 2H), 6.54 (d, J=9.4 Hz, 1H).

Step 4. Formation of 2-chloro-6-fluoroquinoline

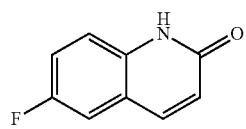

6-fluoro-1,2-dihydroquinolin-2-one (7.8 g, 47.8 mmol) was suspended in phosphorus oxychloride (72.2 g, 470.9 mmol) and stirred for 4 hours at 100° C. in an oil bath. The reaction mixture was concentrated under vacuum to remove the excess phosphorus oxychloride and then ice-water (200 ml) was added. The precipitate that formed was washed with water (2×80 ml) and dried to give 2-chloro-6-fluoroquinoline as a off-white solid (6.8 g, 78%); (ES, m/z): [M+H]⁺ 182; ¹H NMR (300 MHz, DMSO): δ 8.43 (d, J=8.4 Hz, 1H), 8.01 (dd, J=5.4 Hz, 9.3 Hz, 1H), 7.87 (dd, J=3.0 Hz, 9.3 Hz, 1H), 7.72-7.78 (m, 1H), 7.45 (d, J=8.4 Hz, 1H).

Step 5. Formation of 6-fluoro-2-(piperazin-1-yl)quinoline

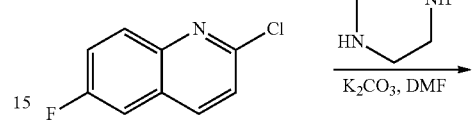

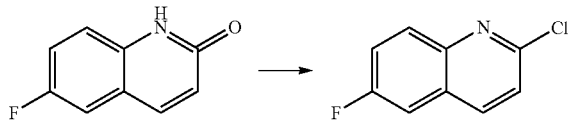

To a solution of 2-chloro-6-fluoroquinoline (6.8 g, 37.4 mmol) in N,N-dimethylformamide (200 ml) in a round-bottomed flask was added potassium carbonate (10.4 g, 75.2 mmol) and piperazine (19.2 g, 222.9 mmol) at room temperature. After heating the contents to 130° C. for 5 hours, the reaction mixture was concentrated under vacuum to a minimum volume and then quenched with water (300 ml) and extracted with dichloromethane (3×200 ml). The combined organic layers were washed with brine (100 ml), dried over anhydrous sodium sulfate, filtered, and concentrated under vacuum. The crude material was purified by silica gel chromatography using 1-2.5% methanol in dichloromethane to elute. The product containing fractions were combined and concentrated to afford 6-fluoro-2-(piperazin-1-yl)quinoline as a brown solid (4.5 g, 52%); (ES, m/z): [M+H]⁺ 232; ¹H NMR (300 MHz, CDCl₃): δ 7.86 (d, J=9.3 Hz, 1H), 7.62-7.72 (m, 1H), 7.32-7.36 (m, 1H), 7.24-7.29 (m, 1H), 7.01 (d, J=9.3 Hz, 1H), 3.73 (t, J=5.1 Hz, 4H), 3.05 (t, J=5.1 Hz, 4H).

Step 6. Formation of 1-[4-(6-fluoroquinolin-2-yl)piperazin-1-yl]-2-[(4-[[4-nitro-3-(trifluoromethyl)phenyl]amino]cyclohexyl)oxy]ethan-1-one (#97)

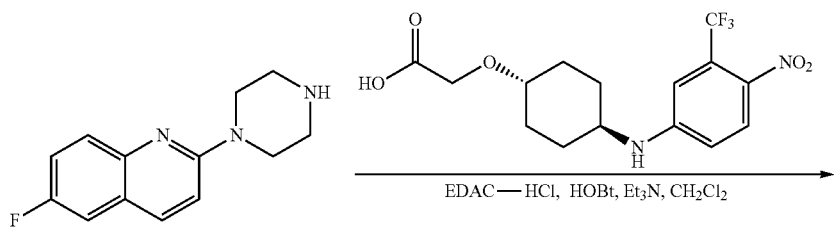

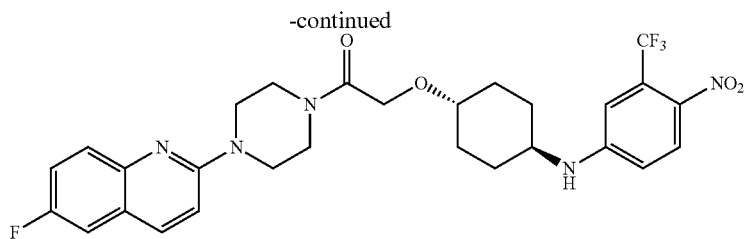

To a solution of 2-[(4-[[4-nitro-3-(trifluoromethyl)phenyl]amino]cyclohexyl)oxy]acetic acid (100 mg, 0.28 mmol) in dichloromethane (20 ml) was added EDAC.HCl (79.1 mg, 0.41 mmol), HOBt (55.9 mg, 0.41 mmol), triethylamine (83.7 mg, 0.83 mmol) and 6-fluoro-2-(piperazin-1-yl)quinoline (70.2 mg, 0.30 mmol) at room temperature. After stirred overnight, the reaction mixture was then diluted with dichloromethane (100 ml) and washed with water (2×100 ml), dried over anhydrous magnesium sulfate, filtered, and concentrated under vacuum to give a residue, which was purified by a silica gel column with 2% methanol in dichloromethane to afford 1-[4-(6-fluoroquinolin-2-yl)piperazin-1-yl]-2-[(4-[[4-nitro-3-(trifluoromethyl)phenyl]amino]cyclohexyl)oxy]ethan-1-one as a yellow solid (80 mg, 48%); (ES, m/z): [M+H]$^+$ 576.20; $^1$H NMR (400 MHz, CDCl$_3$): δ 8.02 (d, J=8.8 Hz, 1H), 7.94-7.99 (m, 1H), 7.72-7.78 (m, 1H), 7.31-7.37 (m, 2H), 7.02 (t, J=8.0 Hz, 1H), 6.87 (s, 1H), 6.64 (dd, J=2.4 Hz, 9.2 Hz, 1H), 4.48 (d, J=7.6 Hz, 1H), 4.28 (s, 2H), 3.75-3.81 (m, 7H), 3.41-3.49 (m, 2H), 2.17-2.19 (m, 4H), 1.50-1.58 (m, 2H), 1.28-1.36 (m, 3H).

EXAMPLE 9: Preparation of Compound 90

Compound 090

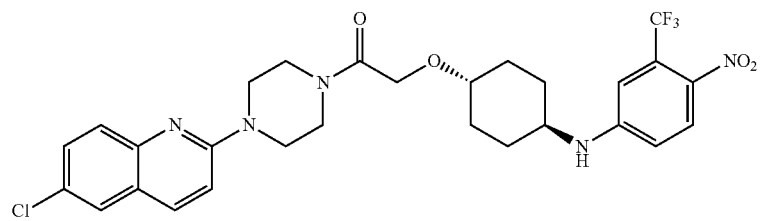

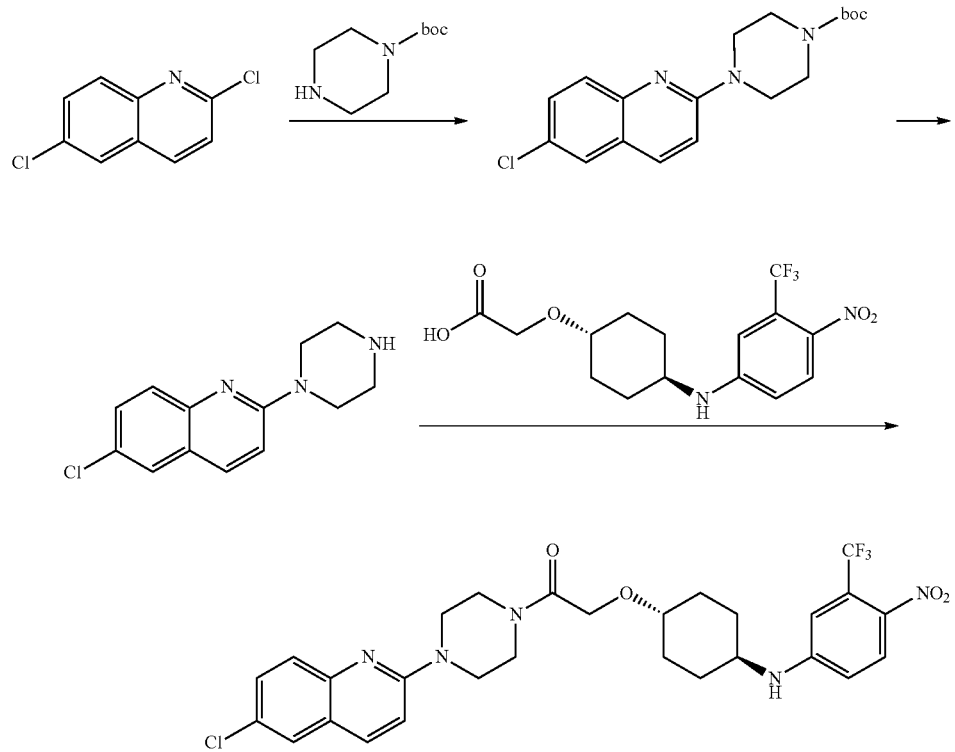

Step 1. Formation of tert-butyl 4-(6-chloroquinolin-2-yl)piperazine-1-carboxylate

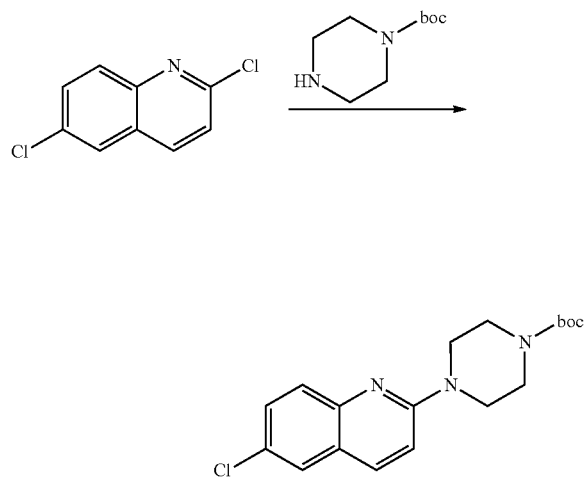

To a solution of 2,6-dichloroquinoline (1.5 g, 7.6 mmol) in DMF (50 ml) was added tert-butyl piperazine-1-carboxylate (7.1 g, 38.1 mmol, 5 eq), and potassium carbonate (2.1 g, 15.1 mmol, 2 eq). The mixture was stirred for 4 hours at 140° C. and then quenched by the addition of water (300 ml) and then extracted with ethyl acetate (3×100 ml). The organic layers were combined, washed with saturated aqueous sodium chloride (3×300 ml), dried over anhydrous sodium sulfate, filtered, and concentrated under vacuum to give a residue. The crude material was purified by silica gel chromatography using 1-10% ethyl acetate in petroleum ether to elute. The product-containing fractions were combined and concentrated under vacuum to afford tert-butyl 4-(6-chloroquinolin-2-yl)piperazine-1-carboxylate as a light yellow solid (1.6 g, 61%). (ES, m/z): [M+H]$^+$ 348; $^1$H NMR (300 MHz, DMSO): δ 8.03 (d, J=9.3 Hz, 1H), 7.81 (d, J=2.1 Hz, 1H), 7.50-7.58 (m, 2H), 7.29 (d, J=9.3 Hz, 1H), 3.68-3.71 (t, J=5.1 Hz, 4H), 3.43-3.47 (t, J=4.5 Hz, 4H), 1.43 (s, 9H).

Step 2. Formation of N-(2-aminoethyl)-6-chloro-N-(2-chloroethyl)quinolin-2-amine

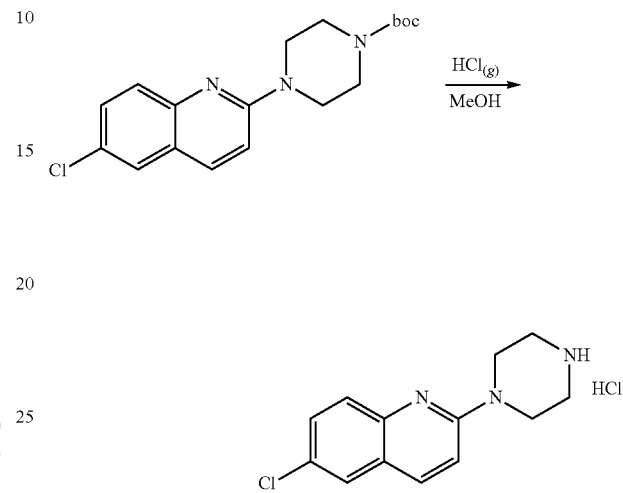

HCl (gas) was transferred into a solution of tert-butyl 4-(6-chloro quinolin-2-yl)piperazine-1-carboxylate (1.6 g, 4.6 mmol) in methanol (40 ml) at room temperature with stirring for 1 hour and then concentrated under vacuum to afford N-(2-aminoethyl)-6-chloro-N-(2-chloroethyl)quinolin-2-amine as a white solid (1.1 g, 84%). (ES, m/z): [M+H]$^+$ 248

Step 3. Formation of 1-[4-(6-chloroquinolin-2-yl)piperazin-1-yl]-2-[(4-[[4-nitro-3-(trifluoromethyl)phenyl]amino]cyclohexyl)oxy]ethan-1-one (#90)

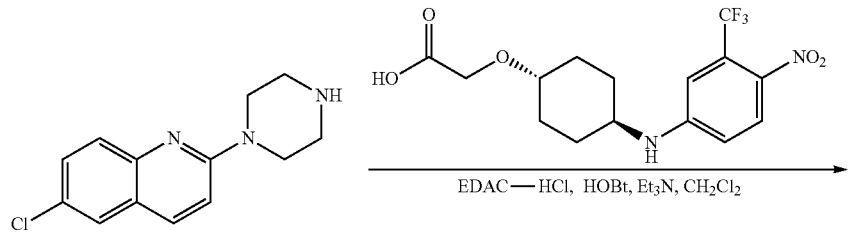

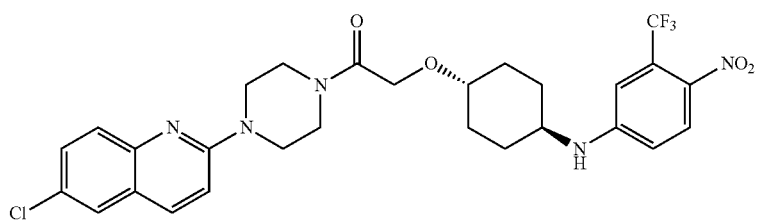

To a solution of 2-[(4-[4-nitro-3-(trifluoromethyl)phenyl]aminocyclohexyl)oxy]acetic acid (100 mg, 0.28 mmol) in dichloromethane (20 ml) was added EDAC.HCl (79.4 mg, 0.41 mmol, 1.5 eq), HOBt (56 mg, 0.41 mmol, 1.5 eq), triethylamine (111.6 mg, 1.10 mmol, 4 eq), and N-(2-aminoethyl)-6-chloro-N-(2-chloroethyl)quinolin-2-amine (93.8 mg, 0.33 mmol, 1.2 eq). The resulting solution was stirred overnight at room temperature and then quenched by the addition of water (50 ml), extracted with dichloromethane (3×30 ml). The organic layers were combined, dried over anhydrous sodium sulfate, filtered, and concentrated under vacuum to give a residue. The crude material was purified by Pre-TLC using 4% methanol in dichloromethane to elute. The product-containing fractions were combined and concentrated under vacuum to afford 1-[4-(6-chloroquinolin-2-yl)piperazin-1-yl]-2-[(4-[[4-nitro-3-(trifluoromethyl)phenyl]amino]cyclohexyl)oxy]ethan-1-one as a yellow solid (69.8 mg, 42%). (ES, m/z): [M+H]$^+$ 592.35; $^1$H NMR (300 MHz, CDCl$_3$): δ 8.00 (d, J=9.0 Hz, 1H), 7.86 (d, J=7.8 Hz, 1H), 7.61 (s, 2H), 7.52 (s, 1H), 7.01 (d, J=9.0 Hz, 1H), 6.91 (s, 1H), 6.84 (d, J=2.4 Hz, 1H), 6.61-6.65 (m, 1H), 4.45 (d, J=7.5 Hz, 1H), 4.26 (s, 2H), 3.75-3.78 (m, 7H), 3.37-3.50 (m, 2H), 2.14 (d, J=10.5 Hz, 4H), 1.44-1.51 (m, 2H), 1.24-1.35 (m, 2H).

EXAMPLE 10: Preparation of Compound 89

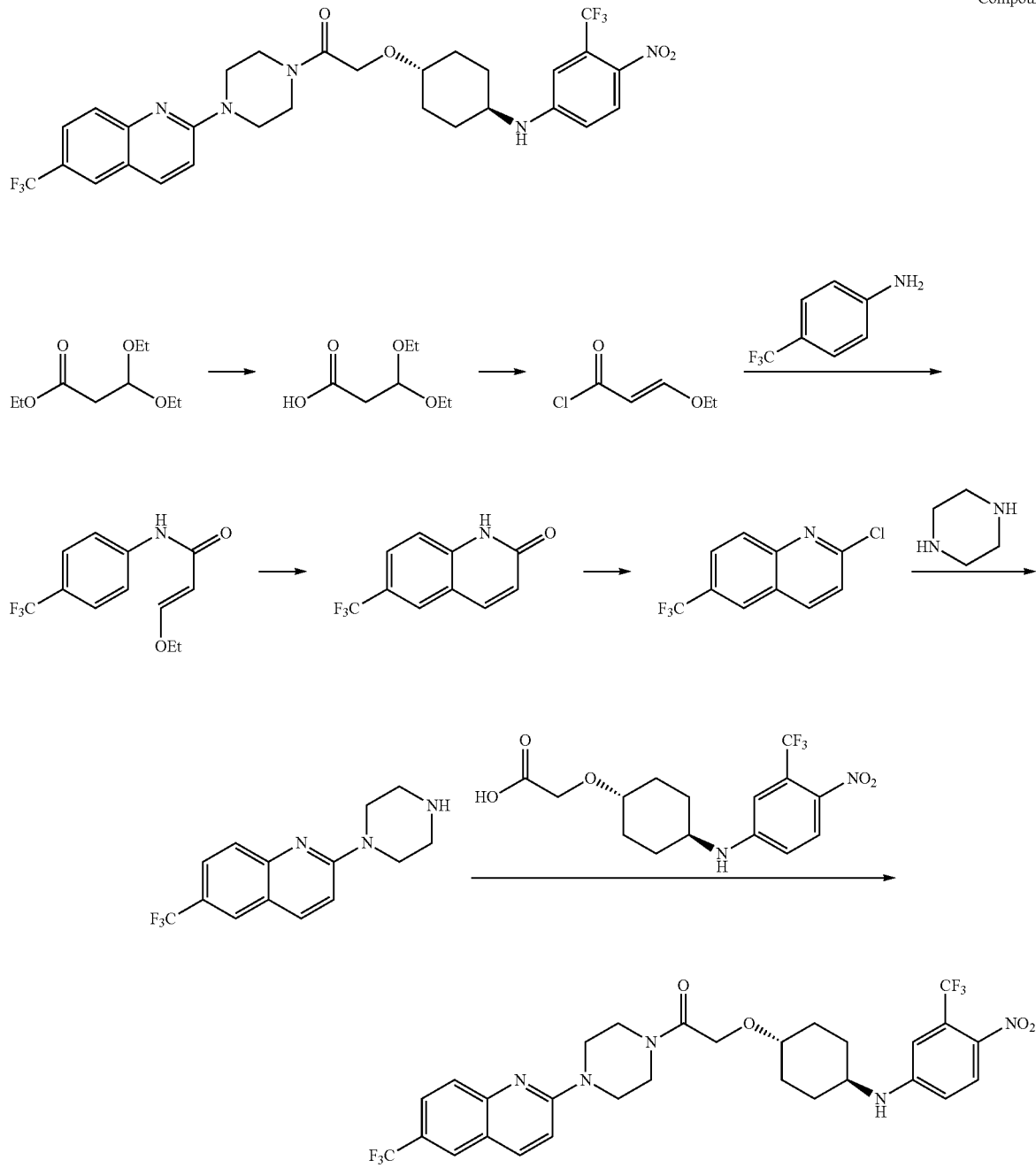

Step 1. Formation of 3,3-diethoxypropanoic acid

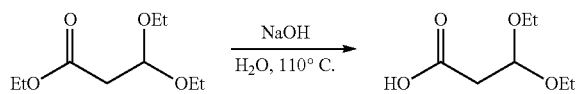 [SMILES: CCOC(=O)CC(OCC)OCC ; "NaOH" ; CCOC(CC(=O)O)OCC]

To a solution of ethyl 3,3-diethoxypropanoate (20 g, 105 mmol) in water (80 ml) was added sodium hydroxide (5 g, 125 mmol, 1.2 eq). The resulting solution was stirred for 1 hour at 110° C. in an oil bath and then adjusted to pH 5 with aqueous hydrogen chloride (3N). The crude product was then extracted with tetrahydrofuran (3×80 ml) and the organic layers were combined, dried over anhydrous sodium sulfate, and filtered before being concentrated under vacuum. The crude residue was purified by silica gel chromatography using 3-50% ethyl acetate in petroleum ether to elute. The product-containing fractions were combined and concentrated under vacuum to afford 3,3-diethoxypropanoic acid as light yellow oil (12 g, 70%); $^1$H NMR (300 MHz, DMSO): δ 4.80-4.82 (t, J=5.7 Hz, 1H), 3.41-3.61 (m, 4H), 2.49 (d, J=5.7 Hz, 2H), 1.06-1.24 (m, 6H).

Step 2. Formation of (2E)-3-ethoxyprop-2-enoyl chloride

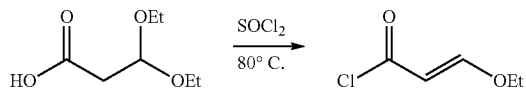 [SMILES: CCOC(CC(=O)O)OCC ; "SOCl2" ; CCO/C=C/C(=O)Cl]

3,3-diethoxypropanoic acid (5 g, 30.83 mmol) was added to thionyl chloride (20 ml) with stirring at 0° C. and then heated to 80° C. for 1 hour (oil bath). The resulting mixture was then concentrated under vacuum to afford (2E)-3-ethoxyprop-2-enoyl chloride as dark red oil (4 g, crude).

Step 3. Formation of (2E)-3-ethoxy-N-(4-methylphenyl)prop-2-enamide

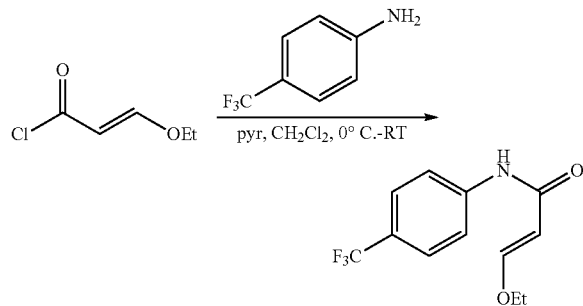

To a solution of 4-(trifluoromethyl)aniline (2.56 g, 15.9 mmol) in dichloromethane (40 ml) was added pyridine (3.77 g, 47.7 mmol). The solution was cooled to 0° C. before a solution of 3,3-diethoxypropanoyl chloride (4 g, crude) in dichloromethane (10 ml) was added dropwise with stirring. The resulting solution was stirred for 4 hours at 20° C. and then washed with water (200 ml). The resulting mixture was extracted with dichloromethane (3×80 ml) and the organic layers were combined and concentrated under vacuum. The crude residue was purified by Pre-TLC with 1-20% ethyl acetate in petroleum ether to elute. The product-containing fractions were combined and concentrated under vacuum to afford (2E)-3-ethoxy-N-(4-trifluoromethylphenyl)prop-2-enamide as a yellow solid (4.0 g). (ES, m/z): [M+H]$^+$ 260; $^1$H NMR (300 MHz, DMSO): δ 10.10 (s, 1H), 7.83 (d, J=8.4 Hz, 2H), 7.72 (s, 1H), 7.60 (d, J=8.7 Hz, 1H), 7.50-7.56 (m, 1H), 5.52 (d, J=12.4 Hz, 1H), 3.90-4.01 (m, 2H), 1.15-1.30 (m, 3H).

Step 4. Formation of 6-(trifluoromethyl)-1,2-dihydroquinolin-2-one

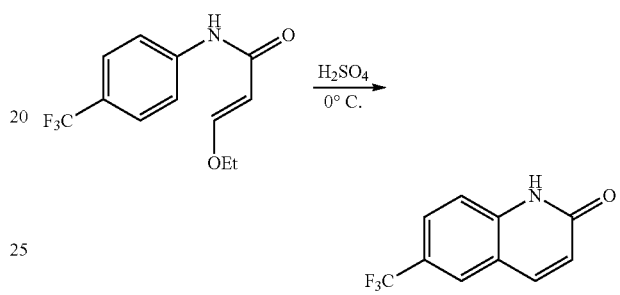

(2E)-3-ethoxy-N-(4-trifluoromethylphenyl)prop-2-enamide (3.44 g, 16.8 mmol) was added in several batches to sulfuric acid (20 ml) at 0° C. and then stirred for 2 hours at 0° C. The resulting mixture was quenched with ice-water (100 ml). The product was precipitated from water and collected by filtration to afford 6-(trifluoromethyl)-1,2-dihydroquinolin-2-one as a yellow solid (2.0 g, 56%). (ES, m/z): [M+H]$^+$ 214. $^1$H NMR (300 MHz, DMSO): δ 8.14 (s, 1H), 8.03 (d, J=9.6 Hz, 1H), 7.80-7.83 (m, 1H), 7.45 (d, J=8.4 Hz, 1H), 6.61-6.65 (t, J=9.6 Hz, 1H).

Step 5. Formation of 2-chloro-6-(trifluoromethyl)quinoline

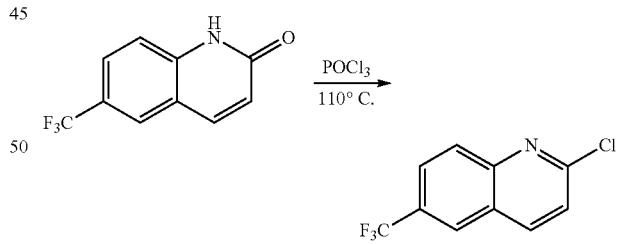

6-(trifluoromethyl)-1,2-dihydroquinolin-2-one (1.0 g, 4.7 mmol) was dissolved in POCl$_3$ (15 ml) and stirred for 2 h at 110° C. (oil bath). The resulting mixture was dissolved in ice-water (100 ml) and adjusted pH to 8 with aqueous Na$_2$CO$_3$ solution (3N). The crude product was then extracted with dichloromethane (3×80 ml) and the organic layers were combined, dried over anhydrous magnesium sulfate, filtered, and concentrated under vacuum to afford 2-chloro-6-(trifluoromethyl)quinoline as a dark red solid (944 mg, 87%). (ES, m/z): [M+H]$^+$ 232. $^1$H NMR (300 MHz, DMSO): δ 8.59-8.66 (m, 2H), 8.01-8.17 (m, 2H), 7.75 (d, J=8.7 Hz, 1H).

Step 6. Formation of 2-(piperazin-1-yl)-6-(trifluoromethyl)quinoline

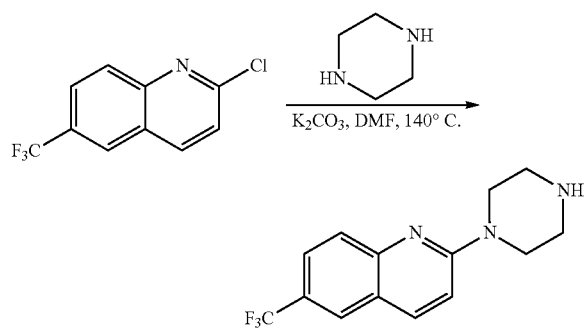

To a solution of 2-methyl-6-(trifluoromethyl)quinoline (1.5 g, 7.10 mmol) in 1N,N-dimethylformamide (50 ml) was added piperazine (2.8 g, 32.51 mmol) and potassium carbonate (1.8 g, 12.93 mmol). The resulting solution was stirred for 3 hours at 140° C. and then quenched by the addition of water (200 ml). The crude product was extracted with ethyl acetate (3×100 ml) and the organic layers were combined. The resulting mixture was washed with saturated aqueous sodium chloride (3×100 ml), dried over anhydrous sodium sulfate, filtered, and then concentrated under vacuum. The crude residue was purified by silica gel chromatography using 1-5% methanol in dichloromethane to elute. The product-containing fractions were combined and concentrated to afford 2-(piperazin-1-yl)-6-(trifluoromethyl) quinoline as a brown solid (1.3 g, 65%). (ES, m/z): [M+H]$^+$ 282; $^1$H NMR (300 MHz, DMSO): δ 8.17-8.23 (t, J=9.3, 2H), 7.66-7.77 (m, 2H), 7.63 (d, J=9.3 Hz, 1H), 3.78-3.81 (t, J=4.5 Hz, 4H), 2.92-2.96 (t, J=4.5 Hz, 4H).

Step 7. Formation of 2-[(4-[[4-nitro-3-(trifluoromethyl)phenyl]amino]cyclohexyl)oxy]-1-[4-[6-trifluoro-methyl)quinolin-2-yl]piperazin-1-yl]ethan-1-one (#89)

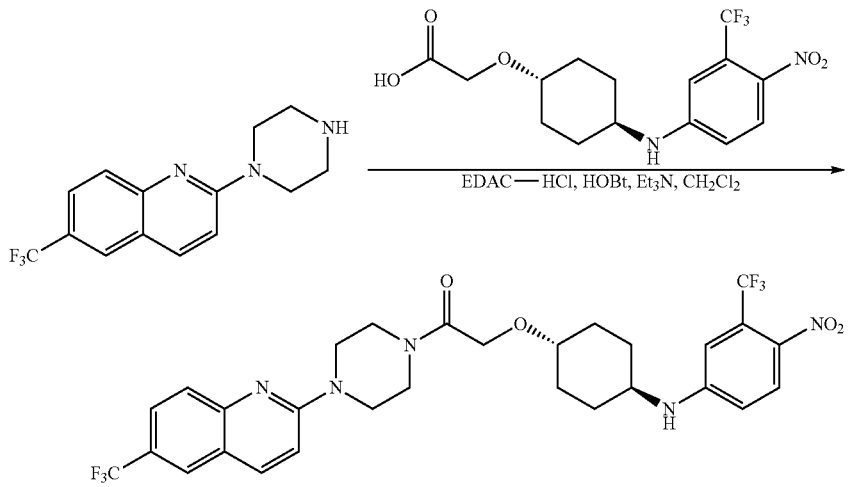

To a solution of 2-[(4-[4-nitro-3-(trifluoromethyl)phenyl]aminocyclohexyl)oxy]acetic acid (100 mg, 0.28 mmol) in dichloromethane (20 ml) was added 2-(piperazin-1-yl)-6-(trifluoromethyl)quinoline (93.1 mg, 0.33 mmol, 1.2 eq), EDAC.HCl (79 mg, 0.41 mmol, 1.5 eq), HOBt (56 mg, 0.41 mmol, 1.5 eq), Et$_3$N (84 mg, 0.83 mmol, 3 eq). The resulting solution was stirred overnight at room temperature and then quenched by the addition of water (50 ml), extracted with of dichloromethane (3×30 ml) and the organic layers were combined and dried over anhydrous sodium sulfate. The organic solution was filtered and then concentrated under vacuum. The crude material was purified by Pre-TLC using 4% methanol in dichloromethane to elute. Concentration of the product-containing fractions afforded 2-[(4-[[4-nitro-3-(trifluoromethyl)phenyl]amino]cyclohexyl)oxy]-1-[4-[6-(trifluoromethyl)quinolin-2-yl]piperazin-1-yl]ethan-1-one as a yellow solid (77 mg, 45%).

(ES, m/z): [M+H]$^+$ 626.40. $^1$H NMR (300 MHz, CD$_3$OD): δ 8.13 (d, J=9.0 Hz, 1H), 8.02-8.05 (t, J=4.5 Hz, 2H), 7.42-7.79 (m, 2H), 7.29 (d, J=9.3 Hz, 1H), 6.99 (d, J=2.4 Hz, 1H), 6.78-6.81 (dd, J=2.4, 9.2 Hz, 1H), 4.34 (s, 2H), 3.88-3.94 (m, 4H), 3.72-3.78 (m, 4H), 3.45-3.50 (m, 2H), 2.10-2.20 (m, 4H), 1.34-1.54 (m, 4H).

EXAMPLE 11: Preparation of Compound 09
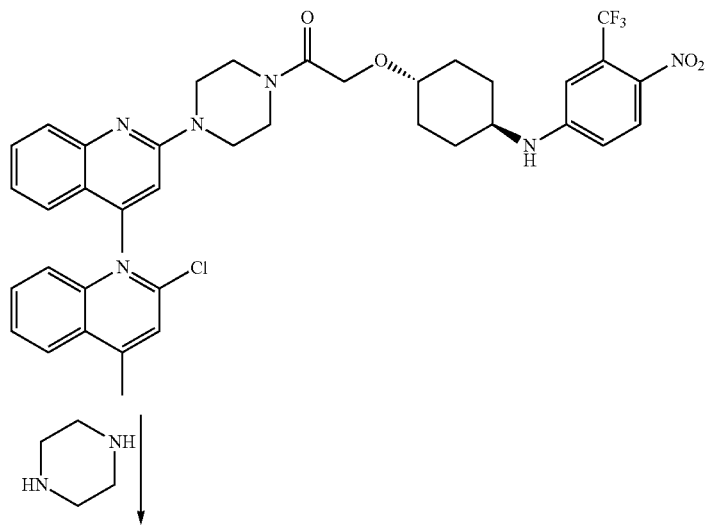
Compound 98
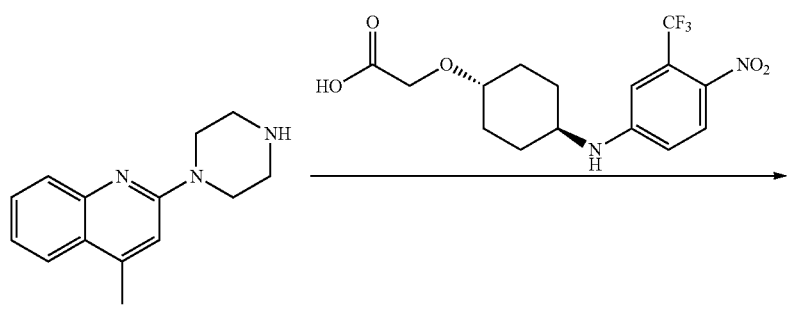
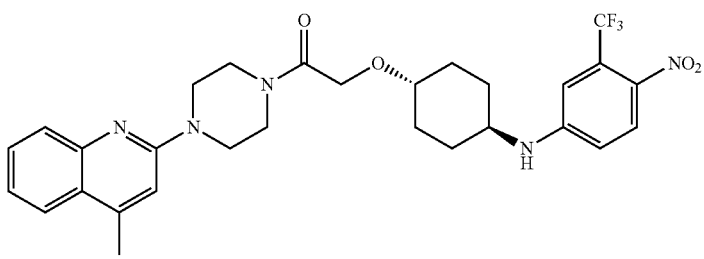
Step 1. Formation of
4-methyl-2-(piperazin-1-yl)quinoline
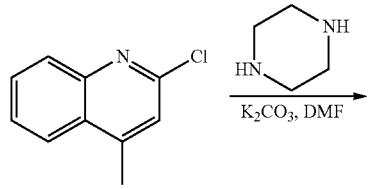
-continued
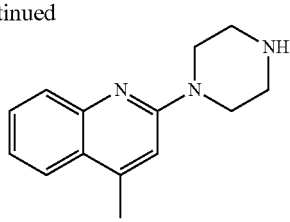
To a solution of 2-chloro-4-methylquinoline (2 g, 11 mmol) in N,N-dimethylformamide (40 ml) was added piperazine (4.86 g, 56.4 mmol, 5 eq) and potassium carbonate (2.34 g, 16.8 mmol, 1.5 eq). The mixture was stirred overnight at 140° C., quenched by the addition of water (200 ml), and extracted with ethyl acetate (3×100 ml). The organic layers were combined and washed with saturated aqueous sodium chloride (200 ml). The ethyl acetate solution was dried over anhydrous sodium sulfate, filtered, and concentrated under vacuum. The crude material was purified by silica gel chromatography using 1-10% methanol in dichloromethane to elute. The product-containing fractions were combined and concentrated to afford 4-methyl-2-(piperazin-1-yl)quinoline as colorless oil (2.2 g, 86%); (ES, m/z) [M+H]$^+$ 228; $^1$H NMR (300 MHz, CDCl$_3$): δ 7.70-7.78 (m, 2H), 7.50-7.55 (t, J=7.5 Hz, 1H), 7.22-7.27 (t, J=6.9 Hz, 1H), 6.83 (s, 2H), 3.70-3.73 (t, J=4.8 Hz, 1H), 3.00-3.03 (t, J=5.1 Hz, 1H), 2.59 (s, 3H).

Step 2. Formation of 1-[4-(4-methylquinolin-2-yl)piperazin-1-yl]-2-[(4-[[4-nitro-3-(trifluoromethyl)phenyl]amino]cyclohexyl)oxy]ethan-1-one (#98)

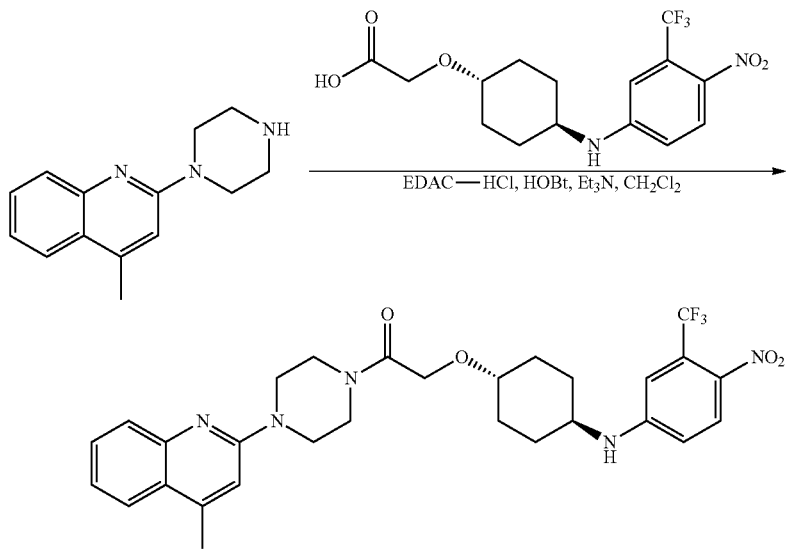

To a solution of 4-methyl-2-(piperazin-1-yl)quinoline (100 mg, 0.44 mmol) in dichloromethane (20 ml) was added EDAC.HCl (126 mg, 0.66 mmol, 1.5 eq), HOBt (88.8 mg, 0.66 mmol, 1.5 eq), triethylamine (133 mg, 1.31 mmol, 3 eq) and 2-[(4-[4-nitro-3-(trifluoromethyl)phenyl]aminocyclohexyl)oxy]acetic acid (190 mg, 0.52 mmol, 1.2 eq). The resulting solution was stirred overnight at room temperature and then quenched by the addition of water (50 ml) and extracted with dichloromethane (3×30 ml). The organic layers were combined, dried over anhydrous sodium sulfate, filtered, and then concentrated under vacuum to give a residue. The crude material was purified by Pre-TLC with 50% ethyl acetate in dichloromethane to afford 1-[4-(4-methylquinolin-2-yl)piperazin-1-yl]-2-[(4-[[4-nitro-3-(trifluoro-methyl)phenyl]amino]cyclohexyl)oxy]ethan-1-one as a yellow solid (117 mg, 47%); (ES, m/z) [M+H]$^+$ 572.20; $^1$H NMR (300 MHz, CDCl$_3$): δ 8.02 (d, J=9.0 Hz, 1H), 7.81 (d, J=8.4 Hz, 1H), 7.74 (s, 1H), 7.54-7.62 (m, 1H), 7.32-7.38 (m, 1H), 6.87 (s, 2H), 6.63-6.67 (m, 1H), 4.48 (d, J=7.5 Hz, 1H), 4.28 (s, 2H), 3.75-3.85 (m, 7H), 3.39-3.52 (m, 2H), 2.65 (s, 3H), 2.16 (d, J=9.9 Hz, 1H), 1.46-1.53 (m, 2H), 1.25-1.36 (m, 2H).

EXAMPLE 12: Preparation of Compound 24

Compound 24

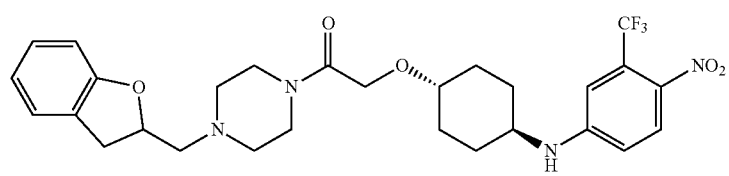

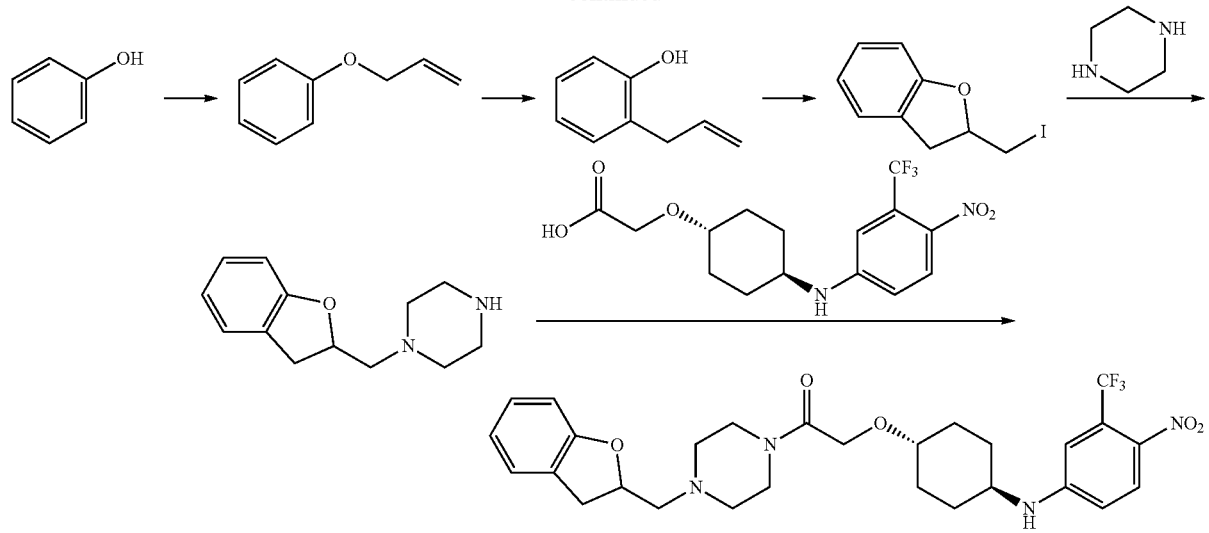

Step 1. Formation of allyloxybenzene

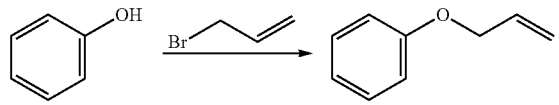

To a round-bottomed flask containing a solution of phenol (30 g, 319 mmol) in acetonitrile (150 ml) at room temperature was added potassium carbonate (66 g, 478 mmol) and allyl bromide (49.8 g, 412 mmol). The mixture was heated to 50° C. and stirred for 3.5 hours. The solids were filtered out and the filtrate was concentrated to a minimum volume. The crude material was diluted with water (200 ml) and extracted with ethyl acetate (3×100 ml). The combined organic layers were washed with brine (2×100 ml), dried over anhydrous magnesium sulfate, filtered, and concentrated to afford crude allyloxybenzene as brown oil (35 g); $^1$H NMR (300 MHz, CDCl$_3$): δ 7.20-7.30 (m, 2H), 6.89-6.96 (m, 3H), 5.99-6.12 (m, 1H), 5.41 (d, J=17.1 Hz, 1H), 5.28 (d, J=10.5 Hz, 1H), 4.52 (d, J=5.1 Hz, 2H).

Step 2. Formation of 2-allylphenol

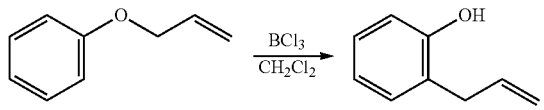

A solution of allyloxybenzene (34 g, crude) in dichloromethane (200 ml) was treated with a 1N solution of BCl$_3$ (279 ml, 279 mmol) in dichloromethane at between −30 to −20° C. under an inert atmosphere of nitrogen. After 30 minutes of stirring, the reaction mixture was then quenched with ice-water (200 ml) and the organic layer was separated. The aqueous layer was extracted with ethyl acetate (2×100 ml). The combined organic layers were washed with saturated aqueous sodium bicarbonate (200 ml), dried over anhydrous magnesium sulfate, filtered, and concentrated under vacuum. The crude material was purified by silica gel chromatography with 0.5-2.5% ethyl acetate in petroleum ether to elute. The product-containing fractions were combined and concentrated under vacuum to afford 2-(prop-2-en-1-yl)phenol as light yellow oil (23 g, 66%); $^1$H NMR (300 MHz, CDCl$_3$): δ 7.09-7.15 (m, 2H), 6.85-6.95 (m, 1H), 6.80 (d, J=7.8 Hz, 1H), 5.93-6.08 (m, 1H), 5.12-5.18 (m, 1H), 5.02-5.09 (m, 1H), 3.41 (d, J=6.3 Hz, 2H).

Step 3. Formation of 2-(iodomethyl)-2,3-dihydro-1-benzofuran

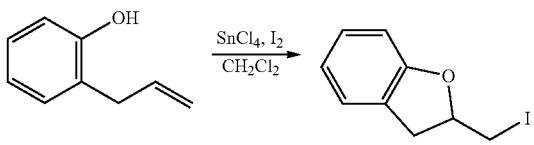

To a solution of 2-allylphenol (10 g, 75 mmol) in dichloromethane (150 ml) was added SnCl$_4$ (29.7 g, 37.3 mmol, 0.5 eq) and iodine (19 g, 75 mmol, 1 eq) at room temperature. After stirring for 5.5 hours, the reaction mixture was diluted with additional dichloromethane (200 ml) and then quenched with water (200 ml). The organic layer was separated and the aqueous layer was adjusted pH to ~8 with sodium bicarbonate and then extracted with dichloromethane (3×150 ml). The organic layers were combined, washed with 5% aqueous Na$_2$S$_2$O$_4$ (200 ml), dried over anhydrous magnesium sulfate, filtered, and then concentrated under vacuum. The crude material was purified by silica gel chromatography using with 0.5-1% ethyl acetate in petroleum ether to elute. The product-containing fractions were combined and concentrated to afford 2-(iodomethyl)-2,3-dihydro-1-benzofuran as brown oil (7 g, 36%); $^1$H NMR (300 MHz, CDCl$_3$): δ 7.09-7.17 (m, 2H), 6.74-6.89 (m, 2H), 4.84-4.93 (m, 1H), 3.30-3.47 (m, 3H), 3.00-3.08 (m, 1H).

Step 4. Formation of 1-(2,3-dihydro-1-benzofuran-2-ylmethyl)piperazine

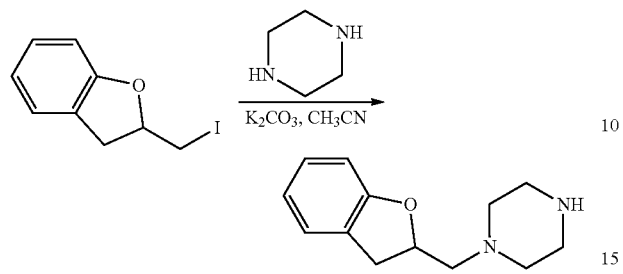

To a solution of 2-(iodomethyl)-2,3-dihydro-1-benzofuran (5.3 g, 20.4 mmol) in acetonitrile (70 ml) was added potassium carbonate (5.6 g, 40.5 mmol, 2 eq) and piperazine (8.8 g, 102.2 mmol, 5 eq). The resulting mixture was heated at reflux for 2 hours. The solids were then filtered off and the filtrate was concentrated under vacuum. The crude material was purified by silica gel chromatography using 0.5-2.5% methanol in dichloromethane to elute. The product-containing fractions were combined and concentrated under vacuum to afford 1-(2,3-dihydro-1-benzofuran-2-ylmethyl)piperazine as brown oil (2.4 g, 54%); (ES, m/z): [M+H]+ 219; $^1$H NMR (300 MHz, CDCl$_3$): δ 7.07-7.17 (m, 2H), 6.78-6.85 (m, 2H), 4.92-5.01 (m, 1H), 3.22 (dd, J=9.0 Hz, 15.6 Hz, 1H), 2.91-2.99 (m, 4H), 2.71-2.82 (m, 1H), 2.53-2.71 (m, 6H).

Step 5. Formation of 1-[4-(2,3-dihydro-1-benzofuran-2-ylmethyl)piperazin-1-yl]-2-[(4-[[4-nitro-3-(trifluoromethyl)phenyl]amino]cyclohexyl)oxy]ethan-1-one (#24)

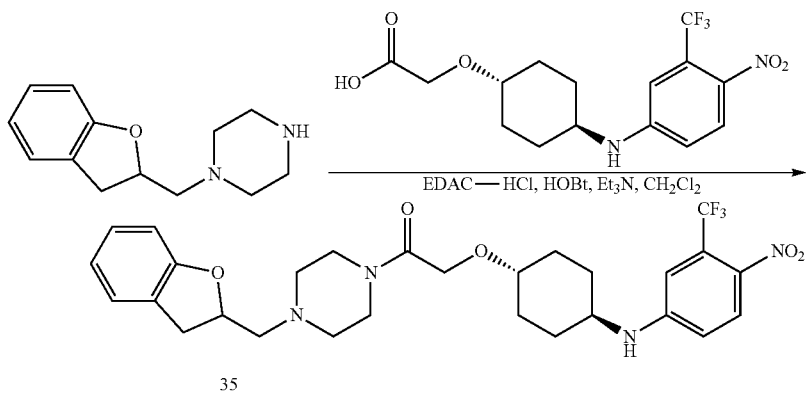

To a solution of 2-[(4-[4-nitro-3-(trifluoromethyl)phenyl]aminocyclohexyl)oxy]acetic acid (900 mg, 2.48 mmol) in dichloromethane (50 ml) was added EDAC.HCl (661 mg, 3.45 mmol), HOBt (464 mg, 3.43 mmol), triethylamine (463 mg, 4.58 mmol) and 1-(2,3-dihydro-1-benzofuran-2-ylmethyl)piperazine (500 mg, 2.29 mmol) in dichloromethane (1 ml) with stirring for overnight at room temperature. Then the mixture was diluted with dichloromethane (300 ml) and washed with water (100 ml). The organic layer was dried over anhydrous magnesium sulfate, filtered, and concentrated under vacuum to give a residue, which was purified by a silica gel column, eluted with 0.5%-3% methanol in dichloromethane to afford 1-[4-(2,3-dihydro-1-benzofuran-2-ylmethyl)piperazin-1-yl]-2-[(4-[[4-nitro-3-(trifluoromethyl)phenyl]amino]cyclohexyl)oxy]ethan-1-one as a yellow solid (462.4 mg, 36%); (ES, m/z): [M+H]+ 563.00; $^1$H NMR (300 MHz, CDCl$_3$): δ 8.00 (d, J=8.7 Hz, 1H), 7.09-7.18 (m, 2H), 6.77-6.88 (m, 3H), 6.61 (dd, J=2.1 Hz, 8.7 Hz, 1H), 5.03 (broad s, 1H), 4.45 (d, J=6.9 Hz, 1H), 4.20 (s, 2H), 3.67-3.78 (m, 3H), 3.40-3.49 (m, 3H), 2.66-2.99 (m. 6H), 2.13-2.23 (m, 4H), 1.41-1.63 (m, 3H), 1.21-1.34 (m, 3H).

EXAMPLE 13: Preparation of Compound 77

Compound 77

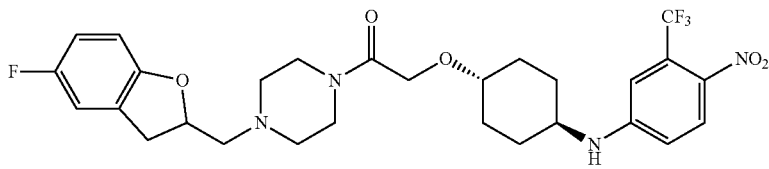

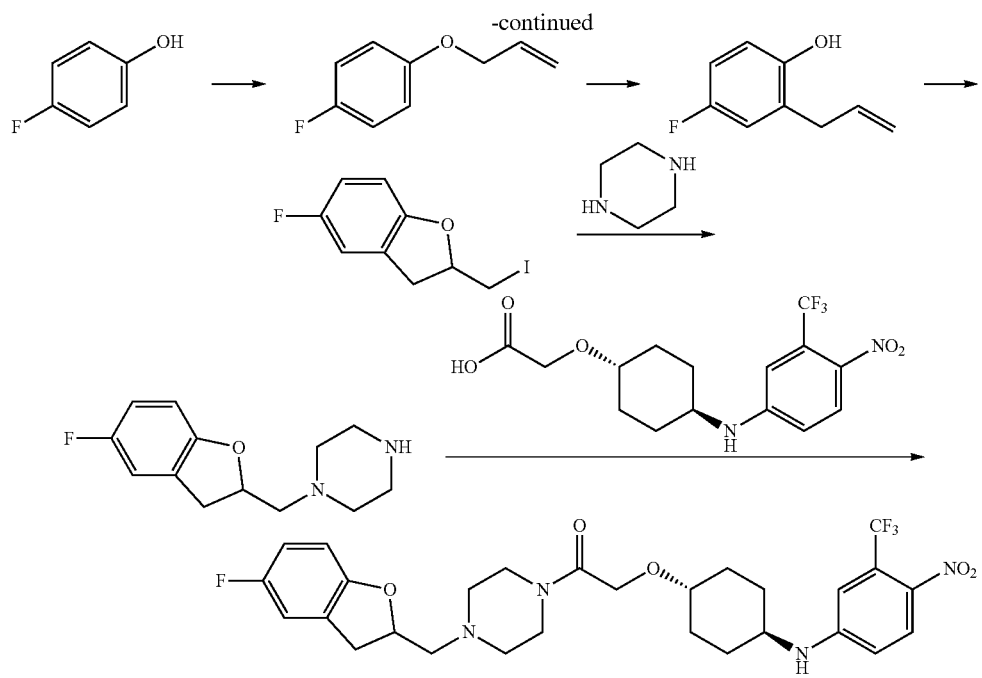

Step 1. Formation of 1-allyloxy-4-fluoro-benzene

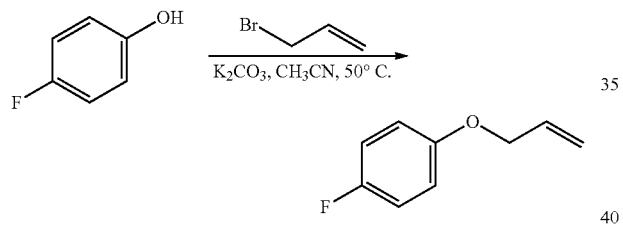

Into a 1 L round-bottomed flask containing 500 ml of acetonitrile was added 4-fluorophenol (30.0 g, 267.6 mmol), 3-bromoprop-1-ene (41.7 g, 344.7 mmol, 1.3 eq), and potassium carbonate (55 g, 398 mmol, 1.5 eq). The mixture was stirred for 3.5 hours at 60° C. (oil bath). The solids were filtered off and the filtrate was concentrated under vacuum leaving 25.0 grams of the crude product as a yellow oil; 61%.

Step 2. Formation of 2-allyl-4-fluoro-phenol

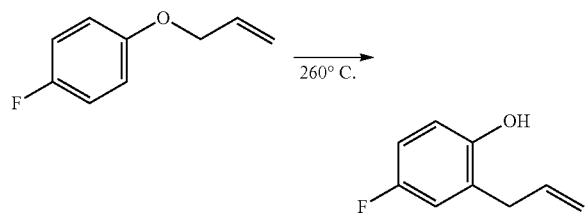

In a 250 ml round-bottomed flask, 1-allyloxy-4-fluoro-benzene (23.0 g, 151 mmol) was heated at 260° C. for 5 hours. The crude product was purified by silica gel chromatography using petroleum ether/ethyl acetate to elute. The product containing fractions were concentrated under vacuum to provide 18.0 grams (78%) of a yellow oil.

Step 3. Formation of 5-fluoro-2-iodomethyl-2,3-dihydro-benzofuran

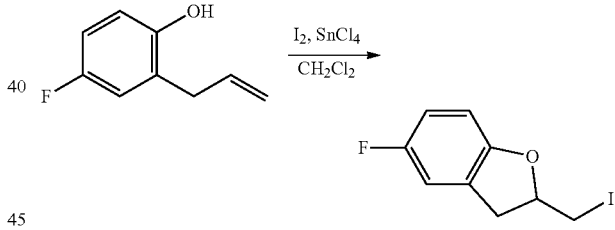

To a solution of 4-fluoro-2-(prop-2-en-1-yl)phenol (5 g, 32.9 mmol) in dichloromethane (125 mL) was added $SnCl_4$ (4.28 g, 16.5 mmol) and iodine (8.36 g, 32.9 mmol) at room temperature. After an additional 18 hours, the reaction was quenched with water (150 ml) and the pH value was adjusted to ~8 with aqueous sodium hydroxide solution (2N). The organic layer was separated and the aqueous layer was extracted with dichloromethane (2×100 mL). The combined organic layer was washed with $Na_2S_2O_4$ (3×100 mL, 5%) to remove iodine and dried over anhydrous magnesium sulfate. The solution was filtered and concentrated under vacuum. The crude residue was purified by silica gel chromatography using 0.5-1% ethyl acetate in petroleum ether to elute. The product-containing fractions were combined and concentrated under vacuum to afford 5-fluoro-2-(iodomethyl)-2,3-dihydro-1-benzofuran as a yellow oil (5 g, 54%); $^1H$ NMR (300 MHz, DMSO): δ 7.03-7.08 (dd, J=5.7 Hz, 8.4 Hz, 1H), 6.93-6.86 (dt, J=2.7 Hz, 8.7 Hz, 1H), 6.76-6.70 (m, 1H), 4.88-4.79 (m, 1H), 3.49-3.60 (m, 2H), 3.41-3.32 (dd, J=7.2 Hz, 16.5 Hz, 1H), 2.96-2.88 (dd, J=7.2 Hz, 16.5 Hz, 1H).

Step 4. Formation of 1-(5-fluoro-2,3-dihydro-benzofuran-2-ylmethyl)-piperazine

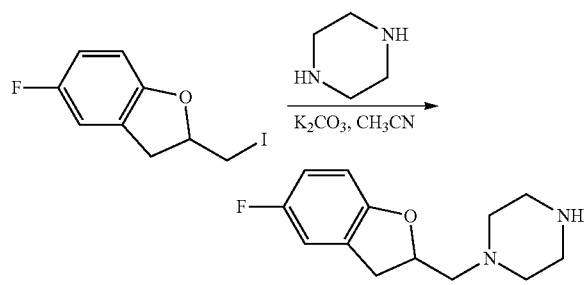

Into a 100 ml round-bottomed flask containing 40 ml of acetonitrile was added 5-fluoro-2-iodomethyl-2,3-dihydro-benzofuran (5.7 g, 20.5 mmol), piperazine (6.6 g, 76.6 mmol, 4 eq), and potassium carbonate (4.2 g, 30.4 mmol, 1.5 eq). The mixture was stirred at room temperature for 4 hours. The reaction contents were diluted with water and then extracted with 3×200 ml of ethyl acetate. The organic layers were combined, dried over sodium sulfate, filtered, and then concentrated under vacuum. The crude material was then purified via silica gel chromatography using methanol/dichloromethane to elute. The product containing fractions were then concentrated under vacuum to provide 2.2 g (45%) of the substituted piperazine as a dark red oil.

Step 5. Formation of 2-chloro-1-[4-(5-fluoro-2,3-dihydro-benzofuran-2-ylmethyl)-piperazin-1-yl]-ethanone (#77)

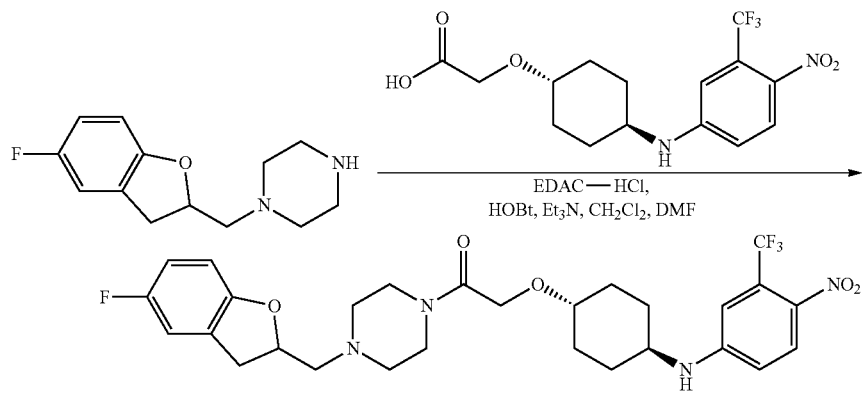

Into a 50 ml round-bottomed flask containing 20 ml of dichloromethane was added 1-(5-fluoro-2,3-dihydro-benzofuran-2-ylmethyl)-piperazine (100 mg, 0.42 mmol), 2-[(4-[[4-nitro-3-(trifluoromethyl)phenyl]amino]cyclohexyl)oxy]acetic acid (230 mg, 0.63 mmol, 1.5 eq), EDAC.HCl (122 mg, 0.64 mmol, 1.5 eq), HOBt (86 mg, 0.64 mmol, 1.5 eq) and triethylamine (128 mg, 1.26 mmol, 3.0 eq). The solution was stirred at room temperature for 16 hours. The crude contents were diluted with water and then extracted with 3×50 ml of ethyl acetate. The organic fractions were combined, dried over magnesium sulfate, filtered, and then concentrated under vacuum. The crude material was then chromatographed on silica gel using methanol/dichloromethane to elute. The product-containing fractions were then combined and concentrated to provide 150 mg of the amide as a light yellow solid (57%). (ES, m/z): [M+H]+ 581.3; $^1$H NMR (300 MHz, CDCl$_3$): δ 8.02 (d, J=9 Hz, 1H), 6.75-6.91 (m, 3H), 6.60-6.71 (m, 2H), 5.00 (broad s, 1H), 4.48 (d, J=7.5 Hz, 1H), 3.66 (s, 2H), 3.48-3.80 (broad m, 4H), 3.22-3.50 (broad m, 3H), 2.95 (m, 1H), 2.75-2.90 (m, 1H), 2.50-2.75 (broad m, 4H), 2.16 (d, J=8.7 Hz, 4H), 1.38-1.58 (dd, J=10.5, 22.5 Hz, 2H), 1.22-1.34 (dd, J=~10.9, 22.5 Hz, 2H).

EXAMPLE 14: Preparation of Compound 76

Compound 76

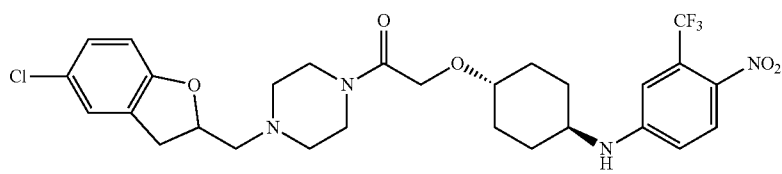

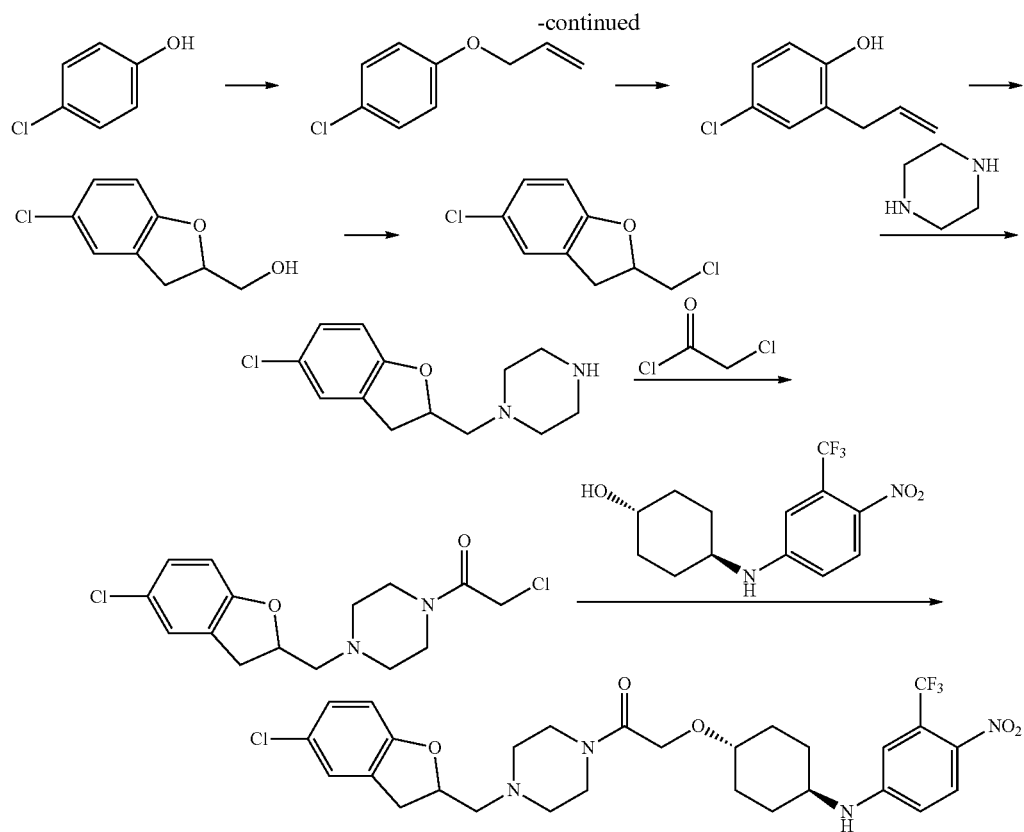

Step 1. Formation of 1-chloro-4-(prop-2-en-1-yloxy)benzene

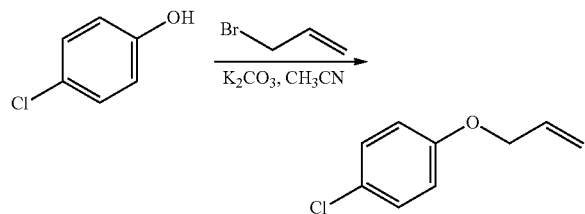

To a solution of 4-chlorophenol (30 g, 233 mmol) in acetonitrile (100 ml) was added potassium carbonate (48.1 g, 349 mmol, 1.5 eq) and allyl bromide (36.28 g, 299.9 mmol, 1.3 eq) dropwise with stirring for 5 hours at 50° C. in an oil bath. The solids were filtered out and the liquid was concentrated under vacuum to afford 1-chloro-4-(prop-2-en-1-yloxy)benzene as yellow oil (34 g, 86%); $^1$H NMR (300 MHz, CDCl$_3$): δ 7.20-7.25 (m, 2H), 6.81-6.86 (m, 2H), 5.96-6.09 (m, 1H), 5.27-5.44 (m, 2H), 4.49-4.51 (m, 2H).

Step 2. Formation of 4-chloro-2-(prop-2-en-1-yl)phenol

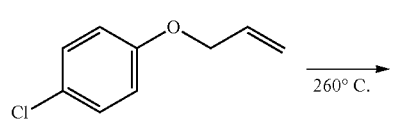

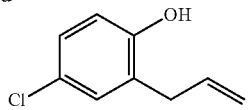

1-chloro-4-(prop-2-en-1-yloxy)benzene (34 g, 202 mmol) was stirred for 7 hours at 260° C. The reaction mixture was purified via silica gel chromatography using 3% ethyl acetate in petroleum ether to elute. The product-containing fractions were combined and concentrated to afford 4-chloro-2-(prop-2-en-1-yl)phenol as light brown oil (17 g, crude); $^1$H NMR (300 MHz, CDCl$_3$): δ 7.03-7.09 (m, 2H), 6.75 (d, J=3.0 Hz, 1H), 5.92-6.05 (m, 1H), 5.13-5.20 (m, 2H), 3.37 (d, J=6.3 Hz, 2H).

Step 3. Formation of (5-chloro-2,3-dihydro-1-benzofuran-2-yl)methanol

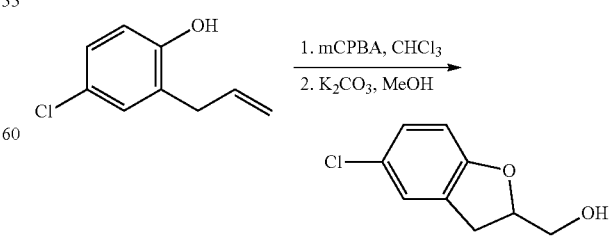

To a solution of 4-chloro-2-(prop-2-en-1-yl)phenol (17 g, crude, nominally 101 mmol) in chloroform (100 ml) was added mCPBA (17.4 g, 101 mmol, 1 eq) with stirring for 1 hour at 50° C. in an oil bath. Then the reaction mixture was concentrated under vacuum and re-dissolved in MeOH (100 ml). Potassium carbonate (27.6 g, 200 mmol, 2 eq) was added and the mixture was stirred for 5 hours at 50° C. The solids were filtered off and the filtrate was concentrated under vacuum. The crude material was purified by silica gel chromatography using 3% ethyl acetate in petroleum ether to elute. The product-containing fractions were combined and concentrated under vacuum to afford (5-chloro-2,3-dihydro-1-benzofuran-2-yl)methanol as yellow oil (6.15 g); $^{1}$H NMR (300 MHz, CDCl$_3$): δ 7.00-7.18 (m, 2H), 6.80 (d, J=8.7 Hz, 1H), 4.88-4.97 (m, 1H), 3.85-3.90 (m, 1H), 3.70-3.79 (m, 1H), 3.19-3.27 (dd, J=9.3 Hz, 15.9 Hz, 1H), 2.98-3.05 (dd, J=7.5 Hz, 15.9 Hz, 1H), 2.10 (broad s, 1H).

Step 4. Formation of 5-chloro-2-(chloromethyl)-2,3-dihydro-1-benzofuran

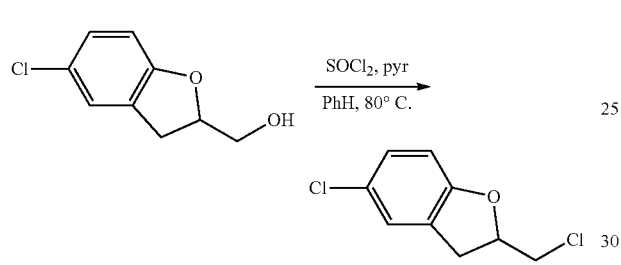

To a solution of (5-chloro-2,3-dihydro-1-benzofuran-2-yl)methanol (3 g, 16 mmol) in benzene (50 ml) was added pyridine (1.55 g, 19.6 mmol, 1.2 eq) and thionyl chloride (2.72 g, 23.0 mmol) dropwise with stirring at 0° C. for 7 hours at 80° C. in an oil bath. The reaction mixture was adjusted to ~pH 8 with aqueous sodium bicarbonate and then extracted with ethyl acetate (3×50 mL). The organic layers were combined, dried over anhydrous magnesium sulfate, filtered, and concentrated under vacuum. The crude material was purified by silica gel chromatography using 3% ethyl acetate in petroleum ether to elute. The product-containing fractions were combined and concentrated under vacuum to afford 5-chloro-2-(chloromethyl)-2,3-dihydro-1-benzofuran as an off-white solid (1.5 g, 46%); $^{1}$H NMR (300 MHz, CDCl$_3$): δ 7.06-7.14 (m, 2H), 6.70 (d, J=8.4 Hz, 1H), 4.99-5.10 (m, 1H), 3.64-3.76 (m, 2H), 3.32-3.40 (dd, J=9.3 Hz, 16.2 Hz, 1H), 3.09-3.17 (dd, J=6.6 Hz, 16.2 Hz, 1H).

Step 5. Formation of 1-[(5-chloro-2,3-dihydro-1-benzofuran-2-yl)methyl]piperazine

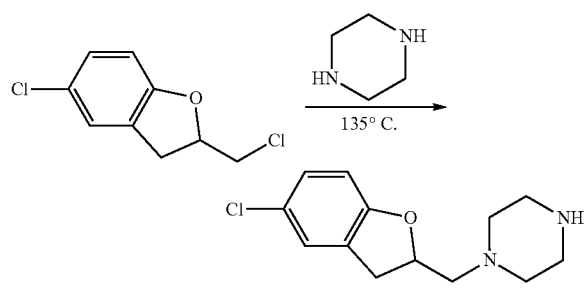

To 5-chloro-2-(chloromethyl)-2,3-dihydro-1-benzofuran (1.6 g, 7.9 mmol) was added piperazine (2.72 g, 31.6 mmol, 4 eq) with stirring for 15 hours at 135° C. in an oil bath. The crude material was purified by silica gel chromatography using 3% dichloromethane in methanol to elute. The product-containing fractions were combined and concentrated under vacuum to afford 1-[(5-chloro-2,3-dihydro-1-benzofuran-2-yl)methyl]piperazine as a light yellow solid (1.3 g, 65%); (ES, m/z): [M+H]$^+$ 253; $^{1}$H NMR (300 MHz, CDCl$_3$): δ 7.03-7.11 (m, 2H), 6.68 (d, J=8.4 Hz, 1H), 4.93-5.03 (m, 1H), 3.20-3.29 (m, 1H), 2.88-2.99 (m, 6H), 2.72-2.79 (m, 1H), 2.49-2.63 (m, 5H).

Step 6. Formation of 2-chloro-1-[4-[(5-chloro-2,3-dihydro-1-benzofuran-2-yl)methyl]piperazin-1-yl]ethan-1-one

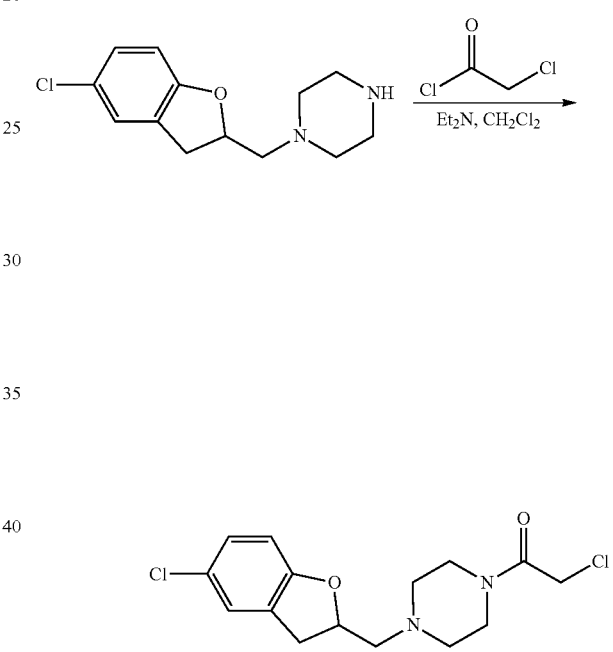

To a solution of 1-[(5-chloro-2,3-dihydro-1-benzofuran-2-yl)methyl]piperazine (1.3 g, 5.1 mmol) in dichloromethane (50 ml) was added triethylamine (782 mg, 7.73 mmol, 1.5 eq) and 2-chloroacetyl chloride (758 mg, 6.71 mmol, 1.3 eq) dropwise with stirring at 0° C. for 1 hour at room temperature. The reaction mixture was quenched by the addition of water (80 ml) and extracted with dichloromethane (3×50 ml). The organic layers were combined, dried over anhydrous magnesium sulfate, filtered, and concentrated under vacuum. The crude material was purified by silica gel chromatography using 3% ethyl acetate in petroleum ether to elute. The product-containing fractions were combined and concentrated under vacuum to afford 2-chloro-1-[4-[(5-chloro-2,3-dihydro-1-benzofuran-2-yl)methyl]piperazin-1-yl]ethan-1-one as yellow oil (1.0 g, 59%); (ES, m/z): [M+H]$^+$ 329; $^{1}$H NMR (300 MHz, CDCl$_3$): δ 7.04-7.12 (m, 2H), 6.69 (d, J=8.4 Hz, 1H), 4.95-5.08 (m, 1H), 4.11 (s, 2H), 3.56-3.73 (m, 5H), 3.23-3.32 (dd, J=9.3 Hz, 15.9 Hz, 1H), 2.91-2.99 (dd, J=7.8 Hz, 15.9 Hz, 1H), 2.77-2.84 (dd, J=7.8 Hz, 13.5 Hz, 1H), 2.48-2.75 (m, 4H).

Step 7. Formation of 1-[4-[(5-chloro-2,3-dihydro-1-benzofuran-2-yl)methyl]piperazin-1-yl]-2-[(4-[[4-nitro-3-(trifluoromethyl)phenyl]amino]cyclohexyl)oxy]ethan-1-one (#76)

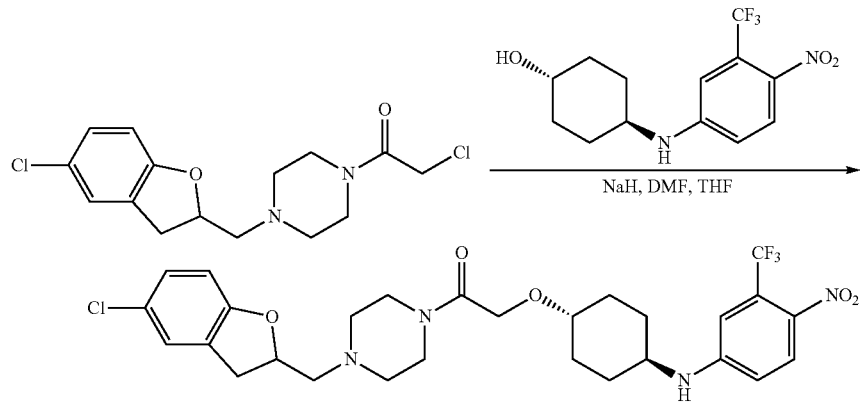

To a solution of 4-[[4-nitro-3-(trifluoromethyl)phenyl]amino]cyclohexan-1-ol (40 mg, 0.13 mmol) in tetrahydrofuran (1 ml) and N,N-dimethylformamide (0.3 ml) was added sodium hydride (26 mg, 1.08 mmol, 8 eq) with stirring for 30 minutes at 0° C. Then 2-chloro-1-[4-[(5-chloro-2,3-dihydro-1-benzofuran-2-yl)methyl]piperazin-1-yl]ethan-1-one (90 mg, 0.27 mmol, 2 eq) in tetrahydrofuran (0.5 ml) was added with stirring for 5 hours at room temperature. The reaction mixture was quenched by water (20 ml) and extracted with ethyl acetate (3×30 ml). The organic layers were combined and dried over anhydrous magnesium sulfate, filtered, and concentrated under vacuum. The crude material was purified by Pre-TLC using 50% ethyl acetate in petroleum ether to elute. The product-containing fractions were combined and concentrated under vacuum to afford 1-[4-[(5-chloro-2,3-dihydro-1-benzofuran-2-yl)methyl]piperazin-1-yl]-2-[(4-[[4-nitro-3-(trifluoromethyl)phenyl]amino]cyclohexyl)oxy]ethan-1-one as a yellow solid (29.8 mg, 38%); (ES, m/z): [M+H]$^+$ 597.35; $^1$H NMR (300 MHz, CDCl$_3$): δ 8.02 (d, J=7.2 Hz, 1H), 7.04-7.12 (m, 2H), 6.84 (d, J=2.4 Hz, 1H), 6.61-6.71 (m, 2H), 5.01 (broad s, 1H), 4.46 (d, J=7.8 Hz, 1H), 4.19 (s, 2H), 3.60-3.73 (m, 3H), 3.40-3.47 (m, 2H), 3.23-3.32 (dd, J=9.3 Hz, 15.9 Hz, 1H), 2.92-2.99 (dd, J=7.8 Hz, 15.9 Hz, 1H), 2.77-2.84 (m, 1H), 2.62-2.77 (m, 4H), 2.12-2.16 (m, 4H), 1.41-1.52 (m, 3H), 1.22-1.30 (m, 3H).

EXAMPLE 15: Preparation of Compound 78

Compound 78

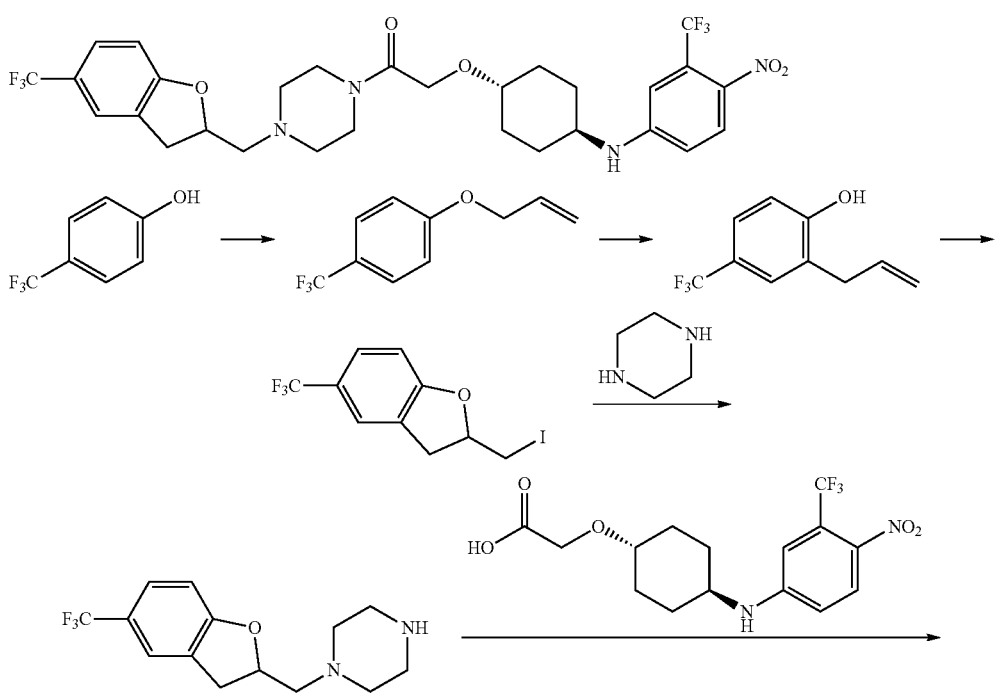

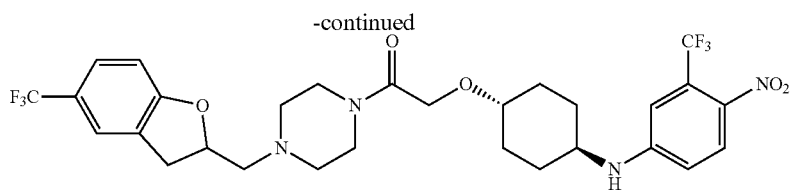

Step 1. Formation of 1-(prop-2-en-1-yloxy)-4-(trifluoromethyl)benzene

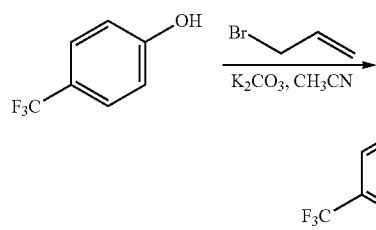

To a solution of 4-(trifluoromethyl)phenol (50 g, 308 mmol) in CH$_3$CN (600 ml) was added potassium carbonate (64 g, 463 mmol, 1.5 eq) and allyl bromide (48 g, 397 mmol, 1.3 eq) with stirring for overnight at 50° C. in an oil bath. The solids were filtered off and the filtrate was concentrated to a minimum volume, which was diluted by water (200 ml) and extracted with ethyl acetate (3×100 ml). The combined organic layers were washed with brine (2×200 ml), dried over anhydrous magnesium sulfate, filtered, and then concentrated under vacuum to afford 1-(prop-2-en-1-yloxy)-4-(trifluoromethyl)benzene as yellow oil (35 g, 56%); $^1$H NMR (300 MHz, CDCl$_3$): δ 7.52 (d, J=8.7 Hz, 2H), 6.96 (d, J=8.7 Hz, 2H), 5.98-6.11 (m, 1H), 5.30-5.46 (m, 2H), 4.57-4.58 (m, 2H).

Step 2. Formation of 2-(prop-2-en-1-yl)-4-(trifluoromethyl)phenol

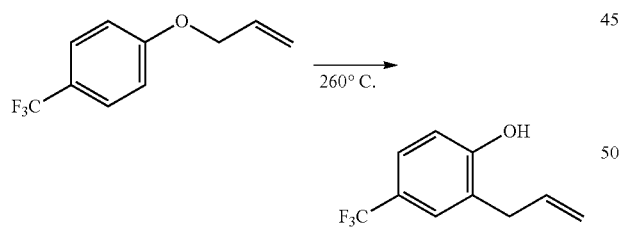

A solution of 1-(prop-2-en-1-yloxy)-4-(trifluoromethyl)benzene (30 g, 148 mmol) in dichloromethane (250 ml) was treated with 1N solution of BCl$_3$ (163 ml, 163 mmol, 1.1 eq) in dichloromethane for 2.5 hours at −20° C. under an inert atmosphere of nitrogen. The reaction mixture was then quenched with ice-water (200 ml) and the organic layer was separated out. The aqueous layer was extracted further with dichloromethane (3×200 ml) and the combined organic layer was washed with saturated aqueous sodium bicarbonate (200 ml) and then dried over anhydrous magnesium sulfate. The solution was filtered and then concentrated under vacuum to afford 2-(prop-2-en-1-yl)-4-(trifluoromethyl)phenol as colorless oil (25 g, 83%); $^1$H NMR (300 MHz, CDCl$_3$): δ 7.38 (d, J=7.5 Hz, 2H), 6.86 (t, J=8.7 Hz, 1H), 5.94-6.07 (m, 1H), 5.60 (s, 1H), 5.15-5.22 (m, 2H), 3.43 (d, J=6.6 Hz, 2H).

Step 3. Formation of 2-(iodomethyl)-5-(trifluoromethyl)-2,3-dihydro-1-benzofuran

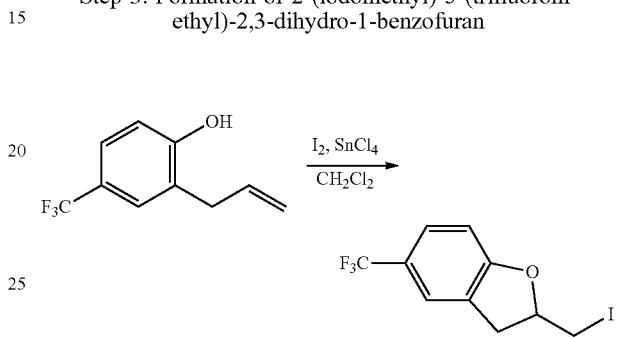

To a solution of 2-(prop-2-en-1-yl)-4-(trifluoromethyl)phenol (4 g, 20 mmol) in dichloromethane (50 ml) was added SnCl$_4$ (2.6 g, 10.0 mmol, 0.5 eq) dropwise and iodine (5.03 g, 19.8 mmol, 1 eq) with stirring for 6 hours at room temperature. The reaction mixture was diluted with dichloromethane (200 ml) and quenched by the addition of water (100 ml). The organic layer was separated and the pH value of the aqueous layer was adjusted to ~8 with aqueous sodium bicarbonate. The aqueous layer was extracted further with dichloromethane (3×100 ml). The organic layers were combined, washed with aqueous Na$_2$S$_2$O$_4$ (5%, 100 ml) to remove remaining iodine, dried over anhydrous magnesium sulfate, filtered, and concentrated under vacuum. The crude material was purified by silica gel chromatography using 1% ethyl acetate in petroleum ether to elute. The product-containing fractions were combined and concentrated under vacuum to afford 2-(iodomethyl)-5-(trifluoromethyl)-2,3-dihydro-1-benzofuran as colorless oil (2.8 g, 43%); $^1$H NMR (300 MHz, CDCl$_3$): δ 7.39 (d, J=5.7 Hz, 2H), 6.83 (d, J=8.7 Hz, 1H), 4.91-5.00 (m, 1H), 3.34-3.48 (m, 3H), 3.05-3.12 (m, 1H).

Step 4. Formation of 1-[[5-(trifluoromethyl)-2,3-dihydro-1-benzofuran-2-yl]methyl]piperazine

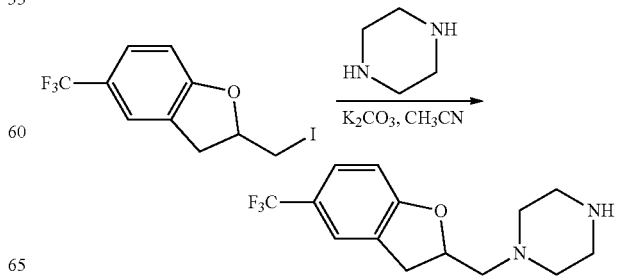

To a solution of 2-(iodomethyl)-5-(trifluoromethyl)-2,3-dihydro-1-benzofuran (2.8 g, 8.5 mmol) in CH$_3$CN (40 ml) was added potassium carbonate (2.36 g, 17.1 mmol, 2 eq) and piperazine (2.94 g, 34.1 mmol, 4 eq) at room temperature. The mixture was heated at reflux for 3 hours, the solids were filtered off, and the filtrate was concentrated under vacuum. The crude material was purified by silica gel chromatography using 1-2.5% methanol in dichloromethane to elute. The product-containing fractions were combined and concentrated under vacuum to afford 1-[[5-(trifluoromethyl)-2,3-dihydro-1-benzofuran-2-yl]methyl]piperazine as light yellow oil (1.25 g, 51%); (ES, m/z): [M+H]$^+$ 287; $^1$H NMR (300 MHz, CDCl$_3$): δ 7.37 (d, J=9.0 Hz, 2H), 6.83 (d, J=8.4 Hz, 1H), 5.00-5.10 (m, 1H), 3.26-3.35 (m, 1H), 2.96-3.04 (m, 1H), 2.88-2.95 (m, 4H), 2.78-2.80 (m, 1H), 2.54-2.69 (m, 4H).

Step 5. Formation of 2-[(4-[[4-nitro-3-(trifluoromethyl)phenyl]amino]cyclohexyl)oxy]-1-(4-[[5-(trifluoromethyl)-2,3-dihydro-1-benzofuran-2-yl]methyl]piperazin-1-yl)ethan-1-one (#78)

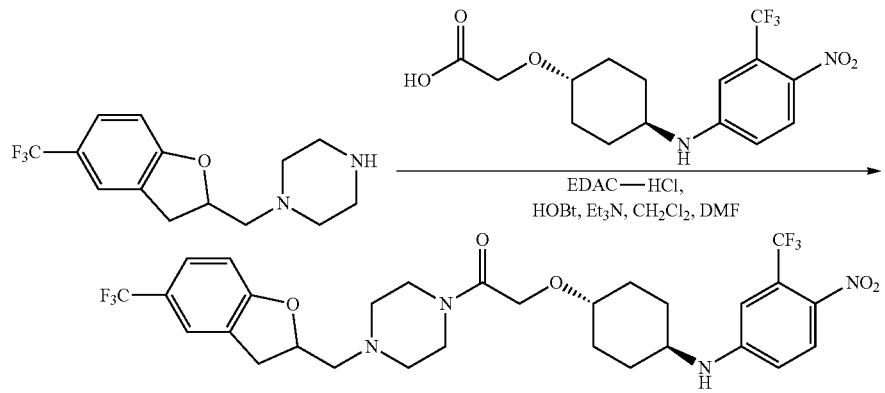

To a solution of 2-[(4-[[4-nitro-3-(trifluoromethyl)phenyl]amino]cyclohexyl)oxy]acetic acid (100 mg, 0.28 mmol) in dichloromethane (30 ml) was added EDAC.HCl (79.6 mg, 0.42 mmol, 1.5 eq), HOBt (55.9 mg, 0.41 mmol, 1.5 eq), triethylamine (55.9 mg, 0.55 mmol, 1.5 eq) and 1-[[5-(trifluoromethyl)-2,3-dihydro-1-benzofuran-2-yl]methyl]piperazine (86.9 mg, 0.30 mmol, 1.1 eq). The solution was stirred at room temperature overnight. The reaction mixture was diluted with water (50 ml) and extracted with ethyl acetate (3×30 ml). The organic layers were combined, dried over anhydrous magnesium sulfate, filtered, and concentrated under vacuum. The crude material was purified by silica gel chromatography using 25% ethyl acetate in dichloromethane to elute. The product-containing fractions were combined and concentrated under vacuum to afford 2-[(4-[[4-nitro-3-(trifluoromethyl)phenyl]amino]cyclohexyl)oxy]-1-(4-[[5-(trifluoromethyl)-2,3-dihydro-1-benzofuran-2-yl]methyl]piperazin-1-yl)ethan-1-one as a yellow solid (69.9 mg, 40%); (ES, m/z): [M+H]$^+$ 631.20; $^1$H NMR (300 MHz, CDCl$_3$): δ 8.01 (d, J=9.0 Hz, 1H), 7.44 (m, 2H), 6.84 (m, 2H), 6.62 (dd, J=2.7 Hz, 9.0 Hz, 1H), 5.10 (broad s, 1H), 4.47 (d, J=8.1 Hz, 1H), 4.22 (s, 2H), 3.61-3.82 (m, 3H), 3.36-3.48 (m, 3H), 3.01-3.07 (dd, J=7.8 Hz, 16.2 Hz, 1H), 2.80-2.95 (m, 1H), 2.54-2.74 (m, 4H), 2.12-2.18 (m, 4H), 1.43-1.59 (m, 3H), 1.24-1.35 (m, 3H).

EXAMPLE 16: Preparation of Compound 83

Compound 83

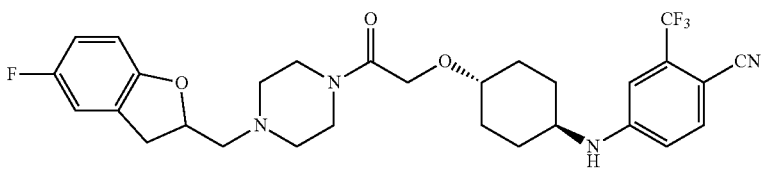

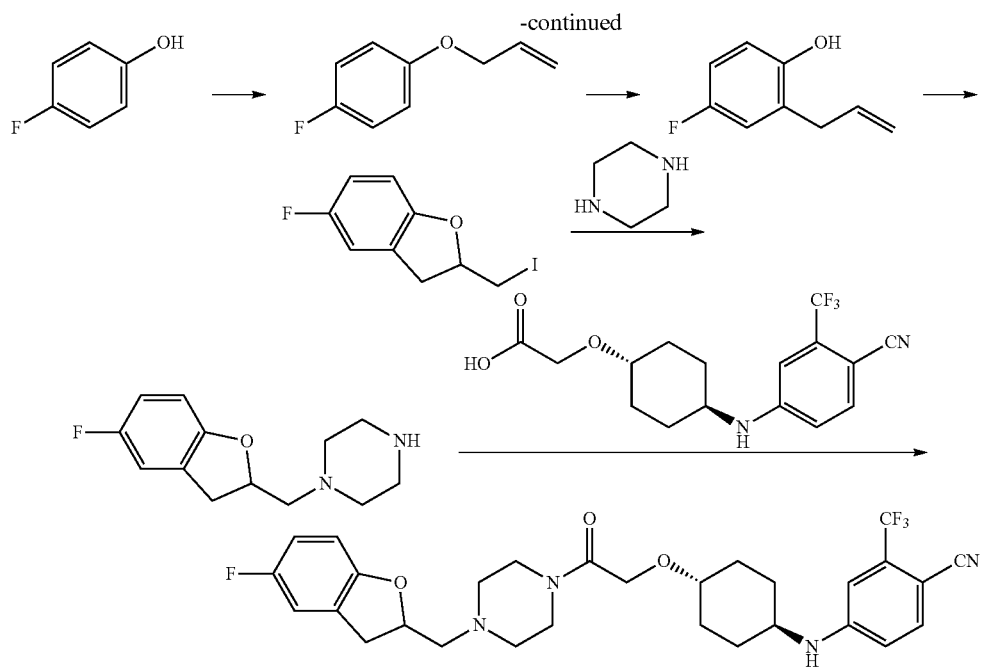

Step 1. Formation of 1-allyloxy-4-fluoro-benzene

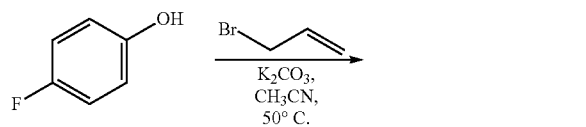

Into a 1 L round-bottomed flask containing 500 ml of acetonitrile was added 4-fluorophenol (30.0 g, 267.6 mmol), 3-bromoprop-1-ene (41.7 g, 344.7 mmol, 1.3 eq), and potassium carbonate (55 g, 398 mmol, 1.5 eq). The mixture was stirred for 3.5 hours at 60° C. (oil bath). The solids were filtered off and the filtrate was concentrated under vacuum leaving 25.0 grams of the crude product as a yellow oil; 61%.

Step 2. Formation of 2-allyl-4-fluoro-phenol

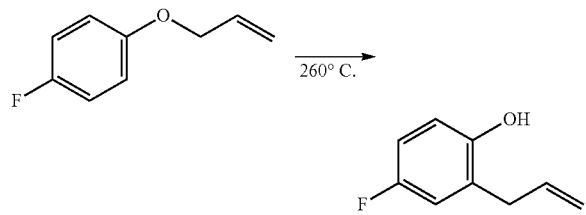

In a 250 ml round-bottomed flask, 1-fluoro-4-(prop-2-en-1-uloxy)benzene (23.0 g, 151 mmol) was heated at 260° C. for 5 hours. The crude product was purified by silica gel chromatography using petroleum ether/ethyl acetate to elute. The product containing fractions were concentrated under vacuum to provide 18.0 grams (78%) of a yellow oil.

Step 3. Formation of 5-fluoro-2-iodomethyl-2,3-dihydro-benzofuran

To a solution of 4-fluoro-2-(prop-2-en-1-yl)phenol (5 g, 32.9 mmol) in dichloromethane (125 mL) was added SnCl$_4$ (4.28 g, 16.5 mmol) and iodine (8.36 g, 32.9 mmol) at room temperature. After an additional 18 hours, the reaction was quenched with water (150 ml) and the pH value was adjusted to 8 with aqueous NaOH solution (2N). The organic layer was separated and the aqueous layer was extracted with dichloromethane (2×100 mL). The combined organic layer was washed with Na$_2$S$_2$O$_4$ (3×100 mL, 5%) to remove iodine and dried over anhydrous magnesium sulfate. The solution was filtered and then concentrated under vacuum. The crude residue was purified by a silica gel column, eluted with 0.5-1% ethyl acetate in petroleum ether to afford 5-fluoro-2-(iodomethyl)-2,3-dihydro-1-benzofuran as a yellow oil (5 g, 54%); $^1$H NMR (300 MHz, DMSO): δ 7.03-7.08 (dd, J=5.7 Hz, 8.4 Hz, 1H), 6.93-6.86 (dt, J=2.7 Hz, 8.7 Hz, 1H), 6.76-6.70 (m, 1H), 4.88-4.79 (m, 1H), 3.49-3.60 (m, 2H), 3.41-3.32 (dd, J=7.2 Hz, 16.5 Hz, 1H), 2.96-2.88 (dd, J=7.2 Hz, 16.5 Hz, 1H).

Step 4. Formation of 1-(5-fluoro-2,3-dihydro-benzofuran-2-ylmethyl)-piperazine

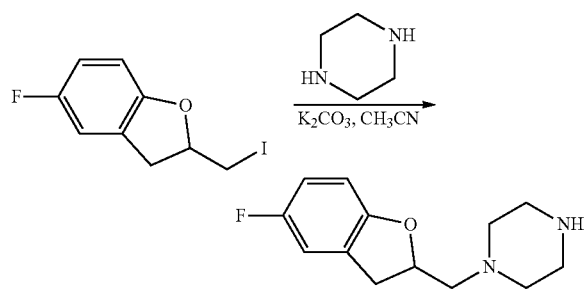

Into a 100 ml round-bottomed flask containing 40 ml of acetonitrile was added 5-Fluoro-2-iodomethyl-2,3-dihydro-benzofuran (5.7 g, 20.5 mmol), piperazine (6.6 g, 76.6 mmol, 4 eq), and potassium carbonate (4.2 g, 30.4 mmol, 1.5 eq). The mixture was stirred at room temperature for 4 hours. The reaction contents were diluted with water and then extracted with 3×200 ml of ethyl acetate. The organic layers were combined, dried over sodium sulfate, filtered, and then concentrated under vacuum. The crude material was then chromatography on silica gel using methanol/dichloromethane to elute. The product containing fractions were then concentrated under vacuum to provide 2.2 g (45%) of the substituted piperazine as a dark red oil.

Step 5. Formation of 4-[[4-(3-[4-[(5-fluoro-2,3-dihydro-1-benzofuran-2-yl)methyl]piperazin-1-yl]-2-oxopropoxy)cyclohexyl]amino]-2-(trifluoromethyl) benzonitrile (#83)

To a solution of 2-[(4-[[4-cyano-3-(trifluoromethyl)phenyl]amino]cyclohexyl)oxy]acetic acid (216 mg, 0.63 mmol, 1.5 eq) in dichloromethane (25 ml) was added EDAC.HCl (122 mg, 0.64 mmol, 1.5 eq), HOBt (86 mg, 0.64 mmol, 1.5 eq), triethylamine (128 mg, 1.26 mmol, 3 eq) and 1-[(5-fluoro-2,3-dihydro-1-benzofuran-2-yl)methyl]piperazine (100 mg, 0.42 mmol) at room temperature. The solution was stirred at room temperature overnight, diluted with dichloromethane (150 ml), and washed with water (80 ml). The organic layer was dried over anhydrous magnesium sulfate, filtered, and concentrated under vacuum. The crude material was purified by silica gel chromatography using 1-2% methanol in dichloromethane to elute. The product-containing fractions were combined and concentrated under vacuum to afford 4-[[4-(3-[4-[(5-fluoro-2,3-dihydro-1-benzofuran-2-yl)methyl]piperazin-1-yl]-2-oxopropoxy)cyclohexyl]amino]-2-(trifluoromethyl) benzonitrile as a white solid (0.18 g, 69%); (ES, m/z): $[M+H]^+$ 561.20; $^1H$ NMR (300 MHz, $CDCl_3$): δ 7.56 (d, J=8.7 Hz, 1H), 6.81-6.92 (m, 3H), 6.64-6.71 (m, 2H), 5.13 (broad s, 1H), 4.29 (d, J=7.8 Hz, 1H), 4.21 (s, 2H), 3.67-3.77 (m, 3H), 3.34-3.47 (m, 3H), 2.92-2.99 (dd, J=−8.1 Hz, −15.9 Hz, 1H), 2.51-2.89 (m, 5H), 2.15-2.25 (broadened d, J=9.9 Hz, 4H), 1.41-1.48 (m, 3H), 1.21-1.32 (m, 3H).

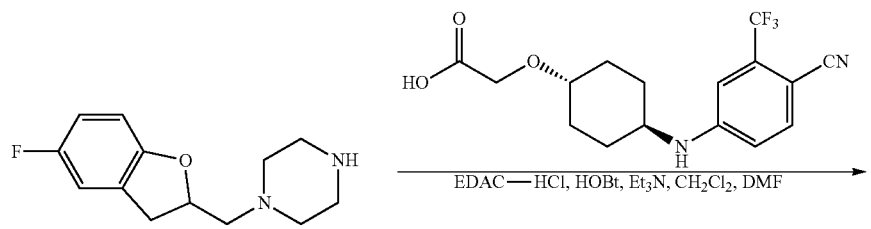

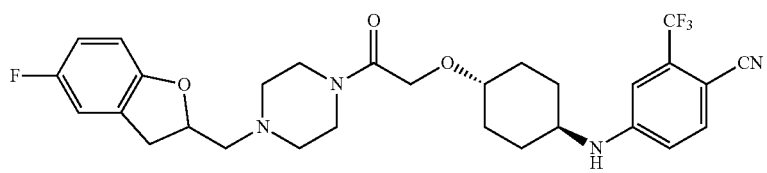

EXAMPLE 17: Preparation of Compound 80

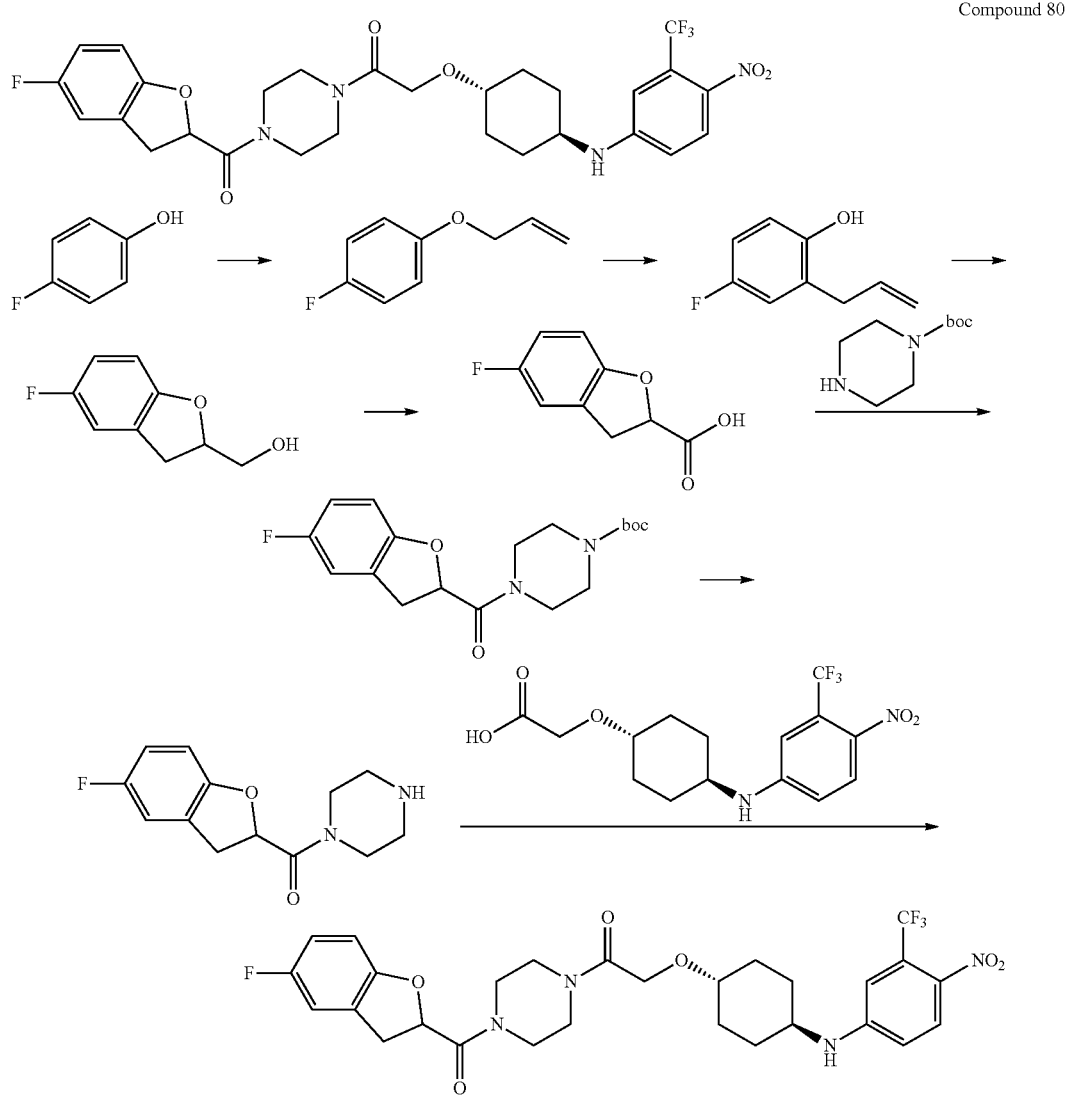

Step 1. Formation of 1-allyloxy-4-fluoro-benzene

Into a 1 L round-bottomed flask containing 500 ml of acetonitrile was added 4-fluorophenol (30.0 g, 267.6 mmol), 3-bromoprop-1-ene (41.7 g, 344.7 mmol, 1.3 eq), and potassium carbonate (55 g, 398 mmol, 1.5 eq). The mixture was stirred for 3.5 hours at 60° C. (oil bath). The solids were filtered off and the filtrate was concentrated under vacuum leaving 25.0 grams of the crude product as a yellow oil; 61%.

Step 2. Formation of 2-allyl-4-fluoro-phenol

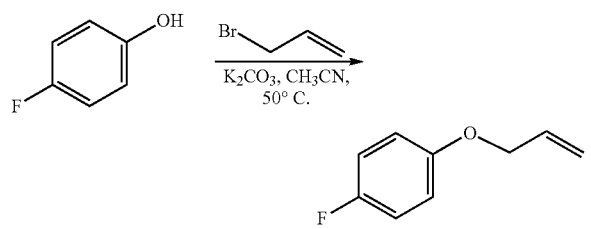

In a 250 ml round-bottomed flask, 1-fluoro-4-(prop-2-en-1-uloxy)benzene (23.0 g, 151 mmol) was heated at 260° C.

for 5 hours. The crude product was purified by silica gel chromatography using petroleum ether/ethyl acetate to elute. The product-containing fractions were concentrated under vacuum to provide 18.0 grams (78%) of a yellow oil.

Step 3. Formation of (5-fluoro-2,3-dihydro-benzofuran-2-yl)-methanol

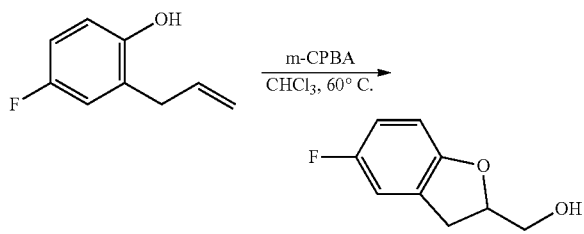

Into a 500 ml round-bottomed flask that contained a solution of 2-allyl-4-fluoro-phenol (10.0 g, 65.7 mmol) in 300 ml of chloroform was added m-CPBA (11 g, 64 mmol, ~0.96 eq). The mixture was heated at 60° C. (oil bath) for 6 hours. The contents were cooled to room temperature and the solids were filtered off and washed with 3×20 ml of chloroform. The filtrate was washed with saturated aqueous NaHCO$_3$ (2×100 mL) to remove traces of m-CPBA, dried over magnesium sulfate, filtered, and then concentrated under vacuum. The crude residue was then chromatographed on silica gel using petroleum ether/ethyl acetate to elute. The product-containing fractions were combined and concentrated under vacuum to afford 8.5 grams of the alcohol as a yellow oil (77%); $^1$H NMR (300 MHz, CDCl$_3$): δ 6.91-6.88 (m, 1H), 6.84-6.78 (m, 1H), 6.72-6.68 (m, 1H), 4.99-4.90 (m, 1H), 3.90-3.85 (dd, J=3.3 Hz, 12 Hz, 1H), 3.78-3.70 (dd, J=3.3 Hz, 12 Hz, 1H), 3.29-3.21 (dd, J=9.3 Hz, 15.9 Hz, 1H), 3.01-3.08 (dd, J=7.5 Hz, 15.9 Hz, 1H).

Step 4. Formation of 5-fluoro-2,3-dihydro-benzofuran-2-carboxylic acid

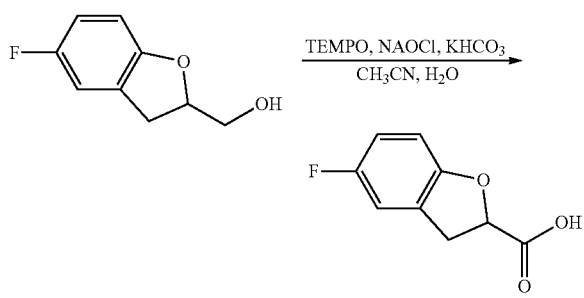

To a 500 ml round-bottomed flask that contained a solution of (5-fluoro-2,3-dihydro-benzofuran-2-yl)-methanol (3.0 g, 17.8 mmol) in 100 ml of acetonitrile was added a solution of potassium bicarbonate (7.14 g, 71.4 mmol, 4 eq) in 30 ml of water. The mixture was cooled to 0° C. and TEMPO (56 mg, 0.36 mmol, 2 mol %) was added, followed by the dropwise addition of NaOCl$_{(aq)}$ (60 ml, 1.1 eq). The mixture was then stirred for 1.5 hours at room temperature. The pH was then adjusted to 4 using aqueous hydrogen chloride (3N). The mixture was then extracted with 3×80 ml of ethyl acetate. The organic fractions were combined, dried over magnesium sulfate, filtered and then concentrated under vacuum to provide 2.0 grams of the crude product as a yellow solid.

Step 6. Formation of 4-(5-fluoro-2,3-dihydro-benzofuran-2-carbonyl)-piperazine-1-carboxylic acid tert-butyl ester

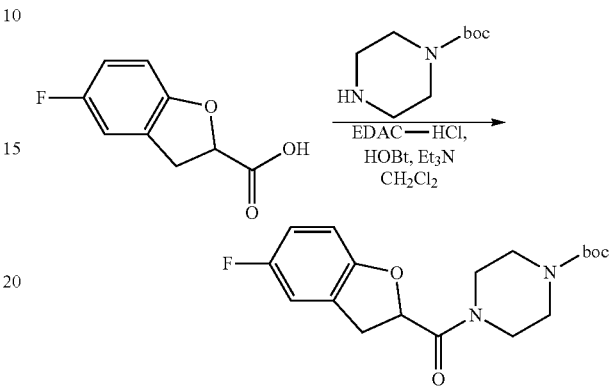

In a 250 ml round-bottomed flask containing a solution of 5-fluoro-2,3-dihydro-benzofuran-2-carboxylic acid (1.8 g, 9.9 mmol) in 100 ml of dichloromethane was added EDAC.HCl (2.85 g, 14.9 mmol, 1.5 eq), HOBt (2.00 g, 14.8 mmol, 1.5 eq), triethylamine (2.00 g, 19.8 mmol, 2.0 eq), and t-butyl piperazine-1-carboxylate (2.20 g, 11.8 mmol, 1.2 eq). The solution was stirred overnight at room temperature before diluting with 50 ml of water. The crude product was then extracted from the mixture using 3×50 ml of dichloromethane. The organic layers were combined, dried over magnesium sulfate, filtered, and then concentrated under vacuum. The crude residue was purified by silica gel chromatography using ethyl acetate/petroleum ether to elute. The product-containing fractions were combined and concentrated under vacuum to afford 1.8 grams of the desired amide as a light yellow solid (52%); $^1$H NMR (300 MHz, CDCl$_3$): δ 6.92 (dd, J=2.4 Hz, 7.8 Hz, 1H), 6.79 (m, 1H), 6.69 (dd, J=4.2 Hz, 8.7 Hz, 1H), 5.40 (dd, J=7.2 Hz, 9.9 Hz, 1H), 3.78-3.91 (m, 3H), 3.46-3.67 (m, 5H), 3.26-3.39 (m, 2H), 1.49 (s, 1H).

Step 7. Formation of (5-fluoro-2,3-dihydro-benzofuran-2-yl)-piperazin-1-yl-methanone

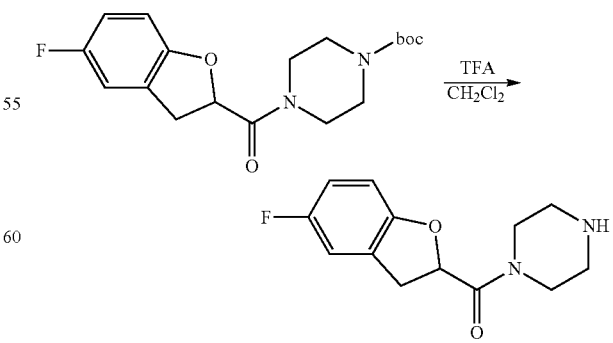

In a 100 ml round-bottomed flask was added 4-(5-Fluoro-2,3-dihydro-benzofuran-2-carbonyl)-piperazine-1-carboxylic acid tert-butyl ester (1.8 g, 5.1 mmol), 50 ml of dichloromethane, and 2 ml of trifluoroacetic acid. The solution was stirred at room temperature overnight. The solution was made basic with the addition of saturated aqueous sodium bicarbonate. The mixture was then extracted with 4×50 ml of dichloromethane. The organic fractions were combined, dried over magnesium sulfate, filtered, and concentrated under vacuum to afford 1.2 grams of the desired amine as a brown oil (94%).

Step 8. Formation of 1-[4-(5-fluoro-2,3-dihydro-benzofuran-2-carbonyl)-piperazin-1-yl]-2-[4-(4-nitro-3-trifluoromethyl-phenylamino)-cyclohexyloxy]-ethanone (#80)

mg, 0.55 mmol, 2.0 eq), and [4-(4-Nitro-3-trifluoromethyl-phenylamino)-cyclohexyloxy]-acetic acid (100 mg, 0.28 mmol). The solution was stirred overnight at room temperature before diluting with 30 ml of water. The crude product was then extracted from the mixture using 3×30 ml of ethyl acetate. The organic layers were combined, dried over magnesium sulfate, filtered, and then concentrated under vacuum. The crude residue was purified by silica gel chromatography using ethyl acetate/dichloromethane to elute. The product-containing fractions were combined and concentrated under vacuum to afford 72 mg of the desired amide as a yellow solid (44%); $^1$H NMR (300 MHz, CDCl$_3$): δ 8.04 (d, J=6.6 Hz, 1H), 6.95 (d, J=5.4, 1H), 6.83 (m, 2H), 6.66 (m, 2H), 5.43 (m, 1H), 4.25 (s, 1H), 3.75-3.95 (m, 4H),

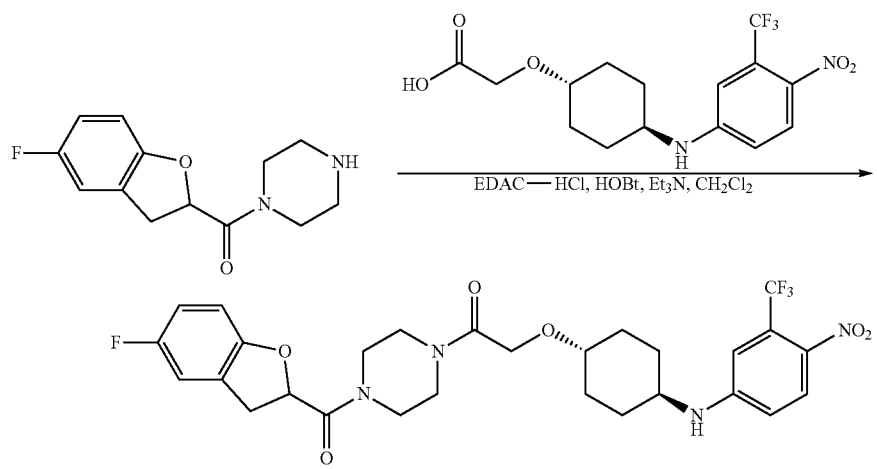

In a 50 ml round-bottomed flask containing a solution of (5-fluoro-2,3-dihydro-benzofuran-2-yl)-piperazin-1-yl-methanone (76 mg, 0.30 mmol, 1.1 eq) in 30 ml of dichloromethane was added EDAC.HCl (76 mg, 0.40 mmol, 1.5 eq), HOBt (56 mg, 0.41 mmol, 1.5 eq), triethylamine (56

3.27-3.80 (m, 8H), 2.12-2.22 (m, 4H), 1.50 (dd, J=7.8 Hz, 16.8 Hz, 2H), 1.31 (dd, J=7.8 Hz, 16.8 Hz, 2H).

EXAMPLE 18: Preparation of Compound 79

Compound 79

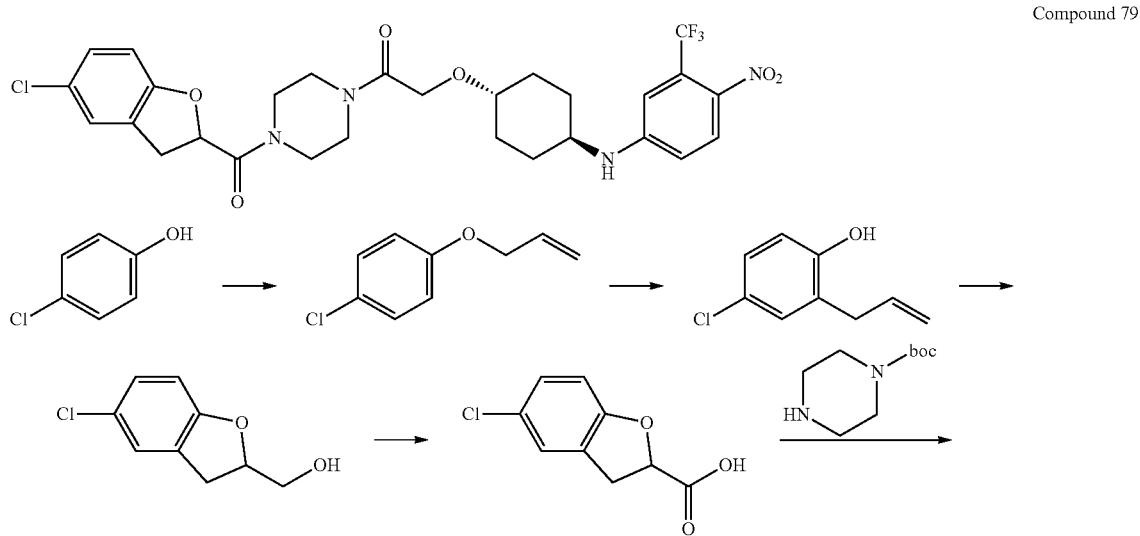

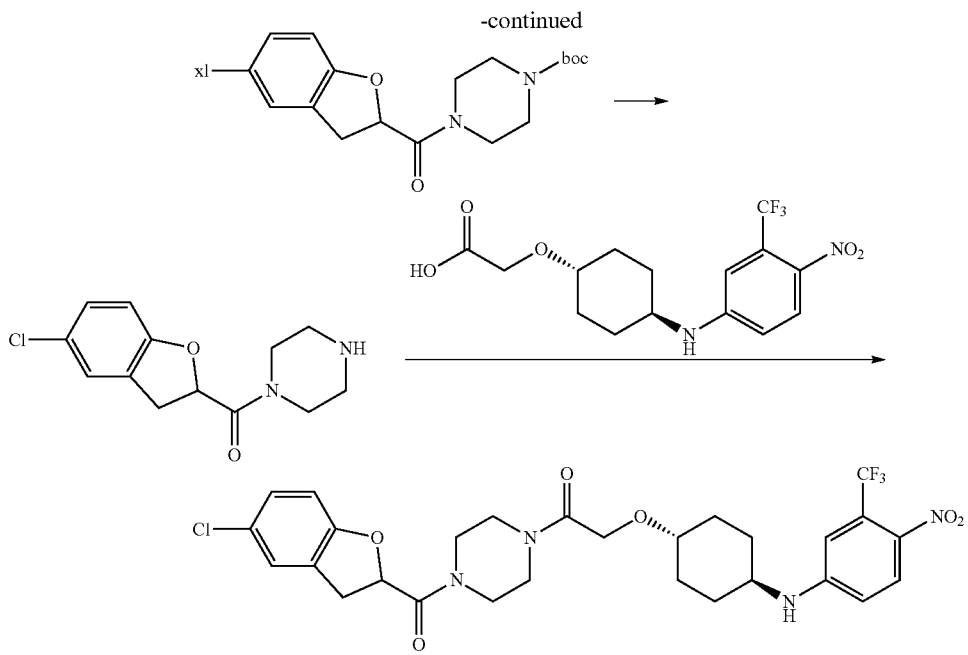

Step 1. Formation of 1-chloro-4-(prop-2-en-1-yloxy)benzene

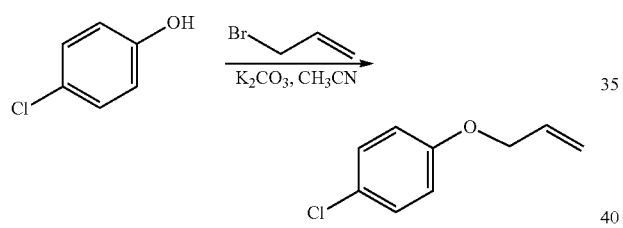

To a solution of 4-chlorophenol (30 g, 233 mmol) in acetonitrile (100 ml) was added potassium carbonate (48.1 g, 349 mmol, 1.5 eq) and allyl bromide (36.28 g, 299.9 mmol, 1.3 eq) dropwise with stirring for 5 hours at 50° C. in an oil bath. The solids were filtered out and the liquid was concentrated under vacuum to afford 1-chloro-4-(prop-2-en-1-yloxy)benzene as yellow oil (34 g, 86%); $^1$H NMR (300 MHz, CDCl$_3$): δ 7.20-7.25 (m, 2H), 6.81-6.86 (m, 2H), 5.96-6.09 (m, 1H), 5.27-5.44 (m, 2H), 4.49-4.51 (m, 2H).

Step 2. Formation of 4-chloro-2-(prop-2-en-1-yl)phenol

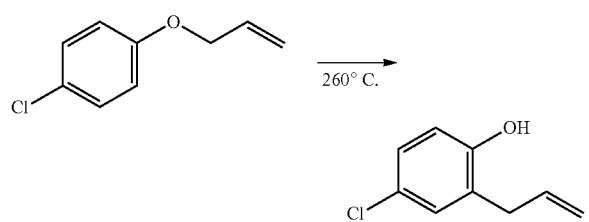

1-chloro-4-(prop-2-en-1-yloxy)benzene (34 g, 202 mmol) was stirred for 7 hours at 260° C. The reaction mixture was purified via silica gel chromatography using 3% ethyl acetate in petroleum ether to elute. The product-containing fractions were combined and concentrated to afford 4-chloro-2-(prop-2-en-1-yl)phenol as light brown oil (17 g, crude); $^1$H NMR (300 MHz, CDCl$_3$): δ 7.03-7.09 (m, 2H), 6.75 (d, J=3.0 Hz, 1H), 5.92-6.05 (m, 1H), 5.13-5.20 (m, 2H), 3.37 (d, J=6.3 Hz, 2H).

Step 3. Formation of (5-chloro-2,3-dihydro-1-benzofuran-2-yl)methanol

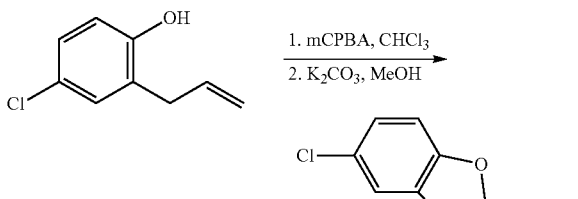

To a solution of 4-chloro-2-(prop-2-en-1-yl)phenol (17 g, crude, nominally 101 mmol) in chloroform (100 ml) was added mCPBA (17.4 g, 101 mmol, 1 eq) with stirring for 1 h at 50° C. in an oil bath. Then the reaction mixture was concentrated under vacuum and re-dissolved in MeOH (100 ml). Potassium carbonate (27.6 g, 200 mmol, 2 eq) was added and the mixture was stirred for 5 hours at 50° C. The solids were filtered off and the filtrate was concentrated under vacuum. The crude material was purified by silica gel chromatography using 3% ethyl acetate in petroleum ether to elute. The product-containing fractions were combined and concentrated under vacuum to afford (5-chloro-2,3-dihydro-1-benzofuran-2-yl)methanol as yellow oil (6.15 g); $^1$H NMR (300 MHz, CDCl$_3$): δ 7.00-7.18 (m, 2H), 6.80 (d, J=8.7 Hz, 1H), 4.88-4.97 (m, 1H), 3.85-3.90 (m, 1H), 3.70-3.79 (m, 1H), 3.19-3.27 (dd, J=9.3 Hz, 15.9 Hz, 1H), 2.98-3.05 (dd, J=7.5 Hz, 15.9 Hz, 1H), 2.10 (broad s, 1H).

Step 4. Formation of 5-chloro-2,3-dihydro-1-benzofuran-2-carboxylic acid

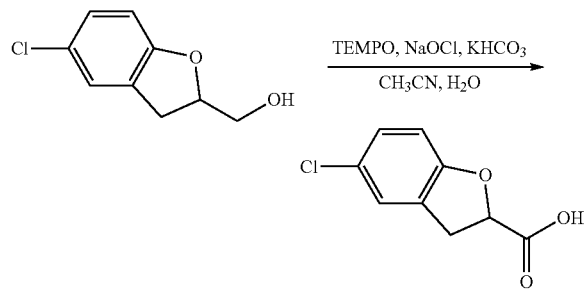

To a solution of (5-chloro-2,3-dihydro-1-benzofuran-2-yl)methanol (2 g, 11 mmol), KHCO$_3$ (4.32 g, 43 mmol, 4 eq) and TEMPO (20 mg, 0.13 mmol, 0.1 eq) in water (8 ml) and CH$_3$CN (18 ml) was added NaOCl (20 ml, aq. 15%, ~4 eq) dropwise with stirring at 0° C. and stirred for 1 hour. The mixture was diluted with water (200 ml) and adjusted to pH ~4 with hydrogen chloride (2N). After extraction with ethyl acetate (3×200 ml), the organic layers were combined, washed with brine (200 ml), dried over anhydrous sodium sulfate, filtered, and then concentrated under vacuum. The crude material was purified by silica gel chromatography using 1% methanol in dichloromethane to elute. The product-containing fractions were combined and concentrated under vacuum to afford 5-chloro-2,3-dihydro-1-benzofuran-2-carboxylic acid as a yellow solid (1.6 g, 74%). $^1$H NMR (300 MHz, CDCl$_3$): δ 7.05-7.22 (m, 2H), 6.83 (d, J=8.4 Hz, 1H), 5.20-5.30 (m, 1H), 3.56-3.65 (m, 1H), 3.33-3.45 (m, 1H) Step 5. Formation of tert-butyl 4-[(5-chloro-2,3-dihydro-1-benzofuran-2-yl)carbonyl]piperazine-1-carboxylate.

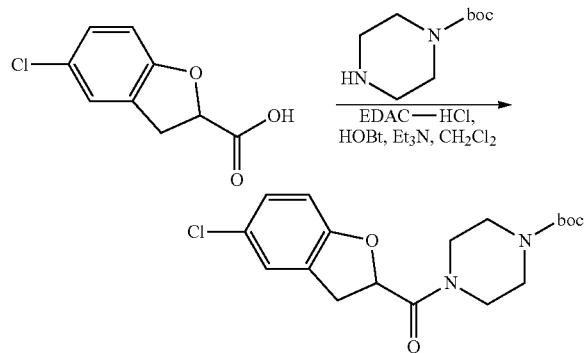

To a solution of 5-chloro-2,3-dihydro-1-benzofuran-2-carboxylic acid (1 g, 5 mmol) in N,N-dimethylformamide (10 ml) was added EDAC.HCl (1.45 g, 7.56 mmol, 1.5 eq), HOBt (1.02 g, 7.55 mmol, 1.5 eq), triethylamine (1.52 g, 15.0 mmol, 3 eq) and tert-butyl piperazine-1-carboxylate (935 mg, 5.02 mmol, 1 eq). The resulting solution was stirred overnight at room temperature, quenched with water (200 ml), and then extracted with ethyl acetate (3×200 ml). The combined organic layer was washed with brine (3×100 ml), dried over anhydrous sodium sulfate, filtered, and concentrated under vacuum. The crude material was purified by silica gel chromatography using 10%-20% ethyl acetate in petroleum ether to elute. The product-containing fractions were combined and concentrated under vacuum to afford tert-butyl 4-[(5-chloro-2,3-dihydro-1-benzofuran-2-yl)carbonyl]piperazine-1-carboxylate as a off-white solid (1.2 g, 65%). (ES, m/z): [M+H]$^+$ 367; $^1$H NMR (300 MHz, CDCl$_3$): δ 7.05-7.22 (m, 2H), 6.72 (d, J=8.4 Hz, 1H), 5.38-5.45 (m, 1H), 3.75-3.90 (m, 3H), 3.25-3.70 (m, 7H), 1.50 (s, 9H).

Step 6. Formation of 1-[(5-chloro-2,3-dihydro-1-benzofuran-2-yl)carbonyl]piperazine

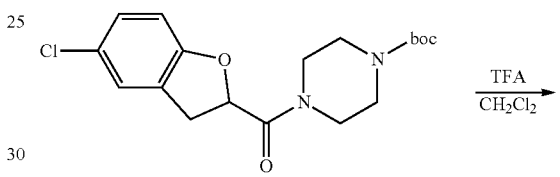

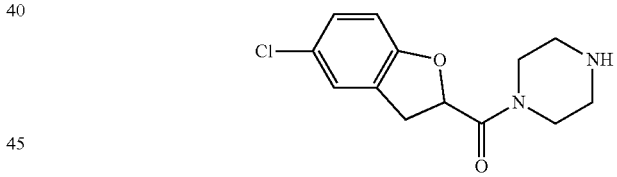

A solution of tert-butyl 4-[(5-chloro-2,3-dihydro-1-benzofuran-2-yl)carbonyl]piperazine-1-carboxylate (400 mg, 1.09 mmol) in dichloromethane (5 ml) was treated with trifluoroacetic acid (1 ml). The resulting solution was stirred for 2 h at room temperature and then concentrated under vacuum to give a residue. The crude material was dissolved into water (20 ml) and the pH was adjusted to ~8 using aqueous sodium bicarbonate. The mixture was extracted with ethyl acetate (3×100 ml). The organic layers were combined, dried over anhydrous sodium sulfate, filtered, and concentrated under vacuum to afford 1-[(5-chloro-2,3-dihydro-1-benzofuran-2-yl)carbonyl]piperazine as light yellow oil (280 mg, 96%). (ES, m/z): [M+H]$^+$ 267; $^1$H NMR (300 MHz, CDCl$_3$): δ 7.20 (s, 1H), 7.05-7.11 (m, 1H), 6.70 (d, J=8.4 Hz, 1H), 5.46-5.55 (m, 1H), 3.85-3.95 (m, 3H), 3.53-3.63 (m, 2H), 3.25-3.35 (m, 1H), 2.90-3.05 (m, 4H).

Step 7. Formation of 1-[4-[(5-chloro-2,3-dihydro-1-benzofuran-2-yl)carbonyl]piperazin-1-yl]-2-[(4-[[4-nitro-3-(trifluoro methyl)phenyl]amino]cyclohexyl)oxy]ethan-1-one (#79)

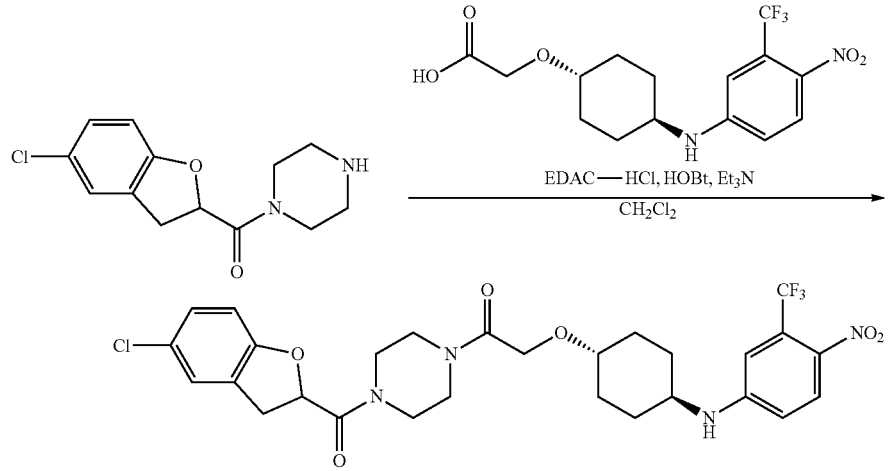

To a solution of 2-[(4-[[4-nitro-3-(trifluoromethyl)phenyl]amino]cyclohexyl)oxy]acetic acid (100 mg, 0.28 mmol) in dichloromethane (20 ml) was added EDAC.HCl (80 mg, 0.42 mmol 1.5 eq), HOBt (56 mg, 0.41 mmol, 1.5 eq), triethylamine (84 mg, 0.83 mmol, 3 eq) and 1-[(5-chloro-2,3-dihydro-1-benzofuran-2-yl)carbonyl]piperazine (74 mg, 0.28 mmol, 1 eq). The resulting solution was stirred overnight at room temperature and then concentrated under vacuum. The crude residue was purified by silica gel chromatography using 5-20% ethyl acetate in dichloromethane to elute. The product-containing fractions were combined and concentrated under vacuum to afford 1-[4-[(5-chloro-2,3-dihydro-1-benzofuran-2-yl)carbonyl]piperazin-1-yl]-2-[(4-[[4-nitro-3-(trifluoromethyl)phenyl]amino]cyclohexyl)oxy]ethan-1-one as a yellow solid (34.9 mg, 19%). (ES, m/z): [M+H]+ 611.25; $^1$H NMR (300 MHz, CDCl$_3$): δ 8.00 (d, J=9.0 Hz, 1H), 7.18 (s, 1H), 7.07 (d, J=8.4 Hz, 1H), 6.85 (d, J=2.1 Hz, 1H), 6.70 (d, J=8.7 Hz, 1H), 6.63 (dd, J=2.1 Hz, 9.0 Hz, 1H), 5.42 (dd, J=7.5 Hz, 9.0 Hz, 1H), 4.23 (s, 2H), 3.82-3.98 (m, 4H), 3.30-3.70 (m, 8H), 2.10-2.20 (m, 4H), 1.42-1.58 (m, 2H), 1.20-1.40 (m, 2H).

EXAMPLE 19: Preparation of Compound 84

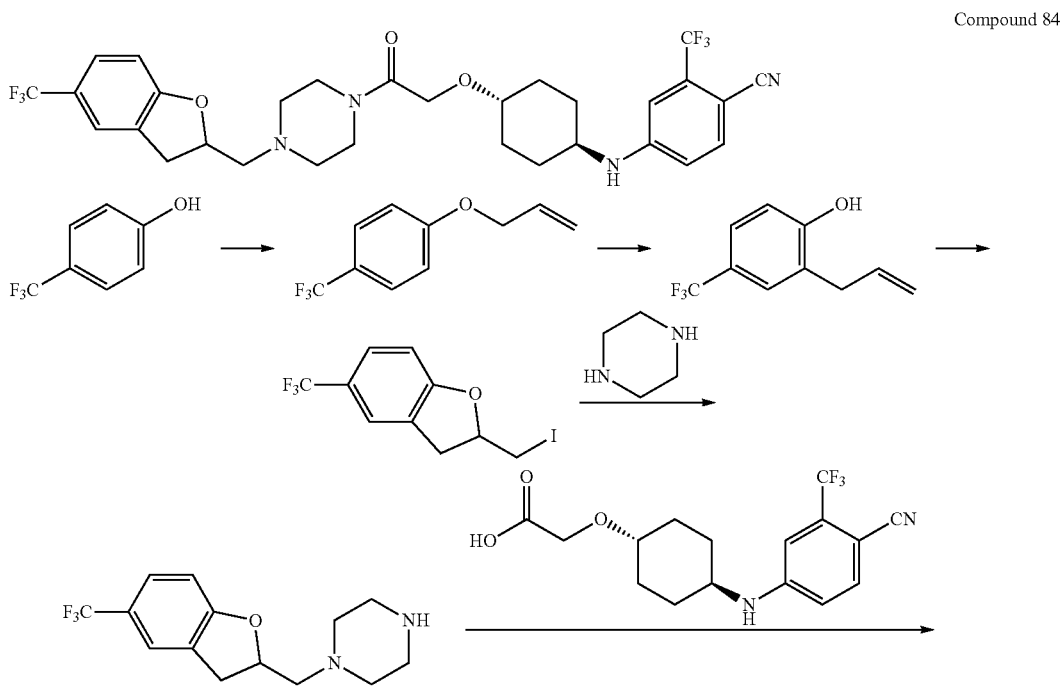

Compound 84

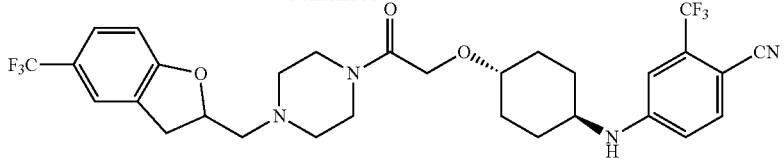

Step 1. Formation of 1-(prop-2-en-1-yloxy)-4-(trifluoromethyl)benzene

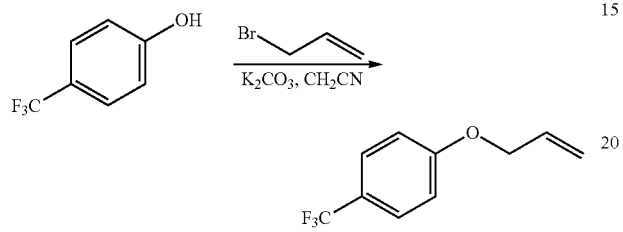

To a solution of 4-(trifluoromethyl)phenol (50 g, 308 mmol) in CH₃CN (600 ml) was added potassium carbonate (64 g, 463 mmol, 1.5 eq) and allyl bromide (48 g, 397 mmol, 1.3 eq) with stirring for overnight at 50° C. in an oil bath. The solids were filtered off and the filtrate was concentrated to a minimum volume, which was diluted by water (200 ml) and extracted with ethyl acetate (3×100 ml). The combined organic layers were washed with brine (2×200 ml), dried over anhydrous magnesium sulfate, filtered, and then concentrated under vacuum to afford 1-(prop-2-en-1-yloxy)-4-(trifluoromethyl)benzene as yellow oil (35 g, 56%), $^1$H NMR (300 MHz, CDCl₃): δ 7.52 (d, J=8.7 Hz, 2H), 6.96 (d, J=8.7 Hz, 2H), 5.98-6.11 (m, 1H), 5.30-5.46 (m, 2H), 4.57-4.58 (m, 2H).

Step 2. Formation of 2-(prop-2-en-1-yl)-4-(trifluoromethyl)phenol

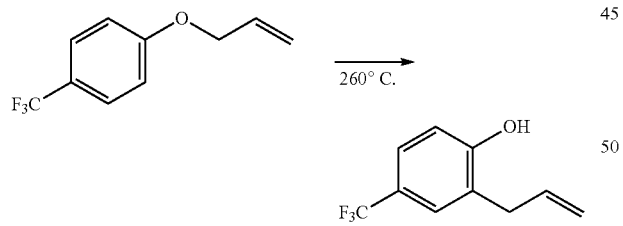

A solution of 1-(prop-2-en-1-yloxy)-4-(trifluoromethyl)benzene (30 g, 148 mmol) in dichloromethane (250 ml) was treated with 1N solution of BCl₃ (163 ml, 163 mmol, 1.1 eq) in dichloromethane for 2.5 h at −20° C. under an inert atmosphere of nitrogen. The reaction mixture was then quenched with ice-water (200 ml) and the organic layer was separated out. The aqueous layer was extracted further with dichloromethane (3×200 ml) and the combined organic layer was washed with saturated aqueous sodium bicarbonate (200 ml) and then dried over anhydrous magnesium sulfate. The solution was filtered and then concentrated under vacuum to afford 2-(prop-2-en-1-yl)-4-(trifluoromethyl)phenol as colorless oil (25 g, 83%); $^1$H NMR (300 MHz, CDCl₃): δ 7.38 (d, J=7.5 Hz, 2H), 6.86 (t, J=8.7 Hz, 1H), 5.94-6.07 (m, 1H), 5.60 (s, 1H), 5.15-5.22 (m, 2H), 3.43 (d, J=6.6 Hz, 2H).

Step 3. Formation of 2-(iodomethyl)-5-(trifluoromethyl)-2,3-dihydro-1-benzofuran

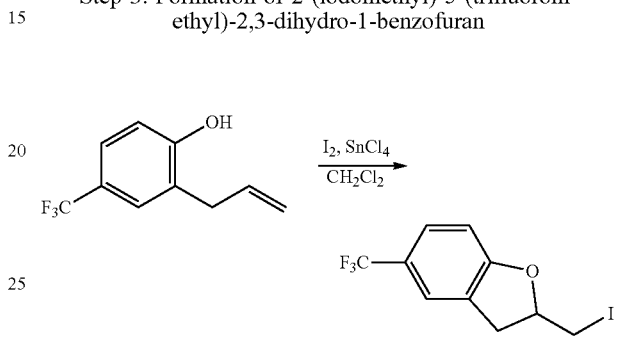

To a solution of 2-(prop-2-en-1-yl)-4-(trifluoromethyl)phenol (4 g, 20 mmol) in dichloromethane (50 ml) was added SnCl₄ (2.6 g, 10.0 mmol, 0.5 eq) dropwise and iodine (5.03 g, 19.8 mmol, 1 eq) with stirring for 6 h at room temperature. The reaction mixture was diluted with dichloromethane (200 ml) and quenched by the addition of water (100 ml). The organic layer was separated and the pH value of the aqueous layer was adjusted to ~8 with aqueous sodium bicarbonate. The aqueous layer was extracted further with dichloromethane (3×100 ml). The organic layers were combined, washed with aqueous Na₂S₂O₄ (5%, 100 ml) to remove remaining iodine, dried over anhydrous magnesium sulfate, filtered, and then concentrated under vacuum. The crude material was purified by silica gel chromatography using 1% ethyl acetate in petroleum ether to elute. The product-containing fractions were combined and concentrated under vacuum to afford 2-(iodomethyl)-5-(trifluoromethyl)-2,3-dihydro-1-benzofuran as colorless oil (2.8 g, 43%); $^1$H NMR (300 MHz, CDCl₃): δ 7.39 (d, J=5.7 Hz, 2H), 6.83 (d, J=8.7 Hz, 1H), 4.91-5.00 (m, 1H), 3.34-3.48 (m, 3H), 3.05-3.12 (m, 1H).

Step 4. Formation of 1-[[5-(trifluoromethyl)-2,3-dihydro-1-benzofuran-2-yl]methyl]piperazine

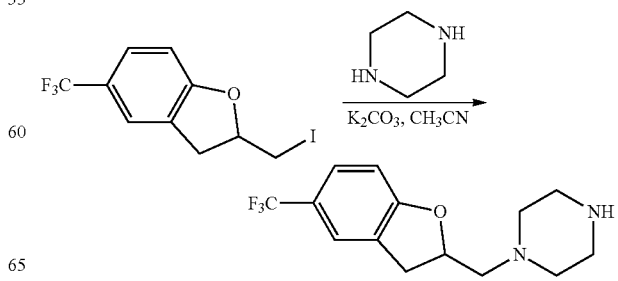

To a solution of 2-(iodomethyl)-5-(trifluoromethyl)-2,3-dihydro-1-benzofuran (2.8 g, 8.5 mmol) in CH₃CN (40 ml) was added potassium carbonate (2.36 g, 17.1 mmol, 2 eq) and piperazine (2.94 g, 34.1 mmol, 4 eq) at room temperature. The mixture was heated at reflux for 3 h, then solids were filtered out and the filtrate was concentrated under vacuum. The crude material was purified by silica gel chromatography using 1-2.5% methanol in dichloromethane to elute. The product-containing fractions were combined and concentrated under vacuum to afford 1-[[5-(trifluoromethyl)-2,3-dihydro-1-benzofuran-2-yl]methyl]piperazine as light yellow oil (1.25 g, 51%); (ES, m/z): [M+H]⁺ 287; ¹H NMR (300 MHz, CDCl₃): δ 7.37 (d, J=9.0 Hz, 2H), 6.83 (d, J=8.4 Hz, 1H), 5.00-5.10 (m, 1H), 3.26-3.35 (m, 1H), 2.96-3.04 (m, 1H), 2.88-2.95 (m, 4H), 2.78-2.80 (m, 1H), 2.54-2.69 (m, 4H).

Step 5. Formation of 4-([4-[2-oxo-2-(4-[[5-(trifluoromethyl)-2,3-dihydro-1-benzofuran-2-yl]methyl]piperazin-1-yl)ethoxy]cyclohexyl]amino)-2-(trifluoromethyl)benzonitrile (#84)

To a solution of 2-[(4-[[4-cyano-3-(trifluoromethyl) phenyl]amino]cyclohexyl)oxy]acetic acid (100 mg, 0.29 mmol) in dichloromethane (30 ml) was added EDAC.HCl (84.2 mg, 0.44 mmol, 1.5 eq), HOBt (59.2 mg, 0.44 mmol, 1.5 eq), triethylamine (59.1 mg, 0.58 mmol, 2 eq) and 1-[[5-(trifluoromethyl)-2,3-dihydro-1-benzofuran-2-yl]methyl]piperazine (92.0 mg, 0.32 mmol, 1.1 eq). The reaction mixture was stirred overnight at room temperature and then quenched by the addition of water (30 ml). The crude product was extracted with ethyl acetate (3×20 ml). The organic layers were combined, dried over anhydrous magnesium sulfate, filtered, and then concentrated under vacuum. The crude material was purified by Pre-TLC with 20% ethyl acetate in dichloromethane to afford 4-([4-[2-oxo-2-(4-[[5-(trifluoromethyl)-2,3-dihydro-1-benzofuran-2-yl]methyl]piperazin-1-yl)ethoxy]cyclohexyl]amino)-2-(trifluoromethyl)benzonitrile as a white solid (76 mg, 43%); (ES, m/z): [M+H]⁺ 611.30; ¹H NMR (300 MHz, CDCl₃): δ 7.55 (d, J=8.7 Hz, 1H), 7.42 (m, 2H), 6.81-6.86 (m, 2H), 6.64-6.68 (dd, J=2.1 Hz, 8.4 Hz, 1H), 5.08-5.13 (m, 1H), 4.29 (d, J=7.8 Hz, 1H), 4.21 (s, 2H), 3.65-3.78 (m, 3H), 3.30-3.48 (m, 3H), 3.01-3.06 (dd, J=8.4 Hz, 15.9 Hz, 2H), 2.51-2.90 (m, 4H), 2.10-2.19 (m, 4H), 1.44-1.58 (m, 3H), 1.21-1.33 (m, 3H).

EXAMPLE 20: Preparation of Compound 75

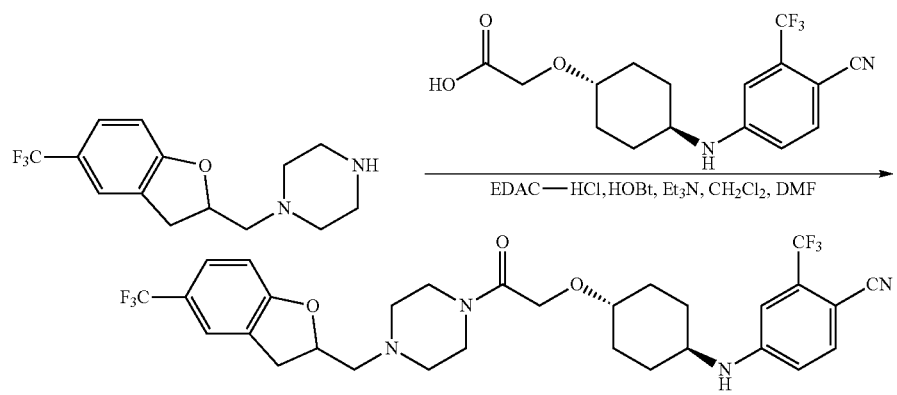

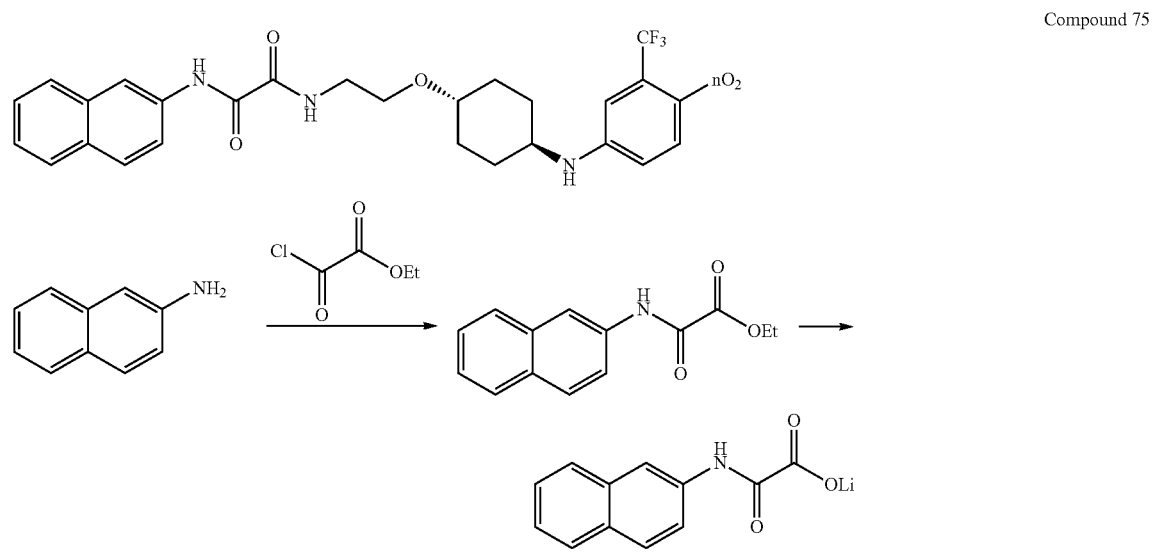

Compound 75

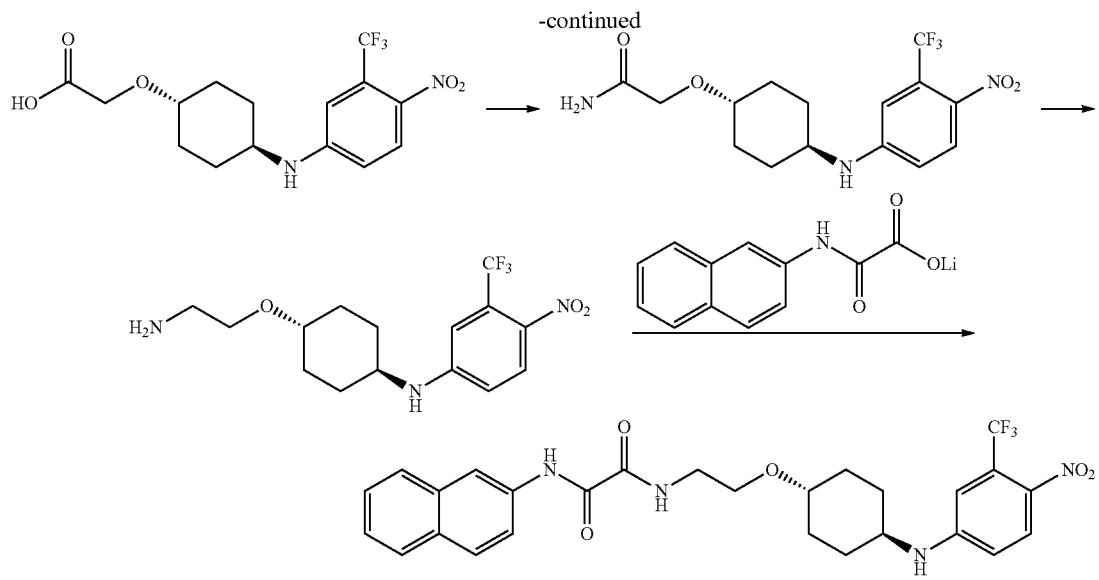

Step 1. Formation of ethyl [(naphthalen-2-yl)carbamoyl]formate

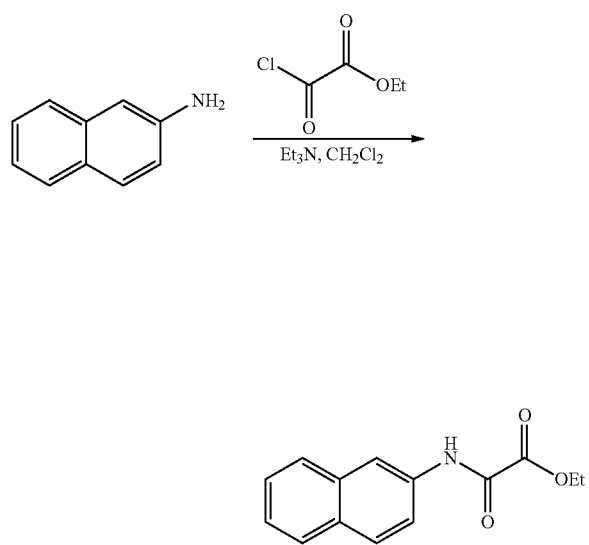

To a solution of naphthalen-2-amine (2 g, 14.0 mmol) in dichloromethane (30 ml) was added triethylamine (4.24 g, 41.9 mmol, 3 eq). Then, ethyl 2-chloro-2-oxoacetate (1.92 g, 14.1 mmol, 1 eq) was added dropwise to the solution kept at 0-5° C. using an ice-bath. The resulting solution was allowed to warm to room temperature while stirring. The reaction was then quenched by the addition of water (50 ml), the product was extracted with dichloromethane (2×50 ml), and the organic layers were combined. The organic solution was washed with saturated aqueous sodium chloride (50 ml), dried over anhydrous sodium sulfate, filtered, and then concentrated under vacuum to afford ethyl [(naphthalen-2-yl)carbamoyl]formate as a black solid (3 g, 88%). (ES, m/z) [M+H]$^+$ 244; $^1$H NMR (300 MHz, CDCl$_3$): δ 9.06 (broad s, 1H), 8.32 (d, J=1.8 Hz, 1H), 7.72-7.88 (m, 3H), 7.59 (dd, J=2.1 Hz, 8.7 Hz, 1H), 7.53 (m, 2H), 4.44 (q, J=7.2 Hz, 2H), 1.43 (t, J=7.2 Hz, 3H).

Step 2. Formation of lithio [(naphthalen-2-yl)carbamoyl]formate

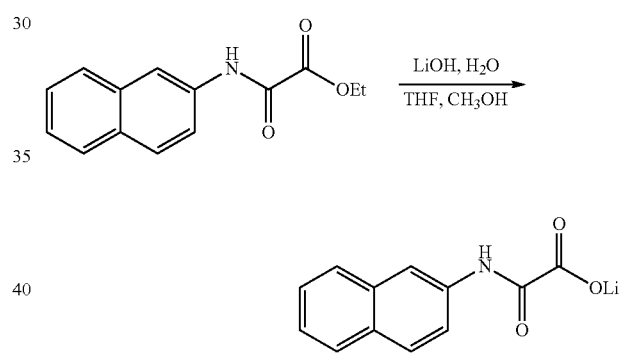

To a solution of ethyl [(naphthalen-2-yl)carbamoyl]formate (320 mg, 1.32 mmol) in tetrahydrofuran (15 ml) and methanol (15 ml) was added a solution of lithium hydroxide (31.6 mg, 1.32 mmol, 1 eq) in water (1 ml). The resulting solution was stirred for 20 min at room temperature and then concentrated under vacuum to afford lithio [(naphthalen-2-yl)carbamoyl]formate as a black solid (290 mg, crude). $^1$H NMR (300 MHz, DMSO): δ 10.46 (s, 1H), 8.44 (s, 1H), 7.80-7.90 (m, 4H), 7.33-7.50 (m, 2H).

Step 3. Formation of 2-[(4-[[4-nitro-3-(trifluoromethyl)phenyl]amino]cyclohexyl)oxy]acetamide

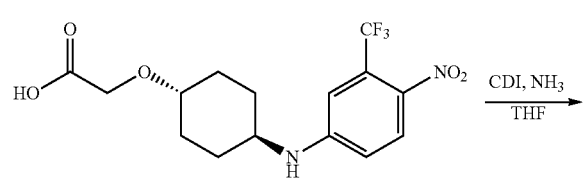

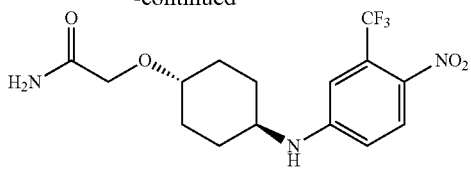

To a heated solution (60° C.) of 2-[(4-[[4-nitro-3-(trifluoromethyl)phenyl]amino]cyclohexyl)oxy]acetic acid (300 mg, 0.83 mmol) in tetrahydrofuran (25 ml) was added CDI (300 mg, 1.85 mmol, 2.2 eq) at reflux and then stirred for 1 hour at 60° C. (oil bath temperature). The resulting solution was poured into ammonia (25 ml) at room temperature and stirred for an additional 1 hour. The contents were diluted with water (100 ml) and the resulting mixture was extracted with ethyl acetate (3×100 ml). The organic layers were combined, washed with saturated aqueous sodium chloride (100 ml), dried over anhydrous sodium sulfate, filtered, and then concentrated under vacuum to afford 2-[(4-[[4-nitro-3-(trifluoromethyl)phenyl]amino]cyclohexyl)oxy]acetamide as yellow solid (220 mg, 74%). (ES, m/z) [M+H]$^+$ 362; $^1$H NMR (300 MHz, DMSO): δ 8.06 (d, J=9.0 Hz, 1H), 7.48 (d, J=7.8 Hz, 1H), 7.27 (d, J=4.2 Hz, 1H), 7.07 (s, 2H), 6.85 (dd, J=2.4 Hz, 9.3 Hz, 1H), 3.82 (s, 2H), 3.40-3.55 (m, 2H), 1.90-2.10 (m, 4H), 1.10-1.50 (m, 4H)

Step 4. Formation of N-[4-(2-aminoethoxy)cyclohexyl]-4-nitro-3-(trifluoromethyl)aniline

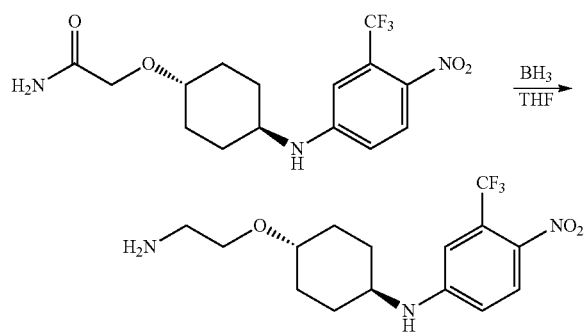

A solution of 2-[(4-[[4-nitro-3-(trifluoromethyl)phenyl]amino]cyclohexyl)oxy]acetamide (220 mg, 0.61 mmol) in borane/THF (1M, 10 ml) was stirred for 10 minutes at 70° C. in an oil bath. The solution was quenched by the addition of aqueous hydrogen chloride (2 ml of a 1M solution), diluted with water (15 ml), and extracted with ethyl acetate (3×15 ml). The aqueous layer was adjusted to pH ~8 with saturated aqueous sodium bicarbonate and extracted further with dichloromethane (3×20 ml). The organic layers were combined and concentrated under vacuum to afford N-[4-(2-aminoethoxy)cyclohexyl]-4-nitro-3-(trifluoromethyl)aniline as yellow oil (180 mg, 85%). (ES, m/z) [M+H]$^+$ 348; $^1$H NMR (300 MHz, DMSO): δ 8.06 (d, J=Hz, 1H), 7.47 (d, J=7.8 Hz, 1H), 7.07 (s, 1H), 6.84 (dd, J=2.7 Hz, 7.8 Hz, 1H), 3.39-3.55 (m, 6H), 2.65-2.70 (t, J=5.7 Hz, 2H), 1.90-2.10 (m, 4H), 1.15-1.40 (m, 4H).

Step 5. Formation of N-(naphthalen-2-yl)-N-[2-[(4-[[4-nitro-3-(trifluoromethyl)phenyl]amino]cyclohexyl)oxy]ethyl]ethanediamide (#75)

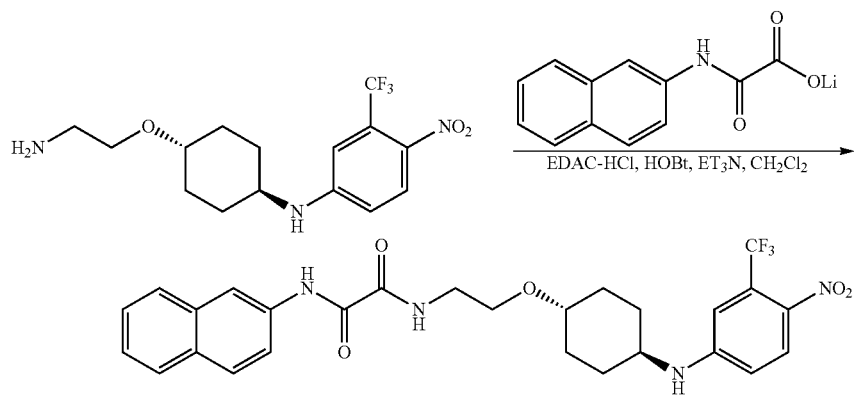

To a solution of lithio [(naphthalen-2-yl)carbamoyl]formate (172 mg, 0.78 mmol, 1.5 eq) in N,N-dimethylformamide (15 ml) was added N-[4-(2-aminoethoxy)cyclohexyl]-4-nitro-3-(trifluoromethyl) aniline (180 mg, 0.52 mmol), EDAC.HCl (149 mg, 0.78 mmol, 1.5 eq), HOBt (105 mg, 0.78 mmol, 1.5 eq) and triethylamine (157 mg, 1.55 mmol, 3 eq). The resulting solution was stirred for 24 hours at room temperature. The solution was diluted with ethyl acetate (200 ml), washed with water (3×100 ml), and then washed with saturated aqueous sodium chloride (100 ml). The organic layer was then dried over anhydrous sodium sulfate, filtered, and concentrated under vacuum. The crude material was purified by silica gel chromatography using 1% methanol in dichloromethane to elute. The product-containing fractions were combined and concentrated under vacuum to afford N-(naphthalen-2-yl)-N-[2-[(4-[[4-nitro-3-(trifluoromethyl)phenyl]amino]cyclohexyl)oxy]ethyl]ethanediamide as a yellow solid (48.6 mg, 17%). (ES, m/z) [M+H]$^+$ 545.25; $^1$H NMR (300 MHz, CDCl$_3$): δ 9.45 (s, 1H), 8.33 (d, J=2.1 Hz, 1H), 8.02 (d, J=9.0 Hz, 1H), 7.80-7.98 (m, 4H), 7.60 (dd, J=2.1 Hz, 8.7 Hz, 1H), 7.40-7.55 (m, 2H), 6.85 (d, J=2.4 Hz, 1H), 6.63 (dd, J=2.4 Hz, 9.0 Hz, 1H), 4.47 (d, J=7.5 Hz, 1H), 3.55-3.70 (m, 4H), 3.30-3.45 (m, 2H), 2.08-2.22 (m, 4H), 1.40-1.53 (m, 2H), 1.20-1.37 (m, 2H).

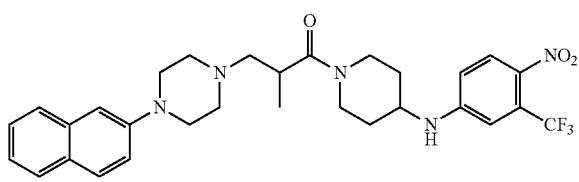 [SMILES: CC(CN1CCN(c2ccc3ccccc3c2)CC1)C(=O)N1CCC(Nc2ccc([N+](=O)[O-])c(C(F)(F)F)c2)CC1]

2-methyl-3-[4-(naphthalen-2-yl)piperazin-1-yl]-1-(4-
[[4-nitro-3-(trifluoromethyl)phenyl]amino]piperidin-
1-yl)propan-1-one (Compound 13)

(ES, m/z): [M+H]⁺ 570; ¹H NMR (300 MHz, DMSO-d6): δ 8.04 (d, J=9.0 Hz, 1H), 7.76-7.68 (m, 3H), 7.49 (d, J=7.5 Hz, 1H), 7.35-7.40 (t, J=7.2 Hz, 2H), 7.22-7.27 (t, J=7.2 Hz, 1H), 7.09-7.15 (m, 2H), 6.90 (dd, J=9.3, 2.1 Hz, 1H), 4.30-4.40 (m, 1H), 3.98-4.11 (m, 1H), 3.68-3.85 (m, 1H), 3.05-3.26 (m, 5H), 2.75-2.96 (m, 1H), 2.54-2.66 (m, 5H), 2.21-2.35 (m, 1H), 1.84-2.05 (m, 2H), 1.14-1.48 (m, 2H), 1.95-1.09 (m, 3H). One proton is not apparent (may be hidden under DMSO or water peak).

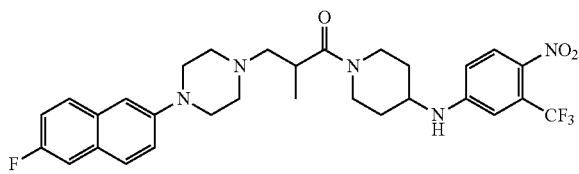 [SMILES: CC(CN1CCN(c2ccc3cc(F)ccc3c2)CC1)C(=O)N1CCC(Nc2ccc([N+](=O)[O-])c(C(F)(F)F)c2)CC1]

3-[4-(6-fluoronaphthalen-2-yl)piperazin-1-yl]-2-
methyl-1-(4-[[4-nitro-3-(trifluoromethyl)phenyl]
amino]piperi-din-1-yl)propan-1-one (#016)

(ES, m/z): [M+H]⁺ 588.55; ¹H NMR (300 MHz, CDCl₃): δ 8.01-8.04 (t, J=5.4 Hz, 1H), 7.66-7.70 (m, 2H), 7.35-7.38 (m, 1H), 7.30 (d, J=6.3 Hz, 1H), 7.19-7.24 (m, 1H), 7.12 (s, 1H), 6.90 (s, 1H), 6.66-6.69 (t, J=7.2 Hz, 1H), 4.50-4.68 (overlapping m, 2H), 4.05-4.09 (t, J=10.5 Hz, 1H), 3.66-3.70 (m, 1H), 3.30 (s, 5H), 3.10 (s, 1H), 2.86-2.95 (m, 2H), 2.60-2.73 (m, 4H). 2.40-2.49 (m, 1H), 2.12-2.49 (m, 2H), 1.45-1.61 (m, 2H), 1.18 (d, J=4.5 Hz, 3H).

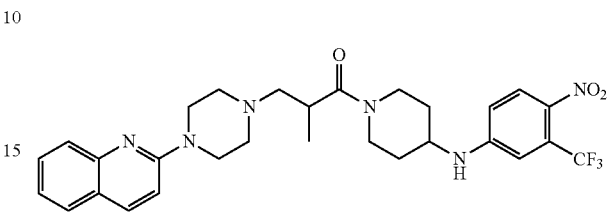

Compound 91: 2-methyl-1-(4-[[4-nitro-3-(trifluo-
romethyl)phenyl]amino]piperidin-1-yl)-3-[4-(quino-
lin-2-yl)piperazin-1-yl]propan-1-one (ES, m/z): [M+H]⁺ 571.15; ¹H NMR (300 MHz, CDCl₃): δ 7.98-8.05 (m, 1H), 7.88 (d, J=9.3 Hz, 1H), 7.70 (d, J=8.1 Hz, 1H), 7.61 (d, J=7.8 Hz, 1H), 7.55 (dd, J=7.5, 7.8 Hz, 1H), 7.22-7.25 (m, 1H), 6.96 (d, J=9.3 Hz, 1H), 6.89 (s, 1H), 6.64 (d, J=8.1 Hz, 1H), 4.60-4.64 (br m, 2H), 4.07 (dd, J=14.1, 17.4 Hz, 1H), 3.76 (br s, 4H), 3.73 (m, 1H), 3.02-3.35 (overlapping m, 2H), 2.90 (overlapping m, 2H), 2.65 (br s, 4H), 2.45 (d, J=10.5 Hz, 1H), 2.01-2.20 (m, 2H), 1.38-1.58 (m, 2H), 1.15 (d, J=4.8 Hz, 3H).

EXAMPLE 21: Preparation of Compound 92

Compound 92

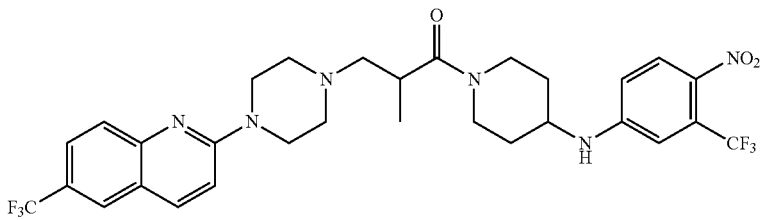

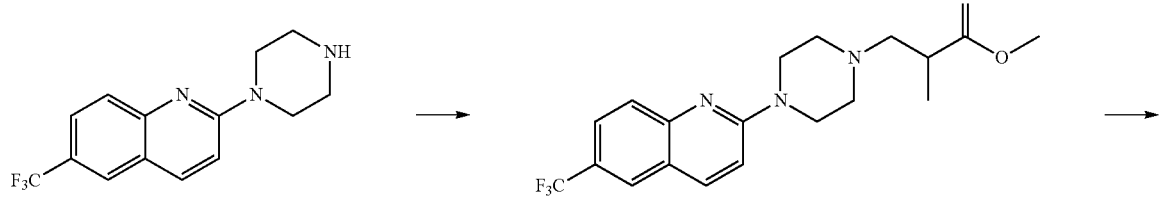

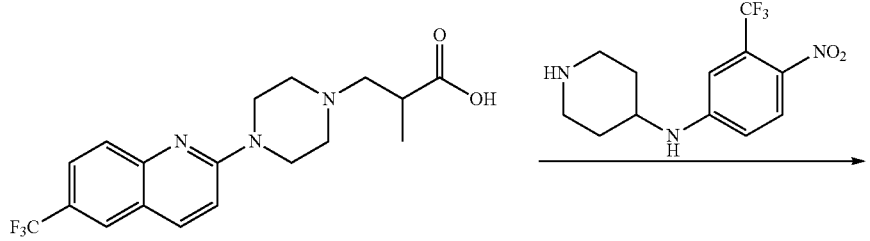

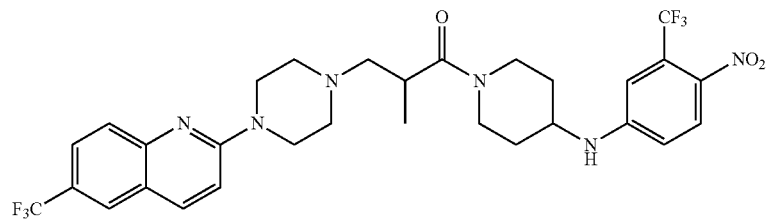

Prep-TLC with 5% methanol in dichloromethane to afford of 2-methyl-1-(4-[[4-nitro-3-(trifluoromethyl)phenyl]amino]piperidin-1-yl)-3-[4-[6-(trifluoromethyl)quinolin-2-yl]piperazin-1-yl]propan-1-one as a yellow solid (111.2 mg, 64%). (ES, m/z): [M+H]⁺ 639.40; ¹H NMR (300 MHz, CDCl₃): δ 7.95-8.08 (m, 1H), 7.72 (overlapping m, 2H), 7.01 (d, J=9.3 Hz, 1H), 6.89 (m, 1H), 6.65 (m, 1H), 4.49-4.70 (m, 2H), 4.08 (m, 1H), 3.72-3.85 (br m, 5H), 3.65 (m, 1H), 3.08 (br s, 1H), 2.88 (br m, 2H), 2.68 (br s, 3H), 2.38 (m, 1H), 2.07-2.20 (overlapping m, 2H), 1.47 (m, 2H), 1.13 (br s, 3H).

Steps 1-6

The formation of 2-piperazin-1-yl-6-trifluoromethyl-quinoline was performed as was described in the synthesis shown for compound 89. The conversion to 2-methyl-3-[4-(6-trifluoromethyl-quinolin-2-yl)-piperazin-1-yl]-propionic acid was performed in a manner analogous to what was described in the synthetic scheme for compound 13.

Step 7. Formation of 2-methyl-1-(4-(4-nitro-3-(trifluoromethyl)phenylamino)piperidin-1-yl)-3-(4-(6-(trifluoromethyl)quinolin-2-yl)piperazin-1-yl)propan-1-one (#92)

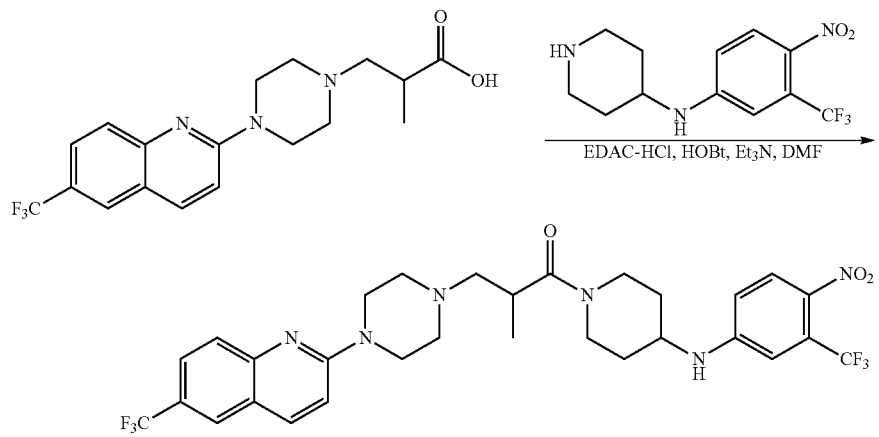

To a solution of 2-methyl-3-[4-[6-(trifluoromethyl) quinolin-2-yl]piperazin-1-yl]propanoic acid (100 mg, 0.27 mmol) in dichloromethane (20 ml) was added EDAC.HCl (79 mg, 0.41 mmol, 1.5 eq.), 1H-1,2,3-benzotriazol-1-ol (55.2 mg, 0.41 mmol, 1.5 eq.), triethylamine (82.6 mg, 0.82 mmol, 3 eq.) and N-[4-nitro-3-(trifluoromethyl)phenyl]piperidin-4-amine (94.5 mg, 0.33 mmol, 1.2 eq.). The resulting solution was stirred overnight at room temperature and then quenched by the addition of water (50 ml) and extracted with dichloromethane (3×30 ml). The organic layers were combined, dried over anhydrous sodium sulfate, and concentrated under vacuum to give a residue, which was purified by

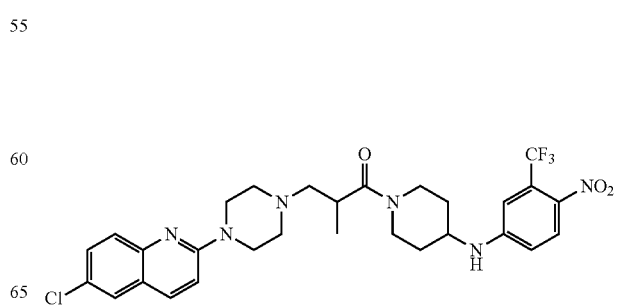

Compound 93: 3-[4-(6-chloroquinolin-2-yl)piperazin-1-yl]-2-methyl-1-(4-[[4-nitro-3-(trifluoromethyl)phenyl]amino]piperidin-1-yl)propan-1-one (ES, m/z): [M+H]⁺ 605.15; ¹H NMR (300 MHz, CDCl₃): δ 8.02 (d, J=9.0 Hz, 1H), 7.80 (d, J=9.3 Hz, 1H), 7.60 (overlapping d, 2H), 7.46 (dd, J=2.1, 9.0 Hz, 1H), 6.98 (d, J=9.0 Hz, 1H), 6.88 (s, 1H), 6.65 (d, J=9.0 Hz, 1H), 4.55-4.67 (overlapping m, 2H), 4.06-4.10 (m, 1H), 3.63-3.82 (m, 5H), 3.22-3.26 (m, 1H), 3.01-3.10 (m, 1H), 2.83-2.97 (m, 2H), 2.63 (s, 4H), 2.39-2.43 (m, 1H), 2.01-2.14 (m, 2H), 1.42-1.50 (m, 2H), 1.14 (d, J=5.1 Hz, 3H).

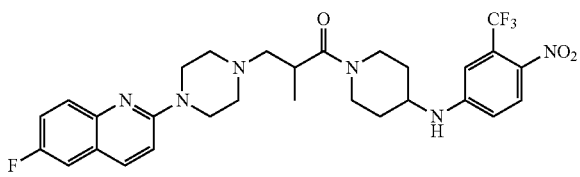 [SMILES: CC(CN1CCN(c2ccc3cc(F)ccc3n2)CC1)C(=O)N1CCC(Nc2ccc([N+](=O)[O-])c(C(F)(F)F)c2)CC1]

Compound 100: 3-[4-(6-fluoroquinolin-2-yl)piperazin-1-yl]-2-methyl-1-(4-[[4-nitro-3-(trifluoromethyl)phenyl]amino]piperidin-1-yl)propan-1-one (ES, m/z): [M+H]⁺ 589.15; ¹H NMR (300 MHz, CDCl₃): δ 8.00 (d, J=8.7 Hz, 1H), 7.84 (d, J=9.3 Hz, 1H), 7.64-7.69 (m, 1H), 7.25-7.34 (m, 2H), 6.98 (d, J=9.0 Hz, 1H), 6.89 (s, 1H), 6.64 (d, J=8.7 Hz, 1H), 4.60 (m, 2H), 4.09 (m, 1H), 3.55-3.81 (overlapping m, 5H), 3.00-3.40 (overlapping m, 2H), 2.90 (br m, 2H), 2.64 (br s, 4H), 2.42 (m, 1H), 2.12 (m, 2H), 1.38-1.55 (br m, 2H), 1.14 (d, J=6.3 Hz, 3H).

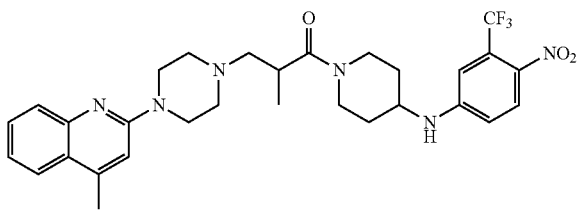 [SMILES: Cc1cc(N2CCN(CC(C)C(=O)N3CCC(Nc4ccc([N+](=O)[O-])c(C(F)(F)F)c4)CC3)CC2)nc2ccccc12]

Compound 101: 2-methyl-3-[4-(4-methylquinolin-2-yl)piperazin-1-yl]-1-(4-[[4-nitro-3-(trifluoromethyl) phenyl]amino]piperidin-1-yl)propan-1-one (ES, m/z): [M+H]⁺ 585.20. ¹H NMR (300 MHz, CDCl₃): δ 8.01 (m, 1H), 7.79 (d, J=7.8 Hz, 1H), 7.75 (m, 1H), 7.57 (br s, 1H), 7.30 (m, 1H), 6.90 (s, 1H), 6.84 (s, 1H), 6.67 (d, J=9.6 Hz, 1H), 4.52-4.90 (m, 2H), 4.11 (m, 1H), 3.76 (br s, 4H), 3.62 (m, 1H), 3.01-3.38 (overlapping m, 2H), 2.78-3.00 (m, 2H), 2.65 (br s, 4H), 2.61 (s, 3H), 2.43 (d, J=12.6 Hz, 1H), 2.06-2.23 (m, 2H), 1.38-1.63 (m, 2H), 1.14 (d, J=6.0 Hz, 3H).

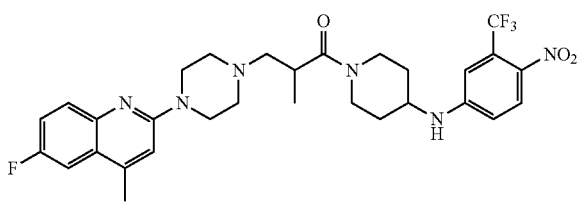 [SMILES: Cc1cc(N2CCN(CC(C)C(=O)N3CCC(Nc4ccc([N+](=O)[O-])c(C(F)(F)F)c4)CC3)CC2)nc2ccc(F)cc12]

Compound 102: 3-[4-(6-fluoro-4-methylquinolin-2-yl)piperazin-1-yl]-2-methyl-1-(4-[[4-nitro-3-(trifluoromethyl) phenyl]amino]piperidin-1-yl)propan-1-one (ES, m/z): [M+H]⁺ 603.15; ¹H NMR (300 MHz, CDCl₃): δ 8.03-7.98 (m, 1H), 7.73-7.65 (m, 1H), 7.39 (dd, J=2.4, 2.7 Hz, 1H), 7.31 (~dd, J=9.3, ~12.9 Hz, 1H—overlaps w/CHCl₃), 6.88 (overlapping s/d, 2H), 6.67 (d, J=6.9 Hz, 1H), 4.80-4.51 (m, 2H), 4.15-4.02 (m, 1H), 3.80-3.55 (br overlapping m, 5H), 3.38-3.08 (br overlapping m, 2H), 3.05-2.80 (br overlapping m, 2H), 2.80-2.60 (m, 3H), 2.55 (s, 3H), 2.43 (m, 1H), 2.25-2.15 (m, 3H), 1.50-1.38 (m, 2H), 1.15 (d, J=5.4 Hz, 3H).

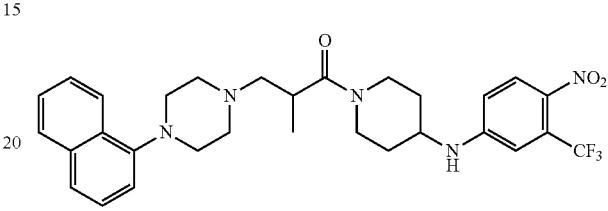

Compound 19: 2-methyl-3-(4-naphthalen-1-yl-piperazin-1-yl)-1-[4-(4-nitro-3-trifluoromethyl-phenylamino)-piperidin-1-yl]-propan-1-one (ES, m/z): [M+H]⁺ 570; ¹H NMR (400 MHz, CDCl₃): δ 8.19 (s, 1H), 8.03 (d, J=8.8 Hz, 1H), 7.84 (dd, J=5.6, 3.6 Hz, 1H), 7.57 (d, J=7.6 Hz, 1H), 7.40-7.50 (m, 3H), 7.08 (s, 1H), 6.91 (d, J=7.6 Hz, 1H), 6.69 (s, 1H), 4.6 (m, 2H), 4.1 (t, J=13.6 Hz, 1H), 3.68 (s, 1H), 2.70-3.40 (overlapping m, 11H), 2.52 (m, 1H), 2.15 (m, 2H), 1.50 (overlapping m, 2H), 1.20 (d, J=6.0 Hz, 3H).

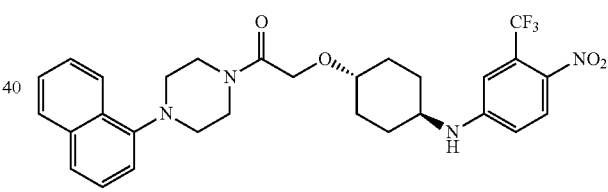

Compound 20: 1-[4-(naphthalen-1-yl)piperazin-1-yl]-2-[(4-[[4-nitro-3-(trifluoromethyl)phenyl]amino] cyclohexyl)oxy]ethan-1-one (ES, m/z): [M+H]⁺ 557; ¹H NMR (400 MHz, CDCl₃): δ 8.20 (d, J=7.5 Hz, 1H); 8.01 (d, J=8.7 Hz, 1H), 7.85 (d, J=7.5 Hz, 1H), 7.61 (d, J=8.4 Hz, 1H), 7.51 (m, 3H), 7.41 (dd, J=7.2, 8.4 Hz, 1H), 7.07 (d, J=7.5 Hz, 1H), 6.85 (s, 1H), 6.6 (d, J=7.8 Hz, 1H), 4.50 (br s, 1H), 4.28 (s, 2H), 3.82 (br m, 2H), 3.45 (br m, 3H), 3.13 (m, 4H), 2.17 (d, J=6.6 Hz, 4H), 1.51 (m, 2H), 1.25 (m, 2H).

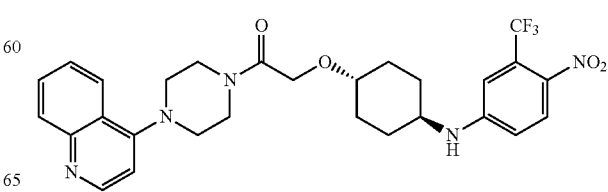

Compound 160: 2-[(4-[[4-nitro-3-(trifluoromethyl)phenyl]amino]cyclohexyl)oxy]-1-[4-(quinolin-4-yl)piperazin-1-yl]ethan-1-one (ES, m/z): [M+H]⁺ 558.40; ¹H NMR (300 MHz, DMSO-d6): δ 8.72 (d, J=4.8 Hz, 1H), 8.11 (t, J=9.3 Hz, 2H), 7.99 (d, J=8.4 Hz, 1H), 7.75 (t, J=8.1 Hz, 1H), 7.60 (t, J=8.1 Hz, 1H), 7.48 (d, J=7.5 Hz, 1H), 7.07 (d, J=1.5 Hz, 1H), 7.02 (d, J=5.1 Hz, 1H), 6.88 (dd, J=9.3, 2.4 Hz, 1H), 4.23 (s, 2H), 3.75 (br s, 4H), 3.49-3.40 (m, 2H), 3.19-3.16 (m, 4H), 2.07-1.95 (m, 4H), 1.45-1.27 (m, 4H).

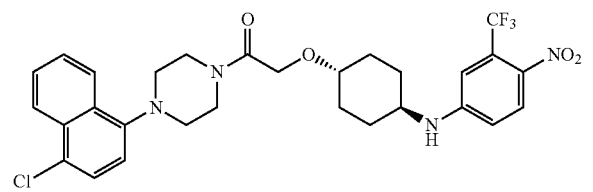 [SMILES: O=C(CO[C@H]1CC[C@H](Nc2ccc([N+](=O)[O-])c(C(F)(F)F)c2)CC1)N1CCN(c2ccc(Cl)c3ccccc23)CC1]

Compound 161: 1-[4-(4-chloronaphthalen-1-yl)piperazin-1-yl]-2-[(4-[[4-nitro-3-(trifluoromethyl)phenyl]amino]cyclohe-xyl)oxy]ethan-1-one (ES, m/z): [M+H]⁺ 591.15; ¹H NMR (300 MHz, CD₃OD): δ 8.33 (dd, J=2.4, 6.0 Hz, 1H), 8.26-8.22 (m, 1H), 8.04 (d, J=9.3 Hz, 1H), 7.67-7.59 (m, 2H), 7.55 (d, J=7.8 Hz, 1H), 7.14 (d, J=8.1 Hz, 1H), 6.99 (d, J=2.4 Hz, 1H), 6.81 (dd, J=2.7, 9.3 Hz, 1H), 4.34 (s, 2H), 3.91-3.71 (m, 2H), 3.64-3.45 (m, 4H), 3.12-2.94 (m, 4H), 2.19-2.09 (m, 4H), 1.58-1.46 (m, 2H), 1.41-1.30 (m, 2H).

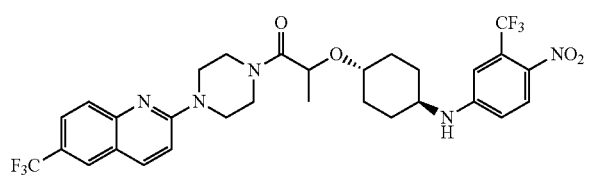 [SMILES: CC(O[C@H]1CC[C@H](Nc2ccc([N+](=O)[O-])c(C(F)(F)F)c2)CC1)C(=O)N1CCN(c2ccc3cc(C(F)(F)F)ccc3n2)CC1]

Compound 249: 2-[[-4-[[4-nitro-3-(trifluoromethyl)phenyl]amino]cyclohexyl]oxy]-1-[4-[6-(trifluoromethyl)quinolin-2-yl]piperazin-1-yl]propan-1-one (ES, m/z): [M+H]⁺ 640.10; ¹H NMR (300 MHz, CD₃OD): δ 8.14 (d, J=9.3 Hz, 1H), 8.02 (m, 2H), 7.78 (dd, J=9.0, 14.1 Hz, 2H), 7.31 (d, J=9.3 Hz, 1H), 6.97 (d, J=2.1 Hz, 1H), 6.78 (d, J=9.3 Hz, 1H), 4.61 (q, J=6.6 Hz, 2H), 3.91-3.76 (m, 8H), 3.46 (m, 2H), 2.16-2.02 (m, 4H), 1.58-1.46 (m, 2H), 1.42 (d, J=6.9 Hz, 3H), 1.38-1.31 (m, 2H).

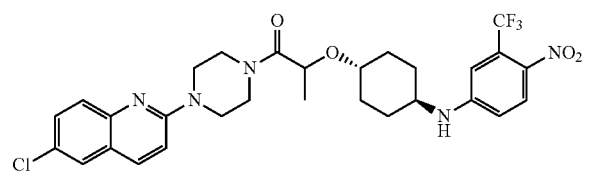 [SMILES: CC(O[C@H]1CC[C@H](Nc2ccc([N+](=O)[O-])c(C(F)(F)F)c2)CC1)C(=O)N1CCN(c2ccc3cc(Cl)ccc3n2)CC1]

Compound 250: 1-[4-(6-chloroquinolin-2-yl)piperazin-1-yl]-2-[[4-[[4-nitro-3-(trifluoromethyl)phenyl]amino]cyclohexyl]oxy]propan-1-one (ES, m/z): [M+H]⁺ 605.95; ¹H NMR (300 MHz, CDCl₃): δ 7.99 (d, J=4.2 Hz, 1H), 7.86 (br s, 1H), 7.62 (s, 2H), 7.52 (br s, 1H), 7.05 (d, J=8.7 Hz, 1H), 6.84 (d, J=2.4 Hz, 1H), 6.64 (dd, J=2.7, 9.0 Hz, 1H), 4.47-4.38 (m, 2H), 3.93-3.79 (overlapping m, 8H), 3.46-3.36 (m, 2H), 2.15 (m, 4H), 1.65-1.53 (m, 2H), 1.47 (d, J=6.9 Hz, 3H), 1.32-1.21 (m, 2H).

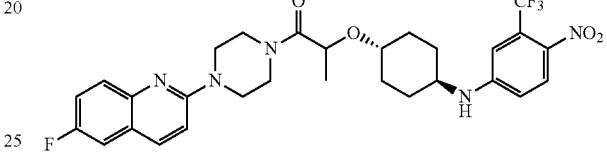

Compound 251: 1-[4-(6-fluoroquinolin-2-yl)piperazin-1-yl]-2-[[4-[[4-nitro-3-(trifluoromethyl)phenyl]amino]cyclohexyl]oxy]propan-1-one (ES, m/z): [M+H]⁺ 590.35; ¹H NMR (300 MHz, CD₃OD): δ 8.03 (d, J=9.0 Hz, 2H), 7.72-7.67 (m, 1H), 7.39-7.32 (m, 2H), 7.25 (d, J=9.3 Hz, 1H), 6.98 (d, J=2.4 Hz, 1H), 6.79 (dd, J=2.7, 9.3 Hz, 1H), 4.61 (q, J=6.9 Hz, 1H), 3.90-3.76 (m, 8H), 3.46 (m, 2H), 2.17-2.07 (m, 4H), 1.58-1.50 (m, 2H), 1.42 (d, J=6.6 Hz, 3H), 1.38-1.30 (m, 2H).

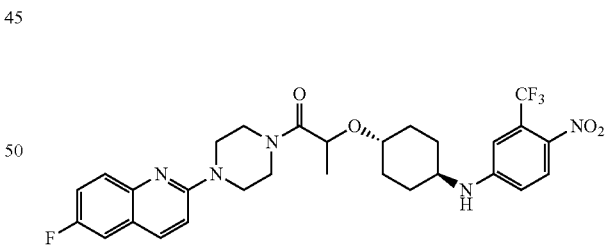

Compound 252: 1-(4-(6-fluoronaphthalen-2-yl)piperazin-1-yl)-2-(-4-(4-nitro-3-(trifluoromethyl)phenylamino)cyclohexyloxy)propan-1-one (ES, m/z): [M+H]⁺ 589.15; ¹H NMR (400 MHz, CD₃OD): δ 8.02 (d, J=9.2 Hz, 1H), 7.75 (m, 2H), 7.44-7.41 (m, 2H), 7.28-7.23 (m, 2H), 6.98 (d, J=2.4 Hz, 1H), 6.78 (dd, J=6.8, 2.4 Hz, 1H), 4.59 (q, J=6.8 Hz, 1H), 3.95-3.75 (m, 4H), 3.50-3.41 (m, 2H), 3.33-3.28 (m, 4H), 2.20-2.05 (m, 4H), 1.60-1.40 (m, 2H), 1.48-1.30 (m, 5H).

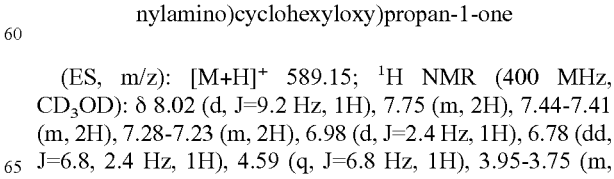

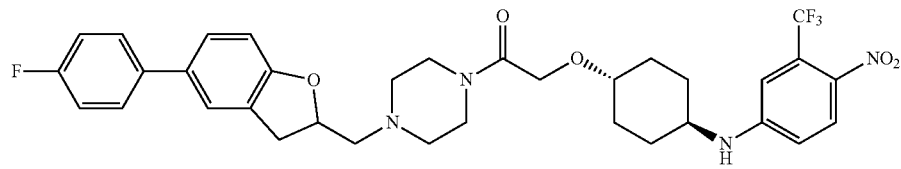 [SMILES: O=C(CO[C@H]1CC[C@H](Nc2ccc([N+](=O)[O-])c(C(F)(F)F)c2)CC1)N1CCN(CC2Cc3cc(-c4ccc(F)cc4)ccc3O2)CC1]

Compound 310: 1-{4-[5-(4-fluoro-phenyl)-2,3-di-hydro-benzofuran-2-ylmethyl]-piperazin-1-yl}-2-[4-(4-nitro-3-trifluoromethyl-phenylamino)-cyclohexyloxy]-ethanone (CI, m/z): [M+H]$^+$ 657; $^1$H NMR (400 MHz, CDCl$_3$) δ ppm 1.27-1.36 (m, 2H), 1.40-1.61 (m, 2H), 2.15 (d, J=9.0 Hz, 4H), 2.50-2.71 (m, 5H), 2.83 (dd, J=13.5, 7.8 Hz, 1H), 3.02 (dd, J=15.6, 7.8 Hz, 1H), 3.21-3.51 (m, 3H), 3.52-3.80 (m, 4H), 4.21 (s, 2H), 4.52 (d, J=7.6 Hz, 1H), 5.03 (dd, J=8.6, 3.8 Hz, 1H), 6.64 (dd, J=9.1, 2.4 Hz, 1H), 6.75-6.92 (m, 2H), 7.09 (t, J=8.7 Hz, 2H), 7.27-7.31 (m, 1H), 7.34 (s, 1H), 7.46 (dd, J=8.6, 5.3 Hz, 2H), 8.02 (d, J=9.0 Hz, 1H).

Compound 261: 1-[4-(5-fluoro-2,3-dihydro-benzofuran-2-ylmethyl)-piperazin-1-yl]-2-{4-[methyl-(4-nitro-3-trifluoromethyl-phenyl)-amino]-cyclohexyloxy}-ethanone (CI, m/z): [M+H]$^+$ 595; $^1$H NMR (400 MHz, CDCl$_3$) δ ppm 1.37-1.52 (m, 2H), 1.58-1.73 (m, 2H), 1.85 (d, J=12.6 Hz, 2H), 2.25 (d, J=11.7 Hz, 2H), 2.51-2.69 (m, 5H), 2.79 (dd, J=13.5, 7.7 Hz, 1H), 2.91 (s, 3H), 2.97 (dd, J=15.9, 8.0 Hz, 1H), 3.27 (dd, J=15.8, 9.0 Hz, 1H), 3.34-3.50 (m, 1H), 3.50-3.81 (m, 5H), 4.21 (s, 2H), 4.99 (qd, J=8.2, 3.9 Hz, 1H), 6.69 (dd, J=8.7, 4.2 Hz, 1H), 6.73-6.82 (m, 2H), 6.87 (d, J=8.0 Hz, 1H), 6.99 (d, J=2.4 Hz, 1H), 8.06 (d, J=9.3 Hz, 1H).

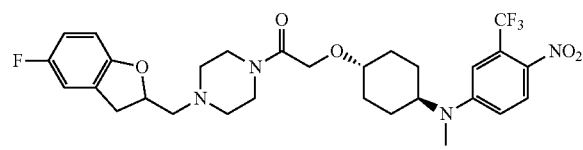 [SMILES: CN(c1ccc([N+](=O)[O-])c(C(F)(F)F)c1)[C@H]1CC[C@H](OCC(=O)N2CCN(CC3Cc4cc(F)ccc4O3)CC2)CC1]

EXAMPLE 22: Preparation of Compound 68

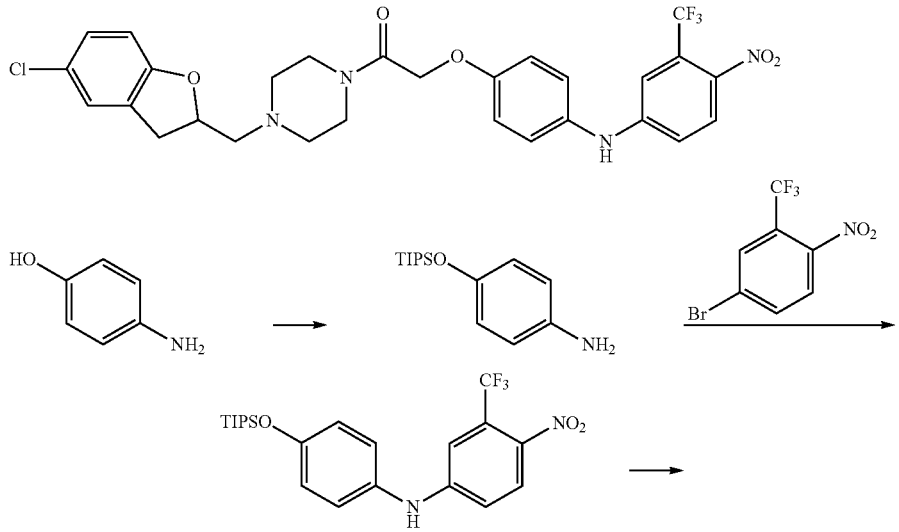

Compound 68

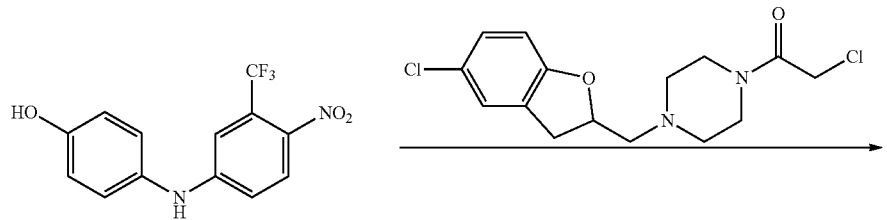

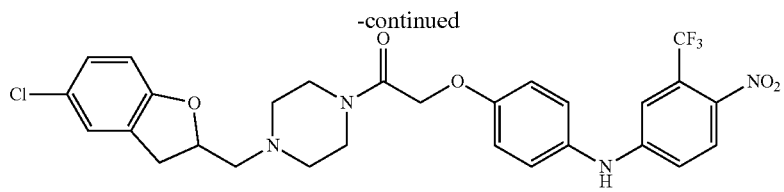

Steps 1-6

The formation of 2-chloro-1-[4-[(5-chloro-2,3-dihydro-1-benzofuran-2-yl)methyl]piperazin-1-yl]ethan-1-one was performed as described in the synthesis of compound 76.

Step 7. Formation of 4-[[tris(propan-2-yl)silyl]oxy]aniline

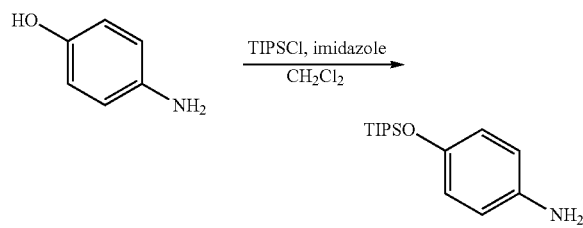

To a solution of 4-aminophenol (20 g, 183 mmol) in dichloromethane (300 ml) was added 1H-imidazole (16.2 g, 240 mmol, 1.3 eq.). Triisopropyl chlorosilane (53.1 g, 275 mmol, 1.5 eq.) was added dropwise with stirring for 2 hours at room temperature. The reaction mixture was filtered and the filtrate was concentrated under vacuum to give a residue, which was purified by silica gel column chromatography using 25% ethyl acetate in petroleum ether to afford 4-[[tris(propan-2-yl)silyl]oxy]aniline as brown oil (34 g, 70%); (ES, m/z): [M+H]$^+$266; $^1$H NMR (300 MHz, CDCl$_3$): δ 6.66-6.72 (m, 2H), 6.55-6.59 (m, 2H), 3.23 (s, 2H), 1.20-1.30 (m, 3H), 1.13 (s, 18H).

Step 8. Formation of 4-nitro-3-(trifluoromethyl)-N-(4-[[tris(propan-2-yl)silyl]oxy]phenyl)aniline

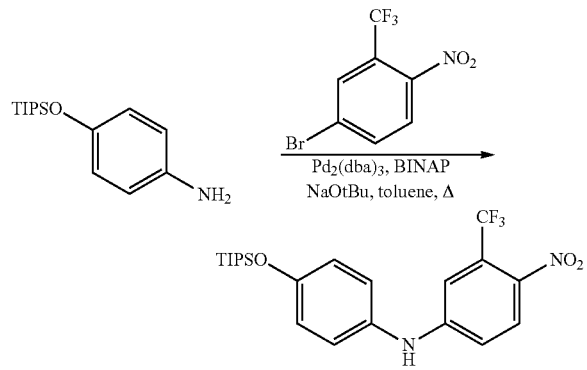

To a solution of 4-[[tris(propan-2-yl)silyl]oxy]aniline (15 g, 56 mmol) in toluene (100 ml) was added 4-bromo-1-nitro-2-(trifluoromethyl)benzene (22.84 g, 84.6 mmol, 1.5 eq.), Pd$_2$(dba)$_3$ (2.34 g, 2.3 mmol, 4 mol %), BINAP (710 mg, 1.1 mmol, 2 mol %) and t-BuONa (10.87 g, 113.2 mmol, 2 eq.). The mixture was stirred under nitrogen overnight at 100° C. (oil bath). The reaction mixture was concentrated under vacuum to give a residue, which was purified by silica gel column chromatography using 10% ethyl acetate in petroleum ether to afford 4-nitro-3-(trifluoromethyl)-N-(4-[[tris(propan-2-yl)silyl]oxy]phenyl)aniline as a orange solid (8 g, 31%); (ES, m/z): [M+H]$^+$ 455; $^1$H NMR (300 MHz, CDCl$_3$): δ 7.97 (d, J=6.0 Hz, 1H), 7.05-7.09 (m, 3H), 6.87-6.96 (m, 3H), 6.18 (s, 1H), 1.26-1.33 (m, 3H), 1.13 (s, 18H).

Step 9. Formation of 4-[[4-nitro-3-(trifluoromethyl)phenyl]amino]phenol

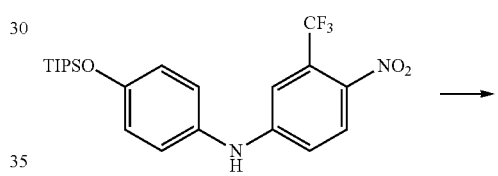

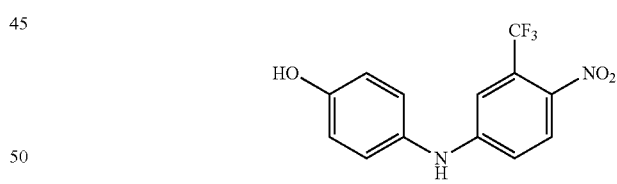

To a solution of 4-nitro-3-(trifluoromethyl)-N-(4-[[tris(propan-2-yl)silyl]oxy]phenyl)aniline (3 g, 6.6 mmol) in tetrahydrofuran (60 ml) was added TBAF (2.59 g, 9.9 mmol) with stirring for 1 hour at room temperature. The reaction mixture was diluted with water (100 ml) and extracted with dichloromethane (3×50 ml), dried over anhydrous magnesium sulfate, and concentrated under vacuum to give a residue, which was applied onto a silica gel column and eluted with 30% ethyl acetate in petroleum ether to afford 4-[[4-nitro-3-(trifluoromethyl) phenyl]amino]phenol as a orange solid (1.5 g, 76%); (ES, m/z): [M+H]$^+$ 299; $^1$H NMR (300 MHz, DMSO-d6): δ 9.53 (s, 1H), 9.28 (s, 1H), 8.07 (d, J=9.0 Hz, 1H), 7.18 (d, J=2.4 Hz, 1H), 7.07 (d, J=8.7 Hz, 2H), 7.01-7.05 (m, 1H), 6.81 (d, J=8.7 Hz, 2H).

Step 10. Formation of 1-[4-[(5-chloro-2,3-dihydro-1-benzofuran-2-yl)methyl]piperazin-1-yl]-2-(4-[[4-nitro-3-(trifluoromethyl) phenyl]amino]phenoxy)ethan-1-one (#68)

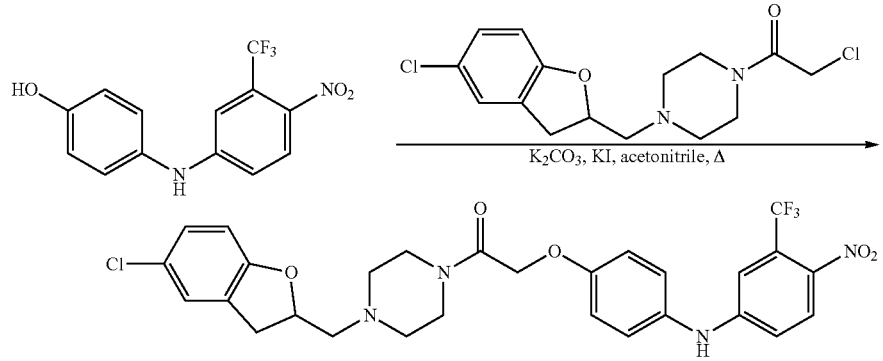

To a solution of 1-[(5-chloro-2,3-dihydro-1-benzofuran-2-yl)methyl]-4-(2-chloroethyl) piperazine (200 mg, 0.61 mmol) in acetonitrile (5 ml) was added potassium carbonate (139 mg, 1.01 mmol, 1.6 eq.), 4-[4-nitro-3-(trifluoromethyl) phenyl]aminophenol (200 mg, 0.67 mmol, 1.1 eq.) and KI (56 mg, 0.34 mmol, 0.6 eq.) with stirring for 3 hours at 70° C. (oil bath). The reaction mixture was concentrated under vacuum to give a residue, which was purified by silica gel column chromatography using 2% dichloromethane in methanol to afford 1-[4-[(5-chloro-2,3-dihydro-1-benzofuran-2-yl)methyl]piperazin-1-yl]-2-(4-[[4-nitro-3-(trifluoromethyl)phenyl]amino]phenoxy)ethan-1-one as a orange solid (150.3 mg, 36%); (ES, m/z): [M+H]$^+$ 591.15; $^1$H NMR (300 MHz, CDCl$_3$): δ 7.98 (d, J=9.0 Hz, 1H), 6.91-7.11 (m, 4H), 7.08 (d, J=8.7 Hz, 1H), 7.01 (d, J=8.7 Hz, 2H), 6.92 (dd, J=2.7, 9.0 Hz, 1H), 6.69 (d, J=8.4 Hz, 1H), 6.32 (s, 1H), 4.93-5.09 (m, 1H), 4.75 (s, 2H), 3.65-3.78 (m, 4H), 3.28 (dd, J=9.3, 15.9 Hz, 1H), 2.97 (dd, J=8.1, 15.6 Hz, 1H), 2.79 (dd, J=7.5, 13.5 Hz, 1H), 2.60-2.75 (m, 5H).

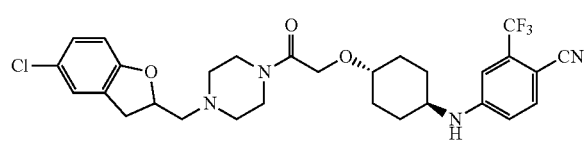 [SMILES: N#Cc1ccc(N[C@H]2CC[C@H](OCC(=O)N3CCN(CC4Cc5cc(Cl)ccc5O4)CC3)CC2)cc1C(F)(F)F]

Compound 82: 4-[[4-(3-[4-[(5-chloro-2,3-dihydro-1-benzofuran-2-yl)methyl]-piperazin-1-yl]-2-oxopropoxy)cyclohexyl]amino]-2-(trifluoromethyl)benzonitrile (ES, m/z): [M+H]$^+$ 577.20; $^1$H NMR (300 MHz, CDCl$_3$): δ 7.55 (d, J=8.7 Hz, 1H), 7.13 (s, 1H), 7.07 (d, J=8.7 Hz, 1H), 6.81 (s, 1H), 6.64-6.71 (m, 2H), 5.03 (br s, 1H), 4.34-4.36 (m, 1H), 4.19 (s, 2H), 3.60-3.80 (m, 3H), 3.32-3.43 (m, 3H), 2.81-3.07 (m, 2H), 2.62-2.83 (m, 4H), 2.12-2.15 (m, 4H), 1.65-1.79 (m, 2H), 1.26-1.48 (m, 4H).

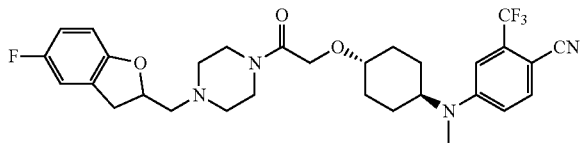 [SMILES: CN(c1ccc(C#N)c(C(F)(F)F)c1)[C@H]1CC[C@H](OCC(=O)N2CCN(CC3Cc4cc(F)ccc4O3)CC2)CC1]

Compound 280: 4-[(4-{2-[4-(5-fluoro-2,3-dihydro-benzofuran-2-ylmethyl)-piperazin-1-yl]-2-oxo-ethoxy}-cyclohexyl)-methyl-amino]-2-trifluoromethyl-benzonitrile (ES, m/z): [M+H]$^+$ 575; $^1$H NMR (400 MHz, CDCl$_3$) δ ppm 1.45 (m, 2H), 1.60 (m, 2H), 1.83 (d, J=12.5 Hz, 2H), 2.24 (d, J=12.0 Hz, 2H), 2.49-2.68 (m, 5H), 2.73-2.81 (m, 1H), 2.86 (s, 3H), 2.99 (d, J=8.0 Hz, 1H), 3.17-3.31 (m, 1H), 3.39 (s, 1H), 3.52-3.79 (m, 5H), 4.20 (s, 2H), 4.83-5.11 (m, 1H), 6.68 (dd, J=8.7, 4.2 Hz, 1H), 6.73-6.83 (m, 2H), 6.84-6.90 (m, 1H), 6.95 (d, J=2.3 Hz, 1H), 7.58 (d, J=8.9 Hz, 1H).

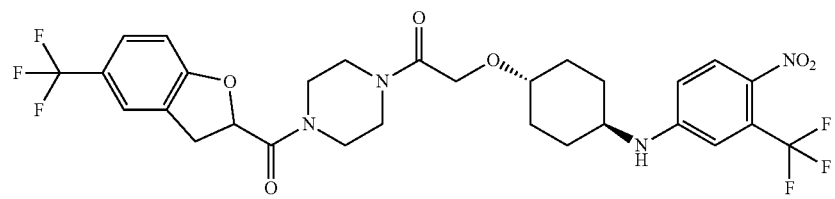 [SMILES: O=C(CO[C@H]1CC[C@H](Nc2ccc([N+](=O)[O-])c(C(F)(F)F)c2)CC1)N1CCN(C(=O)C2Cc3cc(C(F)(F)F)ccc3O2)CC1]

Compound 81: 2-[4-(4-nitro-3-trifluoromethyl-phenylamino)-cyclohexyloxy]-1-[4-(5-trifluoromethyl-2,3-dihydro-benzofuran-2-carbonyl)-piperazin-1-yl]-ethanone (ES, m/z): [M+H]$^+$ 645.25; $^1$H NMR (300 MHz, CDCl$_3$): δ 8.03 (d, J=8.4 Hz, 1H), 7.48 (s, 1H), 7.42 (d, J=8.4 Hz, 1H), 6.83-6.91 (m, 2H), 6.64 (dd, J=9.0, 2.7 Hz, 1H), 5.45-5.55 (m, 1H), 4.24 (s, 2H), 3.82-4.00 (m, 4H), 3.30-3.75 (m, 8H), 2.14 (d, J=6.3 Hz, 4H), 1.40-1.60 (m, 2H), 1.25-1.40 (m, 2H).

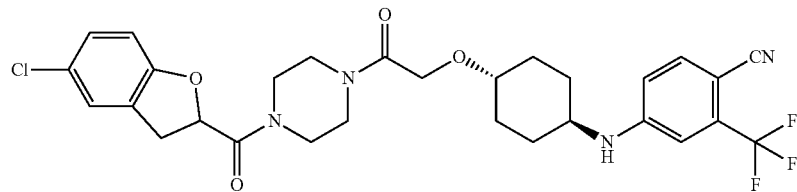 [SMILES: N#Cc1ccc(N[C@H]2CC[C@H](OCC(=O)N3CCN(C(=O)C4Cc5cc(Cl)ccc5O4)CC3)CC2)cc1C(F)(F)F]

Compound 85: 4-(4-{2-[4-(5-chloro-2,3-dihydro-benzofuran-2-carbonyl)-piperazin-1-yl]-2-oxo-ethoxy}-cyclohexylamino)-2-trifluoromethyl-benzonitrile (ES, m/z): [M+H]$^+$ 591.30; $^1$H NMR (300 MHz, CDCl$_3$): δ 7.54 (d, J=8.7 Hz, 1H), 7.18 (s, 1H), 7.08 (dd, J=8.4, 2.1 Hz, 1H), 6.82 (d, J=1.8 Hz, 1H), 6.62-6.74 (t, J=9.0 Hz, 2H), 5.36-5.45 (m, 1H), 4.23 (s, 2H), 3.85-3.95 (m, 4H), 3.25-3.75 (m, 8H), 2.13 (d, J=10.2 Hz, 4H), 1.40-1.55 (m, 2H), 1.20-1.35 (m, 2H).

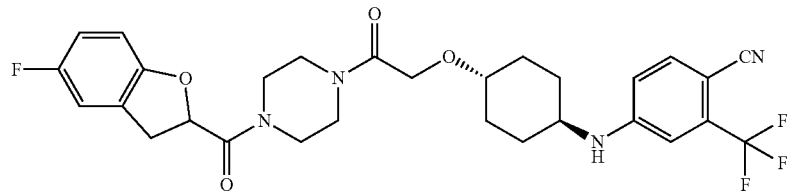 [SMILES: N#Cc1ccc(N[C@H]2CC[C@H](OCC(=O)N3CCN(C(=O)C4Cc5cc(F)ccc5O4)CC3)CC2)cc1C(F)(F)F]

Compound 86: 4-(4-{2-[4-(5-fluoro-2,3-dihydro-benzofuran-2-carbonyl)-piperazin-1-yl]-2-oxo-ethoxy}-cyclohexylamino)-2-trifluoromethyl-benzonitrile (ES, m/z): [M+H]$^+$ 575.20; $^1$H NMR (400 MHz, CDCl$_3$): δ 7.57 (d, J=8.8 Hz, 1H), 6.94 (d, J=6.4 Hz, 1H), 6.81-6.85 (m, 2H), 6.66-6.71 (m, 2H), 5.41-5.46 (m, 1H), 4.31 (d, J 7.2 Hz, 1H), 4.25 (s, 2H), 3.85-3.94 (m, 4H), 3.29-3.77 (m, 8H), 2.15-2.17 (m, 4H), 1.45-1.52 (m, 2H), 1.21-1.33 (m, 2H).

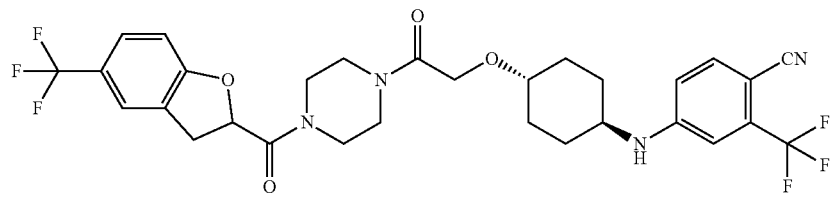 [SMILES: N#Cc1ccc(N[C@H]2CC[C@H](OCC(=O)N3CCN(C(=O)C4Cc5cc(C(F)(F)F)ccc5O4)CC3)CC2)cc1C(F)(F)F]

Compound 87: 2-[4-(4-cyano-3-trifluoromethyl-phenylamino)-cyclohexyloxy]-1-[4-(5-trifluoromethyl-2,3-dihydro-benzofuran-2-carbonyl)-piperazin-1-yl]-ethanone (ES, m/z): [M+H]$^+$ 625.40; $^1$H NMR (300 MHz, CDCl$_3$): δ 7.54 (d, J=8.4 Hz, 1H), 7.48 (s, 1H), 7.42 (d, J=8.4 Hz, 1H), 6.80-6.90 (m, 2H), 6.67 (d, J=8.7 Hz, 1H), 5.45-5.55 (m, 1H), 4.23 (s, 2H), 3.80-4.00 (m, 4H), 3.30-3.70 (m, 8H), 2.14 (d, J=10.8 Hz, 4H), 1.40-1.55 (m, 2H), 1.20-1.35 (m, 2H).

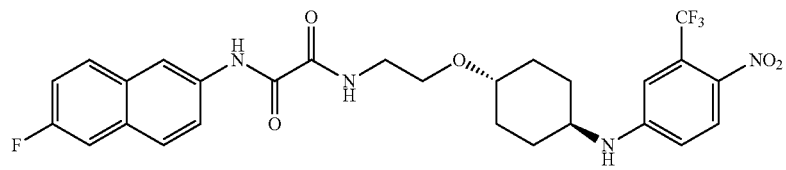 [SMILES: O=C(NCCO[C@H]1CC[C@H](Nc2ccc([N+](=O)[O-])c(C(F)(F)F)c2)CC1)C(=O)Nc1ccc2cc(F)ccc2c1]

Compound 172: N-(7-fluoronaphthalen-2-yl)-N-2-[(4-[[4-nitro-3-(trifluoromethyl) phenyl]amino]cyclohexan-1-e)oxy]ethyl]ethanediamide (ES, m/z): [M+H]$^+$ 561.00; $^1$H NMR (300 MHz, CDCl$_3$): δ 9.41 (s, 1H), 8.34 (s, 1H), 8.01 (d, J=9.0 Hz, 1H), 7.78-7.90 (m, 3H), 7.58 (m, 1H), 7.42 (dd, J=2.4 Hz, 9.6 Hz, 1H), 7.31 (m, 1H), 6.84 (d, J=2.4 Hz, 1H), 6.62 (dd, J=2.7 Hz, 9.0 Hz, 1H), 3.59-3.65 (m, 4H), 3.33-3.41 (m, 2H), 2.11-2.18 (m, 4H), 1.41-1.53 (m, 2H), 1.24-1.35 (m, 2H).

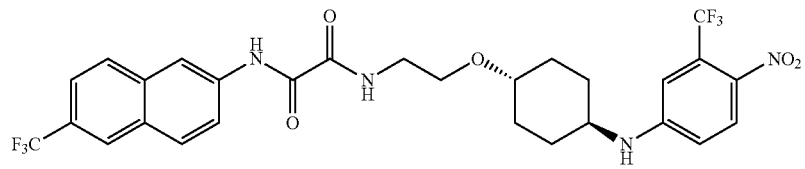 [SMILES: O=C(NCCO[C@H]1CC[C@H](Nc2ccc([N+](=O)[O-])c(C(F)(F)F)c2)CC1)C(=O)Nc1ccc2cc(C(F)(F)F)ccc2c1]

Compound 173: N-[2-[(4-[[4-nitro-3-(trifluoromethyl) phenyl]amino]cyclohexyl)oxy]ethyl]-N-6-(trifluoromethyl) naphthalen-2-yl]ethanediamide (ES, m/z): [M+H]+ 613.15; 1H NMR (400 MHz, CDCl$_3$): δ 9.47 (s, 1H), 8.42 (s, 1H), 8.12 (s, 1H), 8.02 (d, J=8.8 Hz, 1H), 7.96-7.89 (m, 3H), 7.69-7.65 (m, 2H), 6.85 (s, 1H), 6.64 (d, J=8.0 Hz, 1H), 3.66-3.58 (m, 4H), 3.46-3.32 (m, 2H), 2.20-2.10 (m, 4H), 1.51-1.43 (m, 2H), 1.34-1.25 (m, 2H).

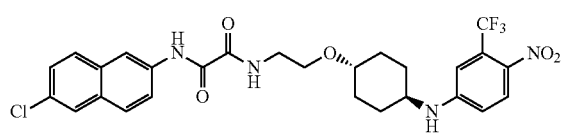 [SMILES: O=C(NCCO[C@H]1CC[C@H](Nc2ccc([N+](=O)[O-])c(C(F)(F)F)c2)CC1)C(=O)Nc1ccc2cc(Cl)ccc2c1]

Compound 174: N-(6-chloronaphthalen-2-yl)-N-[2-[(4-[[4-nitro-3-(trifluoromethyl) phenyl]amino]cyclohexyl)oxy]ethyl]ethanediamide (ES, m/z): [M−H]$^-$ 577.30; $^1$H NMR (300 MHz, CDCl$_3$): δ 9.41 (s, 1H), 8.33 (d, J=1.5 Hz, 1H), 8.02 (d, J=9.0 Hz, 1H), 7.92-7.75 (m, 4H), 7.62 (dd, J=2.1 Hz, 8.7 Hz, 1H), 7.46 (dd, J=2.1 Hz, 8.7 Hz, 1H), 6.86 (s, 1H), 6.65 (d, J=8.4 Hz, 1H), 3.66-3.56 (m, 4H), 3.45-3.35 (m, 2H), 2.18 (m, 4H), 1.52-1.42 (m, 2H), 1.35-1.22 (m, 2H).

EXAMPLE 23: Preparation of Compound 238

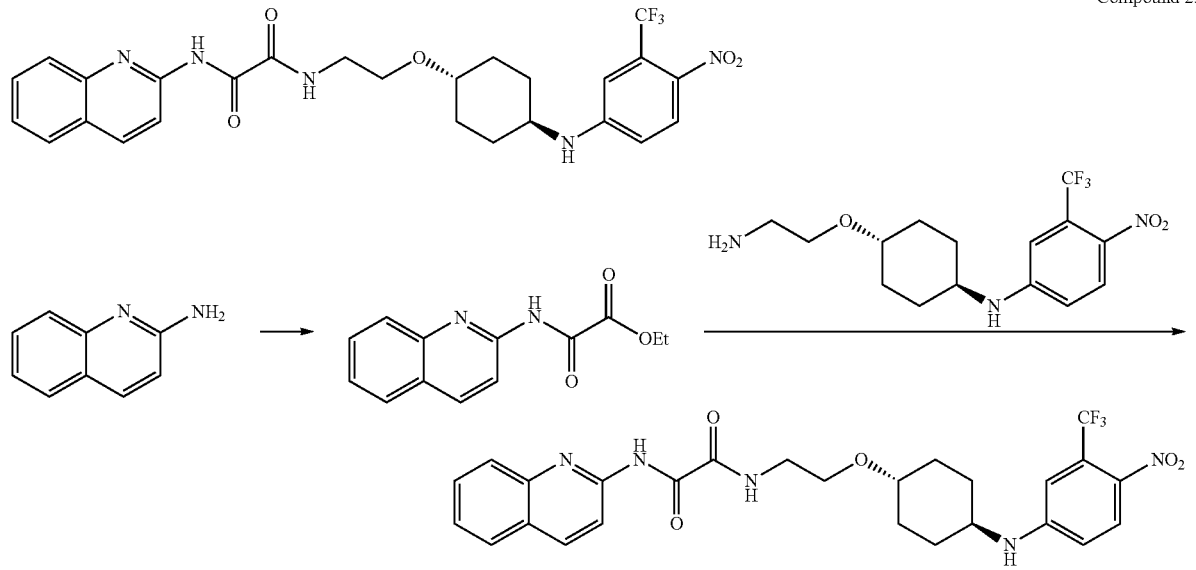

Step 1. Formation of ethyl 2-oxo-2-(quinolin-2-ylamino)acetate

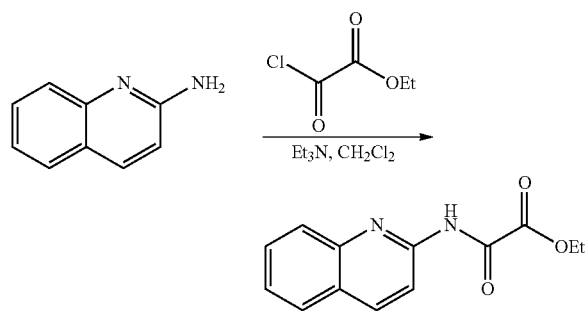

To a mixture of quinolin-2-amine (200 mg, 1.4 mmol) and triethylamine (210 mg, 2.1 mmol) in dichloromethane (10 mL) was added dropwise ethyl 2-chloro-2-oxoacetate (227 mg, 1.67 mmol). After stirring for 1 hour at room temperature, the reaction was quenched with water (50 mL) and extracted with ethyl acetate (3×50 mL). The combined organic layers were dried over anhydrous sodium sulfate, filtered, and concentrated under vacuum to give a residue, which was purified by silica gel column chromatography using 1% ethyl acetate in petroleum ether to afford ethyl 2-oxo-2-(quinolin-2-ylamino)acetate as yellow solid (210 mg, 62%). (ES, m/z): [M+H]$^+$ 245.1; $^1$H NMR (400 MHz, CDCl$_3$): δ 9.65 (br s, 1H), 8.44 (d, J=8.8 Hz, 1H), 8.24 (d, J=8.8 Hz, 1H), 7.90 (d, J=8.4 Hz, 1H), 7.82 (d, J=8.0 Hz, 1H), 7.74-7.69 (m, 1H), 7.53-7.49 (m, 1H), 4.46 (q, J=7.2 Hz, 2H), 1.46 (t, J=7.2 Hz, 3H).

Step 2. Formation of N$^1$-(2-(-4-(4-nitro-3-(trifluoromethyl)phenylamino) cyclohexyloxy)ethyl)-N$^2$-(quinolin-2-yl)oxalamide (#238)

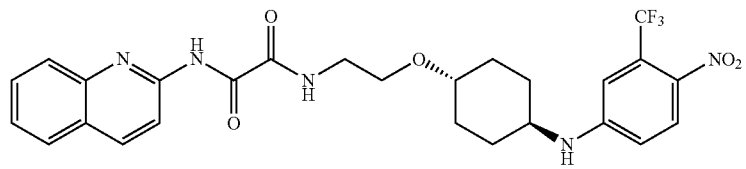

The mixture of ethyl 2-oxo-2-(quinolin-2-ylamino)acetate (56 mg, 0.23 mmol) and N-(-4-(2-aminoethoxy)cyclohexyl)-4-nitro-3-(trifluoromethyl)benzenamine (80 mg, 0.23 mmol) in tetrahydrofuran (2 mL) was stirred overnight at room temperature and then concentrated under vacuum to give a residue, which was purified by HPLC to afford N$^1$-(2-(-4-(4-nitro-3-(trifluoromethyl)phenylamino) cyclohexyloxy)ethyl)-N$^2$-(quinolin-2-yl)oxalamide as a yellow solid (58.8 mg, 46%). (ES, m/z): [M+H]$^+$ 546.10; $^1$H NMR (400 MHz, CDCl$_3$): δ 10.11 (br s, 1H), 8.41 (d, J=8.8 Hz, 1H), 8.26 (d, J=8.8 Hz, 1H), 8.01 (d, J=8.8 Hz, 1H), 7.93 (d, J=8.8 Hz, 1H), 7.82 (d, J=7.6 Hz, 2H), 7.73 (t, J=7.2 Hz, 1H), 7.52 (t, J=7.2 Hz, 1H), 6.85 (d, J=2.4 Hz, 1H), 6.65 (dd, J=8.8, 2.4 Hz, 1H), 4.48 (d, J=7.2 Hz, 1H), 3.68-3.58 (m, 4H), 3.42-3.36 (m, 2H), 2.19-2.10 (m, 4H), 1.48-1.38 (m, 2H), 1.34-1.24 (m, 2H).

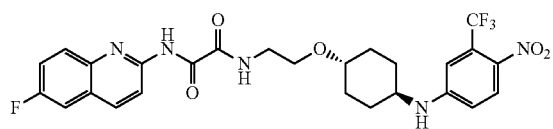 [SMILES: O=C(NCCO[C@H]1CC[C@H](Nc2ccc([N+](=O)[O-])c(C(F)(F)F)c2)CC1)C(=O)Nc1ccc2cc(F)ccc2n1]

Compound 239: N$^1$-(6-fluoroquinolin-2-yl)-N$^2$-(2-(-4-(4-nitro-3-(trifluoromethyl) phenylamino)cyclohexyloxy)ethyl)oxalamide (ES, m/z): [M+H]$^+$ 564.10; $^1$H NMR (300 MHz, CDCl$_3$): δ 10.05 (s, 1H), 8.44 (d, J=9.0 Hz, 1H), 8.20 (d, J=9.0 Hz, 1H), 8.02 (d, J=9.0 Hz, 1H), 7.95-7.91 (m, 1H), 7.83 (m, 1H), 7.53-7.43 (m, 2H), 6.85 (d, J=2.4 Hz, 1H), 6.66 (dd, J=2.7, 9.0, 1H), 4.47 (br s, 1H), 3.68-3.59 (m, 4H), 3.41-3.33 (m, 2H), 2.18-2.10 (m, 4H), 1.53-1.40 (m, 2H), 1.37-1.23 (m, 2H).

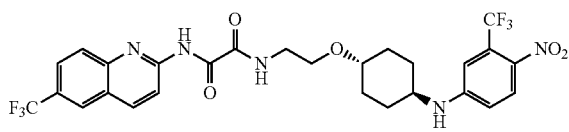 [SMILES: O=C(NCCO[C@H]1CC[C@H](Nc2ccc([N+](=O)[O-])c(C(F)(F)F)c2)CC1)C(=O)Nc1ccc2cc(C(F)(F)F)ccc2n1]

Compound 240: N$^1$-(2-(-4-(4-nitro-3-(trifluoromethyl)phenylamino)cyclohexyloxy)ethyl)-N$^2$-(6-(trifluoromethyl) quinolin-2-yl)oxalamide (ES, m/z): [M+H]$^+$ 614.2; $^1$H NMR (300 MHz, CDCl$_3$): δ 10.19 (br s, 1H), 8.54 (d, J=9.0 Hz, 1H), 8.34 (d, J=9.0 Hz, 1H), 8.14 (s, 1H), 8.06-8.00 (m, 2H), 7.91 (dd, J=1.8, 9.0 Hz, 1H), 7.82 (m, 1H), 6.85 (d, J=2.4 Hz, 1H), 6.63 (dd, J=9.0, 2.4 Hz, 1H), 3.66-3.60 (m, 4H), 3.45-3.33 (m, 2H), 2.18-2.11 (m, 4H), 1.54-1.35 (m, 2H), 1.32-1.23 (m, 2H).

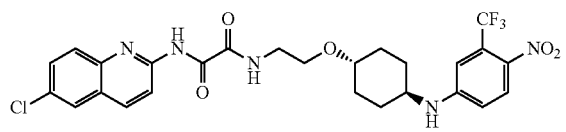 [SMILES: O=C(NCCO[C@H]1CC[C@H](Nc2ccc([N+](=O)[O-])c(C(F)(F)F)c2)CC1)C(=O)Nc1ccc2cc(Cl)ccc2n1]

Compound 241: N$^1$-(6-chloroquinolin-2-yl)-N$^2$-(2-(-4-(4-nitro-3-(trifluoromethyl) phenylamino)cyclohexyloxy)ethyl)oxalamide (ES, m/z): [M+H]$^+$ 580.10; $^1$H NMR (300 MHz, CDCl$_3$): δ 10.02 (s, 1H), 8.44 (d, J=9.0 Hz, 1H), 8.16 (d, J=9.0 Hz, 1H), 8.02 (d, J=9.0 Hz, 1H), 7.89-7.80 (m, 3H), 7.65 (dd, J=9.3, 2.4 Hz, 1H), 6.85 (d, J=2.1 Hz, 1H), 6.63 (dd, J=9.0, 2.4 Hz, 1H), 4.47 (br s, 1H), 3.66-3.59 (m, 4H), 3.41-3.33 (m, 2H), 2.18-2.10 (m, 4H), 1.53-1.40 (m, 2H), 1.37-1.23 (m, 2H).

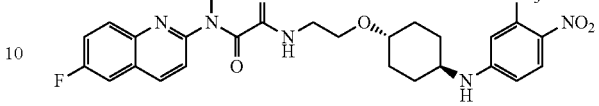

Compound 242: N-(6-fluoroquinolin-2-yl)-N-methyl-N-2-[[-4-[[4-nitro-3-(trifluoromethyl)phenyl]amino]cyclohexyl]oxy]ethyl)ethanediamide (ES, m/z): [M+H]$^+$ 578.05; $^1$H NMR (300 MHz, CDCl$_3$): δ 8.21 (d, J=8.7 Hz, 1H), 8.04-7.97 (m, 2H), 7.51-7.40 (m, 4H), 6.85 (d, J=2.1 Hz, 1H), 6.66 (dd, J=2.4, 9.0 Hz, 1H), 3.55 (overlapping s and m, 5H), 3.42-3.32 (overlapping m, 4H), 2.17-2.07 (m, 4H), 1.50-1.42 (m, 2H), 1.38-1.23 (m, 2H).

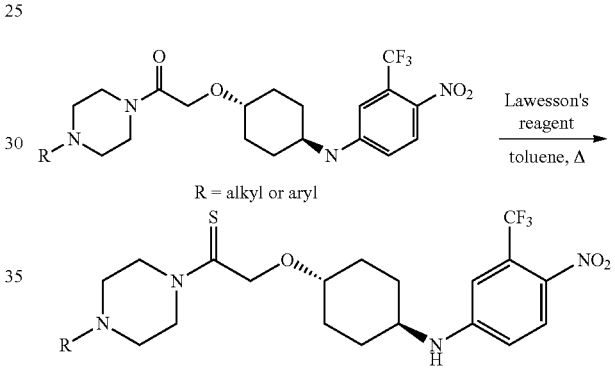

EXAMPLE 24: Compounds 263, 264, & 265

Formation of 1-[4-(6-fluoro-naphthalen-2-yl)-piperazin-1-yl]-2-[4-(4-nitro-3-trifluoromethyl-henylamino)-cyclohexyloxy]-ethanethione (#263)

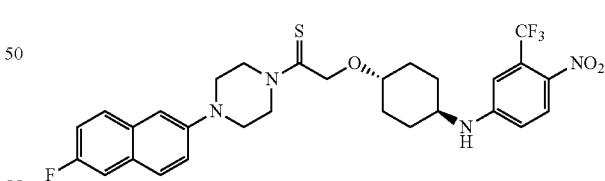

The amide (9 mg) was placed into a conical vial with a stir bar. Lawesson's reagent (1.5 eq.) and ~0.5 ml of toluene were added, and the contents were then heated at 95° C. The solid did not completely dissolve and the mixture was heated overnight. After ~16 hours, diluted the contents with EtOAc and then stirred vigorously with water. Separated, dried the EtOAc layer over Na$_2$SO$_4$, filtered, and concentrated. Chromatographed the crude material on silica gel using Methanol/dichloromethane to elute. The product containing fractions were combined and concentrated under vacuum to afford a yellow solid. (ES, m/z) [M+H]$^+$ 593.21; $^1$H NMR (400 MHz, CDCl₃): δ 8.00 (d, J=8.8 Hz, 1H), 7.70 (m, 2H), 7.38 (dd, J=9.2, 2.4 Hz, 1H), 7.30 (dd, J=9.2, 2.4 Hz, 1H), 7.22 (dt, J=8.8, 2.8 Hz, 1H), 7.14 (d, J=2.4 Hz, 1H), 6.83 (d, J=2.8 Hz, 1H), 6.62 (dd, J=9.2, 2.4 Hz, 1H), 4.66 (s, 2H), 4.44 (m, 3H), 4.12 (m, 2H), 3.60 (m, 1H), 3.38 (m, 5H), 2.15 (m, 4H), 1.45 (m, 2H), 1.30 (m, 2H).

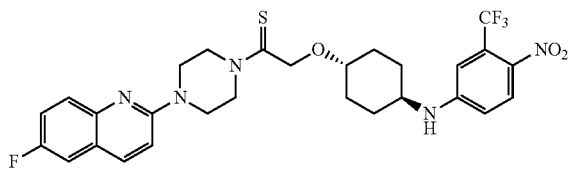 [SMILES: O=[N+]([O-])c1ccc(N[C@H]2CC[C@H](OCC(=S)N3CCN(c4ccc5cc(F)ccc5n4)CC3)CC2)cc1C(F)(F)F]

Compound 264: 1-[4-(6-fluoro-quinolin-2-yl)-piperazin-1-yl]-2-[4-(4-nitro-3-trifluoro-methyl-phenylamino)-cyclohexyloxy]-ethanethione (ES, m/z) [M+H]⁺ 594.21; ¹H NMR (400 MHz, CDCl₃): δ 8.00 (d, J=9.2 Hz, 1H), 7.71 (dd, J=9.2, 5.3 Hz, 1H), 7.26-7.30 (m, 1H), 7.03 (d, J=9.2 Hz, 1H), 6.83 (d, J=2.5 Hz, 1H), 6.62 (dd, J=9.1, 2.6 Hz, 1H), 4.66 (s, 2H), 4.37-4.44 (m, 3H), 4.06-4.10 (m, 2H), 3.84-3.91 (m, 4H), 3.56-3.64 (m, 1H), 3.32-3.43 (m, 1H), 2.08-2.21 (m, 4H), 1.40-1.51 (m, 2H), 1.26-1.36 (m, 4H).

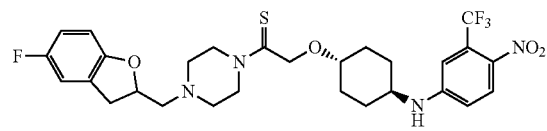 [SMILES: O=[N+]([O-])c1ccc(N[C@H]2CC[C@H](OCC(=S)N3CCN(CC4Cc5cc(F)ccc5O4)CC3)CC2)cc1C(F)(F)F]

Compound 265: 1-[4-(5-fluoro-2,3-dihydro-benzofuran-2-ylmethyl)-piperazin-1-yl]-2-[4-(4-nitro-3-trifluoromethyl-phenylamino)-cyclohexyloxy]-ethanethione (ES, m/z) [M+H]⁺ 599.22; ¹H NMR (400 MHz, CDCl₃): δ 8.01 (d, J=9.0 Hz, 1H), 6.87 (dd, J=8.0, 2.5 Hz, 1H), 6.84 (d, J=2.7 Hz, 1H), 6.79 (td, J=8.9, 2.7 Hz, 1H), 6.68 (dd, J 8.6, 4.1 Hz, 1H), 6.62 (dd, J=9.1, 2.6 Hz, 1H), 4.95-5.03 (m, 1H), 4.60 (s, 2H), 4.44 (m, J 7.6 Hz, 1H), 4.23-4.35 (m, 2H), 3.93 (t, J=5.1 Hz, 2H), 3.57 (tt, J=10.1, 3.8 Hz, 1H), 3.32-3.42 (m, 1H), 3.27 (dd, J=15.7, 9.1 Hz, 1H), 2.97 (dd, J=15.9, 7.9 Hz, 1H), 2.80 (dd, J 13.6, 7.7 Hz, 1H), 2.59-2.76 (m, 5H), 2.08-2.18 (m, 4H), 1.36-1.49 (m, 2H), 1.27-1.36 (m, 2H).

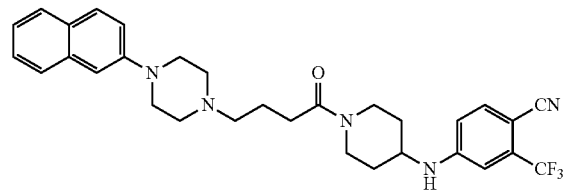 [SMILES: N#Cc1ccc(NC2CCN(C(=O)CCCN3CCN(c4ccc5ccccc5c4)CC3)CC2)cc1C(F)(F)F]

4-[(1-[4-[4-(naphthalen-2-yl)piperazin-1-yl]butanoyl]piperidin-4-yl)amino]-2-(trifluoromethyl)benzonitrile (#15)

(ES, m/z): [M+H]⁺ 550.40; ¹H NMR (400 MHz, DMSO-d6): δ 7.65-7.81 (m, 4H), 7.30-7.46 (m, 2H), 7.14-7.29 (m, 3H), 7.06 (s, 1H), 6.90 (d, J=8.4 Hz, 1H), 4.25 (d, J=13.2 Hz, 1H), 3.85 (d, J=13.6 Hz, 1H), 3.63-3.73 (m, 1H), 3.11-3.25 (m, 5H), 2.75-2.90 (t, J=11.2 Hz, 1H), 2.52-2.62 (m, 4H), 2.27-2.42 (m, 4H), 1.82-1.99 (t, J=16.4 Hz, 2H), 1.65-1.80 (m, 2H), 1.15-1.40 (m, 2H).

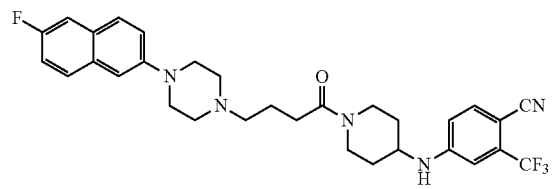 [SMILES: N#Cc1ccc(NC2CCN(C(=O)CCCN3CCN(c4ccc5cc(F)ccc5c4)CC3)CC2)cc1C(F)(F)F]

Compound 18: 4-[(1-[4-[4-(6-fluoronaphthalen-2-yl)piperazin-1-yl]butanoyl]-piperidin-4-yl)amino]-2-(trifluoromethyl)benzonitrile (ES, m/z): [M+H]⁺ 568.3; ¹H NMR (300 MHz, CDCl₃): δ 7.63-7.74 (m, 1H), 7.53 (d, J=8.1 Hz, 1H), 7.35-7.39 (m, 1H), 7.19-7.30 (m, 2H), 6.85 (d, J=2.1 Hz, 1H), 6.69-6.72 (dd, J=2.1, 10.5 Hz, 1H), 4.69 (d, J=7.5 Hz, 1H), 4.53-4.58 (m, 1H), 3.87-3.92 (m, 1H), 3.45-3.61 (m, 4H), 3.09-3.28 (m, 4H), 2.70-2.88 (m, 3H), 2.01-2.20 (m, 4H), 1.75-1.85 (m, 1H).

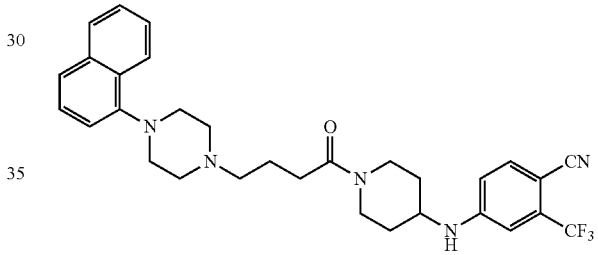

Compound 21: 4-[(1-[4-[4-(naphthalen-1-yl)piperazin-1-yl]butanoyl]piperidin-4-yl)amino]-2-(trifluoromethyl)benzonitrile (ES, m/z): [M+H]⁺ 550; ¹H NMR (300 MHz, CDCl₃): δ 8.05 (d, J=6.3 Hz, 1H), 7.85 (m, 1H), 7.65 (d, J=8.4 Hz, 1H), 7.54 (m, 3H), 7.43 (t, J=8.1 Hz, 1H), 7.16 (d, J=7.5 Hz, 1H), 6.86 (d, J=2.1 Hz, 1H), 6.70 (dd, J=6.3, 8.4 Hz, 1H), 4.52 (d, J=13.5 Hz, 1H), 3.85 (m, 3H), 3.60 (m, 1H), 3.31 (m, 4H), 3.22 (m, 4H), 2.88 (m, 1H), 2.60 (m, 2H), 2.20 (m, 4H), 1.48 (m, 4H).

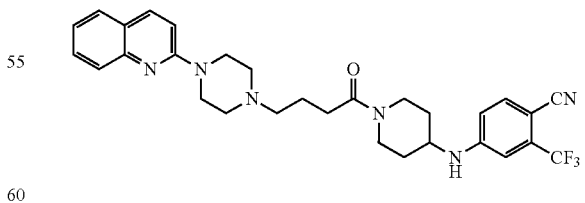

Compound 94: 4-[(1-[4-[4-(quinolin-2-yl)piperazin-1-yl]butanoyl]piperidin-4-yl)amino]-2-(trifluoromethyl)benzonitrile (ES, m/z): [M+H]⁺ 551.15; ¹H NMR (300 MHz, CDCl₃): δ 7.88-7.95 (d, J=9.0 Hz, 1H), 7.69 (d, J=8.4 Hz, 1H), 7.52-7.62 (m, 3H), 7.23 (d, J=7.2 Hz, 1H), 6.97 (d, J=9.0 Hz, 1H), 6.85 (d, J=2.1 Hz, 1H), 6.69 (dd, J=2.1, 5.7 Hz, 1H), 4.55 (d, J=14.4 Hz, 1H), 4.47 (d, J=7.8 Hz, 1H), 3.93 (d, J=14.4 Hz, 1H), 3.77-3.80 (t, J=4.8 Hz, 4H), 3.58-3.61 (m, 1H), 3.18-3.26 (t, J=11.7 Hz, 1H), 2.82-2.90 (t, J=11.7 Hz, 1H), 2.65 (t, J=4.5 Hz, 4H), 2.44-2.54 (m, 4H), 2.06-2.15 (m, 2H), 1.88-1.98 (m, 2H), 1.43-1.47 (m, 2H).

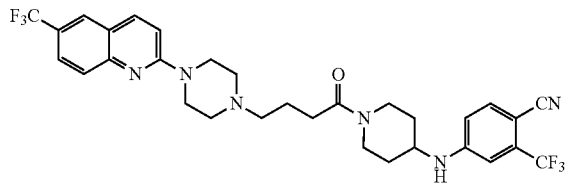 [SMILES: N#Cc1ccc(NC2CCN(C(=O)CCCN3CCN(c4ccc5cc(C(F)(F)F)ccc5n4)CC3)CC2)cc1C(F)(F)F]

Compound 95: 2-(trifluoromethyl)-4-[[1-(4-[4-[6-(trifluoromethyl)quinolin-2-yl]piperazin-1-yl]butanoyl]piperidin-4-yl]amino]benzonitrile (ES, m/z) [M+H]⁺ 619.36; ¹H NMR (300 MHz, CDCl3): δ 7.95 (d, J=8.7 Hz, 1H), 7.89 (s or fine coupling, 1H), 7.72 (m, 2H), 7.56 (d, J=8.7 Hz, 1H), 7.03 (d, J=9.3 Hz, 1H), 6.85 (d, J=2.1 Hz, 1H), 6.78 (dd, J=2.1, 8.4 Hz, 1H), 4.55-4.60 (m, 1H), 4.39-4.41 (m, 1H), 3.85-3.97 (m, 5H), 3.56-3.70 (m, 1H), 3.23 (t, J=12.0 Hz, 1H), 2.86 (t, J=11.4 Hz, 1H), 2.44-2.76 (m, 7H), 2.08-2.16 (m, 2H), 1.96-2.11 (m, 2H), 1.43-1.47 (m, 2H).

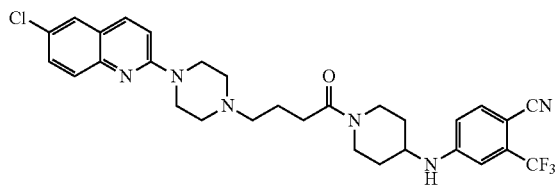 [SMILES: N#Cc1ccc(NC2CCN(C(=O)CCCN3CCN(c4ccc5cc(Cl)ccc5n4)CC3)CC2)cc1C(F)(F)F]

4-[(1-[4-[4-(6-chloroquinolin-2-yl)piperazin-1-yl]butanoyl]piperidin-4-yl)amino]-2-(trifluoromethyl)benzonitrile (#96)

(ES, m/z): [M+H]⁺ 585.20; ¹H NMR (300 MHz, CDCl₃): δ 7.80 (d, J=9.3 Hz, 1H), 7.53-7.65 (m, 3H), 7.44 (dd, J=2.1 Hz, 9.0 Hz, 1H), 7.00 (d, J=9.3 Hz, 1H), 6.85 (s, 1H), 6.66 (dd, J=2.1 Hz, 8.4 Hz, 1H), 4.57 (d, J=13.5 Hz, 1H), 4.42 (d, J=7.5 Hz, 1H), 3.96 (d, J=13.8 Hz, 1H), 3.70-3.85 (br s, 4H), 3.52-3.65 (m, 1H), 3.18 (t, J=11.7 Hz, 1H), 2.83 (t, J=12.0 Hz, 1H), 2.55-2.70 (br s, 4H), 2.40-2.55 (m, 4H), 2.03-2.15 (m, 2H), 1.86-1.96 (m, 2H), 1.35-1.45 (m, 2H).

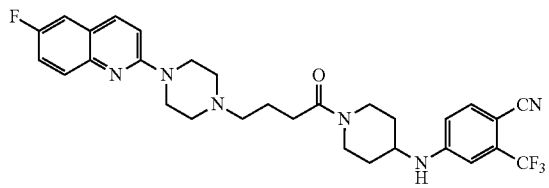 [SMILES: N#Cc1ccc(NC2CCN(C(=O)CCCN3CCN(c4ccc5cc(F)ccc5n4)CC3)CC2)cc1C(F)(F)F]

Compound 103: 4-[(1-[4-[4-(6-fluoroquinolin-2-yl)piperazin-1-yl]butanoyl]piperidin-4-yl)amino]-2-(trifluoromethyl) benzonitrile (ES, m/z): [M+H]⁺ 569.15; ¹H NMR (300 MHz, CDCl₃): δ 7.83 (d, J=9.0 Hz, 1H), 7.67 (dd, J=5.4, 9.0 Hz, 1H), 7.55 (d, J=8.7 Hz, 1H), 7.22-7.34 (m, 2H), 6.99 (d, J=9.3 Hz, 1H), 6.85 (d, J=2.4 Hz, 1H), 6.70 (dd, J=2.7, 8.4 Hz, 1H), 4.57 (br d, J=14.1 Hz, 1H), 4.45 (d, J=7.8 Hz, 1H), 3.95 (br d, J=12.9 Hz, 1H), 3.77 (br s, 4H), 3.55-3.64 (m, 1H), 3.22 (dd, J=11.7, 12.0 Hz, 1H), 2.87 (dd, J=11.1, 11.4 Hz, 1H), 2.67 (br s, 4H), 2.44-2.54 (m, 4H), 2.11-2.15 (m, 2H), 1.92-1.96 (m, 2H), 1.41-1.47 (m, 2H).

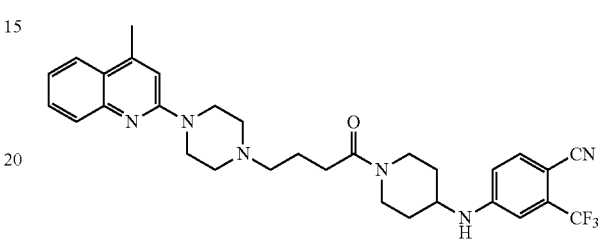

Compound 104: 4-[(1-[4-[4-(4-methylquinolin-2-yl)piperazin-1-yl]butanoyl]piperidin-4-yl)amino]-2-(trifluoromethyl) benzonitrile (ES, m/z): [M+H]⁺ 565.10. ¹H NMR (300 MHz, CDCl₃): δ 7.79 (d, J=8.1 Hz, 1H), 7.72 (d, J=8.4 Hz, 1H), 7.57 (m, 2H), 7.25-7.30 (m, 1H), 6.85 (m, 2H), 6.70 (dd, J=2.1, 87 Hz, 1H), 4.57 (br d, J=13.8 Hz, 1H), 4.85 (d, J=6.3 Hz, 1H), 3.95 (br d, J=13.2 Hz, 1H), 3.83 (br s, 4H), 3.59-3.62 (m, 1H), 3.19-3.26 (dd, J=11.4, 12.0 Hz, 1H), 2.86 (dd, J=11.1, 12.0 Hz, 1H), 2.70 (br s, 4H), 2.40-2.61 (m, 6H), 2.06-2.15 (m, 2H), 1.94-2.01 (m, 2H), 1.35-1.58 (m, 2H).

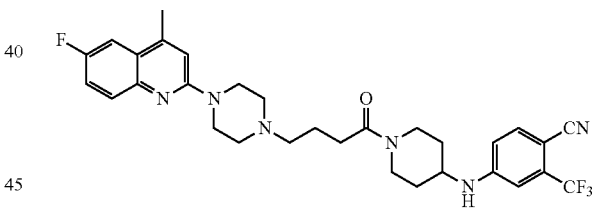

ethyl 4-[4-(6-fluoro-4-methylquinolin-2-yl)piperazin-1-yl]butanoate (#105)

(ES, m/z): [M+H]⁺ 583.00; ¹H NMR (300 MHz, CDCl₃): δ 7.70 (dd, J=5.4, 9.3 Hz, 1H), 7.56 (d, J=8.7 Hz, 1H), 7.41 (dd, J=2.7, 9.9 Hz, 1H), 7.32 (dd, J=2.7, 8.7 Hz, 1H), 6.86 (s, 2H), 6.72 (dd, J=2.1, 8.7 Hz, 1H), 4.59-4.49 (overlapping m, 2H), 3.94 (d, J=13.8 Hz, 1H), 3.76 (br s, 4H), 3.65-3.55 (m, 1H), 3.27 (d, J=11.1, 12.0 Hz, 1H), 2.91 (dd, J=11.4, 11.7 Hz, 1H), 2.66 (br s, 4H), 2.65-2.43 (m, 7H), 2.15 (m, 2H), 2.00-1.88 (m, 2H), 1.47-1.40 (m, 2H).

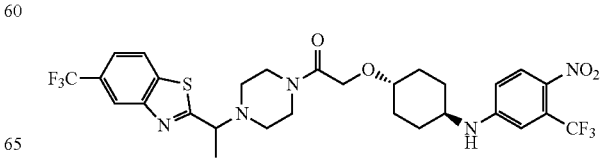

Compound 343: 2-[4-(4-nitro-3-trifluoromethyl-phenylamino)-cyclohexyloxy]-1-{4-[1-(5-trifluoromethyl-benzothiazol-2-yl)-ethyl]-piperazin-1-yl}-ethanone (CI, m/z): [M+H]⁺ 660; ¹H NMR (400 MHz, CDCl₃) δ 1.24-1.36 (m, 2H), 1.37-1.52 (m, 2H), 1.59 (br s, 3H), 2.14 (d, J=9.2 Hz, 4H), 2.51-2.82 (m, 4H), 3.28-3.48 (m, 3H), 3.55-3.80 (m, 4H), 4.20 (s, 2H), 4.44 (d, J=7.4 Hz, 1H), 6.63 (dd, J=9.0, 2.6 Hz, 1H), 6.85 (d, J=2.2 Hz, 1H), 7.62 (d, J=8.1 Hz, 1H), 8.00 (dd, J=12.7, 8.6 Hz, 2H), 8.20-8.28 (m, 1H).

EXAMPLE 25: Preparation of Compound 365

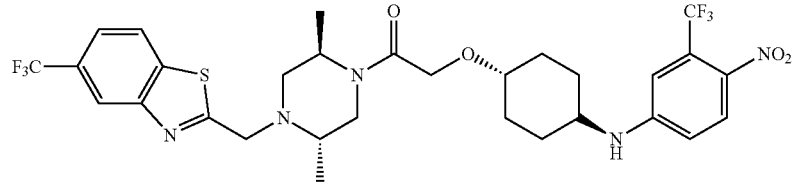

Compound 365

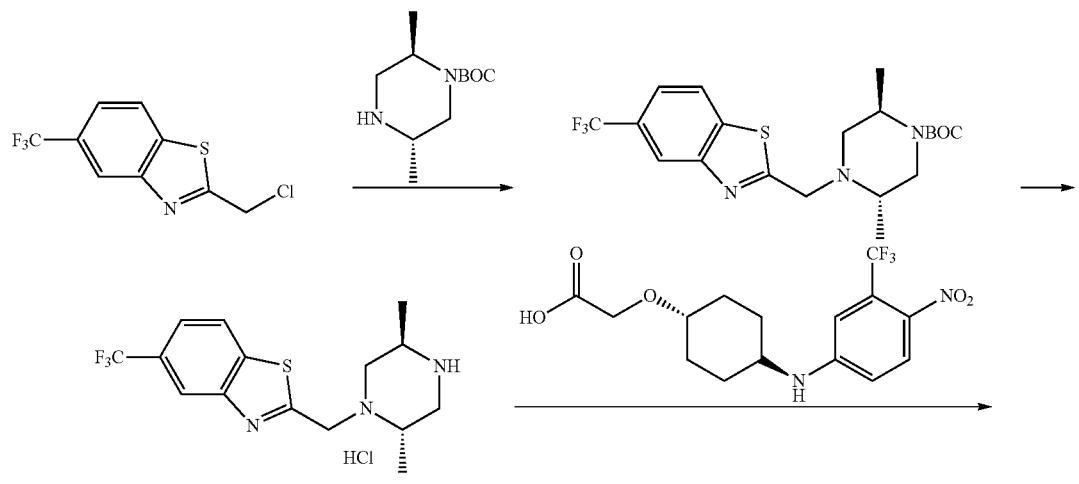

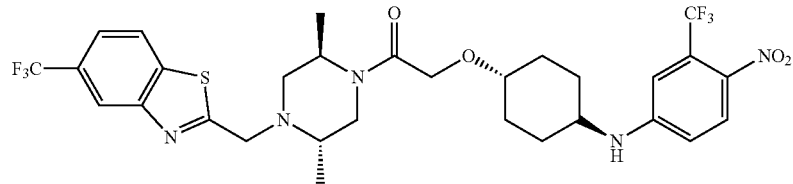

Steps 1-2

The formation of 2-chloromethyl-5-trifluoromethyl-benzothiazole hydrochloride was performed in a manner analogous to that described for compound 235 with a difference being the use of BOC-piperazine in lieu of piperazine.

Steps 3-4

The formation of 2-((2S,5R)-2,5-dimethyl-piperazin-1-ylmethyl)-5-trifluoromethyl-benzothiazole hydrochloride was performed in a manner analogous to that described for compound 285.

Step 5. Formation of 1-[(2R,5S)-2,5-dimethyl-4-(5-trifluoromethyl-benzothiazol-2-ylmethyl)-piperazin-1-yl]-2-[4-(4-nitro-3-trifluoromethyl-phenylamino)-cyclohexyloxy]-ethanone (#365)

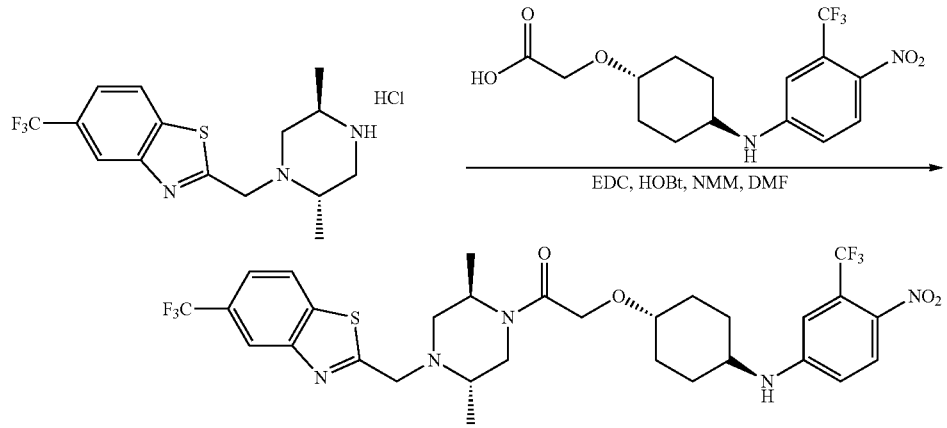

To a solution of [4-(4-nitro-3-trifluoromethyl-phenylamino)-cyclohexyloxy]-acetic acid (172 mg, 0.476 mmol, 2 eq.) in DMF (5 ml) was added EDAC hydrochloride (68 mg, 0.36 mmol, 1.5 eq.), HOBt (55 mg, 0.36 mmol, 1.5 eq.) and 4-methylmorpholine (0.13 ml, 1.2 mmol, 5 eq.). The resulting solution was stirred for 30 min then 2-((2S, 5R)-2,5-dimethyl-piperazin-1-ylmethyl)-5-trifluoromethyl-benzothiazole hydrochloride (87 mg, 0.24 mmol, 1 eq.) was added. The solution was stirred overnight at room temperature and diluted with EtOAc (25 ml) and washed with water (25 ml), saturated aqueous lithium chloride (25 ml) and brine (25 ml), dried over anhydrous sodium sulfate, filtered, and concentrated under vacuum to give a residue, which was applied onto a silica gel column with Heptanes-EtOAc to afford 1-[(2R,5S)-2,5-dimethyl-4-(5-trifluoromethyl-benzothiazol-2-ylmethyl)-piperazin-1-yl]-2-[4-(4-nitro-3-trifluoromethyl-phenylamino)-cyclohexyloxy]-ethanone as a yellow solid (86.1 mg, 53.7%). (CI, m/z): [M+H]⁺ 674; ¹H NMR (400 MHz, CDCl₃) δ 1.02-1.53 (m, 10H), 2.18 (br s, 4H), 2.47 (d, J=11.7 Hz, 1H), 2.99 (d, J=8.8 Hz, 1H), 3.23 (br s, 1H), 3.31-3.53 (m, 2H), 3.85-4.13 (m, 4H), 4.20 (br s, 3H), 4.46 (d, J=7.6 Hz, 1H), 6.64 (dd, J=9.1, 2.5 Hz, 1H), 6.85 (d, J=2.2 Hz, 1H), 7.63 (d, J=8.3 Hz, 1H), 8.01 (t, J=8.3 Hz, 2H), 8.21 (s, 1H).

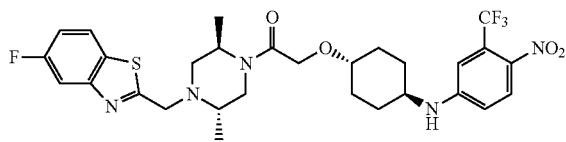 [SMILES: C[C@@H]1CN(Cc2nc3cc(F)ccc3s2)[C@@H](C)CN1C(=O)CO[C@H]1CC[C@H](Nc2ccc([N+](=O)[O-])c(C(F)(F)F)c2)CC1]

Compound 370: 1-[(2R,5S)-4-(5-fluoro-benzothiazol-2-ylmethyl)-2,5-dimethyl-piperazin-1-yl]-2-[4-(4-nitro-3-trifluoromethyl-phenylamino)-cyclohexyloxy]-ethanone (CI, m/z): [M+H]⁺ 624; ¹H NMR (400 MHz, CDCl₃) δ 0.94-1.83 (m, 10H), 2.16 (d, J=10.0 Hz, 4H), 2.53 (br s, 1H), 2.99 (d, J=8.6 Hz, 1H), 3.13-3.51 (m, 4H), 3.54-4.39 (m, 6H), 4.51 (d, J=7.2 Hz, 1H), 6.64 (dd, J=9.1, 2.4 Hz, 1H), 6.85 (d, J=2.2 Hz, 1H), 7.17 (td, J=8.8, 2.2 Hz, 1H), 7.64 (dd, J=9.4, 2.2 Hz, 1H), 7.81 (dd, J=8.7, 5.1 Hz, 1H), 8.02 (d, J=9.0 Hz, 1H).

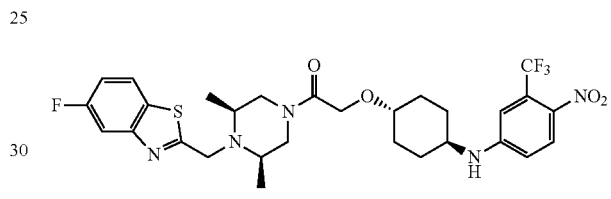

Compound 371: 1-[(3S,5R)-4-(5-fluoro-benzothiazol-2-ylmethyl)-2,5-dimethyl-piperazin-1-yl]-2-[4-(4-nitro-3-trifluoromethyl-phenylamino)-cyclohexyloxy]-ethanone (CI, m/z): [M+H]⁺ 624; ¹H NMR (400 MHz, CDCl₃) δ 1.19 (d, J=4.6 Hz, 6H), 1.25-1.36 (m, 2H), 1.37-1.53 (m, 2H), 2.05-2.24 (m, 4H), 2.45-2.63 (m, 1H), 2.77 (d, J=3.7 Hz, 2H), 2.87-3.07 (m, 1H), 3.23-3.52 (m, 2H), 3.83 (d, J=13.0 Hz, 1H), 4.13-4.29 (m, 4H), 4.41 (d, J=13.0 Hz, 1H), 4.48 (d, J=7.7 Hz, 1H), 6.63 (dd, J=9.1, 2.5 Hz, 1H), 6.85 (d, J=2.3 Hz, 1H), 7.13 (td, J=8.8, 2.4 Hz, 1H), 7.63 (dd, J=9.5, 2.4 Hz, 1H), 7.78 (dd, J 8.8, 5.2 Hz, 1H), 8.02 (d, J=9.0 Hz, 1H).

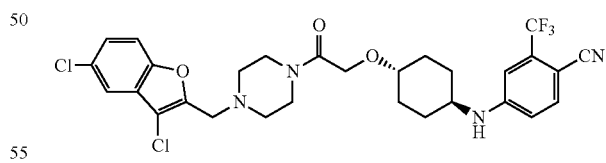

Compound 315: 4-(4-{2-[4-(3,5-dichloro-benzofuran-2-ylmethyl)-piperazin-1-yl]-2-oxo-ethoxy}-cyclohexylamino)-2-trifluoromethyl-benzonitrile (ES, m/z): [M+H]⁺ 609; ¹H NMR (400 MHz, CDCl₃) δ 1.16-1.27 (m, 2H), 1.36-1.52 (m, 2H), 2.10 (d, J=9.0 Hz, 4H), 2.59 (br s, 4H), 3.19-3.46 (m, 2H), 3.51-3.70 (m, 4H), 3.81 (s, 2H), 4.14-4.21 (m, 2H), 4.28 (d, J=7.6 Hz, 1H), 6.65 (dd, J=8.6, 2.2 Hz, 1H), 6.81 (d, J=2.1 Hz, 1H), 7.31 (dd, J=8.8, 2.1 Hz, 1H), 7.36-7.44 (m, 1H), 7.47-7.60 (m, 2H).

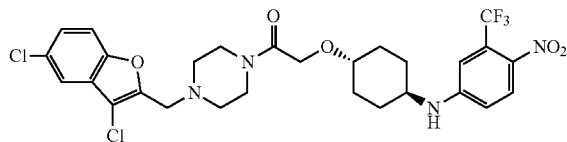 [SMILES: O=C(CO[C@H]1CC[C@H](Nc2ccc([N+](=O)[O-])c(C(F)(F)F)c2)CC1)N1CCN(Cc2oc3ccc(Cl)cc3c2Cl)CC1]

Compound 316: 1-[4-(3,5-dichloro-benzofuran-2-ylmethyl)-piperazin-1-yl]-2-[4-(4-nitro-3-trifluoromethyl-phenylamino)-cyclohexyloxy]-ethanone (ES, m/z): [M+H]$^+$ 629; $^1$H NMR (400 MHz, CDCl$_3$) δ 1.17-1.28 (m, 2H), 1.37-1.51 (m, 2H), 2.12 (d, J=11.0 Hz, 4H), 2.59 (br s, 4H), 3.29-3.45 (m, 2H), 3.52-3.71 (m, 4H), 3.81 (s, 2H), 4.18 (s, 2H), 4.41 (d, J=7.5 Hz, 1H), 6.63 (dd, J=9.1, 2.5 Hz, 1H), 6.85 (d, J=2.3 Hz, 1H), 7.31 (dd, J=8.8, 2.1 Hz, 1H), 7.37-7.46 (m, 1H), 7.54 (d, J=2.0 Hz, 1H), 8.02 (d, J=9.0 Hz, 1H).

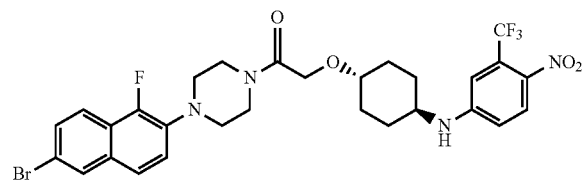 [SMILES: O=C(CO[C@H]1CC[C@H](Nc2ccc([N+](=O)[O-])c(C(F)(F)F)c2)CC1)N1CCN(c2ccc3cc(Br)ccc3c2F)CC1]

Compound 267: 1-[4-(6-bromo-1-fluoro-naphthalen-2-yl)-piperazin-1-yl]-2-[4-(4-nitro-3-trifluoromethyl-phenylamino)-cyclohexyloxy]-ethanone (CI, m/z): [M+H]$^+$ 653.1; $^1$H NMR (400 MHz, CDCl$_3$): δ 8.01 (d, J=9.0 Hz, 1H), 7.90 (m, 1H), 7.89 (d, J=8.8 Hz, 1H), 7.56 (dd, J=8.9, 1.9 Hz, 1H), 7.50 (d, J=9.0 Hz, 1H), 7.23 (dd, J=8.8, 8.4 Hz, 1H), 6.84 (d, J=2.3 Hz, 1H), 6.63 (dd, J=8.9, 2.6 Hz, 1H), 4.43 (d, J=7.7 Hz, 1H), 4.26 (s, 2H), 3.70-3.90 (m, 4H), 3.31-3.54 (m, 2H), 3.24 (m, 4H), 2.21 (m, 4H), 1.45 (m, 2H), 1.28 (m, 2H).

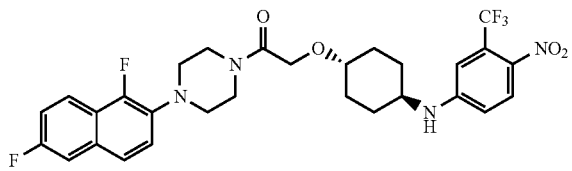 [SMILES: O=C(CO[C@H]1CC[C@H](Nc2ccc([N+](=O)[O-])c(C(F)(F)F)c2)CC1)N1CCN(c2ccc3cc(F)ccc3c2F)CC1]

Compound 289: 1-[4-(1,6-difluoro-naphthalen-2-yl)-piperazin-1-yl]-2-[4-(4-nitro-3-trifluoromethyl-phenylamino)-cyclohexyloxy]-ethanone (CI, m/z): [M+H]$^+$ 593; $^1$H NMR (400 MHz, CDCl$_3$): δ 1.26-1.39 (m, 2H), 1.41-1.55 (m, 2H), 2.17 (d, J=10.4 Hz, 4H), 3.22 (br s, 4H), 3.31-3.58 (m, 2H), 3.67-3.95 (m, 4H), 4.27 (s, 2H), 4.47 (d, J=7.7 Hz, 1H), 6.64 (dd, J=9.0, 2.5 Hz, 1H), 6.86 (d, J=2.3 Hz, 1H), 7.29-7.33 (m, 2H), 7.41 (d, J=9.6 Hz, 1H), 7.54 (d, J=8.9 Hz, 1H), 7.88-8.10 (m, 2H).

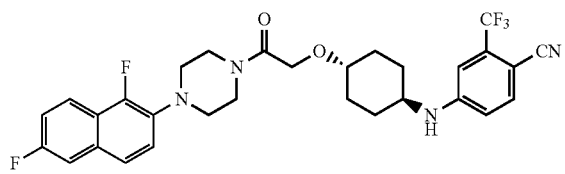 [SMILES: N#Cc1ccc(N[C@H]2CC[C@H](OCC(=O)N3CCN(c4ccc5cc(F)ccc5c4F)CC3)CC2)cc1C(F)(F)F]

Compound 290: 4-(4-{2-[4-(1,6-difluoro-naphthalen-2-yl)-piperazin-1-yl]-2-oxo-ethoxy}-cyclohexylamino)-2-trifluoromethyl-benzonitrile (CI, m/z): [M+H]$^+$ 573; $^1$H NMR (400 MHz, CDCl$_3$): δ 1.28-1.37 (m, 2H), 1.48 (br s, 2H), 2.08-2.28 (m, 4H), 3.22 (br s, 4H), 3.29-3.55 (m, 2H), 3.64-3.96 (m, 4H), 4.27 (s, 3H), 6.53-6.70 (m, 1H), 6.82 (d, J=2.0 Hz, 1H), 7.28 (m, 2H), 7.36-7.45 (m, 1H), 7.54 (t, J=8.0 Hz, 2H), 7.95-8.10 (m, 1H).

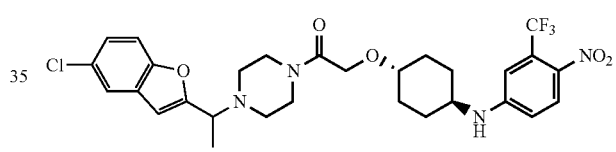

Compound 300: 1-[4-(5-chloro-benzofuran-2-ylmethyl)-piperazin-1-yl]-2-[4-(4-nitro-3-trifluoromethyl-phenylamino)-cyclohexyloxy]-ethanone (ES, m/z): [M+H]$^+$ 609; $^1$H NMR (400 MHz, CDCl$_3$): δ 1.11-1.25 (m, 2H), 1.33-1.45 (m, 2H), 1.52 (s, 3H), 2.08 (m, 4H), 2.40-2.71 (m, 4H), 3.24-3.43 (m, 2H), 3.46-3.74 (m, 4H), 3.90 (q, J=7.0 Hz, 1H), 4.14 (br s, 2H), 4.48 (d, J=7.6 Hz, 1H), 6.49 (s, 1H), 6.61 (dd, J=9.1, 2.5 Hz, 1H), 6.84 (d, J=2.3 Hz, 1H), 7.20 (dd, J=8.7, 2.10 Hz, 1H), 7.38 (s, 1H), 7.50 (s, 1H), 8.02 (d, J=8.9 Hz, 1H).

EXAMPLE 26: Preparation of Compound 327

Compound 327

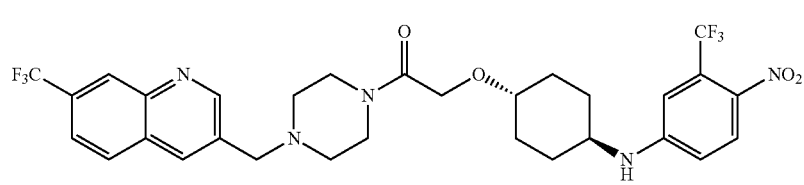

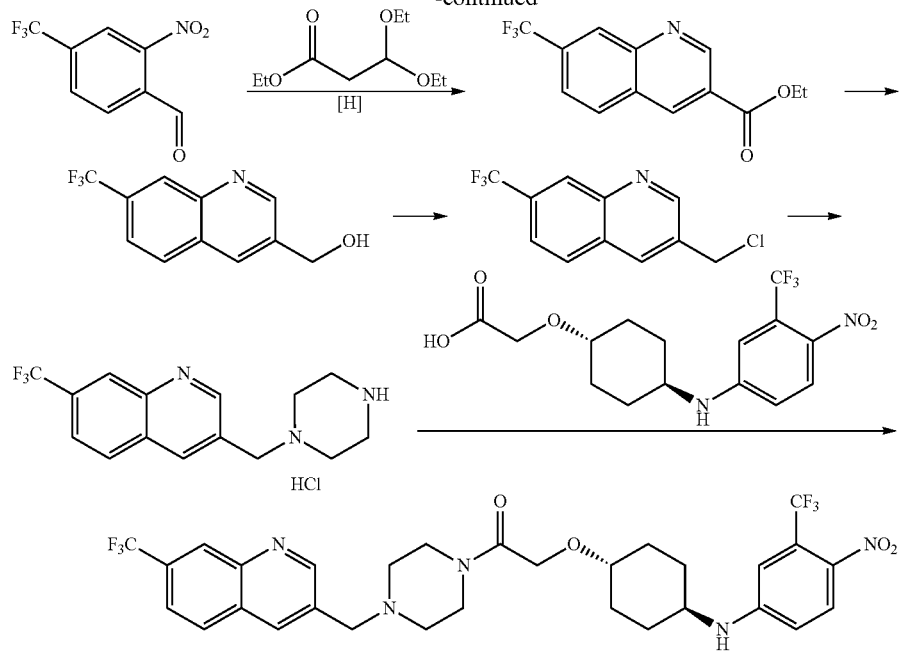

Formation of 2-[4-(4-nitro-3-trifluoromethyl-phenylamino)-cyclohexyloxy]-1-[4-(7-trifluoromethyl-quinolin-3-ylmethyl)-piperazin-1-yl]-ethanone

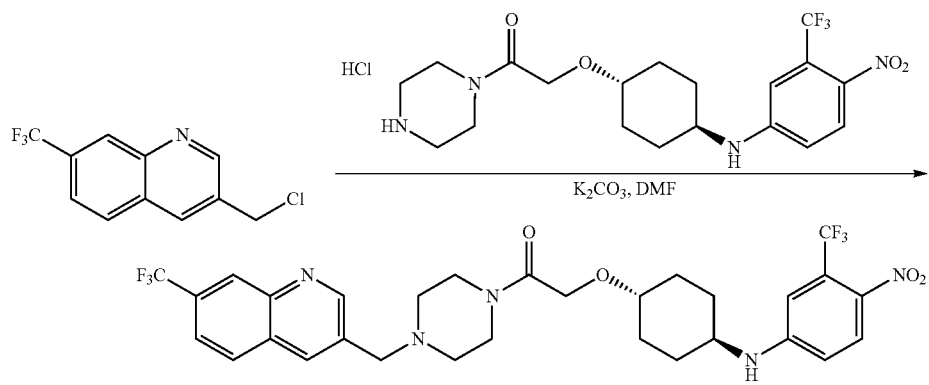

To a solution of 3-chloromethyl-7-trifluoromethyl-quinoline (140 mg, 0.57 mmol, 1.1 eq.) in DMF (10 ml) was added potassium carbonate (345 mg, 2.5 mmol, 5 eq.) then 2-[4-(4-Nitro-3-trifluoromethyl-phenylamino)-cyclohexyloxy]-1-piperazin-1-yl-ethanone hydrochloride (233 mg, 0.5 mmol, 1 eq.) was added. The solution was stirred overnight at 70° C. and diluted with EtOAc (25 ml) and washed with water (25 ml), saturated aqueous lithium chloride (25 ml) and brine (25 ml), dried over anhydrous sodium sulfate, filtered, and concentrated under vacuum to give a residue, which was applied onto a silica gel column and eluted with methanol in dichloromethane. The semi-purified material was further purified by HPLC to afford 2-[4-(4-nitro-3-trifluoromethyl-phenylamino)-cyclohexyloxy]-1-[4-(7-trifluoromethyl-quinolin-3-ylmethyl)-piperazin-1-yl]-ethanone as a yellow solid (111.2 mg, 30%). (CI, m/z): [M+H]+ 640; $^1$H NMR (400 MHz, CDCl$_3$): δ 1.20-1.36 (m, 2H), 1.40-1.54 (m, 2H), 2.08-2.21 (m, 4H), 2.46-2.61 (m, 4H), 3.32-3.49 (m, 2H), 3.53-3.62 (m, 2H), 3.63-3.71 (m, 2H), 3.76 (s, 2H), 4.20 (s, 2H), 4.46 (d, J=7.6 Hz, 1H), 6.63 (dd, J=9.1, 2.6 Hz, 1H), 6.85 (d, J=2.5 Hz, 1H), 7.75 (dd, J=8.5, 1.6 Hz, 1H) 7.94 (d, J=8.5 Hz, 1H), 8.02 (d, J=9.0 Hz, 1H), 8.13 (d, J=1.2 Hz, 1H), 8.43 (s, 1H), 9.03 (d, J=2.1 Hz, 1H).

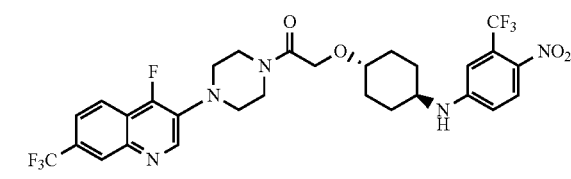 [SMILES: O=C(CO[C@H]1CC[C@H](Nc2ccc([N+](=O)[O-])c(C(F)(F)F)c2)CC1)N1CCN(c2cnc3cc(C(F)(F)F)ccc3c2F)CC1]

Compound 328: 2-[4-(4-nitro-3-trifluoromethyl-phenylamino)-cyclohexyloxy]-1-[4-(7-trifluoromethyl-quinolin-2-ylmethyl)-piperazin-1-yl]-ethanone (CI, m/z): [M+H]$^+$ 640; $^1$H NMR (400 MHz, CDCl$_3$): δ 1.28-1.35 (m, 2H), 1.39-1.54 (m, 2H), 2.14 (d, J=9.3 Hz, 4H), 2.59 (t, J=5.0 Hz, 4H), 3.31-3.50 (m, 2H), 3.53-3.74 (m, 4H), 3.90 (s, 2H), 4.20 (s, 2H), 4.46 (d, J=7.6 Hz, 1H), 6.64 (dd, J=9.1, 2.5 Hz, 1H), 6.85 (d, J=2.3 Hz, 1H), 7.65-7.80 (m, 2H), 7.95 (d, J=8.5 Hz, 1H), 8.02 (d, J=9.0 Hz, 1H), 8.22 (d, J=8.5 Hz, 1H), 8.41 (s, 1H).

Compound 232: 2-[4-(4-nitro-3-trifluoromethyl-phenylamino)-cyclohexyloxy]-1-[4-(6-trifluoromethyl-naphthalen-2-yl)-piperazin-1-yl]-ethanone (CI, m/z): [M+H]$^+$ 640; $^1$H NMR (400 MHz, CDCl$_3$) δ ppm 1.30 (d, J=12.6 Hz, 2H), 1.50 (d, J=12.6 Hz, 2H), 2.17 (d, J=10.4 Hz, 4H), 3.19-3.59 (m, 6H), 3.68-3.95 (m, 4H), 4.28 (s, 2H), 4.44 (d, J=7.6 Hz, 1H), 6.64 (dd, J=9.1, 2.5 Hz, 1H), 6.85 (d, J=2.3 Hz, 1H), 7.15 (d, J=1.9 Hz, 1H), 7.35 (dd, J=9.0, 2.3 Hz, 1H), 7.59 (d, J=8.7 Hz, 1H), 7.69-7.88 (m, 2H), 7.94-8.09 (m, 2H).

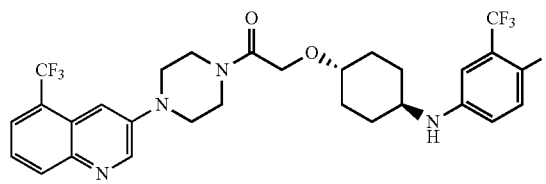

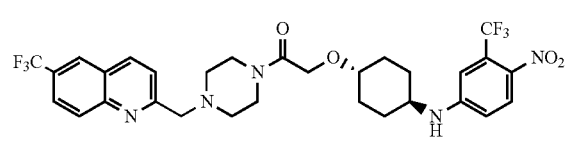 [SMILES: O=C(CO[C@H]1CC[C@H](Nc2ccc([N+](=O)[O-])c(C(F)(F)F)c2)CC1)N1CCN(Cc2ccc3cc(C(F)(F)F)ccc3n2)CC1]

Compound 329: 2-[4-(4-nitro-3-trifluoromethyl-phenylamino)-cyclohexyloxy]-1-[4-(5-trifluoromethyl-quinolin-2-ylmethyl)-piperazin-1-yl]-ethanone (CI, m/z): [M+H]$^+$ 640; $^1$H NMR (400 MHz, CDCl$_3$): δ 1.28-1.36 (m, 2H), 1.39-1.54 (m, 2H), 2.14 (d, J=9.1 Hz, 4H), 2.58 (t, J=4.6 Hz, 4H), 3.29-3.49 (m, 2H), 3.50-3.78 (m, 4H), 3.89 (s, 2H), 4.20 (s, 2H), 4.47 (d, J=7.6 Hz, 1H), 6.64 (dd, J=9.1, 2.5 Hz, 1H), 6.85 (m, 1H), 7.66-7.82 (m, 2H), 7.92 (d, J=7.3 Hz, 1H), 8.02 (d, J=9.1 Hz, 1H), 8.27 (d, J=8.5 Hz, 1H), 8.50 (d, J=8.0 Hz, 1H).

Compound 332: 2-[4-(4-nitro-3-trifluoromethyl-phenylamino)-cyclohexyloxy]-1-[4-(6-trifluoromethyl-quinolin-2-ylmethyl)-piperazin-1-yl]-ethanone (CI, m/z): [M+H]$^+$ 640; $^1$H NMR (400 MHz, CDCl$_3$): δ 1.29-1.36 (m, 2H), 1.39-1.52 (m, 2H), 2.14 (d, J=9.5 Hz, 4H), 2.58 (t, J=5.0 Hz, 4H), 3.27-3.48 (m, 2H), 3.54-3.75 (m, 4H), 3.90 (s, 2H), 4.20 (s, 2H), 4.45 (d, J=7.6 Hz, 1H), 6.64 (dd, J=9.1, 2.5 Hz, 1H), 6.85 (d, J=2.4 Hz, 1H), 7.75 (d, J=8.5 Hz, 1H), 7.90 (dd, J=8.8, 1.8 Hz, 1H), 8.02 (d, J=9.0 Hz, 1H), 8.10-8.21 (m, 2H), 8.25 (d, J=8.5 Hz, 1H).

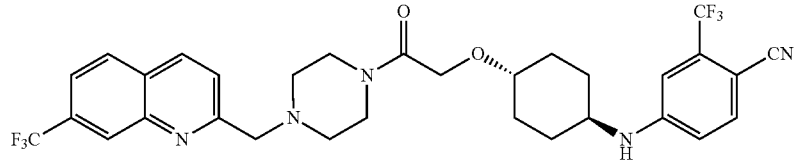 [SMILES: N#Cc1ccc(N[C@H]2CC[C@H](OCC(=O)N3CCN(Cc4ccc5ccc(C(F)(F)F)cc5n4)CC3)CC2)cc1C(F)(F)F]

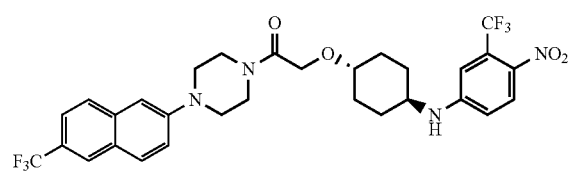

Compound 333: 4-(4-{2-oxo-2-[4-(7-trifluoromethyl-quinolin-2-ylmethyl)-piperazin-1-yl]ethoxy}-cyclohexylamino)-2-trifluoromethyl-benzonitrile (CI, m/z): [M+H]$^+$ 620; $^1$H NMR (400 MHz, CDCl$_3$): δ 1.28-1.35 (m, 2H), 1.37-1.51 (m, 2H), 2.13 (d, J=9.8 Hz, 4H), 2.58 (t, J=5.0 Hz, 4H), 3.24-3.48 (m, 2H), 3.50-3.77 (m, 4H), 3.90 (s, 2H), 4.16 (s, 2H), 4.29 (d, J=7.6 Hz, 1H), 6.66 (dd, J=8.6, 2.2 Hz, 1H), 6.81 (d, J=2.2 Hz, 1H), 7.55 (d, J=8.6 Hz, 1H), 7.65-7.80 (m, 2H), 7.95 (d, J=8.5 Hz, 1H), 8.22 (d, J=8.5 Hz, 1H), 8.41 (s, 1H).

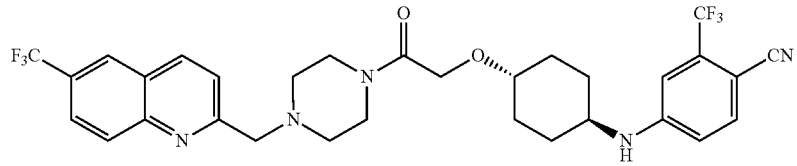 [SMILES: N#Cc1ccc(N[C@H]2CC[C@H](OCC(=O)N3CCN(Cc4ccc5cc(C(F)(F)F)ccc5n4)CC3)CC2)cc1C(F)(F)F]

Compound 334: 4-(4-{2-oxo-2-[4-(6-trifluoromethyl-quinolin-2-ylmethyl)-piperazin-1-yl]-ethoxy}-cyclohexylamino)-2-trifluoromethyl-benzonitrile (CI, m/z): [M+H]$^+$ 620; $^1$H NMR (400 MHz, CDCl$_3$): δ 1.28-1.36 (m, 2H), 1.38-1.52 (m, 2H), 2.13 (d, J=9.7 Hz, 4H), 2.58 (t, J=4.9 Hz, 4H), 3.25-3.48 (m, 2H), 3.52-3.74 (m, 4H), 3.90 (s, 2H), 4.20 (s, 2H), 4.29 (d, J=7.6 Hz, 1H), 6.66 (dd, J=8.6, 2.12 Hz, 1H), 6.81 (d, J=2.0 Hz, 1H), 7.55 (d, J=8.5 Hz, 1H), 7.75 (d, J=8.5 Hz, 1H), 7.90 (d, J=8.8 Hz, 1H), 8.08-8.21 (m, 2H), 8.25 (d, J=8.5 Hz, 1H).

EXAMPLE 27: Preparation of Compound 342

Compound 342

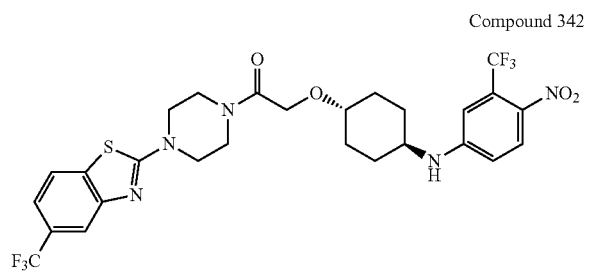 [SMILES: O=C(CO[C@H]1CC[C@H](Nc2ccc([N+](=O)[O-])c(C(F)(F)F)c2)CC1)N1CCN(c2nc3cc(C(F)(F)F)ccc3s2)CC1]

Steps 1-4

The formation of 2-bromo-5-trifluoromethyl-benzothiazole was performed in a manner analogous to that described for compound 237.

Step 5. Formation of 2-[4-(4-nitro-3-trifluoromethyl-phenylamino)-cyclohexyloxy]-1-[4-(5-trifluoromethyl-benzothiazol-2-yl)-piperazin-1-yl]-ethanone (#342)

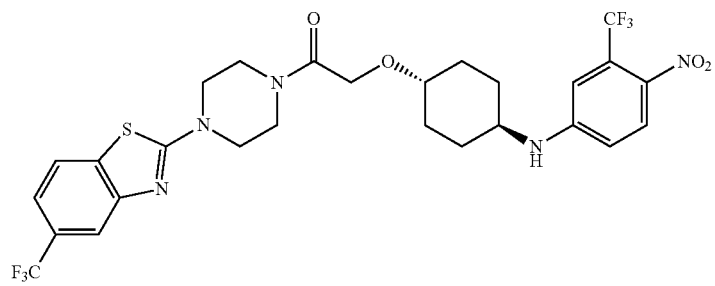

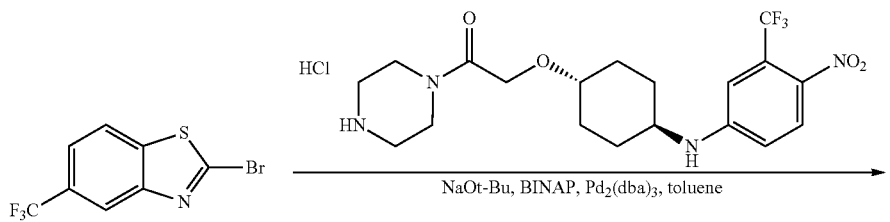

To a solution of 2-bromo-5-trifluoromethyl-benzothiazole (430 mg, 1.4 mmol, 1 eq.) in toluene (15 ml) was added sodium tert-butoxide (546 mg, 5.7 mmol, 4 eq.), BINAP (10 mg, 0.015 mmol, 0.01 eq.) and 2-[4-(4-nitro-3-trifluoromethyl-phenylamino)-cyclohexyloxy]-1-piperazin-1-yl-ethanone hydrochloride (1.33 g, 2.84 mmol, 2 eq.). The solution was flushed with nitrogen and evacuated three times before adding Pd$_2$(dba)$_3$-CHCl$_3$ (31 mg, 0.03 mmol, 0.02 eq.) and flushing/evacuating a final time. The slurry was heated to for 18 hours at 70° C. before concentrating in vacuo. The residue was applied onto a silica gel column and eluted with Heptanes/EtOAc to afford 2-[4-(4-nitro-3-trifluoromethyl-phenylamino)-cyclohexyloxy]-1-[4-(5-trifluoromethyl-benzothiazol-2-yl)-piperazin-1-yl]-ethanone as a yellow solid (662 mg, 73.8%). (CI, m/z): [M+H]$^+$ 632; $^1$H NMR (400 MHz, CDCl$_3$): δ 1.29-1.38 (m, 2H), 1.41-1.56 (m, 2H), 2.16 (d, J=8.9 Hz, 4H), 3.26-3.53 (m, 2H), 3.55-3.90 (m, 8H), 4.26 (s, 2H), 4.47 (d, J=7.6 Hz, 1H), 6.63 (dd, J=9.1, 2.5 Hz, 1H), 6.85 (d, J=2.3 Hz, 1H), 7.36 (d, J=8.2 Hz, 1H), 7.72 (d, J=8.2 Hz, 1H), 7.81 (s, 1H), 8.01 (d, J=9.0 Hz, 1H).

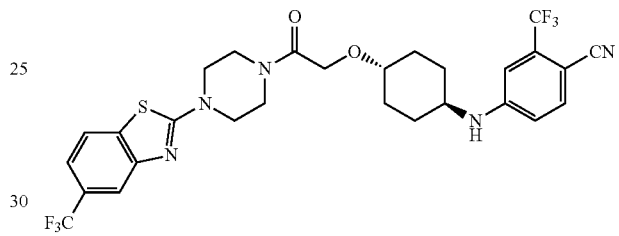

4-(4-{2-oxo-2-[4-(5-trifluoromethyl-benzothiazol-2-yl)-piperazin-1-yl]-ethoxy}-cyclohexylamino)-2-trifluoromethyl-benzonitrile (#358)

(CI, m/z): [M+H]$^+$ 612; $^1$H NMR (400 MHz, CDCl$_3$): δ 1.18-1.35 (m, 2H), 1.36-1.53 (m, 2H), 2.15 (d, J=10.5 Hz,

4H), 3.24-3.52 (m, 2H), 3.54-3.87 (m, 8H), 4.30 (d, J=7.6 Hz, 3H), 6.66 (dd, J=8.6, 2.2 Hz, 1H), 6.81 (d, J=2.2 Hz, 1H), 7.36 (d, J=7.6 Hz, 1H), 7.55 (d, J=8.6 Hz, 1H), 7.72 (d, J=8.2 Hz, 1H), 7.82 (s, 1H).

Compound 364: 2-[4-(4-trifluoromethanesulfonyl-phenylamino)-cyclohexyloxy]-1-[4-(5-trifluoromethyl-benzothiazol-2-yl)-piperazin-1-yl]-ethanone

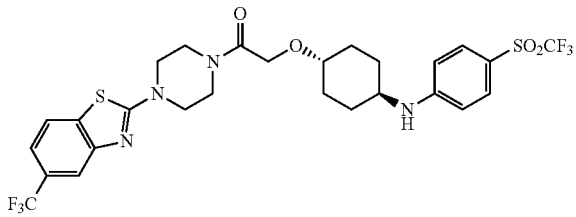

(CI, m/z): [M+H]⁺ 651; ¹H NMR (400 MHz, CDCl₃): δ 1.28-1.39 (m, 2H), 1.41-1.56 (m, 2H), 2.16 (d, J=10.7 Hz, 4H), 3.30-3.54 (m, 2H), 3.61-3.90 (m, 8H), 4.26 (s, 2H), 4.45 (d, J=7.6 Hz, 1H), 6.63 (d, J=8.9 Hz, 2H), 7.36 (d, J=8.2 Hz, 1H), 7.65-7.78 (m, 3H), 7.81 (s, 1H).

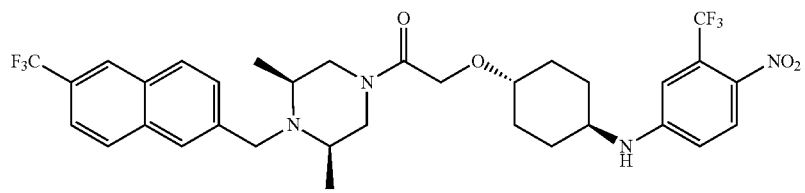 [SMILES: C[C@@H]1CN(C(=O)CO[C@H]2CC[C@H](Nc3ccc([N+](=O)[O-])c(C(F)(F)F)c3)CC2)C[C@H](C)N1Cc1ccc2cc(C(F)(F)F)ccc2c1]

1-[(3S,5R)-4-(6-fluoro-naphthalen-2-ylmethyl)-3,5-dimethyl-piperazin-1-yl]-2-[4-(4-nitro-3-trifluoromethyl-phenylamino)-cyclohexyloxy]-ethanone (#372)

(CI, m/z): [M+H]⁺ 617; ¹H NMR (400 MHz, CDCl₃): δ 1.12 (dd, J=8.8, 5.8 Hz, 6H), 1.28-1.35 (m, 2H), 1.38-1.51 (m, 2H), 2.05-2.21 (m, 4H), 2.65 (d, J=9.7 Hz, 3H), 2.84-3.12 (m, 1H), 3.20-3.50 (m, 2H), 3.77 (d, J=13.0 Hz, 1H), 3.96 (s, 2H), 4.15-4.25 (m, 2H), 4.33 (d, J=8.2 Hz, 1H), 4.43 (d, J=7.6 Hz, 1H), 6.63 (dd, J=9.0, 2.5 Hz, 1H), 6.85 (d, J 2.3 Hz, 1H), 7.17-7.27 (m, 1H), 7.43 (dd, J=9.8, 2.2 Hz, 1H), 7.50 (d, J=8.4 Hz, 1H), 7.73 (d, J=8.5 Hz, 1H), 7.76-7.88 (m, 2H), 8.03 (d, J=9.0 Hz, 1H).

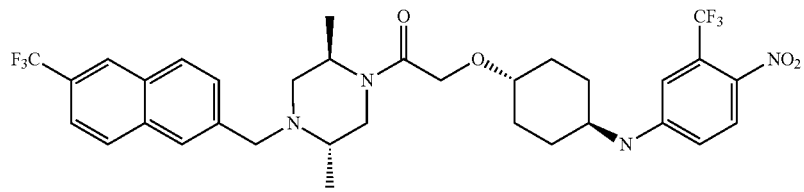 [SMILES: C[C@@H]1CN(Cc2ccc3cc(C(F)(F)F)ccc3c2)[C@@H](C)CN1C(=O)CO[C@H]1CC[C@H](Nc2ccc([N+](=O)[O-])c(C(F)(F)F)c2)CC1]

Compound 357: 1-[(2R,5S)-4-(6-fluoro-naphthalen-2-ylmethyl)-2,5-dimethyl-piperazin-1-yl]-2-[4-(4-nitro-3-trifluoromethyl-phenylamino)-cyclohexyloxy]-ethanone (CI, m/z): [M+H]⁺ 617; ¹H NMR (400 MHz, CDCl₃): δ 0.79-0.92 (m, 2H), 1.04 (br s, 2H), 1.13-1.38 (m, 6H), 1.38-1.52 (m, 3H), 2.15 (d, J=8.7 Hz, 4H), 2.31 (d, J=11.8 Hz, 1H), 2.78 (d, J=8.5 Hz, 1H), 3.08 (br s, 1H), 3.30-3.52 (m, 2H), 3.62 (d, J=13.4 Hz, 1H), 3.79 (d, J=13.5 Hz, 1H), 3.97-4.32 (m, 2H), 4.46 (d, J=7.6 Hz, 1H), 6.64 (dd, J=9.0, 2.51 Hz, 1H), 6.85 (d, J=2.3 Hz, 1H), 7.21-7.27 (m, 1H), 7.45 (dd, J=9.8, 2.3 Hz, 1H), 7.58 (d, J=8.5 Hz, 1H), 7.65-7.86 (m, 3H), 8.02 (d, J=9.0 Hz, 1H).

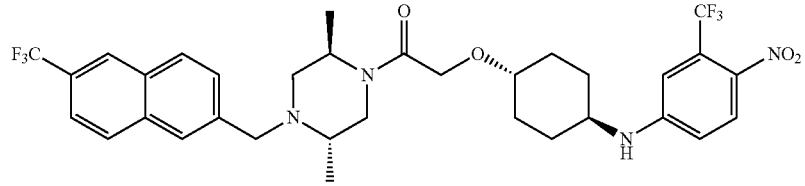 [SMILES: C[C@@H]1CN(Cc2ccc3cc(C(F)(F)F)ccc3c2)[C@@H](C)CN1C(=O)CO[C@H]1CC[C@H](Nc2ccc([N+](=O)[O-])c(C(F)(F)F)c2)CC1]

1-[(2R,5S)-2,5-dimethyl-4-(6-trifluoromethyl-naphthalen-2-ylmethyl)-piperazin-1-yl]-2-[4-(4-nitro-3-trifluoromethyl-phenylamino)-cyclohexyloxy]-ethanone (#373)

(ES, m/z): [M+H]⁺ 667; ¹H NMR (400 MHz, CDCl₃): δ 1.05 (br s, 3H), 1.32 (m, 5H), 1.42-1.52 (m, 2H), 2.15 (d, J=7.0 Hz, 4H), 2.30 (d, J=11.7 Hz, 1H), 2.80 (d, J=9.1 Hz, 1H), 3.09 (br s, 1H), 3.33-3.53 (m, 3H) 3.67 (d, J=13.7 Hz, 2H), 3.84 (d, J=13.7 Hz, 1H), 4.08-4.34 (m, 3H), 4.47 (d, J=7.6 Hz, 1H), 6.64 (dd, J=9.0, 2.5 Hz, 1H), 6.85 (d, J=2.3 Hz, 1H), 7.66 (t, J=8.2 Hz, 2H), 7.82 (s, 1H), 7.92 (s, 2H), 8.02 (d, J=9.0 Hz, 1H), 8.14 (s, 1H).

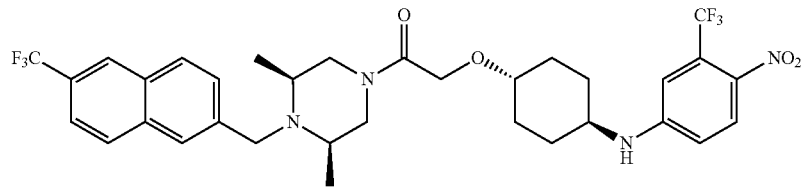 [SMILES: C[C@@H]1CN(C(=O)CO[C@H]2CC[C@H](Nc3ccc([N+](=O)[O-])c(C(F)(F)F)c3)CC2)C[C@H](C)N1Cc1ccc2cc(C(F)(F)F)ccc2c1]

Compound 374: 1-[(3S,5R)-3,5-dimethyl-4-(6-trifluoromethyl-naphthalen-2-ylmethyl)-piperazin-1-yl]-2-[4-(4-nitro-3-trifluoromethyl-phenylamino)-cyclohexyloxy]-ethan one (ES, m/z): [M+H]⁺ 667; ¹H NMR (400 MHz, CDCl₃): δ 1.09 (t, J=6.7 Hz, 6H), 1.31 (br s, 2H), 1.39-1.52 (m, 2H), 2.13 (t, J=10.6 Hz, 4H), 2.53-2.75 (m, 3H), 2.95-3.09 (m, 1H), 3.25-3.54 (m, 2H), 3.79 (d, J=12.6 Hz, 1H), 3.98 (d, J=2.9 Hz, 2H), 4.15-4.26 (m, 2H), 4.35 (d, J=8.5 Hz, 1H), 4.45 (d, J=7.6 Hz, 1H), 6.63 (dd, J=9.1, 2.4 Hz, 1H), 6.85 (d, J=2.2 Hz, 1H), 7.62 (dd, J=16.7, 8.2 Hz, 2H), 7.79-7.97 (m, 3H), 8.02 (d, J=9.0 Hz, 1H), 8.13 (s, 1H).

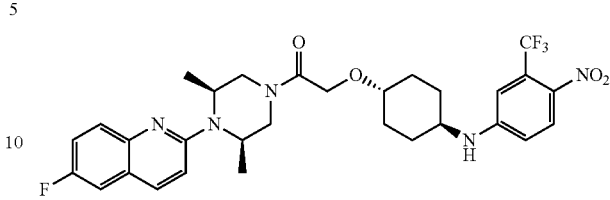

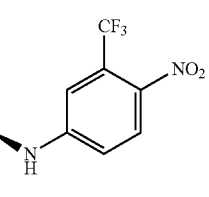

Compound 381: 1-[(3S,5R)-4-(6-fluoro-quinolin-2-yl)-3,5-dimethyl-piperazin-1-yl]-2-[4-(4-nitro-3-trifluoromethyl-phenylamino)-cyclohexyloxy]-ethanone (CI, m/z): [M+H]⁺ 604; ¹H NMR (400 MHz, CDCl₃): δ 1.32 (dd, J=15.7, 6.7 Hz, 8H), 1.43-1.53 (m, 2H), 2.01-2.33 (m, 4H), 3.06 (dd, J=13.0, 4.2 Hz, 1H), 3.27-3.58 (m, 3H), 3.93 (d, J=13.3 Hz, 1H), 4.21-4.40 (m, 2H), 4.41-4.56 (m, 2H), 4.63 (br s, 1H), 4.86 (br s, 1H), 6.64 (dd, J=9.1, 2.5 Hz, 1H), 6.86 (d, J=2.3 Hz, 1H), 6.95 (d, J=9.3 Hz, 1H), 7.25 (m, 1H), 7.32 (td, J=8.8, 2.9 Hz, 1H), 7.68 (dd, J=9.1, 5.2 Hz, 1H), 7.89 (d, J=9.2 Hz, 1H), 8.02 (d, J=9.1 Hz, 1H).

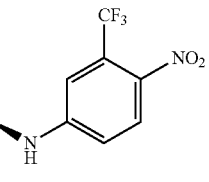

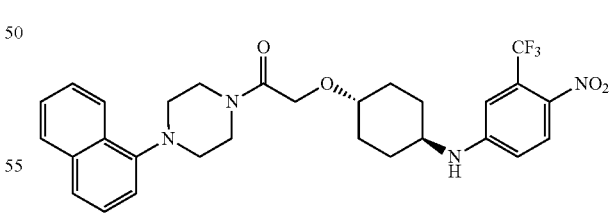

Compound 20: 1-[4-(naphthalen-1-yl)piperazin-1-yl]-2-[(4-[[4-nitro-3-(trifluoromethyl)phenyl]amino] cyclohexyl)oxy]ethan-1-one (ES, m/z): [M+H]⁺ 557; ¹H NMR (400 MHz, CDCl₃): δ 8.20 (d, J=7.5 Hz, 1H); 8.01 (d, J=8.7 Hz, 1H), 7.85 (d, J=7.5 Hz, 1H), 7.61 (d, J=8.4 Hz, 1H), 7.51 (m, 3H), 7.41 (dd, J 7.2, 8.4 Hz, 1H), 7.07 (d, J=7.5 Hz, 1H), 6.85 (s, 1H), 6.6 (d, J=7.8 Hz, 1H), 4.50 (br s, 1H), 4.28 (s, 2H), 3.82 (br m, 2H), 3.45 (br m, 3H), 3.13 (m, 4H), 2.17 (d, J=6.6 Hz, 4H), 1.51 (m, 2H), 1.25 (m, 2H).

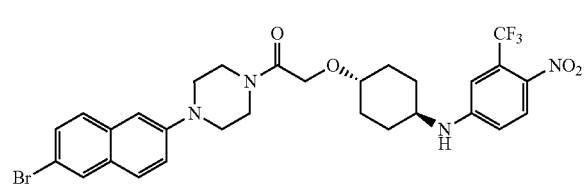

Compound 268: 1-[4-(6-bromo-naphthalen-2-yl)-piperazin-1-yl]-2-[4-(4-nitro-3-trifluoromethyl-phenylamino)-cyclohexyloxy]-ethanone (CI, m/z): [M+H]$^+$ 635.1; $^1$H NMR (400 MHz, CDCl$_3$): δ 8.01 (d, J=8.8 Hz, 1H), 7.88 (d, J=1.8 Hz, 1H), 7.67 (d, J=9.2 Hz, 1H), 7.57 (d, J=8.8 Hz, 1H), 7.48 (dd, J=9.2, 2.0 Hz, 1H), 7.08 (d, J=2.2 Hz, 1H), 6.84 (d, J=2.4 Hz, 1H), 6.63 (dd, J=9.1, 2.6 Hz, 1H), 4.44 (d, J=7.7 Hz, 1H), 4.26 (s, 2H), 3.68-3.88 (m, 4H), 3.34-3.52 (m, 2H), 3.23-3.33 (m, 4H), 2.16 (d, J=10.0 Hz, 4H), 1.47 (s, 2H), 1.20-1.37 (m, 2H).

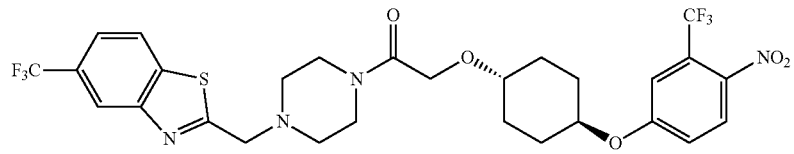 [SMILES: O=C(CO[C@H]1CC[C@H](Oc2ccc([N+](=O)[O-])c(C(F)(F)F)c2)CC1)N1CCN(Cc2nc3cc(C(F)(F)F)ccc3s2)CC1]

Compound 311: 2-[4-(4-nitro-3-trifluoromethyl-phenoxy)-cyclohexyloxy]-1-[4-(5-trifluoromethyl-benzothiazol-2-ylmethyl)-piperazin-1-yl]-ethanone (CI, m/z): [M+H]$^+$ 647.2; $^1$H NMR (400 MHz, CDCl$_3$): δ 8.23 (s, 1H), 8.01 (d, J=9.2 Hz, 2H), 7.62 (dd, J=8.4, 1.2 Hz, 1H), 7.22-7.31 (m, 1H, overlaps CHCl$_3$), 7.07 (dd, J=9.0, 2.7 Hz, 1H), 4.42-4.53 (m, 1H), 4.19 (s, 2H), 4.03 (s, 2H), 3.60-3.76 (m, 4H), 3.51-3.61 (m, 1H), 2.69 (t, J=5.0 Hz, 4H), 1.99-2.16 (m, 4H), 1.52-1.71 (m, 4H).

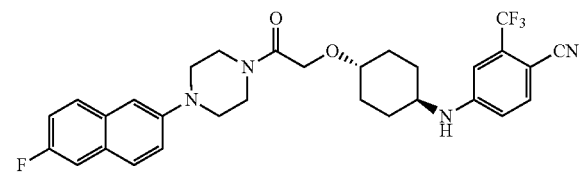 [SMILES: N#Cc1ccc(N[C@H]2CC[C@H](OCC(=O)N3CCN(c4ccc5cc(F)ccc5c4)CC3)CC2)cc1C(F)(F)F]

Compound 279: 4-(4-{2-[4-(6-fluoro-naphthalen-2-yl)-piperazin-1-yl]-2-oxo-ethoxy}-cyclohexylamino)-2-trifluoromethyl-benzonitrile (CI, m/z): [M+H]$^+$ 555.0; $^1$H NMR (DMSO-d6): δ 7.75-7.83 (m, 2H), 7.69 (d, J=8.7 Hz, 1H), 7.55 (dd, J=10.2, 2.4 Hz, 1H), 7.46 (d, J=8.9 Hz, 1H), 7.31 (td, J=8.9, 2.6 Hz, 1H), 7.26 (s, 1H), 7.10 (d, J=7.8 Hz, 1H), 7.02 (s, 1H), 6.85 (d, J=8.8 Hz, 1H), 4.21 (s, 2H), 3.58-3.66 (m, 4H), 3.34-3.46 (m, 2H), 3.24 (d, J=17.6 Hz, 4H), 1.99-2.07 (m, 2H), 1.89-1.98 (m, 2H), 1.28-1.43 (m, 2H), 1.15-1.28 (m, 2H).

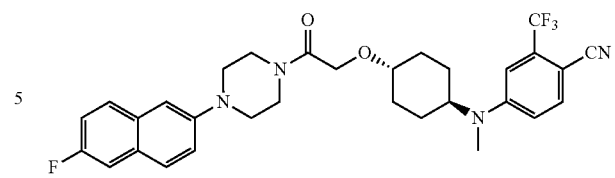

Compound 293: 4-[(4-{2-[4-(6-fluoro-naphthalen-2-yl)-piperazin-1-yl]-2-oxo-ethoxy}-cyclohexyl)-methyl-amino]-2-trifluoromethyl-benzonitrile (CI, m/z): [M+H]$^+$ 569.0; $^1$H NMR (CDCl$_3$): δ 7.65-7.72 (m, 2H), 7.58 (d, J=8.8 Hz, 1H), 7.36 (dd, J=9.8, 2.5 Hz, 1H), 7.29 (dd, J=9.1, 2.2 Hz, 1H), 7.21 (td, J=8.8, 2.6 Hz, 1H), 7.13 (d, J=2.5 Hz, 1H), 6.94 (d, J=2.7 Hz, 1H), 6.80 (dd, J=9.0, 2.7 Hz, 1H), 4.26 (s, 2H), 3.75-3.85 (m, 4H), 3.66-3.71 (m, 1H), 3.38-3.45 (m, 1H), 3.23-3.30 (m, 4H), 2.86 (s, 3H), 2.19-2.29 (m, 2H), 1.75-1.88 (m, 2H), 1.57-1.68 (m, 2H), 1.39-1.52 (m, 2H).

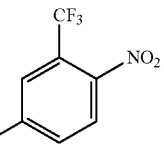

Compound 305: 4-(4-{2-[4-(3-chloro-5-trifluoromethyl-benzofuran-2-ylmethyl)-piperazin-1-yl]-2-oxo-ethoxy}-cyclohexylamino)-2-trifluoromethyl-benzonitrile (CI, m/z): [M+H]$^+$ 643.0; $^1$H NMR (CDCl$_3$): δ 7.76-7.90 (m, 1H), 7.47-7.65 (m, 3H), 6.78 (d, J=2.0 Hz, 1H), 6.62 (dd, J=8.6, 2.1 Hz, 1H), 4.27 (d, J=7.5 Hz, 1H), 4.15 (s, 2H), 3.82 (s, 2H), 3.61-3.70 (m, 2H), 3.53-3.60 (m, 2H), 3.23-3.44 (m, 2H), 2.58 (br. s., 4H), 1.99-2.18 (m, 4H), 1.34-1.51 (m, 2H), 1.12-1.32 (m, 2H).

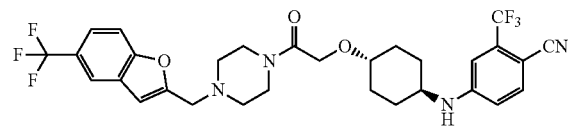 [SMILES: N#Cc1ccc(N[C@H]2CC[C@H](OCC(=O)N3CCN(Cc4cc5cc(C(F)(F)F)ccc5o4)CC3)CC2)cc1C(F)(F)F]

Compound 306: 4-(4-{2-oxo-2-[4-(5-trifluoromethyl-benzofuran-2-ylmethyl)-piperazin-1-yl]-ethoxy}-cyclohexylamino)-2-trifluoromethyl-benzonitrile (CI, m/z): [M+H]⁺ 609.0; ¹H NMR (CDCl₃): δ 7.84 (s, 1H), 7.49-7.62 (m, 3H), 6.81 (d, J=2.0 Hz, 1H), 6.70 (s, 1H), 6.65 (dd, J=8.6, 2.2 Hz, 1H), 4.27 (d, J=7.7 Hz, 1H), 4.19 (s, 2H), 3.76 (s, 2H), 3.65-3.72 (m, 2H), 3.57-3.63 (m, 2H), 3.28-3.46 (m, 2H), 2.57 (t, J=4.9 Hz, 4H), 2.05-2.22 (m, 4H), 1.36-1.51 (m, 2H), 1.15-1.32 (m, 2H).

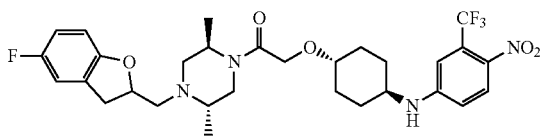 [SMILES: C[C@@H]1CN(CC2Cc3cc(F)ccc3O2)[C@@H](C)CN1C(=O)CO[C@H]1CC[C@H](Nc2ccc([N+](=O)[O-])c(C(F)(F)F)c2)CC1]

Compound 307: 1-[(2R,5S)-4-(5-fluoro-2,3-dihydro-benzofuran-2-ylmethyl)-2,5-dimethyl-piperazin-1-yl]-2-[4-(4-nitro-3-trifluoromethyl-phenylamino)-cyclohexyloxy]-ethanone (mixture of stereoisomers)

(CI, m/z): [M+H]⁺ 609.0; ¹H NMR (CDCl₃): δ 8.02 (d, J=9.0 Hz, 1H), 6.82-6.93 (m, 2H), 6.74-6.82 (m, 1H), 6.59-6.68 (m, 2H), 4.80-4.99 (m, 1H), 4.53 (d, J=7.6 Hz, 1H), 4.06-4.31 (m, 3H), 3.85-4.04 (m, 1H), 3.33-3.53 (m, 3H), 3.18-3.32 (m, 2H), 2.99-3.13 (m, 2H), 2.83-2.94 (m, 1H), 2.58-2.80 (m, 2H), 2.38-2.56 (m, 1H), 2.15 (d, J=9.7 Hz, 4H), 1.41-1.55 (m, 2H), 1.21-1.39 (m, 4H), 1.14 (d, J=5.4 Hz, 1H), 0.88-1.05 (m, 3H).

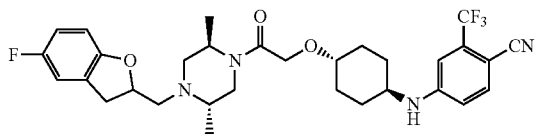 [SMILES: C[C@@H]1CN(CC2Cc3cc(F)ccc3O2)[C@@H](C)CN1C(=O)CO[C@H]1CC[C@H](Nc2ccc(C#N)c(C(F)(F)F)c2)CC1]

Compound 308: 4-(4-{2-[(2R,5S)-4-(5-fluoro-2,3-dihydro-benzofuran-2-ylmethyl)-2,5-dimethyl-piperazin-1-yl]-2-oxo-ethoxy}-cyclohexylamino)-2-trifluoromethyl-benzonitrile (mixture of stereoisomers)

(CI, m/z): [M+H]⁺ 589.0; ¹H NMR (CDCl₃): δ 7.54 (d, J=8.5 Hz, 1H), 6.87 (d, J=8.0 Hz, 1H), 6.80-6.84 (m, 1H), 6.77 (dd, J=8.3, 3.7 Hz, 1H), 6.60-6.70 (m, 2H), 4.78-4.99 (m, 1H), 4.40 (d, J=7.6 Hz, 1H), 4.07-4.28 (m, 2H), 3.31-3.54 (m, 3H), 3.18-3.31 (m, 1H), 3.07 (d, J=8.0 Hz, 2H), 2.88 (d, J=11.2 Hz, 1H), 2.57-2.79 (m, 2H), 2.37-2.55 (m, 1H), 2.13 (m, 6H), 1.36-1.55 (m, 3H), 1.20-1.35 (m, 3H), 1.13 (d, J=4.9 Hz, 1H), 0.85-1.05 (m, 3H).

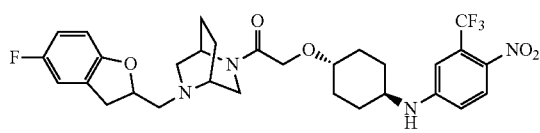 [SMILES: O=C(CO[C@H]1CC[C@H](Nc2ccc([N+](=O)[O-])c(C(F)(F)F)c2)CC1)N1CC2CCC1CN2CC1Cc2cc(F)ccc2O1]

Compound 309: 1-[5-(5-fluoro-2,3-dihydro-benzofuran-2-ylmethyl)-2,5-diaza-bicyclo[2.2.2]oct-2-yl]-2-[4-(4-nitro-3-trifluoromethyl-phenylamino)-cyclohexyloxy]-ethanone (CI, m/z): [M+H]⁺ 607.0; ¹H NMR (CDCl₃): δ 8.02 (d, J=9.0 Hz, 1H), 6.83-6.91 (m, 2H), 6.73-6.82 (m, 1H), 6.60-6.69 (m, 2H), 4.81-4.96 (m, 1H), 4.45-4.58 (m, 1H), 4.07-4.20 (m, 3H), 3.85 (overlapping m, 2H), 3.50 (d, J=5.2 Hz, 2H), 3.34-3.46 (m, 3H), 3.16-3.31 (m, 1H), 3.02-3.13 (m, 2H), 2.92-3.01 (m, 2H), 2.77-2.90 (m, 1H), 2.08-2.25 (m, 4H), 1.76-1.98 (m, 1H), 1.39-1.57 (m, 1H), 1.16-1.36 (m, 4H).

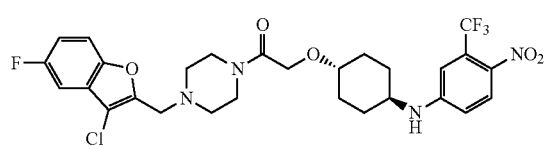 [SMILES: O=C(CO[C@H]1CC[C@H](Nc2ccc([N+](=O)[O-])c(C(F)(F)F)c2)CC1)N1CCN(Cc2oc3ccc(F)cc3c2Cl)CC1]

Compound 312: 1-[4-(3-chloro-5-fluoro-benzofuran-2-ylmethyl)-piperazin-1-yl]-2-[4-(4-nitro-3-trifluoromethyl-phenylamino)-cyclohexyloxy]-ethanone (CI, m/z): [M+H]⁺ 613.0; ¹H NMR (CDCl₃): δ 8.02 (d, J=9.0 Hz, 1H), 7.41 (dd, J=9.0, 3.9 Hz, 1H), 7.22 (dd, J=7.9, 2.6 Hz, 1H), 7.07 (td, J=9.0, 2.6 Hz, 1H), 6.85 (d, J=2.3 Hz, 1H), 6.63 (dd, J=9.0, 2.5 Hz, 1H), 4.49 (d, J=7.5 Hz, 1H), 4.18 (s, 2H), 3.80 (s, 2H), 3.63-3.73 (m, 2H), 3.53-3.62 (m, 2H), 3.30-3.48 (m, 2H), 2.59 (t, J=4.7 Hz, 4H), 2.02-2.22 (m, 4H), 1.36-1.54 (m, 2H), 1.16-1.34 (m, 2H)

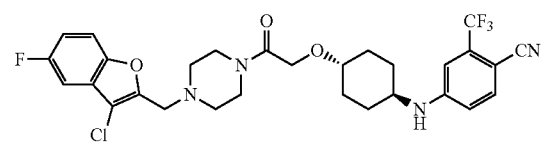 [SMILES: N#Cc1ccc(N[C@H]2CC[C@H](OCC(=O)N3CCN(Cc4oc5ccc(F)cc5c4Cl)CC3)CC2)cc1C(F)(F)F]

Compound 313: 4-(4-{2-[4-(3-chloro-5-fluoro-benzofuran-2-ylmethyl)-piperazin-1-yl]-2-oxo-ethoxy}-cyclohexylamino)-2-trifluoromethyl-benzonitrile (CI, m/z): [M+H]⁺ 593.0; ¹H NMR (CDCl₃): δ 7.55 (d, J=8.6 Hz, 1H), 7.42 (dd, J=8.9, 3.9 Hz, 1H), 7.22 (dd, J=7.9, 2.5 Hz, 1H), 7.07 (td, J=9.0, 2.6 Hz, 1H), 6.81 (d, J=2.1 Hz, 1H), 6.65 (dd, J=8.6, 2.2 Hz, 1H), 4.25-4.35 (m, 1H), 4.18 (s, 2H), 3.80 (s, 2H), 3.64-3.72 (m, 2H), 3.53-3.62 (m, 2H), 3.26-3.49 (m, 2H), 2.51-2.68 (m, 4H), 2.04-2.22 (m, 5H), 1.36-1.52 (m, 2H), 1.15-1.31 (m, 2H).

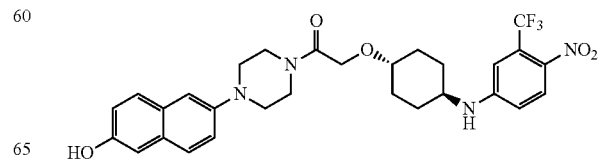

Compound 314: 1-[4-(6-hydroxy-naphthalen-2-yl)-piperazin-1-yl]-2-[4-(4-nitro-3-trifluoromethyl-phenylamino)-cyclohexyloxy]-ethanone (CI, m/z): [M+H]+ 573.0; 1H NMR (DMSO-d6): δ 8.05 (d, J=9.2 Hz, 1H), 7.57 (dd, J=5.6, 4.8 Hz, 2H), 7.45 (br. s., 1H), 7.27 (dd, J=9.0, 1.6 Hz, 1H), 7.08 (d, J=14.1 Hz, 2H), 6.94-7.02 (m, 2H), 6.85 (dd, J=9.3, 2.3 Hz, 1H), 4.21 (s, 2H), 3.62 (br s, 4H), 3.43-3.53 (m, 1H), 3.36-3.42 (m, 1H), 3.01-3.23 (m, 4H), 1.89-2.10 (m, 4H), 1.38 (m, 2H), 1.25 (m, 2H).

EXAMPLE 28: Preparation of Compound 111

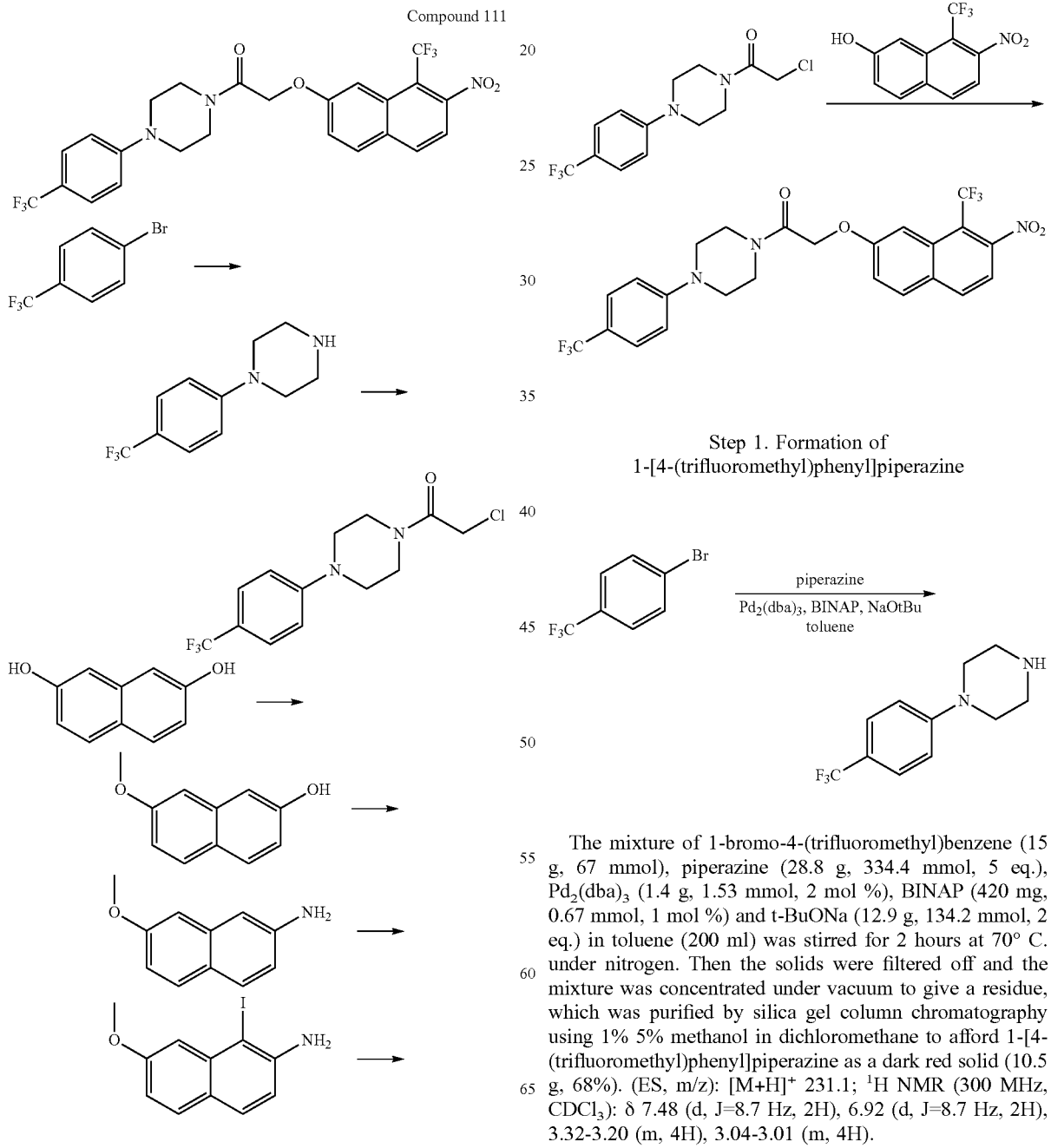

Step 1. Formation of 1-[4-(trifluoromethyl)phenyl]piperazine

The mixture of 1-bromo-4-(trifluoromethyl)benzene (15 g, 67 mmol), piperazine (28.8 g, 334.4 mmol, 5 eq.), Pd$_2$(dba)$_3$ (1.4 g, 1.53 mmol, 2 mol %), BINAP (420 mg, 0.67 mmol, 1 mol %) and t-BuONa (12.9 g, 134.2 mmol, 2 eq.) in toluene (200 ml) was stirred for 2 hours at 70° C. under nitrogen. Then the solids were filtered off and the mixture was concentrated under vacuum to give a residue, which was purified by silica gel column chromatography using 1% 5% methanol in dichloromethane to afford 1-[4-(trifluoromethyl)phenyl]piperazine as a dark red solid (10.5 g, 68%). (ES, m/z): [M+H]+ 231.1; 1H NMR (300 MHz, CDCl$_3$): δ 7.48 (d, J=8.7 Hz, 2H), 6.92 (d, J=8.7 Hz, 2H), 3.32-3.20 (m, 4H), 3.04-3.01 (m, 4H).

Step 2. Formation of 2-chloro-1-[4-[4-(trifluoromethyl)phenyl]piperazin-1-yl]ethan-1-one

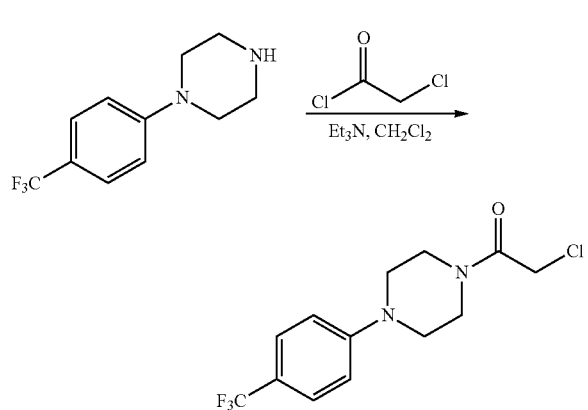

To a mixture of 1-[4-(trifluoromethyl)phenyl]piperazine (600 mg, 2.61 mmol) and triethylamine (660 mg, 6.52 mmol) in dichloromethane (20 ml) was added 2-chloroacetyl chloride (380 mg, 3.36 mmol) dropwise at 0° C. The resulting solution was stirred for 1 hour at room temperature. The reaction mixture was then quenched by water (80 ml) and extracted with dichloromethane (3×30 ml). The organic layers were combined, dried over anhydrous magnesium sulfate, and concentrated under vacuum. The residue was purified by silica gel column chromatography using 1-10% ethyl acetate in petroleum ether to afford 2-chloro-1-[4-[4-(trifluoromethyl)phenyl]piperazin-1-yl]ethan-1-one as a white solid (479 mg, 60%). (ES, m/z): [M+H]$^+$ 307.1; $^1$H NMR (300 MHz, CDCl$_3$): δ 7.52 (d, J=8.4 Hz, 2H), 6.97 (d, J=8.7 Hz, 2H), 4.12 (s, 1H), 3.81 (t, J=5.1 Hz, 2H), 3.72 (t, J=5.1 Hz, 2H), 3.36 (t, J=5.1 Hz, 2H), 3.30 (t, J=5.1 Hz, 2H).

Step 3. Formation of 7-methoxynaphthalen-2-ol

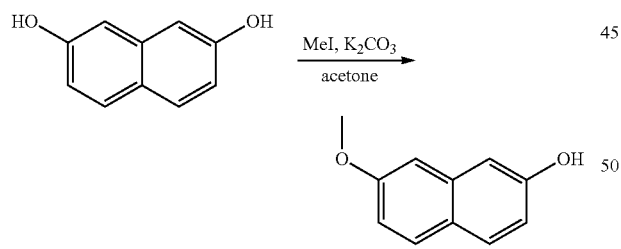

To a mixture of naphthalene-2,7-diol (25 g, 156.08 mmol) and K$_2$CO$_3$ (32.3 g, 232.02 mmol) in acetone (300 ml) was added iodomethane (22.2 g, 156.41 mmol) dropwise with stirring at 0° C. The resulting solution was stirred overnight at room temperature. The solids were filtered off and the filtrate was concentrated under vacuum to give a residue, which was purified by silica gel column chromatography using 1%-10% ethyl acetate in petroleum ether to afford 7-methoxynaphthalen-2-ol as a light yellow solid (10 g, 37%). (ES, m/z): [M+H]$^+$ 175.1; $^1$H NMR (400 MHz, DMSO-d6): δ 9.65 (s, 1H), 7.65 (d, J=8.8 Hz, 2H), 6.79 (dd, J=13.6, 1.6 Hz, 2H), 6.92-6.89 (m, 2H), 3.84 (s, 3H).

Step 4. Formation of 7-methoxynaphthalen-2-amine

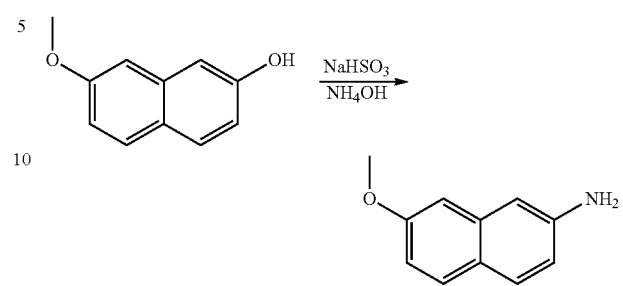

The solution of 7-methoxynaphthalen-2-ol (6.5 g, 37.31 mmol) and NaHSO$_3$ (11.6 g, 111.54 mmol) in ammonium hydroxide (100 ml) was stirred for 2 days at 140° C. in a sealed tube and then cooled to room temperature. The solids were collected by filtration to afford 7-methoxynaphthalen-2-amine as an off-white solid (4.5 g, 70%). (ES, m/z): [M+H]$^+$ 174.1; $^1$H NMR (300 MHz, CDCl$_3$): δ 7.57 (d, J=8.7 Hz, 2H), 6.97-6.87 (m, 3H), 6.79 (dd, J=8.7, 2.1 Hz, 1H), 3.90 (s, 3H), 3.84 (br s, 2H).

Step 5. Formation of 1-iodo-7-methoxynaphthalen-2-amine

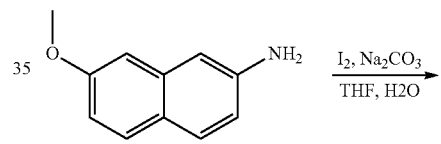

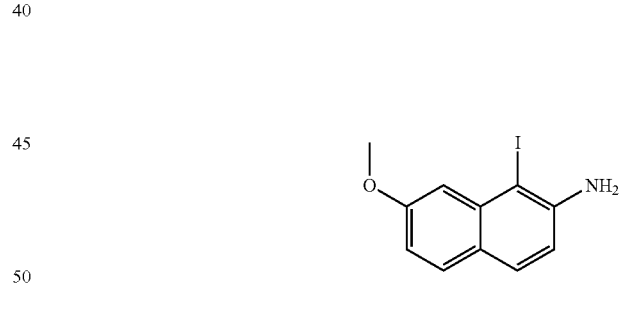

To a mixture of 7-methoxynaphthalen-2-amine (5 g, 29 mmol) and sodium carbonate (6.1 g, 57.6 mmol) in tetrahydrofuran (200 ml) and water (20 ml) was added iodine (7.0 g, 27.67 mmol) in portions at 0° C. The resulting solution was stirred overnight at room temperature and then diluted with water (250 ml), extracted with ethyl acetate (3×200 ml). The combined organic layers were dried over anhydrous magnesium sulfate, filtered, and concentrated under vacuum to give a residue, which was purified by silica gel column chromatography using 5% ethyl acetate in petroleum ether to afford 1-iodo-7-methoxynaphthalen-2-amine as a yellow solid (5.2 g, 60%). (ES, m/z): [M+H]$^+$ 300.1; $^1$H NMR (300 MHz, CDCl$_3$): δ 7.54 (dd, J=8.7, 5.4 Hz, 2H), 7.30 (d, J=2.4 Hz, 1H), 6.91 (dd, J=8.7, 2.4 Hz, 1H), 6.84 (d, J=8.4 Hz, 1H), 4.04 (br s, 2H), 3.96 (s, 3H).

Step 6. Formation of 1-iodo-7-methoxy-2-nitronaphthalene

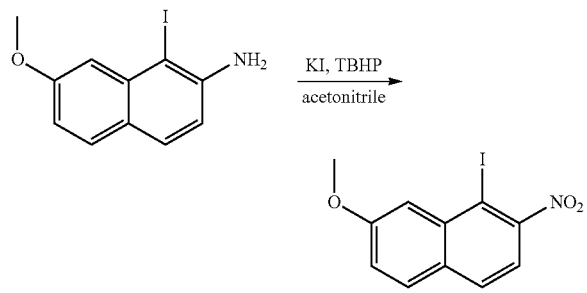

To a solution of 1-iodo-7-methoxynaphthalen-2-amine (10 g, 33.43 mmol) and potassium iodide (300 mg, 1.81 mmol) in acetonitrile (150 ml) was added dropwise TBHP (12 mL) with stirring. The resulting solution was refluxed for 3 days, then quenched by saturated aqueous $Na_2S_2O_3$ (50 ml) and extracted with ethyl acetate (3×150 ml). The combined organic layers were dried over anhydrous magnesium sulfate, filtered, and concentrated under vacuum to give a residue, which was purified by silica gel column chromatography using 1%-10% ethyl acetate in petroleum ether to afford 1-iodo-7-methoxy-2-nitronaphthalene as a yellow solid (2.5 g, 23%). $^1$H NMR (300 MHz, $CDCl_3$): δ 7.86 (d, J=8.7 Hz, 1H), 7.78 (dd, J=9.0, 1.8 Hz, 1H), 7.68 (d, J=2.4 Hz, 1H), 7.54 (dd, J=8.7, 1.8 Hz, 1H), 7.78 (dd, J=9.0, 2.4 Hz, 1H), 4.04 (s, 3H).

Step 7. Formation of 7-methoxy-2-nitro-1-(trifluoromethyl)naphthalene

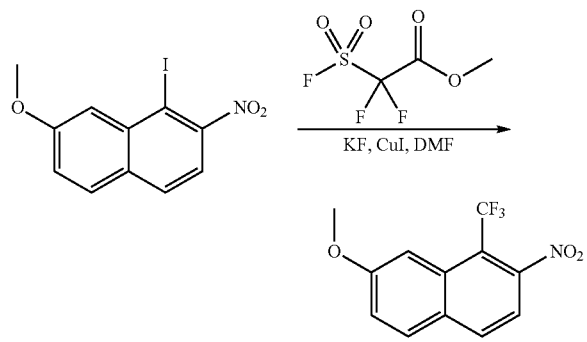

The mixture of 1-iodo-7-methoxy-2-nitronaphthalene (3.7 g, 11.24 mmol), CuI (2.3 g, 12.08 mmol) and KF (1 g, 17.24 mmol) in N,N-dimethylformamide (50 ml) was stirred for 0.5 h at 120° C. before the addition of 2,2-difluoro-2-(fluorosulfonyl)acetate (2.3 g, 11.97 mmol). The resulting solution was stirred for another 0.5 h at 120° C. and then quenched by water (300 ml). The crude product was extracted with dichloromethane (3×100 ml) and the organic fractions were combined and washed by brine (3×150 ml). The organic layers were dried over anhydrous magnesium sulfate, filtered, and concentrated under vacuum to give a residue, which was purified by silica gel column chromatography using 1%-10% ethyl acetate in petroleum ether to afford 7-methoxy-2-nitro-1-(trifluoromethyl)naphthalene as a off-white solid (2 g, 66%). $^1$H NMR (300 MHz, DMSO): δ 8.48 (d, J=8.7 Hz, 1H), 8.21 (d, J=9.3 Hz, 1H), 7.84 (d, J=8.7 Hz, 1H), 7.56 (dd, J=9.0, 2.1 Hz, 1H), 7.41 (s, 1H), 3.96 (s, 3H).

Step 8. Formation of 7-amino-8-(trifluoromethyl)naphthalen-2-ol

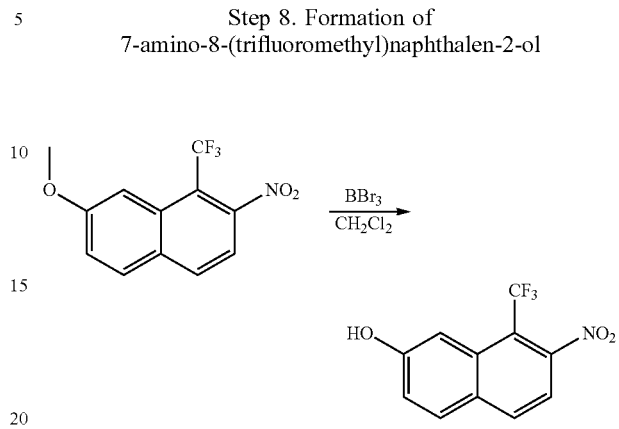

To a solution of 7-methoxy-1-(trifluoromethyl)naphthalen-2-amine (2 g, 8.29 mmol) in dichloromethane (20 ml) was added dropwise $BBr_3$ (4 ml, 42 mmol, 5 eq.) with stirring at −78° C. The resulting solution was stirred overnight at room temperature and then quenched by ice-water (50 ml) and extracted with dichloromethane (3×50 ml). The combined organic layers were dried over anhydrous magnesium sulfate, filtered, and concentrated under vacuum to afford 7-amino-8-(trifluoromethyl)naphthalen-2-ol as a brown solid (1.3 g, 69%).

(ES, m/z): [M−H]⁻ 256.0; $^1$H NMR (300 MHz, DMSO-d6): δ 10.16 (s, 1H), 8.41 (d, J=8.7 Hz, 1H), 8.13 (d, J=9.0 Hz, 1H), 7.73 (d, J=8.7 Hz, 1H), 7.47 (s, 1H), 7.40 (dd, J=9.0, 2.1 Hz, 1H).

Step 9. Formation of 2-[[7-nitro-8-(trifluoromethyl)naphthalen-2-yl]oxy]-1-[4-[4-(trifluoromethyl)phenyl]piperazin-1-yl]ethan-1-one (#111)

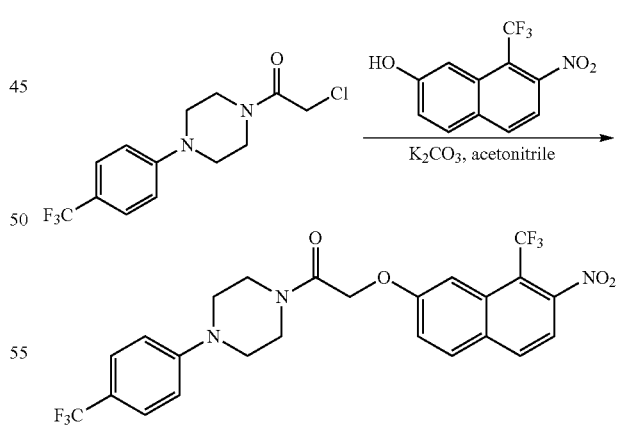

The mixture of 7-nitro-8-(trifluoromethyl)naphthalen-2-ol (50 mg, 0.19 mmol), 2-chloro-1-4-[4-(trifluoromethyl)phenyl]piperazin-1-yletham-1-one (65.4 mg, 0.21 mmol, 1.1 eq.) and potassium carbonate (29.5 mg, 0.21 mmol, 1.1 eq.) in acetonitrile (15 ml) was heated at reflux for 5 hours. The solids were filtered off and the filtrate was concentrated under vacuum to give a residue, which was purified by silica gel column chromatography using methanol in dichloromethane to afford 2-[[7-nitro-8-(trifluoromethyl)naphthalen-2-yl]oxy]-1-[4-[4-(trifluoromethyl)phenyl]piperazin-1-yl]ethan-1-one as a light yellow solid (46.8 mg, 46%). (ES, m/z): [M+H]⁺ 528.10; ¹H NMR (400 MHz, CDCl₃): δ 8.07 (d, J=8.8 Hz, 1H), 6.92 (d, J=9.2 Hz, 1H), 7.55-7.38 (m, 5H), 6.95 (d, J=8.4 Hz, 2H), 4.93 (s, 2H), 3.84-3.82 (m, 4H), 3.34-3.29 (m, 4H).

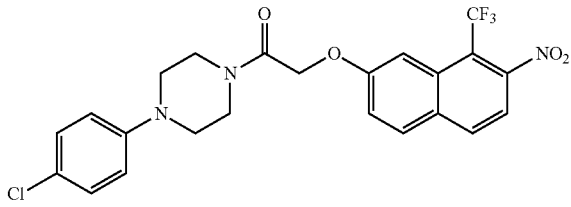 [SMILES: O=C(COc1ccc2ccc([N+](=O)[O-])c(C(F)(F)F)c2c1)N1CCN(c2ccc(Cl)cc2)CC1]

Compound 112: 1-[4-(4-chlorophenyl)piperazin-1-yl]-2-[[7-nitro-8-(trifluoromethyl)naphthalen-2-yl]oxy]ethan-1-one (ES, m/z): [M+H]⁺ 493.85; ¹H NMR (400 MHz, CDCl₃): δ 8.08 (d, J=8.8 Hz, 1H), 7.92 (d, J=8.8 Hz, 1H), 7.56 (s, 1H), 7.45 (d, J=9.2 Hz, 1H), 7.40 (d, J=8.8 Hz, 1H), 7.26 (d, J=8.4 Hz, 2H), 6.99 (d, J=8.4 Hz, 2H), 4.92 (s, 2H), 3.91-3.86 (m, 4H), 3.24-3.19 (m, 4H).

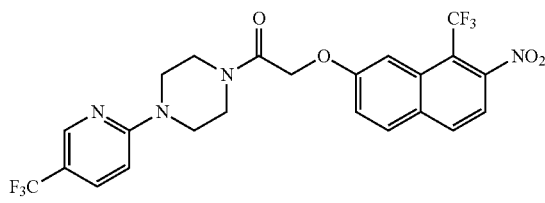 [SMILES: O=C(COc1ccc2ccc([N+](=O)[O-])c(C(F)(F)F)c2c1)N1CCN(c2ccc(C(F)(F)F)cn2)CC1]

Compound 113: 2-[[7-nitro-8-(trifluoromethyl)naphthalen-2-yl]oxy]-1-[4-[5-(trifluoromethyl)pyridin-2-yl]piperazin-1-yl]ethan-1-one (ES, m/z): [M+H]⁺ 529.05; ¹H NMR (400 MHz, CDCl₃): δ 8.42 (s, 1H), 8.07 (d, J=8.8 Hz, 1H), 7.91 (d, J=8.8 Hz, 1H), 7.71 (dd, J=9.2, 2.0 Hz, 1H), 7.56 (s, 1H), 7.46 (d, J=8.8 Hz, 1H), 7.40 (d, J=8.4 Hz, 1H), 6.69 (d, J=8.8 Hz, 1H), 4.93 (s, 2H), 3.83-3.76 (m, 6H), 3.66-3.64 (m. 2H).

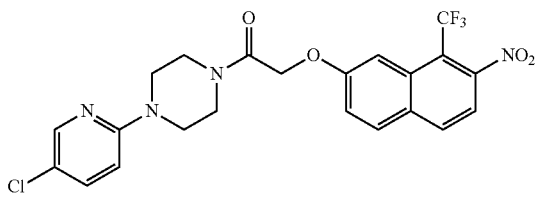 [SMILES: O=C(COc1ccc2ccc([N+](=O)[O-])c(C(F)(F)F)c2c1)N1CCN(c2ccc(Cl)cn2)CC1]

Compound 114: 1-[4-(5-chloropyridin-2-yl)piperazin-1-yl]-2-[[7-nitro-8-(trifluoromethyl)naphthalen-2-yl]oxy]ethan-1-one (ES, m/z): [M+H]⁺ 495.00; ¹H NMR (400 MHz, CDCl₃): δ 8.16 (d, J=2.4 Hz, 1H), 8.07 (d, J=8.8 Hz, 1H), 7.91 (d, J=9.2 Hz, 1H), 7.58-7.55 (m, 2H), 7.45 (dd, J=9.2, 2.4 Hz, 1H), 7.40 (d, J=8.8 Hz, 1H), 6.69 (d, J=9.2 Hz, 1H), 4.92 (s, 2H), 3.81 (br s, 6H), 3.56 (br s, 2H).

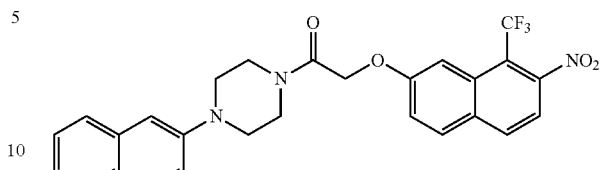

Compound 127: 1-[4-(naphthalen-2-yl)piperazin-1-yl]-2-[[7-nitro-8-(trifluoromethyl)naphthalen-2-yl]oxy]ethan-1-one (ES, m/z): [M+H]⁺ 510.05; ¹H NMR (300 MHz, CDCl₃): δ 8.07 (d, J=8.7 Hz, 1H), 7.92 (d, J=9.0 Hz, 1H), 7.78-7.69 (m, 3H), 7.57 (s, 1H), 7.49-7.31 (m, 4H), 7.28 (m, 1H), 7.16 (s, 1H), 4.94 (s, 2H), 3.89-3.83 (m, 4H), 3.34-3.29 (m, 4H).

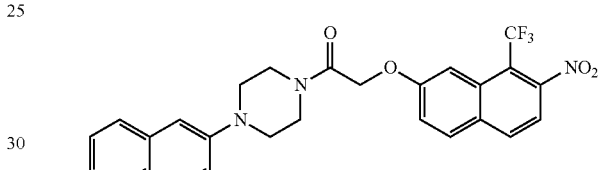

Compound 128: 1-[4-(6-fluoronaphthalen-2-yl)piperazin-1-yl]-2-[[7-nitro-8-(trifluoromethyl)naphthalen-2-yl]oxy]ethan-1-one (ES, m/z): [M+H]⁺ 528.00; ¹H NMR (400 MHz, CDCl₃): δ 8.07 (d, J=8.4 Hz, 1H), 7.92 (d, J=9.2 Hz, 1H), 7.78-7.73 (m, 2H), 7.58 (s, 1H), 7.47 (d, J=8.8 Hz, 1H), 7.41-7.36 (m, 3H), 7.32 (d, J=9.2 Hz, 1H), 7.23-7.20 (m, 1H), 4.94 (s, 2H), 3.93-3.88 (m, 4H), 3.33-3.28 (m, 4H).

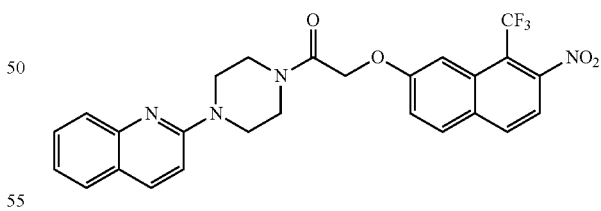

Compound 129: 2-[[7-nitro-8-(trifluoromethyl)naphthalen-2-yl]oxy]-1-[4-(quinolin-2-yl)piperazin-1-yl]ethan-1-one (ES, m/z): [M+H]⁺ 511.25; ¹H NMR (400 MHz, CDCl₃): δ 8.08 (d, J=8.8 Hz, 1H), 8.06-7.94 (m, 1H), 7.91 (d, J=8.8 Hz, 1H), 7.71-7.60 (m, 3H), 7.57 (s, 1H), 7.47 (d, J=9.2 Hz, 1H), 7.40 (d, J=9.0 Hz, 1H), 7.38-7.31 (m, 1H), 7.00 (d, J=9.2 Hz, 1H), 4.95 (s, 2H), 4.02-3.77 (m, 8H).

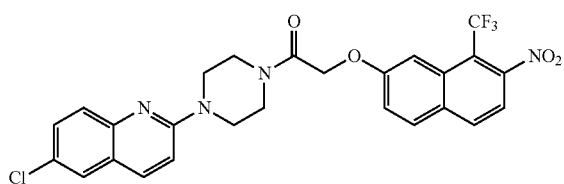 [SMILES: O=C(COc1ccc2ccc([N+](=O)[O-])c(C(F)(F)F)c2c1)N1CCN(c2ccc3cc(Cl)ccc3n2)CC1]

Compound 130: 1-[4-(6-chloroquinolin-2-yl)piperazin-1-yl]-2-[[7-nitro-8-(trifluoromethyl)naphthalen-2-yl]oxy]ethan-1-one (ES, m/z): [M+H]⁺ 545.25; ¹H NMR (300 MHz, CDCl₃): δ 8.06 (d, J=8.7 Hz, 1H), 7.91 (d, J=9.3 Hz, 1H), 7.86 (d, J=9.0 Hz, 1H), 7.65-7.57 (m, 3H), 7.51-7.48 (m, 2H), 7.39 (d, J=9.0 Hz, 1H), 7.00 (d, J=9.3 Hz, 1H), 4.94 (s, 2H), 3.87-3.74 (m, 8H).

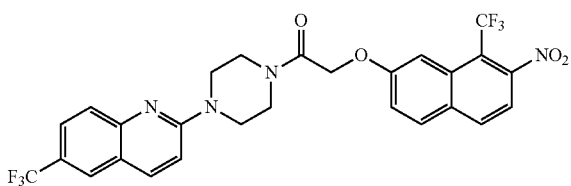 [SMILES: O=C(COc1ccc2ccc([N+](=O)[O-])c(C(F)(F)F)c2c1)N1CCN(c2ccc3cc(C(F)(F)F)ccc3n2)CC1]

Compound 131: 2-[[7-nitro-8-(trifluoromethyl)naphthalen-2-yl]oxy]-1-[4-[6-(trifluoromethyl)quinolin-2-yl]piperazin-1-yl]ethan-1-one (ES, m/z): [M+H]⁺ 579.00; ¹H NMR (300 MHz, CDCl₃): δ 8.10 (d, J=8.7 Hz, 1H), 8.02 (d, J=9.0 Hz, 1H), 7.96-7.93 (m, 2H), 7.85-7.75 (m, 2H), 7.60 (s, 1H), 7.50 (dd, J=9.3, 2.1 Hz, 1H), 7.42 (d, J=8.7 Hz, 1H), 7.08 (d, J=9.0 Hz, 1H), 4.98 (s, 2H), 3.99-3.89 (m, 2H), 3.85-3.80 (m, 6H).

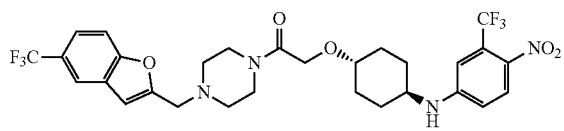 [SMILES: O=C(CO[C@H]1CC[C@H](Nc2ccc([N+](=O)[O-])c(C(F)(F)F)c2)CC1)N1CCN(Cc2cc3cc(C(F)(F)F)ccc3o2)CC1]

Compound 180: 2-[(4-[[4-nitro-3-(trifluoromethyl)phenyl]amino]cyclohexyl)oxy]-1-(4-[[5-(trifluoromethyl)-1-benzofuran-2-yl]methyl]piperazin-1-yl)ethan-1-one (ES, m/z): [M+H]⁺ 629.10; ¹H NMR (300 MHz, CDCl₃): δ 8.01 (d, J=9.0 Hz, 1H), 7.85 (s, 1H), 7.56 (s, 2H), 6.84 (d, J=2.4 Hz, 1H), 6.70 (s, 1H), 6.60 (dd, J=2.7 Hz, 9.0 Hz, 1H), 4.42 (d, J=7.5 Hz, 1H), 4.18 (s, 2H), 3.60-3.90 (m, 5H), 3.36-3.40 (m, 3H), 2.55 (br s, 4H), 2.09-2.14 (m, 4H), 1.38-1.56 (m, 2H), 1.19-1.30 (m, 2H).

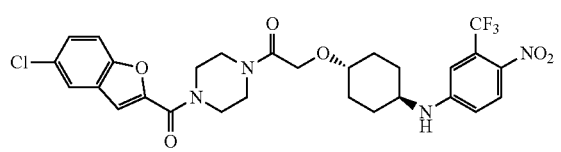 [SMILES: O=C(CO[C@H]1CC[C@H](Nc2ccc([N+](=O)[O-])c(C(F)(F)F)c2)CC1)N1CCN(C(=O)c2cc3cc(Cl)ccc3o2)CC1]

Compound 181: 1-[4-[(5-chloro-1-benzofuran-2-yl)carbonyl]piperazin-1-yl]-2-[(4-[[4-nitro-3-(trifluoromethyl)phenyl]amino]cyclohexyl)oxy]ethan-1-one (ES, m/z): [M+H]⁺ 609.00; ¹H NMR (400 MHz, CDCl₃): δ 8.04 (d, J=8.8 Hz, 1H), 7.67 (d, J=1.5 Hz, 1H), 7.47 (dd, J=1.6, 8.8 Hz, 1H), 7.41 (dd, J=2.0, 8.8 Hz, 1H), 7.32 (s, 1H), 6.88 (s, 1H), 6.67 (d, J=7.6 Hz, 1H), 4.27 (s, 2H), 3.80 (br s, 4H), 3.60-3.76 (m, 4H), 3.39-3.48 (m, 2H), 2.07-2.19 (m, 4H), 1.49-1.54 (m, 2H), 1.28-1.36 (m, 2H).

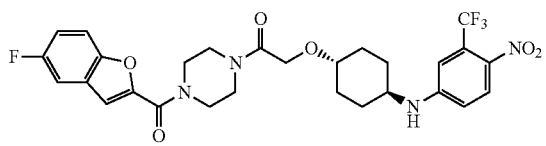 [SMILES: O=C(CO[C@H]1CC[C@H](Nc2ccc([N+](=O)[O-])c(C(F)(F)F)c2)CC1)N1CCN(C(=O)c2cc3cc(F)ccc3o2)CC1]

Compound 182: 1-[4-[(5-fluoro-1-benzofuran-2-yl)carbonyl]piperazin-1-yl]-2-[(4-[[4-nitro-3-(trifluoromethyl)phenyl]amino]cyclohexyl)oxy]ethan-1-one (ES, m/z): [M+H]⁺ 593.15; ¹H NMR (300 MHz, CDCl₃): δ 8.02 (d, J=9.0 Hz, 1H), 7.47 (dd, J=4.2 Hz, 9.3 Hz, 1H), 7.26-7.36 (m, 2H), 7.11-7.19 (m, 1H), 6.86 (s, 1H), 6.65 (d, J=9.9 Hz, 1H), 4.25 (s, 2H), 3.91 (br s, 4H), 3.65-3.79 (m, 4H), 3.39-3.45 (m, 2H), 2.14-2.20 (m, 4H), 1.43-1.54 (m, 2H), 1.28-1.35 (m, 2H).

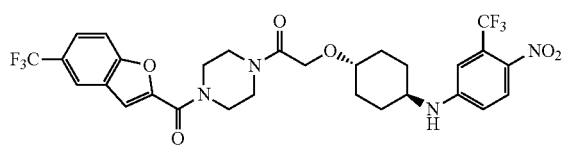 [SMILES: O=C(CO[C@H]1CC[C@H](Nc2ccc([N+](=O)[O-])c(C(F)(F)F)c2)CC1)N1CCN(C(=O)c2cc3cc(C(F)(F)F)ccc3o2)CC1]

Compound 183: 2-[(4-[[4-nitro-3-(trifluoromethyl)phenyl]amino]cyclohexan-1-e)oxy]-1-(4-[[5-(trifluoromethyl)-1-benzofuran-2-yl]carbonyl]piperazin-1-yl) ethan-1-one (ES, m/z): [M+H]⁺ 643.00; ¹H NMR (300 MHz, CDCl₃): δ 8.02 (m, 2H), 7.71-7.61 (m, 2H), 7.44 (s, 1H), 6.87 (s, 1H), 6.68 (d, J=9.6 Hz, 1H), 4.25 (s, 2H), 3.98-3.82 (br s, 4H), 3.80-3.68 (m, 4H), 3.52-3.37 (m, 2H), 2.17-2.05 (m, 4H), 1.53-1.43 (m, 2H), 1.37-1.25 (m, 2H).

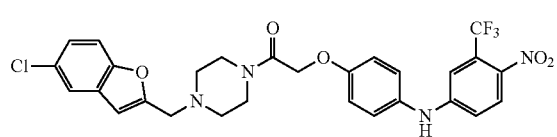 [SMILES: O=C(COc1ccc(Nc2ccc([N+](=O)[O-])c(C(F)(F)F)c2)cc1)N1CCN(Cc2cc3cc(Cl)ccc3o2)CC1]

1-[4-[(5-chloro-1-benzofuran-2-yl)methyl]piperazin-1-yl]-2-(4-[[4-nitro-3-(trifluoromethyl)phenyl]amino]phenoxy)ethan-1-one (#184)

(ES, m/z): [M+H]⁺ 589.05; ¹H NMR (300 MHz, CDCl₃): δ 7.97 (d, J=9.0 Hz, 1H), 7.49 (d, J=1.8 Hz, 1H), 7.39 (d, J=8.7 Hz, 1H), 7.21-7.25 (m, 1H), 7.09-7.11 (m, 3H), 6.95 (m, 2H), 6.89 (dd, J=2.4, 9.0 Hz, 1H), 6.56 (s, 1H), 6.31 (s, 1H), 4.71 (s, 2H), 3.55-3.66 (overlapping m, 6H), 2.56 (br s, 4H).

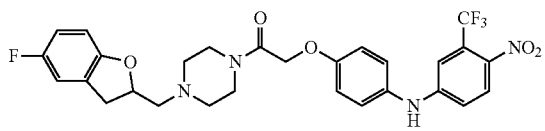 [SMILES: O=C(COc1ccc(Nc2ccc([N+](=O)[O-])c(C(F)(F)F)c2)cc1)N1CCN(CC2Cc3cc(F)ccc3O2)CC1]

Compound 185: 1-[4-[(5-fluoro-2,3-dihydro-1-benzofuran-2-yl)methyl]piperazin-1-yl]-2-(4-[[4-nitro-3-(trifluoromethyl) phenyl]amino]phenoxy)ethan-1-one (ES, m/z): [M+H]⁺ 575.25; ¹H NMR (300 MHz, CDCl₃): δ 7.97 (d, J=9.0 Hz, 1H), 7.11-7.16 (m, 3H), 6.98 (m, 2H), 6.82-6.92 (m, 2H), 6.75-6.79 (m, 1H), 6.65 (dd, J=4.2 Hz, 8.7 Hz, 1H), 6.41 (s, 1H), 4.99 (m, 1H), 4.73 (s, 2H), 3.63-3.70 (m, 4H), 3.26 (dd, J=9.3, 15.6 Hz, 1H), 2.95 (dd, J=7.8, 15.9 Hz, 1H), 2.78 (dd, J=7.8, 13.2 Hz, 1H), 2.59-2.63 (m, 5H).

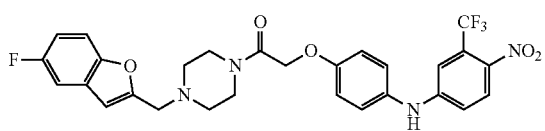 [SMILES: O=C(COc1ccc(Nc2ccc([N+](=O)[O-])c(C(F)(F)F)c2)cc1)N1CCN(Cc2cc3cc(F)ccc3o2)CC1]

Compound 186: 1-[4-[(5-fluoro-1-benzofuran-2-yl)methyl]piperazin-1-yl]-2-(4-[[4-nitro-3-(trifluoromethyl)phenyl]amino]phenyl)ethan-1-one (ES, m/z): [M+H]⁺ 573.20; ¹H NMR (300 MHz, CDCl₃): δ 7.96 (d, J=9.0 Hz, 1H), 7.42 (dd, J=4.2 Hz, 9.0 Hz, 1H), 7.18 (dd, J=2.4, 8.4 Hz, 1H), 7.17-7.09 (m, 3H), 6.99 (m, 3H), 6.90 (dd, J=2.4, 9.0 Hz, 1H), 6.63 (s, 1H), 6.30 (s, 1H), 4.72 (s, 2H), 3.81-3.62 (m, 6H), 2.57 (br s, 4H).

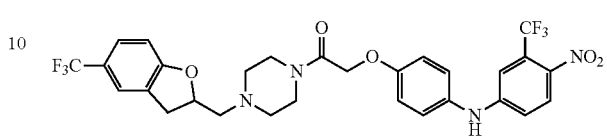

Compound 187: 2-(4-[[4-nitro-3-(trifluoromethyl) phenyl]amino]phenoxy)-1-(4-[[5-(trifluoromethyl)-2,3-dihydro-1-benzofuran-2-yl]methyl]piperazin-1-yl)ethan-1-one (ES, m/z): [M+H]⁺ 525.25; ¹H NMR (300 MHz, CDCl₃): δ 7.97 (d, J=9.0 Hz, 1H), 7.39 (overlapping s & d, 2H), 7.11-7.15 (m, 3H), 7.01 (m, 2H), 6.89-6.93 (dd, J=2.4, 9.0 Hz, 1H), 6.83 (d, J=8.1 Hz, 1H), 6.29 (s, 1H), 5.01 (m, 1H), 4.73 (s, 2H), 3.64-3.70 (m, 4H), 3.33 (dd, J=9.0, 15.9 Hz, 1H), 3.00 (dd, J=9.3, 15.9 Hz, 1H), 2.79 (dd, J=7.2, 13.2 Hz, 1H), 2.49-2.63 (m, 5H).

EXAMPLE 29: Preparation of Compound 188

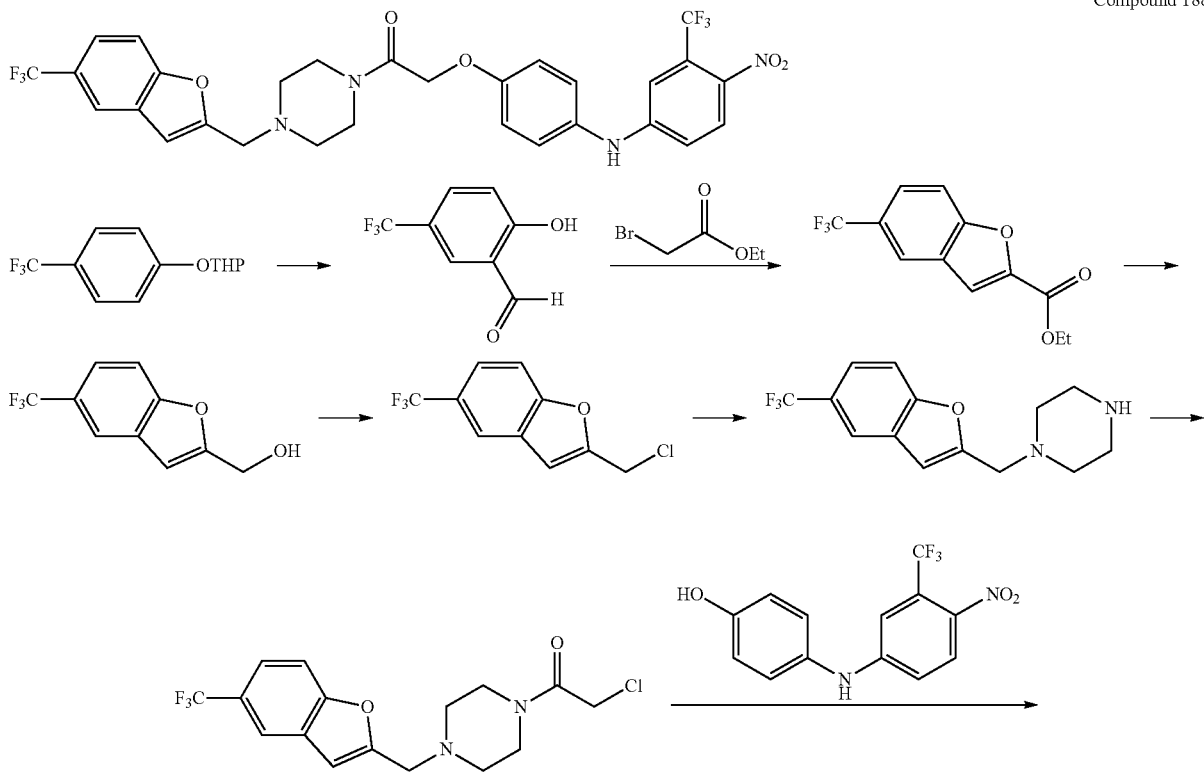

Compound 188

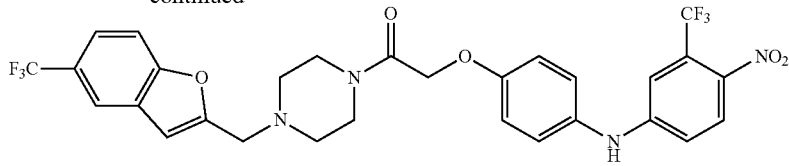

Steps 1-6

Starting from the THP-protected 4-(trifluoromethyl)phenol, 2-chloro-1-(4-[[5-(trifluoromethyl)-1-benzofuran-2-yl]methyl]piperazin-1-yl)ethan-1-one was made in a manner analogous to what was described in the synthesis of compound 184.

Step 7. Formation of 2-(4-[[4-nitro-3-(trifluoromethyl)phenyl]amino]phenoxy)-1-(4-[[5-(trifluoromethyl)-1-benzofuran-2-yl]methyl]piperazin-1-yl)ethan-1-one (#188)

Compound 189: 1-[4-[(5-chloro-1-benzofuran-2-yl)carbonyl]piperazin-1-yl]-2-(4-[[4-nitro-3-(trifluoromethyl)phenyl]amino]phenoxy)ethan-1-one (ES, m/z): [M+H]$^+$ 603.00; $^1$H NMR (300 MHz, CDCl$_3$): δ 7.99 (d, J=9.0 Hz, 1H), 7.65 (d, J=1.8 Hz, 1H), 7.45 (d, J=9.0 Hz, 1H), 7.38 (dd, J=2.1, 9.0 Hz, 1H), 7.33 (s, 1H), 7.14-7.18 (m, 3H), 7.01 (d, J=9.0 Hz, 2H), 6.90 (dd, J=2.7 Hz, 9.0 Hz, 1H), 6.24 (br s, 1H), 4.78 (s, 2H), 3.88 (br s, 4H), 3.77 (br s, 4H).

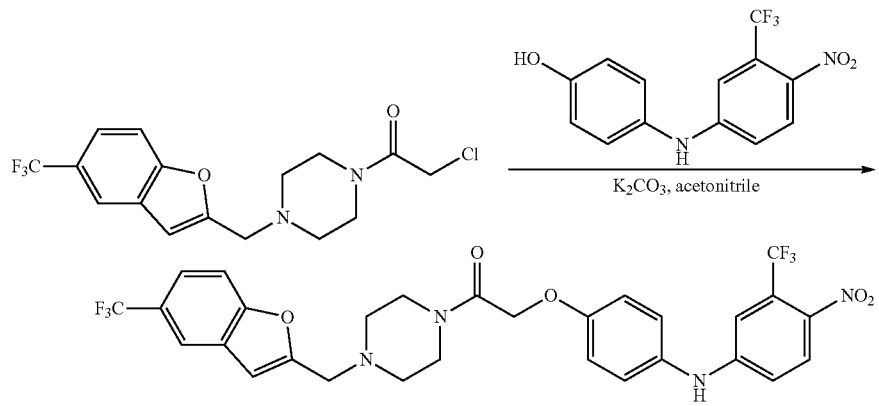

To a solution of 2-chloro-1-(4-[[5-(trifluoromethyl)-1-benzofuran-2-yl]methyl]piperazin-1-yl)ethan-1-one (100 mg, 0.28 mmol) in acetonitrile (10 ml) was added potassium carbonate (57.5 mg, 0.42 mmol) and 4-[4-nitro-3-(trifluoromethyl)phenyl]aminophenol (83 mg, 0.28 mmol). The mixture was stirred and heated at 80° C. (oil bath) for 3 hours. The solids were filtered off and the filtrate was concentrated under vacuum to give a residue, which was purified by Prep-TLC with 60% ethyl acetate in petroleum ether to afford 2-(4-[[4-nitro-3-(trifluoromethyl)phenyl]amino]phenoxy)-1-(4-[[5-(trifluoromethyl)-1-benzofuran-2-yl]methyl]piperazin-1-yl)ethan-1-one as a yellow solid (125.8 mg, 73%); (ES, m/z): [M+H]$^+$ 623.20; $^1$H NMR (400 MHz, CDCl$_3$): δ 8.00 (d, J=8.8 Hz, 1H), 7.86 (s, 1H), 7.60 (m, 2H), 7.14 (overlapping s & d, 3H), 7.00 (d, J=8.4 Hz, 2H), 6.92 (d, J=8.8 Hz, 1H), 6.72 (s, 1H), 6.29 (s, 1H), 4.74 (s, 2H), 3.91-3.53 (m, 6H), 2.60 (br s, 4H).

Compound 190: 4-[[4-nitro-3-(trifluoromethyl)phenyl]amino]phenyl 4-[(5-fluoro-1-benzofuran-2-yl)carbonyl]piperazine-1-carboxylate (ES, m/z): [M+H]$^+$ 587.15; $^1$H NMR (300 MHz, CDCl$_3$): δ 7.98 (d, J=9.0 Hz, 1H), 7.49 (dd, J=3.6, 8.7 Hz, 1H), 7.45-7.31 (m, 2H), 7.15 (overlapping m, 4H), 7.01 (d, J=8.7 Hz, 2H), 6.92 (d, J=9.0 Hz, 1H), 6.38 (s, 1H), 4.79 (s, 2H), 3.90 (br s, 4H), 3.78 (br s, 4H).

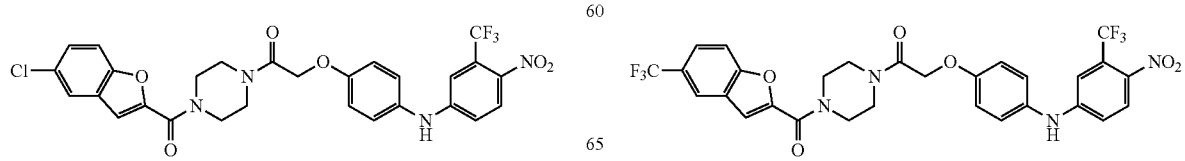

Compound 191: 2-(4-[[4-nitro-3-(trifluoromethyl)phenyl]amino]phenoxy)-1-(4-[[5-(trifluoromethyl)-1-benzofuran-2-yl]carbonyl]piperazin-1-yl)ethan-1-one (ES, m/z): [M+H]⁺ 637.10; ¹H NMR (300 MHz, DMSO-d6): δ 9.39 (s, 1H), 8.21 (s, 1H), 8.10 (d, J=9.0 Hz, 1H), 7.93 (d, J=8.7 Hz, 1H), 7.81 (d, J=8.7 Hz, 1H), 7.57 (s, 1H), 7.19-7.24 (m, 3H), 7.00-7.09 (m, 3H), 4.91 (s, 2H), 3.70-3.97 (m, 4H), 3.55-3.70 (m, 4H).

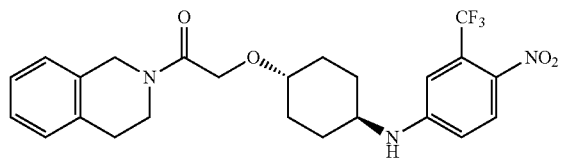 [SMILES: O=C(CO[C@H]1CC[C@H](Nc2ccc([N+](=O)[O-])c(C(F)(F)F)c2)CC1)N1CCc2ccccc2C1]

2-[[4-[[4-nitro-3-(trifluoromethyl)phenyl]amino]cyclohexyl]oxy]-1-(1,2,3,4-tetrahydroisoquinolin-2-yl)ethan-1-one (#192)

(ES, m/z): [M+H]⁺ 478.10; ¹H NMR (300 MHz, CDCl₃): δ 8.02 (d, J=9.0 Hz, 1H), 7.22-7.17 (m, 4H), 6.84 (s, 1H), 6.64 (d, J=9.0 Hz, 1H), 4.74 (m, 2H), 4.28 (s, 2H), 3.84-3.72 (m, 2H), 3.51-3.33 (m, 2H), 2.97-2.84 (m, 2H), 2.13 (m, 4H), 1.50-1.43 (m, 2H), 1.29-1.25 (m, 2H).

EXAMPLE 30: Preparation of Compound 193

Compound 193

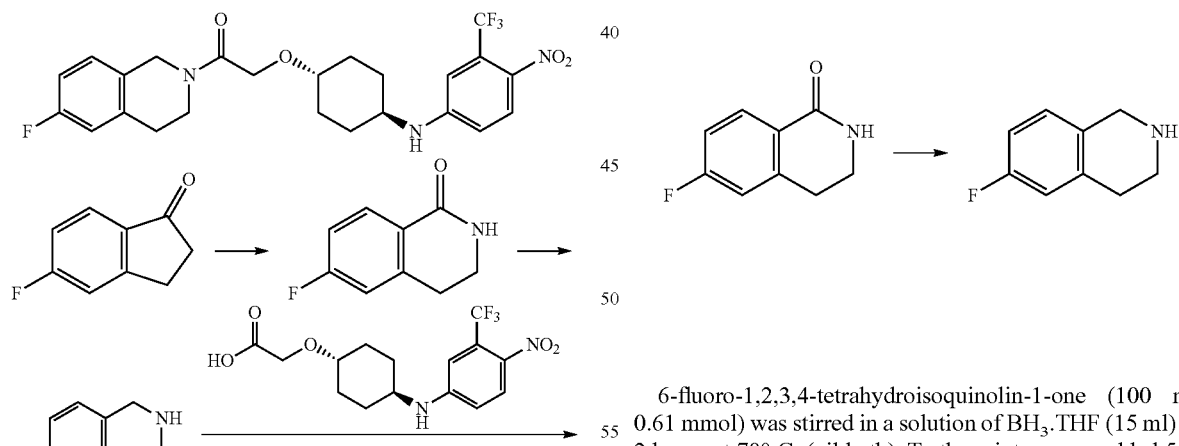

Step 1. Formation of 6-fluoro-1,2,3,4-tetrahydroisoquinolin-1-one

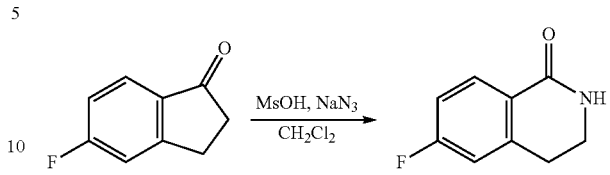

To a solution of 5-fluoro-2,3-dihydro-1H-inden-1-one (4.5 g, 29.97 mmol) in dichloromethane (50 ml) was added methanesulfonic acid (40 ml). This was followed by the addition of sodium azide (2.73 g, 42.0 mmol) in several batches with stirring over 2 hours at 0° C. The reaction mixture was then quenched with aqueous sodium hydroxide and extracted with dichloromethane (2×100 ml). The organic layers were combined, dried over anhydrous sodium sulfate, filtered, and concentrated under vacuum to give a residue, which was purified by silica gel column chromatography using 10% 100% ethyl acetate in petroleum ether to afford 6-fluoro-1,2,3,4-tetrahydroisoquinolin-1-one as a white solid (2.5 g, 51%); (ES, m/z): [M+H]⁺ 166; ¹H NMR (300 MHz, CDCl₃): δ 8.11 (dd, J=6.0, 8.7 Hz, 1H), 7.07-7.00 (m, 1H), 6.94 (dd, J=2.4, 8.7 Hz, 1H), 6.57 (br s, 1H), 3.61 (t, J=6.6, 2H), 3.03 (t, J=6.6, 2H).

Step 2. Formation of 6-fluoro-1,2,3,4-tetrahydroisoquinoline 6-fluoro-1,2,3,4-tetrahydroisoquinolin-1-one (100 mg, 0.61 mmol) was stirred in a solution of BH₃.THF (15 ml) for 2 hours at 70° C. (oil bath). To the mixture was added 5 ml of methanol. The solvent was then removed and the residue was heated at 105° C. in aqueous hydrochloric acid (30 ml, 1M) for 2 hours. The reaction mixture was cooled, basified with aqueous saturated sodium bicarbonate solution, and extracted with ethyl acetate (2×30 ml). The organic fractions were combined, dried over anhydrous sodium sulfate, filtered, and evaporated to afford 6-fluoro-1,2,3,4-tetrahydroisoquinoline as yellow oil (60 mg, 66%); (ES, m/z): [M+H]⁺ 152; ¹H NMR (300 MHz, DMSO-d6): δ 7.05 (t, J=7.2, 1H), 6.94-6.87 (m, 2H), 3.79 (s, 2H), 2.92 (t, J=6.0, 2H), 2.69 (t, J=5.7, 2H).

Step 3. Formation of 1-(6-fluoro-1,2,3,4-tetrahydroisoquinolin-2-yl)-2-[[4-[[4-nitro-3-(trifluoromethyl)phenyl]amino]cyclohexyl]oxy]ethan-1-one (#193)

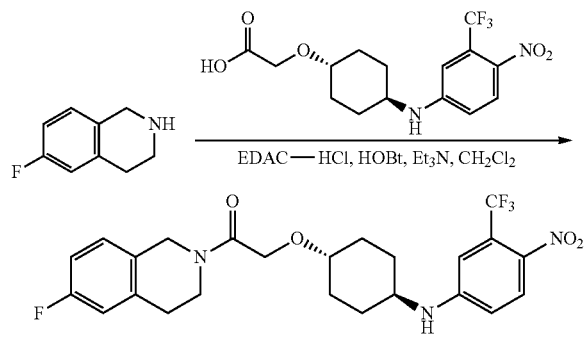

To a solution of 2-[[4-[[4-nitro-3-(trifluoromethyl)phenyl]amino]cyclohexyl]oxy]acetic acid (144 mg, 0.40 mmol) in dichloromethane (15 ml) was added EDAC.HCl (114 mg, 0.59 mmol), HOBt (80 mg, 0.59 mmol) and triethylamine (120 mg, 1.19 mmol) with stirring for 30 minutes. Then 6-fluoro-1,2,3,4-tetrahydroisoquinoline (60 mg, 0.40 mmol) was added to the reaction mixture and the contents were stirred overnight at room temperature. The reaction mixture was diluted with water (100 ml) and extracted with dichloromethane (3×80 ml). The organic fractions were combined, dried over anhydrous sodium sulfate, filtered, and evaporated to give a residue, which was purified by silica gel column chromatography using 5% ethyl acetate in dichloromethane to afford 1-(6-fluoro-1,2,3,4-tetrahydroisoquinolin-2-yl)-2-[[4-[[4-nitro-3-(trifluoromethyl)phenyl]amino]cyclohexyl]oxy]ethan-1-one as a yellow solid (93.8 mg, 48%); (ES, m/z): [M+H]$^+$ 496.00; $^1$H NMR (300 MHz, CDCl$_3$): δ 8.01 (d, J=9.0 Hz, 1H), 7.09 (m, 1H), 6.95-6.82 (m, 3H), 6.65 (d, J=9.0 Hz, 1H), 4.69 (m, 2H), 4.28 (s, 2H), 3.84-3.70 (m, 2H), 3.48-3.33 (m, 2H), 2.93-2.83 (m, 2H), 2.16-2.13 (m, 4H), 1.52-1.40 (m, 2H), 1.34-1.16 (m, 2H).

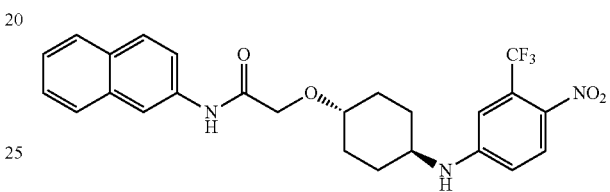

2-[(4-[[4-nitro-3-(trifluoromethyl)phenyl]amino]cyclohexyl)oxy]-1-[6-(trifluoromethyl)-1,2,3,4-tetrahydroisoquinolin-2-yl]ethan-1-one (#194)

(ES, m/z): [M+H]$^+$ 546.00; $^1$H NMR (300 MHz, CDCl$_3$): δ 8.02 (d, J=9.0 Hz, 1H), 7.57-7.42 (m, 2H), 7.28-7.22 (m, 1H), 6.84 (s, 1H), 6.64 (d, J=9.0 Hz, 2H), 4.78 (s, 2H), 4.29 (s, 2H), 3.91-3.73 (m, 2H), 3.46-3.36 (m, 2H), 3.00-2.89 (m, 2H), 2.20-2.10 (m, 4H), 1.54-1.38 (m, 2H), 1.34-1.14 (m, 2H).

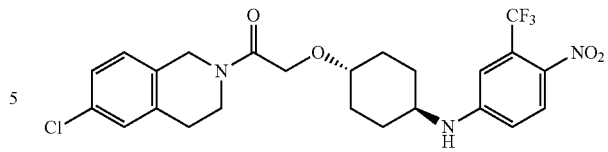

Compound 195: 1-(6-chloro-1,2,3,4-tetrahydroisoquinolin-2-yl)-2-[[4-[[4-nitro-3-(trifluoromethyl)phenyl]amino]cyclohexyl]oxy]ethan-1-one (ES, m/z): [M+H]$^+$ 512.10; $^1$H NMR (300 MHz, CDCl$_3$): δ 8.02 (d, J=9.0 Hz, 1H), 7.20-7.16 (m, 2H), 7.10-7.05 (m, 1H), 6.84 (s, 1H), 6.64 (d, J=8.7 Hz, 1H), 4.69 (m, 2H), 4.27 (s, 2H), 3.84-3.72 (m, 2H), 3.45-3.39 (m, 2H), 2.92-2.85 (m, 2H), 2.16-2.13 (m, 4H), 1.53-1.42 (m, 2H), 1.30-1.26 (m, 2H).

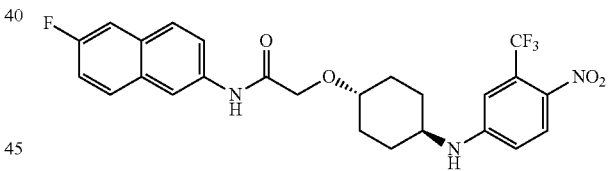

Compound 200: N-(naphthalen-2-yl)-2-[[4-[[4-nitro-3-(trifluoromethyl)phenyl]amino]cyclohexyl]oxy]acetamide (ES, m/z): [M+H]$^+$ 488.05; $^1$H NMR (300 MHz, CDCl$_3$): δ 8.45 (s, 1H), 8.25 (d, J=1.5 Hz, 1H), 8.03 (d, J=9.0 Hz, 1H), 7.84-7.78 (m, 3H), 7.55-7.39 (m, 3H), 6.87 (d, J=2.1 Hz, 1H), 6.67 (dd, J=2.4, 9.0 Hz, 1H), 4.16 (s, 2H), 3.54-3.41 (m, 2H), 2.22 (m, 4H), 1.65-1.52 (m, 2H), 1.39-1.20 (m, 2H).

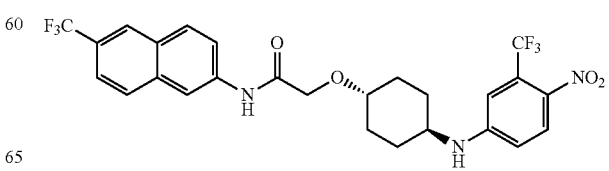

Compound 201: N-(6-fluoronaphthalen-2-yl)-2-[[4-[[4-nitro-3-(trifluoromethyl)phenyl]amino]cyclohexyl]oxy]acetamide (ES, m/z): [M+H]$^+$ 506.10; $^1$H NMR (300 MHz, CDCl$_3$): δ 8.45 (s, 1H), 8.31 (d, J=2.1 Hz, 1H), 8.07 (d, J=9.0 Hz, 1H), 7.86-7.78 (m, 2H), 7.58 (dd, J=1.8, 8.7 Hz, 1H), 7.47 (dd, J=2.7, 9.9 Hz, 1H), 7.33-7.26 (m, 1H), 6.91 (d, J=2.4 Hz, 1H), 6.71 (dd, J=2.4, 9.0 Hz, 1H), 4.20 (s, 2H), 3.59-3.45 (m, 2H), 2.27 (m, 4H), 1.68 (m, 2H), 1.43-1.29 (m, 2H).

Compound 202: 2-[[4-[[4-nitro-3-(trifluoromethyl)phenyl]amino]cyclohexyl]oxy]-N-[6-(trifluoromethyl)naphthalen-2-yl]acetamide (ES, m/z): [M+H]⁺ 556.10; ¹H NMR (300 MHz, CDCl₃): δ 8.51 (s, 1H), 8.38 (s, 1H), 8.10 (s, 1H), 8.04 (d, J=9.0 Hz, 1H), 7.93 (d, J=8.7 Hz, 2H), 7.66 (td, J=2.1, 9.3 Hz, 2H), 6.87 (d, J=2.4 Hz, 1H), 6.68 (dd, J=2.4, 9.0 Hz, 1H), 4.18 (s, 2H), 3.57-3.41 (m, 2H), 2.25 (m, 4H), 1.65-1.55 (m, 2H), 1.37-1.26 (m, 2H).

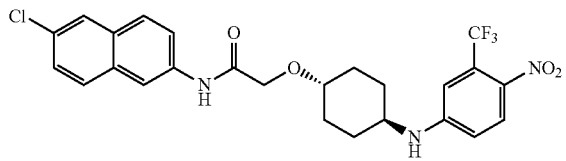 [SMILES: O=C(CO[C@H]1CC[C@H](Nc2ccc([N+](=O)[O-])c(C(F)(F)F)c2)CC1)Nc1ccc2cc(Cl)ccc2c1]

Compound 203: N-(6-chloronaphthalen-2-yl)-2-[[4-[[4-nitro-3-(trifluoromethyl)phenyl]amino]cyclohexyl]oxy]acetamide (ES, m/z): [M+H]⁺ 522.05; ¹H NMR (300 MHz, CDCl₃): δ 8.44 (s, 1H), 8.27 (d, J=1.5 Hz, 1H), 8.03 (d, J=9.0 Hz, 1H), 7.87-7.72 (m, 3H), 7.55 (dd, J=2.1, 8.7 Hz, 1H), 7.43 (dd, J=1.8, 8.7 Hz, 1H), 6.87 (d, J=2.1 Hz, 1H), 6.67 (dd, J=2.4, 9.0 Hz, 1H), 4.16 (s, 2H), 3.57-3.39 (m, 2H), 2.23 (m, 4H), 1.64-1.53 (m, 2H), 1.40-1.26 (m, 2H).

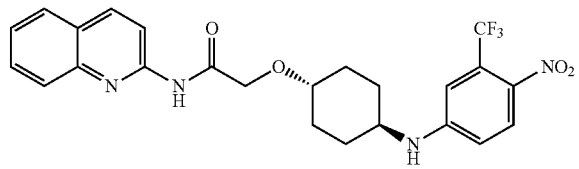 [SMILES: O=C(CO[C@H]1CC[C@H](Nc2ccc([N+](=O)[O-])c(C(F)(F)F)c2)CC1)Nc1ccc2ccccc2n1]

Compound 208: N-(quinolin-2-yl)-2-[[4-[[4-nitro-3-(trifluoromethyl)phenyl]amino]cyclohexyl]oxy]acetamide (ES, m/z): [M+H]⁺ 489.05; ¹H NMR (300 MHz, DMSO-d6): δ 10.15 (s, 1H), 8.39 (d, J=9.0 Hz, 1H), 8.31 (d, J=8.7 Hz, 1H), 8.06 (d, J=9.3 Hz, 1H), 7.93 (d, J=5.2 Hz, 1H), 7.83 (d, J=8.4 Hz, 1H), 7.72 (t, J=7.5 Hz, 1H), 7.53-7.46 (m, 2H), 7.08 (s, 1H), 6.87 (dd, J=2.1, 9.6 Hz, 1H), 4.23 (s, 2H), 3.57-3.47 (m, 2H), 2.16-1.97 (m, 4H), 1.52-1.41 (m, 2H), 1.33-1.25 (m, 2H).

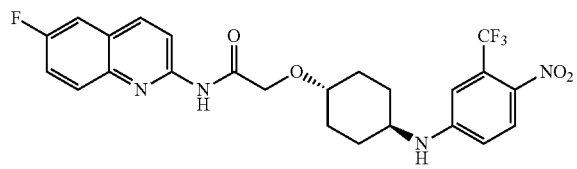 [SMILES: O=C(CO[C@H]1CC[C@H](Nc2ccc([N+](=O)[O-])c(C(F)(F)F)c2)CC1)Nc1ccc2cc(F)ccc2n1]

Compound 209: N-(6-fluoroquinolin-2-yl)-2-[[4-[[4-nitro-3-(trifluoromethyl) phenyl]amino]cyclohexyl]oxy]acetamide (ES, m/z): [M+H]⁺ 507.05; ¹H NMR (400 MHz, DMSO-d6): δ 10.21 (s, 1H), 8.40 (d, J=8.8 Hz, 1H), 8.32 (d, J=8.8 Hz, 1H) 8.07 (d, J=9.2 Hz, 1H), 7.88 (dd, J=5.2, 9.2 Hz, 1H), 7.77 (dd, J=2.0, 9.2 Hz, 1H), 7.65 (td, J=2.4, 8.8 Hz, 1H), 7.48 (d, J=7.6 Hz, 1H), 7.08 (s, 1H), 6.87 (d, J=5.2 Hz, 1H), 4.23 (s, 2H), 3.55-3.45 (m, 2H), 2.10-1.98 (m, 4H), 1.50-1.42 (m, 2H), 1.32-1.23 (m, 2H).

EXAMPLE 31: Preparation of Compound 210

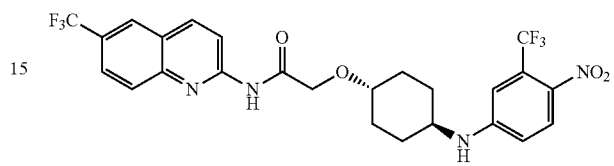

Steps 1-5

The formation of 2-chloro-6-(trifluoromethyl)quinoline is described in the synthesis of compound 89.

Step 6. Formation of 6-(trifluoromethyl)quinolin-2-amine

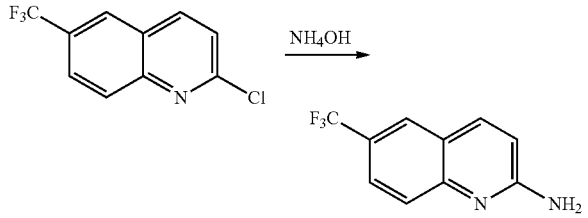

A solution of 2-chloro-6-(trifluoromethyl)quinoline (1 g, 4.3 mmol) in ammonium hydroxide (50 ml) was stirred overnight at 130° C. The resulting mixture was then concentrated under vacuum to give a residue, which was purified by silica gel column chromatography using 1%~2% methanol in dichloromethane to afford 6-(trifluoromethyl)quinolin-2-amine as an off-white solid (350 mg, 38%). (ES, m/z): [M+H]⁺ 212; ¹H NMR (300 MHz, CDCl₃): δ 7.97-7.86 (m, 2H), 7.71 (s, 2H), 6.85 (d, J=9.0 Hz, 1H), 5.26 (s, 2H).

Step 7. Formation of 2-[[4-[[4-nitro-3-(trifluoromethyl)phenyl]amino]cyclohexyl]oxy]-N-[6-(trifluoromethyl)quino-lin-2-yl]acetamide (#210)

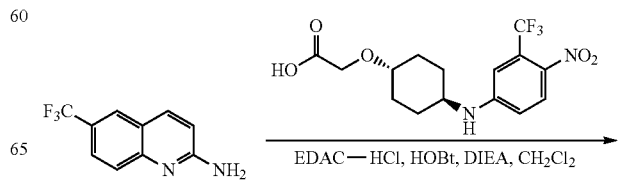

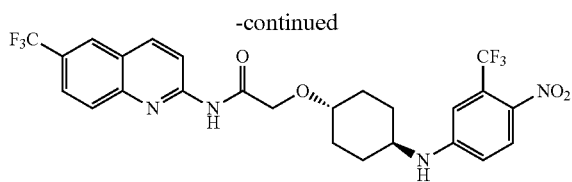

To a solution of 2-[[4-[[4-nitro-3-(trifluoromethyl)phenyl]amino]cyclohexyl]oxy]acetic acid (100 mg, 0.28 mmol) in dichloromethane (30 ml) was added EDAC.HCl (81 mg, 0.42 mmol), HOBt (57 mg, 0.42 mmol) and triethylamine (85 mg, 0.84 mmol). After 15 minutes 6-(trifluoromethyl)quinolin-2-amine (68 mg, 0.32 mmol) was added and the resulting solution was stirred overnight at room temperature. The contents were then quenched with water (100 ml) and extracted with dichloromethane (3×50 ml). The organic layers were combined and dried over anhydrous magnesium sulfate. The solids were filtered off and the filtrate was concentrated under vacuum to give a residue, which was purified by silica gel column chromatography using 3% methanol in dichloromethane to afford 2-[[4-[[4-nitro-3-(trifluoromethyl)phenyl]amino]cyclohexyl-oxy]-N-[6-(trifluoromethyl)quinolin-2-yl]acetamide as a yellow solid (80.6 mg, 52%). (ES, m/z): [M+H]$^+$ 557.20; $^1$H NMR (300 MHz, CD$_3$OD): δ 8.51-8.47 (m, 2H), 8.29 (s, 1H), 8.05-7.99 (m, 2H), 7.93 (dd, J=1.8, 9.0 Hz, 1H), 7.01 (d, J=2.4 Hz, 1H), 6.83 (dd, J=2.4, 9.0 Hz, 1H), 4.27 (s, 2H), 3.63-3.45 (m, 2H), 2.27-2.14 (m, 4H), 1.70-1.56 (m, 2H), 1.46-1.34 (m, 2H).

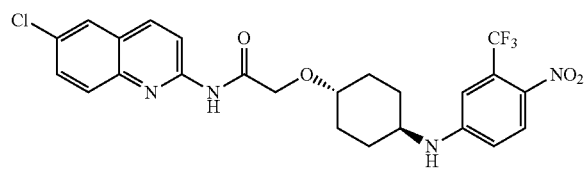 [SMILES: O=C(CO[C@H]1CC[C@H](Nc2ccc([N+](=O)[O-])c(C(F)(F)F)c2)CC1)Nc1ccc2cc(Cl)ccc2n1]

Compound 211: N-(6-chloroquinolin-2-yl)-2-[[4-[[4-nitro-3-(trifluoromethyl) phenyl]amino]cyclohexyl]oxy]acetamide (ES, m/z): [M+H]$^+$ 523.10; $^1$H NMR (300 MHz, DMSO-d6): δ0.24 (s, 1H), 8.39 (m, 2H), 8.07 (overlapping d, 2H), 7.83 (d, J=9.0 Hz, 1H), 7.72 (dd, J=2.1, 9.0 Hz, 1H), 7.47 (d, J=8.1 Hz, 1H), 7.08 (s, 1H), 6.88 (d, J=2.4, 9.3 Hz, 1H), 4.23 (s, 2H), 3.3.49 (br m, 2H), 2.0 (br m, 4H), 1.51-1.40 (m, 2H), 1.33-1.21 (m, 2H).

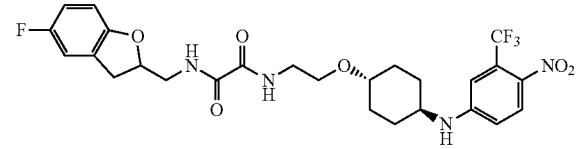 [SMILES: O=C(NCCO[C@H]1CC[C@H](Nc2ccc([N+](=O)[O-])c(C(F)(F)F)c2)CC1)C(=O)NCC1Cc2cc(F)ccc2O1]

N$^1$-(2,3-dihydro-1-benzofuran-2-ylmethyl)-N$^2$-[2-[(4-[[4-nitro-3-(trifluoromethyl)phenyl]amino]cyclohexyl)oxy]ethyl]ethanediamide (#216)

(ES, m/z): [M+H]$^+$ m/z 551.20; $^1$H NMR (300 MHz, CDCl$_3$): δ 8.02 (d, J=9.0 Hz, 1H), 7.82 (br s, 1H), 7.73 (br s, 1H), 7.14 (m, 2H), 6.88-6.80 (m, 3H), 6.63 (d, J=8.7 Hz, 1H), 4.92-4.85 (m, 1H), 3.83-3.72 (m, 1H), 3.60-3.57 (m, 2H), 3.53-3.50 (m, 3H), 3.46-3.31 (m, 3H), 2.91 (dd, J=7.2, 16.2 Hz, 1H), 2.16-2.07 (m, 4H), 1.49-1.41 (m, 2H), 1.29-1.25 (m, 2H).

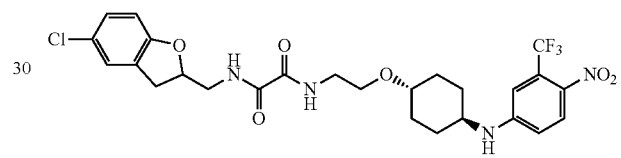

Compound 217: 1-[4-[(5-fluoro-2,3-dihydro-1-benzofuran-2-yl)methyl]piperazin-1-yl]-3-[(4-[[4-nitro-3-(trifluoromethyl) phenyl]amino]cyclohexyl)oxy]propan-2-one (ES, m/z): [M+H]$^+$ 569.35; $^1$H NMR (300 MHz, CDCl$_3$): δ 8.02 (d, J=9.0 Hz, 1H), 7.79 (br s, 1H), 7.78 (br s, 1H), 6.87-6.78 (m, 3H), 6.71-6.62 (m, 2H), 4.92 (m, 1H), 3.74 (m, 1H), 3.58-3.29 (overlapping m, 8H), 2.91 (dd, J=7.2, 15.3 Hz, 1H), 2.11 (m, 4H), 1.46-1.42 (m, 2H), 1.29-1.25 (m, 2H).

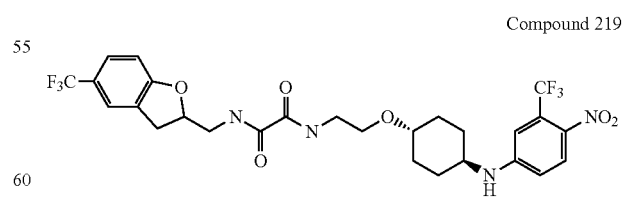

Compound 218: N$^1$-[(5-chloro-2,3-dihydro-1-benzofuran-2-yl)methyl]-N$^2$-[2-[(4-[[4-nitro-3-(trifluoromethyl)phenyl]amino]cyclohexyl)oxy]ethyl]ethanediamide (ES, m/z): [M+H]$^+$ 585.30; $^1$H NMR (300 MHz, CDCl$_3$): δ 8.02 (d, J=9.0 Hz, 1H), 7.79 (m, 1H), 7.71 (m, 1H), 7.11 (s, 1H), 7.07 (dd, J=8.4, 2.1 Hz, 1H), 6.84 (s, 1H), 6.69 (d, J=8.4 Hz, 1H), 6.64 (dd, J=2.4, 8.7 Hz, 1H), 4.91 (m, 1H), 3.72 (m, 1H), 3.58 (m, 2H), 3.52 (m, 3H), 3.35 (br m, 3H), 2.91 (dd, J=7.2, 15.3 Hz, 1H), 2.13 (m, 4H), 1.49-1.41 (m, 2H), 1.29-1.25 (m, 2H).

EXAMPLE 32: Preparation of Compound 219

Compound 219

The formation of N$^1$-[2-[(4-[[4-nitro-3-(trifluoromethyl) phenyl]amino]cyclohexyl)oxy]ethyl]-N$^2$-[[5-(trifluoromethyl)-2,3-dihydro-1-benzofuran-2-yl]methyl]ethanediamide (#219) was conducted in a manner analogous to what was described for the synthesis of compound 216.

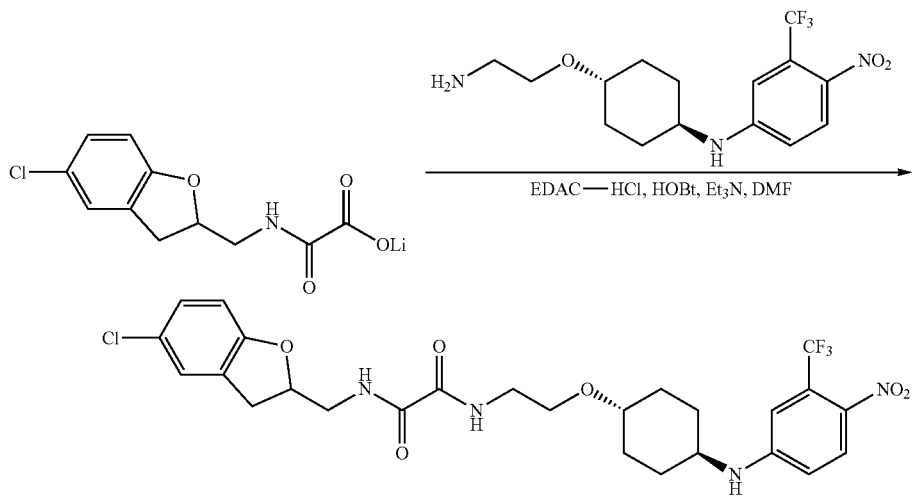

The mixture of lithio ([[5-(trifluoromethyl)-2,3-dihydro-1-benzofuran-2-yl]methyl]carbamoyl)formate (170 mg, 0.58 mmol), EDAC.HCl (166 mg, 0.87 mmol), HOBt (58.3 mg, 0.43 mmol) and triethylamine (87.3 mg, 0.86 mmol) in N,N-dimethylformamide (10 ml) was stirred for 1 hour before the addition of N-[4-(2-aminoethoxy)cyclohexyl]-4-nitro-3-(trifluoromethyl)aniline (100 mg, 0.29 mmol). The resulting solution was stirred overnight at room temperature, diluted with water (100 ml), and extracted with dichloromethane (3×50 ml). The organic fractions were combined, dried over anhydrous sodium sulfate, filtered, and concentrated under vacuum. The residue was purified by HPLC to afford $N^1$-[2-[(4-[[4-nitro-3-(trifluoromethyl)phenyl]amino]cyclohexyl)oxy]ethyl]-$N^2$-[[5-(trifluoromethyl)-2,3-dihydro-1-benzofuran-2-yl]methyl]ethanediamide as a yellow solid (52 mg, 29%). (ES, m/z): [M+H]$^+$ 619.10; $^1$H NMR (300 MHz, CDCl$_3$): δ 8.02 (d, J=9.3 Hz, 1H), 7.80 (br s, 1H), 7.72 (br s, 1H), 7.41 (m, 2H), 6.84 (m, 2H), 6.63 (dd, J=9.0, 2.4 Hz, 1H), 5.00 (m, 1H), 3.78 (m, 1H), 3.60-3.55 (m, 3H), 3.53-3.50 (m, 2H), 3.35 (br m, 3H), 2.98 (dd, J=16.2, 7.2 Hz, 1H), 2.12 (m, 4H), 1.46-1.34 (m, 2H), 1.29-1.22 (m, 2H).

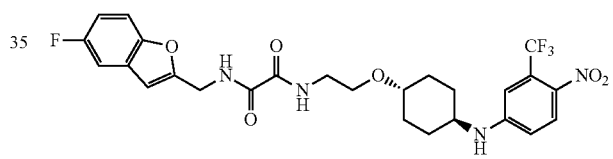

Compound 220: $N^1$-(benzofuran-2-ylmethyl)-$N^2$-(2-(4-(4-nitro-3-(trifluoromethyl) phenylamino)cyclohexyloxy)ethyl)oxalamide (ES, m/z): [M+H]$^+$ 549.35; $^1$H NMR (300 MHz, CDCl$_3$): δ 8.02 (d, J=9.0 Hz, 1H), 7.85 (br s, 1H), 7.75 (br s, 1H), 07.52 (d, J=6.6 Hz, 1H), 7.45 (d, J=8.4 Hz, 1H), 7.28-7.20 (m, 3H), 6.84 (s, 1H), 6.66 (s, 1H), 6.62 (d, J=2.4 Hz, 1H), 4.65 (d, J=6.0 Hz, 2H), 3.59 (m, 2H), 3.51 (m, 2H), 3.36 (br m, 2H), 2.11 (m, 4H), 1.49-1.38 (m, 2H), 1.33-1.25 (m, 2H).

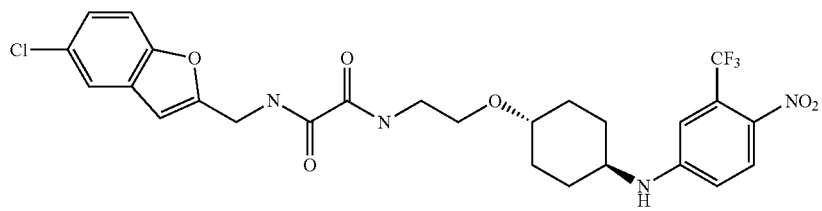

Compound 221: $N^1$-((5-fluorobenzofuran-2-yl)methyl)-$N^2$-(2-(4-(4-nitro-3-(trifluoromethyl)phenylamino)cyclohexyloxy)ethyl)oxalamide (ES, m/z): [M+H]$^+$ 567.00; $^1$H NMR (400 MHz, CDCl$_3$): δ 8.01 (d, J=8.4 Hz, 1H), 7.89 (br s, 1H), 7.74 (br s, 1H), 7.36 (dd, J=8.8, 4.0 Hz, 1H), 7.17 (dd, J=8.4, 2.4 Hz, 1H), 6.98 (td, J=9.2, 2.8 Hz, 1H), 6.84 (d, J=2.0 Hz, 1H), 6.65 (overlapping signals, 2H), 4.64 (d, J=6.4 Hz, 2H), 3.60-3.49 (m, 4H), 3.42-3.30 (m, 2H), 2.15-2.06 (m, 4H), 1.45-1.39 (m, 2H), 1.32-1.23 (m, 2H).

EXAMPLE 33: Preparation of Compound 222

Compound 222

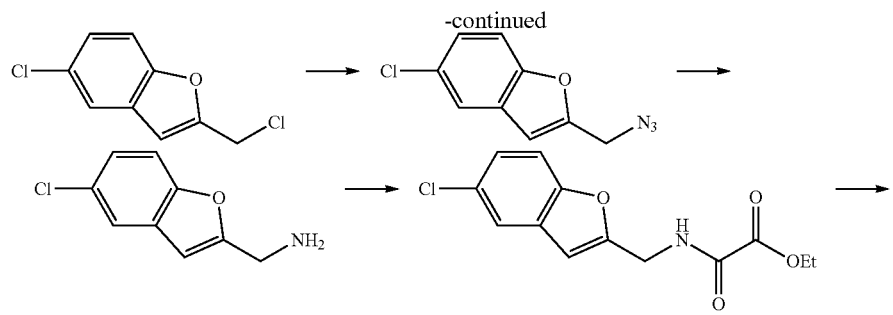

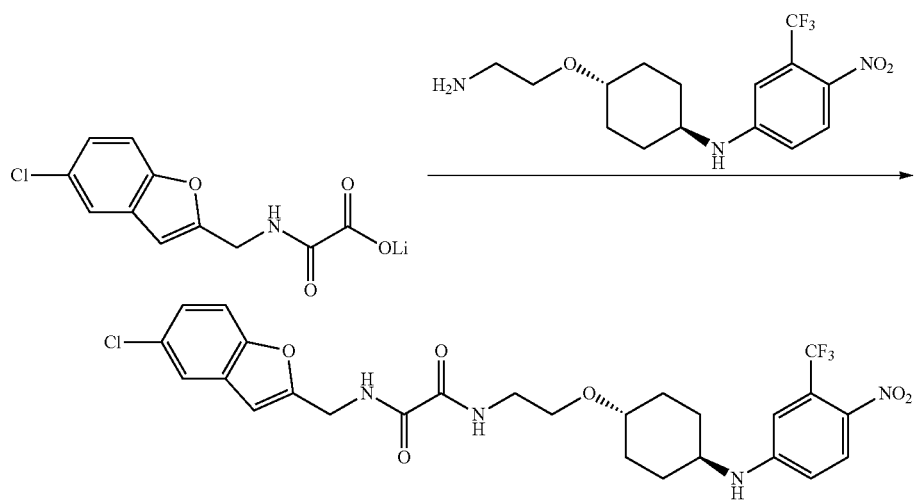

Steps 1-3

The formation of 5-chloro-2-(chloromethyl)-1-benzofuran is described in the synthesis of compound 184.

Step 4. Formation of 2-(azidomethyl)-5-chloro-1-benzofuran

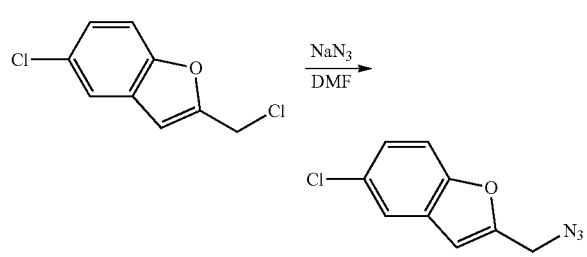

To a solution of 5-chloro-2-(chloromethyl)-1-benzofuran (500 mg, 2.49 mmol) in N,N-di methylformamide (10 ml) was added NaN$_3$ (320 mg, 4.92 mmol) and the contents were stirred overnight at 70° C. The resulting solution was diluted with saturated aqueous sodium bicarbonate (150 ml) and extracted with dichloromethane (3×70 ml). The organic layers were combined, dried over anhydrous sodium sulfate, filtered, and concentrated under vacuum. The residue was purified by silica gel column chromatography eluting with petroleum ether to afford 2-(azidomethyl)-5-chloro-1-benzofuran as light brown oil (500 mg, 97%). $^1$H NMR (300 MHz, CDCl$_3$): δ 7.54 (s, 1H), 7.40 (d, J=9.0 Hz, 1H), 7.25 (d, J=9.0 Hz, 1H), 6.66 (s, 1H), 4.50 (s, 2H).

Step 5. Formation of (5-chloro-1-benzofuran-2-yl)methanamine

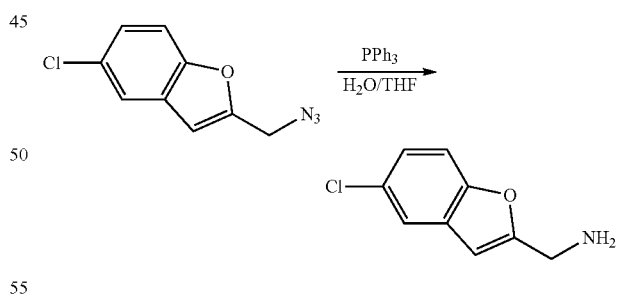

To a solution of 2-(azidomethyl)-5-chloro-1-benzofuran (500 mg, 2.44 mmol) in tetrahydrofuran (10 ml) and water (1 ml) was added PPh$_3$ (759 mg, 2.89 mmol) and the contents were stirred for 3 hours at 60° C. The resulting mixture was concentrated under vacuum to give a residue, which was purified by silica gel column chromatography eluting with methanol in dichloromethane to afford (5-chloro-1-benzofuran-2-yl)methanamine as a colorless liquid (420 mg, crude). (ES, m/z): [M+H]$^+$ 182.0; $^1$H NMR (400 MHz, CDCl$_3$): δ 7.55-7.58 (m, 1H), 7.50-7.47 (m, 1H), 7.21 (d, J=8.8 Hz, 1H), 6.50 (s, 1H), 3.99 (s, 2H).

Step 6. Formation of ethyl [[(5-chloro-1-benzofuran-2-yl)methyl]carbamoyl]formate

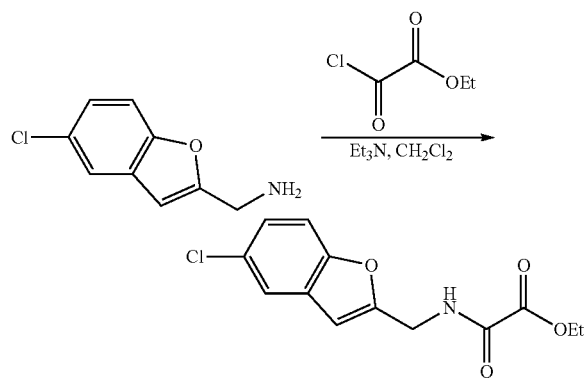

To a solution of (5-chloro-1-benzofuran-2-yl)methanamine (420 mg, crude) in dichloromethane (50 ml) was added triethylamine (315 mg, 3.12 mmol). Then ethyl 2-chloro-2-oxoacetate (378 mg, 2.77 mmol) was added dropwise and the contents were stirred for 30 minutes at 0° C. The resulting solution was quenched with water (100 ml) and extracted with dichloromethane (3×70 ml). The organic fractions were combined, dried over anhydrous sodium sulfate, filtered, and concentrated under vacuum. The residue was purified by silica gel column chromatography eluting with 20% ethyl acetate in petroleum ether to afford ethyl [[(5-chloro-1-benzofuran-2-yl)methyl]carbamoyl]formate as an off-white solid (600 mg).

(ES, m/z): [M+H]$^+$ 282.0; $^1$H NMR (400 MHz, CDCl$_3$): δ 7.52 (s, 2H), 7.38 (d, J=8.4 Hz, 1H), 7.26 (d, J=8.8 Hz, 1H), 6.64 (s, 1H), 4.68 (d, J=4.2 Hz, 2H), 4.39 (q, J=7.2 Hz, 2H), 1.37 (t, J=7.2 Hz, 3H).

Step 7. Formation of lithio [[(5-chloro-1-benzofuran-2-yl)methyl]carbamoyl]formate

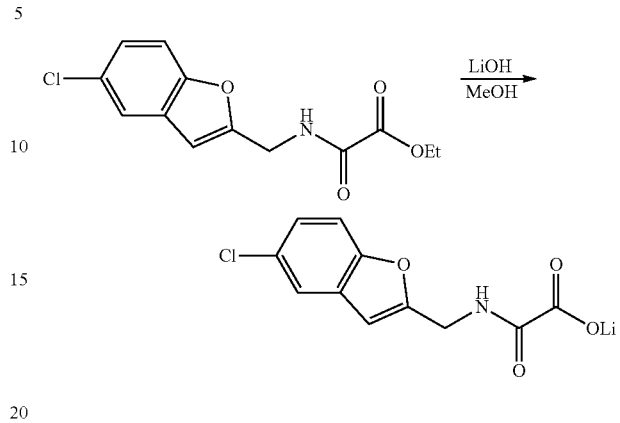

To a solution of ethyl [[(5-chloro-1-benzofuran-2-yl)methyl]carbamoyl]formate (200 mg, 0.71 mmol) in methanol (5 ml) and water (0.1 ml) was added lithium hydroxide monohydrate (20 mg, 0.84 mmol) and the contents were stirred for 30 minutes at room temperature. The resulting mixture was concentrated under vacuum to afford lithio [[(5-chloro-1-benzofuran-2-yl)methyl]carbamoyl]formate as a white solid (160 mg, crude). $^1$H NMR (300 MHz, DMSO-d6): δ 8.88 (s, 1H), 7.62 (s, 1H), 7.53 (d, J=8.7 Hz, 1H), 7.26 (d, J=8.7 Hz, 1H), 6.66 (s, 1H), 4.37 (s, 2H).

Step 8. Formation of N$^1$-[(5-chloro-1-benzofuran-2-yl)methyl]-N$^2$-2-[(4-[[4-nitro-3-(trifluoromethyl)phenyl]amino]cyclohexyl)oxy]ethyl]ethanediamide (#222)

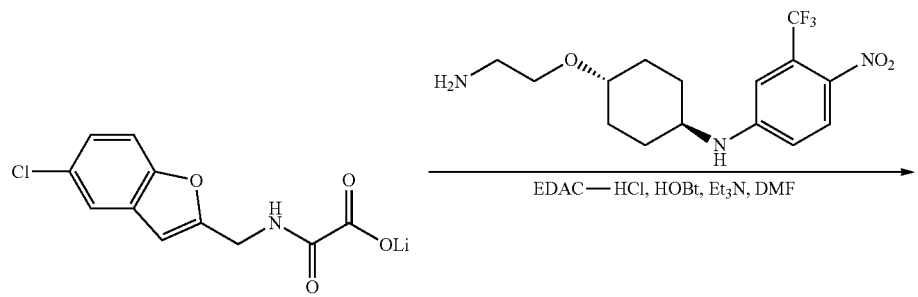

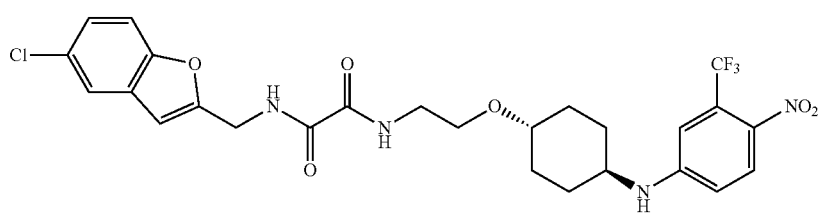

To a solution of lithio [[(5-chloro-1-benzofuran-2-yl)methyl]carbamoyl]formate (148 mg, 0.57 mmol) in N,N-dimethylformamide (10 ml) was added EDAC.HCl (166 mg, 0.87 mmol), HOBt (58.3 mg, 0.43 mmol), and triethylamine (87.3 mg, 0.86 mmol). The solution was stirred for 1 hour at room temperature before the addition of N-[4-(2-aminoethoxy) cyclohexyl]-4-nitro-3-(trifluoromethyl)aniline (100 mg, 0.29 mmol). The contents were then stirred overnight at room temperature. The resulting solution was quenched with water (100 ml) and extracted with dichloromethane (3×60 ml). The organic layers were combined, dried over anhydrous sodium sulfate, filtered, and concentrated under vacuum to give a residue, which was purified by HPLC to afford N$^1$-[(5-chloro-1-benzofuran-2-yl)methyl]-N$^2$-2-[(4-[[4-nitro-3-(trifluoromethyl)phenyl]amino]cyclohexyl)oxy]ethyl]ethanediamide as a yellow solid (41 mg, 24%). (ES, m/z): [M+H]$^+$ 583.20; $^1$H NMR (400 MHz, CDCl$_3$): δ 8.02 (d, J=7.6 Hz, 1H), 7.85 (br s, 1H), 7.73 (br s, 1H), 7.49 (s, 1H), 7.36 (d, J=8.8 Hz, 1H), 7.23 (m, 1H), 6.84 (s, 1H), 6.63 (d, J=8.4 Hz, 1H), 6.60 (s, 1H), 4.64 (d, J=6.0 Hz, 2H), 3.58 (m, 2H), 3.52 (m, 2H), 3.41-3.30 (m, 2H), 2.10 (m, 4H), 1.48-1.42 (m, 2H), 1.29-1.23 (m, 2H).

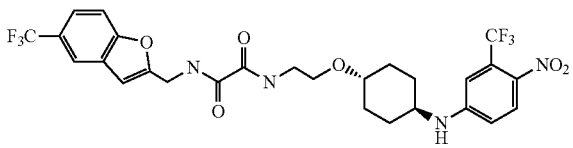 [SMILES: O=C(NCCO[C@H]1CC[C@H](Nc2ccc([N+](=O)[O-])c(C(F)(F)F)c2)CC1)C(=O)NCc1cc2cc(C(F)(F)F)ccc2o1]

N$^1$-(2-(4-(4-nitro-3-(trifluoromethyl)phenylamino) cyclohexyloxy) ethyl)-N$^2$-((5-(trifluoromethyl) benzofuran-2-yl)methyl)oxalamide (#223)

(ES, m/z): [M+H]$^+$ 617.25; $^1$H NMR (400 MHz, CDCl$_3$): δ 8.02 (d, J=9.2 Hz, 1H), 7.91 (br s, 1H), 7.83 (s, 1H), 7.76 (br s, 1H), □7.54 (s, 2H), 6.84 (s, 1H), 6.73 (s, 1H), 6.64-6.62 (dd, J=1.6, 8.8 Hz, 1H), 4.68 (d, J=6.0 Hz, 2H), 3.61-3.52 (m, 4H), 3.40-3.33 (m, 2H), 2.16-2.08 (m, 4H), 1.46-1.43 (m, 2H), 1.29-1.26 (m, 2H).

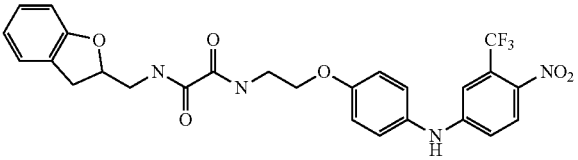 [SMILES: O=C(NCCOc1ccc(Nc2ccc([N+](=O)[O-])c(C(F)(F)F)c2)cc1)C(=O)NCC1Cc2ccccc2O1]

N$^1$-((2,3-dihydrobenzofuran-2-yl)methyl)-N$^2$-(2-(4-(4-nitro-3-(trifluoromethyl)phenylamino)phenoxy) ethyl)oxalamide (#224).

(ES, m/z): [M+H]$^+$ 545.25; $^1$H NMR (300 MHz, CDCl$_3$): δ 7.98 (d, J=9.0 Hz, 1H), 7.82 (d, J=5.4 Hz, 2H), 7.17-7.10 (m, 5H), 6.97-6.78 (m, 5H), 6.19 (br s, 1H), 4.95-4.86 (m, 1H), 4.10 (t, J=5.1 Hz, 2H), 3.81-3.73 (m, 3H), 3.54-3.49 (m, 1H), 3.36-3.28 (m, 1H), 2.96-2.89 (m, 1H).

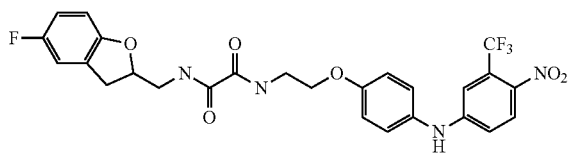 [SMILES: O=C(NCCOc1ccc(Nc2ccc([N+](=O)[O-])c(C(F)(F)F)c2)cc1)C(=O)NCC1Cc2cc(F)ccc2O1]

Compound 225: N$^1$-((5-fluoro-2,3-dihydrobenzofuran-2-yl)methyl)-N$^2$-(2-(4-(4-nitro-3-(trifluoromethyl)phenylamino)phenoxy)ethyl)oxalamide (ES, m/z): [M+H]$^+$ 563.25; $^1$H NMR (300 MHz, CDCl$_3$): δ 8.00 (d, J=9.3 Hz, 1H), 7.96-7.80 (m, 2H), □7.14 (d, J=9.0 Hz, 2H), 7.10 (s, 1H), 6.96-6.77 (m, 5H), 6.69 (dd, J=8.7, 4.2 Hz, 1H), 6.19 (br s, 1H), 4.94-4.88 (m, 1H), 4.11 (t, J=5.1 Hz, 2H), 3.76 (t, J=5.4 Hz, 2H), 3.72-3.69 (m, 1H), 3.55-3.48 (m, 1H), 3.29-3.26 (m, 1H), 2.90 (dd, J=16.2, 7.2 Hz, 1H).

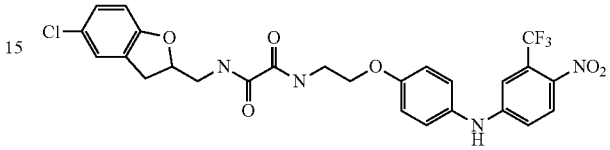

Compound 226: N$^1$-((5-chloro-2,3-dihydrobenzofuran-2-yl)methyl)-N$^2$-(2-(4-(4-nitro-3-(trifluoromethyl)phenylamino)phenoxy)ethyl)oxalamide (ES, m/z): [M+H]$^+$ 579.20; $^1$H NMR (400 MHz, CDCl$_3$): δ 7.97 (d, J=8.8 Hz, 1H), 7.80 (d, J=8.8 Hz, 2H), □7.16-7.07 (m, 5H), 6.95 (d, J=8.4 Hz, 2H), 6.89 (d, J=8.4 Hz, 1H), 6.70 (d, J=8.4 Hz, 1H), 6.18 (br s, 1H), 4.94-4.92 (m, 1H), 4.11 (d, J=4.4 Hz, 2H), 3.78-3.71 (m, 3H), 3.54-3.47 (m, 1H), 3.33-3.27 (m, 1H), 2.94-2.88 (m, 1H).

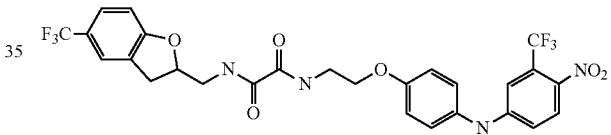

Compound 227: N$^1$-(2-(4-(4-nitro-3-(trifluoromethyl)phenylamino)phenoxy)ethyl)-N$^2$-((5-(trifluoromethyl)-2,3-dihydro benzofuran-2-yl)methyl)ethanediamide (ES, m/z): [M+H]$^+$ 613.25; $^1$H NMR (300 MHz, CDCl$_3$): δ 8.01 (d, J=9.0 Hz, 1H), 7.93 (br s, 2H), 7.51 (s, 2H), 7.20-7.13 (m, 3H), 6.99-6.82 (m, 4H), 6.22 (s, 1H), 5.04-5.02 (m, 1H), 4.15-4.12 (m, 2H), 3.93-3.77 (m, 3H), 3.60-3.52 (m, 1H), 3.44-3.36 (m, 1H), 3.08-2.96 (m, 1H).

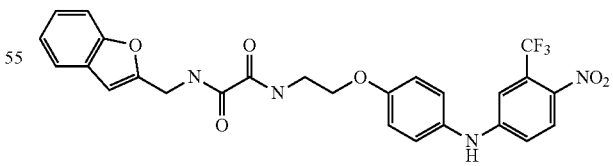

Compound 228: N$^1$-(benzofuran-2-ylmethyl)-N$^2$-(2-(4-(4-nitro-3-(trifluoromethyl) phenylamino)phenoxy)ethyl)oxalamide (ES, m/z): [M+H]$^+$ 543.50; $^1$H NMR (300 MHz, CDCl$_3$): δ 7.96 (d, J=9.0 Hz, 1H), 7.86 (br s, 2H), □7.52 (d, J=7.2 Hz, 1H), 7.45 (d, J=7.8 Hz, 1H), 7.31-7.09 (m, 5H), 6.96-6.88 (m, 3H), 6.66 (s, 1H), 6.20 (br s, 1H), 4.66 (d, J=6.0 Hz, 2H), 4.10 (t, J=5.1 Hz, 2H), 3.78 (t, J=5.4 Hz, 2H).

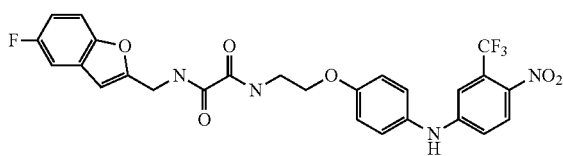 [SMILES: O=C(NCCOc1ccc(Nc2ccc([N+](=O)[O-])c(C(F)(F)F)c2)cc1)C(=O)NCc1cc2cc(F)ccc2o1]

Compound 229: $N^1$-((5-fluorobenzofuran-2-yl)methyl)-$N^2$-(2-(4-(4-nitro-3-(trifluoromethyl)phenylamino)phenoxy)ethyl)oxalamide (ES, m/z): [M−H]⁻ 559.25; ¹H NMR (400 MHz, CDCl₃): δ 7.97 (d, J=9.2 Hz, 1H), 7.88 (s, 2H), 7.38 (d, J=4.0 Hz, 1H), 7.19-7.09 (m, 4H), 7.02-6.87 (m, 4H), 6.63 (s, 1H), 4.64 (d, J=6.4 Hz, 2H), 4.10 (t, J=5.2 Hz, 2H), 3.77 (m, 2H).

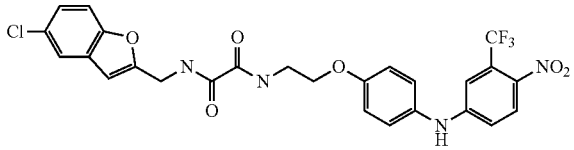 [SMILES: O=C(NCCOc1ccc(Nc2ccc([N+](=O)[O-])c(C(F)(F)F)c2)cc1)C(=O)NCc1cc2cc(Cl)ccc2o1]

Compound 230: $N^1$-((5-chlorobenzofuran-2-yl)methyl)-$N^2$-(2-(4-(4-nitro-3-(trifluoromethyl)phenylamino)phenoxy)ethyl)oxalamide (ES, m/z): [M−H]⁻ 575.29; ¹H NMR (400 MHz, CDCl₃): δ 8.02 (d, J=8.4 Hz, 1H), 7.99 (s, 2H), □7.52 (s, 1H), 7.36 (d, J=8.8 Hz, 1H), 7.26-7.22 (m, 1H), 7.16-7.10 (m, 3H), 6.96-6.88 (m, 3H), 6.61 (s, 1H), 6.17 (br s, 1H), 4.64 (d, J=5.6 Hz, 2H), 4.10 (t, J=4.8 Hz, 2H), 3.77 (m, 2H).

EXAMPLE 34: Preparation of Compound 231

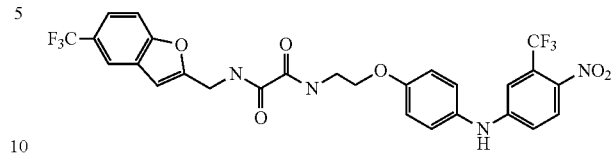

Steps 1-7

The formation of [4-(2-amino-ethoxy)-phenyl]-(4-nitro-3-trifluoromethyl-phenyl)-amine was performed in a manner analogous to what is described in the synthesis of compound 224 and the formation of lithium 2-((5-trifluoromethylbenzofuran-2-yl)methylamino)-2-oxoacetate was performed in a manner analogous to what is described in the synthesis of compound 223.

Step 8. Formation of $N^1$-[2-(4-[[4-nitro-3-(trifluoromethyl)phenyl]amino]phenoxy)ethyl]-$N^2$-[5-(trifluoromethyl)-1-benzofuran-2-yl]methyl]ethanediamide (#231)

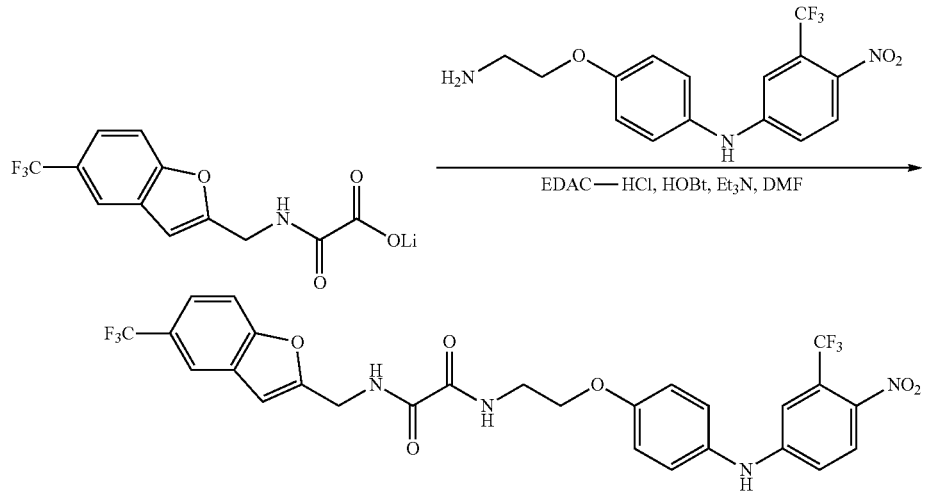

The mixture of lithio ([[5-(trifluoromethyl)-1-benzofuran-2-yl]methyl]carbamoyl)formate (130 mg, crude), EDAC.HCl (166 mg, 0.87 mmol), HOBt (58.3 mg, 0.43 mmol), and triethylamine (87.3 mg, 0.86 mmol) in N,N-dimethylformamide (10 ml) was stirred for 1 hour at room temperature before the addition of N-[4-(2-aminoethoxy)phenyl]-4-nitro-3-(trifluoromethyl)aniline (100 mg, 0.29 mmol). The resulting solution was stirred overnight at room temperature and then quenched by the addition of water (100 ml) and extracted with dichloromethane (3×20 ml). The organic layers were combined, dried over sodium sulfate, filtered, and concentrated under vacuum to give a residue, which was purified by Prep-HPLC to afford $N^1$-[2-(4-[[4-nitro-3-(trifluoromethyl)phenyl]amino]phenoxy)ethyl]-$N^2$-

[5-(trifluoromethyl)-1-benzofuran-2-yl]methyl]ethanediamide as a yellow solid (9.3 mg, 5%).

(ES, m/z): [M−H]⁻ 609.25; ¹H NMR (300 MHz, CDCl₃): δ 8.01 (d, J=9.0 Hz, 1H), 7.90 (br s, 2H), 7.87 (s, 1H), 7.57 (s, 2H), 7.19-7.12 (m, 3H), 7.00-6.90 (m, 3H), 6.76 (s, 1H), 6.20 (s, 1H), 4.71 (d, J=6.0 Hz, 2H), 4.14 (t, J=5.1 Hz, 2H), 3.81 (m, 2H).

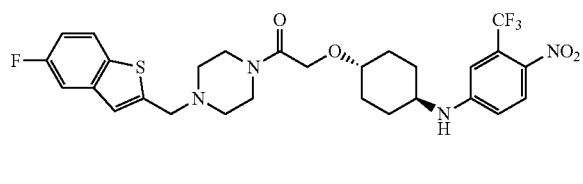 [SMILES: O=C(CO[C@H]1CC[C@H](Nc2ccc([N+](=O)[O-])c(C(F)(F)F)c2)CC1)N1CCN(Cc2cc3cc(F)ccc3s2)CC1]

Compound 234: 1-[4-[(5-fluoro-1-benzothiophen-2-yl)methyl]piperazin-1-yl]-2-[[4-[[4-nitro-3-(trifluoromethyl)phenyl]amino]cyclohexyl]oxy]ethan-1-one (ES, m/z): [M+H]⁺ 595.00; ¹H NMR (400 MHz, CDCl₃): δ 8.01 (d, J=9.2 Hz, 1H), 7.70 (br s, 1H), 7.36 (s, 1H), 7.18-7.02 (m, 2H), 6.84 (d, J=2.0 Hz, 1H), 6.62 (dd, J=9.2, 2.4 Hz, 1H), 4.42 (m, 1H), 4.18 (s, 2H), 3.81 (s, 2H), 3.68-3.52 (overlapping m, 4H), 3.40 (m, 2H), 2.55 (m, 3H), 2.2 (m, 4H), 1.54 (m, 2H), 1.26 (m, 2H).

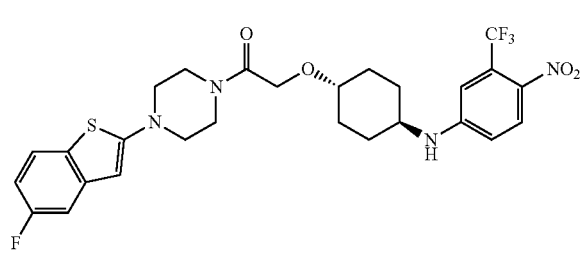 [SMILES: O=C(CO[C@H]1CC[C@H](Nc2ccc([N+](=O)[O-])c(C(F)(F)F)c2)CC1)N1CCN(c2cc3cc(F)ccc3s2)CC1]

Compound 236: 1-(4-(5-fluorobenzo[b]thiophen-2-yl)piperazin-1-yl)-2-((4-((4-nitro-3-(trifluoromethyl)phenyl) amino)cyclohexyl)oxy)ethanone (ES, m/z): [M+H]⁺ 581.00; ¹H NMR (300 MHz, CDCl₃): δ 8.05 (d, J=9.0 Hz, 1H), 7.71 (dd, J=5.1, 8.7 Hz, 1H), 7.45 (d, J=7.8 Hz, 1H), 7.25 (dd, J=2.4, 10.2 Hz, 1H), 7.07 (s, 1H), 6.93-6.83 (m, 2H), 6.35 (s, 1H), 4.21 (s, 2H), 3.62-3.55 (m, 4H), 3.48-3.24 (m, 6H), 2.05-1.94 (m, 4H), 1.43-1.18 (m, 4H).

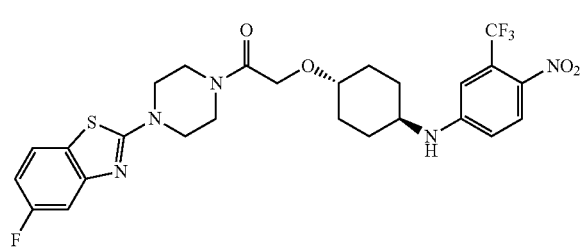 [SMILES: O=C(CO[C@H]1CC[C@H](Nc2ccc([N+](=O)[O-])c(C(F)(F)F)c2)CC1)N1CCN(c2nc3cc(F)ccc3s2)CC1]

1-[4-(5-fluoro-1,3-benzothiazol-2-yl)piperazin-1-yl]-2-[[4-[[4-nitro-3-(trifluoromethyl)pheny-1]amino]cyclohexyl]oxy]ethan-1-one (#237)

(ES, m/z): [M+H]⁺ 582.05; ¹H NMR (400 MHz, CDCl₃): δ 8.01 (d, J=9.2 Hz, 1H), 7.52 (dd, J=8.8, 5.6 Hz, 1H), 7.28-7.25 (m, 1H), 6.89-6.84 (m, 2H), 6.63 (dd, J=9.2, 2.8 Hz, 1H), 4.47 (m, 1H), 4.24 (s, 2H), 3.75 (m, 6H), 3.64 (m, 2H), 3.45 (m, 2H), 2.12 (m, 4H), 1.47 (m, 2H), 1.29 (m, 2H).

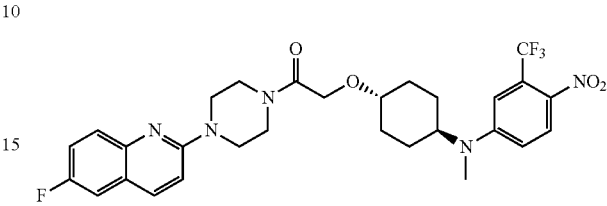

Compound 247: 1-(4-(6-fluoroquinolin-2-yl)piperazin-1-yl)-2-(4-(methyl(4-nitro-3-(trifluoromethyl)phenyl) amino)cyclohexyloxy)ethanone (ES, m/z): [M+H]⁺ 589.95; ¹H NMR (300 MHz, CD₃OD): δ 8.05-8.00 (m, 2H), 7.71-7.68 (m, 1H), 7.37 (d, J=9.0 Hz, 2H), 7.25 (d, J=9.0 Hz, 1H), 7.08-7.01 (m, 2H), 4.34 (s, 2H), 3.88-3.71 (m, 9H), 3.50-3.32 (m, 1H), 2.95 (s, 3H), 2.27-2.23 (m, 2H), 1.85-1.71 (m, 4H), 1.60-1.47 (m, 2H).

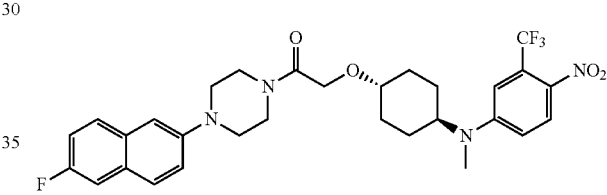

Compound 248: 1-(4-(6-fluoronaphthalen-2-yl)piperazin-1-yl)-2-(4-(methyl(4-nitro-3-(trifluoromethyl)phenyl)amino)cyclohexyloxy)ethanone (ES, m/z): [M+H]⁺ 589.15; ¹H NMR (300 MHz, CDCl₃): δ 8.05 (d, J=9.3 Hz, 1H), 7.75-7.69 (m, 2H), 7.41-7.21 (m, 4H), 6.98 (s, 1H), 6.77 (dd, J=9.3, 3.0 Hz, 1H), 4.28 (s, 2H), 3.90-3.85 (m, 4H), 3.74-3.71 (m, 1H), 3.45-3.40 (m, 1H), 3.32-3.31 (m, 4H), 2.90 (s, 3H), 2.28-2.24 (m, 2H), 1.90-1.84 (m, 2H), 1.70-1.46 (m, 4H).

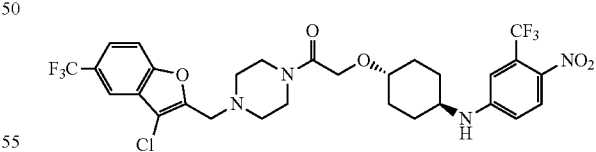

Compound 253: 1-(4-[[3-chloro-5-(trifluoromethyl)-1-benzofuran-2-yl]methyl]piperazin-1-yl)-2-[[4-[[4-nitro-3-(trifluoromethyl)phenyl]amino]cyclohexyl]oxy]ethan-1-one (ES, m/z): [M+H]⁺ 663.30; ¹H NMR (300 MHz, CD₃OD): δ 8.03 (d, J=9.0 Hz, 1H), 7.91 (s, 1H), 7.74 (m, 2H), 6.98 (d, J=2.7 Hz, 1H), 6.77 (dd, J=9.0, 2.7 Hz, 1H), 4.24 (s, 2H), 3.92 (s, 2H), 3.62 (m, 4H), 3.41 (m, 2H), 2.65 (m, 4H), 2.09 (m, 4H), 1.54-1.2 (m, 4H).

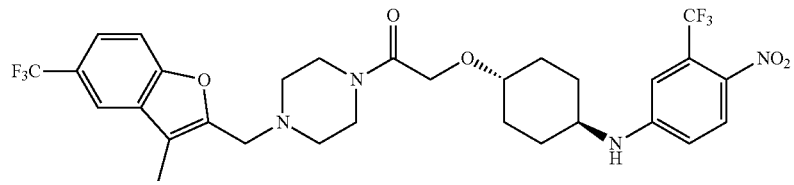 [SMILES: Cc1c(CN2CCN(C(=O)CO[C@H]3CC[C@H](Nc4ccc([N+](=O)[O-])c(C(F)(F)F)c4)CC3)CC2)oc2ccc(C(F)(F)F)cc12]

Compound 254: 2-[[4-[[4-nitro-3-(trifluoromethyl)phenyl]amino]cyclohexyl]oxy]-1-(4-[1-[5-(trifluoromethyl)-1-benzofuran-2-yl]ethyl]piperazin-1-yl)ethan-1-one (ES, m/z): [M+H]$^+$ 643.30; $^1$H NMR (300 MHz, DMSO-d6): δ 8.07-8.02 (overlapping d, 2H), 7.78 (d, J=8.7 Hz, 1H), 7.58 (dd, J=9.0, 1.5 Hz, 1H), 7.41 (d, J=7.8 Hz, 1H), 7.05 (d, J=1.5 Hz, 1H), 6.90 (s, 1H), 6.82 (dd, J=9.3, 2.4 Hz, 1H), 4.08 (m, 3H), 3.42 (m, 5H), 3.27 (m, 1H), 2.50 (s, 2H), 2.40 (m, 2H), 1.90 (m, 4H), 1.45 (d, J=7.2 Hz, 3H), 1.34-1.23 (m, 5H).

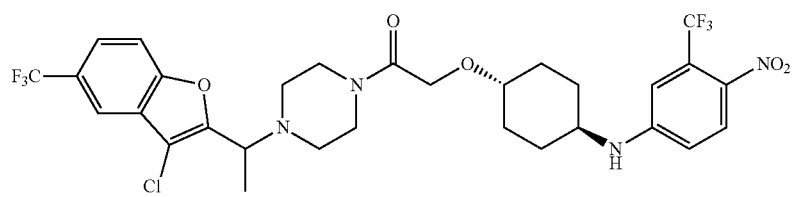 [SMILES: CC(c1oc2ccc(C(F)(F)F)cc2c1Cl)N1CCN(C(=O)CO[C@H]2CC[C@H](Nc3ccc([N+](=O)[O-])c(C(F)(F)F)c3)CC2)CC1]

Compound 255: 2-1-(4-[1-[3-chloro-5-(trifluoromethyl)-1-benzofuran-2-yl]ethyl]piperazin-1-yl)-2-[[4-[[4-nitro-3-(trifluoromethyl)phenyl]amino]cyclohexyl]oxy]ethan-1-one (ES, m/z): [M+H]$^+$ 677.10; $^1$H NMR (300 MHz, CD$_3$OD): δ 7.98 (d, J=9.0 Hz, 1H), 7.93 (s, 1H), 7.75 (m, 2H), 6.92 (d, J=2.4 Hz, 1H), 6.71 (dd, J=9.0, 2.4 Hz, 1H), 4.72 (br s, 1H), 4.17 (s, 2H), 3.69 (br s, 4H), 3.32 (m, 2H), 3.00 (br m, 4H), 1.98 (m, 4H), 1.72 (d, J=6.3 Hz, 3H), 1.30 (br overlapping m, 4H).

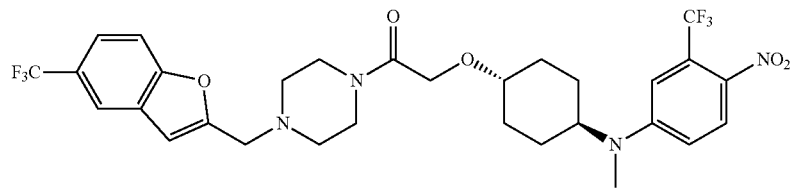 [SMILES: CN(c1ccc([N+](=O)[O-])c(C(F)(F)F)c1)[C@H]1CC[C@H](OCC(=O)N2CCN(Cc3cc4cc(C(F)(F)F)ccc4o3)CC2)CC1]

Compound 256: 2-[[4-[methyl[4-nitro-3-(trifluoromethyl)phenyl]amino]cyclohexyl]oxy]-1-(4-[[5-(trifluorom-ethyl)-1-benzofuran-2-yl]methyl]piperazin-1-yl)ethan-1-one (ES, m/z): [M+H]$^+$ 643.10; $^1$H NMR (300 MHz, CD$_3$OD): δ 7.95 (d, J=9.3 Hz, 1H), 7.81 (s, 1H), 7.52 (d, J=8.7 Hz, 1H), 7.45 (d, J=8.4 Hz, 1H), 6.92 (m, 2H), 6.77 (s, 1H), 4.12 (s, 2H), 3.73 (s, 3H), 3.49 (m, 4H), 3.25 (m, 1H), 2.81 (s, 3H), 2.52 (m, 4H), 2.06 (m, 2H), 1.69-1.43 (m, 4H), 1.41-1.29 (m, 2H).

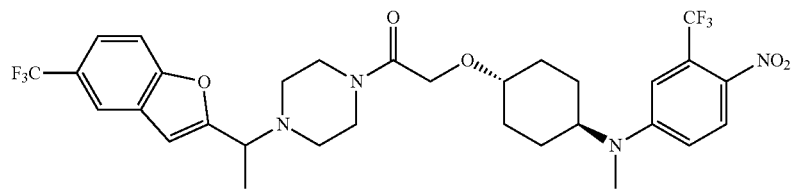 [SMILES: CC(c1cc2cc(C(F)(F)F)ccc2o1)N1CCN(C(=O)CO[C@H]2CC[C@H](N(C)c3ccc([N+](=O)[O-])c(C(F)(F)F)c3)CC2)CC1]

Compound 257: 2-[[4-[methyl[4-nitro-3-(trifluoromethyl)phenyl]amino]cyclohexyl]oxy]-1-(4-[1-[5-(trifluoro-methyl)-1-benzofuran-2-yl]ethyl]piperazin-1-yl)ethan-1-one (ES, m/z): [M+H]$^+$ 657.15; $^1$H NMR (300 MHz, DMSO-d6): δ 8.06 (d, J=9.0 Hz, 1H), 8.02 (s, 1H), 7.78 (d, J=8.7 Hz, 1H), 7.57 (dd, J=8.7, 1.8 Hz, 1H), 7.08 (overlapping s & d, 2H), 6.90 (s, 1H), 4.05 (overlapping s & m, 3H), 3.87 (m, 1H), 3.45 (m, 4H), 3.23 (m, 1H), 2.85 (s, 3H), 2.50 (m, 2H), 2.38 (m, 2H), 1.97 (m, 2H), 1.55 (m, 4H), 1.45 (d, J=6.9 Hz, 3H), 1.38 (m, 2H).

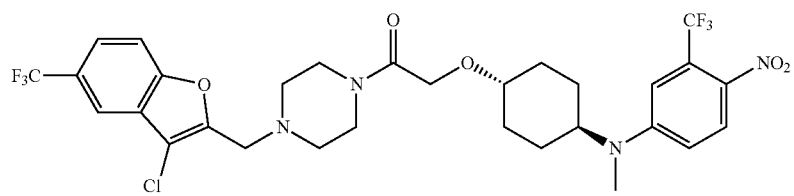 [SMILES: CN(c1ccc([N+](=O)[O-])c(C(F)(F)F)c1)[C@H]1CC[C@H](OCC(=O)N2CCN(Cc3oc4ccc(C(F)(F)F)cc4c3Cl)CC2)CC1]

Compound 258: 1-(4-[[3-chloro-5-(trifluoromethyl)-1-benzofuran-2-yl]methyl]piperazin-1-yl)-2-[[4-[methyl[4-nitro-3-(trifluoromethyl)phenyl]amino]cyclohexyl]oxy]ethan-1-one (ES, m/z): [M+H]$^+$ 677.25; $^1$H NMR (300 MHz, CDCl$_3$) δ 8.06 (d, J=9.3 Hz, 1H), 7.88 (s, 1H), 7.60 (m, 2H), 6.98 (d, J=1.5 Hz, 1H), 6.76 (dd, J=6.6, 3.0 Hz, 1H), 4.17 (s, 2H), 3.85 (br s, 2H), 3.66 (m, 4H), 3.35 (m, 2H), 2.87 (s, 3H), 2.62 (m, 4H), 2.19 (m, 2H), 1.80 (m, 2H), 1.65-1.35 (overlapping m, 4H).

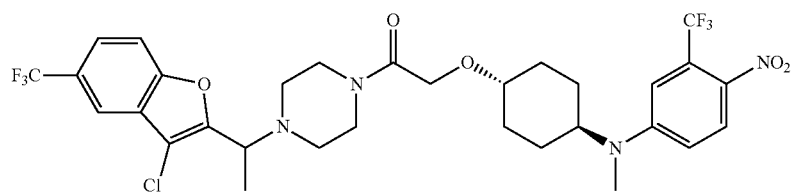 [SMILES: CC(c1oc2ccc(C(F)(F)F)cc2c1Cl)N1CCN(C(=O)CO[C@H]2CC[C@H](N(C)c3ccc([N+](=O)[O-])c(C(F)(F)F)c3)CC2)CC1]

Compound 259: 1-(4-[1-[3-chloro-5-(trifluoromethyl)-1-benzofuran-2-yl]ethyl]piperazin-1-yl)-2-[[4-[methyl-[4-nitro-3-(trifluoromethyl)phenyl]amino]cyclohexyl]oxy]ethan-1-one (ES, m/z): [M+H]$^+$ 691.10; $^1$H NMR (300 MHz, DMSO-d6): δ 8.07 (d, J=9.0 Hz, 1H), 7.92-7.88 (m, 2H), 7.74 (d, J=1.2, 9.0 Hz, 1H), 7.06 (overlapping s & d, 2H), 4.15 (q, J=7.2 Hz, 1H), 4.08 (s, 2H), 3.84 (m, 1H), 3.42 (m, 4H), 3.20 (m, 1H), 2.83 (s, 3H), 2.50 (br m, 4H), 1.95 (m, 2H), 1.51 (d, J=6.9 Hz, 3H), 1.50-1.21 (m, 6H).

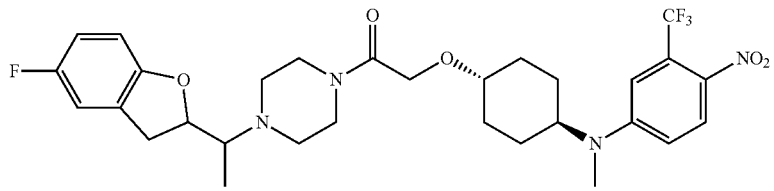 [SMILES: CC(C1Cc2cc(F)ccc2O1)N1CCN(C(=O)CO[C@H]2CC[C@H](N(C)c3ccc([N+](=O)[O-])c(C(F)(F)F)c3)CC2)CC1]

Compounds 262 & 262-10: 1-(4-((S)-1-((R)-5-fluoro-2,3-dihydrobenzofuran-2-yl)ethyl) piperazin-1-yl)-2-(4-(4-nitro-3-(trifluoromethyl)phenylamino) cyclohexyloxy) ethanone & 1-(4-((S)-1-((S)-5-fluoro-2,3-dihydrobenzofuran-2-yl)ethyl)piperazin-1-yl)-2-(4-(4-nitro-3-(trifluoromethyl)phenylamino) cyclohexyloxy)ethanone (E/S, m/z): [M+H]$^+$ 595.10; $^1$H NMR (300 MHz, CDCl$_3$): δ 8.05 (d, J=9.3 Hz, 1H), 6.99 (d, J=2.4 Hz, 1H), 6.87 (d, J=7.8 Hz, 1H), 6.78 (m, 2H), 6.65 (dd, J=4.2, 8.7 Hz, 1H), 4.80 (br m, 1H), 4.21 (s, 2H), 3.80-3.50 (overlapping m, 5H), 3.40 (m, 1H), 3.32-3.08 (m, 4H), 2.90 (s, 3H), 2.78-2.48 (overlapping m, 4H), 2.24 (m, 2H), 1.85 (m, 2H), 1.70-1.40 (m, 4H), 1.10 (d, J=5.1 Hz, 3H).

(ES, m/z): [M+H]$^+$ 609.20; $^1$H NMR (300 MHz, CDCl$_3$): δ 8.05 (d, J=9.3 Hz, 1H), 6.99 (d, J=2.4 Hz, 1H), 6.88 (d, J=7.2 Hz, 1H), 6.76 (dd, J=3.0, 9.3 Hz, 2H), 6.63 (m, 1H), 4.80 (br m, 1H), 4.19 (s, 2H), 3.72 (m, 1H), 3.65-3.34 (overlapping m, 6H), 3.14 (apparent d, J=9.0 Hz, 2H), 2.90 (s, 3H), 2.85 (m, 1H), 2.69 (m, 3H), 2.23 (m, 2H), 1.84 (m, 2H), 1.72-1.39 (overlapping m, 4H), 1.12 (d, J=Hz, 3H).
Relative stereochemical assignments are tentative.

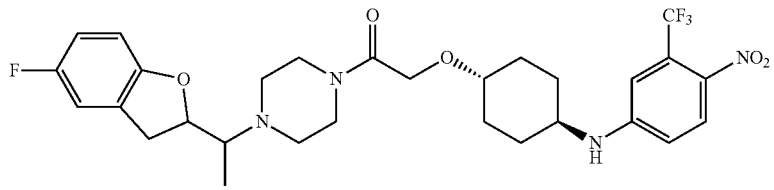 [SMILES: CC(C1Cc2cc(F)ccc2O1)N1CCN(C(=O)CO[C@H]2CC[C@H](Nc3ccc([N+](=O)[O-])c(C(F)(F)F)c3)CC2)CC1]

Compounds 260 & 260-10: 1-(4-((S)-1-((R)-5-fluoro-2,3-dihydrobenzofuran-2-yl)ethyl) piperazin-1-yl)-2-(4-(4-nitro-3-(trifluoromethyl)phenylamino) cyclohexyloxy)ethanone & 1-(4-((S)-1-((S)-5-fluoro-2,3-dihydrobenzofuran-2-yl)ethyl)piperazin-1-yl)-2-(4-(4-nitro-3-(trifluoromethyl)phenylamino) cyclohexyloxy)ethanone (E/S, m/z): [M+H]$^+$ 595.10; $^1$H NMR (300 MHz, CDCl$_3$): δ 8.02 (d, J=9.0 Hz, 1H), 6.88 (m, 2H), 6.79 (dd, J=8.4, 9.6 Hz, 1H), 6.65 (m, 2H), 4.82 (br s, 1H), 4.46 (d, J=7.5 Hz, 1H), 4.20 (s, 2H), 3.75-3.10 (m, 8H), 2.80-2.45 (m, 4H), 2.14 (m, 4H), 1.50 (m, 2H), 1.30 (m, 2H), 1.10-1.08 (d, J=9.0 Hz, 3H).

(E/S, m/z): [M+H]$^+$ 595.10; $^1$H NMR (300 MHz, CDCl$_3$): δ 8.03 (d, J=9.0 Hz, 1H), 6.88 (m, 2H), 6.79 (m, 1H), 6.64 (m, 2H), 4.80 (br s, 1H), 4.46 (d, J=7.8 Hz, 1H), 4.19 (s, 2H), 3.69-3.32 (br m, 6H), 3.13 (m, 2H), 2.86 (m, 1H), 2.67 (br s, 3H), 2.14 (m, 4H), 1.46 (m, 2H), 1.28 (m, 2H), 1.12 (d, J=6.0 Hz, 3H).
Relative stereochemical assignments are tentative.

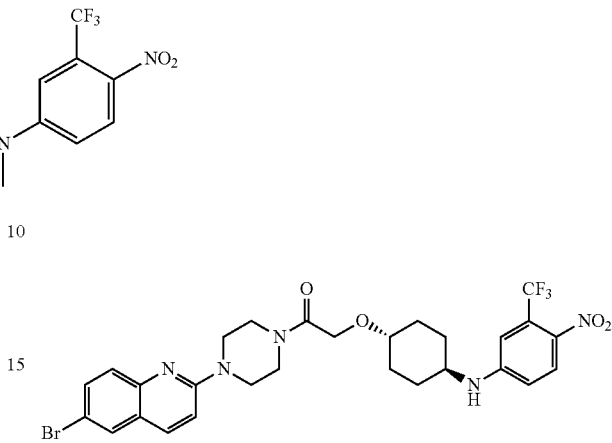

Compound 266: 2-[[4-[(4-nitro-3-trifluoromethyl-phenyl)amino]cyclohexyl]oxy]-1-[4-(6-bromoquinolin-2-yl)piperazin-1-yl]ethan-1-one (CI, m/z): [M+H]$^+$ 636; $^1$H NMR (400 MHz, DMSO-d6): δ 8.05 (dd, J=9.2 Hz, 2.0 Hz, 1H), 7.97 (d, J=2.3 Hz, 1H), 7.63 (dd, J=8.9 Hz, 2.3 Hz, 1H), 7.51 (d, J=8.9 Hz, 1H), 7.45 (d, J=7.8 Hz, 1H), 7.32 (d, J=9.3 Hz, 1H), 7.07 (s, 1H), 6.85 (dd, J=9.7 Hz, 2.4 Hz, 1H), 4.22 (s, 2H), 3.80-3.68 (m, 4H), 3.62-3.54 (m, 4H), 3.52-3.43 (m, 1H), 3.42-3.34 (m, 1H), 2.09-1.91 (m, 4H), 1.45-1.18 (m, 4H).

Compound 269: 2-[(4-[methyl-[4-nitro-3-(trifluoromethyl)phenyl]amino]cyclohexyl)-oxy]1-[4-(6-bromoquinolin-2-yl)piperazin-1-yl]ethan-1-one (CI, m/z): [M+H]$^+$ 650; $^1$H NMR (400 MHz, DMSO-d6): δ 8.06 (dd, J=9.2 Hz, 3.0 Hz, 2H), 7.97 (d, J=2.2 Hz, 1H), 7.63 (dd, J=8.9 Hz, 2.3 Hz, 1H), 7.51 (d, J=8.9 Hz, 1H), 7.33 (d, J=9.2 Hz, 1H), 7.14-7.05 (m, 2H), 4.23 (s, 2H), 3.99-3.90 (m, 1H), 3.81-3.68 (m, 4H), 3.63-3.55 (m, 4H), 3.42-3.34 (m, 1H), 2.90 (s, 3H), 2.16-2.06 (m, 2H), 1.72-1.56 (m, 4H), 1.52-1.38 (m, 2H).

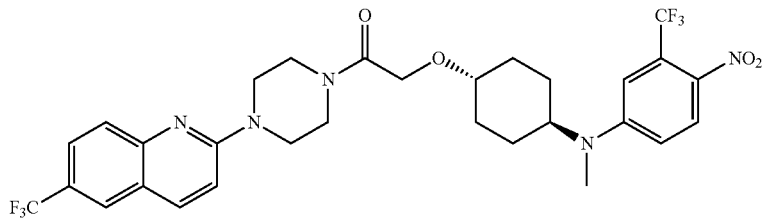 [SMILES: CN(c1ccc([N+](=O)[O-])c(C(F)(F)F)c1)[C@H]1CC[C@H](OCC(=O)N2CCN(c3ccc4cc(C(F)(F)F)ccc4n3)CC2)CC1]

Compound 245: 2-[[(1r,4r)-4-[methyl[4-nitro-3-(trifluoromethyl)phenyl]amino]cyclohexyl]oxy]-1-[4-[6-(trifluoromethyl)quinolin-2-yl]piperazin-1-yl]ethan-1-one (ES, m/z): [M+H]$^+$ 640.35; $^1$H NMR (300 MHz, CD$_3$OD): δ 8.16 (d, J=9.3 Hz, 1H), 8.09 (d, J=9.3 Hz, 1H), 8.05 (s, 1H), 7.76 (m, 2H), 7.33 (d, J=9.3 Hz, 1H), 7.09 (m, 2H), 4.37 (s, 2H), 3.92 (overlapping m, 5H), 3.77 (m, 4H), 3.49 (br m, 1H), 2.97 (s, 3H), 2.27 (m, 2H), 1.90-1.70 (m, 4H), 1.62-1.48 (m, 2H).

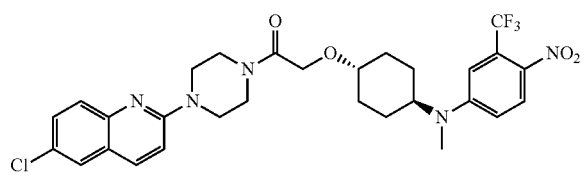 [SMILES: CN(c1ccc([N+](=O)[O-])c(C(F)(F)F)c1)[C@H]1CC[C@H](OCC(=O)N2CCN(c3ccc4cc(Cl)ccc4n3)CC2)CC1]

Compound 246: 1-[4-(6-chloroquinolin-2-yl)piperazin-1-yl]-2-[[4-[methyl[4-nitro-3-(trifluoromethyl)phenyl]amino]cyclohexyl]oxy]ethan-1-one (ES, m/z): [M+H]$^+$ 606.30; $^1$H NMR (400 MHz, CDCl$_3$): δ 8.05 (d, J=9.6 Hz, 1H), 7.87 (s, 1H), 7.70-7.35 (overlapping m, 3H), 7.00 (d, J=8.8 Hz, 1H), 6.98 (d, J=2.4 Hz, 1H), 6.77 (dd, J=2.8, 9.2 Hz, 1H), 4.27 (s, 2H), 3.94-3.68 (overlapping m, 9H), 3.42 (m, 1H), 2.90 (s, 3H), 2.28 (m, 2H), 1.85 (m, 2H), 1.69-1.40 (m, 4H).

Compound 247: 1-(4-(6-fluoroquinolin-2-yl)piperazin-1-yl)-2-(4-(methyl(4-nitro-3-(trifluoromethyl)phenyl)amino)cyclohexyloxy)ethanone (ES, m/z): [M+H]$^+$ 589.95; $^1$H NMR (300 MHz, CD$_3$OD): δ 8.05-8.00 (m, 2H), 7.71-7.68 (m, 1H), 7.37 (d, J=9.0 Hz, 2H), 7.25 (d, J=9.0 Hz, 1H), 7.08-7.01 (m, 2H), 4.34 (s, 2H), 3.88-3.71 (m, 9H), 3.50-3.32 (m, 1H), 2.95 (s, 3H), 2.27-2.23 (m, 2H), 1.85-1.71 (m, 4H), 1.60-1.47 (m, 2H).

Compound 248: 1-(4-(6-fluoronaphthalen-2-yl)piperazin-1-yl)-2-(4-(methyl(4-nitro-3-(trifluoromethyl)phenyl)amino)cyclohexyloxy)ethanone (ES, m/z): [M+H]$^+$ 589.15; $^1$H NMR (300 MHz, CDCl$_3$): δ 8.05 (d, J=9.3 Hz, 1H), 7.73 (overlapping m, 2H), 7.41-7.21 (overlapping m, 4H), 6.98 (s, 1H), 6.77 (dd, J=9.3, 3.0 Hz, 1H), 4.28 (s, 2H), 3.88 (m, 4H), 3.73 (m, 1H), 3.43 (m, 1H), 3.32 (m, 4H), 2.90 (s, 3H), 2.26 (m, 2H), 1.84 (m, 2H), 1.72 (m, 2H), 1.48 (m, 2H).

Compound 178: 1-[4-[(5-chloro-1-benzofuran-2-yl)methyl]piperazin-1-yl]-2-[(4-[[4-nitro-3-(trifluoromethyl) phenyl]amino]cyclohexyl)oxy]ethan-1-one (ES, m/z): [M+H]$^+$ 594.95; $^1$H NMR (400 MHz, CDCl$_3$): δ 8.04 (d, J=9.2 Hz, 1H), 7.51 (s, 1H), 7.41 (d, J=8.8 Hz, 1H), 7.19-7.26 (m, 1H), 6.84 (s, 1H), 6.63 (m, 2H), 4.44 (d, J=7.2 Hz, 1H), 4.18 (s, 2H), 3.51-3.85 (m, 6H), 3.39-3.42 (m, 2H), 2.56 (br s, 4H), 2.03-2.14 (m, 4H), 1.41-1.59 (m, 2H), 1.12-1.28 (m, 2H).

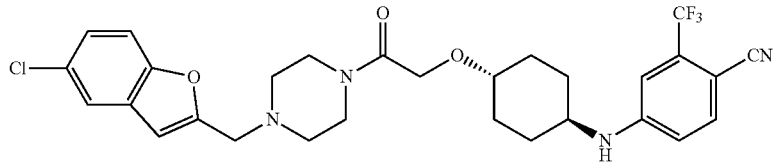 [SMILES: N#Cc1ccc(N[C@H]2CC[C@H](OCC(=O)N3CCN(Cc4cc5cc(Cl)ccc5o4)CC3)CC2)cc1C(F)(F)F]

Compound 274: 2-[(4-[[4-cyano-3-(trifluoromethyl)phenyl]amino]cyclohexyl)-oxy]1-[4-(5-chlorobenzofuran-2-ylmethyl)piperazin-1-yl]ethan-1-one (CI, m/z): [M+H]⁺ 575; ¹H NMR (400 MHz, DMSO-d6): δ 7.69 (d, J=8.8 Hz, 1H), 7.66 (d, J=2.3 Hz, 1H), 7.58 (d, J=8.7 Hz, 1H), 7.28 (dd, J=8.7 Hz, 2.2 Hz, 1H), 7.08 (d, J=7.8 Hz, 1H), 7.01 (s, 1H), 6.84 (dd, J=8.7 Hz, 2.2 Hz, 1H), 6.79 (s, 1H), 4.11 (s, 2H), 3.72 (s, 2H) 3.49-3.26 (m, 6H), 2.52-2.40 (m, 4H), 2.02-1.86 (m, 4H), 1.39-1.25 (m, 2H), 1.23-1.11 (m, 2H).

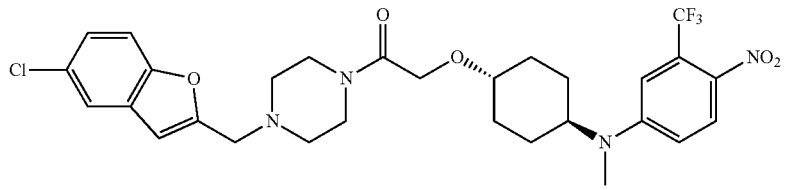 [SMILES: CN(c1ccc([N+](=O)[O-])c(C(F)(F)F)c1)[C@H]1CC[C@H](OCC(=O)N2CCN(Cc3cc4cc(Cl)ccc4o3)CC2)CC1]

Compound 275: 2-[(4-[methyl[4-nitro-3-(trifluoromethyl)phenyl]amino]cyclohexyl)-oxy]1-[4-(5-chlorobenzofuran-2-ylmethyl)piperazin-1-yl]ethan-1-one (CI, m/z): [M+H]⁺ 609; ¹H NMR (400 MHz, DMSO-d6): δ 8.07 (d, J=9.2 Hz, 1H), 7.67 (d, J=2.2 Hz, 1H), 7.58 (d, J=8.7 Hz, 1H), 7.28 (dd, J=8.7 Hz, 2.2 Hz, 1H), 7.12-7.05 (m, 2H), 6.80 (s, 1H), 4.12 (s, 2H), 3.96-3.87 (m, 1H), 3.73 (s, 2H), 3.50-3.40 (m, 4H), 3.34-3.25 (m, 1H), 2.89 (s, 3H), 2.53-2.40 (m, 4H), 2.08-1.99 (m, 2H), 1.69-1.53 (m, 4H), 1.46-1.33 (m, 2H).

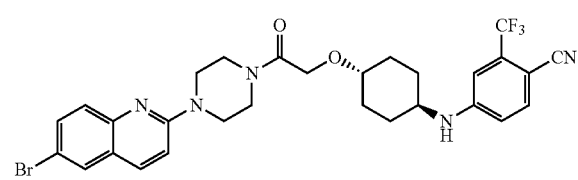

Compound 271: 2-[(4-[[4-cyano-3-(trifluoromethyl)phenyl]amino]cyclohexyl)oxy]-1-[4-(6-bromoquinolin-2-yl)piperazin-1-yl]ethan-1-one (CI, m/z): [M+H]⁺ 616; ¹H NMR (400 MHz, DMSO-d6): δ 8.06 (d, J=9.2 Hz, 1H), 7.97 (d, J=2.3 Hz, 1H), 7.69 (d, J=8.7 Hz, 1H), 7.63 (dd, J=8.9 Hz, 2.3 Hz, 1H), 7.51 (d, J=8.9 Hz, 1H), 7.32 (d, J=9.3 Hz, 1H), 7.10 (d, J=7.8 Hz, 1H), 7.01 (s, 1H), 6.85 (dd, J=8.7 Hz, 2.2 Hz, 1H), 4.21 (s, 2H), 3.79-3.68 (m, 4H), 3.62-3.55 (m, 4H), 3.47-3.32 (m, 2H), 2.07-2.00 (m, 2H), 1.98-1.90 (m, 2H), 1.43-1.31 (m, 2H), 1.28-1.16 (m, 2H).

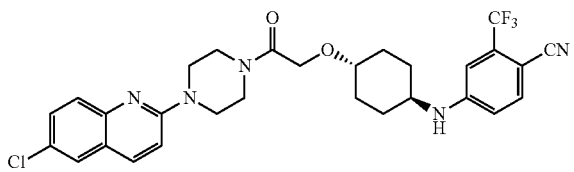 [SMILES: N#Cc1ccc(N[C@H]2CC[C@H](OCC(=O)N3CCN(c4ccc5cc(Cl)ccc5n4)CC3)CC2)cc1C(F)(F)F]

Compound 272: 2-[(4-[[4-cyano-3-(trifluoromethyl)phenyl]amino]cyclohexyl)oxy]-1-[4-(6-chloroquinolin-2-yl)piperazin-1-yl]ethan-1-one (CI, m/z): [M+H]⁺ 572; ¹H NMR (400 MHz, DMSO-d6): δ 8.06 (d, J=9.2 Hz, 1H), 7.83 (d, J=2.4 Hz, 1H), 7.69 (d, J=8.7 Hz, 1H), 7.58 (d, J=9.0 Hz, 1H), 7.52 (dd, J=8.9 Hz, 2.4 Hz, 1H), 7.33 (d, J=9.3 Hz, 1H), 7.10 (d, J=7.8 Hz, 1H), 7.01 (s, 1H), 6.85 (dd, J=8.7 Hz, 2.3 Hz, 1H), 4.21 (s, 2H), 3.79-3.68 (m, 4H), 3.62-3.54 (m, 4H), 3.47-3.32 (m, 2H), 2.08-2.00 (m, 2H), 1.98-1.90 (m, 2H), 1.44-1.31 (m, 2H), 1.28-1.16 (m, 2H).

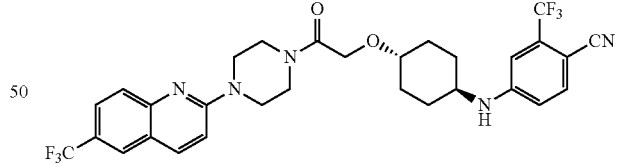

Compound 273: 2-[(4-[[4-cyano-3-(trifluoromethyl)phenyl]amino]cyclohexyl)oxy]-1-[4-[6-(trifluoromethyl)quinolin-2-yl]piperazin-1-yl]ethan-1-one (CI, m/z): [M+H]⁺ 606; ¹H NMR (400 MHz, DMSO-d6): δ 8.23 (d, J=9.3 Hz, 1H), 8.17 (s, 1H), 7.66 (dd, J=8.9 Hz, 2.1 Hz, 1H), 7.72-7.66 (m, 3H), 7.39 (d, J=9.3 Hz, 1H), 7.10 (d, J=7.8 Hz, 1H), 7.01 (s, 1H), 6.85 (dd, J=8.7 Hz, 2.2 Hz, 1H), 4.22 (s, 2H), 3.86-3.75 (m, 4H), 3.63-3.56 (m, 4H), 3.47-3.32 (m, 2H), 2.08-2.00 (m, 2H), 1.98-1.90 (m, 2H), 1.44-1.31 (m, 2H), 1.28-1.16 (m, 2H).

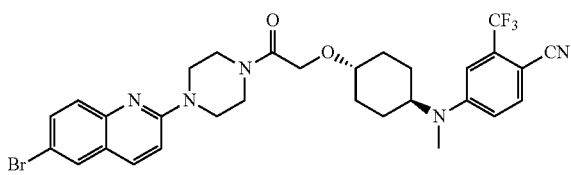 [SMILES: CN(c1ccc(C#N)c(C(F)(F)F)c1)[C@H]1CC[C@H](OCC(=O)N2CCN(c3ccc4cc(Br)ccc4n3)CC2)CC1]

Compound 281: 2-[(4-[methyl[4-cyano-3-(trifluoromethyl)phenyl]amino]cyclohexyl)-oxy]-1-[4-(6-bromoquinolin-2-yl)piperazin-1-yl]ethan-1-one (CI, m/z): [M+H]⁺ 630; ¹H NMR (400 MHz, DMSO-d6): δ 8.06 (d, J=9.2 Hz, 1H), 7.97 (d, J=2.2 Hz, 1H), 7.76 (d, J=8.8 Hz, 1H), 7.63 (dd, J=8.9 Hz, 2.3 Hz, 1H), 7.51 (d, J=8.9 Hz, 1H), 7.33 (d, J=9.3 Hz, 1H), 7.13-7.07 (m, 2H), 4.22 (s, 2H), 3.94-3.84 (m, 1H), 3.79-3.69 (m, 4H), 3.63-3.55 (m, 4H), 3.41-3.32 (m, 1H), 2.85 (s, 3H), 2.14-2.05 (m, 2H), 1.69-1.55 (m, 4H), 1.51-1.38 (m, 2H).

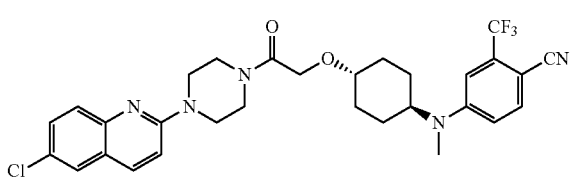 [SMILES: CN(c1ccc(C#N)c(C(F)(F)F)c1)[C@H]1CC[C@H](OCC(=O)N2CCN(c3ccc4cc(Cl)ccc4n3)CC2)CC1]

Compound 282: 2-[(4-[methyl[4-cyano-3-(trifluoromethyl)phenyl]amino]cyclohexyl)-oxy]1-[4-(6-chloroquinolin-2-yl)-piperazin-1-yl]ethan-1-one (CI, m/z): [M+H]⁺ 586; ¹H NMR (400 MHz, DMSO-d6): δ 8.06 (d, J=9.3 Hz, 1H), 7.83 (d, J=2.1 Hz, 1H), 7.76 (d, J=8.5 Hz, 1H), 7.6-7.50 (m, 2H), 7.33 (d, J=9.2 Hz, 1H), 7.14-7.05 (m, 2H), 4.22 (s, 2H), 3.94-3.84 (m, 1H), 3.81-3.68 (m, 4H), 3.63-3.55 (m, 4H), 3.41-3.32 (m, 1H), 2.85 (s, 3H), 2.14-2.05 (m, 2H), 1.69-1.55 (m, 4H), 1.51-1.38 (m, 2H).

EXAMPLE 35: Preparation of Compound 283

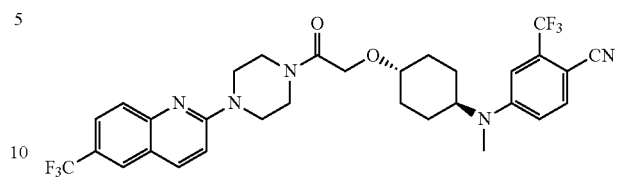

Compound 283

Formation of 2-[(4-[methyl[4-cyano-3-(trifluoromethyl)phenyl]amino]cyclohexyl)-oxy]1-[4-[6-(trifluoromethyl)quinolin-2-yl]-piperazin-1-yl]ethan-1-one (#283)

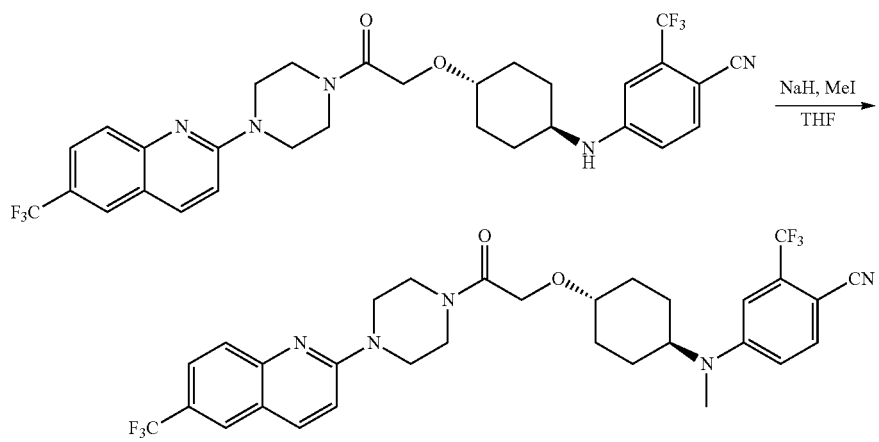

To a solution of 2-[(4-[[4-cyano-3-(trifluoromethyl)phenyl]amino]-cyclohexyl)oxy]-1-[4-[6-(trifluoromethyl)quinolin-2-yl]piperazin-1-yl]ethan-1-one (100 mg, 0.16 mmol) in THF (3 ml) was added sodium hydride (25 mg, 0.63 mmol, 3.9 eq.) and the mixture was stirred for 30 minutes. The mixture was then treated with iodomethane (100 mg, 0.7 mmol, 4 eq.) and stirred for 5 days. The resulting mixture was diluted with water (30 ml), and extracted with ethyl acetate (30 mL). The organic layer was separated, washed with brine, dried over anhydrous sodium sulfate, filtered, and concentrated under vacuum to give a residue from which the product was purified by silica gel column flash chromatography eluting with ethyl acetate/heptanes to afford 2-[(4-[methyl[4-cyano-3-(trifluoromethyl)phenyl]-aminol-cyclohexyl)oxy]-1-[4-[6-(trifluoromethyl)quinolin-2-yl)piperazin-1-yl]ethan-1-one as a yellow solid (100 mg, 98%). (CI, m/z): [M+H]⁺ 620; ¹H NMR (400 MHz, DMSO-d6): δ 8.24 (d, J=9.3 Hz, 1H), 8.17 (s, 1H), 7.76 (d, J=8.7 Hz, 2H), 7.70 (d, J=8.7 Hz, 1H), 7.40 (d, J=9.3 Hz, 1H), 7.13-7.07 (m, 2H), 4.23 (s, 2H), 3.94-3.76 (m, 5H), 3.63-3.57 (m, 4H), 3.41-3.32 (m, 1H), 2.85 (s, 3H), 2.14-2.05 (m, 2H), 1.69-1.57 (m, 4H), 1.50-1.38 (m, 2H).

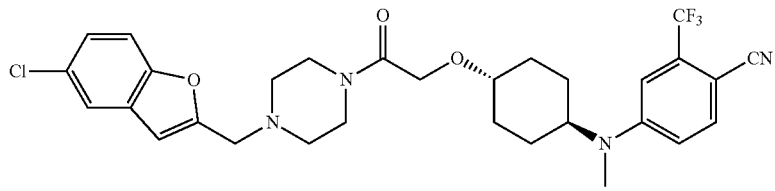 [SMILES: CN(c1ccc(C#N)c(C(F)(F)F)c1)[C@H]1CC[C@H](OCC(=O)N2CCN(Cc3cc4cc(Cl)ccc4o3)CC2)CC1]

Compound 284: 2-[(4-[methyl[4-cyano-3-(trifluoromethyl)phenyl]amino]cyclohexyl)-oxy]1-[4-(6-chlorobenzofuran-2-ylmethyl)-piperazin-1-yl]ethan-1-one (CI, m/z): [M+H]$^+$ 589 $^1$H NMR (400 MHz, DMSO-d6): δ 7.76 (d, J=9.0 Hz, 1H), 7.67 (s, 1H), 7.58 (d, J=8.7 Hz, 1H), 7.28 (d, J=8.5 Hz, 1H), 7.12-7.04 (m, 2H), 6.79 (s, 1H), 4.12 (s, 2H), 3.91-3.80 (m, 1H), 3.73 (s, 2H), 3.51-3.39 (m, 4H), 3.33-3.23 (m, 1H), 2.83 (s, 3H), 2.54-2.38 (m, 4H), 2.07-1.97 (m, 2H), 1.66-1.49 (m, 4H), 1.46-1.31 (m, 2H).

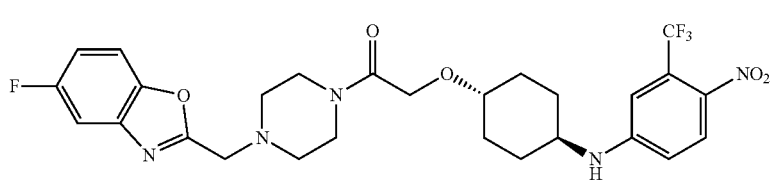

Compound 285

Step 5. Formation of 2-[(4-[[4-nitro-3-(trifluoromethyl)phenyl]amino]cyclohexyl)-oxy]1-[4-(5-fluorobenzoxazol-2-ylmethyl)piperazin-1-yl]ethan-1-one (#285)

(CI, m/z): [M+H]$^+$ 580; $^1$H NMR (400 MHz, DMSO-d6): δ 8.05 (d, J=9.3 Hz, 1H), 7.77 (dd, J=4.3 Hz, 9.4 Hz, 1H), 7.62 (dd, J=8.7 Hz, 2.6 Hz, 1H), 7.43 (d, J=7.7 Hz, 1H), 7.26 (td, J=9.6 Hz, 2.6 Hz, 1H), 7.06 (s, 1H), 6.84 (dd, J=9.3 Hz, 2.5 Hz, 1H), 4.12 (s, 2H), 3.92 (s, 2H), 3.51-3.38 (m, 5H), 3.36-3.26 (m, 1H), 2.60-2.50 (m, 4H), 2.04-1.88 (m, 4H), 1.40-1.15 (m, 4H).

Compound 286: 2-[(4-[[4-cyano-3-(trifluoromethyl)phenyl]amino]cyclohexyl)-oxy]1-[4-(5-fluorobenzoxazol-2-ylmethyl)piperazin-1-yl]ethan-1-one (CI, m/z): [M+H]$^+$ 560; $^1$H NMR (400 MHz, DMSO-d6): δ 7.77 (dd, J=4.3 Hz, 9.0 Hz, 1H), 7.69 (d, J=8.7 Hz, 1H), 7.62 (dd, J=8.8 Hz, 2.6 Hz, 1H), 7.26 (td, J=9.0 Hz, 2.6 Hz, 1H), 7.08 (d, J=7.8 Hz, 1H), 7.01 (s, 1H), 6.84 (dd, J=8.7 Hz, 2.2 Hz, 1H), 4.12 (s, 2H), 3.92 (s, 2H), 3.51-3.27 (m, 6H), 2.60-2.50 (m, 4H), 2.02-1.86 (m, 4H), 1.38-1.26 (m, 2H), 1.24-1.12 (m, 2H).

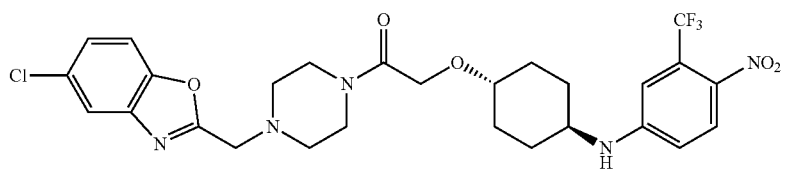

Compound 287: 2-[(4-[[4-nitro-3-(trifluoromethyl)phenyl]amino]cyclohexyl)-oxy]1-[4-(5-chlorobenzoxazol-2-ylmethyl)piperazin-1-yl]ethan-1-one (CI, m/z): [M+H]$^+$ 595; $^1$H NMR (400 MHz, DMSO-d6): δ 8.05 (d, J=9.2 Hz, 1H), 7.86 (d, J=2.1 Hz, 1H), 7.78 (d, J=8.7 Hz, 1H), 7.47-7.40 (m, 2H), 7.06 (s, 1H), 6.84 (dd, J=9.3 Hz, 2.4 Hz, 1H), 4.12 (s, 2H), 3.93 (s, 2H), 3.52-3.38 (m, 5H), 3.36-3.26 (m, 1H), 2.60-2.50 (m, 4H), 2.04-1.88 (m, 4H), 1.40-1.15 (m, 4H).

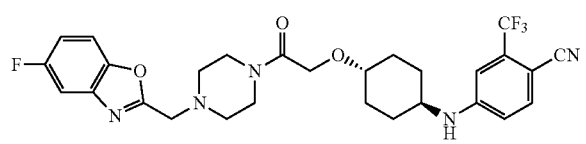 [SMILES: N#Cc1ccc(N[C@H]2CC[C@H](OCC(=O)N3CCN(Cc4nc5cc(F)ccc5o4)CC3)CC2)cc1C(F)(F)F]

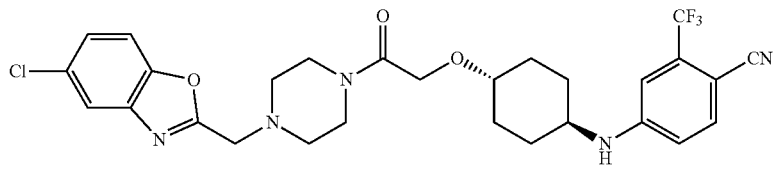 [SMILES: N#Cc1ccc(N[C@H]2CC[C@H](OCC(=O)N3CCN(Cc4nc5cc(Cl)ccc5o4)CC3)CC2)cc1C(F)(F)F]

Compound 288: 2-[(4-[[4-cyano-3-(trifluoromethyl)phenyl]amino]cyclohexyl)-oxy]1-[4-(5-chlorobenzoxazol-2-ylmethyl)piperazin-1-yl]ethan-1-one (CI, m/z): [M+H]$^+$ 576; $^1$H NMR (400 MHz, DMSO-d6): δ 7.86 (d, J=2.1 Hz, 1H), 7.77 (d, J=8.7 Hz, 1H), 7.69 (d, J=7.7 Hz, 1H), 7.44 (dd, J=8.7 Hz, 2.3 Hz, 1H), 7.08 (d, J=7.8 Hz, 1H), 7.01 (s, 1H), 6.84 (dd, J=8.7 Hz, 2.2 Hz, 1H), 4.12 (s, 2H), 3.93 (s, 2H), 3.50-3.26 (m, 6H), 2.60-2.50 (m, 4H), 2.02-1.86 (m, 4H), 1.38-1.26 (m, 2H), 1.24-1.12 (m, 2H).

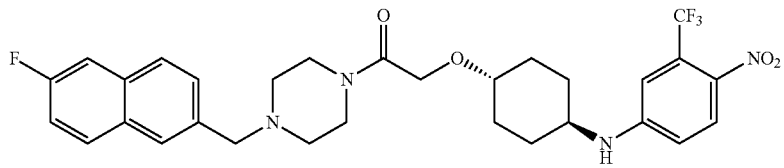 [SMILES: O=C(CO[C@H]1CC[C@H](Nc2ccc([N+](=O)[O-])c(C(F)(F)F)c2)CC1)N1CCN(Cc2ccc3cc(F)ccc3c2)CC1]

Compound 297: 2-[(4-[[4-nitro-3-(trifluoromethyl)phenyl]amino]cyclohexyl)-oxy]1-[4-(6-fluoronaphthalen-2-ylmethyl)piperazin-1-yl]ethan-1-one (CI, m/z): [M+H]$^+$ 589; $^1$H NMR (400 MHz, DMSO-d6): δ 8.05 (d, J=9.2 Hz, 1H), 7.98 (dd, J=9.1 Hz, 5.9 Hz, 1H), 7.88 (d, J=8.5 Hz, 1H), 7.85 (s, 1H), 7.68 (dd, J=10.4 Hz, 2.6 Hz, 1H), 7.54 (d, J=8.5 Hz, 1H), 7.46-7.37 (m, 2H), 7.06 (s, 1H), 6.84 (dd, J=9.3 Hz, 2.5 Hz, 1H), 4.12 (s, 2H), 3.65 (s, 2H), 3.51-3.39 (m, 5H), 3.32-3.27 (m, 1H), 2.45-2.33 (m, 4H), 2.04-1.88 (m, 4H), 1.41-1.14 (m, 4H).

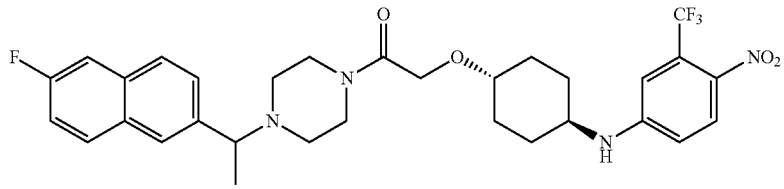 [SMILES: CC(c1ccc2cc(F)ccc2c1)N1CCN(C(=O)CO[C@H]2CC[C@H](Nc3ccc([N+](=O)[O-])c(C(F)(F)F)c3)CC2)CC1]

Compound 298: 2-[(4-[[4-nitro-3-(trifluoromethyl)phenyl]amino]cyclohexyl)-oxy]1-[4-[1-(6-fluoronaphthalen-2-yl)ethyl]piperazin-1-yl]ethan-1-one (CI, m/z): [M+H]$^+$ 603; $^1$H NMR (400 MHz, DMSO-d6): δ 8.05 (d, J=9.2 Hz, 1H), 7.98 (dd, J=9.1 Hz, 5.8 Hz, 1H), 7.87 (d, J=8.6 Hz, 1H), 7.83 (s, 1H), 7.66 (dd, J=10.4 Hz, 2.6 Hz, 1H), 7.56 (d, J=8.4 Hz, 1H), 7.44-7.36 (m, 2H), 7.05 (s, 1H), 6.83 (dd, J=9.3 Hz, 2.5 Hz, 1H), 4.08 (s, 2H), 3.62 (q, J=6.7 Hz, 1H), 3.48-3.35 (m, 5H), 3.34-3.24 (m, 1H), 2.47-2.26 (m, 4H), 2.00-1.85 (m, 4H), 1.39 (d, J=6.7 Hz, 3H), 1.35-1.12 (m, 4H).

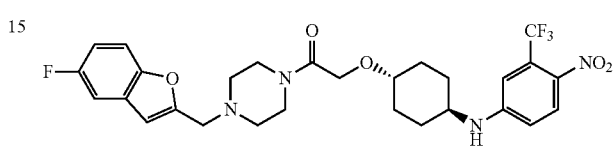

Compound 179: 1-[4-[(5-fluoro-1-benzofuran-2-yl)methyl]piperazin-1-yl]-2-[(4-[[4-nitro-3-(trifluoromethyl) phenyl]amino]cyclohexyl)oxy]ethan-1-one (ES, m/z): [M+H]$^+$ 579.15; $^1$H NMR (300 MHz, CDCl$_3$): δ 8.02 (d, J=9.0 Hz, 1H), 7.41 (dd, J=3.9 Hz, 9.0 Hz, 1H), 7.27 (d, J=10.2 Hz, 1H), 7.07-7.14 (m, 1H), 6.97 (s, 1H), 6.83 (d, J=5.4 Hz, 1H), 6.60 (dd, J=2.7 Hz, 9.0 Hz, 1H), 4.37 (s, 2H), 4.17 (s, 2H), 4.01 (br s, 4H), 3.11-3.37 (overlapping m, 6H), 2.00-2.15 (m, 4H), 1.15-1.44 (m, 4H).

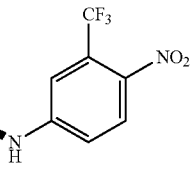

Compound 304: 2-[(4-[[4-nitro-3-(trifluoromethyl)phenyl]amino]cyclohexyl)-oxy]1-[4-[1-(5-fluorobenzofuran-2-yl)ethyl]piperazin-1-yl]ethan-1-one (CI, m/z): [M+H]$^+$ 593; $^1$H NMR (400 MHz, DMSO-d6): δ 8.05 (d, J=9.2 Hz, 1H), 7.56 (dd, J=8.9 Hz, 4.2 Hz, 1H), 7.43-7.36 (m, 2H), 7.10-7.03 (m, 2H), 6.82 (dd, J=9.2 Hz, 2.4 Hz, 1H), 6.75 (s, 1H), 4.08 (s, 2H), 3.98 (q, J=7.0 Hz, 1H), 3.48-3.35 (m, 5H), 3.33-3.23 (m, 1H), 2.58-2.45 (m, 2H), 2.43-2.32 (m, 2H), 2.00-1.83 (m, 4H), 1.42 (d, J=7.0 Hz, 3H), 1.34-1.09 (m, 4H).

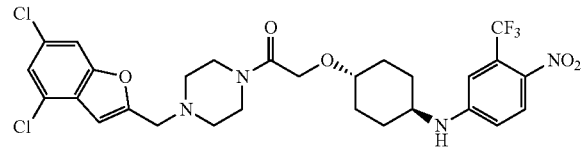 [SMILES: O=C(CO[C@H]1CC[C@H](Nc2ccc([N+](=O)[O-])c(C(F)(F)F)c2)CC1)N1CCN(Cc2cc3c(Cl)cc(Cl)cc3o2)CC1]

Compound 318: 2-[(4-[[4-nitro-3-(trifluoromethyl)phenyl]amino]cyclohexyl)-oxy]1-[4-(4,6-dichlorobenzofuran-2-ylmethyl)piperazin-1-yl]ethan-1-one (CI, m/z): [M+H]⁺ 629; ¹H NMR (400 MHz, DMSO-d6): δ 8.06 (d, J=9.2 Hz, 1H), 7.70 (d, J=2.0 Hz, 1H), 7.51 (d, J=2.0 Hz, 1H), 7.43 (d, J=7.7 Hz, 1H), 7.06 (s, 1H), 6.91 (s, 1H), 6.84 (dd, J=9.2 Hz, 2.3 Hz, 1H), 4.12 (s, 2H), 3.77 (s, 2H), 3.50-3.38 (m, 5H), 3.36-3.27 (m, 1H), 2.53-2.39 (m, 4H), 2.03-1.87 (m, 4H), 1.39-1.14 (m, 4H).

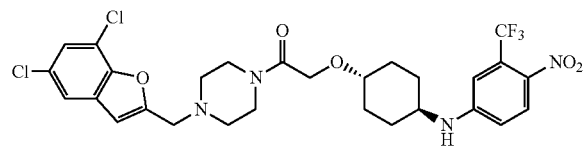

Compound 319: 2-[(4-[[4-nitro-3-(trifluoromethyl)phenyl]amino]cyclohexyl)-oxy]1-[4-(5,7-dichlorobenzofuran-2-ylmethyl)piperazin-1-yl]ethan-1-one (CI, m/z): [M+H]⁺ 629; ¹H NMR (400 MHz, DMSO-d6): δ 8.05 (d, J=9.2 Hz, 1H), 7.81 (s, 1H), 7.45 (d, J=1.6 Hz, 1H), 7.43 (d, J=7.8 Hz, 1H), 7.06 (s, 1H), 6.90 (s, 1H), 6.84 (dd, J=9.3 Hz, 2.5 Hz, 1H), 4.12 (s, 2H), 3.75 (s, 2H), 3.50-3.38 (m, 5H), 3.36-3.27 (m, 1H), 2.52-2.40 (m, 4H), 2.03-1.87 (m, 4H), 1.39-1.14 (m, 4H).

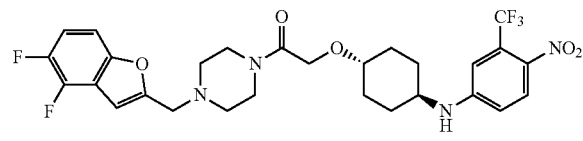 [SMILES: O=C(CO[C@H]1CC[C@H](Nc2ccc([N+](=O)[O-])c(C(F)(F)F)c2)CC1)N1CCN(Cc2cc3c(F)c(F)ccc3o2)CC1]

Compound 320: 2-[(4-[[4-nitro-3-(trifluoromethyl)phenyl]amino]cyclohexyl)-oxy]1-[4-(4,5-difluorobenzofuran-2-ylmethyl)piperazin-1-yl]ethan-1-one (CI, m/z): [M+H]⁺ 597; ¹H NMR (400 MHz, DMSO-d6): δ 8.05 (d, J=9.2 Hz, 1H), 7.48-7.40 (m, 2H), 7.38-7.29 (m, 1H), 7.06 (s, 1H), 7.01 (s, 1H), 6.84 (dd, J=9.3 Hz, 2.5 Hz, 1H), 4.12 (s, 2H), 3.73 (s, 2H), 3.49-3.39 (m, 5H), 3.35-3.27 (m, 1H), 2.52-2.41 (m, 4H), 2.03-1.88 (m, 4H), 1.39-1.14 (m, 4H).

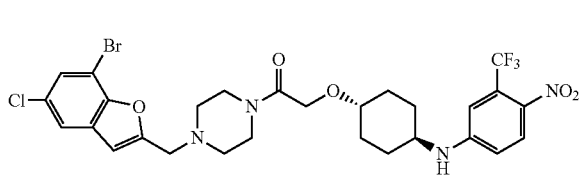 [SMILES: O=C(CO[C@H]1CC[C@H](Nc2ccc([N+](=O)[O-])c(C(F)(F)F)c2)CC1)N1CCN(Cc2cc3cc(Cl)cc(Br)c3o2)CC1]

Compound 321: 2-[(4-[[4-nitro-3-(trifluoromethyl)phenyl]amino]cyclohexyl)-oxy]1-[4-(5-chloro-7-bromobenzofuran-2-ylmethyl)piperazin-1-yl]ethan-1-one (CI, m/z): [M+H]⁺ 673; ¹H NMR (400 MHz, DMSO-d6): δ 8.05 (d, J=9.2 Hz, 1H), 7.72 (d, J=2.0 Hz, 1H), 7.60 (d, J=2.0 Hz, 1H), 7.43 (d, J=7.8 Hz, 1H), 7.06 (s, 1H), 6.93 (s, 1H), 6.84 (dd, J=9.3 Hz, 2.3 Hz, 1H), 4.12 (s, 2H), 3.77 (s, 2H), 3.50-3.38 (m, 5H), 3.36-3.26 (m, 1H), 2.53-2.40 (m, 4H), 2.03-1.87 (m, 4H), 1.38-1.13 (m, 4H).

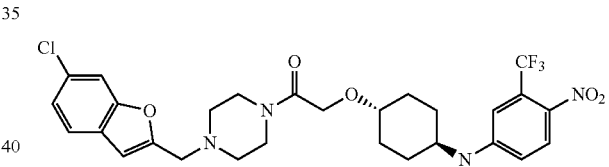

Compound 322: 2-[(4-[[4-nitro-3-(trifluoromethyl)phenyl]amino]cyclohexyl)-oxy]1-[4-(6-chlorobenzofuran-2-ylmethyl)piperazin-1-yl]ethan-1-one (CI, m/z): [M+H]⁺ 595; ¹H NMR (400 MHz, DMSO-d6): δ 8.05 (d, J=9.2 Hz, 1H), 7.73 (s, 1H), 7.61 (d, J=8.1 Hz, 1H), 7.43 (d, J=7.8 Hz, 1H), 7.26 (d, J=8.5 Hz, 1H), 7.06 (s, 1H), 6.87-6.80 (m, 2H), 4.12 (s, 2H), 3.72 (s, 2H) 3.48-3.38 (m, 5H), 3.36-3.27 (m, 1H), 2.52-2.39 (m, 4H), 2.03-1.87 (m, 4H), 1.39-1.14 (m, 4H).

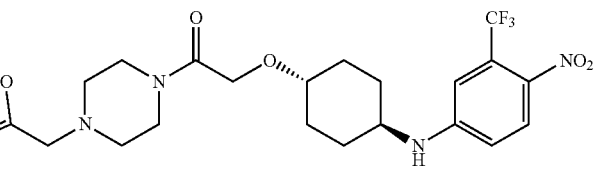

Compound 323: 2-[(4-[[4-nitro-3-(trifluoromethyl)phenyl]amino]cyclohexyl)-oxy]1-[4-(5-methoxybenzofuran-2-ylmethyl)piperazin-1-yl]ethan-1-one (CI, m/z): [M+H]⁺ 591; ¹H NMR (400 MHz, DMSO-d6): δ 8.05 (d, J=9.2 Hz, 1H), 7.42 (d, J=9.0 Hz, 2H), 7.10 (d, J=2.6 Hz, 1H), 7.06 (s, 1H), 6.85 (dd, J=8.9 Hz, 2.6 Hz, 2H), 6.71 (s, 1H), 4.12 (s, 2H), 3.75 (s, 3H), 3.68 (s, 2H), 3.48-3.38 (m, 5H), 3.36-3.27 (m, 1H), 2.50-2.38 (m, 4H), 2.03-1.88 (m, 4H), 1.38-1.14 (m, 4H).

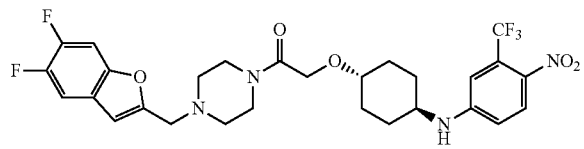 [SMILES: O=C(CO[C@H]1CC[C@H](Nc2ccc([N+](=O)[O-])c(C(F)(F)F)c2)CC1)N1CCN(Cc2cc3cc(F)c(F)cc3o2)CC1]

Compound 325: 2-[(4-[[4-nitro-3-(trifluoromethyl)phenyl]amino]cyclohexyl)-oxy]1-[4-(5,6-difluorobenzofuran-2-ylmethyl)piperazin-1-yl]ethan-1-one (CI, m/z): [M+H]⁺ 596; ¹H NMR (400 MHz, DMSO-d6): δ 8.05 (d, J=9.2 Hz, 1H), 7.80 (dd, J=10.6 Hz, 6.6 Hz, 1H), 7.65 (dd, J=10.5 Hz, 8.2 Hz, 1H), 7.43 (d, J=7.8 Hz, 1H), 7.06 (s, 1H), 6.86-6.80 (m, 2H), 4.12 (s, 2H), 3.71 (s, 2H), 3.48-3.39 (m, 5H), 3.35-3.28 (m, 1H), 2.50-2.39 (m, 4H), 2.03-1.88 (m, 4H), 1.39-1.15 (m, 4H).

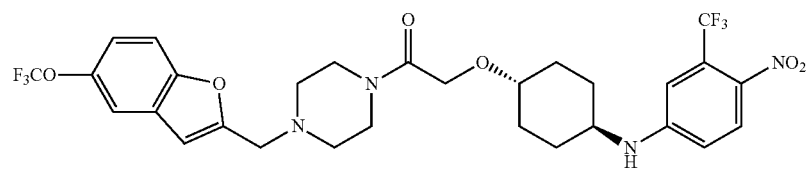 [SMILES: O=C(CO[C@H]1CC[C@H](Nc2ccc([N+](=O)[O-])c(C(F)(F)F)c2)CC1)N1CCN(Cc2cc3cc(OC(F)(F)F)ccc3o2)CC1]

Compound 326: 2-[(4-[[4-nitro-3-(trifluoromethyl)phenyl]amino]cyclohexyl)-oxy]1-[4-[5-(trifluoromethoxy)benzofuran-2-ylmethyl]piperazin-1-yl]ethan-1-one (CI, m/z): [M+H]⁺ 645; ¹H NMR (400 MHz, DMSO-d6): δ 8.05 (d, J=9.2 Hz, 1H), 7.67 (d, J=8.9 Hz, 1H), 7.63 (s, 1H), 7.42 (d, J=7.8 Hz, 1H), 7.25 (dd, J=8.9 Hz, 2.5 Hz, 1H), 7.06 (s, 1H), 6.87 (s, 1H), 6.84 (dd, J=9.2 Hz, 2.5 Hz, 1H), 4.12 (s, 2H), 3.74 (s, 2H), 3.49-3.39 (m, 5H), 3.35-3.27 (m, 1H), 2.51-2.41 (m, 4H), 2.02-1.86 (m, 4H), 1.38-1.14 (m, 4H).

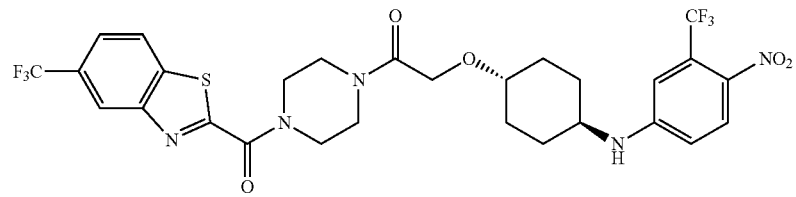 [SMILES: O=C(CO[C@H]1CC[C@H](Nc2ccc([N+](=O)[O-])c(C(F)(F)F)c2)CC1)N1CCN(C(=O)c2nc3cc(C(F)(F)F)ccc3s2)CC1]

Compound 338: 2-[(4-[[4-nitro-3-(trifluoromethyl)phenyl]amino]cyclohexyl)-oxy]1-[4-[5-(trifluoromethyl)benzothiazole-2-carbonyl]piperazin-1-yl]ethan-1-one (CI, m/z): [M+H]⁺ 660; ¹H NMR (400 MHz, DMSO-d6): δ 8.52 (s, 1H), 8.48 (d, J=8.5 Hz, 1H), 8.05 (d, J=9.2 Hz, 1H), 7.92 (dd, J=8.5 Hz, 1.4 Hz, 1H), 7.45 (d, J=7.7 Hz, 1H), 7.07 (s, 1H), 6.85 (d, J=9.0 Hz, 1H), 4.37-4.26 (m, 2H), 4.21 (s, 2H), 3.81-3.62 (m, 2H), 3.67-3.56 (m, 4H), 3.52-3.34 (m, 2H), 2.09-1.90 (m, 4H), 1.45-1.14 (m, 4H).

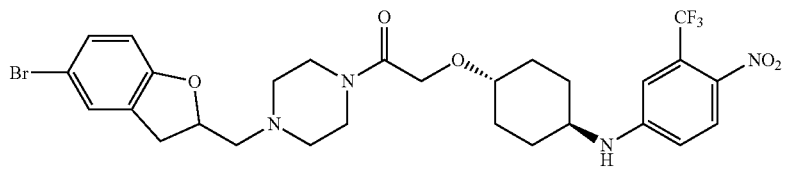 [SMILES: O=C(CO[C@H]1CC[C@H](Nc2ccc([N+](=O)[O-])c(C(F)(F)F)c2)CC1)N1CCN(CC2Cc3cc(Br)ccc3O2)CC1]

Compound 299: 2-[(4-[[4-nitro-3-(trifluoromethyl)phenyl]amino]-cyclohexyl)oxy]-1-[4-(5-bromobenzofuran-2-ylmethyl)-piperazin-1-yl]ethan-1-one (CI, m/z): [M+H]$^+$ 641; $^1$H NMR (400 MHz, DMSO-d6): δ 8.05 (d, J=9.2 Hz, 1H), 7.44 (d, J=7.7 Hz, 1H), 7.37 (s, 1H), 7.22 (dd, J=8.5 Hz, 2.2 Hz, 1H), 7.07 (s, 1H), 6.85 (dd, J=9.2 Hz, 2.3 Hz, 1H), 6.71 (d, J=8.4 Hz, 1H), 5.04-4.90 (m, 1H) 4.13 (s, 2H), 3.52-3.22 (m, 6H) 2.99-2.91 (m, 1H), 2.69-2.62 (m, 1H), 2.59-2.41 (m, 6H), 2.06-1.90 (m, 4H), 1.42-1.16 (m, 4H).

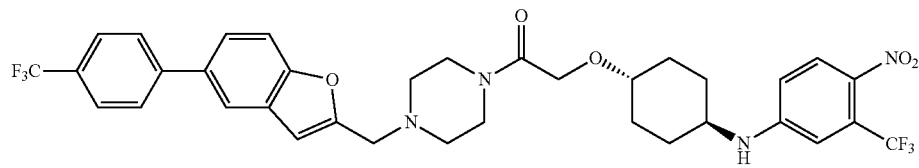 [SMILES: O=C(CO[C@H]1CC[C@H](Nc2ccc([N+](=O)[O-])c(C(F)(F)F)c2)CC1)N1CCN(Cc2cc3cc(-c4ccc(C(F)(F)F)cc4)ccc3o2)CC1]

Compound 380: 2-[(4-[[4-nitro-3-(trifluoromethyl)phenyl]amino]cyclohexyl)-oxy]1-[4-[5-[4-(trifluoromethyl)phenyl]2,3-dihydrobenzofuran-2-ylmethyl]piperazin-1-yl]ethan-1-one (CI, m/z): [M+H]$^+$ 706; $^1$H NMR (400 MHz, CD$_2$Cl$_2$): δ 8.01 (d, J=9.1 Hz, 1H), 7.69-7.64 (m, 4H), 7.46 (s, 1H), 7.39 (d, J=8.2 Hz, 1H), 6.87 (d, J=2.5 Hz, 1H), 6.84 (d, J=8.3 Hz, 1H), 6.67 (dd, J=9.1 Hz, 2.6 Hz, 1H), 4.63 (d, J=8.0 Hz, 1H), 4.17 (s, 2H), 3.66-3.29 (m, 6H), 3.08-3.02 (m, 1H), 2.86-2.49 (m, 5H), 2.18-2.06 (m, 4H), 1.59-1.20 (m, 7H).

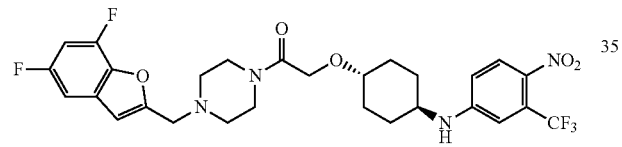

Compound 375: 1-[4-(5,7-difluoro-benzooxazol-2-ylmethyl)-piperazin-1-yl]-2-[4-(4-nitro-3-trifluoromethyl-phenylamino)-cyclohexyloxy]-ethanone (CI, m/z): [M+H]$^+$ 597; $^1$H NMR (400 MHz, DMSO-d$_6$): δ 8.05 (d, J=9.23 Hz, 1H), 7.43 (d, J=7.86 Hz, 1H), 7.31 (dd, J=8.44, 2.44 Hz, 1H), 7.24 (ddd, J=11.08, 9.81, 2.39 Hz, 1H), 7.06 (s, 1H), 6.92 (d, J=2.98 Hz, 1H), 6.84 (dd, J=9.27, 2.49 Hz, 1H), 4.12 (s, 2H), 3.76 (s, 2H), 3.44 (br. s., 5H), 2.44 (br. s., 4H), 1.95-2.02 (m, 2H), 1.92 (d, J=11.86 Hz, 2H), 1.27-1.39 (m, 2H), 1.17-1.26 (m, 2H); $^{19}$F NMR (376 MHz, DMSO-d$_6$): δ ppm −133.63 (dt, J=11.21, 2.97 Hz, 1F) −117.37--117.11 (m, 1F) −59.15 (s, 3F).

EXAMPLE 36: Preparation of Compound 376

Compound 376

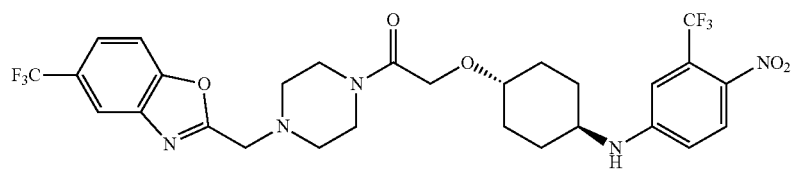

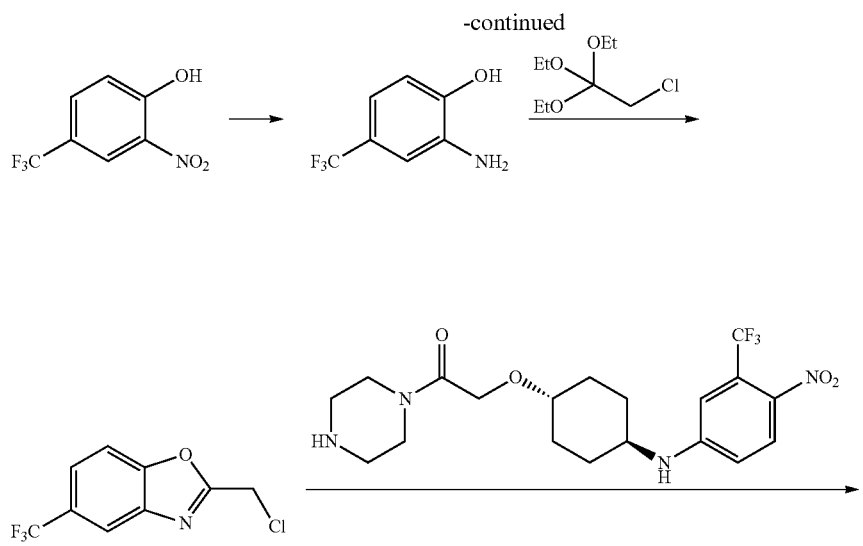

Step 1. Formation of 2-amino-4-trifluoromethylphenol

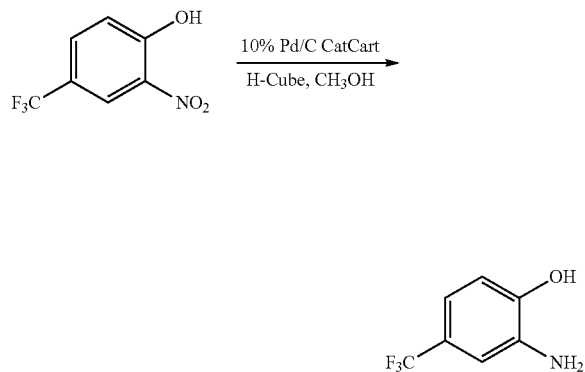

2-Nitro-4-trifluoromethylphenol (340 µL, 2.41 mmol) was dissolved in methanol (50 mL) and processed through the H-Cube with a 10% Pd/C Catalyst cartridge at ambient temperature and pressure. The eluent was concentrated under reduced pressure to provide 2-amino-4-trifluoromethylphenol as a light brown solid (438 mg, 100%). (CI, m/z): [M+H]$^+$ 178, [M−H]$^−$ 176; $^1$H NMR (CDCl$_3$): δ 6.96 (d, J=2.0 Hz, 1H), 6.89-6.94 (m, 1H), 6.74 (d, J=8.2 Hz, 1H), 4.10 (br s, 2H).

Step 2. Formation of 2-chloromethyl-5-trifluoromethyl-benzoxazole

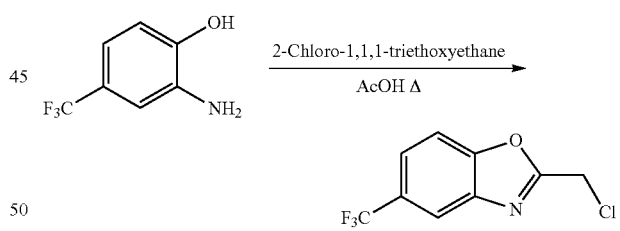

2-Chloro-1,1,1-triethoxyethane (410 µL, 2.15 mmol) was added to a suspension of 2-amino-4-trifluoromethylphenol (370 mg, 1.79 mmol) in acetic acid (7 mL); during the addition the solution began to clear. The solution was heated at 120° C. (external temperature). After three hours the reaction mixture was cooled and the volatiles were removed under reduced pressure. Purification by silica gel chromatography, eluting with a gradient of 0 to 10% ethyl acetate in heptanes, gave 2-chloromethyl-5-trifluoromethyl-benzoxazole as a yellow oil (324 mg, 77%). (CI, m/z): [M+H]$^+$ 236; $^1$H NMR (CDCl$_3$): δ 8.05 (s, 1H), 7.66-7.73 (m, 2H), 4.79 (s, 2H); $^{19}$F NMR (376 MHz, CDCl$_3$): δ ppm −61.26 (s, 3F).

Step 3. Formation of 2-[4-(4-nitro-3-trifluoromethyl-phenylamino)-cyclohexyloxy]-1-[4-(5-trifluoromethyl-benzooxazol-2-ylmethyl)-piperazin-1-yl]-ethanone (#376)

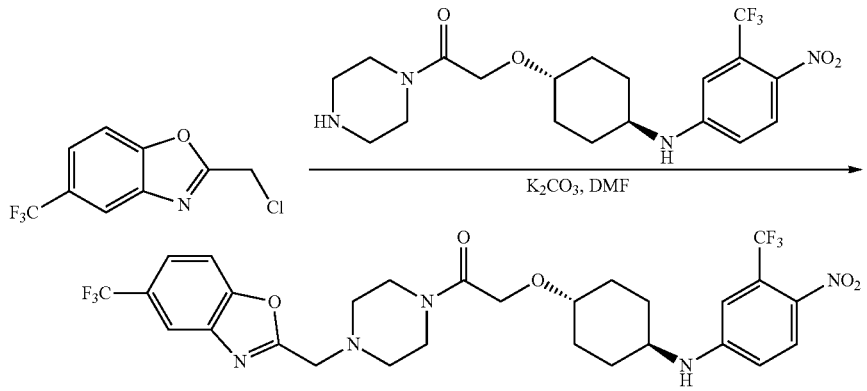

A mixture of 2-chloromethyl-5-trifluoromethyl-benzoxazole (50 mg, 0.214 mmol), 2-[4-(4-Nitro-3-trifluoromethyl-phenylamino)-cyclohexyloxy]-1-piperazin-1-yl-ethanone hydrochloride (100 mg, 0.214 mmol), potassium carbonate (60 mg, 0.428 mmol), and DMF (1 mL) was heated at 100° C. for two hours before the reaction mixture was cooled, diluted with EtOAc (60 mL), washed with water (2×40 mL), washed with brine (1×40 mL), dried over sodium sulfate, filtered, and concentrated under reduced pressure to an orange residue that was purified by silica gel chromatography, eluting with a gradient of 0 to 100% EtOAc in heptanes, to provide 2-[4-(4-nitro-3-trifluoromethyl-phenylamino)-cyclohexyloxy]-1-[4-(5-trifluoromethyl-benzooxazol-2-ylmethyl)-piperazin-1-yl]-ethanone as a stiff, orange solid (69 mg, 51%). (CI, m/z): [M+H]+ 360; $^1$H NMR (400 MHz, DMSO-$d_6$): δ 8.17 (s, 1H), 8.05 (d, J=9.23 Hz, 1H), 7.97 (d, J=8.54 Hz, 1H), 7.77 (dd, J=8.57, 1.44 Hz, 1H), 7.43 (d, J=7.71 Hz, 1H), 7.06 (s, 1H), 6.84 (dd, J=9.30, 2.51 Hz, 1H), 3.99 (s, 2H) 4.12 (s, 2H), 3.45 (br s, 5H), 2.52-2.64 (m, 4H), 1.95-2.04 (m, 2H), 1.92 (d, J=10.59 Hz, 2H), 1.28-1.40 (m, 2H), 1.19-1.27 (m, 2H); $^{19}$F NMR (376 MHz, DMSO-$d_6$): δ ppm −59.45 (s, 3F) −59.17 (s, 3F).

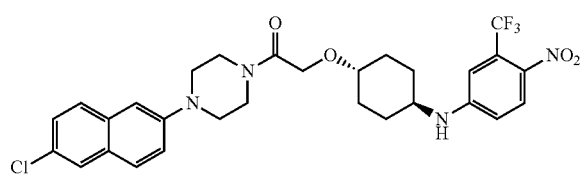 [SMILES: O=C(CO[C@H]1CC[C@H](Nc2ccc([N+](=O)[O-])c(C(F)(F)F)c2)CC1)N1CCN(c2ccc3cc(Cl)ccc3c2)CC1]

Compound 233: 1-[4-(6-chloro-2-naphthyl)piperazin-1-yl]-2-[4-[4-nitro-3-(trifluoromethyl)anilino]cyclohexoxy]ethanone (CI, m/z): [M+H]+ 591; $^1$H NMR (400 MHz, CD$_3$OD): δ 8.02 (d, J=9.1 Hz, 1H), 7.72 (d, J=1.9 Hz, 1H), 7.66 (dd, J=17.5, 9.0 Hz, 2H), 7.37 (dd, J=8.8, 2.1 Hz, 1H), 7.29 (dd, J=9.0, 2.4 Hz, 1H), 7.10 (d, J=2.3 Hz, 1H), 6.85 (d, J=2.5 Hz, 1H), 6.64 (dd, J=9.1, 2.6 Hz, 1H), 4.45 (d, J=7.9 Hz, 1H), 4.27 (s, 2H), 3.72-3.88 (m, 4H), 3.35-3.55 (m, 2H), 3.30 (d, J=4.3 Hz, 4H), 2.17 (d, J=10.2 Hz, 4H), 1.43-1.55 (m, 2H), 1.24-1.37 (m, 2H).

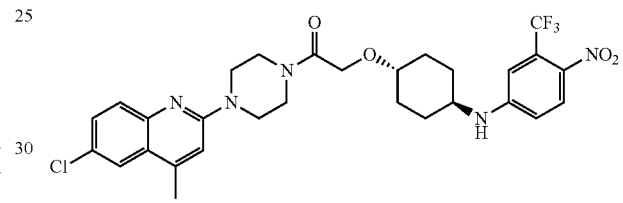

1-[4-(6-chloro-4-methyl-2-quinolyl)piperazin-1-yl]-2-[4-[4-nitro-3-(trifluoromethyl)anilino]cyclohexoxy]ethanone (#270)

(CI, m/z): [M+H]+ 606; $^1$H NMR (400 MHz, CD$_3$OD): δ 8.02 (d, J=9.1 Hz, 1H), 7.76 (d, J=2.3 Hz, 1H), 7.65 (d, J=8.9 Hz, 1H), 7.49 (dd, J=8.9, 2.4 Hz, 1H), 6.82-6.90 (m, 2H), 6.64 (dd, J=9.1, 2.6 Hz, 1H), 4.46 (d, J=7.7 Hz, 1H), 3.65-3.89 (m, 8H), 4.27 (s, 2H), 3.32-3.54 (m, 2H), 2.59 (d, J=0.6 Hz, 3H), 2.16 (d, J=10.1 Hz, 4H), 1.43-1.55 (m, 2H), 1.25-1.36 (m, 2H).

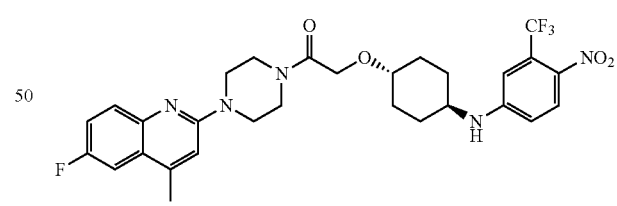

1-[4-(6-fluoro-4-methyl-2-quinolyl)piperazin-1-yl]-2-[4-[4-nitro-3-(trifluoromethyl)anilino]cyclohexoxy]ethanone (#99)

(CI, m/z): [M+H]+ 590; $^1$H NMR (400 MHz, CD$_3$OD): δ 8.02 (d, J=9.1 Hz, 1H), 7.71 (dd, J=9.1, 5.4 Hz, 1H), 7.42 (dd, J=9.8, 2.8 Hz, 1H), 7.30-7.37 (m, 1H), 6.89 (s, 1H), 6.85 (d, J=2.6 Hz, 1H), 6.64 (dd, J=9.1, 2.6 Hz, 1H), 4.46 (d, J=7.6 Hz, 1H), 4.27 (s, 2H), 3.65-3.86 (m, 8H), 3.33-3.55 (m, 2H), 2.59 (s, 3H), 2.10-2.25 (m, 4H), 1.44-1.55 (m, 2H), 1.23-1.37 (m, 2H).

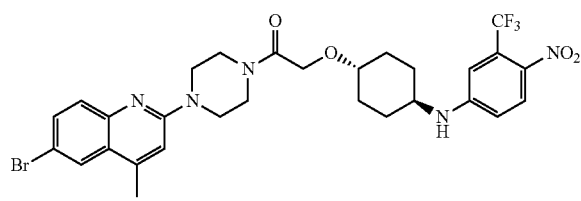 [SMILES: Cc1cc(N2CCN(C(=O)CO[C@H]3CC[C@H](Nc4ccc([N+](=O)[O-])c(C(F)(F)F)c4)CC3)CC2)nc2ccc(Cl)cc12]

Compound 277: 1-[4-(6-bromo-4-methyl-2-quinolyl)piperazin-1-yl]-2-[4-[4-nitro-3-(trifluoromethyl)anilino]cyclohexoxy]ethanone (CI, m/z): [M+2]⁺652; ¹H NMR (400 MHz, CD₃OD): δ 8.02 (d, J=9.1 Hz, 1H), 7.92 (d, J=2.0 Hz, 1H), 7.54-7.66 (m, 2H), 6.83-6.88 (m, 2H), 6.64 (dd, J=9.1, 2.6 Hz, 1H), 4.45 (d, J=7.5 Hz, 1H), 4.27 (s, 2H), 3.67-3.89 (m, 8H), 3.34-3.54 (m, 2H), 2.59 (s, 3H), 2.16 (d, J=10.3 Hz, 4H), 1.44-1.55 (m, 2H), 1.23-1.37 (m, 2H).

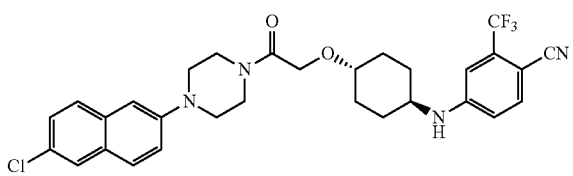 [SMILES: N#Cc1ccc(N[C@H]2CC[C@H](OCC(=O)N3CCN(c4ccc5cc(Cl)ccc5c4)CC3)CC2)cc1C(F)(F)F]

Compound 278: 4-[[4-[2-[4-(6-chloro-2-naphthyl)piperazin-1-yl]-2-oxo-ethoxy]cyclohexyl]amino]-2-methyl-benzonitrile (CI, m/z): [M+H]⁺ 571; ¹H NMR (400 MHz, CD₃OD): δ 7.72 (d, J=1.9 Hz, 1H), 7.66 (dd, J=17.6, 9.0 Hz, 2H), 7.55 (d, J=8.5 Hz, 1H), 7.37 (dd, J=8.7, 2.1 Hz, 1H), 7.28-7.31 (m, 1H), 7.10 (d, J=2.2 Hz, 1H), 6.81 (d, J=2.3 Hz, 1H), 6.66 (dd, J=8.6, 2.4 Hz, 1H), 4.24-4.35 (m, 3H), 3.73-3.89 (m, 4H), 3.22-3.54 (m, 6H), 2.10-2.25 (m, 4H), 1.41-1.54 (m, 2H), 1.21-1.35 (m, 2H).

EXAMPLE 37: Preparation of Compound 235

Compound 235

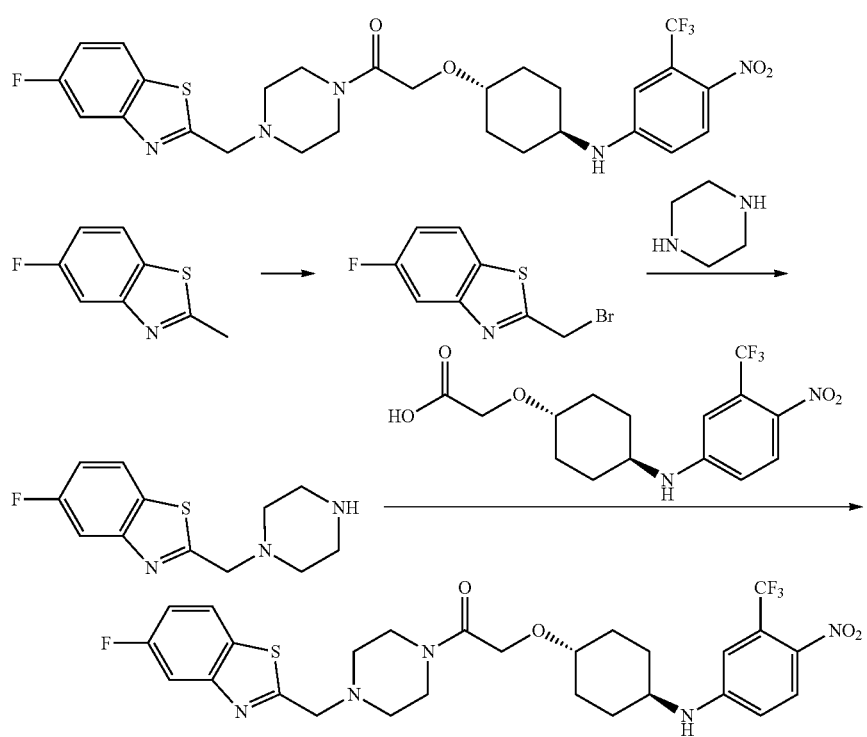

Step 1. Formation of 2-(bromomethyl)-5-fluoro-1,3-benzothiazole

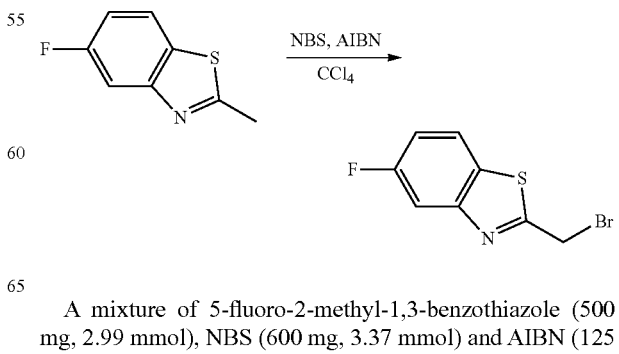

A mixture of 5-fluoro-2-methyl-1,3-benzothiazole (500 mg, 2.99 mmol), NBS (600 mg, 3.37 mmol) and AIBN (125 mg, 0.76 mmol) in carbon tetrachloride (25 ml) was heated at reflux for 20 hours under nitrogen with stirring. The solution was then concentrated to give a residue which was purified by silica gel column chromatography using 1% ethyl acetate in petroleum ether to afford 2-(bromomethyl)-5-fluoro-1,3-benzothiazole as a yellow solid (150 mg, 20%). $^1$H NMR (400 MHz, CDCl$_3$): δ 7.81 (dd, J=8.8, 5.2 Hz, 1H), 7.70 (dd, J=9.2, 2.4 Hz, 1H), 7.23-7.16 (m, 1H), 4.80 (s, 2H).

Step 2. Formation of 5-fluoro-2-(piperazin-1-ylmethyl)-1,3-benzothiazole

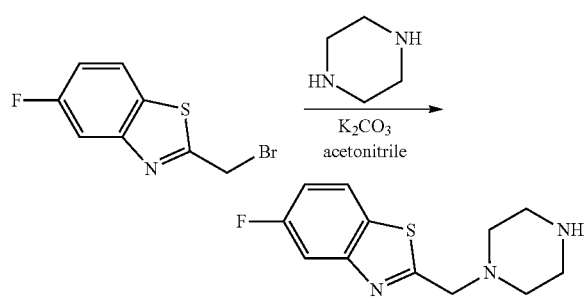

A mixture of 2-(bromomethyl)-5-fluoro-1,3-benzothiazole (150 mg, 0.61 mmol), potassium carbonate (253 mg, 1.83 mmol) and piperazine (263 mg, 3.05 mmol) in acetonitrile (30 ml) was heated at reflux for 4.5 hours with stirring and was then concentrated under vacuum. The residue was dissolved in dichloromethane (100 ml), washed with brine (3×50 mL), dried over anhydrous sodium sulfate, filtered and concentrated under vacuum to afford 5-fluoro-2-(piperazin-1-ylmethyl)-1,3-benzothiazole as a yellow crude solid (130 mg). (ES, m/z): [M+H]$^+$ 252.1; $^1$H NMR (400 MHz, CDCl$_3$): δ 7.81 (dd, J=8.8, 5.2 Hz, 1H), 7.70 (dd, J 9.6, 2.4 Hz, 1H), 7.16-7.11 (m, 1H), 3.93 (s, 2H), 2.97-2.93 (m, 4H), 2.64-2.63 (m, 4H), 1.98 (s, 1H).

Step 3. Formation of 1-(4-((5-fluorobenzo[d]thiazol-2-yl)methyl)piperazin-1-yl)-2-(-4-(4-nitro-3-(trifluoromethyl)phenylamino)cyclohexyloxy)ethanone (#235)

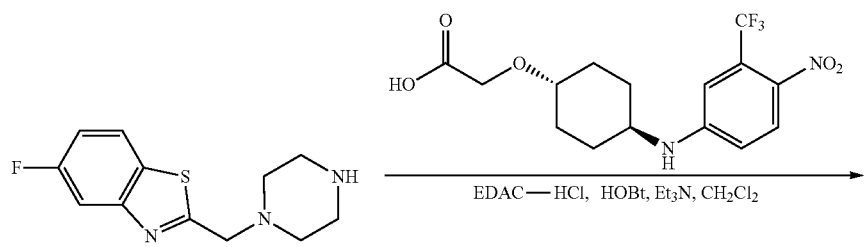

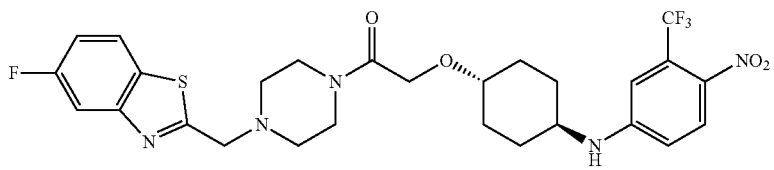

A mixture of 5-fluoro-2-(piperazin-1-ylmethyl)-1,3-benzothiazole (130 mg, 0.52 mmol), EDAC.HCl (149 mg, 0.78 mmol), HOBt (105 mg, 0.78 mmol) and triethylamine (157 mg, 1.55 mmol) in dichloromethane (30 ml) was stirred for 1 hour at room temperature before the addition of 2-(-4-(4-nitro-3-(trifluoromethyl)phenylamino)cyclohexyloxy)acetic acid (187 mg, 0.52 mmol). After stirring overnight at room temperature, the solution was diluted with dichloromethane (100 ml) and washed with water (50 ml), dried over anhydrous sodium sulfate, filtered, and concentrated under vacuum to give a residue, which was purified by HPLC to afford 1-(4-((5-fluorobenzo[d]thiazol-2-yl)methyl)piperazin-1-yl)-2-(-4-(4-nitro-3-(trifluoromethyl)phenylamino)cyclohexyloxy)ethanone as a yellow solid (162.0 mg, 53%).

(ES, m/z): [M+H]$^+$ 596.00; $^1$H NMR (300 MHz, CDCl$_3$): δ 8.01 (d, J=9.0 Hz, 1H), 7.87 (dd, J=8.7, 4.8 Hz, 1H), 7.72 (dd, J=9.0, 2.4 Hz, 1H), 7.29-7.23 (m, 1H), 6.84 (d, J=2.1 Hz, 1H), 6.62 (dd, J=9.0, 2.1 Hz, 1H), 5.52 (br s, 1H), 4.47 (s, 2H), 4.20 (s, 2H), 3.93-3.90 (m, 4H), 3.43-3.33 (m, 2H), 3.22-3.19 (m, 4H), 2.11-2.01 (m, 4H), 1.48-1.37 (m, 2H), 1.32-1.21 (m, 2H).

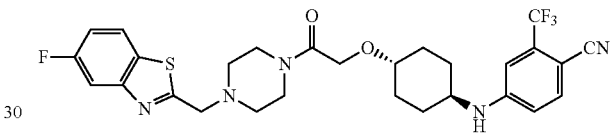

Compound 294: 4-[[4-[2-[4-[(5-fluoro-1,3-benzothiazol-2-yl)methyl]piperazin-1-yl]-2-oxo-ethoxy]cyclohexyl]amino]-2-(trifluoromethyl)benzonitrile (CI, m/z): [M+H]$^+$ 576; $^1$H NMR (400 MHz, CD$_3$OD): δ 0.7.81 (dd, J=8.8, 5.1 Hz, 1H), 7.66 (dd, J=9.4, 2.4 Hz, 1H), 7.55 (d, J=8.6 Hz, 1H), 7.17 (td, J=8.8, 2.5 Hz, 1H), 6.81 (d, J 2.3 Hz, 1H), 6.66 (dd, J=8.6, 2.4 Hz, 1H), 4.34 (d, J=7.4 Hz, 1H), 4.20 (s, 2H), 3.99 (s, 2H), 3.54-3.78 (m, 4H), 3.28-3.50 (m, 2H), 2.67 (t, J=4.9 Hz, 4H), 2.13 (d, J=8.8 Hz, 4H), 1.38-1.53 (m, 2H), 1.23-1.29 (m, 2H).

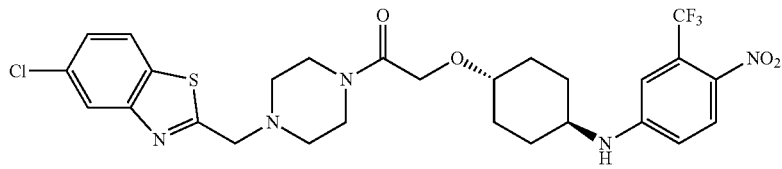 [SMILES: O=C(CO[C@H]1CC[C@H](Nc2ccc([N+](=O)[O-])c(C(F)(F)F)c2)CC1)N1CCN(Cc2nc3cc(Cl)ccc3s2)CC1]

Compound 291: 1-[4-[(5-chloro-1,3-benzothiazol-2-yl)methyl]piperazin-1-yl]-2-[4-[4-nitro-3-(trifluoromethyl)anilino]cyclohexoxy]ethanone (CI, m/z): [M+H]$^+$ 612; $^1$H NMR (400 MHz, CD$_3$OD): δ 8.02 (d, J=9.0 Hz, 1H), 7.96 (d, J=1.9 Hz, 1H), 7.79 (d, J=8.5 Hz, 1H), 7.37 (dd, J=8.5, 1.9 Hz, 1H), 6.85 (d, J=2.2 Hz, 1H), 6.64 (dd, J=9.0, 2.4 Hz, 1H), 4.48 (d, J=7.6 Hz, 1H), 4.21 (s, 2H), 3.99 (s, 2H), 3.58-3.77 (m, 4H), 3.33-3.49 (m, 2H), 2.67 (t, J=4.9 Hz, 4H), 2.14 (d, J=11.0 Hz, 4H), 1.41-1.53 (m, 2H), 1.23-1.34 (m, 2H).

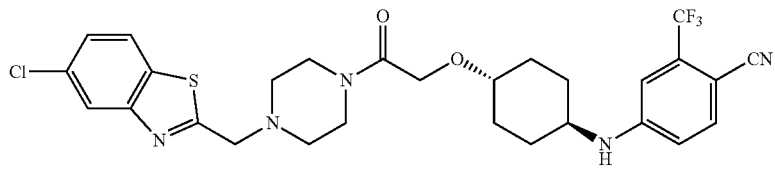

Compound 292: 4-[[4-[2-[4-[(5-chloro-1,3-benzothiazol-2-yl)methyl]piperazin-1-yl]-2-oxo-ethoxy]cyclohexyl]amino]-2-(trifluoromethyl)benzonitrile (CI, m/z): [M+H]$^+$ 592; $^1$H NMR (400 MHz, CD$_3$OD): δ 7.96 (d, J=1.9 Hz, 1H), 7.79 (d, J=8.5 Hz, 1H), 7.55 (d, J=8.6 Hz, 1H), 7.37 (dd, J=8.5, 2.0 Hz, 1H), 6.81 (d, J=2.3 Hz, 1H), 6.66 (dd, J=8.6, 2.3 Hz, 1H), 4.30 (d, J=7.7 Hz, 1H), 4.20 (s, 2H), 3.99 (s, 2H), 3.55-3.76 (m, 4H), 3.28-3.49 (m, 2H), 2.58-2.74 (m, 4H), 2.13 (d, J=8.5 Hz, 4H), 1.38-1.53 (m, 2H), 1.18-1.35 (m, 2H).

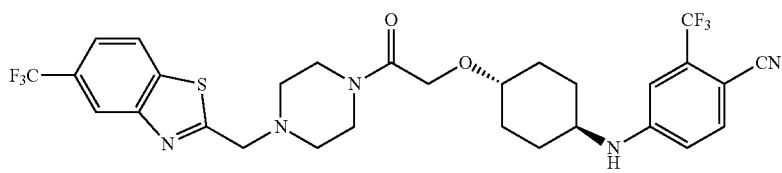 [SMILES: N#Cc1ccc(N[C@H]2CC[C@H](OCC(=O)N3CCN(Cc4nc5cc(C(F)(F)F)ccc5s4)CC3)CC2)cc1C(F)(F)F]

Compound 301: 4-[[4-[2-oxo-2-[4-[[5-(trifluoromethyl)-1,3-benzothiazol-2-yl]methyl]piperazin-1-yl]ethoxy]cyclohexyl]amino]-2-(trifluoromethyl)benzonitrile (CI, m/z): [M+H]$^+$ 626; $^1$H NMR (400 MHz, CD$_3$OD): δ 8.24 (s, 1H), 8.00 (d, J=8.3 Hz, 1H), 7.63 (dd, J=8.4, 1.4 Hz, 1H), 7.55 (d, J=8.6 Hz, 1H), 6.81 (d, J=2.4 Hz, 1H), 6.66 (dd, J=8.6, 2.4 Hz, 1H), 4.31 (d, J=7.3 Hz, 1H), 4.21 (s, 2H), 4.02 (s, 2H), 3.59-3.77 (m, 4H), 3.30-3.48 (m, 2H), 2.59-2.80 (m, 4H), 2.13 (d, J=9.9 Hz, 4H), 1.38-1.54 (m, 2H), 1.22-1.32 (m, 2H).

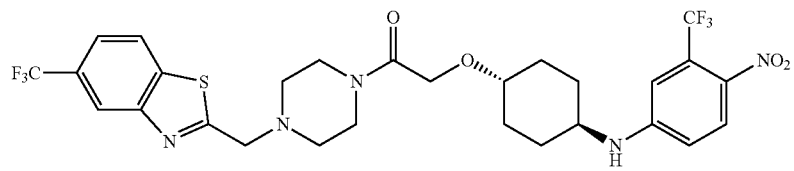 [SMILES: O=C(CO[C@H]1CC[C@H](Nc2ccc([N+](=O)[O-])c(C(F)(F)F)c2)CC1)N1CCN(Cc2nc3cc(C(F)(F)F)ccc3s2)CC1]

Compound 302: 2-[4-[4-nitro-3-(trifluoromethyl)anilino]cyclohexoxy]-1-[4-[[5-(trifluoromethyl)-1,3-benzothiazol-2-yl]methyl]piperazin-1-yl]ethanone (CI, m/z): [M+H]$^+$ 646; $^1$H NMR (400 MHz, CD$_3$OD): δ 8.24 (s, 1H), 8.01 (t, J=8.2 Hz, 2H), 7.63 (dd, J=8.5, 1.4 Hz, 1H), 6.85 (d, J=2.6 Hz, 1H), 6.64 (dd, J=9.1, 2.6 Hz, 1H), 4.39-4.57 (m, 1H), 4.21 (s, 2H), 4.03 (s, 2H), 3.59-3.80 (m, 4H), 3.33-3.50 (m, 2H), 2.68 (t, J=5.0 Hz, 4H), 2.14 (d, J=11.0 Hz, 4H), 1.41-1.53 (m, 2H), 1.30 (m., 2H).

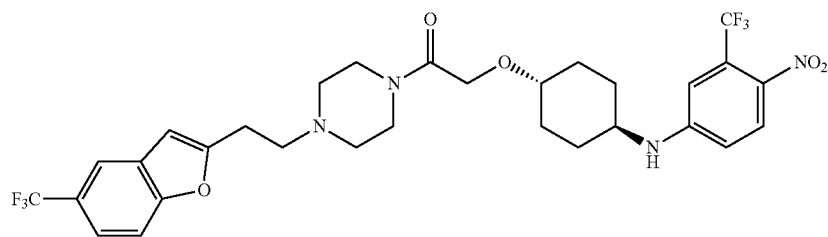 [SMILES: O=C(CO[C@H]1CC[C@H](Nc2ccc([N+](=O)[O-])c(C(F)(F)F)c2)CC1)N1CCN(CCc2cc3cc(C(F)(F)F)ccc3o2)CC1]

Compound 324: 2-[4-[4-nitro-3-(trifluoromethyl)anilino]cyclohexoxy]-1-[4-[2-[5-(trifluoromethyl)benzofuran-2-yl]ethyl]piperazin-1-yl]ethanone (CI, m/z): [M+H]$^+$ 643; $^1$H NMR (400 MHz, CD$_3$OD): δ 8.02 (d, J=9.0 Hz, 1H), 7.79 (s, 1H), 7.49 (d, J=1.1 Hz, 2H), 6.85 (d, J=2.5 Hz, 1H), 6.63 (dd, J=9.1, 2.6 Hz, 1H), 6.53 (s, 1H), 4.51 (d, J=7.6 Hz, 1H), 4.20 (s, 2H), 3.52-3.71 (m, 4H), 3.32-3.50 (m, 2H), 2.97-3.08 (m, 2H), 2.77-2.88 (m, 2H), 2.54 (t, J=4.8 Hz, 4H), 2.15 (d, J=10.6 Hz, 4H), 1.40-1.55 (m, 2H), 1.27-1.34 (m, 2H).

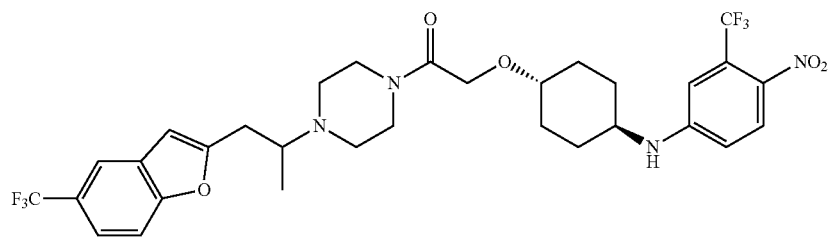 [SMILES: CC(Cc1cc2cc(C(F)(F)F)ccc2o1)N1CCN(C(=O)CO[C@H]2CC[C@H](Nc3ccc([N+](=O)[O-])c(C(F)(F)F)c3)CC2)CC1]

Compound 330: 1-[4-[1-methyl-2-[5-(trifluoromethyl)benzofuran-2-yl]ethyl]piperazin-1-yl]-2-[4-[4-nitro-3-(trifluoromethyl)anilino]cyclohexoxy]ethanone (CI, m/z): [M+H]$^+$ 657; $^1$H NMR (400 MHz, CD$_3$OD): δ 8.02 (d, J=9.1 Hz, 1H), 7.79 (s, 1H), 7.49 (d, J=1.1 Hz, 2H), 6.85 (d, J=2.4 Hz, 1H), 6.64 (dd, J=9.1, 2.6 Hz, 1H), 6.52 (s, 1H), 4.45 (d, J=7.5 Hz, 1H), 4.16-4.23 (m, 2H), 3.63-3.51 (m, 4H), 3.46-3.38 (m, 2H), 3.21-3.16 (m, 1H), 3.04-3.09 (m, 1H), 3.02-3.10 (m, 1H), 2.74 (dd, J=14.9, 8.2 Hz, 1H), 2.55-2.65 (m, 3H), 2.13-2.16 (m, 4H), 1.43-1.51 (m, 2H), 1.24-1.34 (m, 2H), 1.09 (d, J=6.6 Hz, 3H).

EXAMPLE 38: Preparation of Compound 331
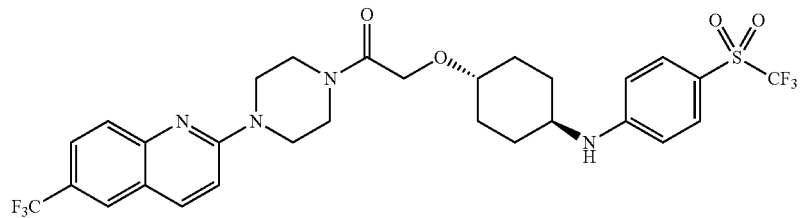
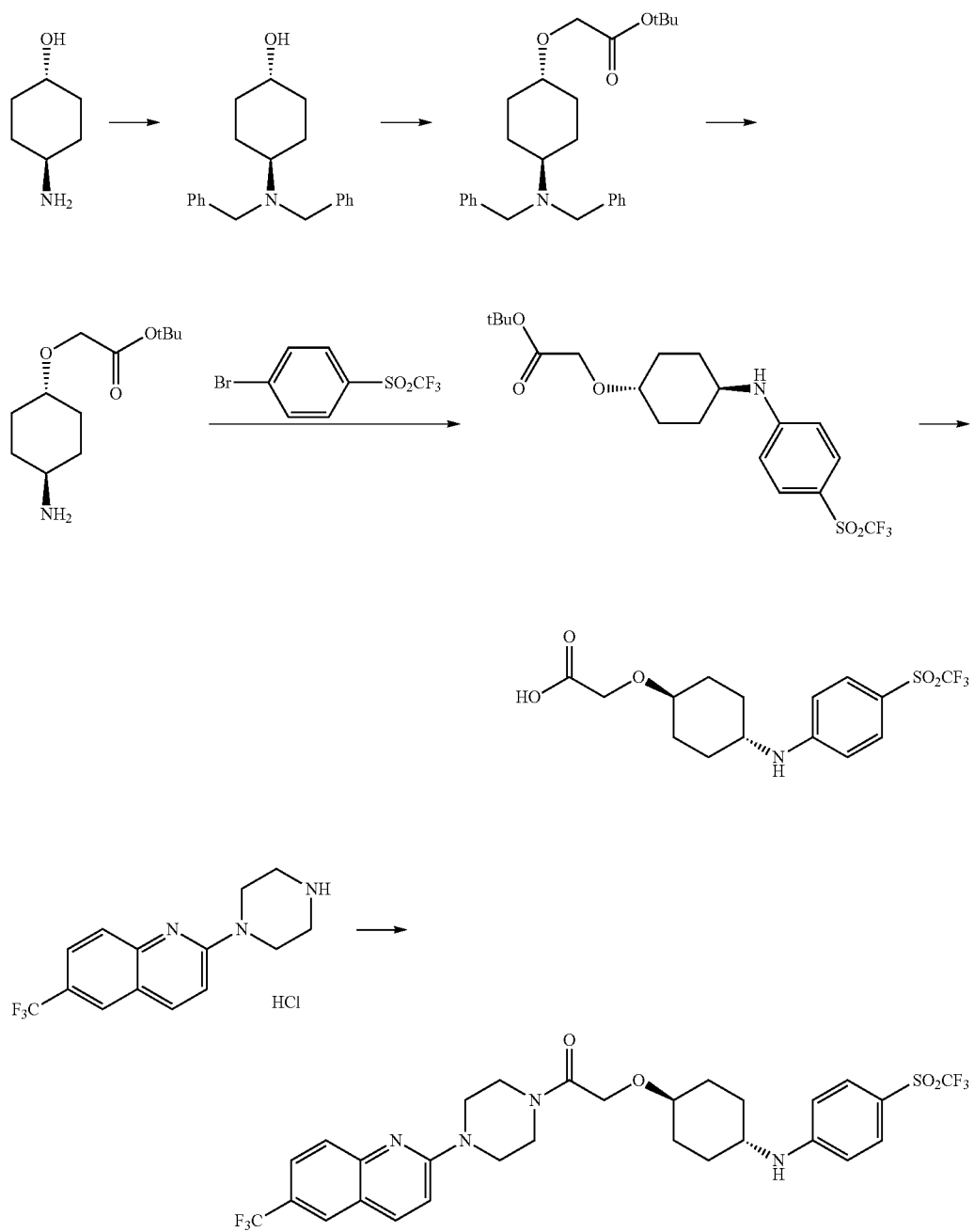

Steps 1-7

The formation of 2-piperazin-1-yl-6-(trifluoromethyl)quinoline hydrochloride is described in the synthesis of compound 89 with the difference being the use of BOC-piperazine in lieu of piperazine.

Step 8. Formation of (trans)-4,-4(dibenzylamino)cyclohexanol

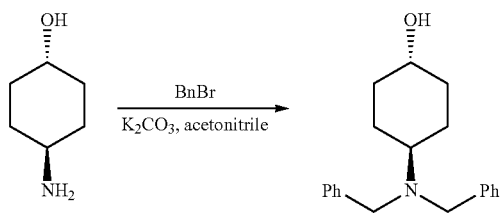

To a stirred solution of (trans)-4-aminocyclohexanol (5 g, 43 mmol, 1 eq.) in 200 mL of acetonitrile was added potassium carbonate (21 g, 152 mmol, 1 eq.) and benzylbromide (10.3 mL, 86.8 mmol, 2 eq.). The mixture was stirred at room temperature for 16 hours and then filtered. The filter cake was washed with dichloromethane and the filtrate was concentrated under vacuum. The crude material was dissolved with dichloromethane, washed with water and then saturated ammonium chloride, dried over sodium sulfate, and concentrated. The crude material was purified by silica gel column chromatography using ethyl acetate/heptanes to elute. The product containing fractions were combined and concentrated under vacuum to afford (trans)-4,-4 (dibenzylamino)cyclohexanol as a white solid (8.9 g, 70%); (CI, m/z): [M+H]$^+$ 296; $^1$H NMR (400 MHz, CDCl$_3$): δ 7.34-7.39 (m, 4H), 7.27-7.33 (m, 4H), 7.18-7.25 (m, 2H), 3.62 (s, 4H), 3.50-3.60 (m, 1H), 2.48-2.59 (m, 1H), 2.01 (m, 2H), 1.86-1.95 (m, 2H), 1.58 (br s, 1H), 1.38-1.50 (m, 2H), 1.14-1.26 (m, 2H).

Step 9. Formation of tert-butyl 2-[4-(dibenzylamino)cyclohexoxy]acetate

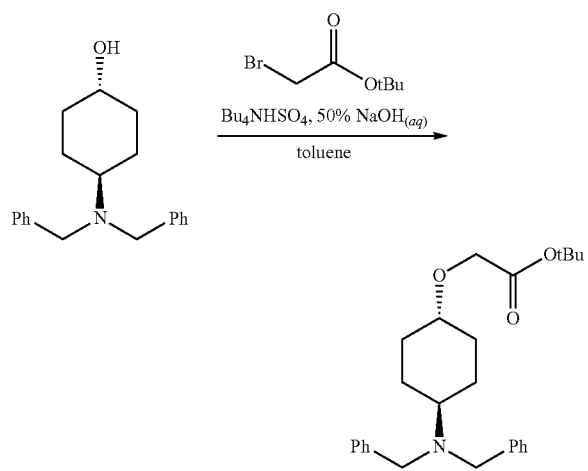

(Trans)-4,-4(dibenzylamino)cyclohexanol (8 g, 27 mmol, 1 eq.) was dissolved in toluene (100 mL) and mixed with tetrabutylammonium hydrogen sulfate (0.46 g, 1.35 mmol, 0.05 eq.) and tert-butyl bromoacetate (6 mL, 40.61 mmol, 1.5 eq.). Sodium hydroxide solution (26 mL, 50% aq.) was added dropwise with vigorous stirring. The mixture was stirred for 3 days at room temperature. After phase separation, the organic phase was washed with water and saturated sodium chloride solution, dried over sodium sulfate, and then concentrated under vacuum. The resulting crude product was purified by silica gel column chromatography using ethyl acetate/heptanes to elute. The product containing fractions were combined and concentrated under vacuum to afford tert-butyl 2-[4-(dibenzylamino)cyclohexoxy]acetate (6.2 g, 56%); (CI, m/z): [M+H]$^+$ 410; $^1$H NMR (400 MHz, CDCl$_3$): δ 7.33-7.39 (m, 4H), 7.27-7.32 (m, 4H), 7.18-7.24 (m, 2H), 3.97 (s, 2H), 3.61 (s, 4H), 3.21-3.31 (m, 1H), 2.48-2.59 (m, 1H), 2.05-2.15 (m, 2H), 1.88-1.98 (m, 2H), 1.48 (s, 9H), 1.33-1.45 (m, 2H), 1.15-1.27 (m, 2H).

Step 10. Formation of tert-butyl 2-(4-aminocyclohexoxy)acetate

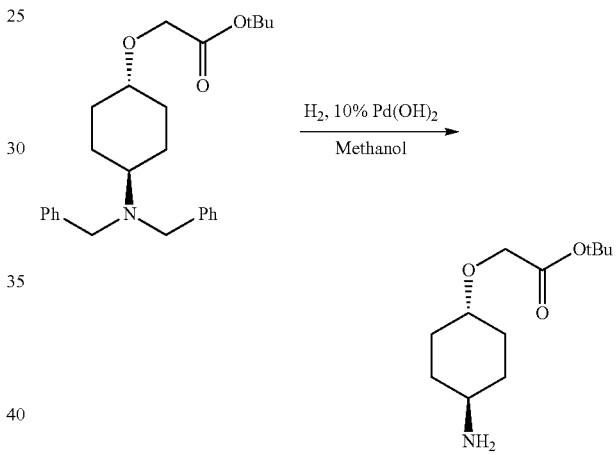

Tert-butyl 2-[4-(dibenzylamino)cyclohexoxy]acetate (6 g, 15 mmol, 1 eq.) was dissolved in methanol (200 mL) and pumped through the H-Cube® hydrogenation instrument containing a 10% Pd(OH)$_2$ catalyst cartridge (CatCart) and using full hydrogen flow, ambient pressure, at 40° C. for 3 hours. The solvent was removed under vacuum to provide tert-butyl 2-(4-aminocyclohexoxy)acetate (3.3 g, 98%); (CI, m/z): [M+H]$^+$ 230; $^1$H NMR (400 MHz, CDCl$_3$): δ 3.99 (s, 2H), 3.31 (tt, J=10.7, 4.2 Hz, 1H), 2.71 (tt, J=10.8, 3.9 Hz, 1H), 2.00-2.11 (m, 2H), 1.83-1.93 (m, 2H), 1.46-1.51 (m, 9H), 1.29-1.44 (m, 4H), 1.06-1.19 (m, 2H).

Step 11. Formation of tert-butyl 2-[4-[4-(trifluoromethylsulfonyl)anilino]cyclohexoxy]acetate

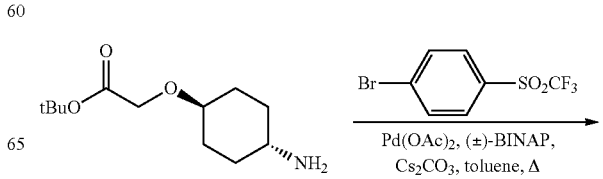

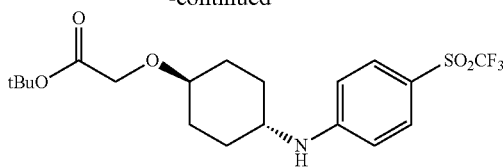

A suspension of tert-butyl 2-(4-aminocyclohexoxy)acetate (0.5 g, 1.7 mmol, 1 eq.), 1-bromo-4-(trifluoromethylsulfonyl)benzene (0.4 g, 1.7 mmol, 1 eq.), cesium carbonate (1.4 g, 4.3 mmol, 2.5 eq.), and BINAP (54 mg, 0.08 mmol, 0.05 eq.), in toluene (15 mL), was bubbled with nitrogen for 10 minutes before the addition of Pd(OAc)$_2$ (19 mg, 0.08 mmol, 0.05 eq.) to the reaction mixture. Nitrogen gas was bubbled through the reaction mixture for another 10 minutes and the contents were heated at 100° C. under nitrogen atmosphere for 3 hours. The contents were cooled to room temperature, diluted with ethyl acetate, filtered through Celite®, and concentrated. The crude material was purified by silica gel column chromatography using ethyl acetate/heptanes to elute. The product containing fractions were combined and concentrated to obtain tert-butyl 2-[4-[4-(trifluoromethylsulfonyl)anilino]cyclohexoxy]acetate (0.73 g, 77%); (CI, m/z): [M+H]$^+$ 438; $^1$H NMR (400 MHz, CDCl$_3$): δ 7.74 (d, J=8.9 Hz, 2H), 6.56-6.70 (m, 2H), 4.44 (d, J=7.4 Hz, 1H), 4.02 (s, 2H), 3.32-3.49 (m, 2H), 2.07-2.25 (m, 4H), 1.44-1.55 (m, 11H), 1.21-1.35 (m, 2H).

Step 12. Formation of trufluoro acetic acid salt of 2-[4-[4-(trifluoromethylsulfonyl)anilino]cyclohexoxy]acetic acid

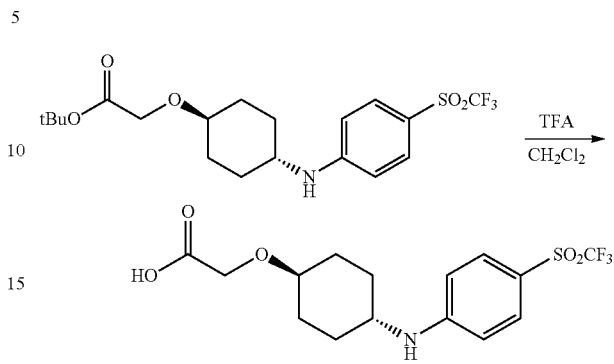

To a solution of tert-butyl 2-[4-[4-(trifluoromethylsulfonyl)anilino]cyclohexoxy]acetate (0.7 g, 1.6 mmol, 1 eq.) in trifluroacetic acid (3 mL) was stirred at room temperature for 2 hours. The mixture was concentrated under vacuum to remove excess trifluoroacetic acid. The crude material was dried under high vacuum overnight to obtain 2-[4-[4-(trifluoromethylsulfonyl) anilino]cyclohexoxy]acetic acid as light brown syrup. (0.79 g, 100%); (CI, m/z): [M+H]$^+$ 382; $^1$H NMR (400 MHz, CD$_3$OD): δ 7.65 (d, J=9.0 Hz, 2H), 6.76 (d, J=9.2 Hz, 2H), 4.13 (s, 2H), 3.37-3.51 (m, 2H), 2.03-2.20 (m, 4H), 1.26-1.54 (m, 4H).

Step 13. Formation of 1-[4-[6-(trifluoromethyl)-2-quinolyl]piperazin-1-yl]-2-[4-[4-(trifluoromethylsulfonyl)anilino]cyclohexoxy]ethanone (#331)

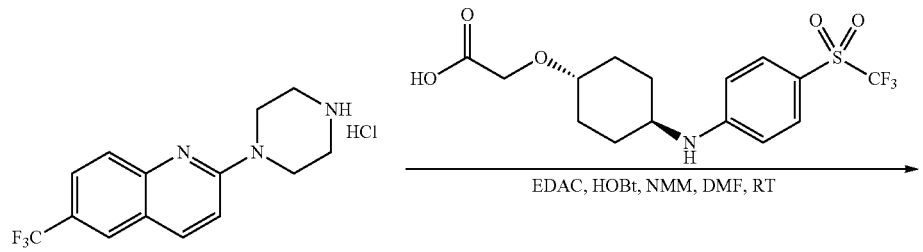

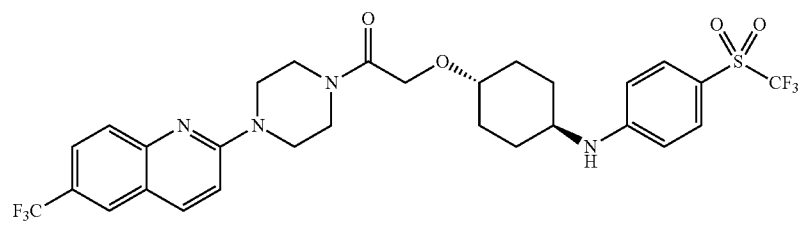

To a solution of 2-[4-[4-(trifluoromethylsulfonyl)anilino]cyclohexoxy]acetic acid (75 mg, 0.19 mmol, 1 eq.) in DMF (1 ml) was added EDAC.HCl (56 mg, 0.29 mmol, 1.5 eq.), HOBt (39 mg, 0.29 mmol, 1.5 eq.), 4-methylmorpholine (0.21 mL, 1.96 mmol, 10 eq.), and 2-piperazin-1-yl-6-(trifluoromethyl)quinoline hydrochloride (62 mg, 0.19 mmol, 1 eq.). The resulting solution was stirred overnight at room temperature and concentrated to remove DMF under vacuum. The resulting crude material was diluted with water, extracted with ethyl acetate, dried over sodium sulfate and concentrated to get crude. The crude material was purified by silica gel column chromatography using ethyl acetate/dichloromethane to elute. The product containing fractions were combined and concentrated under vacuum to afford 89 mg of 1-[4-[6-(trifluoromethyl)-2-quinolyl]piperazin-1-yl]-2-[4-[4-(trifluoromethylsulfonyl) anilino]cyclohexoxy]ethanone as white solid (70%); (CI, m/z): [M+H]$^+$ 645; $^1$H NMR (400 MHz, CD$_3$OD): δ 7.99 (d, J=9.2 Hz, 1H), 7.92 (s, 1H), 7.69-7.81 (m, 4H), 7.06 (d, J=9.2 Hz, 1H), 6.63 (d, J=9.0 Hz, 2H), 4.44 (d, J=7.6 Hz, 1H), 4.27 (s, 2H), 3.86-3.97 (m, 2H), 3.80 (m, 4H), 3.69-3.76 (m, 2H), 3.35-3.55 (m, 2H), 2.12-2.25 (m, 4H), 1.45-1.55 (m, 2H), 1.26-1.35 (m, 2H).

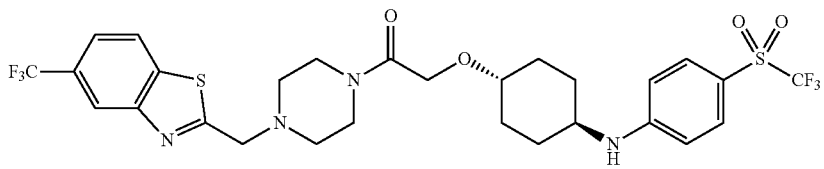 [SMILES: O=C(CO[C@H]1CC[C@H](Nc2ccc(S(=O)(=O)C(F)(F)F)cc2)CC1)N1CCN(Cc2nc3cc(C(F)(F)F)ccc3s2)CC1]

Compound 344: 1-[4-[[5-(trifluoromethyl)-1,3-benzothiazol-2-yl]methyl]piperazin-1-yl]-2-[4-[4-(trifluoromethylsulfonyl)anilino]cyclohexoxy]ethanone (CI, m/z): [M+H]$^+$ 665; $^1$H NMR (400 MHz, CD$_3$OD): δ 8.24 (s, 1H), 8.00 (d, J=8.3 Hz, 1H), 7.74 (d, J=8.9 Hz, 2H), 7.63 (dd, J=8.4, 1.4 Hz, 1H), 6.60-6.68 (m, 2H), 4.43 (d, J 7.3 Hz, 1H), 4.21 (s, 2H), 4.02 (s, 2H), 3.60-3.75 (m, 4H), 3.35-3.48 (m, 2H), 2.65-2.72 (m, 4H), 2.11-2.20 (m, 4H), 1.41-1.52 (m, 2H), 1.27-1.33 (m, 2H).

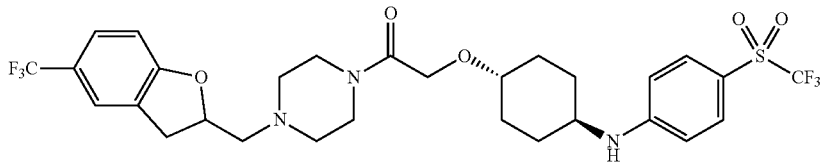 [SMILES: O=C(CO[C@H]1CC[C@H](Nc2ccc(S(=O)(=O)C(F)(F)F)cc2)CC1)N1CCN(CC2Cc3cc(C(F)(F)F)ccc3O2)CC1]

Compound 378: 1-[4-[[5-(trifluoromethyl)-2,3-dihydrobenzofuran-2-yl]methyl]piperazin-1-yl]-2-[4-[4-(trifluoromethylsulfonyl)anilino]cyclohexoxy]ethanone (CI, m/z): [M+H]$^+$ 650; $^1$H NMR (400 MHz, CD$_3$OD): δ 7.71 (d, J=8.8 Hz, 2H), 7.33-7.44 (m, 2H), 6.81 (d, J=8.2 Hz, 1H), 6.55-6.65 (m, 2H), 4.95-5.11 (m, 1H), 4.44 (d, J=7.6 Hz, 1H), 4.18 (s, 2H), 3.52-3.69 (m, 4H), 3.24-3.45 (m, 3H), 3.00 (dd, J=15.8, 7.7 Hz, 1H), 2.77 (dd, J=13.6, 7.5 Hz, 1H), 2.51-2.67 (m, 5H), 2.12 (m, 4H), 1.38-1.50 (m, 2H), 1.23-1.31 (m, 2H).

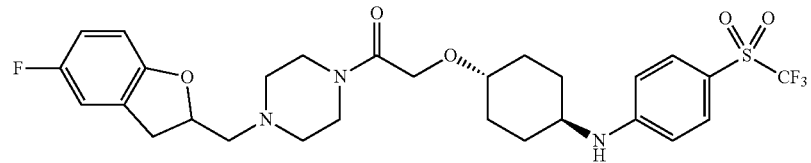 [SMILES: O=C(CO[C@H]1CC[C@H](Nc2ccc(S(=O)(=O)C(F)(F)F)cc2)CC1)N1CCN(CC2Cc3cc(F)ccc3O2)CC1]

Compound 379: 1-[4-[(5-fluoro-2,3-dihydrobenzo-furan-2-yl)methyl]piperazin-1-yl]-2-[4-[4-(trifluoromethylsulfonyl)anilino]cyclohexoxy]ethanone (CI, m/z): [M+H]⁺ 600; ¹H NMR (400 MHz, CD₃OD): δ 7.74 (d, J=8.9 Hz, 2H), 6.88 (dd, J=7.9, 2.6 Hz, 1H), 6.76-6.83 (m, 1H), 6.69 (dd, J=8.6, 4.2 Hz, 1H), 6.61-6.66 (m, 2H), 4.92-5.04 (m, 1H), 4.43 (d, J=7.3 Hz, 1H), 4.20 (s, 2H), 3.54-3.71 (m, 4H), 3.34-3.49 (m, 2H), 3.27 (dd, J=15.8, 9.1 Hz, 1H), 2.97 (dd, J=15.6, 8.1 Hz, 1H), 2.79 (dd, J=13.5, 7.6 Hz, 1H), 2.53-2.68 (m, 5H), 2.09-2.21 (m, 4H), 1.41-1.52 (m, 2H), 1.27-1.34 (m, 2H).

J=8.1, 1.2 Hz, 1H), 7.46-7.61 (m, 3H), 7.38 (d, J=2.7 Hz, 1H), 6.81 (d, J=2.3 Hz, 1H), 6.66 (dd, J=8.6, 2.4 Hz, 1H), 4.32 (d, J=7.6 Hz, 1H), 4.27 (s, 2H), 3.77-3.92 (m, 4H), 3.27-3.49 (m, 6H), 2.08-2.22 (m, 4H), 1.43-1.55 (m, 2H), 1.26-1.34 (m, 2H).

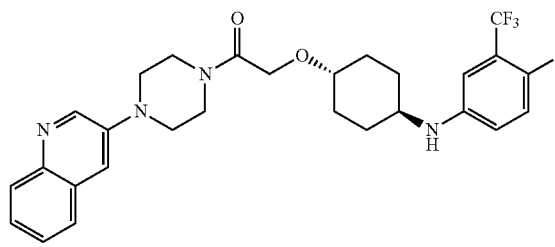

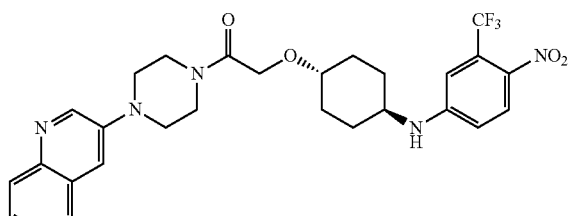

Compound 335: 4-[[4-[2-oxo-2-[4-(3-quinolyl)piperazin-1-yl]ethoxy]cyclohexyl]amino]-2-(trifluoromethyl)benzonitrile (CI, m/z): [M+H]⁺ 538; ¹H NMR (400 MHz, CD₃OD): δ 8.81 (d, J=2.8 Hz, 1H), 8.02 (d, J=8.3 Hz, 1H), 7.70 (dd, Compound 336: 2-[4-[4-nitro-3-(trifluoromethyl)anilino]cyclohexoxy]-1-[4-(3-quinolyl)piperazin-1-yl]ethanone (CI, m/z): [M+H]⁺ 558; ¹H NMR (400 MHz, CD₃OD): δ 8.81 (d, J=2.8 Hz, 1H), 8.02 (d, J=9.0 Hz, 2H), 7.71 (dd, J=8.1, 1.1 Hz, 1H), 7.48-7.60 (m, 2H), 7.38 (d, J=2.8 Hz, 1H), 6.85 (d, J=2.5 Hz, 1H), 6.64 (dd, J=9.1, 2.6 Hz, 1H), 4.46 (d, J=7.6 Hz, 1H), 4.27 (s, 2H), 3.77-3.92 (m, 4H), 3.37-3.53 (m, 2H), 3.32 (m, 4H), 2.10-2.24 (m, 4H), 1.46-1.56 (m, 2H), 1.27-1.35 (m, 2H).

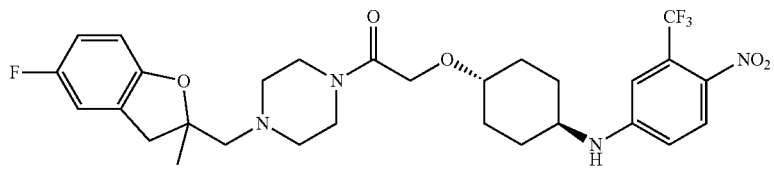 [SMILES: CC1(CN2CCN(C(=O)CO[C@H]3CC[C@H](Nc4ccc([N+](=O)[O-])c(C(F)(F)F)c4)CC3)CC2)Cc2cc(F)ccc2O1]

Compound 377: 1-[4-[(5-fluoro-2-methyl-3H-benzofuran-2-yl)methyl]piperazin-1-yl]-2-[4-[4-nitro-3-(trifluoromethyl)anilino]cyclohexoxy]ethanone (CI, m/z): [M+H]⁺ 595; ¹H NMR (400 MHz, CD₃OD): δ 8.01 (d, J=9.1 Hz, 1H), 6.82-6.90 (m, 2H), 6.78 (td, J=8.9, 2.8 Hz, 1H), 6.55-6.66 (m, 2H), 4.59 (d, J=7.7 Hz, 1H), 4.17 (s, 2H), 3.32-3.61 (m, 6H), 3.26 (d, J=15.7 Hz, 1H), 2.88 (d, J=15.7 Hz, 1H), 2.49-2.68 (m, 6H), 2.13 (d, J=10.6 Hz, 4H), 1.38-1.53 (m, 5H), 1.25-1.33 (m, 2H).

EXAMPLE 39: Preparation of Compound 400

Compound 400

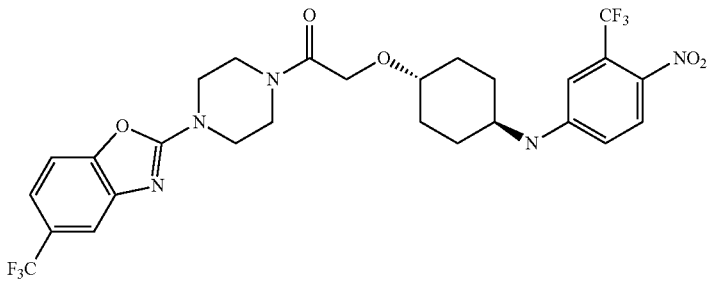

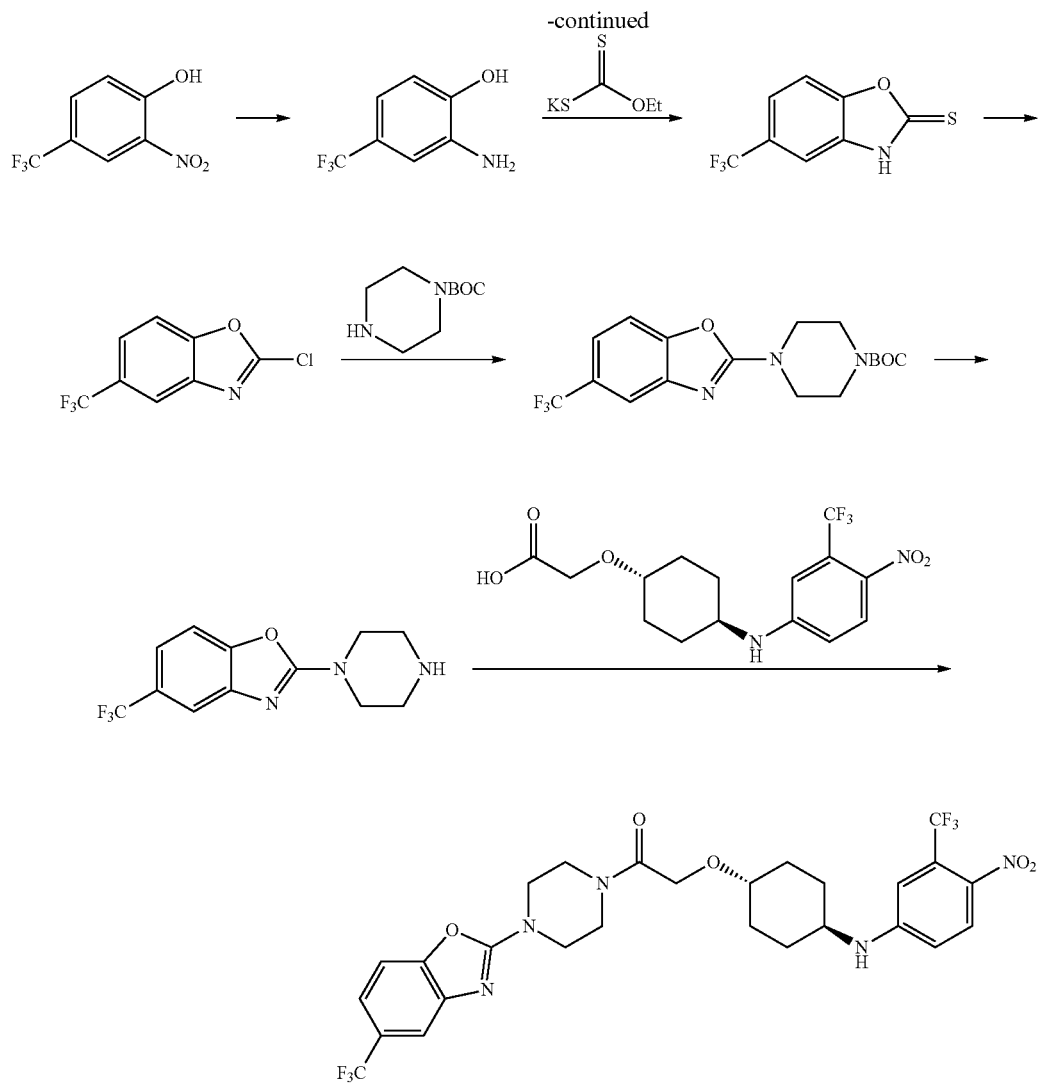

2-[4-(4-nitro-3-trifluoromethyl-phenylamino)-cyclo-hexyloxy]-1-[4-(5-trifluoromethyl-benzooxazol-2-yl)-piperazin-1-yl]-ethanone (CI, m/z): [M+H]$^+$ 616; $^1$H NMR (DMSO-d$_6$): δ 8.05 (d, J=9.2 Hz, 1H), 7.63 (dd, J=5.1, 3.3 Hz, 2H), 7.45 (d, J=7.4 Hz, 1H), 7.40 (dd, J=8.7, 1.5 Hz, 1H), 7.06 (s, 1H), 6.85 (dd, J=9.3, 2.4 Hz, 1H), 4.22 (s, 2H), 3.57-3.74 (m, 8H), 3.43-3.51 (m, 1H), 3.34-3.43 (m, 1H), 2.04 (d, J=12.9 Hz, 2H), 1.96 (d, J=12.3 Hz, 2H), 1.31-1.44 (m, 2H), 1.19-1.30 (m, 2H); $^{19}$F NMR (376 MHz, DMSO-d$_6$): δ −59.45 (s, 3H), −59.15 (s, 3H).

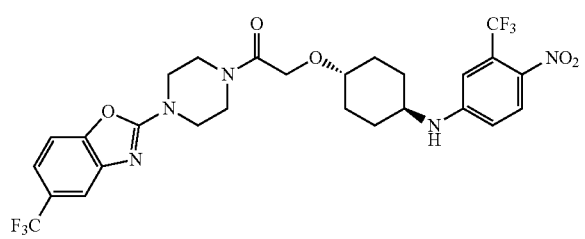 [SMILES: O=C(CO[C@H]1CC[C@H](Nc2ccc([N+](=O)[O-])c(C(F)(F)F)c2)CC1)N1CCN(c2nc3cc(C(F)(F)F)ccc3o2)CC1]

2-[4-(4-nitro-3-trifluoromethyl-phenylamino)-cyclo-hexyloxy]-1-[4-(5-trifluoromethoxy-benzooxazol-2-yl)-piperazin-1-yl]ethanone (CI, m/z): [M+H]$^+$ 632; $^1$H NMR (DMSO-d$_6$): δ 8.05 (d, J=9.2 Hz, 1H), 7.51 (d, J=8.6 Hz, 1H), 7.45 (d, J=7.8 Hz, 1H), 7.31 (d, J=1.4 Hz, 1H), 7.06 (s, 1H), 7.01 (dd, J=8.6, 1.5 Hz, 1H), 6.85 (dd, J=9.3, 2.5 Hz, 1H), 4.21 (s, 2H), 3.56-3.72 (m, 8H), 3.43-3.52 (m, 1H), 3.36-3.42 (m, 1H), 2.04 (d, J=9.5 Hz, 2H), 1.96 (d, J=12.7 Hz, 2H), 1.32-1.44 (m, 2H), 1.19-1.31 (m, 2H); $^{19}$F NMR (376 MHz, DMSO-d$_6$): δ −59.15 (s, 3H), −57.15 (s, 3H).

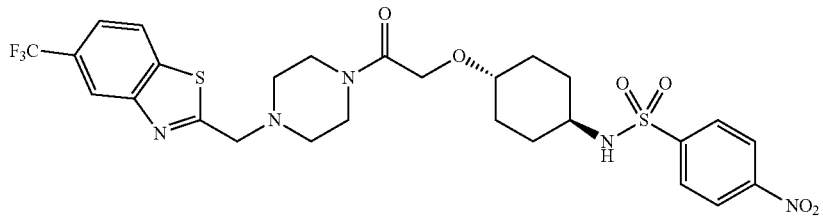 [SMILES: O=C(CO[C@H]1CC[C@H](NS(=O)(=O)c2ccc([N+](=O)[O-])cc2)CC1)N1CCN(Cc2nc3cc(C(F)(F)F)ccc3s2)CC1]

4-nitro-N-[4-[2-oxo-2-[4-[[5-(trifluoromethyl)-1,3-benzothiazol-2-yl]methyl]piperazin-1-yl]ethoxy]cyclohexyl]benzenesulfonamide (#403)

(CI, m/z): [M+H]+ 642; ¹H NMR (400 MHz, CDCl₃): δ 8.33-8.42 (m, 2H), 8.23 (s, 1H), 8.04-8.10 (m, 2H), 7.99 (d, J=8.4 Hz, 1H), 7.63 (dd, J=8.4, 1.4 Hz, 1H), 4.64 (d, J=7.6 Hz, 1H), 4.14 (s, 2H), 4.00 (s, 2H), 3.63-3.73 (m, 2H), 3.54-3.62 (m, 2H), 3.17-3.37 (m, 2H), 2.50-2.76 (m, 4H), 1.86-2.03 (m, 4H), 1.18-1.37 (m, 4H).

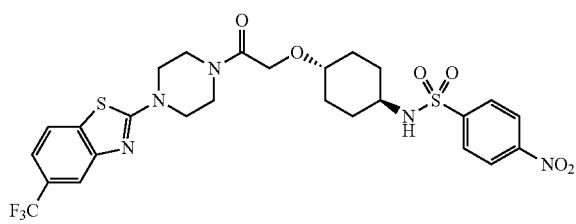 [SMILES: O=C(CO[C@H]1CC[C@H](NS(=O)(=O)c2ccc([N+](=O)[O-])cc2)CC1)N1CCN(c2nc3cc(C(F)(F)F)ccc3s2)CC1]

Compound 402: 4-nitro-N-[4-[2-oxo-2-[4-[5-(trifluoromethyl)-1,3-benzothiazol-2-yl]piperazin-1-yl]ethoxy]cyclohexyl]benzenesulfonamide (CI, m/z): [M+H]+ 628; ¹H NMR (400 MHz, DMSO-d₆): δ 8.36-8.47 (m, 2H), 7.98-8.11 (m, 4H), 7.72 (d, J=1.2 Hz, 1H), 7.39 (dd, J=8.3, 1.2 Hz, 1H), 4.13 (s, 2H), 3.50-3.69 (m, 8H), 3.18-3.27 (m, 1H), 2.99-3.12 (m, 1H), 1.83-1.96 (m, 2H), 1.57-1.69 (m, 2H), 1.10-1.27 (m, 4H).

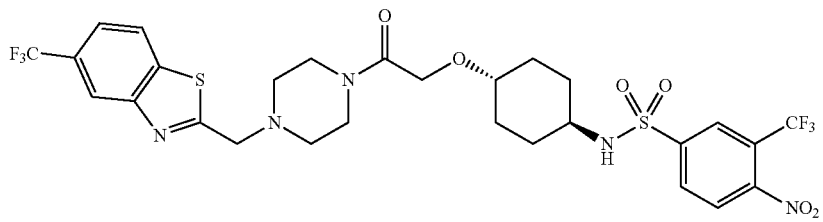 [SMILES: O=C(CO[C@H]1CC[C@H](NS(=O)(=O)c2ccc([N+](=O)[O-])c(C(F)(F)F)c2)CC1)N1CCN(Cc2nc3cc(C(F)(F)F)ccc3s2)CC1]

Compound 405: 4-nitro-N-[4-[2-oxo-2-[4-[[5-(trifluoromethyl)-1,3-benzothiazol-2-yl]methyl]piperazin-1-yl]ethoxy]cyclohexyl]-3-(trifluoromethyl)benzenesulfonamide (CI, m/z): [M+H]+ 710; ¹H NMR (400 MHz, CDCl₃): δ 8.32 (d, J=1.71 Hz, 1H), 8.21-8.25 (m, 2H), 8.00 (dd, J=8.4, 2.7 Hz, 2H), 7.63 (dd, J=8.4, 1.3 Hz, 1H), 4.77 (d, J=7.7 Hz, 1H), 4.15 (s, 2H), 4.01 (s, 2H), 3.55-3.73 (m, 4H), 3.21-3.38 (m, 2H), 2.66 (br s, 4H), 1.87-2.07 (m, 4H), 1.21-1.41 (m, 4H).

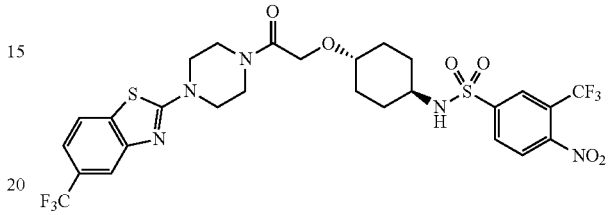

Compound 404: 4-nitro-N-[4-[2-oxo-2-[4-[5-(trifluoromethyl)-1,3-benzothiazol-2-yl]piperazin-1-yl]ethoxy]cyclohexyl]-3-(trifluoromethyl)benzenesulfonamide (CI, m/z): [M+H]+ 696; ¹H NMR (400 MHz, DMSO-d₆): δ 8.31-8.42 (m, 3H), 8.19 (d, J=7.1 Hz, 1H), 8.03 (d, J=8.2 Hz, 1H), 7.73 (br s, 1H), 7.39 (dd, J=8.2, 1.2 Hz, 1H), 4.14 (s, 2H), 3.52-3.68 (m, 8H), 3.19-3.29 (m, 1H), 3.06-3.17 (m, 1H), 1.84-1.96 (m, 2H), 1.58-1.71 (m, 2H), 1.17-1.26 (m, 4H).

Biological Activity Examples

Method A: Screening Method to Test Activity of Compounds Against *Haemonchus contortus*.

Twenty L1 *Haemonchus contortus* larvae were added to wells of a microtitre plate containing a nutrient medium and the test compound in DMSO. An analysis was conducted at 4 days to determine the extent of development of the larvae. Larvae exposed to DMSO alone served as controls. Compounds numbers 13, 14, 16, 17, 18, 24, 68, 75, 76, 77, 78, 79, 80, 81, 82, 83, 84, 85, 86, 87, 88, 89, 90, 91, 92, 93, 96, 97, 98, 99, 100, 103, 131, 172, 173, 174, 178, 179, 180, 181, 182, 183, 184, 185, 186, 187, 188, 189, 191, 194, 216, 217, 218, 219, 220, 222, 223, 225, 226, 227, 232, 233, 234, 235, 236, 237, 238, 239, 240, 241, 245, 246, 247, 248, 249, 250, 251, 252, 253, 254, 255, 256, 257, 258, 260, 260-10, 261, 262, 262-10, 263, 264, 265, 266, 267, 268, 269, 270, 271, 272, 273, 274, 275, 276, 277, 278, 279, 280, 281, 282, 283, 285, 287, 288, 289, 290, 291, 292, 293, 294, 297, 298, 299, 300, 301, 302, 304, 305, 306, 307, 308, 309, 310, 311, 312, 313, 315, 316, 318, 319, 320, 321, 322, 323, 324, 325, 326, 327, 328, 329, 330, 331, 332, 333, 334, 335, 336, 338, 342, 343, 344, 357, 358, 364, 365, 370, 371, 372, 373, 374, 375, 377, 381, 399, 400, and 401 gave at least 90% motility inhibition at a test concentration of less than or equal to 5 ppm when assessed at the 4 day time point.

Method B: Screening Method to Test Activity of Compounds Against an Anthelmintic-Resistant Isolate of *Haemonchus contortus*.

The conditions described in method A were used against an isolate of *H. contortus* found to be functionally resistant against the benzimidazole class of anthelmintics (e.g. 127-fold resistance to thiabendazole). Analogs 14, 16, 17, 24, 76, 77, 78, 79, 83, 84, 88, 89, 90, 97, 99, 178, 179, 180, 183, 185, 187, 188, 191, 217, 219, 232, 233, 234, 235, 236, 237, 245, 246, 247, 248, 260, 260-10, 261, 262, 262-10, 265, 266, 269, 270, 271, 272, 273, 278, 279, 281, 282, 283, 287, 289, 290, 291, 293, 297, 298, 299, 300, 301, 302, 304, 307, 310, 311, 320, 325, 326, 327, 328, 329, 330, 331, 332, 335, 342, 343, 344, 357, 358, 364, 365, & 370 were evaluated and found to be of similar efficacy to that observed against the wild-type strain of *H. contortus*.

Method C: Screening Method to Test Activity of Compounds Against *Cooperia oncophora* In Vitro.

Twenty L1 *Cooperia oncophora* larvae were added to the wells of a microtitre plate containing a nutrient medium and the test compound in DMSO. An analysis was conducted at 4 days to determine the extent of development of the larvae. Larvae exposed to DMSO alone served as controls. Compounds 76, 77, 78, 89, 90, 97, 99, 178, 180, 183, 234, 235, 237, 245, 246, 260, 261, 262, 266, 269, 270, 271, 272, 273, 278, 281, 282, 283, 289, 290, 291, 297, 298, 299, 300, 301, 302, 303, 304, 307, 310, 320, 325, 326, 328, 331, 342, 343, 344 gave at least 90% inhibition of motility at a test concentration of less than 5 ppm when assessed at the 4 day time point.

Method D: Method to Test Activity of Compounds Against *Haemonchus contortus* In Vivo in Mongolian Jirds (*Meriones unguiculatus*).

Mongolian jirds, at least five weeks old, that have been immunosuppressed were artificially infected with ensheathed *Haemonchus contortus* third instar larvae. Six days after infection, the jirds were treated by oral gavage with the test compounds, dissolved in a mixture of DMSO/corn oil, at doses of 30 mg/kg. Jirds treated only with the placebo (DMSO/corn oil carrier) served as controls. On day 9 (3 days after treatment) the jirds were euthanized and necropsied for recovery of parasites from the stomach. Efficacy was calculated as the average % reduction in the number of worms in each test group compared with the average number of worms from the control group. Compounds numbers 235, 272, 278, 325, and 327 provided a 70-90% reduction in nematode infestation in Mongolian jirds treated by oral gavage with the test article at a dose of 30 mg/kg. Compounds numbers 77, 78, 89, 180, 245, 261, 273, 283, 302, and 342 provided a >90% reduction in nematode infestation in Mongolian jirds treated by oral gavage with the test article at a dose of 30 mg/kg.

Method E: Method to test activity of compounds against *Trichostrongylus colubriformis* in vivo in Mongolian jirds (*Meriones unguiculatus*).

Mongolian jirds, at least five weeks old, that have been immunosuppressed were artificially infected with ensheathed *Trichostrongylus colubriformis* third instar larvae. Six days after infection, the jirds were treated by oral gavage with the test compounds, dissolved in a mixture of DMSO/corn oil, at doses of 30 mg/kg. Jirds treated only with the placebo (DMSO/corn oil carrier) served as controls. On day 9 (3 days after treatment) the jirds were euthanized and necropsied for recovery of parasites from the stomach. Efficacy was calculated as the average % reduction in the number of worms in each test group compared with the average number of worms from the control group. In this method, a reduction in nematode infestation is achieved with compounds of formula (I), especially from table 1. Compounds numbers 77 & 89 provided a 60-80% reduction in nematode infestation in Mongolian jirds treated by oral gavage with the test article at a dose of 30 mg/kg. In particular, compounds numbers 78, 302, and 342 provided a >80% reduction in nematode infestation in Mongolian jirds treated by oral gavage with the test article at a dose of 30 mg/kg.

Method F: Screening Method to Test Activity of Compounds Against Microfilaria of *Dirofilaria immitis*.

Microfilaria of *Dirofilaria immitis* were added to the wells of a microtitre plate containing buffer and the test compounds in DMSO. An assessment was conducted at 24 hours to determine survival of the microfilaria. Microfilaria exposed to DMSO alone served as controls. Compounds 15, 76, 77, 78, 79, 83, 84, 87, 88, 89, 93, 94, 95, 96, 98, 100, 103, 104, 114, 160, 161, 182, 188, 189, 230, 231, 232, 257, 269, 277, 279, 284, 287, 294, and 304 were found to have $EC_{50}$ values of less than 5 ppm, compounds 13, 14, 17, 18, 19, 20, 24, 81, 92, 97, 99, 101, 102, 172, 178, 179, 180, 181, 183, 184, 186, 187, 192, 193, 194, 195, 210, 216, 217, 218, 219, 220, 221, 225, 226, 227, 229, 233, 235, 236, 242, 245, 246, 247, 249, 250, 251, 252, 254, 255, 256, 258, 260, 262, 263, 265, 270, 271, 272, 273, 274, 275, 278, 290, 292, 297, 298, and 260-10 returned $EC_{50}$ values of less than 1 ppm, and compounds 90, 185, 222, 223, 234, 237, 248, 253, 261, 266, 299, 300, 301, 302, 305, 306, 307, 308, 309, 310, and 262-10 returned $EC_{50}$ values of less than 0.1 ppm.

Method G: Permeability of Compounds.

Permeability of a compound across the epithelium cells along the gastrointestinal tract is an important limiting factor for the oral absorption and systemic availability of the compound. An in vitro model utilizing Caco-2/TC7 cells is employed to assess the permeability characteristics of new chemical entities (NCEs). For orally administered compounds, absorption depends on the intrinsic permeability across the intestinal epithelium and whether the active agent is a substrate or inhibitor of uptake or efflux transporters.

The permeability studies were performed under standard conditions in the apical to basolateral (A→B) direction with a pH gradient and a BSA gradient (standard apical medium (0.5% BSA at pH 6.5)/standard basal medium (5% BSA at pH 7.4)); conditions that most closely reflect the conditions in the in vivo situation. Samples were deproteinized by the addition of 404 µl acetonitrile to 200 µl sample, followed by a 20-minute centrifugation at 1730 g. Compound solubilisation: compound solutions at final concentrations of 20 µM were prepared following dilutions of stock solutions (starting from 10 mM in DMSO) in HBSS. Final concentration of DMSO was adjusted to 1%. Analytical conditions: Supernatants recovered following centrifugation were analysed by LC/MS/MS using a reverse phase column and the mobile phases delivered at 0.3 ml/minute in a gradient: water (A) and acetonitrile (B) (each with 0.1% formic acid).

The permeability of standard compounds in the CACO-2/TC7 in vitro model for permeability is shown in table 9. Every experiment (n) represents the mean of 3 filters per experiment.

TABLE 9

Permeability as measured in the CACO-2/TC7 model.

| Compound # | Permeability (A-B) [×10⁻⁷ cm/sec] |
|---|---|
| 335 | 150 |
| 235 | 138 |
| 235 | 138 |
| 80 | 121 |
| 285 | 120 |
| 334 | 119 |
| 323 | 119 |
| 287 | 110 |
| 301 | 99 |
| 24 | 97 |
| 274 | 92 |
| 325 | 90 |
| 304 | 90 |
| 306 | 90 |
| 292 | 83 |
| 294 | 82 |
| 261 | 82 |
| 333 | 81 |
| 254 | 80 |
| 322 | 79 |
| 336 | 79 |
| 221 | 75 |
| 328 | 72 |
| 82 | 71 |
| 327 | 69 |
| 320 | 68 |
| 332 | 65 |
| 291 | 62 |
| 297 | 57 |
| 329 | 56 |
| 187 | 55 |
| 256 | 54 |
| 84 | 53 |
| 222 | 50 |
| 178 | 49 |
| 234 | 40 |
| CC-1 | 25 |

Relative to the prior art compound CC-1 (described in WO2009/077527), compounds 234, 178, & 222 were 50-100% more permeable, compounds 84, 256, 187, 329, 297, 291, 332, 320, 327, 82, 328, & 221 were 100-200% more permeable, compounds 336, 322, 254, 333, 261, 294, 292, 306, 304, 325, 274, 24, & 301 were 200-300% more permeable, and compounds 287, 323, 334, 285, 80, 235, & 335 were over 300% more permeable in the intestinal cell model.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An anthelmintic compound of formula (IA-2):

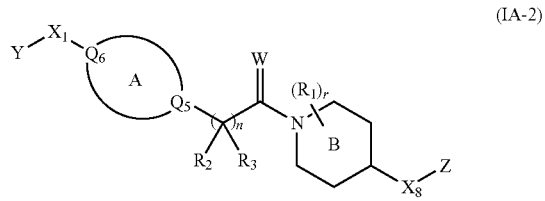

(IA-2)

wherein Y is a bicyclic carbocyclic or a bicyclic heterocyclic group selected from the group consisting of naphthyl, indolyl, benzothiazolyl, benzoxazolyl, benzodioxolyl, benzothienyl, quinuclidinyl, quinolinyl, tetrahydroisoquinolinyl, isoquinolinyl, benzimidazolyl, indolizinyl, benzofuranyl, dihydrobenzofuranyl, chromonyl, coumarinyl, benzopyranyl, cinnolinyl, quinoxalinyl, indazolyl, pyrrolopyridyl, furopyridinyl, dihydroisoindolyl, dihydroquinazolinyl and tetrahydroquinolinyl optionally substituted by one or more of halogen, nitro, cyano, hydroxy, hydroxyalkyl, amino, alkylamino, dialkylamino, aminoalkyl, alkyl, haloalkyl, alkoxy, haloalkoxy, alkylthio, $SF_5$, haloalkylthio, alkylsulfinyl, haloalkylsulfinyl, alkyl sulfonyl or haloalkylsulfonyl;

Z is phenyl optionally substituted with one or more halogen, nitro, cyano, or haloalkyl;

$X_1$ is a bond, $X_8$ is —O—, or —NH—, which is optionally substituted with alkyl;

Ring A is L1:

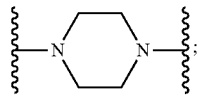

L1

W is O or S;

$R_2$ and $R_3$ are independently hydrogen or alkyl;

n is 1, 2 or 3; and r is 0 to 5.

2. A composition for the treatment of a parasitic infection or infestation in an animal, comprising an effective amount of at least one anthelmintic compound of claim 1 in combination with a pharmaceutically acceptable carrier.

3. The composition of claim 2, wherein the composition comprises an additional parasiticidal active agent.

4. A method for the treatment of a parasitic infection or infestation in an animal, comprising administering an effective amount of the anthelmintic compound of claim 1 to the animal.

5. The compound of claim 1, wherein $X_8$ is —O—, —NH— or —N(CH$_3$)—.

6. The compound of claim 5, wherein:
$R_2$ and $R_3$ are independently hydrogen or $C_1$-$C_3$alkyl; and
$X_8$ is —NH— or —N(CH$_3$)—.

7. The compound of claim 6, wherein Y is naphthyl, benzothiazolyl, benzoxazolyl, benzothienyl, quinolinyl, isoquinolinyl, indolizinyl, benzofuranyl or dihydrobenzofuranyl optionally substituted by one or more halogen, alkyl, haloalkyl, alkylthio, haloalkylthio, alkoxy, haloalkoxy, $SF_5$, alkylsulfinyl, haloalkylsulfinyl, alkylsulfonyl or haloalkylsulfonyl; and Z is phenyl optionally substituted with one or more halogen, nitro, cyano or $CF_3$.

8. The compound of claim 7, wherein Y is naphthyl, benzothiazolyl, benzoxazolyl, quinolinyl, isoquinolinyl, indolizinyl, benzofuranyl or dihydrobenzofuranyl optionally substituted with one or more halogen, haloalkyl, haloalkylthio, $SF_5$ or haloalkoxy; and Z is phenyl substituted with one or more fluoro, nitro or $CF_3$.

9. The compound of claim 7, wherein Y is naphthyl, benzothiazolyl, benzoxazolyl, quinolinyl, isoquinolinyl, indolizinyl, benzofuranyl or dihydrobenzofuranyl optionally substituted with one or more halogen haloalkyl, haloalkoxy, $SF_5$ or haloalkylthio; and Z is phenyl substituted with one or more fluoro, cyano or $CF_3$.

10. The compound of claim 8, wherein Y is naphthyl, benzothiazolyl, benzoxazolyl, quinolinyl, isoquinolinyl, indolizinyl, benzofuranyl or dihydrobenzofuranyl optionally substituted with one or more halogen, $CF_3$, —$OCF_3$, —$SCF_3$ or $SF_5$; and Z is phenyl substituted with nitro and $CF_3$.

11. The compound of claim 9, wherein Y is naphthyl, benzothiazolyl, benzoxazolyl, quinolinyl, isoquinolinyl benzofuranyl or dihydrobenzofuranyl, optionally substituted with one or more halogen, $CF_3$, —$OCF_3$, —$SCF_3$ or —$SF_5$; and Z is phenyl substituted with cyano and $CF_3$.

12. The compound of claim 8, wherein:
Y is naphthyl, quinolinyl, benzothiazolyl or benzoxazolyl optionally substituted with one or more halogen, or $C_1$-$C_3$haloalkyl;
$X_8$ is —NH—;
$R_2$ and $R_3$ are each independently hydrogen or $C_1$-$C_3$alkyl;
Z is phenyl optionally substituted with one or more of F, nitro, cyano or $CF_3$; and
n is 2 or 3.

13. The compound of claim 12, wherein:
Y is naphthyl optionally substituted with one or more F, Cl or $CF_3$;
$R_2$ and $R_3$ are independently hydrogen or $CH_3$;
Z is phenyl substituted with one or more nitro, cyano or $CF_3$.

14. The compound of claim 12, wherein:
Y is quinolinyl optionally substituted with one or more F, Cl or $CF_3$;
$R_2$ and $R_3$ are independently hydrogen or $CH_3$;
Z is phenyl substituted with one or more nitro, cyano or $CF_3$.

15. The compound of claim 12, wherein:
Y is benzothiazole optionally substituted with one or more F, Cl or $CF_3$;
$R_2$ and $R_3$ are independently hydrogen or $CH_3$;
Z is phenyl substituted with one or more nitro, cyano or $CF_3$.

16. The compound of claim 12, wherein:
Y is benzoxazole optionally substituted with one or more F, Cl or $CF_3$;
$R_2$ and $R_3$ are independently hydrogen or $CH_3$;
Z is phenyl substituted with one or more nitro, cyano or $CF_3$.

* * * * *